US011535666B2

(12) United States Patent
Chen et al.

(10) Patent No.: US 11,535,666 B2
(45) Date of Patent: Dec. 27, 2022

(54) TRIFUNCTIONAL MOLECULE AND APPLICATION THEREOF

(71) Applicant: CYTOCARES (SHANGHAI) INC., Shanghai (CN)

(72) Inventors: Shuai Chen, Shanghai (CN); Huaxing Zhu, Shanghai (CN); Yuanping Liao, Shanghai (CN)

(73) Assignee: CYTOCARES (SHANGHAI) INC., Shanghai (CN)

( * ) Notice: Subject to any disclaimer, the term of this patent is extended or adjusted under 35 U.S.C. 154(b) by 363 days.

(21) Appl. No.: 16/474,555

(22) PCT Filed: Aug. 9, 2017

(86) PCT No.: PCT/CN2017/096594
§ 371 (c)(1),
(2) Date: Nov. 12, 2019

(87) PCT Pub. No.: WO2018/120843
PCT Pub. Date: Jul. 5, 2018

(65) Prior Publication Data

US 2020/0207851 A1 Jul. 2, 2020

(30) Foreign Application Priority Data

Dec. 30, 2016 (CN) ......................... 201611256659.9
Dec. 30, 2016 (CN) ......................... 201611258643.1
Dec. 30, 2016 (CN) ......................... 201611258691.0
Dec. 30, 2016 (CN) ......................... 201611260817.8

(51) Int. Cl.
*C07K 16/28* (2006.01)
*A61P 35/00* (2006.01)

(52) U.S. Cl.
CPC .......... *C07K 16/2803* (2013.01); *A61P 35/00* (2018.01); *C07K 16/2809* (2013.01); *C07K 16/2818* (2013.01); *C07K 2317/31* (2013.01); *C07K 2317/53* (2013.01); *C07K 2317/622* (2013.01); *C07K 2317/75* (2013.01); *C07K 2317/76* (2013.01)

(58) Field of Classification Search
None
See application file for complete search history.

(56) References Cited

U.S. PATENT DOCUMENTS

2002/0051780 A1* 5/2002 Lindhofer .............. C07K 16/30 424/130.1
2014/0294833 A1* 10/2014 Desjarlais .......... C07K 16/2803 424/136.1

FOREIGN PATENT DOCUMENTS

| | | | | |
|---|---|---|---|---|
| CN | 1380341 A | | 11/2002 | |
| CN | 1563092 A | | 1/2005 | |
| CN | 104788573 A | | 7/2015 | |
| CN | 106117366 A | | 11/2016 | |
| CN | 106188305 A | | 12/2016 | |
| CN | 106589129 A | | 4/2017 | |
| WO | WO 2004/106381 | * | 12/2004 | ............. C07K 16/28 |
| WO | WO 2016069993 A1 | | 5/2016 | |
| WO | WO 2016/139463 | * | 9/2016 | ............. C12N 15/86 |

OTHER PUBLICATIONS

Reusch, U. et al., "Effect of Tetravalent Bispecific CD19 XCD3 Recombinant Antibody Construct and CD28 Costimulation on Lysis of Malignant B Cells from Patients with Chronic Lymphocytic Leukemia by Autologous T Cells", Int. J. Cancer, Jun. 16, 2004 (Jun. 16, 2004), vol. 112, pp. 509-518.

* cited by examiner

*Primary Examiner* — Nelson B Moseley, II
(74) *Attorney, Agent, or Firm* — Rothwell, Figg, Ernst & Manbeck, P.C.

(57) ABSTRACT

This disclosure belongs to the field of biomedical technology, and particularly refers to a trifunctional molecule and the application thereof. The structure of the trifunctional molecule includes a first functional domain, a second functional domain and a third functional domain. These domains are capable of simultaneously binding to CD19, CD3, and T cell positive (negative) costimulatory factors, thereby producing the first and second signal required for T cell activation. The trifunctional molecule is a recombinant protein peptide chain, which can be produced by a eukaryotic cell expression system. The product has a single structure, simple purification process, high protein yield, and preparation process and product stability. The trifunctional molecule is superior to the anti-CD19/anti-CD3 BiTE bispecific antibody in killing CD19-positive target cells. Compared with the CAR-T technology targeting CD19, the trifunctional molecule is more convenient to use, the dose is controllable, and the side effects of CAR-T are avoided.

12 Claims, 28 Drawing Sheets

Specification includes a Sequence Listing.

SEQUENCE LISTING

```
<160> NUMBER OF SEQ ID NOS: 357

<210> SEQ ID NO 1
<211> LENGTH: 756
<212> TYPE: PRT
<213> ORGANISM: Artificial
<220> FEATURE:
<223> OTHER INFORMATION: The amino acid sequence of CD19-CD3-CD28 TsAb_M
      monomer

<400> SEQUENCE: 1

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
```

-continued

```
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495
```

```
Leu Lys Gly Gly Gly Gly Ser Gly Gly Gly Gly Ser Gly Gly Gly Gly
            500                 505                 510

Ser Gln Val Gln Leu Val Gln Ser Gly Ala Glu Val Lys Lys Pro Gly
        515                 520                 525

Ala Ser Val Lys Val Ser Cys Lys Ala Ser Gly Tyr Thr Phe Thr Ser
    530                 535                 540

Tyr Tyr Ile His Trp Val Arg Gln Ala Pro Gly Gln Gly Leu Glu Trp
545                 550                 555                 560

Ile Gly Cys Ile Tyr Pro Gly Asn Val Asn Thr Asn Tyr Asn Glu Lys
                565                 570                 575

Phe Lys Asp Arg Ala Thr Leu Thr Val Asp Thr Ser Ile Ser Thr Ala
            580                 585                 590

Tyr Met Glu Leu Ser Arg Leu Arg Ser Asp Asp Thr Ala Val Tyr Phe
        595                 600                 605

Cys Thr Arg Ser His Tyr Gly Leu Asp Trp Asn Phe Asp Val Trp Gly
    610                 615                 620

Gln Gly Thr Thr Val Thr Val Ser Ser Gly Gly Gly Gly Ser Gly Gly
625                 630                 635                 640

Gly Gly Ser Gly Gly Gly Gly Ser Asp Ile Gln Met Thr Gln Ser Pro
                645                 650                 655

Ser Ser Leu Ser Ala Ser Val Gly Asp Arg Val Thr Ile Thr Cys His
            660                 665                 670

Ala Ser Gln Asn Ile Tyr Val Trp Leu Asn Trp Tyr Gln Gln Lys Pro
        675                 680                 685

Gly Lys Ala Pro Lys Leu Leu Ile Tyr Lys Ala Ser Asn Leu His Thr
    690                 695                 700

Gly Val Pro Ser Arg Phe Ser Gly Ser Gly Ser Gly Thr Asp Phe Thr
705                 710                 715                 720

Leu Thr Ile Ser Ser Leu Gln Pro Glu Asp Phe Ala Thr Tyr Tyr Cys
                725                 730                 735

Gln Gln Gly Gln Thr Tyr Pro Tyr Thr Phe Gly Gly Gly Thr Lys Val
            740                 745                 750

Glu Ile Lys Arg
        755


<210> SEQ ID NO 2
<211> LENGTH: 2268
<212> TYPE: DNA
<213> ORGANISM: Artificial
<220> FEATURE:
<223> OTHER INFORMATION: The nucleotide sequence of CCD19-CD3-CD28
      TsAb_M monomer

<400> SEQUENCE: 2

gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480
```

```
aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggtggcggag ggtccgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaaccccct gaccttcggc gccggcacca agctggagct gaagggaggc   1500

ggaggttccg gcggtggggg atcggggggt ggagggagtc aggtgcagct ggtgcagagc   1560

ggcgccgagg tgaagaagcc cggcgccagc gtgaaggtga gctgcaaggc cagcggctac   1620

accttcacca gctactacat ccactgggtg cgccaggccc ccggccaggg cctggagtgg   1680

atcggctgca tctaccccgg caacgtgaac accaactaca acgagaagtt caaggaccgc   1740

gccaccctga ccgtggacac cagcatcagc accgcctaca tggagctgag ccgcctgcgc   1800

agcgacgaca ccgccgtgta cttctgcacc cgcagccact acggcctgga ctggaacttc   1860

gacgtgtggg gccagggcac caccgtgacc gtgagcagcg gcggcggcgg cagcggcggc   1920

ggcggcagcg gcggcggcgg cagcgacatc cagatgaccc agagccccag cagcctgagc   1980

gccagcgtgg gcgaccgcgt gaccatcacc tgccacgcca gccagaacat ctacgtgtgg   2040

ctgaactggt accagcagaa gcccggcaag gcccccaagc tgctgatcta caaggccagc   2100

aacctgcaca ccggcgtgcc cagccgcttc agcggcagcg gcagcggcac cgacttcacc   2160

ctgaccatca gcagcctgca gcccgaggac ttcgccacct actactgcca gcagggccag   2220

acctacccct acaccttcgg cggcggcacc aaggtggaga tcaagcgc                2268
```

<210> SEQ ID NO 3
<211> LENGTH: 822
<212> TYPE: PRT
<213> ORGANISM: Artificial
<220> FEATURE:
<223> OTHER INFORMATION: The amino acid sequence of CD19-CD3-CD28 TsAb_D dimer

<400> SEQUENCE: 3

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45
```

-continued

```
Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460
```

-continued

```
Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Gln Val Gln Leu Val Gln Ser Gly Ala Glu Val Lys Lys
            580                 585                 590

Pro Gly Ala Ser Val Lys Val Ser Cys Lys Ala Ser Gly Tyr Thr Phe
        595                 600                 605

Thr Ser Tyr Tyr Ile His Trp Val Arg Gln Ala Pro Gly Gln Gly Leu
    610                 615                 620

Glu Trp Ile Gly Cys Ile Tyr Pro Gly Asn Val Asn Thr Asn Tyr Asn
625                 630                 635                 640

Glu Lys Phe Lys Asp Arg Ala Thr Leu Thr Val Asp Thr Ser Ile Ser
                645                 650                 655

Thr Ala Tyr Met Glu Leu Ser Arg Leu Arg Ser Asp Asp Thr Ala Val
            660                 665                 670

Tyr Phe Cys Thr Arg Ser His Tyr Gly Leu Asp Trp Asn Phe Asp Val
        675                 680                 685

Trp Gly Gln Gly Thr Thr Val Thr Val Ser Ser Gly Gly Gly Gly Ser
    690                 695                 700

Gly Gly Gly Gly Ser Gly Gly Gly Gly Ser Asp Ile Gln Met Thr Gln
705                 710                 715                 720

Ser Pro Ser Ser Leu Ser Ala Ser Val Gly Asp Arg Val Thr Ile Thr
                725                 730                 735

Cys His Ala Ser Gln Asn Ile Tyr Val Trp Leu Asn Trp Tyr Gln Gln
            740                 745                 750

Lys Pro Gly Lys Ala Pro Lys Leu Leu Ile Tyr Lys Ala Ser Asn Leu
        755                 760                 765

His Thr Gly Val Pro Ser Arg Phe Ser Gly Ser Gly Ser Gly Thr Asp
    770                 775                 780

Phe Thr Leu Thr Ile Ser Ser Leu Gln Pro Glu Asp Phe Ala Thr Tyr
785                 790                 795                 800

Tyr Cys Gln Gln Gly Gln Thr Tyr Pro Tyr Thr Phe Gly Gly Gly Thr
                805                 810                 815

Lys Val Glu Ile Lys Arg
            820
```

<210> SEQ ID NO 4
<211> LENGTH: 2466
<212> TYPE: DNA
<213> ORGANISM: Artificial
<220> FEATURE:
<223> OTHER INFORMATION: The nucleotide sequence of CD19-CD3-CD28 TsAb_D
dimer

<400> SEQUENCE: 4

-continued

```
gacatccagc tgacccagag ccccgccagc ctggccgtga gcctgggcca gcgcgccacc     60
atcagctgca aggccagcca gagcgtggac tacgacggcg acagctacct gaactggtac    120
cagcagatcc ccggccagcc ccccaagctg ctgatctacg acgccagcaa cctggtgagc    180
ggcatccccc cccgcttcag cggcagcggc agcggcaccg acttcaccct gaacatccac    240
cccgtggaga aggtggacgc cgccacctac cactgccagc agagcaccga ggacccctgg    300
accttcggcg gcggcaccaa gctggagatc aagggcggcg gcggcagcgg cggcggcggc    360
agcggcggcg gcggcagcca ggtgcagctg cagcagagcg gcgccgagct ggtgcgcccc    420
ggcagcagcg tgaagatcag ctgcaaggcc agcggctacg ccttcagcag ctactggatg    480
aactgggtga agcagcgccc cggccagggc ctggagtgga tcggccagat ctggcccggc    540
gacggcgaca ccaactacaa cggcaagttc aagggcaagg ccaccctgac cgccgacgag    600
agcagcagca ccgcctacat gcagctgagc agcctggcca gcgaggacag cgccgtgtac    660
ttctgcgccc gccgcgagac caccaccgtg ggccgctact actacgccat ggactactgg    720
ggccagggca ccaccgtgac cgtgagcagc ggtggcggag ggtccgacat caagctgcag    780
cagagcggcg ccgagctggc ccgccccggc gccagcgtga agatgagctg caagaccagc    840
ggctacacct tcacccgcta caccatgcac tgggtgaagc agcgccccgg ccagggcctg    900
gagtggatcg gctacatcaa ccccagccgc ggctacacca actacaacca gaagttcaag    960
gacaaggcca ccctgaccac cgacaagagc agcagcaccg cctacatgca gctgagcagc   1020
ctgaccagcg aggacagcgc cgtgtactac tgcgcccgct actacgacga ccactactgc   1080
ctggactact ggggccaggg caccaccctg accgtgagca gcgtggaggg cggcagcggc   1140
ggcagcggcg gcagcggcgg cagcggcggc gtggacgaca tccagctgac ccagagcccc   1200
gccatcatga gcgccagccc cggcgagaag gtgaccatga cctgccgcgc cagcagcagc   1260
gtgagctaca tgaactggta ccagcagaag agcggcacca gccccaagcg ctggatctac   1320
gacaccagca aggtggccag cggcgtgccc taccgcttca gcggcagcgg cagcggcacc   1380
agctacagcc tgaccatcag cagcatggag gccgaggacg ccgccaccta ctactgccag   1440
cagtggagca gcaaccccct gaccttcggc gccggcacca agctggagct gaaggccagc   1500
aagagcaaga aggagatctt ccgctggccc gagagcccca aggcccaggc cagcagcgtg   1560
cccaccgccc agccccaggc cgagggcagc ctggccaagg ccaccaccgc ccccgccacc   1620
acccgcaaca ccggccgcgg cggcgaggag aagaagaagg agaaggagaa ggaggagcag   1680
gaggagcgcg agaccaagac ccccgagtgc cccagccaca cccagcccct gggcgtgcag   1740
gtgcagctgg tgcagagcgg cgccgaggtg aagaagcccg gcgccagcgt gaaggtgagc   1800
tgcaaggcca gcggctacac cttcaccagc tactacatcc actgggtgcg ccaggccccc   1860
ggccagggcc tggagtggat cggctgcatc taccccggca acgtgaacac caactacaac   1920
gagaagttca aggaccgcgc caccctgacc gtggacacca gcatcagcac cgcctacatg   1980
gagctgagcc gcctgcgcag cgacgacacc gccgtgtact tctgcacccg cagccactac   2040
ggcctggact ggaacttcga cgtgtggggc cagggcacca ccgtgaccgt gagcagcggc   2100
ggcggcggca gcggcggcgg cggcagcggc ggcggcggca gcgacatcca gatgacccag   2160
agccccagca gcctgagcgc cagcgtgggc gaccgcgtga ccatcacctg ccacgccagc   2220
cagaacatct acgtgtggct gaactggtac cagcagaagc ccggcaaggc ccccaagctg   2280
ctgatctaca aggccagcaa cctgcacacc ggcgtgccca gccgcttcag cggcagcggc   2340
```

```
agcggcaccg acttcaccct gaccatcagc agcctgcagc ccgaggactt cgccacctac   2400

tactgccagc agggccagac ctacccctac accttcggcg gcggcaccaa ggtggagatc   2460

aagcgc                                                              2466


<210> SEQ ID NO 5
<211> LENGTH: 250
<212> TYPE: PRT
<213> ORGANISM: Artificial
<220> FEATURE:
<223> OTHER INFORMATION: The amino acid sequence of anti-CD19 scFv

<400> SEQUENCE: 5

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser
                245                 250


<210> SEQ ID NO 6
<211> LENGTH: 124
<212> TYPE: PRT
<213> ORGANISM: Artificial
<220> FEATURE:
<223> OTHER INFORMATION: The amino acid sequence of anti-CD19 scFv heavy
      chain variable region

<400> SEQUENCE: 6

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
```

```
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120


<210> SEQ ID NO 7
<211> LENGTH: 111
<212> TYPE: PRT
<213> ORGANISM: Artificial
<220> FEATURE:
<223> OTHER INFORMATION: The amino acid sequence of anti-CD19 scFv light
      chain variable region

<400> SEQUENCE: 7

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110


<210> SEQ ID NO 8
<211> LENGTH: 243
<212> TYPE: PRT
<213> ORGANISM: Artificial
<220> FEATURE:
<223> OTHER INFORMATION: The amino acid sequence of anti-CD3 scFv

<400> SEQUENCE: 8

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

```
Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys


<210> SEQ ID NO 9
<211> LENGTH: 119
<212> TYPE: PRT
<213> ORGANISM: Artificial
<220> FEATURE:
<223> OTHER INFORMATION: The amino acid sequence of anti-CD3 scFv heavy
      chain variable region

<400> SEQUENCE: 9

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115


<210> SEQ ID NO 10
<211> LENGTH: 106
<212> TYPE: PRT
<213> ORGANISM: Artificial
<220> FEATURE:
<223> OTHER INFORMATION: The amino acid sequence of anti-CD3 scFv light
      chain variable region

<400> SEQUENCE: 10

Asp Ile Gln Leu Thr Gln Ser Pro Ala Ile Met Ser Ala Ser Pro Gly
1               5                   10                  15
```

```
Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105


<210> SEQ ID NO 11
<211> LENGTH: 243
<212> TYPE: PRT
<213> ORGANISM: Artificial
<220> FEATURE:
<223> OTHER INFORMATION: The amino acid sequence of anti-CD28 scFv

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys His Ala
145                 150                 155                 160

Ser Gln Asn Ile Tyr Val Trp Leu Asn Trp Tyr Gln Gln Lys Pro Gly
                165                 170                 175

Lys Ala Pro Lys Leu Leu Ile Tyr Lys Ala Ser Asn Leu His Thr Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Gly Gln Thr Tyr Pro Tyr Thr Phe Gly Gly Gly Thr Lys Val Glu
225                 230                 235                 240

Ile Lys Arg


<210> SEQ ID NO 12
<211> LENGTH: 120
<212> TYPE: PRT
```

<213> ORGANISM: Artificial
<220> FEATURE:
<223> OTHER INFORMATION: The amino acid sequence of anti-CD28 scFv heavy
      chain variable region

<400> SEQUENCE: 12

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser
        115                 120
```

<210> SEQ ID NO 13
<211> LENGTH: 108
<212> TYPE: PRT
<213> ORGANISM: Artificial
<220> FEATURE:
<223> OTHER INFORMATION: The amino acid sequence of anti-CD28 scFv light
      chain variable region

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg
            100                 105
```

<210> SEQ ID NO 14
<211> LENGTH: 750
<212> TYPE: DNA
<213> ORGANISM: Artificial
<220> FEATURE:
<223> OTHER INFORMATION: The nucleotide sequence of anti-CD19 scFv

<400> SEQUENCE: 14

```
gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180
```

```
ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc                                     750
```

```
<210> SEQ ID NO 15
<211> LENGTH: 372
<212> TYPE: DNA
<213> ORGANISM: Artificial
<220> FEATURE:
<223> OTHER INFORMATION: The nucleotide sequence of anti-CD19 scFv heavy
      chain variable region

<400> SEQUENCE: 15

caggtgcagc tgcagcagag cggcgccgag ctggtgcgcc ccggcagcag cgtgaagatc     60

agctgcaagg ccagcggcta cgccttcagc agctactgga tgaactgggt gaagcagcgc    120

cccggccagg gcctggagtg gatcggccag atctggcccg gcgacggcga caccaactac    180

aacggcaagt tcaagggcaa ggccaccctg accgccgacg agagcagcag caccgcctac    240

atgcagctga gcagcctggc cagcgaggac agcgccgtgt acttctgcgc ccgccgcgag    300

accaccaccg tgggccgcta ctactacgcc atggactact ggggccaggg caccaccgtg    360

accgtgagca gc                                                        372
```

```
<210> SEQ ID NO 16
<211> LENGTH: 333
<212> TYPE: DNA
<213> ORGANISM: Artificial
<220> FEATURE:
<223> OTHER INFORMATION: The nucleotide sequence of anti-CD19 scFv light
      chain variable region

<400> SEQUENCE: 16

gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180

ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aag                                 333
```

```
<210> SEQ ID NO 17
<211> LENGTH: 729
<212> TYPE: DNA
<213> ORGANISM: Artificial
<220> FEATURE:
<223> OTHER INFORMATION: The nucleotide sequence of anti-CD3 scFv

<400> SEQUENCE: 17

gacatcaagc tgcagcagag cggcgccgag ctggcccgcc ccggcgccag cgtgaagatg     60
```

agctgcaaga ccagcggcta caccttcacc cgctacacca tgcactgggt gaagcagcgc 120
cccggccagg gcctggagtg gatcggctac atcaacccca gccgcggcta caccaactac 180
aaccagaagt tcaaggacaa ggccaccctg accaccgaca agagcagcag caccgcctac 240
atgcagctga gcagcctgac cagcgaggac agcgccgtgt actactgcgc ccgctactac 300
gacgaccact actgcctgga ctactggggc cagggcacca ccctgaccgt gagcagcgtg 360
gagggcggca gcggcggcag cggcggcagc ggcggcagcg gcggcgtgga cgacatccag 420
ctgacccaga gccccgccat catgagcgcc agccccggcg agaaggtgac catgacctgc 480
cgcgccagca gcagcgtgag ctacatgaac tggtaccagc agaagagcgg caccagcccc 540
aagcgctgga tctacgacac cagcaaggtg gccagcggcg tgccctaccg cttcagcggc 600
agcggcagcg gcaccagcta cagcctgacc atcagcagca tggaggccga ggacgccgcc 660
acctactact gccagcagtg gagcagcaac cccctgacct tcggcgccgg caccaagctg 720
gagctgaag 729

<210> SEQ ID NO 18
<211> LENGTH: 357
<212> TYPE: DNA
<213> ORGANISM: Artificial
<220> FEATURE:
<223> OTHER INFORMATION: The nucleotide sequence of anti-CD3 scFv heavy chain variable region

<400> SEQUENCE: 18
gacatcaagc tgcagcagag cggcgccgag ctggcccgcc ccggcgccag cgtgaagatg 60
agctgcaaga ccagcggcta caccttcacc cgctacacca tgcactgggt gaagcagcgc 120
cccggccagg gcctggagtg gatcggctac atcaacccca gccgcggcta caccaactac 180
aaccagaagt tcaaggacaa ggccaccctg accaccgaca agagcagcag caccgcctac 240
atgcagctga gcagcctgac cagcgaggac agcgccgtgt actactgcgc ccgctactac 300
gacgaccact actgcctgga ctactggggc cagggcacca ccctgaccgt gagcagc 357

<210> SEQ ID NO 19
<211> LENGTH: 318
<212> TYPE: DNA
<213> ORGANISM: Artificial
<220> FEATURE:
<223> OTHER INFORMATION: The nucleotide sequence of anti-CD3 scFv light chain variable region

<400> SEQUENCE: 19
gacatccagc tgacccagag ccccgccatc atgagcgcca gccccggcga gaaggtgacc 60
atgacctgcc gcgccagcag cagcgtgagc tacatgaact ggtaccagca gaagagcggc 120
accagcccca agcgctggat ctacgacacc agcaaggtgg ccagcggcgt gccctaccgc 180
ttcagcggca gcggcagcgg caccagctac agcctgacca tcagcagcat ggaggccgag 240
gacgccgcca cctactactg ccagcagtgg agcagcaacc ccctgacctt cggcgccggc 300
accaagctgg agctgaag 318

<210> SEQ ID NO 20
<211> LENGTH: 729
<212> TYPE: DNA
<213> ORGANISM: Artificial
<220> FEATURE:
<223> OTHER INFORMATION: The nucleotide sequence of anti-CD28

<400> SEQUENCE: 20
caggtgcagc tggtgcagag cggcgccgag gtgaagaagc ccggcgccag cgtgaaggtg 60
agctgcaagg ccagcggcta caccttcacc agctactaca tccactgggt gcgccaggcc 120
cccggccagg gcctggagtg gatcggctgc atctaccccg gcaacgtgaa caccaactac 180
aacgagaagt tcaaggaccg cgccaccctg accgtggaca ccagcatcag caccgcctac 240
atggagctga gccgcctgcg cagcgacgac accgccgtgt acttctgcac ccgcagccac 300
tacggcctgg actggaactt cgacgtgtgg ggccagggca ccaccgtgac cgtgagcagc 360
ggcggcggcg gcagcggcgg cggcggcagc ggcggcggcg gcagcgacat ccagatgacc 420
cagagcccca gcagcctgag cgccagcgtg ggcgaccgcg tgaccatcac ctgccacgcc 480
agccagaaca tctacgtgtg gctgaactgg taccagcaga agcccggcaa ggcccccaag 540
ctgctgatct acaaggccag caacctgcac accggcgtgc ccagccgctt cagcggcagc 600
ggcagcggca ccgacttcac cctgaccatc agcagcctgc agcccgagga cttcgccacc 660
tactactgcc agcagggcca gacctacccc tacaccttcg gcggcggcac caaggtggag 720
atcaagcgc 729

<210> SEQ ID NO 21
<211> LENGTH: 360
<212> TYPE: DNA
<213> ORGANISM: Artificial
<220> FEATURE:
<223> OTHER INFORMATION: The nucleotide sequence of anti-CD28 heavy chain variable region

<400> SEQUENCE: 21
caggtgcagc tggtgcagag cggcgccgag gtgaagaagc ccggcgccag cgtgaaggtg 60
agctgcaagg ccagcggcta caccttcacc agctactaca tccactgggt gcgccaggcc 120
cccggccagg gcctggagtg gatcggctgc atctaccccg gcaacgtgaa caccaactac 180
aacgagaagt tcaaggaccg cgccaccctg accgtggaca ccagcatcag caccgcctac 240
atggagctga gccgcctgcg cagcgacgac accgccgtgt acttctgcac ccgcagccac 300
tacggcctgg actggaactt cgacgtgtgg ggccagggca ccaccgtgac cgtgagcagc 360

<210> SEQ ID NO 22
<211> LENGTH: 324
<212> TYPE: DNA
<213> ORGANISM: Artificial
<220> FEATURE:
<223> OTHER INFORMATION: The nucleotide sequence of anti-CD28 scFv light chain variable region

<400> SEQUENCE: 22
gacatccaga tgacccagag ccccagcagc ctgagcgcca gcgtgggcga ccgcgtgacc 60
atcacctgcc acgccagcca gaacatctac gtgtggctga actggtacca gcagaagccc 120
ggcaaggccc ccaagctgct gatctacaag gccagcaacc tgcacaccgg cgtgcccagc 180
cgcttcagcg gcagcggcag cggcaccgac ttcaccctga ccatcagcag cctgcagccc 240
gaggacttcg ccacctacta ctgccagcag ggccagacct acccctacac cttcggcggc 300
ggcaccaagg tggagatcaa gcgc 324

<210> SEQ ID NO 23
<211> LENGTH: 5
<212> TYPE: PRT
<213> ORGANISM: Artificial

<220> FEATURE:
<223> OTHER INFORMATION: The amino acid sequence of CD19-CD3-CD28 TsAb_M
monomer linker (Linker 1)

<400> SEQUENCE: 23

Gly Gly Gly Gly Ser
1 5

<210> SEQ ID NO 24
<211> LENGTH: 15
<212> TYPE: DNA
<213> ORGANISM: Artificial
<220> FEATURE:
<223> OTHER INFORMATION: The nucleotide sequence of CD19-CD3-CD28 TsAb_M
monomer linker (Linker 1)

<400> SEQUENCE: 24
ggtggcggag ggtcc 15

<210> SEQ ID NO 25
<211> LENGTH: 15
<212> TYPE: PRT
<213> ORGANISM: Artificial
<220> FEATURE:
<223> OTHER INFORMATION: The amino acid sequence of CD19-CD3-CD28 TsAb_M
monomer linker (Linker 2)

<400> SEQUENCE: 25

Gly Gly Gly Gly Ser Gly Gly Gly Gly Ser Gly Gly Gly Gly Ser
1 5 10 15

<210> SEQ ID NO 26
<211> LENGTH: 45
<212> TYPE: DNA
<213> ORGANISM: Artificial
<220> FEATURE:
<223> OTHER INFORMATION: The nucleotide sequence of CD19-CD3-CD28 TsAb_M
monomer linker (Linker 2)

<400> SEQUENCE: 26
ggaggcggag gttccggcgg tgggggatcg gggggtggag ggagt 45

<210> SEQ ID NO 27
<211> LENGTH: 5
<212> TYPE: PRT
<213> ORGANISM: Artificial
<220> FEATURE:
<223> OTHER INFORMATION: The amino acid sequence of CD19-CD3-CD28 TsAb_D
dimer linker (Linker 1)

<400> SEQUENCE: 27

Gly Gly Gly Gly Ser
1 5

<210> SEQ ID NO 28
<211> LENGTH: 15
<212> TYPE: DNA
<213> ORGANISM: Artificial
<220> FEATURE:
<223> OTHER INFORMATION: The nucleotide sequence of CD19-CD3-CD28 TsAb_D
dimer linker (Linker 1)

<400> SEQUENCE: 28
ggtggcggag ggtcc 15

<210> SEQ ID NO 29
<211> LENGTH: 81

<212> TYPE: PRT
<213> ORGANISM: Artificial
<220> FEATURE:
<223> OTHER INFORMATION: The amino acid sequence of CD19-CD3-CD28 TsAb_D
      dimer linker (Linker 2)

<400> SEQUENCE: 29

Ala Ser Lys Ser Lys Lys Glu Ile Phe Arg Trp Pro Glu Ser Pro Lys
1               5                   10                  15

Ala Gln Ala Ser Ser Val Pro Thr Ala Gln Pro Gln Ala Glu Gly Ser
            20                  25                  30

Leu Ala Lys Ala Thr Thr Ala Pro Ala Thr Thr Arg Asn Thr Gly Arg
        35                  40                  45

Gly Gly Glu Glu Lys Lys Lys Glu Lys Glu Lys Glu Glu Gln Glu Glu
    50                  55                  60

Arg Glu Thr Lys Thr Pro Glu Cys Pro Ser His Thr Gln Pro Leu Gly
65                  70                  75                  80

Val

<210> SEQ ID NO 30
<211> LENGTH: 243
<212> TYPE: DNA
<213> ORGANISM: Artificial
<220> FEATURE:
<223> OTHER INFORMATION: The nucleotide sequence of CD19-CD3-CD28 TsAb_D
      dimer linker (Linker 2)

<400> SEQUENCE: 30
gccagcaaga gcaagaagga gatcttccgc tggcccgaga gccccaaggc ccaggccagc      60
agcgtgccca ccgcccagcc ccaggccgag ggcagcctgg ccaaggccac caccgccccc     120
gccaccaccc gcaacaccgg ccgcggcggc gaggagaaga agaaggagaa ggagaaggag     180
gagcaggagg agcgcgagac caagaccccc gagtgcccca gccacaccca gcccctgggc     240
gtg                                                                   243

<210> SEQ ID NO 31
<211> LENGTH: 19
<212> TYPE: PRT
<213> ORGANISM: Artificial
<220> FEATURE:
<223> OTHER INFORMATION: The amino acid sequence of the secretory signal
      peptide

<400> SEQUENCE: 31

Met Thr Arg Leu Thr Val Leu Ala Leu Leu Ala Gly Leu Leu Ala Ser
1               5                   10                  15

Ser Arg Ala

<210> SEQ ID NO 32
<211> LENGTH: 57
<212> TYPE: DNA
<213> ORGANISM: Artificial
<220> FEATURE:
<223> OTHER INFORMATION: The nucleotide sequence of the secretory signal
      peptide

<400> SEQUENCE: 32
atgacccggc tgaccgtgct ggccctgctg gccggcctgc tggcctcctc cagggcc         57

<210> SEQ ID NO 33
<211> LENGTH: 59
<212> TYPE: DNA

<213> ORGANISM: Artificial
<220> FEATURE:
<223> OTHER INFORMATION: pcDNA3.1-Sig-F

<400> SEQUENCE: 33
gtgctggata tctgcagaat tcgccgccac catgacccgg ctgaccgtgc tggccctgc 59

<210> SEQ ID NO 34
<211> LENGTH: 49
<212> TYPE: DNA
<213> ORGANISM: Artificial
<220> FEATURE:
<223> OTHER INFORMATION: Sig-R

<400> SEQUENCE: 34
ggccctggag gaggccagca ggccggccag cagggccagc acggtcagc 49

<210> SEQ ID NO 35
<211> LENGTH: 42
<212> TYPE: DNA
<213> ORGANISM: Artificial
<220> FEATURE:
<223> OTHER INFORMATION: Sig-CD19-F

<400> SEQUENCE: 35
ctgctggcct cctccagggc cgacatccag ctgacccaga gc 42

<210> SEQ ID NO 36
<211> LENGTH: 23
<212> TYPE: DNA
<213> ORGANISM: Artificial
<220> FEATURE:
<223> OTHER INFORMATION: CD19-R

<400> SEQUENCE: 36
gctgctcacg gtcacggtgg tgc 23

<210> SEQ ID NO 37
<211> LENGTH: 56
<212> TYPE: DNA
<213> ORGANISM: Artificial
<220> FEATURE:
<223> OTHER INFORMATION: CD19-G4S-CD3-F

<400> SEQUENCE: 37
ccaccgtgac cgtgagcagc ggtggcggag ggtccgacat caagctgcag cagagc 56

<210> SEQ ID NO 38
<211> LENGTH: 20
<212> TYPE: DNA
<213> ORGANISM: Artificial
<220> FEATURE:
<223> OTHER INFORMATION: CD3-R

<400> SEQUENCE: 38
cttcagctcc agcttggtgc 20

<210> SEQ ID NO 39
<211> LENGTH: 86
<212> TYPE: DNA
<213> ORGANISM: Artificial
<220> FEATURE:
<223> OTHER INFORMATION: CD3-(GGGGS)3-CD28-F

<400> SEQUENCE: 39
gcaccaagct ggagctgaag ggaggcggag gttccggcgg tgggggatcg gggggtggag 60
ggagtcaggt gcagctggtg cagagc 86

<210> SEQ ID NO 40
<211> LENGTH: 51
<212> TYPE: DNA
<213> ORGANISM: Artificial
<220> FEATURE:
<223> OTHER INFORMATION: pcDNA3.1-CD28-R

<400> SEQUENCE: 40
ctgatcagcg gtttaaactt aagctttcag cgcttgatct ccaccttggt g 51

<210> SEQ ID NO 41
<211> LENGTH: 41
<212> TYPE: DNA
<213> ORGANISM: Artificial
<220> FEATURE:
<223> OTHER INFORMATION: CD3-IgD-F

<400> SEQUENCE: 41
gcaccaagct ggagctgaag gccagcaaga gcaagaagga g 41

<210> SEQ ID NO 42
<211> LENGTH: 21
<212> TYPE: DNA
<213> ORGANISM: Artificial
<220> FEATURE:
<223> OTHER INFORMATION: IgD-R

<400> SEQUENCE: 42
cacgcccagg ggctgggtgt g 21

<210> SEQ ID NO 43
<211> LENGTH: 42
<212> TYPE: DNA
<213> ORGANISM: Artificial
<220> FEATURE:
<223> OTHER INFORMATION: IgD-CD28-F

<400> SEQUENCE: 43
cacacccagc ccctgggcgt gcaggtgcag ctggtgcaga gc 42

<210> SEQ ID NO 44
<211> LENGTH: 5
<212> TYPE: PRT
<213> ORGANISM: Artificial
<220> FEATURE:
<223> OTHER INFORMATION: The amino acid sequence of CD19-CD3-4-1BB
      TsAb_M monomer linker (Linker 1)

<400> SEQUENCE: 44

Gly Gly Gly Gly Ser
1               5

<210> SEQ ID NO 45
<211> LENGTH: 15
<212> TYPE: DNA
<213> ORGANISM: Artificial
<220> FEATURE:
<223> OTHER INFORMATION: The nucleotide sequence of CD19-CD3-4-1BB
      TsAb_M monomer linker (Linker 1)

<400> SEQUENCE: 45
ggtggcggag ggtcc 15

<210> SEQ ID NO 46
<211> LENGTH: 15
<212> TYPE: PRT
<213> ORGANISM: Artificial
<220> FEATURE:
<223> OTHER INFORMATION: The amino acid sequence of CD19-CD3-4-1BB
TsAb_M monomer linker (Linker 2)

<400> SEQUENCE: 46

Gly Gly Gly Gly Ser Gly Gly Gly Gly Ser Gly Gly Gly Gly Ser
1 5 10 15

<210> SEQ ID NO 47
<211> LENGTH: 45
<212> TYPE: DNA
<213> ORGANISM: Artificial
<220> FEATURE:
<223> OTHER INFORMATION: The nucleotide sequence of CD19-CD3-4-1BB
TsAb_M monomer linker (Linker 2)

<400> SEQUENCE: 47
ggaggcggag gttccggcgg tgggggatcg gggggtggag ggagt 45

<210> SEQ ID NO 48
<211> LENGTH: 5
<212> TYPE: PRT
<213> ORGANISM: Artificial
<220> FEATURE:
<223> OTHER INFORMATION: The amino acid sequence of CD19-CD3-4-1BB
TsAb_D dimer linker (Linker 1)

<400> SEQUENCE: 48

Gly Gly Gly Gly Ser
1 5

<210> SEQ ID NO 49
<211> LENGTH: 15
<212> TYPE: DNA
<213> ORGANISM: Artificial
<220> FEATURE:
<223> OTHER INFORMATION: The nucleotide sequence of CD19-CD3-4-1BB
TsAb_D dimer linker (Linker 1)

<400> SEQUENCE: 49
ggtggcggag ggtcc 15

<210> SEQ ID NO 50
<211> LENGTH: 81
<212> TYPE: PRT
<213> ORGANISM: Artificial
<220> FEATURE:
<223> OTHER INFORMATION: The amino acid sequence of CD19-CD3-4-1BB
TsAb_D dimer linker

<400> SEQUENCE: 50

Ala Ser Lys Ser Lys Lys Glu Ile Phe Arg Trp Pro Glu Ser Pro Lys
1 5 10 15

Ala Gln Ala Ser Ser Val Pro Thr Ala Gln Pro Gln Ala Glu Gly Ser
20 25 30

Leu Ala Lys Ala Thr Thr Ala Pro Ala Thr Thr Arg Asn Thr Gly Arg
35 40 45

Gly Gly Glu Glu Lys Lys Lys Glu Lys Glu Lys Glu Glu Gln Glu Glu
50 55 60

Arg Glu Thr Lys Thr Pro Glu Cys Pro Ser His Thr Gln Pro Leu Gly
65 70 75 80

-continued

Val

<210> SEQ ID NO 51
<211> LENGTH: 243
<212> TYPE: DNA
<213> ORGANISM: Artificial
<220> FEATURE:
<223> OTHER INFORMATION: The nucleotide sequence of CD19-CD3-4-1BB TsAb_D dimer linker (Linker 2)

<400> SEQUENCE: 51
gccagcaaga gcaagaagga gatcttccgc tggcccgaga gccccaaggc ccaggccagc 60
agcgtgccca ccgcccagcc ccaggccgag ggcagcctgg ccaaggccac caccgccccc 120
gccaccaccc gcaacaccgg ccgcggcggc gaggagaaga agaaggagaa ggagaaggag 180
gagcaggagg agcgcgagac caagaccccc gagtgcccca gccacaccca gcccctgggc 240
gtg 243

<210> SEQ ID NO 52
<211> LENGTH: 134
<212> TYPE: PRT
<213> ORGANISM: Artificial
<220> FEATURE:
<223> OTHER INFORMATION: The amino acid sequence of the human T cell positive costimulatory molecule CD28 extracellular domain

<400> SEQUENCE: 52

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro
    130

<210> SEQ ID NO 53
<211> LENGTH: 163
<212> TYPE: PRT
<213> ORGANISM: Artificial
<220> FEATURE:
<223> OTHER INFORMATION: The amino acid sequence of the human T cell positive costimulatory molecule 4-1BB extracellular domain

<400> SEQUENCE: 53

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val

```
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln


<210> SEQ ID NO 54
<211> LENGTH: 120
<212> TYPE: PRT
<213> ORGANISM: Artificial
<220> FEATURE:
<223> OTHER INFORMATION: The amino acid sequence of the human T cell
      positive costimulatory molecule ICOS extracellular domain

<400> SEQUENCE: 54

Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
            100                 105                 110

Ser Gln Leu Cys Cys Gln Leu Lys
        115                 120


<210> SEQ ID NO 55
<211> LENGTH: 186
<212> TYPE: PRT
<213> ORGANISM: Artificial
<220> FEATURE:
<223> OTHER INFORMATION: The amino acid sequence of the human T cell
      positive costimulatory molecule OX40 extracellular domain

<400> SEQUENCE: 55

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45
```

```
Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala
            180                 185


<210> SEQ ID NO 56
<211> LENGTH: 137
<212> TYPE: PRT
<213> ORGANISM: Artificial
<220> FEATURE:
<223> OTHER INFORMATION: The amino acid sequence of the human T cell
      positive costimulatory molecule GITR extracellular domain

<400> SEQUENCE: 56

Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
            20                  25                  30

Cys Arg Asp Tyr Pro Gly Glu Glu Cys Cys Ser Glu Trp Asp Cys Met
        35                  40                  45

Cys Val Gln Pro Glu Phe His Cys Gly Asp Pro Cys Cys Thr Thr Cys
    50                  55                  60

Arg His His Pro Cys Pro Pro Gly Gln Gly Val Gln Ser Gln Gly Lys
65                  70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
            100                 105                 110

Gly Phe Leu Thr Val Phe Pro Gly Asn Lys Thr His Asn Ala Val Cys
        115                 120                 125

Val Pro Gly Ser Pro Pro Ala Glu Pro
    130                 135


<210> SEQ ID NO 57
<211> LENGTH: 215
<212> TYPE: PRT
<213> ORGANISM: Artificial
<220> FEATURE:
<223> OTHER INFORMATION: The amino acid sequence of the human T cell
      positive costimulatory molecule CD40L extracellular domain

<400> SEQUENCE: 57

His Arg Arg Leu Asp Lys Ile Glu Asp Glu Arg Asn Leu His Glu Asp
1               5                   10                  15
```

```
Phe Val Phe Met Lys Thr Ile Gln Arg Cys Asn Thr Gly Glu Arg Ser
            20                  25                  30

Leu Ser Leu Leu Asn Cys Glu Glu Ile Lys Ser Gln Phe Glu Gly Phe
        35                  40                  45

Val Lys Asp Ile Met Leu Asn Lys Glu Glu Thr Lys Lys Glu Asn Ser
    50                  55                  60

Phe Glu Met Gln Lys Gly Asp Gln Asn Pro Gln Ile Ala Ala His Val
65                  70                  75                  80

Ile Ser Glu Ala Ser Ser Lys Thr Thr Ser Val Leu Gln Trp Ala Glu
                85                  90                  95

Lys Gly Tyr Tyr Thr Met Ser Asn Asn Leu Val Thr Leu Glu Asn Gly
            100                 105                 110

Lys Gln Leu Thr Val Lys Arg Gln Gly Leu Tyr Tyr Ile Tyr Ala Gln
        115                 120                 125

Val Thr Phe Cys Ser Asn Arg Glu Ala Ser Ser Gln Ala Pro Phe Ile
    130                 135                 140

Ala Ser Leu Cys Leu Lys Ser Pro Gly Arg Phe Glu Arg Ile Leu Leu
145                 150                 155                 160

Arg Ala Ala Asn Thr His Ser Ser Ala Lys Pro Cys Gly Gln Gln Ser
                165                 170                 175

Ile His Leu Gly Gly Val Phe Glu Leu Gln Pro Gly Ala Ser Val Phe
            180                 185                 190

Val Asn Val Thr Asp Pro Ser Gln Val Ser His Gly Thr Gly Phe Thr
        195                 200                 205

Ser Phe Gly Leu Leu Lys Leu
    210                 215
```

<210> SEQ ID NO 58
<211> LENGTH: 172
<212> TYPE: PRT
<213> ORGANISM: Artificial
<220> FEATURE:
<223> OTHER INFORMATION: The amino acid sequence of the human T cell positive costimulatory molecule CD27 extracellular domain

<400> SEQUENCE: 58

```
Ala Thr Pro Ala Pro Lys Ser Cys Pro Glu Arg His Tyr Trp Ala Gln
1               5                   10                  15

Gly Lys Leu Cys Cys Gln Met Cys Glu Pro Gly Thr Phe Leu Val Lys
            20                  25                  30

Asp Cys Asp Gln His Arg Lys Ala Ala Gln Cys Asp Pro Cys Ile Pro
        35                  40                  45

Gly Val Ser Phe Ser Pro Asp His His Thr Arg Pro His Cys Glu Ser
    50                  55                  60

Cys Arg His Cys Asn Ser Gly Leu Leu Val Arg Asn Cys Thr Ile Thr
65                  70                  75                  80

Ala Asn Ala Glu Cys Ala Cys Arg Asn Gly Trp Gln Cys Arg Asp Lys
                85                  90                  95

Glu Cys Thr Glu Cys Asp Pro Leu Pro Asn Pro Ser Leu Thr Ala Arg
            100                 105                 110

Ser Ser Gln Ala Leu Ser Pro His Pro Gln Pro Thr His Leu Pro Tyr
        115                 120                 125

Val Ser Glu Met Leu Glu Ala Arg Thr Ala Gly His Met Gln Thr Leu
    130                 135                 140

Ala Asp Phe Arg Gln Leu Pro Ala Arg Thr Leu Ser Thr His Trp Pro
```

-continued

```
145                 150                 155                 160

Pro Gln Arg Ser Leu Cys Ser Ser Asp Phe Ile Arg
                165                 170


<210> SEQ ID NO 59
<211> LENGTH: 759
<212> TYPE: PRT
<213> ORGANISM: Artificial
<220> FEATURE:
<223> OTHER INFORMATION: The amino acid sequence of CD19-CD3-4-1BB
      TsAb_M monomer

<400> SEQUENCE: 59

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335
```

-continued

```
Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Gln Val Gln Leu Gln Gln Trp Gly Ala Gly Leu Leu Lys Pro Ser
        515                 520                 525

Glu Thr Leu Ser Leu Thr Cys Ala Val Tyr Gly Gly Ser Phe Ser Gly
    530                 535                 540

Tyr Tyr Trp Ser Trp Ile Arg Gln Ser Pro Glu Lys Gly Leu Glu Trp
545                 550                 555                 560

Ile Gly Glu Ile Asn His Gly Gly Tyr Val Thr Tyr Asn Pro Ser Leu
                565                 570                 575

Glu Ser Arg Val Thr Ile Ser Val Asp Thr Ser Lys Asn Gln Phe Ser
            580                 585                 590

Leu Lys Leu Ser Ser Val Thr Ala Ala Asp Thr Ala Val Tyr Tyr Cys
        595                 600                 605

Ala Arg Asp Tyr Gly Pro Gly Asn Tyr Asp Trp Tyr Phe Asp Leu Trp
    610                 615                 620

Gly Arg Gly Thr Leu Val Thr Val Ser Ser Gly Gly Gly Gly Ser Gly
625                 630                 635                 640

Gly Gly Gly Ser Gly Gly Gly Gly Ser Glu Ile Val Leu Thr Gln Ser
                645                 650                 655

Pro Ala Thr Leu Ser Leu Ser Pro Gly Glu Arg Ala Thr Leu Ser Cys
            660                 665                 670

Arg Ala Ser Gln Ser Val Ser Ser Tyr Leu Ala Trp Tyr Gln Gln Lys
        675                 680                 685

Pro Gly Gln Ala Pro Arg Leu Leu Ile Tyr Asp Ala Ser Asn Arg Ala
    690                 695                 700

Thr Gly Ile Pro Ala Arg Phe Ser Gly Ser Gly Ser Gly Thr Asp Phe
705                 710                 715                 720

Thr Leu Thr Ile Ser Ser Leu Glu Pro Glu Asp Phe Ala Val Tyr Tyr
                725                 730                 735

Cys Gln Gln Arg Ser Asn Trp Pro Pro Ala Leu Thr Phe Cys Gly Gly
            740                 745                 750

Thr Lys Val Glu Ile Lys Arg
```

755

<210> SEQ ID NO 60
<211> LENGTH: 2277
<212> TYPE: DNA
<213> ORGANISM: Artificial
<220> FEATURE:
<223> OTHER INFORMATION: The nucleotide sequence of CD19-CD3-4-1BB
TsAb_M monomer

<400> SEQUENCE: 60
gacatccagc tgacccagag ccccgccagc ctggccgtga gcctgggcca gcgcgccacc 60
atcagctgca aggccagcca gagcgtggac tacgacggcg acagctacct gaactggtac 120
cagcagatcc ccggccagcc ccccaagctg ctgatctacg acgccagcaa cctggtgagc 180
ggcatccccc cccgcttcag cggcagcggc agcggcaccg acttcaccct gaacatccac 240
cccgtggaga aggtggacgc cgccacctac cactgccagc agagcaccga ggacccctgg 300
accttcggcg gcggcaccaa gctggagatc aagggcggcg gcggcagcgg cggcggcggc 360
agcggcggcg gcggcagcca ggtgcagctg cagcagagcg gcgccgagct ggtgcgcccc 420
ggcagcagcg tgaagatcag ctgcaaggcc agcggctacg ccttcagcag ctactggatg 480
aactgggtga agcagcgccc cggccagggc ctggagtgga tcggccagat ctggcccggc 540
gacggcgaca ccaactacaa cggcaagttc aagggcaagg ccaccctgac cgccgacgag 600
agcagcagca ccgcctacat gcagctgagc agcctggcca gcgaggacag cgccgtgtac 660
ttctgcgccc gccgcgagac caccaccgtg ggccgctact actacgccat ggactactgg 720
ggccagggca ccaccgtgac cgtgagcagc ggtggcggag ggtccgacat caagctgcag 780
cagagcggcg ccgagctggc ccgccccggc gccagcgtga agatgagctg caagaccagc 840
ggctacacct tcacccgcta caccatgcac tgggtgaagc agcgccccgg ccagggcctg 900
gagtggatcg gctacatcaa ccccagccgc ggctacacca actacaacca gaagttcaag 960
gacaaggcca ccctgaccac cgacaagagc agcagcaccg cctacatgca gctgagcagc 1020
ctgaccagcg aggacagcgc cgtgtactac tgcgcccgct actacgacga ccactactgc 1080
ctggactact ggggccaggg caccaccctg accgtgagca gcgtggaggg cggcagcggc 1140
ggcagcggcg gcagcggcgg cagcggcggc gtggacgaca tccagctgac ccagagcccc 1200
gccatcatga gcgccagccc cggcgagaag gtgaccatga cctgccgcgc cagcagcagc 1260
gtgagctaca tgaactggta ccagcagaag agcggcacca gccccaagcg ctggatctac 1320
gacaccagca aggtggccag cggcgtgccc taccgcttca gcggcagcgg cagcggcacc 1380
agctacagcc tgaccatcag cagcatggag gccgaggacg ccgccaccta ctactgccag 1440
cagtggagca gcaaccccct gaccttcggc gccggcacca agctggagct gaagggaggc 1500
ggaggttccg gcggtggggg atcgggggt ggagggagtc aggtgcagct gcagcagtgg 1560
ggcgccggcc tgctgaagcc cagcgagacc ctgagcctga cctgcgccgt gtacggcggc 1620
agcttcagcg gctactactg gagctggatc cgccagagcc ccgagaaggg cctggagtgg 1680
atcggcgaga tcaaccacgg cggctacgtg acctacaacc ccagcctgga gagccgcgtg 1740
accatcagcg tggacaccag caagaaccag ttcagcctga agctgagcag cgtgaccgcc 1800
gccgacaccg ccgtgtacta ctgcgcccgc gactacggcc ccggcaacta cgactggtac 1860
ttcgacctgt ggggccgcgg caccctggtg accgtgagca gcggcggcgg cggcagcggc 1920
ggcggcggca gcggcggcgg cggcagcgag atcgtgctga cccagagccc cgccaccctg 1980

```
agcctgagcc ccggcgagcg cgccaccctg agctgccgcg ccagccagag cgtgagcagc   2040

tacctggcct ggtaccagca gaagcccggc caggcccccc gcctgctgat ctacgacgcc   2100

agcaaccgcg ccaccggcat ccccgcccgc ttcagcggca gcggcagcgg caccgacttc   2160

accctgacca tcagcagcct ggagcccgag gacttcgccg tgtactactg ccagcagcgc   2220

agcaactggc cccccgccct gaccttctgc ggcggcacca aggtggagat caagcgc      2277
```

<210> SEQ ID NO 61
<211> LENGTH: 825
<212> TYPE: PRT
<213> ORGANISM: Artificial
<220> FEATURE:
<223> OTHER INFORMATION: The amino acid sequence of CD19-CD3-4-1BB
      TsAb_D dimer

<400> SEQUENCE: 61

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
```

-continued 305 310 315 320

Asp Lys Ala Thr Leu Thr Thr Asp Lys Ser Ser Ser Thr Ala Tyr Met
325 330 335

Gln Leu Ser Ser Leu Thr Ser Glu Asp Ser Ala Val Tyr Tyr Cys Ala
340 345 350

Arg Tyr Tyr Asp Asp His Tyr Cys Leu Asp Tyr Trp Gly Gln Gly Thr
355 360 365

Thr Leu Thr Val Ser Ser Val Glu Gly Gly Ser Gly Gly Ser Gly Gly
370 375 380

Ser Gly Gly Ser Gly Gly Val Asp Asp Ile Gln Leu Thr Gln Ser Pro
385 390 395 400

Ala Ile Met Ser Ala Ser Pro Gly Glu Lys Val Thr Met Thr Cys Arg
405 410 415

Ala Ser Ser Ser Val Ser Tyr Met Asn Trp Tyr Gln Gln Lys Ser Gly
420 425 430

Thr Ser Pro Lys Arg Trp Ile Tyr Asp Thr Ser Lys Val Ala Ser Gly
435 440 445

Val Pro Tyr Arg Phe Ser Gly Ser Gly Ser Gly Thr Ser Tyr Ser Leu
450 455 460

Thr Ile Ser Ser Met Glu Ala Glu Asp Ala Ala Thr Tyr Tyr Cys Gln
465 470 475 480

Gln Trp Ser Ser Asn Pro Leu Thr Phe Gly Ala Gly Thr Lys Leu Glu
485 490 495

Leu Lys Ala Ser Lys Ser Lys Lys Glu Ile Phe Arg Trp Pro Glu Ser
500 505 510

Pro Lys Ala Gln Ala Ser Ser Val Pro Thr Ala Gln Pro Gln Ala Glu
515 520 525

Gly Ser Leu Ala Lys Ala Thr Thr Ala Pro Ala Thr Thr Arg Asn Thr
530 535 540

Gly Arg Gly Gly Glu Glu Lys Lys Lys Glu Lys Glu Lys Glu Glu Gln
545 550 555 560

Glu Glu Arg Glu Thr Lys Thr Pro Glu Cys Pro Ser His Thr Gln Pro
565 570 575

Leu Gly Val Gln Val Gln Leu Gln Gln Trp Gly Ala Gly Leu Leu Lys
580 585 590

Pro Ser Glu Thr Leu Ser Leu Thr Cys Ala Val Tyr Gly Gly Ser Phe
595 600 605

Ser Gly Tyr Tyr Trp Ser Trp Ile Arg Gln Ser Pro Glu Lys Gly Leu
610 615 620

Glu Trp Ile Gly Glu Ile Asn His Gly Gly Tyr Val Thr Tyr Asn Pro
625 630 635 640

Ser Leu Glu Ser Arg Val Thr Ile Ser Val Asp Thr Ser Lys Asn Gln
645 650 655

Phe Ser Leu Lys Leu Ser Ser Val Thr Ala Ala Asp Thr Ala Val Tyr
660 665 670

Tyr Cys Ala Arg Asp Tyr Gly Pro Gly Asn Tyr Asp Trp Tyr Phe Asp
675 680 685

Leu Trp Gly Arg Gly Thr Leu Val Thr Val Ser Ser Gly Gly Gly Gly
690 695 700

Ser Gly Gly Gly Gly Ser Gly Gly Gly Gly Ser Glu Ile Val Leu Thr
705 710 715 720

Gln Ser Pro Ala Thr Leu Ser Leu Ser Pro Gly Glu Arg Ala Thr Leu
725 730 735

```
Ser Cys Arg Ala Ser Gln Ser Val Ser Ser Tyr Leu Ala Trp Tyr Gln
            740                 745                 750

Gln Lys Pro Gly Gln Ala Pro Arg Leu Leu Ile Tyr Asp Ala Ser Asn
        755                 760                 765

Arg Ala Thr Gly Ile Pro Ala Arg Phe Ser Gly Ser Gly Ser Gly Thr
    770                 775                 780

Asp Phe Thr Leu Thr Ile Ser Ser Leu Glu Pro Glu Asp Phe Ala Val
785                 790                 795                 800

Tyr Tyr Cys Gln Gln Arg Ser Asn Trp Pro Pro Ala Leu Thr Phe Cys
                805                 810                 815

Gly Gly Thr Lys Val Glu Ile Lys Arg
            820                 825


<210> SEQ ID NO 62
<211> LENGTH: 2475
<212> TYPE: DNA
<213> ORGANISM: Artificial
<220> FEATURE:
<223> OTHER INFORMATION: The nucleotide sequence of CD19-CD3-4-1BB
      TsAb_D dimer

<400> SEQUENCE: 62

gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180

ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggtggcggag ggtccgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaaccccct gaccttcggc gccggcacca agctggagct gaaggccagc   1500
```

```
aagagcaaga aggagatctt ccgctggccc gagagcccca aggcccaggc cagcagcgtg   1560
cccaccgccc agccccaggc cgagggcagc ctggccaagg ccaccaccgc ccccgccacc   1620
acccgcaaca ccggccgcgg cggcgaggag aagaagaagg agaaggagaa ggaggagcag   1680
gaggagcgcg agaccaagac ccccgagtgc cccagccaca cccagcccct gggcgtgcag   1740
gtgcagctgc agcagtgggg cgccggcctg ctgaagccca gcgagaccct gagcctgacc   1800
tgcgccgtgt acggcggcag cttcagcggc tactactgga gctggatccg ccagagcccc   1860
gagaagggcc tggagtggat cggcgagatc aaccacggcg gctacgtgac ctacaacccc   1920
agcctggaga gccgcgtgac catcagcgtg gacaccagca agaaccagtt cagcctgaag   1980
ctgagcagcg tgaccgccgc cgacaccgcc gtgtactact gcgcccgcga ctacggcccc   2040
ggcaactacg actggtactt cgacctgtgg ggccgcggca ccctggtgac cgtgagcagc   2100
ggcggcggcg gcagcggcgg cggcggcagc ggcggcggcg gcagcgagat cgtgctgacc   2160
cagagccccg ccaccctgag cctgagcccc ggcgagcgcg ccaccctgag ctgccgcgcc   2220
agccagagcg tgagcagcta cctggcctgg taccagcaga agcccggcca ggcccccgc    2280
ctgctgatct acgacgccag caaccgcgcc accggcatcc ccgcccgctt cagcggcagc   2340
ggcagcggca ccgacttcac cctgaccatc agcagcctgg agcccgagga cttcgccgtg   2400
tactactgcc agcagcgcag caactggccc cccgccctga ccttctgcgg cggcaccaag   2460
gtggagatca agcgc                                                    2475
```

<210> SEQ ID NO 63
<211> LENGTH: 760
<212> TYPE: PRT
<213> ORGANISM: Artificial
<220> FEATURE:
<223> OTHER INFORMATION: The amino acid sequence of CD19-CD3-ICOS TsAb_M monomer

<400> SEQUENCE: 63

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175
```

-continued

```
Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Gln Val Gln Leu Val Gln Ser Gly Ala Glu Val Lys Lys Pro Gly
        515                 520                 525

Ala Ser Val Lys Val Ser Cys Lys Ala Ser Gly Tyr Thr Phe Thr Gly
    530                 535                 540

Tyr Tyr Met His Trp Val Arg Gln Ala Pro Gly Gln Gly Leu Glu Trp
545                 550                 555                 560

Met Gly Trp Ile Asn Pro His Ser Gly Gly Thr Asn Tyr Ala Gln Lys
                565                 570                 575

Phe Gln Gly Arg Val Thr Met Thr Arg Asp Thr Ser Ile Ser Thr Ala
            580                 585                 590

Tyr Met Glu Leu Ser Arg Leu Arg Ser Asp Asp Thr Ala Val Tyr Tyr
```

```
        595                 600                 605

Cys Ala Arg Thr Tyr Tyr Tyr Asp Ser Ser Gly Tyr Tyr His Asp Ala
    610                 615                 620

Phe Asp Ile Trp Gly Gln Gly Thr Met Val Thr Val Ser Ser Gly Gly
625                 630                 635                 640

Gly Gly Ser Gly Gly Gly Gly Ser Gly Gly Gly Gly Ser Asp Ile Gln
                645                 650                 655

Met Thr Gln Ser Pro Ser Ser Val Ser Ala Ser Val Gly Asp Arg Val
            660                 665                 670

Thr Ile Thr Cys Arg Ala Ser Gln Gly Ile Ser Arg Leu Leu Ala Trp
        675                 680                 685

Tyr Gln Gln Lys Pro Gly Lys Ala Pro Lys Leu Leu Ile Tyr Val Ala
    690                 695                 700

Ser Ser Leu Gln Ser Gly Val Pro Ser Arg Phe Ser Gly Ser Gly Ser
705                 710                 715                 720

Gly Thr Asp Phe Thr Leu Thr Ile Ser Ser Leu Gln Pro Glu Asp Phe
                725                 730                 735

Ala Thr Tyr Tyr Cys Gln Gln Ala Asn Ser Phe Pro Trp Thr Phe Gly
            740                 745                 750

Gln Gly Thr Lys Val Glu Ile Lys
        755                 760


<210> SEQ ID NO 64
<211> LENGTH: 2280
<212> TYPE: DNA
<213> ORGANISM: Artificial
<220> FEATURE:
<223> OTHER INFORMATION: The nucleotide sequence of CD19-CD3-ICOS TsAb_M
      monomer

<400> SEQUENCE: 64

gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600

agcagcagca ccgcctacat gcagctgagc agcctggcca gcgaggacag cgccgtgtac     660

ttctgcgccc gccgcgagac caccaccgtg ggccgctact actacgccat ggactactgg     720

ggccagggca ccaccgtgac cgtgagcagc ggtggcggag ggtccgacat caagctgcag     780

cagagcggcg ccgagctggc ccgccccggc gccagcgtga agatgagctg caagaccagc     840

ggctacacct tcacccgcta caccatgcac tgggtgaagc agcgccccgg ccagggcctg     900

gagtggatcg gctacatcaa ccccagccgc ggctacacca actacaacca gaagttcaag     960

gacaaggcca ccctgaccac cgacaagagc agcagcaccg cctacatgca gctgagcagc    1020

ctgaccagcg aggacagcgc cgtgtactac tgcgcccgct actacgacga ccactactgc    1080
```

-continued ctggactact ggggccaggg caccaccctg accgtgagca gcgtggaggg cggcagcggc 1140
ggcagcggcg gcagcggcgg cagcggcggc gtggacgaca tccagctgac ccagagcccc 1200
gccatcatga gcgccagccc cggcgagaag gtgaccatga cctgccgcgc cagcagcagc 1260
gtgagctaca tgaactggta ccagcagaag agcggcacca gccccaagcg ctggatctac 1320
gacaccagca aggtggccag cggcgtgccc taccgcttca gcggcagcgg cagcggcacc 1380
agctacagcc tgaccatcag cagcatggag gccgaggacg ccgccaccta ctactgccag 1440
cagtggagca gcaacccct gaccttcggc gccggcacca agctggagct gaagggaggc 1500
ggaggttccg gcggtggggg atcggggggt ggagggagtc aggtgcagct ggtgcagagc 1560
ggcgccgagg tgaagaagcc cggcgccagc gtgaaggtga gctgcaaggc cagcggctac 1620
accttcaccg gctactacat gcactgggtg cgccaggccc ccggccaggg cctggagtgg 1680
atgggctgga tcaaccccca cagcggcggc accaactacg cccagaagtt ccagggccgc 1740
gtgaccatga cccgcgacac cagcatcagc accgcctaca tggagctgag ccgcctgcgc 1800
agcgacgaca ccgccgtgta ctactgcgcc cgcacctact actacgacag cagcggctac 1860
taccacgacg ccttcgacat ctggggccag ggcaccatgg tgaccgtgag cagcggcggc 1920
ggcggcagcg gcggcggcgg cagcggcggc ggcggcagcg acatccagat gacccagagc 1980
cccagcagcg tgagcgccag cgtgggcgac cgcgtgacca tcacctgccg cgccagccag 2040
ggcatcagcc gcctgctggc ctggtaccag cagaagcccg gcaaggcccc caagctgctg 2100
atctacgtgg ccagcagcct gcagagcggc gtgcccagcc gcttcagcgg cagcggcagc 2160
ggcaccgact tcaccctgac catcagcagc ctgcagcccg aggacttcgc cacctactac 2220
tgccagcagg ccaacagctt cccctggacc ttcggccagg gcaccaaggt ggagatcaag 2280

<210> SEQ ID NO 65
<211> LENGTH: 826
<212> TYPE: PRT
<213> ORGANISM: Artificial
<220> FEATURE:
<223> OTHER INFORMATION: The amino acid sequence of CD19-CD3-ICOS TsAb_D dimer

<400> SEQUENCE: 65

Asp Ile Gln Leu Thr Gln Ser Pro Ala Ser Leu Ala Val Ser Leu Gly
1 5 10 15

Gln Arg Ala Thr Ile Ser Cys Lys Ala Ser Gln Ser Val Asp Tyr Asp
20 25 30

Gly Asp Ser Tyr Leu Asn Trp Tyr Gln Gln Ile Pro Gly Gln Pro Pro
35 40 45

Lys Leu Leu Ile Tyr Asp Ala Ser Asn Leu Val Ser Gly Ile Pro Pro
50 55 60

Arg Phe Ser Gly Ser Gly Ser Gly Thr Asp Phe Thr Leu Asn Ile His
65 70 75 80

Pro Val Glu Lys Val Asp Ala Ala Thr Tyr His Cys Gln Gln Ser Thr
85 90 95

Glu Asp Pro Trp Thr Phe Gly Gly Gly Thr Lys Leu Glu Ile Lys Gly
100 105 110

Gly Gly Gly Ser Gly Gly Gly Gly Ser Gly Gly Gly Gly Ser Gln Val
115 120 125

Gln Leu Gln Gln Ser Gly Ala Glu Leu Val Arg Pro Gly Ser Ser Val
130 135 140

Lys Ile Ser Cys Lys Ala Ser Gly Tyr Ala Phe Ser Ser Tyr Trp Met

-continued

```
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575
```

```
Leu Gly Val Gln Val Gln Leu Val Gln Ser Gly Ala Glu Val Lys Lys
            580                 585                 590

Pro Gly Ala Ser Val Lys Val Ser Cys Lys Ala Ser Gly Tyr Thr Phe
        595                 600                 605

Thr Gly Tyr Tyr Met His Trp Val Arg Gln Ala Pro Gly Gln Gly Leu
    610                 615                 620

Glu Trp Met Gly Trp Ile Asn Pro His Ser Gly Gly Thr Asn Tyr Ala
625                 630                 635                 640

Gln Lys Phe Gln Gly Arg Val Thr Met Thr Arg Asp Thr Ser Ile Ser
                645                 650                 655

Thr Ala Tyr Met Glu Leu Ser Arg Leu Arg Ser Asp Asp Thr Ala Val
            660                 665                 670

Tyr Tyr Cys Ala Arg Thr Tyr Tyr Tyr Asp Ser Ser Gly Tyr Tyr His
        675                 680                 685

Asp Ala Phe Asp Ile Trp Gly Gln Gly Thr Met Val Thr Val Ser Ser
    690                 695                 700

Gly Gly Gly Gly Ser Gly Gly Gly Gly Ser Gly Gly Gly Gly Ser Asp
705                 710                 715                 720

Ile Gln Met Thr Gln Ser Pro Ser Ser Val Ser Ala Ser Val Gly Asp
                725                 730                 735

Arg Val Thr Ile Thr Cys Arg Ala Ser Gln Gly Ile Ser Arg Leu Leu
            740                 745                 750

Ala Trp Tyr Gln Gln Lys Pro Gly Lys Ala Pro Lys Leu Leu Ile Tyr
        755                 760                 765

Val Ala Ser Ser Leu Gln Ser Gly Val Pro Ser Arg Phe Ser Gly Ser
    770                 775                 780

Gly Ser Gly Thr Asp Phe Thr Leu Thr Ile Ser Ser Leu Gln Pro Glu
785                 790                 795                 800

Asp Phe Ala Thr Tyr Tyr Cys Gln Gln Ala Asn Ser Phe Pro Trp Thr
                805                 810                 815

Phe Gly Gln Gly Thr Lys Val Glu Ile Lys
            820                 825
```

<210> SEQ ID NO 66
<211> LENGTH: 2478
<212> TYPE: DNA
<213> ORGANISM: Artificial
<220> FEATURE:
<223> OTHER INFORMATION: The nucleotide sequence of CD19-CD3-ICOS TsAb_D dimer

<400> SEQUENCE: 66

```
gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600
```

```
agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggtggcggag ggtccgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaacccct gaccttcggc gccggcacca agctggagct gaaggccagc   1500

aagagcaaga aggagatctt ccgctggccc gagagcccca aggcccaggc cagcagcgtg   1560

cccaccgccc agccccaggc cgagggcagc ctggccaagg ccaccaccgc ccccgccacc   1620

acccgcaaca ccggccgcgg cggcgaggag aagaagaagg agaaggagaa ggaggagcag   1680

gaggagcgcg agaccaagac ccccgagtgc cccagccaca cccagcccct gggcgtgcag   1740

gtgcagctgg tgcagagcgg cgccgaggtg aagaagcccg gcgccagcgt gaaggtgagc   1800

tgcaaggcca gcggctacac cttcaccggc tactacatgc actgggtgcg ccaggccccc   1860

ggccagggcc tggagtggat gggctggatc aacccccaca gcggcggcac caactacgcc   1920

cagaagttcc agggccgcgt gaccatgacc cgcgacacca gcatcagcac cgcctacatg   1980

gagctgagcc gcctgcgcag cgacgacacc gccgtgtact actgcgcccg cacctactac   2040

tacgacagca gcggctacta ccacgacgcc ttcgacatct ggggccaggg caccatggtg   2100

accgtgagca gcggcggcgg cggcagcggc ggcggcggca gcggcggcgg cggcagcgac   2160

atccagatga cccagagccc cagcagcgtg agcgccagcg tgggcgaccg cgtgaccatc   2220

acctgccgcg ccagccaggg catcagccgc ctgctggcct ggtaccagca gaagcccggc   2280

aaggccccca agctgctgat ctacgtggcc agcagcctgc agagcggcgt gcccagccgc   2340

ttcagcggca gcggcagcgg caccgacttc accctgacca tcagcagcct gcagcccgag   2400

gacttcgcca cctactactg ccagcaggcc aacagcttcc cctggacctt cggccagggc   2460

accaaggtgg agatcaag                                                  2478
```

```
<210> SEQ ID NO 67
<211> LENGTH: 755
<212> TYPE: PRT
<213> ORGANISM: Artificial
<220> FEATURE:
<223> OTHER INFORMATION: The amino acid sequence of CD19-CD3-OX40 TsAb_M
      monomer

<400> SEQUENCE: 67

Asp Ile Gln Leu Thr Gln Ser Pro Ala Ser Leu Ala Val Ser Leu Gly
1               5                   10                  15
```

-continued

```
Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
```

-continued

```
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Gln Leu Val Glu Ser Gly Gly Gly Leu Val Gln Pro Gly Gly Ser
        515                 520                 525

Leu Arg Leu Ser Cys Ala Ala Ser Gly Phe Thr Phe Ser Ser Tyr Ser
    530                 535                 540

Met Asn Trp Val Arg Gln Ala Pro Gly Lys Gly Leu Glu Trp Val Ser
545                 550                 555                 560

Tyr Ile Ser Ser Ser Ser Ser Thr Ile Tyr Tyr Ala Asp Ser Val Lys
                565                 570                 575

Gly Arg Phe Thr Ile Ser Arg Asp Asn Ala Lys Asn Ser Leu Tyr Leu
            580                 585                 590

Gln Met Asn Ser Leu Arg Asp Glu Asp Thr Ala Val Tyr Tyr Cys Ala
        595                 600                 605

Arg Gly Val Tyr His Asn Gly Trp Ser Phe Phe Asp Tyr Trp Gly Gln
    610                 615                 620

Gly Thr Leu Leu Thr Val Ser Ser Gly Gly Gly Gly Ser Gly Gly Gly
625                 630                 635                 640

Gly Ser Gly Gly Gly Gly Ser Asp Ile Gln Met Thr Gln Ser Pro Ser
                645                 650                 655

Ser Leu Ser Ala Ser Val Gly Asn Arg Val Thr Ile Thr Cys Arg Ala
            660                 665                 670

Ser Gln Asp Ile Ser Ser Trp Leu Ala Trp Tyr Gln Gln Lys Pro Glu
        675                 680                 685

Lys Ala Pro Lys Ser Leu Ile Tyr Ala Ala Ser Ser Leu Gln Ser Gly
    690                 695                 700

Val Pro Ser Arg Phe Ser Gly Ser Gly Ser Gly Thr Asp Phe Thr Leu
705                 710                 715                 720

Thr Ile Ser Ser Leu Gln Pro Glu Asp Phe Ala Thr Tyr Tyr Cys Gln
                725                 730                 735

Gln Tyr Asn Ser Tyr Pro Leu Thr Phe Gly Gln Gly Thr Arg Leu Glu
            740                 745                 750

Ile Lys Arg
        755
```

<210> SEQ ID NO 68
<211> LENGTH: 2265
<212> TYPE: DNA
<213> ORGANISM: Artificial
<220> FEATURE:
<223> OTHER INFORMATION: The nucleotide sequence of CD19-CD3-OX40 TsAb_M monomer

<400> SEQUENCE: 68

```
gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180
```

-continued

```
ggcatccccc cccgcttcag cggcagcggc agcggcaccg acttcaccct gaacatccac    240
cccgtggaga aggtggacgc cgccacctac cactgccagc agagcaccga ggacccctgg    300
accttcggcg gcggcaccaa gctggagatc aagggcggcg gcggcagcgg cggcggcggc    360
agcggcggcg gcggcagcca ggtgcagctg cagcagagcg gcgccgagct ggtgcgcccc    420
ggcagcagcg tgaagatcag ctgcaaggcc agcggctacg ccttcagcag ctactggatg    480
aactgggtga agcagcgccc cggccagggc ctggagtgga tcggccagat ctggcccggc    540
gacggcgaca ccaactacaa cggcaagttc aagggcaagg ccaccctgac cgccgacgag    600
agcagcagca ccgcctacat gcagctgagc agcctggcca gcgaggacag cgccgtgtac    660
ttctgcgccc gccgcgagac caccaccgtg ggccgctact actacgccat ggactactgg    720
ggccagggca ccaccgtgac cgtgagcagc ggtggcggag ggtccgacat caagctgcag    780
cagagcggcg ccgagctggc ccgccccggc gccagcgtga agatgagctg caagaccagc    840
ggctacacct tcacccgcta caccatgcac tgggtgaagc agcgccccgg ccagggcctg    900
gagtggatcg gctacatcaa ccccagccgc ggctacacca actacaacca gaagttcaag    960
gacaaggcca ccctgaccac cgacaagagc agcagcaccg cctacatgca gctgagcagc   1020
ctgaccagcg aggacagcgc cgtgtactac tgcgcccgct actacgacga ccactactgc   1080
ctggactact ggggccaggg caccaccctg accgtgagca gcgtggaggg cggcagcggc   1140
ggcagcggcg gcagcggcgg cagcggcggc gtggacgaca tccagctgac ccagagcccc   1200
gccatcatga gcgccagccc cggcgagaag gtgaccatga cctgccgcgc cagcagcagc   1260
gtgagctaca tgaactggta ccagcagaag agcggcacca gccccaagcg ctggatctac   1320
gacaccagca aggtggccag cggcgtgccc taccgcttca gcggcagcgg cagcggcacc   1380
agctacagcc tgaccatcag cagcatggag gccgaggacg ccgccaccta ctactgccag   1440
cagtggagca gcaacccccct gaccttcggc gccggcacca agctggagct gaagggaggc   1500
ggaggttccg gcggtggggg atcgggggggt ggagggagtc agctggtgga gagcggcggc   1560
ggcctggtgc agcccggcgg cagcctgcgc ctgagctgcg ccgccagcgg cttcaccttc   1620
agcagctaca gcatgaactg ggtgcgccag gcccccggca agggcctgga gtgggtgagc   1680
tacatcagca gcagcagcag caccatctac tacgccgaca gcgtgaaggg ccgcttcacc   1740
atcagccgcg acaacgccaa gaacagcctg tacctgcaga tgaacagcct gcgcgacgag   1800
gacaccgccg tgtactactg cgcccgcggc gtgtaccaca acggctggag cttcttcgac   1860
tactggggcc agggcaccct gctgaccgtg agcagcggcg gcggcggcag cggcggcggc   1920
ggcagcggcg gcggcggcag cgacatccag atgacccaga gccccagcag cctgagcgcc   1980
agcgtgggca accgcgtgac catcacctgc cgcgccagcc aggacatcag cagctggctg   2040
gcctggtacc agcagaagcc cgagaaggcc cccaagagcc tgatctacgc cgccagcagc   2100
ctgcagagcg gcgtgcccag ccgcttcagc ggcagcggca gcggcaccga cttcaccctg   2160
accatcagca gcctgcagcc cgaggacttc gccacctact actgccagca gtacaacagc   2220
taccccctga ccttcggcca gggcacccgc ctggagatca agcgc                   2265
```

<210> SEQ ID NO 69
<211> LENGTH: 821
<212> TYPE: PRT
<213> ORGANISM: Artificial
<220> FEATURE:
<223> OTHER INFORMATION: The amino acid sequence of CD19-CD3-OX40 TsAb_D dimer

<400> SEQUENCE: 69

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

```
Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Gln Leu Val Glu Ser Gly Gly Gly Leu Val Gln Pro Gly
            580                 585                 590

Gly Ser Leu Arg Leu Ser Cys Ala Ala Ser Gly Phe Thr Phe Ser Ser
        595                 600                 605

Tyr Ser Met Asn Trp Val Arg Gln Ala Pro Gly Lys Gly Leu Glu Trp
    610                 615                 620

Val Ser Tyr Ile Ser Ser Ser Ser Ser Thr Ile Tyr Tyr Ala Asp Ser
625                 630                 635                 640

Val Lys Gly Arg Phe Thr Ile Ser Arg Asp Asn Ala Lys Asn Ser Leu
                645                 650                 655

Tyr Leu Gln Met Asn Ser Leu Arg Asp Glu Asp Thr Ala Val Tyr Tyr
            660                 665                 670

Cys Ala Arg Gly Val Tyr His Asn Gly Trp Ser Phe Phe Asp Tyr Trp
        675                 680                 685

Gly Gln Gly Thr Leu Leu Thr Val Ser Ser Gly Gly Gly Gly Ser Gly
    690                 695                 700

Gly Gly Gly Ser Gly Gly Gly Gly Ser Asp Ile Gln Met Thr Gln Ser
705                 710                 715                 720

Pro Ser Ser Leu Ser Ala Ser Val Gly Asn Arg Val Thr Ile Thr Cys
                725                 730                 735

Arg Ala Ser Gln Asp Ile Ser Ser Trp Leu Ala Trp Tyr Gln Gln Lys
            740                 745                 750

Pro Glu Lys Ala Pro Lys Ser Leu Ile Tyr Ala Ala Ser Ser Leu Gln
        755                 760                 765

Ser Gly Val Pro Ser Arg Phe Ser Gly Ser Gly Ser Gly Thr Asp Phe
    770                 775                 780

Thr Leu Thr Ile Ser Ser Leu Gln Pro Glu Asp Phe Ala Thr Tyr Tyr
785                 790                 795                 800

Cys Gln Gln Tyr Asn Ser Tyr Pro Leu Thr Phe Gly Gln Gly Thr Arg
                805                 810                 815

Leu Glu Ile Lys Arg
            820
```

<210> SEQ ID NO 70
<211> LENGTH: 2463
<212> TYPE: DNA
<213> ORGANISM: Artificial
<220> FEATURE:
<223> OTHER INFORMATION: The nucleotide sequence of CD19-CD3-OX40 TsAb_D
dimer

<400> SEQUENCE: 70

```
gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600

agcagcagca ccgcctacat gcagctgagc agcctggcca gcgaggacag cgccgtgtac     660

ttctgcgccc gccgcgagac caccaccgtg ggccgctact actacgccat ggactactgg     720

ggccagggca ccaccgtgac cgtgagcagc ggtggcggag ggtccgacat caagctgcag     780

cagagcggcg ccgagctggc ccgccccggc gccagcgtga agatgagctg caagaccagc     840

ggctacacct tcacccgcta caccatgcac tgggtgaagc agcgccccgg ccagggcctg     900

gagtggatcg gctacatcaa ccccagccgc ggctacacca actacaacca gaagttcaag     960

gacaaggcca ccctgaccac cgacaagagc agcagcaccg cctacatgca gctgagcagc    1020

ctgaccagcg aggacagcgc cgtgtactac tgcgcccgct actacgacga ccactactgc    1080

ctggactact ggggccaggg caccaccctg accgtgagca gcgtggaggg cggcagcggc    1140

ggcagcggcg gcagcggcgg cagcggcggc gtggacgaca tccagctgac ccagagcccc    1200

gccatcatga gcgccagccc cggcgagaag gtgaccatga cctgccgcgc cagcagcagc    1260

gtgagctaca tgaactggta ccagcagaag agcggcacca gccccaagcg ctggatctac    1320

gacaccagca aggtggccag cggcgtgccc taccgcttca gcggcagcgg cagcggcacc    1380

agctacagcc tgaccatcag cagcatggag gccgaggacg ccgccaccta ctactgccag    1440

cagtggagca gcaaccccct gaccttcggc gccggcacca agctggagct gaaggccagc    1500

aagagcaaga aggagatctt ccgctggccc gagagcccca aggcccaggc cagcagcgtg    1560

cccaccgccc agccccaggc cgagggcagc ctggccaagg ccaccaccgc cccccgccacc   1620

acccgcaaca ccggccgcgg cggcgaggag aagaagaagg agaaggagaa ggaggagcag    1680

gaggagcgcg agaccaagac ccccgagtgc cccagccaca cccagcccct gggcgtgcag    1740

ctggtggaga gcggcggcgg cctggtgcag cccggcggca gcctgcgcct gagctgcgcc    1800

gccagcggct tcaccttcag cagctacagc atgaactggg tgcgccaggc ccccggcaag    1860

ggcctggagt gggtgagcta catcagcagc agcagcagca ccatctacta cgccgacagc    1920

gtgaagggcc gcttcaccat cagccgcgac aacgccaaga acagcctgta cctgcagatg    1980

aacagcctgc gcgacgagga caccgccgtg tactactgcg cccgcggcgt gtaccacaac    2040
```

```
ggctggagct tcttcgacta ctggggccag ggcaccctgc tgaccgtgag cagcggcggc   2100

ggcggcagcg gcggcggcgg cagcggcggc ggcggcagcg acatccagat gacccagagc   2160

cccagcagcc tgagcgccag cgtgggcaac cgcgtgacca tcacctgccg cgccagccag   2220

gacatcagca gctggctggc ctggtaccag cagaagcccg agaaggcccc caagagcctg   2280

atctacgccg ccagcagcct gcagagcggc gtgcccagcc gcttcagcgg cagcggcagc   2340

ggcaccgact tcaccctgac catcagcagc ctgcagcccg aggacttcgc cacctactac   2400

tgccagcagt acaacagcta ccccctgacc ttcggccagg gcacccgcct ggagatcaag   2460

cgc                                                                 2463


<210> SEQ ID NO 71
<211> LENGTH: 754
<212> TYPE: PRT
<213> ORGANISM: Artificial
<220> FEATURE:
<223> OTHER INFORMATION: The amino acid sequence of CD19-CD3-GITR TsAb_M
      monomer

<400> SEQUENCE: 71

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
```

-continued

```
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Gln Val Thr Leu Lys Glu Ser Gly Pro Gly Ile Leu Lys Pro Ser
        515                 520                 525

Gln Thr Leu Ser Leu Thr Cys Ser Phe Ser Gly Phe Ser Leu Ser Thr
    530                 535                 540

Ser Gly Met Gly Val Gly Trp Ile Arg Gln Pro Ser Gly Lys Gly Leu
545                 550                 555                 560

Glu Trp Leu Ala His Ile Trp Trp Asp Asp Asp Lys Tyr Tyr Asn Pro
                565                 570                 575

Ser Leu Lys Ser Gln Leu Thr Ile Ser Lys Asp Thr Ser Arg Asn Gln
            580                 585                 590

Val Phe Leu Lys Ile Thr Ser Val Asp Thr Ala Asp Ala Ala Thr Tyr
        595                 600                 605

Tyr Cys Ala Arg Thr Arg Arg Tyr Phe Pro Phe Ala Tyr Trp Gly Gln
    610                 615                 620

Gly Thr Leu Val Thr Val Ser Ser Gly Gly Gly Gly Ser Gly Gly Gly
625                 630                 635                 640

Gly Ser Gly Gly Gly Gly Ser Asp Ile Val Met Thr Gln Ser Gln Lys
                645                 650                 655

Phe Met Ser Thr Ser Val Gly Asp Arg Val Ser Val Thr Cys Lys Ala
            660                 665                 670

Ser Gln Asn Val Gly Thr Asn Val Ala Trp Tyr Gln Gln Lys Pro Gly
        675                 680                 685

Gln Ser Pro Lys Ala Leu Ile Tyr Ser Ala Ser Tyr Arg Tyr Ser Gly
    690                 695                 700
```

Val Pro Asp Arg Phe Thr Gly Ser Gly Ser Gly Thr Asp Phe Thr Leu
705 710 715 720

Thr Ile Asn Asn Val His Ser Glu Asp Leu Ala Glu Tyr Phe Cys Gln
725 730 735

Gln Tyr Asn Thr Asp Pro Leu Thr Phe Gly Ala Gly Thr Lys Leu Glu
740 745 750

Ile Lys

<210> SEQ ID NO 72
<211> LENGTH: 2262
<212> TYPE: DNA
<213> ORGANISM: Artificial
<220> FEATURE:
<223> OTHER INFORMATION: The nucleotide sequence of CD19-CD3-GITR TsAb_M
monomer

<400> SEQUENCE: 72
gacatccagc tgacccagag ccccgccagc ctggccgtga gcctgggcca gcgcgccacc 60
atcagctgca aggccagcca gagcgtggac tacgacggcg acagctacct gaactggtac 120
cagcagatcc ccggccagcc ccccaagctg ctgatctacg acgccagcaa cctggtgagc 180
ggcatccccc cccgcttcag cggcagcggc agcggcaccg acttcaccct gaacatccac 240
cccgtggaga aggtggacgc cgccacctac cactgccagc agagcaccga ggacccctgg 300
accttcggcg gcggcaccaa gctggagatc aagggcggcg gcggcagcgg cggcggcggc 360
agcggcggcg gcggcagcca ggtgcagctg cagcagagcg gcgccgagct ggtgcgcccc 420
ggcagcagcg tgaagatcag ctgcaaggcc agcggctacg ccttcagcag ctactggatg 480
aactgggtga agcagcgccc cggccagggc ctggagtgga tcggccagat ctggcccggc 540
gacggcgaca ccaactacaa cggcaagttc aagggcaagg ccaccctgac cgccgacgag 600
agcagcagca ccgcctacat gcagctgagc agcctggcca gcgaggacag cgccgtgtac 660
ttctgcgccc gccgcgagac caccaccgtg ggccgctact actacgccat ggactactgg 720
ggccagggca ccaccgtgac cgtgagcagc ggtggcggag ggtccgacat caagctgcag 780
cagagcggcg ccgagctggc ccgccccggc gccagcgtga agatgagctg caagaccagc 840
ggctacacct tcacccgcta caccatgcac tgggtgaagc agcgccccgg ccagggcctg 900
gagtggatcg gctacatcaa ccccagccgc ggctacacca actacaacca gaagttcaag 960
gacaaggcca ccctgaccac cgacaagagc agcagcaccg cctacatgca gctgagcagc 1020
ctgaccagcg aggacagcgc cgtgtactac tgcgcccgct actacgacga ccactactgc 1080
ctggactact ggggccaggg caccaccctg accgtgagca gcgtggaggg cggcagcggc 1140
ggcagcggcg gcagcggcgg cagcggcggc gtggacgaca tccagctgac ccagagcccc 1200
gccatcatga gcgccagccc cggcgagaag gtgaccatga cctgccgcgc cagcagcagc 1260
gtgagctaca tgaactggta ccagcagaag agcggcacca gccccaagcg ctggatctac 1320
gacaccagca aggtggccag cggcgtgccc taccgcttca gcggcagcgg cagcggcacc 1380
agctacagcc tgaccatcag cagcatggag gccgaggacg ccgccaccta ctactgccag 1440
cagtggagca gcaaccccct gaccttcggc gccggcacca agctggagct gaagggaggc 1500
ggaggttccg gcggtggggg atcggggggt ggagggagtc aggtgaccct gaaggagagc 1560
ggccccggca tcctgaagcc cagccagacc ctgagcctga cctgcagctt cagcggcttc 1620
agcctgagca ccagcggcat gggcgtgggc tggatccgcc agcccagcgg caagggcctg 1680

```
gagtggctgg cccacatctg gtgggacgac gacaagtact acaaccccag cctgaagagc   1740

cagctgacca tcagcaagga caccagccgc aaccaggtgt tcctgaagat caccagcgtg   1800

gacaccgccg acgccgccac ctactactgc gcccgcaccc gccgctactt ccccttcgcc   1860

tactggggcc agggcaccct ggtgaccgtg agcagcggcg gcggcggcag cggcggcggc   1920

ggcagcggcg gcggcggcag cgacatcgtg atgacccaga gccagaagtt catgagcacc   1980

agcgtgggcg accgcgtgag cgtgacctgc aaggccagcc agaacgtggg caccaacgtg   2040

gcctggtacc agcagaagcc cggccagagc cccaaggccc tgatctacag cgccagctac   2100

cgctacagcg gcgtgcccga ccgcttcacc ggcagcggca gcggcaccga cttcaccctg   2160

accatcaaca acgtgcacag cgaggacctg gccgagtact tctgccagca gtacaacacc   2220

gaccccctga ccttcggcgc cggcaccaag ctggagatca ag                      2262


<210> SEQ ID NO 73
<211> LENGTH: 820
<212> TYPE: PRT
<213> ORGANISM: Artificial
<220> FEATURE:
<223> OTHER INFORMATION: The amino acid sequence of CD19-CD3-GITR TsAb_D
      dimer

<400> SEQUENCE: 73

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255
```

-continued

```
Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Gln Val Thr Leu Lys Glu Ser Gly Pro Gly Ile Leu Lys
            580                 585                 590

Pro Ser Gln Thr Leu Ser Leu Thr Cys Ser Phe Ser Gly Phe Ser Leu
        595                 600                 605

Ser Thr Ser Gly Met Gly Val Gly Trp Ile Arg Gln Pro Ser Gly Lys
    610                 615                 620

Gly Leu Glu Trp Leu Ala His Ile Trp Trp Asp Asp Asp Lys Tyr Tyr
625                 630                 635                 640

Asn Pro Ser Leu Lys Ser Gln Leu Thr Ile Ser Lys Asp Thr Ser Arg
                645                 650                 655

Asn Gln Val Phe Leu Lys Ile Thr Ser Val Asp Thr Ala Asp Ala Ala
            660                 665                 670

Thr Tyr Tyr Cys Ala Arg Thr Arg Arg Tyr Phe Pro Phe Ala Tyr Trp
```

-continued

```
        675                 680                 685

Gly Gln Gly Thr Leu Val Thr Val Ser Ser Gly Gly Gly Gly Ser Gly
    690                 695                 700

Gly Gly Gly Ser Gly Gly Gly Gly Ser Asp Ile Val Met Thr Gln Ser
705                 710                 715                 720

Gln Lys Phe Met Ser Thr Ser Val Gly Asp Arg Val Ser Val Thr Cys
                725                 730                 735

Lys Ala Ser Gln Asn Val Gly Thr Asn Val Ala Trp Tyr Gln Gln Lys
            740                 745                 750

Pro Gly Gln Ser Pro Lys Ala Leu Ile Tyr Ser Ala Ser Tyr Arg Tyr
        755                 760                 765

Ser Gly Val Pro Asp Arg Phe Thr Gly Ser Gly Ser Gly Thr Asp Phe
    770                 775                 780

Thr Leu Thr Ile Asn Asn Val His Ser Glu Asp Leu Ala Glu Tyr Phe
785                 790                 795                 800

Cys Gln Gln Tyr Asn Thr Asp Pro Leu Thr Phe Gly Ala Gly Thr Lys
                805                 810                 815

Leu Glu Ile Lys
            820


<210> SEQ ID NO 74
<211> LENGTH: 2460
<212> TYPE: DNA
<213> ORGANISM: Artificial
<220> FEATURE:
<223> OTHER INFORMATION: The nucleotide sequence of CD19-CD3-GITR TsAb_D
      dimer

<400> SEQUENCE: 74

gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180

ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggtggcggag ggtccgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200
```

gccatcatga gcgccagccc cggcgagaag gtgaccatga cctgccgcgc cagcagcagc 1260
gtgagctaca tgaactggta ccagcagaag agcggcacca gccccaagcg ctggatctac 1320
gacaccagca aggtggccag cggcgtgccc taccgcttca gcggcagcgg cagcggcacc 1380
agctacagcc tgaccatcag cagcatggag gccgaggacg ccgccaccta ctactgccag 1440
cagtggagca gcaacccccct gaccttcggc gccggcacca agctggagct gaaggccagc 1500
aagagcaaga aggagatctt ccgctggccc gagagcccca aggcccaggc cagcagcgtg 1560
cccaccgccc agccccaggc cgagggcagc ctggccaagg ccaccaccgc ccccgccacc 1620
acccgcaaca ccggccgcgg cggcgaggag aagaagaagg agaaggagaa ggaggagcag 1680
gaggagcgcg agaccaagac ccccgagtgc cccagccaca cccagcccct gggcgtgcag 1740
gtgaccctga aggagagcgg ccccggcatc ctgaagccca gccagaccct gagcctgacc 1800
tgcagcttca gcggcttcag cctgagcacc agcggcatgg gcgtgggctg gatccgccag 1860
cccagcggca agggcctgga gtggctggcc cacatctggt gggacgacga caagtactac 1920
aaccccagcc tgaagagcca gctgaccatc agcaaggaca ccagccgcaa ccaggtgttc 1980
ctgaagatca ccagcgtgga caccgccgac gccgccacct actactgcgc ccgcacccgc 2040
cgctacttcc ccttcgccta ctggggccag ggcaccctgg tgaccgtgag cagcggcggc 2100
ggcggcagcg gcggcggcgg cagcggcggc ggcggcagcg acatcgtgat gacccagagc 2160
cagaagttca tgagcaccag cgtgggcgac cgcgtgagcg tgacctgcaa ggccagccag 2220
aacgtgggca ccaacgtggc ctggtaccag cagaagcccg gccagagccc caaggccctg 2280
atctacagcg ccagctaccg ctacagcggc gtgcccgacc gcttcaccgg cagcggcagc 2340
ggcaccgact tcaccctgac catcaacaac gtgcacagcg aggacctggc cgagtacttc 2400
tgccagcagt acaacaccga cccccctgacc ttcggcgccg gcaccaagct ggagatcaag 2460

<210> SEQ ID NO 75
<211> LENGTH: 752
<212> TYPE: PRT
<213> ORGANISM: Artificial
<220> FEATURE:
<223> OTHER INFORMATION: The amino acid sequence of CD19-CD3-CD40L
      TsAb_M monomer

<400> SEQUENCE: 75

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val

```
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Glu Val Gln Leu Leu Glu Ser Gly Gly Gly Leu Val Gln Pro Gly
        515                 520                 525

Gly Ser Leu Arg Leu Ser Cys Ala Ala Ser Gly Phe Thr Phe Ser Ser
    530                 535                 540

Tyr Ala Met Ser Trp Val Arg Gln Ala Pro Gly Lys Gly Leu Glu Trp
545                 550                 555                 560
```

```
Val Ser Ala Ile Ser Gly Ser Gly Gly Ser Thr Tyr Tyr Ala Asp Ser
                565                 570                 575

Val Lys Gly Arg Phe Thr Ile Ser Arg Asp Asn Ser Lys Asn Thr Leu
            580                 585                 590

Tyr Leu Gln Met Asn Ser Leu Arg Ala Glu Asp Thr Ala Val Tyr Tyr
        595                 600                 605

Cys Ala Lys Ser Tyr Gly Ala Phe Asp Tyr Trp Gly Gln Gly Thr Leu
    610                 615                 620

Val Thr Val Ser Ser Gly Gly Gly Gly Ser Gly Gly Gly Gly Ser Gly
625                 630                 635                 640

Gly Gly Gly Ser Asp Ile Gln Met Thr Gln Ser Pro Ser Ser Leu Ser
                645                 650                 655

Ala Ser Val Gly Asp Arg Val Thr Ile Thr Cys Arg Ala Ser Gln Ser
            660                 665                 670

Ile Ser Ser Tyr Leu Asn Trp Tyr Gln Gln Lys Pro Gly Lys Ala Pro
        675                 680                 685

Lys Leu Leu Ile Tyr Ala Ala Ser Ser Leu Gln Ser Gly Val Pro Ser
    690                 695                 700

Arg Phe Ser Gly Ser Gly Ser Gly Thr Asp Phe Thr Leu Thr Ile Ser
705                 710                 715                 720

Ser Leu Gln Pro Glu Asp Phe Ala Thr Tyr Tyr Cys Gln Gln Ser Tyr
                725                 730                 735

Ser Thr Pro Asn Thr Phe Gly Gln Gly Thr Lys Val Glu Ile Lys Arg
            740                 745                 750
```

<210> SEQ ID NO 76
<211> LENGTH: 2256
<212> TYPE: DNA
<213> ORGANISM: Artificial
<220> FEATURE:
<223> OTHER INFORMATION: The nucleotide sequence of CD19-CD3-CD40L
      TsAb_M monomer

<400> SEQUENCE: 76

```
gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600

agcagcagca ccgcctacat gcagctgagc agcctggcca gcgaggacag cgccgtgtac     660

ttctgcgccc gccgcgagac caccaccgtg ggccgctact actacgccat ggactactgg     720

ggccagggca ccaccgtgac cgtgagcagc ggtggcggag ggtccgacat caagctgcag     780

cagagcggcg ccgagctggc ccgccccggc gccagcgtga agatgagctg caagaccagc     840

ggctacacct tcacccgcta caccatgcac tgggtgaagc agcgccccgg ccagggcctg     900

gagtggatcg gctacatcaa ccccagccgc ggctacacca actacaacca gaagttcaag     960
```

```
gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaacccccct gaccttcggc gccggcacca agctggagct gaagggaggc   1500

ggaggttccg gcggtggggg atcgggggt ggagggagtg aggtgcagct gctggagagc   1560

ggcggcggcc tggtgcagcc cggcggcagc ctgcgcctga gctgcgccgc cagcggcttc   1620

accttcagca gctacgccat gagctgggtg cgccaggccc ccggcaaggg cctggagtgg   1680

gtgagcgcca tcagcggcag cggcggcagc acctactacg ccgacagcgt gaagggccgc   1740

ttcaccatca gccgcgacaa cagcaagaac accctgtacc tgcagatgaa cagcctgcgc   1800

gccgaggaca ccgccgtgta ctactgcgcc aagagctacg gcgccttcga ctactggggc   1860

cagggcaccc tggtgaccgt gagcagcggc ggcggcggca gcggcggcgg cggcagcggc   1920

ggcggcggca gcgacatcca gatgacccag agccccagca gcctgagcgc cagcgtgggc   1980

gaccgcgtga ccatcacctg ccgcgccagc cagagcatca gcagctacct gaactggtac   2040

cagcagaagc ccggcaaggc ccccaagctg ctgatctacg ccgccagcag cctgcagagc   2100

ggcgtgccca gccgcttcag cggcagcggc agcggcaccg acttcaccct gaccatcagc   2160

agcctgcagc ccgaggactt cgccacctac tactgccagc agagctacag cacccccaac   2220

accttcggcc agggcaccaa ggtggagatc aagcgc                             2256
```

<210> SEQ ID NO 77
<211> LENGTH: 818
<212> TYPE: PRT
<213> ORGANISM: Artificial
<220> FEATURE:
<223> OTHER INFORMATION: The amino acid sequence of CD19-CD3-CD40L TsAb_D dimer

<400> SEQUENCE: 77

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125
```

```
Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540
```

```
Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Glu Val Gln Leu Leu Glu Ser Gly Gly Gly Leu Val Gln
            580                 585                 590

Pro Gly Gly Ser Leu Arg Leu Ser Cys Ala Ala Ser Gly Phe Thr Phe
        595                 600                 605

Ser Ser Tyr Ala Met Ser Trp Val Arg Gln Ala Pro Gly Lys Gly Leu
    610                 615                 620

Glu Trp Val Ser Ala Ile Ser Gly Ser Gly Gly Ser Thr Tyr Tyr Ala
625                 630                 635                 640

Asp Ser Val Lys Gly Arg Phe Thr Ile Ser Arg Asp Asn Ser Lys Asn
                645                 650                 655

Thr Leu Tyr Leu Gln Met Asn Ser Leu Arg Ala Glu Asp Thr Ala Val
            660                 665                 670

Tyr Tyr Cys Ala Lys Ser Tyr Gly Ala Phe Asp Tyr Trp Gly Gln Gly
        675                 680                 685

Thr Leu Val Thr Val Ser Ser Gly Gly Gly Gly Ser Gly Gly Gly Gly
    690                 695                 700

Ser Gly Gly Gly Gly Ser Asp Ile Gln Met Thr Gln Ser Pro Ser Ser
705                 710                 715                 720

Leu Ser Ala Ser Val Gly Asp Arg Val Thr Ile Thr Cys Arg Ala Ser
                725                 730                 735

Gln Ser Ile Ser Ser Tyr Leu Asn Trp Tyr Gln Gln Lys Pro Gly Lys
            740                 745                 750

Ala Pro Lys Leu Leu Ile Tyr Ala Ala Ser Ser Leu Gln Ser Gly Val
        755                 760                 765

Pro Ser Arg Phe Ser Gly Ser Gly Ser Gly Thr Asp Phe Thr Leu Thr
    770                 775                 780

Ile Ser Ser Leu Gln Pro Glu Asp Phe Ala Thr Tyr Tyr Cys Gln Gln
785                 790                 795                 800

Ser Tyr Ser Thr Pro Asn Thr Phe Gly Gln Gly Thr Lys Val Glu Ile
                805                 810                 815

Lys Arg
```

<210> SEQ ID NO 78
<211> LENGTH: 2454
<212> TYPE: DNA
<213> ORGANISM: Artificial
<220> FEATURE:
<223> OTHER INFORMATION: The nucleotide sequence of CD19-CD3-CD40L TsAb_D dimer

<400> SEQUENCE: 78

```
gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480
```

-continued

```
aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggtggcggag ggtccgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaacccccct gaccttcggc gccggcacca agctggagct gaaggccagc   1500

aagagcaaga aggagatctt ccgctggccc gagagcccca aggcccaggc cagcagcgtg   1560

cccaccgccc agccccaggc cgagggcagc ctggccaagg ccaccaccgc ccccgccacc   1620

acccgcaaca ccggccgcgg cggcgaggag aagaagaagg agaaggagaa ggaggagcag   1680

gaggagcgcg agaccaagac ccccgagtgc cccagccaca cccagcccct gggcgtggag   1740

gtgcagctgc tggagagcgg cggcggcctg gtgcagcccg gcggcagcct gcgcctgagc   1800

tgcgccgcca gcggcttcac cttcagcagc tacgccatga gctgggtgcg ccaggccccc   1860

ggcaagggcc tggagtgggt gagcgccatc agcggcagcg gcggcagcac ctactacgcc   1920

gacagcgtga agggccgctt caccatcagc cgcgacaaca gcaagaacac cctgtacctg   1980

cagatgaaca gcctgcgcgc cgaggacacc gccgtgtact actgcgccaa gagctacggc   2040

gccttcgact actggggcca gggcaccctg gtgaccgtga gcagcggcgg cggcggcagc   2100

ggcggcggcg gcagcggcgg cggcggcagc gacatccaga tgacccagag ccccagcagc   2160

ctgagcgcca gcgtgggcga ccgcgtgacc atcacctgcc gcgccagcca gagcatcagc   2220

agctacctga actggtacca gcagaagccc ggcaaggccc ccaagctgct gatctacgcc   2280

gccagcagcc tgcagagcgg cgtgcccagc cgcttcagcg gcagcggcag cggcaccgac   2340

ttcaccctga ccatcagcag cctgcagccc gaggacttcg ccacctacta ctgccagcag   2400

agctacagca cccccaacac cttcggccag ggcaccaagg tggagatcaa gcgc          2454
```

<210> SEQ ID NO 79
<211> LENGTH: 754
<212> TYPE: PRT
<213> ORGANISM: Artificial
<220> FEATURE:
<223> OTHER INFORMATION: The amino acid sequence of CD19-CD3-CD27
      TsAb_M monomer

<400> SEQUENCE: 79

Asp Ile Gln Leu Thr Gln Ser Pro Ala Ser Leu Ala Val Ser Leu Gly

-continued

```
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430
```

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Gln Val Gln Leu Val Glu Ser Gly Gly Gly Val Val Gln Pro Gly
        515                 520                 525

Arg Ser Leu Arg Leu Ser Cys Ala Ala Ser Gly Phe Thr Phe Ser Ser
    530                 535                 540

Tyr Asp Met His Trp Val Arg Gln Ala Pro Gly Lys Gly Leu Glu Trp
545                 550                 555                 560

Val Ala Val Ile Trp Tyr Asp Gly Ser Asn Lys Tyr Tyr Ala Asp Ser
                565                 570                 575

Val Lys Gly Arg Phe Thr Ile Ser Arg Asp Asn Ser Lys Asn Thr Leu
            580                 585                 590

Tyr Leu Gln Met Asn Ser Leu Arg Ala Glu Asp Thr Ala Val Tyr Tyr
        595                 600                 605

Cys Ala Arg Gly Ser Gly Asn Trp Gly Phe Phe Asp Tyr Trp Gly Gln
    610                 615                 620

Gly Thr Leu Val Thr Val Ser Ser Gly Gly Gly Gly Ser Gly Gly Gly
625                 630                 635                 640

Gly Ser Gly Gly Gly Gly Ser Asp Ile Gln Met Thr Gln Ser Pro Ser
                645                 650                 655

Ser Leu Ser Ala Ser Val Gly Asp Arg Val Thr Ile Thr Cys Arg Ala
            660                 665                 670

Ser Gln Gly Ile Ser Arg Trp Leu Ala Trp Tyr Gln Gln Lys Pro Glu
        675                 680                 685

Lys Ala Pro Lys Ser Leu Ile Tyr Ala Ala Ser Ser Leu Gln Ser Gly
    690                 695                 700

Val Pro Ser Arg Phe Ser Gly Ser Gly Ser Gly Thr Asp Phe Thr Leu
705                 710                 715                 720

Thr Ile Ser Ser Leu Gln Pro Glu Asp Phe Ala Thr Tyr Tyr Cys Gln
                725                 730                 735

Gln Tyr Asn Thr Tyr Pro Arg Thr Phe Gly Gln Gly Thr Lys Val Glu
            740                 745                 750

Ile Lys

<210> SEQ ID NO 80
<211> LENGTH: 2262
<212> TYPE: DNA
<213> ORGANISM: Artificial
<220> FEATURE:
<223> OTHER INFORMATION: The nucleotide sequence of CD19-CD3-CD27 TsAb_M monomer

<400> SEQUENCE: 80
gacatccagc tgacccagag ccccgccagc ctggccgtga gcctgggcca gcgcgccacc 60
atcagctgca aggccagcca gagcgtggac tacgacggcg acagctacct gaactggtac 120
cagcagatcc ccggccagcc ccccaagctg ctgatctacg acgccagcaa cctggtgagc 180
ggcatccccc cccgcttcag cggcagcggc agcggcaccg acttcaccct gaacatccac 240
cccgtggaga aggtggacgc cgccacctac cactgccagc agagcaccga ggacccctgg 300
accttcggcg gcggcaccaa gctggagatc aagggcggcg gcggcagcgg cggcggcggc 360
agcggcggcg gcggcagcca ggtgcagctg cagcagagcg gcgccgagct ggtgcgcccc 420
ggcagcagcg tgaagatcag ctgcaaggcc agcggctacg ccttcagcag ctactggatg 480
aactgggtga agcagcgccc cggccagggc ctggagtgga tcggccagat ctggcccggc 540
gacggcgaca ccaactacaa cggcaagttc aagggcaagg ccaccctgac cgccgacgag 600
agcagcagca ccgcctacat gcagctgagc agcctggcca gcgaggacag cgccgtgtac 660
ttctgcgccc gccgcgagac caccaccgtg ggccgctact actacgccat ggactactgg 720
ggccagggca ccaccgtgac cgtgagcagc ggtggcggag ggtccgacat caagctgcag 780
cagagcggcg ccgagctggc ccgccccggc gccagcgtga agatgagctg caagaccagc 840
ggctacacct tcacccgcta caccatgcac tgggtgaagc agcgccccgg ccagggcctg 900
gagtggatcg gctacatcaa ccccagccgc ggctacacca actacaacca gaagttcaag 960
gacaaggcca ccctgaccac cgacaagagc agcagcaccg cctacatgca gctgagcagc 1020
ctgaccagcg aggacagcgc cgtgtactac tgcgcccgct actacgacga ccactactgc 1080
ctggactact ggggccaggg caccaccctg accgtgagca gcgtggaggg cggcagcggc 1140
ggcagcggcg gcagcggcgg cagcggcggc gtggacgaca tccagctgac ccagagcccc 1200
gccatcatga gcgccagccc cggcgagaag gtgaccatga cctgccgcgc cagcagcagc 1260
gtgagctaca tgaactggta ccagcagaag agcggcacca gccccaagcg ctggatctac 1320
gacaccagca aggtggccag cggcgtgccc taccgcttca gcggcagcgg cagcggcacc 1380
agctacagcc tgaccatcag cagcatggag gccgaggacg ccgccaccta ctactgccag 1440
cagtggagca gcaacccct gaccttcggc gccggcacca agctggagct gaagggaggc 1500
ggaggttccg gcggtggggg atcgggggt ggagggagtc aggtgcagct ggtggagagc 1560
ggcggcggcg tggtgcagcc cggccgcagc ctgcgcctga gctgcgccgc cagcggcttc 1620
accttcagca gctacgacat gcactgggtg cgccaggccc ccggcaaggg cctggagtgg 1680
gtggccgtga tctggtacga cggcagcaac aagtactacg ccgacagcgt gaagggccgc 1740
ttcaccatca gccgcgacaa cagcaagaac accctgtacc tgcagatgaa cagcctgcgc 1800
gccgaggaca ccgccgtgta ctactgcgcc cgcggcagcg gcaactgggg cttcttcgac 1860
tactggggcc agggcaccct ggtgaccgtg agcagcggcg gcggcggcag cggcggcggc 1920
ggcagcggcg gcggcggcag cgacatccag atgacccaga gccccagcag cctgagcgcc 1980
agcgtgggcg accgcgtgac catcacctgc cgcgccagcc agggcatcag ccgctggctg 2040
gcctggtacc agcagaagcc cgagaaggcc cccaagagcc tgatctacgc cgccagcagc 2100
ctgcagagcg gcgtgcccag ccgcttcagc ggcagcggca gcggcaccga cttcaccctg 2160
accatcagca gcctgcagcc cgaggacttc gccacctact actgccagca gtacaacacc 2220
taccccgca ccttcggcca gggcaccaag gtggagatca ag 2262

<210> SEQ ID NO 81
<211> LENGTH: 820
<212> TYPE: PRT
<213> ORGANISM: Artificial
<220> FEATURE:
<223> OTHER INFORMATION: The amino acid sequence of CD19-CD3-CD27 TsAb_D
dimer

<400> SEQUENCE: 81

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
```

```
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Gln Val Gln Leu Val Glu Ser Gly Gly Gly Val Val Gln
            580                 585                 590

Pro Gly Arg Ser Leu Arg Leu Ser Cys Ala Ala Ser Gly Phe Thr Phe
        595                 600                 605

Ser Ser Tyr Asp Met His Trp Val Arg Gln Ala Pro Gly Lys Gly Leu
    610                 615                 620

Glu Trp Val Ala Val Ile Trp Tyr Asp Gly Ser Asn Lys Tyr Tyr Ala
625                 630                 635                 640

Asp Ser Val Lys Gly Arg Phe Thr Ile Ser Arg Asp Asn Ser Lys Asn
                645                 650                 655

Thr Leu Tyr Leu Gln Met Asn Ser Leu Arg Ala Glu Asp Thr Ala Val
            660                 665                 670

Tyr Tyr Cys Ala Arg Gly Ser Gly Asn Trp Gly Phe Phe Asp Tyr Trp
        675                 680                 685

Gly Gln Gly Thr Leu Val Thr Val Ser Ser Gly Gly Gly Gly Ser Gly
    690                 695                 700

Gly Gly Gly Ser Gly Gly Gly Gly Ser Asp Ile Gln Met Thr Gln Ser
705                 710                 715                 720

Pro Ser Ser Leu Ser Ala Ser Val Gly Asp Arg Val Thr Ile Thr Cys
                725                 730                 735

Arg Ala Ser Gln Gly Ile Ser Arg Trp Leu Ala Trp Tyr Gln Gln Lys
            740                 745                 750

Pro Glu Lys Ala Pro Lys Ser Leu Ile Tyr Ala Ala Ser Ser Leu Gln
        755                 760                 765

Ser Gly Val Pro Ser Arg Phe Ser Gly Ser Gly Ser Gly Thr Asp Phe
    770                 775                 780

Thr Leu Thr Ile Ser Ser Leu Gln Pro Glu Asp Phe Ala Thr Tyr Tyr
785                 790                 795                 800

Cys Gln Gln Tyr Asn Thr Tyr Pro Arg Thr Phe Gly Gln Gly Thr Lys
                805                 810                 815

Val Glu Ile Lys
            820
```

<210> SEQ ID NO 82
<211> LENGTH: 2460
<212> TYPE: DNA
<213> ORGANISM: Artificial
<220> FEATURE:
<223> OTHER INFORMATION: The nucleotide sequence of CD19-CD3-CD27 TsAb_D dimer

<400> SEQUENCE: 82

```
gacatccagc tgacccagag ccccgccagc ctggccgtga gcctgggcca gcgcgccacc     60
atcagctgca aggccagcca gagcgtggac tacgacggcg acagctacct gaactggtac    120
cagcagatcc ccggccagcc ccccaagctg ctgatctacg acgccagcaa cctggtgagc    180
ggcatccccc cccgcttcag cggcagcggc agcggcaccg acttcaccct gaacatccac    240
cccgtggaga aggtggacgc cgccacctac cactgccagc agagcaccga ggacccctgg    300
accttcggcg gcggcaccaa gctggagatc aagggcggcg gcggcagcgg cggcggcggc    360
agcggcggcg gcggcagcca ggtgcagctg cagcagagcg gcgccgagct ggtgcgcccc    420
ggcagcagcg tgaagatcag ctgcaaggcc agcggctacg ccttcagcag ctactggatg    480
aactgggtga agcagcgccc cggccagggc ctggagtgga tcggccagat ctggcccggc    540
gacggcgaca ccaactacaa cggcaagttc aagggcaagg ccaccctgac cgccgacgag    600
agcagcagca ccgcctacat gcagctgagc agcctggcca gcgaggacag cgccgtgtac    660
ttctgcgccc gccgcgagac caccaccgtg ggccgctact actacgccat ggactactgg    720
ggccagggca ccaccgtgac cgtgagcagc ggtggcggag ggtccgacat caagctgcag    780
cagagcggcg ccgagctggc ccgccccggc gccagcgtga agatgagctg caagaccagc    840
ggctacacct tcacccgcta caccatgcac tgggtgaagc agcgccccgg ccagggcctg    900
gagtggatcg gctacatcaa ccccagccgc ggctacacca actacaacca gaagttcaag    960
gacaaggcca ccctgaccac cgacaagagc agcagcaccg cctacatgca gctgagcagc   1020
ctgaccagcg aggacagcgc cgtgtactac tgcgcccgct actacgacga ccactactgc   1080
ctggactact ggggccaggg caccaccctg accgtgagca gcgtggaggg cggcagcggc   1140
ggcagcggcg gcagcggcgg cagcggcggc gtggacgaca tccagctgac ccagagcccc   1200
gccatcatga gcgccagccc cggcgagaag gtgaccatga cctgccgcgc cagcagcagc   1260
gtgagctaca tgaactggta ccagcagaag agcggcacca gccccaagcg ctggatctac   1320
gacaccagca aggtggccag cggcgtgccc taccgcttca gcggcagcgg cagcggcacc   1380
agctacagcc tgaccatcag cagcatggag gccgaggacg ccgccaccta ctactgccag   1440
cagtggagca gcaacccccct gaccttcggc gccggcacca agctggagct gaaggccagc   1500
aagagcaaga aggagatctt ccgctggccc gagagcccca aggcccaggc cagcagcgtg   1560
cccaccgccc agccccaggc cgagggcagc ctggccaagg ccaccaccgc ccccgccacc   1620
acccgcaaca ccggccgcgg cggcgaggag aagaagaagg agaaggagaa ggaggagcag   1680
gaggagcgcg agaccaagac ccccgagtgc cccagccaca cccagcccct gggcgtgcag   1740
gtgcagctgg tggagagcgg cggcggcgtg gtgcagcccg gccgcagcct gcgcctgagc   1800
tgcgccgcca gcggcttcac cttcagcagc tacgacatgc actgggtgcg ccaggccccc   1860
ggcaagggcc tggagtgggt ggccgtgatc tggtacgacg gcagcaacaa gtactacgcc   1920
gacagcgtga agggccgctt caccatcagc cgcgacaaca gcaagaacac cctgtacctg   1980
cagatgaaca gcctgcgcgc cgaggacacc gccgtgtact actgcgcccg cggcagcggc   2040
```

```
aactggggct tcttcgacta ctggggccag ggcaccctgg tgaccgtgag cagcggcggc   2100

ggcggcagcg gcggcggcgg cagcggcggc ggcggcagcg acatccagat gacccagagc   2160

cccagcagcc tgagcgccag cgtgggcgac cgcgtgacca tcacctgccg cgccagccag   2220

ggcatcagcc gctggctggc ctggtaccag cagaagcccg agaaggcccc caagagcctg   2280

atctacgccg ccagcagcct gcagagcggc gtgcccagcc gcttcagcgg cagcggcagc   2340

ggcaccgact tcaccctgac catcagcagc ctgcagcccg aggacttcgc cacctactac   2400

tgccagcagt acaacaccta cccccgcacc ttcggccagg gcaccaaggt ggagatcaag   2460


<210> SEQ ID NO 83
<211> LENGTH: 250
<212> TYPE: PRT
<213> ORGANISM: Artificial
<220> FEATURE:
<223> OTHER INFORMATION: The amino acid sequence of anti-CD19 scFv

<400> SEQUENCE: 83

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser
                245                 250


<210> SEQ ID NO 84
<211> LENGTH: 124
<212> TYPE: PRT
<213> ORGANISM: Artificial
<220> FEATURE:
```

<223> OTHER INFORMATION: The amino acid sequence of anti-CD19 scFv heavy chain variable region

<400> SEQUENCE: 84

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 85
<211> LENGTH: 111
<212> TYPE: PRT
<213> ORGANISM: Artificial
<220> FEATURE:
<223> OTHER INFORMATION: The amino acid sequence of anti-CD19 scFv light chain variable region

<400> SEQUENCE: 85

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 86
<211> LENGTH: 243
<212> TYPE: PRT
<213> ORGANISM: Artificial
<220> FEATURE:
<223> OTHER INFORMATION: The amino acid sequence of anti-CD3 scFv

<400> SEQUENCE: 86

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

```
Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys


<210> SEQ ID NO 87
<211> LENGTH: 119
<212> TYPE: PRT
<213> ORGANISM: Artificial
<220> FEATURE:
<223> OTHER INFORMATION: The amino acid sequence of anti-CD3 scFv heavy
      chain variable region

<400> SEQUENCE: 87

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115


<210> SEQ ID NO 88
<211> LENGTH: 106
<212> TYPE: PRT
<213> ORGANISM: Artificial
```

<220> FEATURE:
<223> OTHER INFORMATION: The amino acid sequence of anti-CD3 scFv light chain variable region

<400> SEQUENCE: 88

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105
```

<210> SEQ ID NO 89
<211> LENGTH: 246
<212> TYPE: PRT
<213> ORGANISM: Artificial
<220> FEATURE:
<223> OTHER INFORMATION: The amino acid sequence of anti-4-1BB scFv

<400> SEQUENCE: 89

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Gly Gly Gly Gly Ser Gly Gly
        115                 120                 125

Gly Gly Ser Gly Gly Gly Gly Ser Glu Ile Val Leu Thr Gln Ser Pro
    130                 135                 140

Ala Thr Leu Ser Leu Ser Pro Gly Glu Arg Ala Thr Leu Ser Cys Arg
145                 150                 155                 160

Ala Ser Gln Ser Val Ser Ser Tyr Leu Ala Trp Tyr Gln Gln Lys Pro
                165                 170                 175

Gly Gln Ala Pro Arg Leu Leu Ile Tyr Asp Ala Ser Asn Arg Ala Thr
            180                 185                 190

Gly Ile Pro Ala Arg Phe Ser Gly Ser Gly Ser Gly Thr Asp Phe Thr
        195                 200                 205

Leu Thr Ile Ser Ser Leu Glu Pro Glu Asp Phe Ala Val Tyr Tyr Cys
    210                 215                 220
```

```
Gln Gln Arg Ser Asn Trp Pro Pro Ala Leu Thr Phe Cys Gly Gly Thr
225                 230                 235                 240

Lys Val Glu Ile Lys Arg
                245


<210> SEQ ID NO 90
<211> LENGTH: 121
<212> TYPE: PRT
<213> ORGANISM: Artificial
<220> FEATURE:
<223> OTHER INFORMATION: The amino acid sequence of anti-4-1BB scFv
      heavy chain variable region

<400> SEQUENCE: 90

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
        115                 120


<210> SEQ ID NO 91
<211> LENGTH: 110
<212> TYPE: PRT
<213> ORGANISM: Artificial
<220> FEATURE:
<223> OTHER INFORMATION: The amino acid sequence of anti-4-1BB scFv
      light chain variable region

<400> SEQUENCE: 91

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Cys Gly Gly Thr Lys Val Glu Ile Lys Arg
            100                 105                 110


<210> SEQ ID NO 92
<211> LENGTH: 247
<212> TYPE: PRT
<213> ORGANISM: Artificial
<220> FEATURE:
```

```
<223> OTHER INFORMATION: The amino acid sequence of ICOS scFv

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro His Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Thr Tyr Tyr Tyr Asp Ser Ser Gly Tyr Tyr His Asp Ala Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Asp Ile Gln Met
    130                 135                 140

Thr Gln Ser Pro Ser Ser Val Ser Ala Ser Val Gly Asp Arg Val Thr
145                 150                 155                 160

Ile Thr Cys Arg Ala Ser Gln Gly Ile Ser Arg Leu Leu Ala Trp Tyr
                165                 170                 175

Gln Gln Lys Pro Gly Lys Ala Pro Lys Leu Leu Ile Tyr Val Ala Ser
            180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ala Asn Ser Phe Pro Trp Thr Phe Gly Gln
225                 230                 235                 240

Gly Thr Lys Val Glu Ile Lys
                245


<210> SEQ ID NO 93
<211> LENGTH: 125
<212> TYPE: PRT
<213> ORGANISM: Artificial
<220> FEATURE:
<223> OTHER INFORMATION: The amino acid sequence of ICOS scFv heavy
      chain variable region

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro His Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
```

-continued 85 90 95

Ala Arg Thr Tyr Tyr Tyr Asp Ser Ser Gly Tyr Tyr His Asp Ala Phe
100 105 110

Asp Ile Trp Gly Gln Gly Thr Met Val Thr Val Ser Ser
115 120 125

<210> SEQ ID NO 94
<211> LENGTH: 107
<212> TYPE: PRT
<213> ORGANISM: Artificial
<220> FEATURE:
<223> OTHER INFORMATION: The amino acid sequence of ICOS scFv light chain variable region

<400> SEQUENCE: 94

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Arg Leu
20 25 30

Leu Ala Trp Tyr Gln Gln Lys Pro Gly Lys Ala Pro Lys Leu Leu Ile
35 40 45

Tyr Val Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asn Ser Phe Pro Trp
85 90 95

Thr Phe Gly Gln Gly Thr Lys Val Glu Ile Lys
100 105

<210> SEQ ID NO 95
<211> LENGTH: 242
<212> TYPE: PRT
<213> ORGANISM: Artificial
<220> FEATURE:
<223> OTHER INFORMATION: The amino acid sequence of OX40 scFv

<400> SEQUENCE: 95

Gln Leu Val Glu Ser Gly Gly Gly Leu Val Gln Pro Gly Gly Ser Leu
1 5 10 15

Arg Leu Ser Cys Ala Ala Ser Gly Phe Thr Phe Ser Ser Tyr Ser Met
20 25 30

Asn Trp Val Arg Gln Ala Pro Gly Lys Gly Leu Glu Trp Val Ser Tyr
35 40 45

Ile Ser Ser Ser Ser Ser Thr Ile Tyr Tyr Ala Asp Ser Val Lys Gly
50 55 60

Arg Phe Thr Ile Ser Arg Asp Asn Ala Lys Asn Ser Leu Tyr Leu Gln
65 70 75 80

Met Asn Ser Leu Arg Asp Glu Asp Thr Ala Val Tyr Tyr Cys Ala Arg
85 90 95

Gly Val Tyr His Asn Gly Trp Ser Phe Phe Asp Tyr Trp Gly Gln Gly
100 105 110

Thr Leu Leu Thr Val Ser Ser Gly Gly Gly Gly Ser Gly Gly Gly Gly
115 120 125

Ser Gly Gly Gly Gly Ser Asp Ile Gln Met Thr Gln Ser Pro Ser Ser
130 135 140

Leu Ser Ala Ser Val Gly Asn Arg Val Thr Ile Thr Cys Arg Ala Ser
145 150 155 160

```
Gln Asp Ile Ser Ser Trp Leu Ala Trp Tyr Gln Gln Lys Pro Glu Lys
                165                 170                 175

Ala Pro Lys Ser Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Tyr Asn Ser Tyr Pro Leu Thr Phe Gly Gln Gly Thr Arg Leu Glu Ile
225                 230                 235                 240

Lys Arg


<210> SEQ ID NO 96
<211> LENGTH: 119
<212> TYPE: PRT
<213> ORGANISM: Artificial
<220> FEATURE:
<223> OTHER INFORMATION: The amino acid sequence of OX40 scFv heavy
      chain variable region

<400> SEQUENCE: 96

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ser Met
            20                  25                  30

Asn Trp Val Arg Gln Ala Pro Gly Lys Gly Leu Glu Trp Val Ser Tyr
        35                  40                  45

Ile Ser Ser Ser Ser Ser Thr Ile Tyr Tyr Ala Asp Ser Val Lys Gly
    50                  55                  60

Arg Phe Thr Ile Ser Arg Asp Asn Ala Lys Asn Ser Leu Tyr Leu Gln
65                  70                  75                  80

Met Asn Ser Leu Arg Asp Glu Asp Thr Ala Val Tyr Tyr Cys Ala Arg
                85                  90                  95

Gly Val Tyr His Asn Gly Trp Ser Phe Phe Asp Tyr Trp Gly Gln Gly
            100                 105                 110

Thr Leu Leu Thr Val Ser Ser
        115


<210> SEQ ID NO 97
<211> LENGTH: 108
<212> TYPE: PRT
<213> ORGANISM: Artificial
<220> FEATURE:
<223> OTHER INFORMATION: The amino acid sequence of OX40 scFv light
      chain variable region

<400> SEQUENCE: 97

Asp Ile Gln Met Thr Gln Ser Pro Ser Ser Leu Ser Ala Ser Val Gly
1               5                   10                  15

Asn Arg Val Thr Ile Thr Cys Arg Ala Ser Gln Asp Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Asn Ser Tyr Pro Leu
                85                  90                  95

Thr Phe Gly Gln Gly Thr Arg Leu Glu Ile Lys Arg
            100                 105


<210> SEQ ID NO 98
<211> LENGTH: 241
<212> TYPE: PRT
<213> ORGANISM: Artificial
<220> FEATURE:
<223> OTHER INFORMATION: The amino acid sequence of GITR scFv

<400> SEQUENCE: 98

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Ala Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Val Met Thr Gln Ser Gln Lys Phe
    130                 135                 140

Met Ser Thr Ser Val Gly Asp Arg Val Ser Val Thr Cys Lys Ala Ser
145                 150                 155                 160

Gln Asn Val Gly Thr Asn Val Ala Trp Tyr Gln Gln Lys Pro Gly Gln
                165                 170                 175

Ser Pro Lys Ala Leu Ile Tyr Ser Ala Ser Tyr Arg Tyr Ser Gly Val
            180                 185                 190

Pro Asp Arg Phe Thr Gly Ser Gly Ser Gly Thr Asp Phe Thr Leu Thr
        195                 200                 205

Ile Asn Asn Val His Ser Glu Asp Leu Ala Glu Tyr Phe Cys Gln Gln
    210                 215                 220

Tyr Asn Thr Asp Pro Leu Thr Phe Gly Ala Gly Thr Lys Leu Glu Ile
225                 230                 235                 240

Lys


<210> SEQ ID NO 99
<211> LENGTH: 119
<212> TYPE: PRT
<213> ORGANISM: Artificial
<220> FEATURE:
<223> OTHER INFORMATION: The amino acid sequence of GITR scFv heavy
      chain variable region

<400> SEQUENCE: 99

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30
```

```
Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Ala Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser Ser
        115


<210> SEQ ID NO 100
<211> LENGTH: 107
<212> TYPE: PRT
<213> ORGANISM: Artificial
<220> FEATURE:
<223> OTHER INFORMATION: The amino acid sequence of GITR scFv light
      chain variable region

<400> SEQUENCE: 100

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val His Ser
65                  70                  75                  80

Glu Asp Leu Ala Glu Tyr Phe Cys Gln Gln Tyr Asn Thr Asp Pro Leu
                85                  90                  95

Thr Phe Gly Ala Gly Thr Lys Leu Glu Ile Lys
            100                 105


<210> SEQ ID NO 101
<211> LENGTH: 239
<212> TYPE: PRT
<213> ORGANISM: Artificial
<220> FEATURE:
<223> OTHER INFORMATION: The amino acid sequence of CD40L scFv

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Ser Tyr Gly Ala Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Asp Ile Gln Met Thr Gln Ser Pro Ser Ser Leu Ser Ala
    130                 135                 140

Ser Val Gly Asp Arg Val Thr Ile Thr Cys Arg Ala Ser Gln Ser Ile
145                 150                 155                 160

Ser Ser Tyr Leu Asn Trp Tyr Gln Gln Lys Pro Gly Lys Ala Pro Lys
                165                 170                 175

Leu Leu Ile Tyr Ala Ala Ser Ser Leu Gln Ser Gly Val Pro Ser Arg
            180                 185                 190

Phe Ser Gly Ser Gly Ser Gly Thr Asp Phe Thr Leu Thr Ile Ser Ser
        195                 200                 205

Leu Gln Pro Glu Asp Phe Ala Thr Tyr Tyr Cys Gln Gln Ser Tyr Ser
    210                 215                 220

Thr Pro Asn Thr Phe Gly Gln Gly Thr Lys Val Glu Ile Lys Arg
225                 230                 235


<210> SEQ ID NO 102
<211> LENGTH: 116
<212> TYPE: PRT
<213> ORGANISM: Artificial
<220> FEATURE:
<223> OTHER INFORMATION: The amino acid sequence of CD40L scFv heavy
      chain variable region

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser
        115


<210> SEQ ID NO 103
<211> LENGTH: 108
<212> TYPE: PRT
<213> ORGANISM: Artificial
<220> FEATURE:
<223> OTHER INFORMATION: The amino acid sequence of CD40L scFv light
      chain variable region

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

-continued

```
Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg
            100                 105


<210> SEQ ID NO 104
<211> LENGTH: 241
<212> TYPE: PRT
<213> ORGANISM: Artificial
<220> FEATURE:
<223> OTHER INFORMATION: The amino acid sequence of CD27 scFv

<400> SEQUENCE: 104

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Asn Trp Gly Phe Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Gly Ile Ser Arg Trp Leu Ala Trp Tyr Gln Gln Lys Pro Glu Lys
                165                 170                 175

Ala Pro Lys Ser Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Tyr Asn Thr Tyr Pro Arg Thr Phe Gly Gln Gly Thr Lys Val Glu Ile
225                 230                 235                 240

Lys


<210> SEQ ID NO 105
<211> LENGTH: 119
<212> TYPE: PRT
<213> ORGANISM: Artificial
<220> FEATURE:
<223> OTHER INFORMATION: The amino acid sequence of CD27 scFv heavy
```

chain variable region

<400> SEQUENCE: 105

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Asp Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Ser Gly Asn Trp Gly Phe Phe Asp Tyr Trp Gly Gln Gly
100 105 110

Thr Leu Val Thr Val Ser Ser
115

<210> SEQ ID NO 106
<211> LENGTH: 107
<212> TYPE: PRT
<213> ORGANISM: Artificial
<220> FEATURE:
<223> OTHER INFORMATION: The amino acid sequence of CD27 scFv light chain variable region

<400> SEQUENCE: 106

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Arg Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Thr Tyr Pro Arg
85 90 95

Thr Phe Gly Gln Gly Thr Lys Val Glu Ile Lys
100 105

<210> SEQ ID NO 107
<211> LENGTH: 750
<212> TYPE: DNA
<213> ORGANISM: Artificial
<220> FEATURE:
<223> OTHER INFORMATION: The nucleotide sequence of anti-CD19 scFv

<400> SEQUENCE: 107
gacatccagc tgacccagag ccccgccagc ctggccgtga gcctgggcca gcgcgccacc 60
atcagctgca aggccagcca gagcgtggac tacgacggcg acagctacct gaactggtac 120
cagcagatcc ccggccagcc ccccaagctg ctgatctacg acgccagcaa cctggtgagc 180
ggcatccccc cccgcttcag cggcagcggc agcggcaccg acttcaccct gaacatccac 240
cccgtggaga aggtggacgc cgccacctac cactgccagc agagcaccga ggacccctgg 300

-continued

```
accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc                                     750


<210> SEQ ID NO 108
<211> LENGTH: 372
<212> TYPE: DNA
<213> ORGANISM: Artificial
<220> FEATURE:
<223> OTHER INFORMATION: The nucleotide sequence of anti-CD19 scFv heavy
      chain variable region

<400> SEQUENCE: 108

caggtgcagc tgcagcagag cggcgccgag ctggtgcgcc ccggcagcag cgtgaagatc     60

agctgcaagg ccagcggcta cgccttcagc agctactgga tgaactgggt gaagcagcgc    120

cccggccagg gcctggagtg gatcggccag atctggcccg gcgacggcga caccaactac    180

aacggcaagt tcaagggcaa ggccaccctg accgccgacg agagcagcag caccgcctac    240

atgcagctga gcagcctggc cagcgaggac agcgccgtgt acttctgcgc ccgccgcgag    300

accaccaccg tgggccgcta ctactacgcc atggactact ggggccaggg caccaccgtg    360

accgtgagca gc                                                        372


<210> SEQ ID NO 109
<211> LENGTH: 333
<212> TYPE: DNA
<213> ORGANISM: Artificial
<220> FEATURE:
<223> OTHER INFORMATION: The nucleotide sequence of anti-CD19 scFv light
      chain variable region

<400> SEQUENCE: 109

gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180

ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aag                                 333


<210> SEQ ID NO 110
<211> LENGTH: 729
<212> TYPE: DNA
<213> ORGANISM: Artificial
<220> FEATURE:
<223> OTHER INFORMATION: The nucleotide sequence of anti-CD3 scFv

<400> SEQUENCE: 110

gacatcaagc tgcagcagag cggcgccgag ctggcccgcc ccggcgccag cgtgaagatg     60

agctgcaaga ccagcggcta caccttcacc cgctacacca tgcactgggt gaagcagcgc    120
```

cccggccagg gcctggagtg gatcggctac atcaacccca gccgcggcta caccaactac 180
aaccagaagt tcaaggacaa ggccaccctg accaccgaca agagcagcag caccgcctac 240
atgcagctga gcagcctgac cagcgaggac agcgccgtgt actactgcgc ccgctactac 300
gacgaccact actgcctgga ctactggggc cagggcacca ccctgaccgt gagcagcgtg 360
gagggcggca gcggcggcag cggcggcagc ggcggcagcg gcggcgtgga cgacatccag 420
ctgacccaga gccccgccat catgagcgcc agccccggcg agaaggtgac catgacctgc 480
cgcgccagca gcagcgtgag ctacatgaac tggtaccagc agaagagcgg caccagcccc 540
aagcgctgga tctacgacac cagcaaggtg gccagcggcg tgccctaccg cttcagcggc 600
agcggcagcg gcaccagcta cagcctgacc atcagcagca tggaggccga ggacgccgcc 660
acctactact gccagcagtg gagcagcaac cccctgacct tcggcgccgg caccaagctg 720
gagctgaag 729

<210> SEQ ID NO 111
<211> LENGTH: 357
<212> TYPE: DNA
<213> ORGANISM: Artificial
<220> FEATURE:
<223> OTHER INFORMATION: The nucleotide sequence of anti-CD3 scFv heavy chain variable region

<400> SEQUENCE: 111
gacatcaagc tgcagcagag cggcgccgag ctggcccgcc ccggcgccag cgtgaagatg 60
agctgcaaga ccagcggcta caccttcacc cgctacacca tgcactgggt gaagcagcgc 120
cccggccagg gcctggagtg gatcggctac atcaacccca gccgcggcta caccaactac 180
aaccagaagt tcaaggacaa ggccaccctg accaccgaca agagcagcag caccgcctac 240
atgcagctga gcagcctgac cagcgaggac agcgccgtgt actactgcgc ccgctactac 300
gacgaccact actgcctgga ctactggggc cagggcacca ccctgaccgt gagcagc 357

<210> SEQ ID NO 112
<211> LENGTH: 318
<212> TYPE: DNA
<213> ORGANISM: Artificial
<220> FEATURE:
<223> OTHER INFORMATION: The nucleotide sequence of anti-CD3 scFv light chain variable region

<400> SEQUENCE: 112
gacatccagc tgacccagag ccccgccatc atgagcgcca gccccggcga gaaggtgacc 60
atgacctgcc gcgccagcag cagcgtgagc tacatgaact ggtaccagca gaagagcggc 120
accagcccca agcgctggat ctacgacacc agcaaggtgg ccagcggcgt gccctaccgc 180
ttcagcggca gcggcagcgg caccagctac agcctgacca tcagcagcat ggaggccgag 240
gacgccgcca cctactactg ccagcagtgg agcagcaacc ccctgacctt cggcgccggc 300
accaagctgg agctgaag 318

<210> SEQ ID NO 113
<211> LENGTH: 738
<212> TYPE: DNA
<213> ORGANISM: Artificial
<220> FEATURE:
<223> OTHER INFORMATION: The nucleotide sequence of anti-4-1BB scFv

<400> SEQUENCE: 113
caggtgcagc tgcagcagtg gggcgccggc ctgctgaagc ccagcgagac cctgagcctg 60
acctgcgccg tgtacggcgg cagcttcagc ggctactact ggagctggat ccgccagagc 120
cccgagaagg gcctggagtg gatcggcgag atcaaccacg gcggctacgt gacctacaac 180
cccagcctgg agagccgcgt gaccatcagc gtggacacca gcaagaacca gttcagcctg 240
aagctgagca gcgtgaccgc cgccgacacc gccgtgtact actgcgcccg cgactacggc 300
cccggcaact acgactggta cttcgacctg tggggccgcg gcaccctggt gaccgtgagc 360
agcggcggcg gcggcagcgg cggcggcggc agcggcggcg gcggcagcga gatcgtgctg 420
acccagagcc ccgccaccct gagcctgagc cccggcgagc gcgccaccct gagctgccgc 480
gccagccaga gcgtgagcag ctacctggcc tggtaccagc agaagcccgg ccaggccccc 540
cgcctgctga tctacgacgc cagcaaccgc gccaccggca tccccgcccg cttcagcggc 600
agcggcagcg gcaccgactt caccctgacc atcagcagcc tggagcccga ggacttcgcc 660
gtgtactact gccagcagcg cagcaactgg ccccccgccc tgaccttctg cggcggcacc 720
aaggtggaga tcaagcgc 738

<210> SEQ ID NO 114
<211> LENGTH: 363
<212> TYPE: DNA
<213> ORGANISM: Artificial
<220> FEATURE:
<223> OTHER INFORMATION: The nucleotide sequence of anti-4-1BB scFv
heavy chain variable region

<400> SEQUENCE: 114
caggtgcagc tgcagcagtg gggcgccggc ctgctgaagc ccagcgagac cctgagcctg 60
acctgcgccg tgtacggcgg cagcttcagc ggctactact ggagctggat ccgccagagc 120
cccgagaagg gcctggagtg gatcggcgag atcaaccacg gcggctacgt gacctacaac 180
cccagcctgg agagccgcgt gaccatcagc gtggacacca gcaagaacca gttcagcctg 240
aagctgagca gcgtgaccgc cgccgacacc gccgtgtact actgcgcccg cgactacggc 300
cccggcaact acgactggta cttcgacctg tggggccgcg gcaccctggt gaccgtgagc 360
agc 363

<210> SEQ ID NO 115
<211> LENGTH: 330
<212> TYPE: DNA
<213> ORGANISM: Artificial
<220> FEATURE:
<223> OTHER INFORMATION: The nucleotide sequence of anti-4-1BB scFv
light chain variable region

<400> SEQUENCE: 115
gagatcgtgc tgacccagag ccccgccacc ctgagcctga gccccggcga gcgcgccacc 60
ctgagctgcc gcgccagcca gagcgtgagc agctacctgg cctggtacca gcagaagccc 120
ggccaggccc cccgcctgct gatctacgac gccagcaacc gcgccaccgg catccccgcc 180
cgcttcagcg gcagcggcag cggcaccgac ttcaccctga ccatcagcag cctggagccc 240
gaggacttcg ccgtgtacta ctgccagcag cgcagcaact ggcccccccgc cctgaccttc 300 tgcggcggca ccaaggtgga gatcaagcgc 330

<210> SEQ ID NO 116
<211> LENGTH: 741
<212> TYPE: DNA
<213> ORGANISM: Artificial
<220> FEATURE:

<223> OTHER INFORMATION: The nucleotide sequence of anti-ICOS scFv

<400> SEQUENCE: 116
caggtgcagc tggtgcagag cggcgccgag gtgaagaagc ccggcgccag cgtgaaggtg 60
agctgcaagg ccagcggcta caccttcacc ggctactaca tgcactgggt gcgccaggcc 120
cccggccagg gcctggagtg gatgggctgg atcaaccccc acagcggcgg caccaactac 180
gcccagaagt tccagggccg cgtgaccatg acccgcgaca ccagcatcag caccgcctac 240
atggagctga gccgcctgcg cagcgacgac accgccgtgt actactgcgc ccgcacctac 300
tactacgaca gcagcggcta ctaccacgac gccttcgaca tctggggcca gggcaccatg 360
gtgaccgtga gcagcggcgg cggcggcagc ggcggcggcg gcagcggcgg cggcggcagc 420
gacatccaga tgacccagag ccccagcagc gtgagcgcca gcgtgggcga ccgcgtgacc 480
atcacctgcc gcgccagcca gggcatcagc cgcctgctgg cctggtacca gcagaagccc 540
ggcaaggccc ccaagctgct gatctacgtg gccagcagcc tgcagagcgg cgtgcccagc 600
cgcttcagcg gcagcggcag cggcaccgac ttcaccctga ccatcagcag cctgcagccc 660
gaggacttcg ccacctacta ctgccagcag gccaacagct tcccctggac cttcggccag 720
ggcaccaagg tggagatcaa g 741

<210> SEQ ID NO 117
<211> LENGTH: 375
<212> TYPE: DNA
<213> ORGANISM: Artificial
<220> FEATURE:
<223> OTHER INFORMATION: The nucleotide sequence of anti-ICOS scFv heavy chain variable region

<400> SEQUENCE: 117
caggtgcagc tggtgcagag cggcgccgag gtgaagaagc ccggcgccag cgtgaaggtg 60
agctgcaagg ccagcggcta caccttcacc ggctactaca tgcactgggt gcgccaggcc 120
cccggccagg gcctggagtg gatgggctgg atcaaccccc acagcggcgg caccaactac 180
gcccagaagt tccagggccg cgtgaccatg acccgcgaca ccagcatcag caccgcctac 240
atggagctga gccgcctgcg cagcgacgac accgccgtgt actactgcgc ccgcacctac 300
tactacgaca gcagcggcta ctaccacgac gccttcgaca tctggggcca gggcaccatg 360
gtgaccgtga gcagc 375

<210> SEQ ID NO 118
<211> LENGTH: 321
<212> TYPE: DNA
<213> ORGANISM: Artificial
<220> FEATURE:
<223> OTHER INFORMATION: The nucleotide sequence of anti-ICOS scFv light chain variable region

<400> SEQUENCE: 118
gacatccaga tgacccagag ccccagcagc gtgagcgcca gcgtgggcga ccgcgtgacc 60
atcacctgcc gcgccagcca gggcatcagc cgcctgctgg cctggtacca gcagaagccc 120
ggcaaggccc ccaagctgct gatctacgtg gccagcagcc tgcagagcgg cgtgcccagc 180
cgcttcagcg gcagcggcag cggcaccgac ttcaccctga ccatcagcag cctgcagccc 240
gaggacttcg ccacctacta ctgccagcag gccaacagct tcccctggac cttcggccag 300
ggcaccaagg tggagatcaa g 321

<210> SEQ ID NO 119
<211> LENGTH: 726
<212> TYPE: DNA
<213> ORGANISM: Artificial
<220> FEATURE:
<223> OTHER INFORMATION: The nucleotide sequence of anti-OX40 scFv

<400> SEQUENCE: 119

```
cagctggtgg agagcggcgg cggcctggtg cagcccggcg gcagcctgcg cctgagctgc     60
gccgccagcg gcttcacctt cagcagctac agcatgaact gggtgcgcca ggcccccggc    120
aagggcctgg agtgggtgag ctacatcagc agcagcagca gcaccatcta ctacgccgac    180
agcgtgaagg gccgcttcac catcagccgc gacaacgcca agaacagcct gtacctgcag    240
atgaacagcc tgcgcgacga ggacaccgcc gtgtactact gcgcccgcgg cgtgtaccac    300
aacggctgga gcttcttcga ctactggggc cagggcaccc tgctgaccgt gagcagcggc    360
ggcggcggca gcggcggcgg cggcagcggc ggcggcggca gcgacatcca gatgacccag    420
agccccagca gcctgagcgc cagcgtgggc aaccgcgtga ccatcacctg ccgcgccagc    480
caggacatca gcagctggct ggcctggtac cagcagaagc ccgagaaggc ccccaagagc    540
ctgatctacg ccgccagcag cctgcagagc ggcgtgccca gccgcttcag cggcagcggc    600
agcggcaccg acttcaccct gaccatcagc agcctgcagc ccgaggactt cgccacctac    660
tactgccagc agtacaacag ctacccccctg accttcggcc agggcacccg cctggagatc    720
aagcgc                                                               726
```

<210> SEQ ID NO 120
<211> LENGTH: 357
<212> TYPE: DNA
<213> ORGANISM: Artificial
<220> FEATURE:
<223> OTHER INFORMATION: The nucleotide sequence of anti-OX40 scFv heavy
      chain variable region

<400> SEQUENCE: 120

```
cagctggtgg agagcggcgg cggcctggtg cagcccggcg gcagcctgcg cctgagctgc     60
gccgccagcg gcttcacctt cagcagctac agcatgaact gggtgcgcca ggcccccggc    120
aagggcctgg agtgggtgag ctacatcagc agcagcagca gcaccatcta ctacgccgac    180
agcgtgaagg gccgcttcac catcagccgc gacaacgcca agaacagcct gtacctgcag    240
atgaacagcc tgcgcgacga ggacaccgcc gtgtactact gcgcccgcgg cgtgtaccac    300
aacggctgga gcttcttcga ctactggggc cagggcaccc tgctgaccgt gagcagc       357
```

<210> SEQ ID NO 121
<211> LENGTH: 324
<212> TYPE: DNA
<213> ORGANISM: Artificial
<220> FEATURE:
<223> OTHER INFORMATION: The nucleotide sequence of anti-OX40 scFv light
      chain variable region

<400> SEQUENCE: 121

```
gacatccaga tgacccagag ccccagcagc ctgagcgcca gcgtgggcaa ccgcgtgacc     60
atcacctgcc gcgccagcca ggacatcagc agctggctgg cctggtacca gcagaagccc    120
gagaaggccc ccaagagcct gatctacgcc gccagcagcc tgcagagcgg cgtgcccagc    180
cgcttcagcg gcagcggcag cggcaccgac ttcaccctga ccatcagcag cctgcagccc    240
gaggacttcg ccacctacta ctgccagcag tacaacagct acccccctgac cttcggccag    300
```

```
ggcacccgcc tggagatcaa gcgc                                          324


<210> SEQ ID NO 122
<211> LENGTH: 723
<212> TYPE: DNA
<213> ORGANISM: Artificial
<220> FEATURE:
<223> OTHER INFORMATION: The nucleotide sequence of anti-GITR scFv

<400> SEQUENCE: 122

caggtgaccc tgaaggagag cggccccggc atcctgaagc ccagccagac cctgagcctg     60

acctgcagct tcagcggctt cagcctgagc accagcggca tgggcgtggg ctggatccgc    120

cagcccagcg gcaagggcct ggagtggctg gcccacatct ggtgggacga cgacaagtac    180

tacaacccca gcctgaagag ccagctgacc atcagcaagg acaccagccg caaccaggtg    240

ttcctgaaga tcaccagcgt ggacaccgcc gacgccgcca cctactactg cgcccgcacc    300

cgccgctact tccccttcgc ctactggggc cagggcaccc tggtgaccgt gagcagcggc    360

ggcggcggca gcggcggcgg cggcagcggc ggcggcggca gcgacatcgt gatgacccag    420

agccagaagt tcatgagcac cagcgtgggc gaccgcgtga gcgtgacctg caaggccagc    480

cagaacgtgg gcaccaacgt ggcctggtac cagcagaagc ccggccagag ccccaaggcc    540

ctgatctaca gcgccagcta ccgctacagc ggcgtgcccg accgcttcac cggcagcggc    600

agcggcaccg acttcaccct gaccatcaac aacgtgcaca gcgaggacct ggccgagtac    660

ttctgccagc agtacaacac cgaccccctg accttcggcg ccggcaccaa gctggagatc    720

aag                                                                  723


<210> SEQ ID NO 123
<211> LENGTH: 357
<212> TYPE: DNA
<213> ORGANISM: Artificial
<220> FEATURE:
<223> OTHER INFORMATION: The nucleotide sequence of anti-GITR scFv heavy
      chain variable region

<400> SEQUENCE: 123

caggtgaccc tgaaggagag cggccccggc atcctgaagc ccagccagac cctgagcctg     60

acctgcagct tcagcggctt cagcctgagc accagcggca tgggcgtggg ctggatccgc    120

cagcccagcg gcaagggcct ggagtggctg gcccacatct ggtgggacga cgacaagtac    180

tacaacccca gcctgaagag ccagctgacc atcagcaagg acaccagccg caaccaggtg    240

ttcctgaaga tcaccagcgt ggacaccgcc gacgccgcca cctactactg cgcccgcacc    300

cgccgctact tccccttcgc ctactggggc cagggcaccc tggtgaccgt gagcagc       357


<210> SEQ ID NO 124
<211> LENGTH: 321
<212> TYPE: DNA
<213> ORGANISM: Artificial
<220> FEATURE:
<223> OTHER INFORMATION: The nucleotide sequence of anti-GITR scFv light
      chain variable region

<400> SEQUENCE: 124

gacatcgtga tgacccagag ccagaagttc atgagcacca gcgtgggcga ccgcgtgagc     60

gtgacctgca aggccagcca gaacgtgggc accaacgtgg cctggtacca gcagaagccc    120

ggccagagcc ccaaggccct gatctacagc gccagctacc gctacagcgg cgtgcccgac    180

cgcttcaccg gcagcggcag cggcaccgac ttcaccctga ccatcaacaa cgtgcacagc    240
```

gaggacctgg ccgagtactt ctgccagcag tacaacaccg accccctgac cttcggcgcc 300
ggcaccaagc tggagatcaa g 321

<210> SEQ ID NO 125
<211> LENGTH: 717
<212> TYPE: DNA
<213> ORGANISM: Artificial
<220> FEATURE:
<223> OTHER INFORMATION: The nucleotide sequence of anti-CD40L scFv

<400> SEQUENCE: 125
gaggtgcagc tgctggagag cggcggcggc ctggtgcagc ccggcggcag cctgcgcctg 60
agctgcgccg ccagcggctt caccttcagc agctacgcca tgagctgggt gcgccaggcc 120
cccggcaagg gcctggagtg ggtgagcgcc atcagcggca gcggcggcag cacctactac 180
gccgacagcg tgaagggccg cttcaccatc agccgcgaca acagcaagaa caccctgtac 240
ctgcagatga acagcctgcg cgccgaggac accgccgtgt actactgcgc caagagctac 300
ggcgccttcg actactgggg ccagggcacc ctggtgaccg tgagcagcgg cggcggcggc 360
agcggcggcg gcggcagcgg cggcggcggc agcgacatcc agatgaccca gagccccagc 420
agcctgagcg ccagcgtggg cgaccgcgtg accatcacct gccgcgccag ccagagcatc 480
agcagctacc tgaactggta ccagcagaag cccggcaagg cccccaagct gctgatctac 540
gccgccagca gcctgcagag cggcgtgccc agccgcttca gcggcagcgg cagcggcacc 600
gacttcaccc tgaccatcag cagcctgcag cccgaggact tcgccaccta ctactgccag 660
cagagctaca gcacccccaa caccttcggc cagggcacca aggtggagat caagcgc 717

<210> SEQ ID NO 126
<211> LENGTH: 348
<212> TYPE: DNA
<213> ORGANISM: Artificial
<220> FEATURE:
<223> OTHER INFORMATION: The nucleotide sequence of anti-CD40L scFv
heavy chain variable region

<400> SEQUENCE: 126
gaggtgcagc tgctggagag cggcggcggc ctggtgcagc ccggcggcag cctgcgcctg 60
agctgcgccg ccagcggctt caccttcagc agctacgcca tgagctgggt gcgccaggcc 120
cccggcaagg gcctggagtg ggtgagcgcc atcagcggca gcggcggcag cacctactac 180
gccgacagcg tgaagggccg cttcaccatc agccgcgaca acagcaagaa caccctgtac 240
ctgcagatga acagcctgcg cgccgaggac accgccgtgt actactgcgc caagagctac 300
ggcgccttcg actactgggg ccagggcacc ctggtgaccg tgagcagc 348

<210> SEQ ID NO 127
<211> LENGTH: 324
<212> TYPE: DNA
<213> ORGANISM: Artificial
<220> FEATURE:
<223> OTHER INFORMATION: The nucleotide sequence of anti-CD40L scFv
light chain variable region

<400> SEQUENCE: 127
gacatccaga tgacccagag ccccagcagc ctgagcgcca gcgtgggcga ccgcgtgacc 60
atcacctgcc gcgccagcca gagcatcagc agctacctga actggtacca gcagaagccc 120
ggcaaggccc ccaagctgct gatctacgcc gccagcagcc tgcagagcgg cgtgcccagc 180

```
cgcttcagcg gcagcggcag cggcaccgac ttcaccctga ccatcagcag cctgcagccc    240

gaggacttcg ccacctacta ctgccagcag agctacagca cccccaacac cttcggccag    300

ggcaccaagg tggagatcaa gcgc                                          324


<210> SEQ ID NO 128
<211> LENGTH: 723
<212> TYPE: DNA
<213> ORGANISM: Artificial
<220> FEATURE:
<223> OTHER INFORMATION: The nucleotide sequence of anti-CD27 scFv

<400> SEQUENCE: 128

caggtgcagc tggtggagag cggcggcggc gtggtgcagc ccggccgcag cctgcgcctg     60

agctgcgccg ccagcggctt caccttcagc agctacgaca tgcactgggt gcgccaggcc    120

cccggcaagg gcctggagtg ggtggccgtg atctggtacg acggcagcaa caagtactac    180

gccgacagcg tgaagggccg cttcaccatc agccgcgaca acagcaagaa caccctgtac    240

ctgcagatga acagcctgcg cgccgaggac accgccgtgt actactgcgc ccgcggcagc    300

ggcaactggg gcttcttcga ctactggggc cagggcaccc tggtgaccgt gagcagcggc    360

ggcggcggca gcggcggcgg cggcagcggc ggcggcggca gcgacatcca gatgacccag    420

agccccagca gcctgagcgc cagcgtgggc gaccgcgtga ccatcacctg ccgcgccagc    480

cagggcatca gccgctggct ggcctggtac cagcagaagc ccgagaaggc ccccaagagc    540

ctgatctacg ccgccagcag cctgcagagc ggcgtgccca gccgcttcag cggcagcggc    600

agcggcaccg acttcaccct gaccatcagc agcctgcagc ccgaggactt cgccacctac    660

tactgccagc agtacaacac ctacccccgc accttcggcc agggcaccaa ggtggagatc    720

aag                                                                 723


<210> SEQ ID NO 129
<211> LENGTH: 357
<212> TYPE: DNA
<213> ORGANISM: Artificial
<220> FEATURE:
<223> OTHER INFORMATION: The nucleotide sequence of anti-CD27 scFv heavy
      chain variable region

<400> SEQUENCE: 129

caggtgcagc tggtggagag cggcggcggc gtggtgcagc ccggccgcag cctgcgcctg     60

agctgcgccg ccagcggctt caccttcagc agctacgaca tgcactgggt gcgccaggcc    120

cccggcaagg gcctggagtg ggtggccgtg atctggtacg acggcagcaa caagtactac    180

gccgacagcg tgaagggccg cttcaccatc agccgcgaca acagcaagaa caccctgtac    240

ctgcagatga acagcctgcg cgccgaggac accgccgtgt actactgcgc ccgcggcagc    300

ggcaactggg gcttcttcga ctactggggc cagggcaccc tggtgaccgt gagcagc      357


<210> SEQ ID NO 130
<211> LENGTH: 321
<212> TYPE: DNA
<213> ORGANISM: Artificial
<220> FEATURE:
<223> OTHER INFORMATION: The nucleotide sequence of anti-CD27 scFv light
      chain variable region

<400> SEQUENCE: 130

gacatccaga tgacccagag ccccagcagc ctgagcgcca gcgtgggcga ccgcgtgacc     60

atcacctgcc gcgccagcca gggcatcagc cgctggctgg cctggtacca gcagaagccc    120
```

```
gagaaggccc ccaagagcct gatctacgcc gccagcagcc tgcagagcgg cgtgcccagc    180

cgcttcagcg gcagcggcag cggcaccgac ttcaccctga ccatcagcag cctgcagccc    240

gaggacttcg ccacctacta ctgccagcag tacaacacct acccccgcac cttcggccag    300

ggcaccaagg tggagatcaa g                                              321
```

<210> SEQ ID NO 131
<211> LENGTH: 19
<212> TYPE: PRT
<213> ORGANISM: Artificial
<220> FEATURE:
<223> OTHER INFORMATION: The amino acid sequence of the secretory signal peptide

<400> SEQUENCE: 131

```
Met Thr Arg Leu Thr Val Leu Ala Leu Leu Ala Gly Leu Leu Ala Ser
1               5                   10                  15

Ser Arg Ala
```

<210> SEQ ID NO 132
<211> LENGTH: 57
<212> TYPE: DNA
<213> ORGANISM: Artificial
<220> FEATURE:
<223> OTHER INFORMATION: The nucleotide sequence of the secretory signal peptide

<400> SEQUENCE: 132

```
atgacccggc tgaccgtgct ggccctgctg gccggcctgc tggcctcctc cagggcc       57
```

<210> SEQ ID NO 133
<211> LENGTH: 59
<212> TYPE: DNA
<213> ORGANISM: Artificial
<220> FEATURE:
<223> OTHER INFORMATION: pcDNA3.1-Sig-F

<400> SEQUENCE: 133

```
gtgctggata tctgcagaat tcgccgccac catgacccgg ctgaccgtgc tggccctgc     59
```

<210> SEQ ID NO 134
<211> LENGTH: 49
<212> TYPE: DNA
<213> ORGANISM: Artificial
<220> FEATURE:
<223> OTHER INFORMATION: Sig-R

<400> SEQUENCE: 134

```
ggccctggag gaggccagca ggccggccag cagggccagc acggtcagc                49
```

<210> SEQ ID NO 135
<211> LENGTH: 42
<212> TYPE: DNA
<213> ORGANISM: Artificial
<220> FEATURE:
<223> OTHER INFORMATION: Sig-CD19-F

<400> SEQUENCE: 135

```
ctgctggcct cctccagggc cgacatccag ctgacccaga gc                       42
```

<210> SEQ ID NO 136
<211> LENGTH: 23
<212> TYPE: DNA
<213> ORGANISM: Artificial

<220> FEATURE:
<223> OTHER INFORMATION: CD19-R

<400> SEQUENCE: 136
gctgctcacg gtcacggtgg tgc 23

<210> SEQ ID NO 137
<211> LENGTH: 56
<212> TYPE: DNA
<213> ORGANISM: Artificial
<220> FEATURE:
<223> OTHER INFORMATION: CD19-G4S-CD3-F

<400> SEQUENCE: 137
ccaccgtgac cgtgagcagc ggtggcggag ggtccgacat caagctgcag cagagc 56

<210> SEQ ID NO 138
<211> LENGTH: 20
<212> TYPE: DNA
<213> ORGANISM: Artificial
<220> FEATURE:
<223> OTHER INFORMATION: CD3-R

<400> SEQUENCE: 138
cttcagctcc agcttggtgc 20

<210> SEQ ID NO 139
<211> LENGTH: 72
<212> TYPE: DNA
<213> ORGANISM: Artificial
<220> FEATURE:
<223> OTHER INFORMATION: CD3-(GGGGS)3-4-1BB-F

<400> SEQUENCE: 139
gcaccaagct ggagctgaag ggcggcggcg gcagcggcgg cggcggcagc ggcggcggcg 60
gcagccaggt gc 72

<210> SEQ ID NO 140
<211> LENGTH: 51
<212> TYPE: DNA
<213> ORGANISM: Artificial
<220> FEATURE:
<223> OTHER INFORMATION: pcDNA3.1-4-1BB-R

<400> SEQUENCE: 140
ctgatcagcg gtttaaactt aagctttcag cgcttgatct ccaccttggt g 51

<210> SEQ ID NO 141
<211> LENGTH: 41
<212> TYPE: DNA
<213> ORGANISM: Artificial
<220> FEATURE:
<223> OTHER INFORMATION: CD3-IgD-F

<400> SEQUENCE: 141
gcaccaagct ggagctgaag gccagcaaga gcaagaagga g 41

<210> SEQ ID NO 142
<211> LENGTH: 21
<212> TYPE: DNA
<213> ORGANISM: Artificial
<220> FEATURE:
<223> OTHER INFORMATION: IgD-R

<400> SEQUENCE: 142
cacgcccagg ggctgggtgt g 21

<210> SEQ ID NO 143
<211> LENGTH: 42
<212> TYPE: DNA
<213> ORGANISM: Artificial
<220> FEATURE:
<223> OTHER INFORMATION: IgD-4-1BB-F

<400> SEQUENCE: 143
cacacccagc ccctgggcgt gcaggtgcag ctgcagcagt gg 42

<210> SEQ ID NO 144
<211> LENGTH: 86
<212> TYPE: DNA
<213> ORGANISM: Artificial
<220> FEATURE:
<223> OTHER INFORMATION: CD3-(GGGGS)3-ICOS-F

<400> SEQUENCE: 144
gcaccaagct ggagctgaag ggcggcggcg gcagcggcgg cggcggcagc ggcggcggcg 60
gcagccaggt gcagctggtg cagagc 86

<210> SEQ ID NO 145
<211> LENGTH: 50
<212> TYPE: DNA
<213> ORGANISM: Artificial
<220> FEATURE:
<223> OTHER INFORMATION: pcDNA3.1-ICOS-R

<400> SEQUENCE: 145
ctgatcagcg gtttaaactt aagctttcac ttgatctcca ccttggtgcc 50

<210> SEQ ID NO 146
<211> LENGTH: 42
<212> TYPE: DNA
<213> ORGANISM: Artificial
<220> FEATURE:
<223> OTHER INFORMATION: IgD-ICOS-F

<400> SEQUENCE: 146
cacacccagc ccctgggcgt gcaggtgcag ctggtgcaga gc 42

<210> SEQ ID NO 147
<211> LENGTH: 85
<212> TYPE: DNA
<213> ORGANISM: Artificial
<220> FEATURE:
<223> OTHER INFORMATION: CD3-(GGGGS)3-OX40-F

<400> SEQUENCE: 147
gcaccaagct ggagctgaag ggcggcggcg gcagcggcgg cggcggcagc ggcggcggcg 60
gcagccagct ggtggagagc ggcgg 85

<210> SEQ ID NO 148
<211> LENGTH: 52
<212> TYPE: DNA
<213> ORGANISM: Artificial
<220> FEATURE:
<223> OTHER INFORMATION: pcDNA3.1-OX40-R

<400> SEQUENCE: 148
ctgatcagcg gtttaaactt aagctttcag cgcttgatct ccaggcgggt gc 52

-continued

<210> SEQ ID NO 149
<211> LENGTH: 45
<212> TYPE: DNA
<213> ORGANISM: Artificial
<220> FEATURE:
<223> OTHER INFORMATION: IgD-OX40-F

<400> SEQUENCE: 149
gccacaccca gcccctgggc gtgcagctgg tggagagcgg cggcg 45

<210> SEQ ID NO 150
<211> LENGTH: 85
<212> TYPE: DNA
<213> ORGANISM: Artificial
<220> FEATURE:
<223> OTHER INFORMATION: CD3-(GGGGS)3-GITR-F

<400> SEQUENCE: 150
gcaccaagct ggagctgaag ggcggcggcg gcagcggcgg cggcggcagc ggcggcggcg 60
gcagccaggt gaccctgaag gagag 85

<210> SEQ ID NO 151
<211> LENGTH: 52
<212> TYPE: DNA
<213> ORGANISM: Artificial
<220> FEATURE:
<223> OTHER INFORMATION: pcDNA3.1-GITR-R

<400> SEQUENCE: 151
ctgatcagcg gtttaaactt aagctttcac ttgatctcca gcttggtgcc gg 52

<210> SEQ ID NO 152
<211> LENGTH: 43
<212> TYPE: DNA
<213> ORGANISM: Artificial
<220> FEATURE:
<223> OTHER INFORMATION: IgD-GITR-F

<400> SEQUENCE: 152
gccacaccca gcccctgggc gtgcaggtga ccctgaagga gag 43

<210> SEQ ID NO 153
<211> LENGTH: 87
<212> TYPE: DNA
<213> ORGANISM: Artificial
<220> FEATURE:
<223> OTHER INFORMATION: CD3-(GGGGS)3-CD40L-F

<400> SEQUENCE: 153
ggcaccaagc tggagctgaa gggcggcggc ggcagcggcg gcggcggcag cggcggcggc 60
ggcagcgagg tgcagctgct ggagagc 87

<210> SEQ ID NO 154
<211> LENGTH: 51
<212> TYPE: DNA
<213> ORGANISM: Artificial
<220> FEATURE:
<223> OTHER INFORMATION: pcDNA3.1-CD40L-R

<400> SEQUENCE: 154
ctgatcagcg gtttaaactt aagctttcag cgcttgatct ccaccttggt g 51

<210> SEQ ID NO 155
<211> LENGTH: 43
<212> TYPE: DNA

<213> ORGANISM: Artificial
<220> FEATURE:
<223> OTHER INFORMATION: IgD-CD40L-F

<400> SEQUENCE: 155
gccacaccca gcccctgggc gtggaggtgc agctgctgga gag 43

<210> SEQ ID NO 156
<211> LENGTH: 86
<212> TYPE: DNA
<213> ORGANISM: Artificial
<220> FEATURE:
<223> OTHER INFORMATION: CD3-(GGGGS)3-CD27-F

<400> SEQUENCE: 156
gcaccaagct ggagctgaag ggcggcggcg gcagcggcgg cggcggcagc ggcggcggcg 60
gcagccaggt gcagctggtg gagagc 86

<210> SEQ ID NO 157
<211> LENGTH: 51
<212> TYPE: DNA
<213> ORGANISM: Artificial
<220> FEATURE:
<223> OTHER INFORMATION: pcDNA3.1-CD27-R

<400> SEQUENCE: 157
ctgatcagcg gtttaaactt aagctttcac ttgatctcca ccttggtgcc c 51

<210> SEQ ID NO 158
<211> LENGTH: 43
<212> TYPE: DNA
<213> ORGANISM: Artificial
<220> FEATURE:
<223> OTHER INFORMATION: IgD-CD27-F

<400> SEQUENCE: 158
gccacaccca gcccctgggc gtgcaggtgc agctggtgga gag 43

<210> SEQ ID NO 159
<211> LENGTH: 5
<212> TYPE: PRT
<213> ORGANISM: Artificial
<220> FEATURE:
<223> OTHER INFORMATION: The amino acid sequence of CD19-CD3-4-1BBL
TsM_M monomer linker (Linker 1)

<400> SEQUENCE: 159

Gly Gly Gly Gly Ser
1 5

<210> SEQ ID NO 160
<211> LENGTH: 15
<212> TYPE: DNA
<213> ORGANISM: Artificial
<220> FEATURE:
<223> OTHER INFORMATION: The nucleotide sequence of CD19-CD3-4-1BBL
TsM_M monomer linker (Linker 1)

<400> SEQUENCE: 160
ggcggcggcg gcagc 15

<210> SEQ ID NO 161
<211> LENGTH: 15
<212> TYPE: PRT
<213> ORGANISM: Artificial
<220> FEATURE:

<223> OTHER INFORMATION: The amino acid sequence of CD19-CD3-4-1BBL
TsM_M monomer linker (Linker 2)

<400> SEQUENCE: 161

Gly Gly Gly Gly Ser Gly Gly Gly Gly Ser Gly Gly Gly Gly Ser
1               5                   10                  15

<210> SEQ ID NO 162
<211> LENGTH: 45
<212> TYPE: DNA
<213> ORGANISM: Artificial
<220> FEATURE:
<223> OTHER INFORMATION: The nucleotide sequence of CD19-CD3-4-1BBL
TsM_M monomer linker (Linker 2)

<400> SEQUENCE: 162
ggcggcggcg gcagcggcgg cggcggcagc ggcggcggcg gcagc 45

<210> SEQ ID NO 163
<211> LENGTH: 5
<212> TYPE: PRT
<213> ORGANISM: Artificial
<220> FEATURE:
<223> OTHER INFORMATION: The amino acid sequence of CD19-CD3-4-1BBL
TsM_D dimer linker (Linker 1)

<400> SEQUENCE: 163

Gly Gly Gly Gly Ser
1               5

<210> SEQ ID NO 164
<211> LENGTH: 15
<212> TYPE: DNA
<213> ORGANISM: Artificial
<220> FEATURE:
<223> OTHER INFORMATION: The nucleotide sequence of CD19-CD3-4-1BBL
TsM_D dimer linker (Linker 1)

<400> SEQUENCE: 164
ggcggcggcg gcagc 15

<210> SEQ ID NO 165
<211> LENGTH: 81
<212> TYPE: PRT
<213> ORGANISM: Artificial
<220> FEATURE:
<223> OTHER INFORMATION: The amino acid sequence of CD19-CD3-4-1BBL
TsM_D dimer linker (Linker 2)

<400> SEQUENCE: 165

Ala Ser Lys Ser Lys Lys Glu Ile Phe Arg Trp Pro Glu Ser Pro Lys
1               5                   10                  15

Ala Gln Ala Ser Ser Val Pro Thr Ala Gln Pro Gln Ala Glu Gly Ser
            20                  25                  30

Leu Ala Lys Ala Thr Thr Ala Pro Ala Thr Thr Arg Asn Thr Gly Arg
        35                  40                  45

Gly Gly Glu Glu Lys Lys Lys Glu Lys Glu Lys Glu Glu Gln Glu Glu
    50                  55                  60

Arg Glu Thr Lys Thr Pro Glu Cys Pro Ser His Thr Gln Pro Leu Gly
65                  70                  75                  80

Val

<210> SEQ ID NO 166
<211> LENGTH: 243

<212> TYPE: DNA
<213> ORGANISM: Artificial
<220> FEATURE:
<223> OTHER INFORMATION: The nucleotide sequence of CD19-CD3-4-1BBL
TsM_D dimer linker (Linker 2)

<400> SEQUENCE: 166

```
gccagcaaga gcaagaagga gatcttccgc tggcccgaga gccccaaggc ccaggccagc      60

agcgtgccca ccgcccagcc ccaggccgag ggcagcctgg ccaaggccac caccgccccc     120

gccaccaccc gcaacaccgg ccgcggcggc gaggagaaga agaaggagaa ggagaaggag     180

gagcaggagg agcgcgagac caagaccccc gagtgcccca gccacaccca gcccctgggc     240

gtg                                                                   243
```

<210> SEQ ID NO 167
<211> LENGTH: 232
<212> TYPE: PRT
<213> ORGANISM: Artificial
<220> FEATURE:
<223> OTHER INFORMATION: The amino acid sequence of the T cell positive
costimulatory molecule human 4-1BB

<400> SEQUENCE: 167

```
Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln Ile Ile Ser Phe Phe Leu Ala Leu Thr Ser Thr Ala Leu
                165                 170                 175

Leu Phe Leu Leu Phe Phe Leu Thr Leu Arg Phe Ser Val Val Lys Arg
            180                 185                 190

Gly Arg Lys Lys Leu Leu Tyr Ile Phe Lys Gln Pro Phe Met Arg Pro
        195                 200                 205

Val Gln Thr Thr Gln Glu Glu Asp Gly Cys Ser Cys Arg Phe Pro Glu
    210                 215                 220

Glu Glu Glu Gly Gly Cys Glu Leu
225                 230
```

<210> SEQ ID NO 168
<211> LENGTH: 254
<212> TYPE: PRT
<213> ORGANISM: Artificial -continued
<220> FEATURE:
<223> OTHER INFORMATION: The amino acid sequence of the T cell positive
      costimulatory ligand human 4-1BBL

<400> SEQUENCE: 168

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 169
<211> LENGTH: 179
<212> TYPE: PRT
<213> ORGANISM: Artificial
<220> FEATURE:
<223> OTHER INFORMATION: The amino acid sequence of the T cell positive
      costimulatory molecule human ICOS

<400> SEQUENCE: 169

Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
            100                 105                 110

Ser Gln Leu Cys Cys Gln Leu Lys Phe Trp Leu Pro Ile Gly Cys Ala
        115                 120                 125

Ala Phe Val Val Val Cys Ile Leu Gly Cys Ile Leu Ile Cys Trp Leu
    130                 135                 140

Thr Lys Lys Lys Tyr Ser Ser Ser Val His Asp Pro Asn Gly Glu Tyr
145                 150                 155                 160

Met Phe Met Arg Ala Val Asn Thr Ala Lys Lys Ser Arg Leu Thr Asp
                165                 170                 175

Val Thr Leu

<210> SEQ ID NO 170
<211> LENGTH: 284
<212> TYPE: PRT
<213> ORGANISM: Artificial
<220> FEATURE:
<223> OTHER INFORMATION: The amino acid sequence of the T cell positive
      costimulatory ligand human B7RP-1

<400> SEQUENCE: 170

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asn Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr Trp Ser
225                 230                 235                 240

Ile Leu Ala Val Leu Cys Leu Leu Val Val Val Ala Val Ala Ile Gly
                245                 250                 255

```
Trp Val Cys Arg Asp Arg Cys Leu Gln His Ser Tyr Ala Gly Ala Trp
            260                 265                 270

Ala Val Ser Pro Glu Thr Glu Leu Thr Gly His Val
        275                 280


<210> SEQ ID NO 171
<211> LENGTH: 249
<212> TYPE: PRT
<213> ORGANISM: Artificial
<220> FEATURE:
<223> OTHER INFORMATION: The amino acid sequence of the T cell positive
      costimulatory molecule human OX40

<400> SEQUENCE: 171

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
    210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245


<210> SEQ ID NO 172
<211> LENGTH: 183
<212> TYPE: PRT
<213> ORGANISM: Artificial
<220> FEATURE:
<223> OTHER INFORMATION: The amino acid sequence of the T cell positive
      costimulatory ligand human OX40L

<400> SEQUENCE: 172

Met Glu Arg Val Gln Pro Leu Glu Glu Asn Val Gly Asn Ala Ala Arg
1               5                   10                  15
```

```
Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180
```

```
<210> SEQ ID NO 173
<211> LENGTH: 216
<212> TYPE: PRT
<213> ORGANISM: Artificial
<220> FEATURE:
<223> OTHER INFORMATION: The amino acid sequence of the T cell positive
      costimulatory molecule human GITR

<400> SEQUENCE: 173

Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
            20                  25                  30

Cys Arg Asp Tyr Pro Gly Glu Glu Cys Cys Ser Glu Trp Asp Cys Met
        35                  40                  45

Cys Val Gln Pro Glu Phe His Cys Gly Asp Pro Cys Cys Thr Thr Cys
    50                  55                  60

Arg His His Pro Cys Pro Pro Gly Gln Gly Val Gln Ser Gln Gly Lys
65                  70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
            100                 105                 110

Gly Phe Leu Thr Val Phe Pro Gly Asn Lys Thr His Asn Ala Val Cys
        115                 120                 125

Val Pro Gly Ser Pro Pro Ala Glu Pro Leu Gly Trp Leu Thr Val Val
    130                 135                 140

Leu Leu Ala Val Ala Ala Cys Val Leu Leu Leu Thr Ser Ala Gln Leu
145                 150                 155                 160

Gly Leu His Ile Trp Gln Leu Arg Ser Gln Cys Met Trp Pro Arg Glu
                165                 170                 175

Thr Gln Leu Leu Leu Glu Val Pro Pro Ser Thr Glu Asp Ala Arg Ser
```

```
            180                 185                 190

Cys Gln Phe Pro Glu Glu Glu Arg Gly Glu Arg Ser Ala Glu Glu Lys
        195                 200                 205

Gly Arg Leu Gly Asp Leu Trp Val
    210                 215
```

<210> SEQ ID NO 174
<211> LENGTH: 199
<212> TYPE: PRT
<213> ORGANISM: Artificial
<220> FEATURE:
<223> OTHER INFORMATION: The amino acid sequence of the T cell positive costimulatory ligand human GITRL

<400> SEQUENCE: 174

```
Met Thr Leu His Pro Ser Pro Ile Thr Cys Glu Phe Leu Phe Ser Thr
1               5                   10                  15

Ala Leu Ile Ser Pro Lys Met Cys Leu Ser His Leu Glu Asn Met Pro
            20                  25                  30

Leu Ser His Ser Arg Thr Gln Gly Ala Gln Arg Ser Ser Trp Lys Leu
        35                  40                  45

Trp Leu Phe Cys Ser Ile Val Met Leu Leu Phe Leu Cys Ser Phe Ser
    50                  55                  60

Trp Leu Ile Phe Ile Phe Leu Gln Leu Glu Thr Ala Lys Glu Pro Cys
65                  70                  75                  80

Met Ala Lys Phe Gly Pro Leu Pro Ser Lys Trp Gln Met Ala Ser Ser
                85                  90                  95

Glu Pro Pro Cys Val Asn Lys Val Ser Asp Trp Lys Leu Glu Ile Leu
            100                 105                 110

Gln Asn Gly Leu Tyr Leu Ile Tyr Gly Gln Val Ala Pro Asn Ala Asn
        115                 120                 125

Tyr Asn Asp Val Ala Pro Phe Glu Val Arg Leu Tyr Lys Asn Lys Asp
    130                 135                 140

Met Ile Gln Thr Leu Thr Asn Lys Ser Lys Ile Gln Asn Val Gly Gly
145                 150                 155                 160

Thr Tyr Glu Leu His Val Gly Asp Thr Ile Asp Leu Ile Phe Asn Ser
                165                 170                 175

Glu His Gln Val Leu Lys Asn Asn Thr Tyr Trp Gly Ile Ile Leu Leu
            180                 185                 190

Ala Asn Pro Gln Phe Ile Ser
        195
```

<210> SEQ ID NO 175
<211> LENGTH: 241
<212> TYPE: PRT
<213> ORGANISM: Artificial
<220> FEATURE:
<223> OTHER INFORMATION: The amino acid sequence of the T cell positive costimulatory molecule human CD27

<400> SEQUENCE: 175

```
Ala Thr Pro Ala Pro Lys Ser Cys Pro Glu Arg His Tyr Trp Ala Gln
1               5                   10                  15

Gly Lys Leu Cys Cys Gln Met Cys Glu Pro Gly Thr Phe Leu Val Lys
            20                  25                  30

Asp Cys Asp Gln His Arg Lys Ala Ala Gln Cys Asp Pro Cys Ile Pro
        35                  40                  45

Gly Val Ser Phe Ser Pro Asp His His Thr Arg Pro His Cys Glu Ser
```

```
    50                  55                  60

Cys Arg His Cys Asn Ser Gly Leu Leu Val Arg Asn Cys Thr Ile Thr
65                  70                  75                  80

Ala Asn Ala Glu Cys Ala Cys Arg Asn Gly Trp Gln Cys Arg Asp Lys
                85                  90                  95

Glu Cys Thr Glu Cys Asp Pro Leu Pro Asn Pro Ser Leu Thr Ala Arg
            100                 105                 110

Ser Ser Gln Ala Leu Ser Pro His Pro Gln Pro Thr His Leu Pro Tyr
        115                 120                 125

Val Ser Glu Met Leu Glu Ala Arg Thr Ala Gly His Met Gln Thr Leu
    130                 135                 140

Ala Asp Phe Arg Gln Leu Pro Ala Arg Thr Leu Ser Thr His Trp Pro
145                 150                 155                 160

Pro Gln Arg Ser Leu Cys Ser Ser Asp Phe Ile Arg Ile Leu Val Ile
                165                 170                 175

Phe Ser Gly Met Phe Leu Val Phe Thr Leu Ala Gly Ala Leu Phe Leu
            180                 185                 190

His Gln Arg Arg Lys Tyr Arg Ser Asn Lys Gly Glu Ser Pro Val Glu
        195                 200                 205

Pro Ala Glu Pro Cys His Tyr Ser Cys Pro Arg Glu Glu Glu Gly Ser
    210                 215                 220

Thr Ile Pro Ile Gln Glu Asp Tyr Arg Lys Pro Glu Pro Ala Cys Ser
225                 230                 235                 240

Pro


<210> SEQ ID NO 176
<211> LENGTH: 193
<212> TYPE: PRT
<213> ORGANISM: Artificial
<220> FEATURE:
<223> OTHER INFORMATION: The amino acid sequence of the T cell positive
      costimulatory ligand human CD70

<400> SEQUENCE: 176

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
```

```
                165                 170                 175

Pro Ser Arg Asn Thr Asp Glu Thr Phe Phe Gly Val Gln Trp Val Arg
            180                 185                 190

Pro


<210> SEQ ID NO 177
<211> LENGTH: 718
<212> TYPE: PRT
<213> ORGANISM: Artificial
<220> FEATURE:
<223> OTHER INFORMATION: The amino acid sequence of CD19-CD3-4-1BBL
      TsM_M monomer

<400> SEQUENCE: 177

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
```

```
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Ala Cys Pro Trp Ala Val Ser Gly Ala Arg Ala Ser Pro Gly Ser
        515                 520                 525

Ala Ala Ser Pro Arg Leu Arg Glu Gly Pro Glu Leu Ser Pro Asp Asp
    530                 535                 540

Pro Ala Gly Leu Leu Asp Leu Arg Gln Gly Met Phe Ala Gln Leu Val
545                 550                 555                 560

Ala Gln Asn Val Leu Leu Ile Asp Gly Pro Leu Ser Trp Tyr Ser Asp
                565                 570                 575

Pro Gly Leu Ala Gly Val Ser Leu Thr Gly Gly Leu Ser Tyr Lys Glu
            580                 585                 590

Asp Thr Lys Glu Leu Val Val Ala Lys Ala Gly Val Tyr Tyr Val Phe
        595                 600                 605

Phe Gln Leu Glu Leu Arg Arg Val Val Ala Gly Glu Gly Ser Gly Ser
    610                 615                 620

Val Ser Leu Ala Leu His Leu Gln Pro Leu Arg Ser Ala Ala Gly Ala
625                 630                 635                 640

Ala Ala Leu Ala Leu Thr Val Asp Leu Pro Pro Ala Ser Ser Glu Ala
                645                 650                 655

Arg Asn Ser Ala Phe Gly Phe Gln Gly Arg Leu Leu His Leu Ser Ala
            660                 665                 670

Gly Gln Arg Leu Gly Val His Leu His Thr Glu Ala Arg Ala Arg His
        675                 680                 685

Ala Trp Gln Leu Thr Gln Gly Ala Thr Val Leu Gly Leu Phe Arg Val
    690                 695                 700

Thr Pro Glu Ile Pro Ala Gly Leu Pro Ser Pro Arg Ser Glu
705                 710                 715
```

<210> SEQ ID NO 178
<211> LENGTH: 2154
<212> TYPE: DNA
<213> ORGANISM: Artificial -continued

```
<220> FEATURE:
<223> OTHER INFORMATION: The nucleotide sequence of CD19-CD3-4-1BBL
      TsM_M monomer

<400> SEQUENCE: 178

gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600

agcagcagca ccgcctacat gcagctgagc agcctggcca gcgaggacag cgccgtgtac     660

ttctgcgccc gccgcgagac caccaccgtg ggccgctact actacgccat ggactactgg     720

ggccagggca ccaccgtgac cgtgagcagc ggcggcggcg gcagcgacat caagctgcag     780

cagagcggcg ccgagctggc ccgccccggc gccagcgtga agatgagctg caagaccagc     840

ggctacacct tcacccgcta caccatgcac tgggtgaagc agcgccccgg ccagggcctg     900

gagtggatcg gctacatcaa ccccagccgc ggctacacca actacaacca gaagttcaag     960

gacaaggcca ccctgaccac cgacaagagc agcagcaccg cctacatgca gctgagcagc    1020

ctgaccagcg aggacagcgc cgtgtactac tgcgcccgct actacgacga ccactactgc    1080

ctggactact ggggccaggg caccaccctg accgtgagca gcgtggaggg cggcagcggc    1140

ggcagcggcg gcagcggcgg cagcggcggc gtggacgaca tccagctgac ccagagcccc    1200

gccatcatga gcgccagccc cggcgagaag gtgaccatga cctgccgcgc cagcagcagc    1260

gtgagctaca tgaactggta ccagcagaag agcggcacca gccccaagcg ctggatctac    1320

gacaccagca aggtggccag cggcgtgccc taccgcttca gcggcagcgg cagcggcacc    1380

agctacagcc tgaccatcag cagcatggag gccgaggacg ccgccaccta ctactgccag    1440

cagtggagca gcaacccccct gaccttcggc gccggcacca agctggagct gaagggcggc    1500

ggcggcagcg gcggcggcgg cagcggcggc ggcggcagcg cctgcccctg ggccgtgagc    1560

ggcgcccgcg ccagccccgg cagcgccgcc agcccccgcc tgcgcgaggg ccccgagctg    1620

agccccgacg accccgccgg cctgctggac ctgcgccagg gcatgttcgc ccagctggtg    1680

gcccagaacg tgctgctgat cgacggcccc ctgagctggt acagcgaccc cggcctggcc    1740

ggcgtgagcc tgaccggcgg cctgagctac aaggaggaca ccaaggagct ggtggtggcc    1800

aaggccggcg tgtactacgt gttcttccag ctggagctgc gccgcgtggt ggccggcgag    1860

ggcagcggca gcgtgagcct ggccctgcac ctgcagcccc tgcgcagcgc cgccggcgcc    1920

gccgccctgg ccctgaccgt ggacctgccc cccgccagca gcgaggcccg caacagcgcc    1980

ttcggcttcc agggccgcct gctgcacctg agcgccggcc agcgcctggg cgtgcacctg    2040

cacaccgagg cccgcgcccg ccacgcctgg cagctgaccc agggcgccac cgtgctgggc    2100

ctgttccgcg tgacccccga gatccccgcc ggcctgccca gcccccgcag cgag          2154
```

<210> SEQ ID NO 179
<211> LENGTH: 784
<212> TYPE: PRT
<213> ORGANISM: Artificial
<220> FEATURE:
<223> OTHER INFORMATION: The amino acid sequence of CD19-CD3-4-1BBL TsM_D dimer

<400> SEQUENCE: 179

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365
```

```
Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Ala Cys Pro Trp Ala Val Ser Gly Ala Arg Ala Ser Pro
            580                 585                 590

Gly Ser Ala Ala Ser Pro Arg Leu Arg Glu Gly Pro Glu Leu Ser Pro
        595                 600                 605

Asp Asp Pro Ala Gly Leu Leu Asp Leu Arg Gln Gly Met Phe Ala Gln
    610                 615                 620

Leu Val Ala Gln Asn Val Leu Leu Ile Asp Gly Pro Leu Ser Trp Tyr
625                 630                 635                 640

Ser Asp Pro Gly Leu Ala Gly Val Ser Leu Thr Gly Gly Leu Ser Tyr
                645                 650                 655

Lys Glu Asp Thr Lys Glu Leu Val Val Ala Lys Ala Gly Val Tyr Tyr
            660                 665                 670

Val Phe Phe Gln Leu Glu Leu Arg Arg Val Val Ala Gly Glu Gly Ser
        675                 680                 685

Gly Ser Val Ser Leu Ala Leu His Leu Gln Pro Leu Arg Ser Ala Ala
    690                 695                 700

Gly Ala Ala Ala Leu Ala Leu Thr Val Asp Leu Pro Pro Ala Ser Ser
705                 710                 715                 720

Glu Ala Arg Asn Ser Ala Phe Gly Phe Gln Gly Arg Leu Leu His Leu
                725                 730                 735

Ser Ala Gly Gln Arg Leu Gly Val His Leu His Thr Glu Ala Arg Ala
            740                 745                 750

Arg His Ala Trp Gln Leu Thr Gln Gly Ala Thr Val Leu Gly Leu Phe
        755                 760                 765

Arg Val Thr Pro Glu Ile Pro Ala Gly Leu Pro Ser Pro Arg Ser Glu
    770                 775                 780
```

```
<210> SEQ ID NO 180
<211> LENGTH: 2352
<212> TYPE: DNA
<213> ORGANISM: Artificial
<220> FEATURE:
<223> OTHER INFORMATION: The nucleotide sequence of CD19-CD3-4-1BBL
      TsM_D dimer

<400> SEQUENCE: 180

gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180

ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggcggcggcg gcagcgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaaccccct gaccttcggc gccggcacca agctggagct gaaggccagc   1500

aagagcaaga aggagatctt ccgctggccc gagagcccca aggcccaggc cagcagcgtg   1560

cccaccgccc agccccaggc cgagggcagc ctggccaagg ccaccaccgc ccccgccacc   1620

acccgcaaca ccggccgcgg cggcgaggag aagaagaagg agaaggagaa ggaggagcag   1680

gaggagcgcg agaccaagac ccccgagtgc cccagccaca cccagcccct gggcgtggcc   1740

tgcccctggg ccgtgagcgg cgcccgcgcc agccccggca gcgccgccag cccccgcctg   1800

cgcgagggcc ccgagctgag ccccgacgac cccgccggcc tgctggacct gcgccagggc   1860

atgttcgccc agctggtggc ccagaacgtg ctgctgatcg acggccccct gagctggtac   1920

agcgaccccg gcctggccgg cgtgagcctg accggcggcc tgagctacaa ggaggacacc   1980

aaggagctgg tggtggccaa ggccggcgtg tactacgtgt tcttccagct ggagctgcgc   2040

cgcgtggtgg ccggcgaggg cagcggcagc gtgagcctgg ccctgcacct gcagcccctg   2100
```

```
cgcagcgccg ccggcgccgc cgccctggcc ctgaccgtgg acctgccccc cgccagcagc   2160

gaggcccgca acagcgcctt cggcttccag ggccgcctgc tgcacctgag cgccggccag   2220

cgcctgggcg tgcacctgca caccgaggcc cgcgcccgcc acgcctggca gctgacccag   2280

ggcgccaccg tgctgggcct gttccgcgtg acccccgaga tccccgccgg cctgcccagc   2340

ccccgcagcg ag                                                        2352
```

```
<210> SEQ ID NO 181
<211> LENGTH: 751
<212> TYPE: PRT
<213> ORGANISM: Artificial
<220> FEATURE:
<223> OTHER INFORMATION: The amino acid sequence of CD19-CD3-B7RP-1
      TsM_M monomer

<400> SEQUENCE: 181

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300
```

-continued

```
Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Asp Thr Gln Glu Lys Glu Val Arg Ala Met Val Gly Ser Asp Val
        515                 520                 525

Glu Leu Ser Cys Ala Cys Pro Glu Gly Ser Arg Phe Asp Leu Asn Asp
    530                 535                 540

Val Tyr Val Tyr Trp Gln Thr Ser Glu Ser Lys Thr Val Val Thr Tyr
545                 550                 555                 560

His Ile Pro Gln Asn Ser Ser Leu Glu Asn Val Asp Ser Arg Tyr Arg
                565                 570                 575

Asn Arg Ala Leu Met Ser Pro Ala Gly Met Leu Arg Gly Asp Phe Ser
            580                 585                 590

Leu Arg Leu Phe Asn Val Thr Pro Gln Asp Glu Gln Lys Phe His Cys
        595                 600                 605

Leu Val Leu Ser Gln Ser Leu Gly Phe Gln Glu Val Leu Ser Val Glu
    610                 615                 620

Val Thr Leu His Val Ala Ala Asn Phe Ser Val Pro Val Val Ser Ala
625                 630                 635                 640

Pro His Ser Pro Ser Gln Asp Glu Leu Thr Phe Thr Cys Thr Ser Ile
                645                 650                 655

Asn Gly Tyr Pro Arg Pro Asn Val Tyr Trp Ile Asn Lys Thr Asp Asn
            660                 665                 670

Ser Leu Leu Asp Gln Ala Leu Gln Asn Asp Thr Val Phe Leu Asn Met
        675                 680                 685

Arg Gly Leu Tyr Asp Val Val Ser Val Leu Arg Ile Ala Arg Thr Pro
    690                 695                 700

Ser Val Asn Ile Gly Cys Cys Ile Glu Asn Val Leu Leu Gln Gln Asn
705                 710                 715                 720

Leu Thr Val Gly Ser Gln Thr Gly Asn Asp Ile Gly Glu Arg Asp Lys
```

```
                725                 730                 735

Ile Thr Glu Asn Pro Val Ser Thr Gly Glu Lys Asn Ala Ala Thr
            740                 745                 750


<210> SEQ ID NO 182
<211> LENGTH: 2253
<212> TYPE: DNA
<213> ORGANISM: Artificial
<220> FEATURE:
<223> OTHER INFORMATION: The nucleotide sequence of CD19-CD3-B7RP-1
      TsM_M monomer

<400> SEQUENCE: 182

gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600

agcagcagca ccgcctacat gcagctgagc agcctggcca gcgaggacag cgccgtgtac     660

ttctgcgccc gccgcgagac caccaccgtg ggccgctact actacgccat ggactactgg     720

ggccagggca ccaccgtgac cgtgagcagc ggcggcggcg gcagcgacat caagctgcag     780

cagagcggcg ccgagctggc ccgccccggc gccagcgtga agatgagctg caagaccagc     840

ggctacacct tcacccgcta caccatgcac tgggtgaagc agcgccccgg ccagggcctg     900

gagtggatcg gctacatcaa ccccagccgc ggctacacca actacaacca gaagttcaag     960

gacaaggcca ccctgaccac cgacaagagc agcagcaccg cctacatgca gctgagcagc    1020

ctgaccagcg aggacagcgc cgtgtactac tgcgcccgct actacgacga ccactactgc    1080

ctggactact ggggccaggg caccaccctg accgtgagca gcgtggaggg cggcagcggc    1140

ggcagcggcg gcagcggcgg cagcggcggc gtggacgaca tccagctgac ccagagcccc    1200

gccatcatga gcgccagccc cggcgagaag gtgaccatga cctgccgcgc cagcagcagc    1260

gtgagctaca tgaactggta ccagcagaag agcggcacca gccccaagcg ctggatctac    1320

gacaccagca aggtggccag cggcgtgccc taccgcttca gcggcagcgg cagcggcacc    1380

agctacagcc tgaccatcag cagcatggag gccgaggacg ccgccaccta ctactgccag    1440

cagtggagca gcaacccccct gaccttcggc gccggcacca agctggagct gaagggcggc    1500

ggcggcagcg gcggcggcgg cagcggcggc ggcggcagcg acacccagga gaaggaggtg    1560

cgcgccatgg tgggcagcga cgtggagctg agctgcgcct gccccgaggg cagccgcttc    1620

gacctgaacg acgtgtacgt gtactggcag accagcgaga gcaagaccgt ggtgacctac    1680

cacatccccc agaacagcag cctggagaac gtggacagcc gctaccgcaa ccgcgccctg    1740

atgagccccg ccggcatgct gcgcggcgac ttcagcctgc gcctgttcaa cgtgaccccc    1800

caggacgagc agaagttcca ctgcctggtg ctgagccaga gcctgggctt ccaggaggtg    1860

ctgagcgtgg aggtgaccct gcacgtggcc gccaacttca gcgtgcccgt ggtgagcgcc    1920
```

```
ccccacagcc ccagccagga cgagctgacc ttcacctgca ccagcatcaa cggctacccc   1980

cgccccaacg tgtactggat caacaagacc gacaacagcc tgctggacca ggccctgcag   2040

aacgacaccg tgttcctgaa catgcgcggc ctgtacgacg tggtgagcgt gctgcgcatc   2100

gcccgcaccc ccagcgtgaa catcggctgc tgcatcgaga acgtgctgct gcagcagaac   2160

ctgaccgtgg gcagccagac cggcaacgac atcggcgagc gcgacaagat caccgagaac   2220

cccgtgagca ccggcgagaa gaacgccgcc acc                                2253


<210> SEQ ID NO 183
<211> LENGTH: 817
<212> TYPE: PRT
<213> ORGANISM: Artificial
<220> FEATURE:
<223> OTHER INFORMATION: The amino acid sequence of CD19-CD3-B7RP-1
      TsM_D dimer

<400> SEQUENCE: 183

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
```

-continued

```
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Asp Thr Gln Glu Lys Glu Val Arg Ala Met Val Gly Ser
            580                 585                 590

Asp Val Glu Leu Ser Cys Ala Cys Pro Glu Gly Ser Arg Phe Asp Leu
        595                 600                 605

Asn Asp Val Tyr Val Tyr Trp Gln Thr Ser Glu Ser Lys Thr Val Val
    610                 615                 620

Thr Tyr His Ile Pro Gln Asn Ser Ser Leu Glu Asn Val Asp Ser Arg
625                 630                 635                 640

Tyr Arg Asn Arg Ala Leu Met Ser Pro Ala Gly Met Leu Arg Gly Asp
                645                 650                 655

Phe Ser Leu Arg Leu Phe Asn Val Thr Pro Gln Asp Glu Gln Lys Phe
            660                 665                 670

His Cys Leu Val Leu Ser Gln Ser Leu Gly Phe Gln Glu Val Leu Ser
        675                 680                 685

Val Glu Val Thr Leu His Val Ala Ala Asn Phe Ser Val Pro Val Val
    690                 695                 700

Ser Ala Pro His Ser Pro Ser Gln Asp Glu Leu Thr Phe Thr Cys Thr
705                 710                 715                 720
```

```
Ser Ile Asn Gly Tyr Pro Arg Pro Asn Val Tyr Trp Ile Asn Lys Thr
                725                 730                 735

Asp Asn Ser Leu Leu Asp Gln Ala Leu Gln Asn Asp Thr Val Phe Leu
            740                 745                 750

Asn Met Arg Gly Leu Tyr Asp Val Val Ser Val Leu Arg Ile Ala Arg
        755                 760                 765

Thr Pro Ser Val Asn Ile Gly Cys Cys Ile Glu Asn Val Leu Leu Gln
    770                 775                 780

Gln Asn Leu Thr Val Gly Ser Gln Thr Gly Asn Asp Ile Gly Glu Arg
785                 790                 795                 800

Asp Lys Ile Thr Glu Asn Pro Val Ser Thr Gly Glu Lys Asn Ala Ala
                805                 810                 815

Thr


<210> SEQ ID NO 184
<211> LENGTH: 2451
<212> TYPE: DNA
<213> ORGANISM: Artificial
<220> FEATURE:
<223> OTHER INFORMATION: The nucleotide sequence of CD19-CD3-B7RP-1
      TsM_D dimer

<400> SEQUENCE: 184

gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600

agcagcagca ccgcctacat gcagctgagc agcctggcca gcgaggacag cgccgtgtac     660

ttctgcgccc gccgcgagac caccaccgtg ggccgctact actacgccat ggactactgg     720

ggccagggca ccaccgtgac cgtgagcagc ggcggcggcg gcagcgacat caagctgcag     780

cagagcggcg ccgagctggc ccgccccggc gccagcgtga agatgagctg caagaccagc     840

ggctacacct tcacccgcta caccatgcac tgggtgaagc agcgccccgg ccagggcctg     900

gagtggatcg gctacatcaa ccccagccgc ggctacacca actacaacca gaagttcaag     960

gacaaggcca ccctgaccac cgacaagagc agcagcaccg cctacatgca gctgagcagc    1020

ctgaccagcg aggacagcgc cgtgtactac tgcgcccgct actacgacga ccactactgc    1080

ctggactact ggggccaggg caccaccctg accgtgagca gcgtggaggg cggcagcggc    1140

ggcagcggcg gcagcggcgg cagcggcggc gtggacgaca tccagctgac ccagagcccc    1200

gccatcatga gcgccagccc cggcgagaag gtgaccatga cctgccgcgc cagcagcagc    1260

gtgagctaca tgaactggta ccagcagaag agcggcacca gccccaagcg ctggatctac    1320

gacaccagca aggtggccag cggcgtgccc taccgcttca gcggcagcgg cagcggcacc    1380

agctacagcc tgaccatcag cagcatggag gccgaggacg ccgccaccta ctactgccag    1440
```

```
cagtggagca gcaacccccct gaccttcggc gccggcacca agctggagct gaaggccagc   1500

aagagcaaga aggagatctt ccgctggccc gagagcccca aggcccaggc cagcagcgtg   1560

cccaccgccc agccccaggc cgagggcagc ctggccaagg ccaccaccgc ccccgccacc   1620

acccgcaaca ccggccgcgg cggcgaggag aagaagaagg agaaggagaa ggaggagcag   1680

gaggagcgcg agaccaagac ccccgagtgc cccagccaca cccagcccct gggcgtggac   1740

acccaggaga aggaggtgcg cgccatggtg ggcagcgacg tggagctgag ctgcgcctgc   1800

cccgagggca gccgcttcga cctgaacgac gtgtacgtgt actggcagac cagcgagagc   1860

aagaccgtgg tgacctacca catcccccag aacagcagcc tggagaacgt ggacagccgc   1920

taccgcaacc gcgccctgat gagccccgcc ggcatgctgc gcggcgactt cagcctgcgc   1980

ctgttcaacg tgacccccca ggacgagcag aagttccact gcctggtgct gagccagagc   2040

ctgggcttcc aggaggtgct gagcgtggag gtgaccctgc acgtggccgc caacttcagc   2100

gtgcccgtgg tgagcgcccc ccacagcccc agccaggacg agctgacctt cacctgcacc   2160

agcatcaacg gctacccccg ccccaacgtg tactggatca acaagaccga caacagcctg   2220

ctggaccagg ccctgcagaa cgacaccgtg ttcctgaaca tgcgcggcct gtacgacgtg   2280

gtgagcgtgc tgcgcatcgc ccgcaccccc agcgtgaaca tcggctgctg catcgagaac   2340

gtgctgctgc agcagaacct gaccgtgggc agccagaccg gcaacgacat cggcgagcgc   2400

gacaagatca ccgagaaccc cgtgagcacc ggcgagaaga acgccgccac c             2451
```

<210> SEQ ID NO 185
<211> LENGTH: 646
<212> TYPE: PRT
<213> ORGANISM: Artificial
<220> FEATURE:
<223> OTHER INFORMATION: The amino acid sequence of CD19-CD3-OX40L TsM_M monomer

<400> SEQUENCE: 185

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175
```

-continued

```
Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Gln Val Ser His Arg Tyr Pro Arg Ile Gln Ser Ile Lys Val Gln
        515                 520                 525

Phe Thr Glu Tyr Lys Lys Glu Lys Gly Phe Ile Leu Thr Ser Gln Lys
    530                 535                 540

Glu Asp Glu Ile Met Lys Val Gln Asn Asn Ser Val Ile Ile Asn Cys
545                 550                 555                 560

Asp Gly Phe Tyr Leu Ile Ser Leu Lys Gly Tyr Phe Ser Gln Glu Val
                565                 570                 575

Asn Ile Ser Leu His Tyr Gln Lys Asp Glu Glu Pro Leu Phe Gln Leu
            580                 585                 590

Lys Lys Val Arg Ser Val Asn Ser Leu Met Val Ala Ser Leu Thr Tyr
```

```
        595                 600                 605

Lys Asp Lys Val Tyr Leu Asn Val Thr Thr Asp Asn Thr Ser Leu Asp
    610                 615                 620

Asp Phe His Val Asn Gly Gly Glu Leu Ile Leu Ile His Gln Asn Pro
625                 630                 635                 640

Gly Glu Phe Cys Val Leu
                645


<210> SEQ ID NO 186
<211> LENGTH: 1938
<212> TYPE: DNA
<213> ORGANISM: Artificial
<220> FEATURE:
<223> OTHER INFORMATION: The nucleotide sequence of CD19-CD3-OX40L TsM_M
      monomer

<400> SEQUENCE: 186

gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180

ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggcggcggcg gcagcgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaacccct gaccttcggc gccggcacca agctggagct gaagggcggc   1500

ggcggcagcg gcggcggcgg cagcggcggc ggcggcagcc aggtgagcca ccgctacccc   1560

cgcatccaga gcatcaaggt gcagttcacc gagtacaaga aggagaaggg cttcatcctg   1620

accagccaga aggaggacga gatcatgaag gtgcagaaca acagcgtgat catcaactgc   1680

gacggcttct acctgatcag cctgaagggc tacttcagcc aggaggtgaa catcagcctg   1740
```

```
cactaccaga aggacgagga gcccctgttc cagctgaaga aggtgcgcag cgtgaacagc   1800

ctgatggtgg ccagcctgac ctacaaggac aaggtgtacc tgaacgtgac caccgacaac   1860

accagcctgg acgacttcca cgtgaacggc ggcgagctga tcctgatcca ccagaacccc   1920

ggcgagttct gcgtgctg                                                  1938


<210> SEQ ID NO 187
<211> LENGTH: 712
<212> TYPE: PRT
<213> ORGANISM: Artificial
<220> FEATURE:
<223> OTHER INFORMATION: The amino acid sequence of CD19-CD3-OX40L TsM_D
      dimer

<400> SEQUENCE: 187

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320
```

```
Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Gln Val Ser His Arg Tyr Pro Arg Ile Gln Ser Ile Lys
            580                 585                 590

Val Gln Phe Thr Glu Tyr Lys Lys Glu Lys Gly Phe Ile Leu Thr Ser
        595                 600                 605

Gln Lys Glu Asp Glu Ile Met Lys Val Gln Asn Asn Ser Val Ile Ile
    610                 615                 620

Asn Cys Asp Gly Phe Tyr Leu Ile Ser Leu Lys Gly Tyr Phe Ser Gln
625                 630                 635                 640

Glu Val Asn Ile Ser Leu His Tyr Gln Lys Asp Glu Glu Pro Leu Phe
                645                 650                 655

Gln Leu Lys Lys Val Arg Ser Val Asn Ser Leu Met Val Ala Ser Leu
            660                 665                 670

Thr Tyr Lys Asp Lys Val Tyr Leu Asn Val Thr Thr Asp Asn Thr Ser
        675                 680                 685

Leu Asp Asp Phe His Val Asn Gly Gly Glu Leu Ile Leu Ile His Gln
    690                 695                 700

Asn Pro Gly Glu Phe Cys Val Leu
705                 710
```

<210> SEQ ID NO 188
<211> LENGTH: 2136

<212> TYPE: DNA
<213> ORGANISM: Artificial
<220> FEATURE:
<223> OTHER INFORMATION: The nucleotide sequence of CD19-CD3-OX40L TsM_D
      dimer

<400> SEQUENCE: 188

```
gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180

ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggcggcggcg gcagcgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaacccccct gaccttcggc gccggcacca agctggagct gaaggccagc   1500

aagagcaaga aggagatctt ccgctggccc gagagcccca aggcccaggc cagcagcgtg   1560

cccaccgccc agccccaggc cgagggcagc ctggccaagg ccaccaccgc cccgccacc   1620

acccgcaaca ccggccgcgg cggcgaggag aagaagaagg agaaggagaa ggaggagcag   1680

gaggagcgcg agaccaagac ccccgagtgc cccagccaca cccagcccct gggcgtgcag   1740

gtgagccacc gctacccccg catccagagc atcaaggtgc agttcaccga gtacaagaag   1800

gagaagggct tcatcctgac cagccagaag gaggacgaga tcatgaaggt gcagaacaac   1860

agcgtgatca tcaactgcga cggcttctac ctgatcagcc tgaagggcta cttcagccag   1920

gaggtgaaca tcagcctgca ctaccagaag gacgaggagc ccctgttcca gctgaagaag   1980

gtgcgcagcg tgaacagcct gatggtggcc agcctgacct acaaggacaa ggtgtacctg   2040

aacgtgacca ccgacaacac cagcctggac gacttccacg tgaacggcgg cgagctgatc   2100

ctgatccacc agaaccccgg cgagttctgc gtgctg                              2136
```

<210> SEQ ID NO 189
<211> LENGTH: 641
<212> TYPE: PRT
<213> ORGANISM: Artificial
<220> FEATURE:
<223> OTHER INFORMATION: The amino acid sequence of CD19-CD3-GITRL TsM_M monomer

<400> SEQUENCE: 189

Asp Ile Gln Leu Thr Gln Ser Pro Ala Ser Leu Ala Val Ser Leu Gly
1 5 10 15

Gln Arg Ala Thr Ile Ser Cys Lys Ala Ser Gln Ser Val Asp Tyr Asp
20 25 30

Gly Asp Ser Tyr Leu Asn Trp Tyr Gln Gln Ile Pro Gly Gln Pro Pro
35 40 45

Lys Leu Leu Ile Tyr Asp Ala Ser Asn Leu Val Ser Gly Ile Pro Pro
50 55 60

Arg Phe Ser Gly Ser Gly Ser Gly Thr Asp Phe Thr Leu Asn Ile His
65 70 75 80

Pro Val Glu Lys Val Asp Ala Ala Thr Tyr His Cys Gln Gln Ser Thr
85 90 95

Glu Asp Pro Trp Thr Phe Gly Gly Gly Thr Lys Leu Glu Ile Lys Gly
100 105 110

Gly Gly Gly Ser Gly Gly Gly Gly Ser Gly Gly Gly Gly Ser Gln Val
115 120 125

Gln Leu Gln Gln Ser Gly Ala Glu Leu Val Arg Pro Gly Ser Ser Val
130 135 140

Lys Ile Ser Cys Lys Ala Ser Gly Tyr Ala Phe Ser Ser Tyr Trp Met
145 150 155 160

Asn Trp Val Lys Gln Arg Pro Gly Gln Gly Leu Glu Trp Ile Gly Gln
165 170 175

Ile Trp Pro Gly Asp Gly Asp Thr Asn Tyr Asn Gly Lys Phe Lys Gly
180 185 190

Lys Ala Thr Leu Thr Ala Asp Glu Ser Ser Ser Thr Ala Tyr Met Gln
195 200 205

Leu Ser Ser Leu Ala Ser Glu Asp Ser Ala Val Tyr Phe Cys Ala Arg
210 215 220

Arg Glu Thr Thr Thr Val Gly Arg Tyr Tyr Tyr Ala Met Asp Tyr Trp
225 230 235 240

Gly Gln Gly Thr Thr Val Thr Val Ser Ser Gly Gly Gly Gly Ser Asp
245 250 255

Ile Lys Leu Gln Gln Ser Gly Ala Glu Leu Ala Arg Pro Gly Ala Ser
260 265 270

Val Lys Met Ser Cys Lys Thr Ser Gly Tyr Thr Phe Thr Arg Tyr Thr
275 280 285

Met His Trp Val Lys Gln Arg Pro Gly Gln Gly Leu Glu Trp Ile Gly
290 295 300

Tyr Ile Asn Pro Ser Arg Gly Tyr Thr Asn Tyr Asn Gln Lys Phe Lys
305 310 315 320

Asp Lys Ala Thr Leu Thr Thr Asp Lys Ser Ser Ser Thr Ala Tyr Met
325 330 335

Gln Leu Ser Ser Leu Thr Ser Glu Asp Ser Ala Val Tyr Tyr Cys Ala
340 345 350

Arg Tyr Tyr Asp Asp His Tyr Cys Leu Asp Tyr Trp Gly Gln Gly Thr

```
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Gln Leu Glu Thr Ala Lys Glu Pro Cys Met Ala Lys Phe Gly Pro
        515                 520                 525

Leu Pro Ser Lys Trp Gln Met Ala Ser Ser Glu Pro Pro Cys Val Asn
    530                 535                 540

Lys Val Ser Asp Trp Lys Leu Glu Ile Leu Gln Asn Gly Leu Tyr Leu
545                 550                 555                 560

Ile Tyr Gly Gln Val Ala Pro Asn Ala Asn Tyr Asn Asp Val Ala Pro
                565                 570                 575

Phe Glu Val Arg Leu Tyr Lys Asn Lys Asp Met Ile Gln Thr Leu Thr
            580                 585                 590

Asn Lys Ser Lys Ile Gln Asn Val Gly Gly Thr Tyr Glu Leu His Val
        595                 600                 605

Gly Asp Thr Ile Asp Leu Ile Phe Asn Ser Glu His Gln Val Leu Lys
    610                 615                 620

Asn Asn Thr Tyr Trp Gly Ile Ile Leu Leu Ala Asn Pro Gln Phe Ile
625                 630                 635                 640

Ser


<210> SEQ ID NO 190
<211> LENGTH: 1923
<212> TYPE: DNA
<213> ORGANISM: Artificial
<220> FEATURE:
<223> OTHER INFORMATION: The nucleotide sequence of CD19-CD3-GITRL TsM_M
      monomer

<400> SEQUENCE: 190

gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420
```

ggcagcagcg tgaagatcag ctgcaaggcc agcggctacg ccttcagcag ctactggatg 480
aactgggtga agcagcgccc cggccagggc ctggagtgga tcggccagat ctggcccggc 540
gacggcgaca ccaactacaa cggcaagttc aagggcaagg ccaccctgac cgccgacgag 600
agcagcagca ccgcctacat gcagctgagc agcctggcca gcgaggacag cgccgtgtac 660
ttctgcgccc gccgcgagac caccaccgtg ggccgctact actacgccat ggactactgg 720
ggccagggca ccaccgtgac cgtgagcagc ggcggcggcg gcagcgacat caagctgcag 780
cagagcggcg ccgagctggc ccgccccggc gccagcgtga agatgagctg caagaccagc 840
ggctacacct tcacccgcta caccatgcac tgggtgaagc agcgccccgg ccagggcctg 900
gagtggatcg gctacatcaa ccccagccgc ggctacacca actacaacca gaagttcaag 960
gacaaggcca ccctgaccac cgacaagagc agcagcaccg cctacatgca gctgagcagc 1020
ctgaccagcg aggacagcgc cgtgtactac tgcgcccgct actacgacga ccactactgc 1080
ctggactact ggggccaggg caccaccctg accgtgagca gcgtggaggg cggcagcggc 1140
ggcagcggcg gcagcggcgg cagcggcggc gtggacgaca tccagctgac ccagagcccc 1200
gccatcatga gcgccagccc cggcgagaag gtgaccatga cctgccgcgc cagcagcagc 1260
gtgagctaca tgaactggta ccagcagaag agcggcacca gccccaagcg ctggatctac 1320
gacaccagca aggtggccag cggcgtgccc taccgcttca gcggcagcgg cagcggcacc 1380
agctacagcc tgaccatcag cagcatggag gccgaggacg ccgccaccta ctactgccag 1440
cagtggagca gcaacccct gaccttcggc gccggcacca agctggagct gaagggcggc 1500
ggcggcagcg gcggcggcgg cagcggcggc ggcggcagcc agctggagac cgccaaggag 1560
ccctgcatgg ccaagttcgg cccccctgccc agcaagtggc agatggccag cagcgagccc 1620
ccctgcgtga acaaggtgag cgactggaag ctggagatcc tgcagaacgg cctgtacctg 1680
atctacggcc aggtggcccc caacgccaac tacaacgacg tggcccccctt cgaggtgcgc 1740 ctgtacaaga acaaggacat gatccagacc ctgaccaaca agagcaagat ccagaacgtg 1800
ggcggcacct acgagctgca cgtgggcgac accatcgacc tgatcttcaa cagcgagcac 1860
caggtgctga agaacaacac ctactggggc atcatcctgc tggccaaccc ccagttcatc 1920
agc 1923

<210> SEQ ID NO 191
<211> LENGTH: 707
<212> TYPE: PRT
<213> ORGANISM: Artificial
<220> FEATURE:
<223> OTHER INFORMATION: The amino acid sequence of CD19-CD3-GITRL TsM_D dimer

<400> SEQUENCE: 191

Asp Ile Gln Leu Thr Gln Ser Pro Ala Ser Leu Ala Val Ser Leu Gly
1 5 10 15

Gln Arg Ala Thr Ile Ser Cys Lys Ala Ser Gln Ser Val Asp Tyr Asp
20 25 30

Gly Asp Ser Tyr Leu Asn Trp Tyr Gln Gln Ile Pro Gly Gln Pro Pro
35 40 45

Lys Leu Leu Ile Tyr Asp Ala Ser Asn Leu Val Ser Gly Ile Pro Pro
50 55 60

Arg Phe Ser Gly Ser Gly Ser Gly Thr Asp Phe Thr Leu Asn Ile His
65 70 75 80

```
Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
```

-continued

```
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Gln Leu Glu Thr Ala Lys Glu Pro Cys Met Ala Lys Phe
            580                 585                 590

Gly Pro Leu Pro Ser Lys Trp Gln Met Ala Ser Ser Glu Pro Pro Cys
        595                 600                 605

Val Asn Lys Val Ser Asp Trp Lys Leu Glu Ile Leu Gln Asn Gly Leu
    610                 615                 620

Tyr Leu Ile Tyr Gly Gln Val Ala Pro Asn Ala Asn Tyr Asn Asp Val
625                 630                 635                 640

Ala Pro Phe Glu Val Arg Leu Tyr Lys Asn Lys Asp Met Ile Gln Thr
                645                 650                 655

Leu Thr Asn Lys Ser Lys Ile Gln Asn Val Gly Gly Thr Tyr Glu Leu
            660                 665                 670

His Val Gly Asp Thr Ile Asp Leu Ile Phe Asn Ser Glu His Gln Val
        675                 680                 685

Leu Lys Asn Asn Thr Tyr Trp Gly Ile Ile Leu Leu Ala Asn Pro Gln
    690                 695                 700

Phe Ile Ser
705


<210> SEQ ID NO 192
<211> LENGTH: 2121
<212> TYPE: DNA
<213> ORGANISM: Artificial
<220> FEATURE:
<223> OTHER INFORMATION: The nucleotide sequence of CD19-CD3-GITRL TsM_D
      dimer

<400> SEQUENCE: 192

gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600

agcagcagca ccgcctacat gcagctgagc agcctggcca gcgaggacag cgccgtgtac     660

ttctgcgccc gccgcgagac caccaccgtg ggccgctact actacgccat ggactactgg     720

ggccagggca ccaccgtgac cgtgagcagc ggcggcggcg gcagcgacat caagctgcag     780

cagagcggcg ccgagctggc ccgccccggc gccagcgtga agatgagctg caagaccagc     840
```

```
ggctacacct tcacccgcta caccatgcac tgggtgaagc agcgccccgg ccagggcctg    900
gagtggatcg gctacatcaa ccccagccgc ggctacacca actacaacca gaagttcaag    960
gacaaggcca ccctgaccac cgacaagagc agcagcaccg cctacatgca gctgagcagc   1020
ctgaccagcg aggacagcgc cgtgtactac tgcgcccgct actacgacga ccactactgc   1080
ctggactact ggggccaggg caccaccctg accgtgagca gcgtggaggg cggcagcggc   1140
ggcagcggcg gcagcggcgg cagcggcggc gtggacgaca tccagctgac ccagagcccc   1200
gccatcatga gcgccagccc cggcgagaag gtgaccatga cctgccgcgc cagcagcagc   1260
gtgagctaca tgaactggta ccagcagaag agcggcacca gccccaagcg ctggatctac   1320
gacaccagca aggtggccag cggcgtgccc taccgcttca gcggcagcgg cagcggcacc   1380
agctacagcc tgaccatcag cagcatggag gccgaggacg ccgccaccta ctactgccag   1440
cagtggagca gcaacccccct gaccttcggc gccggcacca agctggagct gaaggccagc   1500
aagagcaaga aggagatctt ccgctggccc gagagcccca aggcccaggc cagcagcgtg   1560
cccaccgccc agccccaggc cgagggcagc ctggccaagg ccaccaccgc ccccgccacc   1620
acccgcaaca ccggccgcgg cggcgaggag aagaagaagg agaaggagaa ggaggagcag   1680
gaggagcgcg agaccaagac ccccgagtgc cccagccaca cccagcccct gggcgtgcag   1740
ctggagaccg ccaaggagcc ctgcatggcc aagttcggcc ccctgcccag caagtggcag   1800
atggccagca gcgagccccc ctgcgtgaac aaggtgagcg actggaagct ggagatcctg   1860
cagaacggcc tgtacctgat ctacggccag gtggccccca acgccaacta caacgacgtg   1920
gccccccttcg aggtgcgcct gtacaagaac aaggacatga tccagaccct gaccaacaag   1980
agcaagatcc agaacgtggg cggcacctac gagctgcacg tgggcgacac catcgacctg   2040
atcttcaaca gcgagcacca ggtgctgaag aacaacacct actggggcat catcctgctg   2100
gccaaccccc agttcatcag c                                             2121
```

<210> SEQ ID NO 193
<211> LENGTH: 668
<212> TYPE: PRT
<213> ORGANISM: Artificial
<220> FEATURE:
<223> OTHER INFORMATION: The amino acid sequence of CD19-CD3-CD70 TsM_M monomer

<400> SEQUENCE: 193

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125
```

```
Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Gln Arg Phe Ala Gln Ala Gln Gln Gln Leu Pro Leu Glu Ser Leu
        515                 520                 525

Gly Trp Asp Val Ala Glu Leu Gln Leu Asn His Thr Gly Pro Gln Gln
    530                 535                 540
```

-continued

```
Asp Pro Arg Leu Tyr Trp Gln Gly Gly Pro Ala Leu Gly Arg Ser Phe
545                 550                 555                 560

Leu His Gly Pro Glu Leu Asp Lys Gly Gln Leu Arg Ile His Arg Asp
                565                 570                 575

Gly Ile Tyr Met Val His Ile Gln Val Thr Leu Ala Ile Cys Ser Ser
            580                 585                 590

Thr Thr Ala Ser Arg His His Pro Thr Thr Leu Ala Val Gly Ile Cys
        595                 600                 605

Ser Pro Ala Ser Arg Ser Ile Ser Leu Leu Arg Leu Ser Phe His Gln
    610                 615                 620

Gly Cys Thr Ile Ala Ser Gln Arg Leu Thr Pro Leu Ala Arg Gly Asp
625                 630                 635                 640

Thr Leu Cys Thr Asn Leu Thr Gly Thr Leu Leu Pro Ser Arg Asn Thr
                645                 650                 655

Asp Glu Thr Phe Phe Gly Val Gln Trp Val Arg Pro
            660                 665
```

<210> SEQ ID NO 194
<211> LENGTH: 2004
<212> TYPE: DNA
<213> ORGANISM: Artificial
<220> FEATURE:
<223> OTHER INFORMATION: The nucleotide sequence of CD19-CD3-CD70 TsM_M monomer

<400> SEQUENCE: 194

```
gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180

ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggcggcggcg gcagcgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320
```

```
gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaacccccct gaccttcggc gccggcacca agctggagct gaagggcggc   1500

ggcggcagcg gcggcggcgg cagcggcggc ggcggcagcc agcgcttcgc ccaggcccag   1560

cagcagctgc ccctggagag cctgggctgg gacgtggccg agctgcagct gaaccacacc   1620

ggcccccagc aggacccccg cctgtactgg cagggcggcc ccgccctggg ccgcagcttc   1680

ctgcacggcc ccgagctgga caagggccag ctgcgcatcc accgcgacgg catctacatg   1740

gtgcacatcc aggtgaccct ggccatctgc agcagcacca ccgccagccg ccaccacccc   1800

accaccctgg ccgtgggcat ctgcagcccc gccagccgca gcatcagcct gctgcgcctg   1860

agcttccacc agggctgcac catcgccagc cagcgcctga ccccccctggc ccgcggcgac   1920

accctgtgca ccaacctgac cggcaccctg ctgcccagcc gcaacaccga cgagaccttc   1980

ttcggcgtgc agtgggtgcg cccc                                          2004
```

```
<210> SEQ ID NO 195
<211> LENGTH: 734
<212> TYPE: PRT
<213> ORGANISM: Artificial
<220> FEATURE:
<223> OTHER INFORMATION: The amino acid sequence of CD19-CD3-CD70 TsM_D
      dimer

<400> SEQUENCE: 195

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240
```

Gly Gln Gly Thr Thr Val Thr Val Ser Ser Gly Gly Gly Gly Ser Asp
245 250 255

Ile Lys Leu Gln Gln Ser Gly Ala Glu Leu Ala Arg Pro Gly Ala Ser
260 265 270

Val Lys Met Ser Cys Lys Thr Ser Gly Tyr Thr Phe Thr Arg Tyr Thr
275 280 285

Met His Trp Val Lys Gln Arg Pro Gly Gln Gly Leu Glu Trp Ile Gly
290 295 300

Tyr Ile Asn Pro Ser Arg Gly Tyr Thr Asn Tyr Asn Gln Lys Phe Lys
305 310 315 320

Asp Lys Ala Thr Leu Thr Thr Asp Lys Ser Ser Ser Thr Ala Tyr Met
325 330 335

Gln Leu Ser Ser Leu Thr Ser Glu Asp Ser Ala Val Tyr Tyr Cys Ala
340 345 350

Arg Tyr Tyr Asp Asp His Tyr Cys Leu Asp Tyr Trp Gly Gln Gly Thr
355 360 365

Thr Leu Thr Val Ser Ser Val Glu Gly Gly Ser Gly Gly Ser Gly Gly
370 375 380

Ser Gly Gly Ser Gly Gly Val Asp Asp Ile Gln Leu Thr Gln Ser Pro
385 390 395 400

Ala Ile Met Ser Ala Ser Pro Gly Glu Lys Val Thr Met Thr Cys Arg
405 410 415

Ala Ser Ser Ser Val Ser Tyr Met Asn Trp Tyr Gln Gln Lys Ser Gly
420 425 430

Thr Ser Pro Lys Arg Trp Ile Tyr Asp Thr Ser Lys Val Ala Ser Gly
435 440 445

Val Pro Tyr Arg Phe Ser Gly Ser Gly Ser Gly Thr Ser Tyr Ser Leu
450 455 460

Thr Ile Ser Ser Met Glu Ala Glu Asp Ala Ala Thr Tyr Tyr Cys Gln
465 470 475 480

Gln Trp Ser Ser Asn Pro Leu Thr Phe Gly Ala Gly Thr Lys Leu Glu
485 490 495

Leu Lys Ala Ser Lys Ser Lys Lys Glu Ile Phe Arg Trp Pro Glu Ser
500 505 510

Pro Lys Ala Gln Ala Ser Ser Val Pro Thr Ala Gln Pro Gln Ala Glu
515 520 525

Gly Ser Leu Ala Lys Ala Thr Thr Ala Pro Ala Thr Thr Arg Asn Thr
530 535 540

Gly Arg Gly Gly Glu Glu Lys Lys Lys Glu Lys Glu Lys Glu Glu Gln
545 550 555 560

Glu Glu Arg Glu Thr Lys Thr Pro Glu Cys Pro Ser His Thr Gln Pro
565 570 575

Leu Gly Val Gln Arg Phe Ala Gln Ala Gln Gln Gln Leu Pro Leu Glu
580 585 590

Ser Leu Gly Trp Asp Val Ala Glu Leu Gln Leu Asn His Thr Gly Pro
595 600 605

Gln Gln Asp Pro Arg Leu Tyr Trp Gln Gly Gly Pro Ala Leu Gly Arg
610 615 620

Ser Phe Leu His Gly Pro Glu Leu Asp Lys Gly Gln Leu Arg Ile His
625 630 635 640

Arg Asp Gly Ile Tyr Met Val His Ile Gln Val Thr Leu Ala Ile Cys
645 650 655

-continued

```
Ser Ser Thr Thr Ala Ser Arg His His Pro Thr Thr Leu Ala Val Gly
            660                 665                 670

Ile Cys Ser Pro Ala Ser Arg Ser Ile Ser Leu Leu Arg Leu Ser Phe
        675                 680                 685

His Gln Gly Cys Thr Ile Ala Ser Gln Arg Leu Thr Pro Leu Ala Arg
    690                 695                 700

Gly Asp Thr Leu Cys Thr Asn Leu Thr Gly Thr Leu Leu Pro Ser Arg
705                 710                 715                 720

Asn Thr Asp Glu Thr Phe Phe Gly Val Gln Trp Val Arg Pro
                725                 730


<210> SEQ ID NO 196
<211> LENGTH: 2202
<212> TYPE: DNA
<213> ORGANISM: Artificial
<220> FEATURE:
<223> OTHER INFORMATION: The nucleotide sequence of CD19-CD3-CD70 TsM_D
      dimer

<400> SEQUENCE: 196

gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600

agcagcagca ccgcctacat gcagctgagc agcctggcca gcgaggacag cgccgtgtac     660

ttctgcgccc gccgcgagac caccaccgtg ggccgctact actacgccat ggactactgg     720

ggccagggca ccaccgtgac cgtgagcagc ggcggcggcg gcagcgacat caagctgcag     780

cagagcggcg ccgagctggc ccgccccggc gccagcgtga agatgagctg caagaccagc     840

ggctacacct tcacccgcta caccatgcac tgggtgaagc agcgccccgg ccagggcctg     900

gagtggatcg gctacatcaa ccccagccgc ggctacacca actacaacca gaagttcaag     960

gacaaggcca ccctgaccac cgacaagagc agcagcaccg cctacatgca gctgagcagc    1020

ctgaccagcg aggacagcgc cgtgtactac tgcgcccgct actacgacga ccactactgc    1080

ctggactact ggggccaggg caccaccctg accgtgagca gcgtggaggg cggcagcggc    1140

ggcagcggcg gcagcggcgg cagcggcggc gtggacgaca tccagctgac ccagagcccc    1200

gccatcatga gcgccagccc cggcgagaag gtgaccatga cctgccgcgc cagcagcagc    1260

gtgagctaca tgaactggta ccagcagaag agcggcacca gccccaagcg ctggatctac    1320

gacaccagca aggtggccag cggcgtgccc taccgcttca gcggcagcgg cagcggcacc    1380

agctacagcc tgaccatcag cagcatggag gccgaggacg ccgccaccta ctactgccag    1440

cagtggagca gcaaccccct gaccttcggc gccggcacca agctggagct gaaggccagc    1500

aagagcaaga aggagatctt ccgctggccc gagagcccca aggcccaggc cagcagcgtg    1560

cccaccgccc agccccaggc cgagggcagc ctggccaagg ccaccaccgc ccccgccacc    1620
```

-continued

```
acccgcaaca ccggccgcgg cggcgaggag aagaagaagg agaaggagaa ggaggagcag   1680

gaggagcgcg agaccaagac ccccgagtgc cccagccaca cccagcccct gggcgtgcag   1740

cgcttcgccc aggcccagca gcagctgccc ctggagagcc tgggctggga cgtggccgag   1800

ctgcagctga accacaccgg cccccagcag gacccccgcc tgtactggca gggcggcccc   1860

gccctgggcc gcagcttcct gcacggcccc gagctggaca agggccagct gcgcatccac   1920

cgcgacggca tctacatggt gcacatccag gtgaccctgg ccatctgcag cagcaccacc   1980

gccagccgcc accaccccac caccctggcc gtgggcatct gcagccccgc cagccgcagc   2040

atcagcctgc tgcgcctgag cttccaccag ggctgcacca tcgccagcca gcgcctgacc   2100

cccctggccc gcggcgacac cctgtgcacc aacctgaccg gcaccctgct gcccagccgc   2160

aacaccgacg agaccttctt cggcgtgcag tgggtgcgcc cc                      2202
```

<210> SEQ ID NO 197
<211> LENGTH: 250
<212> TYPE: PRT
<213> ORGANISM: Artificial
<220> FEATURE:
<223> OTHER INFORMATION: The amino acid sequence of anti-CD19 scFv

<400> SEQUENCE: 197

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser
                245                 250
```

<210> SEQ ID NO 198
<211> LENGTH: 124
<212> TYPE: PRT
<213> ORGANISM: Artificial
<220> FEATURE:
<223> OTHER INFORMATION: The amino acid sequence of anti-CD19 scFv heavy chain variable region

<400> SEQUENCE: 198

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

<210> SEQ ID NO 199
<211> LENGTH: 111
<212> TYPE: PRT
<213> ORGANISM: Artificial
<220> FEATURE:
<223> OTHER INFORMATION: The amino acid sequence of anti-CD19 scFv light chain variable region

<400> SEQUENCE: 199

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110
```

<210> SEQ ID NO 200
<211> LENGTH: 243
<212> TYPE: PRT
<213> ORGANISM: Artificial
<220> FEATURE:
<223> OTHER INFORMATION: The amino acid sequence of anti-CD3 scFv

<400> SEQUENCE: 200

```
Asp Ile Lys Leu Gln Gln Ser Gly Ala Glu Leu Ala Arg Pro Gly Ala
1               5                   10                  15
```

```
Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys
```

```
<210> SEQ ID NO 201
<211> LENGTH: 119
<212> TYPE: PRT
<213> ORGANISM: Artificial
<220> FEATURE:
<223> OTHER INFORMATION: The amino acid sequence of anti-CD3 scFv heavy
      chain variable region

<400> SEQUENCE: 201

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115
```

<210> SEQ ID NO 202
<211> LENGTH: 106
<212> TYPE: PRT
<213> ORGANISM: Artificial
<220> FEATURE:
<223> OTHER INFORMATION: The amino acid sequence of anti-CD3 scFv light chain variable region

<400> SEQUENCE: 202

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105
```

<210> SEQ ID NO 203
<211> LENGTH: 205
<212> TYPE: PRT
<213> ORGANISM: Artificial
<220> FEATURE:
<223> OTHER INFORMATION: The amino acid sequence of 4-1BBL extracellular domain

<400> SEQUENCE: 203

```
Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Arg
    130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
            180                 185                 190
```

```
Pro Glu Ile Pro Ala Gly Leu Pro Ser Pro Arg Ser Glu
        195                 200                 205


<210> SEQ ID NO 204
<211> LENGTH: 238
<212> TYPE: PRT
<213> ORGANISM: Artificial
<220> FEATURE:
<223> OTHER INFORMATION: The amino acid sequence of B7RP-1 extracellular
      domain

<400> SEQUENCE: 204

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asn Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235


<210> SEQ ID NO 205
<211> LENGTH: 133
<212> TYPE: PRT
<213> ORGANISM: Artificial
<220> FEATURE:
<223> OTHER INFORMATION: The amino acid sequence of OX40L extracellular
      domain

<400> SEQUENCE: 205

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45
```

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 206
<211> LENGTH: 128
<212> TYPE: PRT
<213> ORGANISM: Artificial
<220> FEATURE:
<223> OTHER INFORMATION: The amino acid sequence of GITRL extracellular domain

<400> SEQUENCE: 206

Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
            20                  25                  30

Val Ser Asp Trp Lys Leu Glu Ile Leu Gln Asn Gly Leu Tyr Leu Ile
        35                  40                  45

Tyr Gly Gln Val Ala Pro Asn Ala Asn Tyr Asn Asp Val Ala Pro Phe
    50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                85                  90                  95

Asp Thr Ile Asp Leu Ile Phe Asn Ser Glu His Gln Val Leu Lys Asn
            100                 105                 110

Asn Thr Tyr Trp Gly Ile Ile Leu Leu Ala Asn Pro Gln Phe Ile Ser
        115                 120                 125

<210> SEQ ID NO 207
<211> LENGTH: 155
<212> TYPE: PRT
<213> ORGANISM: Artificial
<220> FEATURE:
<223> OTHER INFORMATION: The amino acid sequence of CD70 extracellular domain

<400> SEQUENCE: 207

Gln Arg Phe Ala Gln Ala Gln Gln Gln Leu Pro Leu Glu Ser Leu Gly
1               5                   10                  15

Trp Asp Val Ala Glu Leu Gln Leu Asn His Thr Gly Pro Gln Gln Asp
            20                  25                  30

Pro Arg Leu Tyr Trp Gln Gly Gly Pro Ala Leu Gly Arg Ser Phe Leu
        35                  40                  45

His Gly Pro Glu Leu Asp Lys Gly Gln Leu Arg Ile His Arg Asp Gly
    50                  55                  60

Ile Tyr Met Val His Ile Gln Val Thr Leu Ala Ile Cys Ser Ser Thr
65                  70                  75                  80

-continued

Thr Ala Ser Arg His His Pro Thr Thr Leu Ala Val Gly Ile Cys Ser
85 90 95

Pro Ala Ser Arg Ser Ile Ser Leu Leu Arg Leu Ser Phe His Gln Gly
100 105 110

Cys Thr Ile Ala Ser Gln Arg Leu Thr Pro Leu Ala Arg Gly Asp Thr
115 120 125

Leu Cys Thr Asn Leu Thr Gly Thr Leu Leu Pro Ser Arg Asn Thr Asp
130 135 140

Glu Thr Phe Phe Gly Val Gln Trp Val Arg Pro
145 150 155

<210> SEQ ID NO 208
<211> LENGTH: 750
<212> TYPE: DNA
<213> ORGANISM: Artificial
<220> FEATURE:
<223> OTHER INFORMATION: The nucleotide sequence of anti-CD19 scFv

<400> SEQUENCE: 208
gacatccagc tgacccagag ccccgccagc ctggccgtga gcctgggcca gcgcgccacc 60
atcagctgca aggccagcca gagcgtggac tacgacggcg acagctacct gaactggtac 120
cagcagatcc ccggccagcc ccccaagctg ctgatctacg acgccagcaa cctggtgagc 180
ggcatccccc cccgcttcag cggcagcggc agcggcaccg acttcaccct gaacatccac 240
cccgtggaga aggtggacgc cgccacctac cactgccagc agagcaccga ggacccctgg 300
accttcggcg gcggcaccaa gctggagatc aagggcggcg gcggcagcgg cggcggcggc 360
agcggcggcg gcggcagcca ggtgcagctg cagcagagcg gcgccgagct ggtgcgcccc 420
ggcagcagcg tgaagatcag ctgcaaggcc agcggctacg ccttcagcag ctactggatg 480
aactgggtga agcagcgccc cggccagggc ctggagtgga tcggccagat ctggcccggc 540
gacggcgaca ccaactacaa cggcaagttc aagggcaagg ccaccctgac cgccgacgag 600
agcagcagca ccgcctacat gcagctgagc agcctggcca gcgaggacag cgccgtgtac 660
ttctgcgccc gccgcgagac caccaccgtg ggccgctact actacgccat ggactactgg 720
ggccagggca ccaccgtgac cgtgagcagc 750

<210> SEQ ID NO 209
<211> LENGTH: 372
<212> TYPE: DNA
<213> ORGANISM: Artificial
<220> FEATURE:
<223> OTHER INFORMATION: The nucleotide sequence of anti-CD19 scFv heavy
chain variable region

<400> SEQUENCE: 209
caggtgcagc tgcagcagag cggcgccgag ctggtgcgcc ccggcagcag cgtgaagatc 60
agctgcaagg ccagcggcta cgccttcagc agctactgga tgaactgggt gaagcagcgc 120
cccggccagg gcctggagtg gatcggccag atctggcccg gcgacggcga caccaactac 180
aacggcaagt tcaagggcaa ggccaccctg accgccgacg agagcagcag caccgcctac 240
atgcagctga gcagcctggc cagcgaggac agcgccgtgt acttctgcgc ccgccgcgag 300
accaccaccg tgggccgcta ctactacgcc atggactact ggggccaggg caccaccgtg 360
accgtgagca gc 372

<210> SEQ ID NO 210

<211> LENGTH: 333
<212> TYPE: DNA
<213> ORGANISM: Artificial
<220> FEATURE:
<223> OTHER INFORMATION: The nucleotide sequence of anti-CD19 scFv light chain variable region

<400> SEQUENCE: 210
gacatccagc tgacccagag ccccgccagc ctggccgtga gcctgggcca gcgcgccacc 60
atcagctgca aggccagcca gagcgtggac tacgacggcg acagctacct gaactggtac 120
cagcagatcc ccggccagcc ccccaagctg ctgatctacg acgccagcaa cctggtgagc 180
ggcatccccc cccgcttcag cggcagcggc agcggcaccg acttcaccct gaacatccac 240
cccgtggaga aggtggacgc cgccacctac cactgccagc agagcaccga ggacccctgg 300
accttcggcg gcggcaccaa gctggagatc aag 333

<210> SEQ ID NO 211
<211> LENGTH: 729
<212> TYPE: DNA
<213> ORGANISM: Artificial
<220> FEATURE:
<223> OTHER INFORMATION: The nucleotide sequence of anti-CD3 scFv

<400> SEQUENCE: 211
gacatcaagc tgcagcagag cggcgccgag ctggcccgcc ccggcgccag cgtgaagatg 60
agctgcaaga ccagcggcta caccttcacc cgctacacca tgcactgggt gaagcagcgc 120
cccggccagg gcctggagtg gatcggctac atcaacccca gccgcggcta caccaactac 180
aaccagaagt tcaaggacaa ggccaccctg accaccgaca agagcagcag caccgcctac 240
atgcagctga gcagcctgac cagcgaggac agcgccgtgt actactgcgc ccgctactac 300
gacgaccact actgcctgga ctactggggc cagggcacca ccctgaccgt gagcagcgtg 360
gagggcggca gcggcggcag cggcggcagc ggcggcagcg gcggcgtgga cgacatccag 420
ctgacccaga gccccgccat catgagcgcc agccccggcg agaaggtgac catgacctgc 480
cgcgccagca gcagcgtgag ctacatgaac tggtaccagc agaagagcgg caccagcccc 540
aagcgctgga tctacgacac cagcaaggtg gccagcggcg tgccctaccg cttcagcggc 600
agcggcagcg gcaccagcta cagcctgacc atcagcagca tggaggccga ggacgccgcc 660
acctactact gccagcagtg gagcagcaac cccctgacct tcggcgccgg caccaagctg 720
gagctgaag 729

<210> SEQ ID NO 212
<211> LENGTH: 357
<212> TYPE: DNA
<213> ORGANISM: Artificial
<220> FEATURE:
<223> OTHER INFORMATION: The nucleotide sequence of anti-CD3 scFv heavy chain variable region

<400> SEQUENCE: 212
gacatcaagc tgcagcagag cggcgccgag ctggcccgcc ccggcgccag cgtgaagatg 60
agctgcaaga ccagcggcta caccttcacc cgctacacca tgcactgggt gaagcagcgc 120
cccggccagg gcctggagtg gatcggctac atcaacccca gccgcggcta caccaactac 180
aaccagaagt tcaaggacaa ggccaccctg accaccgaca agagcagcag caccgcctac 240
atgcagctga gcagcctgac cagcgaggac agcgccgtgt actactgcgc ccgctactac 300
gacgaccact actgcctgga ctactggggc cagggcacca ccctgaccgt gagcagc 357

<210> SEQ ID NO 213
<211> LENGTH: 318
<212> TYPE: DNA
<213> ORGANISM: Artificial
<220> FEATURE:
<223> OTHER INFORMATION: The nucleotide sequence of anti-CD3 scFv light chain variable region

<400> SEQUENCE: 213
gacatccagc tgacccagag ccccgccatc atgagcgcca gccccggcga gaaggtgacc 60
atgacctgcc gcgccagcag cagcgtgagc tacatgaact ggtaccagca gaagagcggc 120
accagcccca agcgctggat ctacgacacc agcaaggtgg ccagcggcgt gccctaccgc 180
ttcagcggca gcggcagcgg caccagctac agcctgacca tcagcagcat ggaggccgag 240
gacgccgcca cctactactg ccagcagtgg agcagcaacc ccctgacctt cggcgccggc 300
accaagctgg agctgaag 318

<210> SEQ ID NO 214
<211> LENGTH: 615
<212> TYPE: DNA
<213> ORGANISM: Artificial
<220> FEATURE:
<223> OTHER INFORMATION: The nucleotide sequence of 4-1BBL extracellular region

<400> SEQUENCE: 214
gcctgcccct gggccgtgag cggcgcccgc gccagccccg gcagcgccgc cagcccccgc 60
ctgcgcgagg gccccgagct gagccccgac gaccccgccg gcctgctgga cctgcgccag 120
ggcatgttcg cccagctggt ggcccagaac gtgctgctga tcgacggccc cctgagctgg 180
tacagcgacc ccggcctggc cggcgtgagc ctgaccggcg gcctgagcta caaggaggac 240
accaaggagc tggtggtggc caaggccggc gtgtactacg tgttcttcca gctggagctg 300
cgccgcgtgg tggccggcga gggcagcggc agcgtgagcc tggccctgca cctgcagccc 360
ctgcgcagcg ccgccggcgc cgccgccctg gccctgaccg tggacctgcc ccccgccagc 420
agcgaggccc gcaacagcgc cttcggcttc cagggccgcc tgctgcacct gagcgccggc 480
cagcgcctgg gcgtgcacct gcacaccgag gcccgcgccc gccacgcctg gcagctgacc 540
cagggcgcca ccgtgctggg cctgttccgc gtgacccccg agatccccgc cggcctgccc 600
agcccccgca gcgag 615

<210> SEQ ID NO 215
<211> LENGTH: 714
<212> TYPE: DNA
<213> ORGANISM: Artificial
<220> FEATURE:
<223> OTHER INFORMATION: The nucleotide sequence of B7RP-1 extracellular domain

<400> SEQUENCE: 215
gacacccagg agaaggaggt gcgcgccatg gtgggcagcg acgtggagct gagctgcgcc 60
tgccccgagg gcagccgctt cgacctgaac gacgtgtacg tgtactggca gaccagcgag 120
agcaagaccg tggtgaccta ccacatcccc cagaacagca gcctggagaa cgtggacagc 180
cgctaccgca accgcgccct gatgagcccc gccggcatgc tgcgcggcga cttcagcctg 240
cgcctgttca acgtgacccc ccaggacgag cagaagttcc actgcctggt gctgagccag 300
agcctgggct tccaggaggt gctgagcgtg gaggtgaccc tgcacgtggc cgccaacttc 360
agcgtgcccg tggtgagcgc cccccacagc cccagccagg acgagctgac cttcacctgc 420
accagcatca acggctaccc ccgccccaac gtgtactgga tcaacaagac cgacaacagc 480
ctgctggacc aggccctgca gaacgacacc gtgttcctga acatgcgcgg cctgtacgac 540
gtggtgagcg tgctgcgcat cgcccgcacc cccagcgtga acatcggctg ctgcatcgag 600
aacgtgctgc tgcagcagaa cctgaccgtg ggcagccaga ccggcaacga catcggcgag 660
cgcgacaaga tcaccgagaa ccccgtgagc accggcgaga agaacgccgc cacc 714

<210> SEQ ID NO 216
<211> LENGTH: 399
<212> TYPE: DNA
<213> ORGANISM: Artificial
<220> FEATURE:
<223> OTHER INFORMATION: The nucleotide sequence of OX40L extracellular domain

<400> SEQUENCE: 216
caggtgagcc accgctaccc ccgcatccag agcatcaagg tgcagttcac cgagtacaag 60
aaggagaagg gcttcatcct gaccagccag aaggaggacg agatcatgaa ggtgcagaac 120
aacagcgtga tcatcaactg cgacggcttc tacctgatca gcctgaaggg ctacttcagc 180
caggaggtga acatcagcct gcactaccag aaggacgagg agcccctgtt ccagctgaag 240
aaggtgcgca gcgtgaacag cctgatggtg gccagcctga cctacaagga caaggtgtac 300
ctgaacgtga ccaccgacaa caccagcctg gacgacttcc acgtgaacgg cggcgagctg 360
atcctgatcc accagaaccc cggcgagttc tgcgtgctg 399

<210> SEQ ID NO 217
<211> LENGTH: 384
<212> TYPE: DNA
<213> ORGANISM: Artificial
<220> FEATURE:
<223> OTHER INFORMATION: The nucleotide sequence of GITRL extracellular domain

<400> SEQUENCE: 217
cagctggaga ccgccaagga gccctgcatg gccaagttcg gcccccctgcc cagcaagtgg 60 cagatggcca gcagcgagcc cccctgcgtg aacaaggtga gcgactggaa gctggagatc 120
ctgcagaacg gcctgtacct gatctacggc caggtggccc ccaacgccaa ctacaacgac 180
gtggccccct tcgaggtgcg cctgtacaag aacaaggaca tgatccagac cctgaccaac 240
aagagcaaga tccagaacgt gggcggcacc tacgagctgc acgtgggcga caccatcgac 300
ctgatcttca acagcgagca ccaggtgctg aagaacaaca cctactgggg catcatcctg 360
ctggccaacc cccagttcat cagc 384

<210> SEQ ID NO 218
<211> LENGTH: 465
<212> TYPE: DNA
<213> ORGANISM: Artificial
<220> FEATURE:
<223> OTHER INFORMATION: The nucleotide sequence of CD70 extracellular domain

<400> SEQUENCE: 218
cagcgcttcg cccaggccca gcagcagctg cccctggaga gcctgggctg ggacgtggcc 60
gagctgcagc tgaaccacac cggcccccag caggaccccc gcctgtactg gcagggcggc 120
cccgccctgg gccgcagctt cctgcacggc cccgagctgg acaagggcca gctgcgcatc 180

```
caccgcgacg gcatctacat ggtgcacatc caggtgaccc tggccatctg cagcagcacc    240

accgccagcc gccaccaccc caccaccctg gccgtgggca tctgcagccc cgccagccgc    300

agcatcagcc tgctgcgcct gagcttccac cagggctgca ccatcgccag ccagcgcctg    360

acccccctgg cccgcggcga caccctgtgc accaacctga ccggcaccct gctgcccagc    420

cgcaacaccg acgagacctt cttcggcgtg cagtgggtgc gcccc                    465
```

<210> SEQ ID NO 219
<211> LENGTH: 19
<212> TYPE: PRT
<213> ORGANISM: Artificial
<220> FEATURE:
<223> OTHER INFORMATION: The amino acid sequence of the secretory signal peptide

<400> SEQUENCE: 219

```
Met Thr Arg Leu Thr Val Leu Ala Leu Leu Ala Gly Leu Leu Ala Ser
1               5                   10                  15

Ser Arg Ala
```

<210> SEQ ID NO 220
<211> LENGTH: 57
<212> TYPE: DNA
<213> ORGANISM: Artificial
<220> FEATURE:
<223> OTHER INFORMATION: The nucleotide sequence of the secretory signal peptide

<400> SEQUENCE: 220

```
atgacccgcc tgaccgtgct ggccctgctg gccggcctgc tggccagcag ccgcgcc        57
```

<210> SEQ ID NO 221
<211> LENGTH: 59
<212> TYPE: DNA
<213> ORGANISM: Artificial
<220> FEATURE:
<223> OTHER INFORMATION: pcDNA3.1-Sig-F

<400> SEQUENCE: 221

```
gtgctggata tctgcagaat tcgccgccac catgacccgg ctgaccgtgc tggccctgc      59
```

<210> SEQ ID NO 222
<211> LENGTH: 49
<212> TYPE: DNA
<213> ORGANISM: Artificial
<220> FEATURE:
<223> OTHER INFORMATION: Sig-R

<400> SEQUENCE: 222

```
ggccctggag gaggccagca ggccggccag cagggccagc acggtcagc                49
```

<210> SEQ ID NO 223
<211> LENGTH: 42
<212> TYPE: DNA
<213> ORGANISM: Artificial
<220> FEATURE:
<223> OTHER INFORMATION: Sig-CD19-F

<400> SEQUENCE: 223

```
ctgctggcct cctccagggc cgacatccag ctgacccaga gc                       42
```

<210> SEQ ID NO 224
<211> LENGTH: 23

<212> TYPE: DNA
<213> ORGANISM: Artificial
<220> FEATURE:
<223> OTHER INFORMATION: CD19-R

<400> SEQUENCE: 224
gctgctcacg gtcacggtgg tgc 23

<210> SEQ ID NO 225
<211> LENGTH: 56
<212> TYPE: DNA
<213> ORGANISM: Artificial
<220> FEATURE:
<223> OTHER INFORMATION: CD19-G4S-CD3-F

<400> SEQUENCE: 225
ccaccgtgac cgtgagcagc ggtggcggag ggtccgacat caagctgcag cagagc 56

<210> SEQ ID NO 226
<211> LENGTH: 20
<212> TYPE: DNA
<213> ORGANISM: Artificial
<220> FEATURE:
<223> OTHER INFORMATION: CD3-R

<400> SEQUENCE: 226
cttcagctcc agcttggtgc 20

<210> SEQ ID NO 227
<211> LENGTH: 87
<212> TYPE: DNA
<213> ORGANISM: Artificial
<220> FEATURE:
<223> OTHER INFORMATION: CD3-(GGGGS)3-4-1BBL-F

<400> SEQUENCE: 227
ggcaccaagc tggagctgaa gggcggcggc ggcagcggcg gcggcggcag cggcggcggc 60
ggcagcgcct gcccctgggc cgtgagc 87

<210> SEQ ID NO 228
<211> LENGTH: 53
<212> TYPE: DNA
<213> ORGANISM: Artificial
<220> FEATURE:
<223> OTHER INFORMATION: pcDNA3.1-4-1BBL-R

<400> SEQUENCE: 228
ctgatcagcg gtttaaactt aagctttcac tcgctgcggg ggctgggcag gcc 53

<210> SEQ ID NO 229
<211> LENGTH: 41
<212> TYPE: DNA
<213> ORGANISM: Artificial
<220> FEATURE:
<223> OTHER INFORMATION: CD3-IgD-F

<400> SEQUENCE: 229
gcaccaagct ggagctgaag gccagcaaga gcaagaagga g 41

<210> SEQ ID NO 230
<211> LENGTH: 21
<212> TYPE: DNA
<213> ORGANISM: Artificial
<220> FEATURE:
<223> OTHER INFORMATION: IgD-R

<400> SEQUENCE: 230
cacgcccagg ggctgggtgt g 21

<210> SEQ ID NO 231
<211> LENGTH: 42
<212> TYPE: DNA
<213> ORGANISM: Artificial
<220> FEATURE:
<223> OTHER INFORMATION: IgD-4-1BBL-F

<400> SEQUENCE: 231
cacacccagc ccctgggcgt ggcctgcccc tgggccgtga gc 42

<210> SEQ ID NO 232
<211> LENGTH: 87
<212> TYPE: DNA
<213> ORGANISM: Artificial
<220> FEATURE:
<223> OTHER INFORMATION: CD3-(GGGGS)3-B7RP-1-F

<400> SEQUENCE: 232
ggcaccaagc tggagctgaa gggcggcggc ggcagcggcg gcggcggcag cggcggcggc 60
ggcagcgaca cccaggagaa ggaggtg 87

<210> SEQ ID NO 233
<211> LENGTH: 50
<212> TYPE: DNA
<213> ORGANISM: Artificial
<220> FEATURE:
<223> OTHER INFORMATION: pcDNA3.1-B7RP-1-R

<400> SEQUENCE: 233
ctgatcagcg gtttaaactt aagctttcag gtggcggcgt tcttctcgcc 50

<210> SEQ ID NO 234
<211> LENGTH: 42
<212> TYPE: DNA
<213> ORGANISM: Artificial
<220> FEATURE:
<223> OTHER INFORMATION: IgD-B7RP-1-F

<400> SEQUENCE: 234
cacacccagc ccctgggcgt ggacacccag gagaaggagg tg 42

<210> SEQ ID NO 235
<211> LENGTH: 87
<212> TYPE: DNA
<213> ORGANISM: Artificial
<220> FEATURE:
<223> OTHER INFORMATION: CD3-(GGGGS)3-OX40L-F

<400> SEQUENCE: 235
ggcaccaagc tggagctgaa gggcggcggc ggcagcggcg gcggcggcag cggcggcggc 60
ggcagccagg tgagccaccg ctacccc 87

<210> SEQ ID NO 236
<211> LENGTH: 50
<212> TYPE: DNA
<213> ORGANISM: Artificial
<220> FEATURE:
<223> OTHER INFORMATION: pcDNA3.1-OX40L-R

<400> SEQUENCE: 236
ctgatcagcg gtttaaactt aagctttcac agcacgcaga actcgccggg 50

<210> SEQ ID NO 237
<211> LENGTH: 42
<212> TYPE: DNA
<213> ORGANISM: Artificial
<220> FEATURE:
<223> OTHER INFORMATION: IgD-OX40L-F

<400> SEQUENCE: 237
cacacccagc ccctgggcgt gcaggtgagc caccgctacc cc 42

<210> SEQ ID NO 238
<211> LENGTH: 87
<212> TYPE: DNA
<213> ORGANISM: Artificial
<220> FEATURE:
<223> OTHER INFORMATION: CD3-(GGGGS)3-GITRL-F

<400> SEQUENCE: 238
ggcaccaagc tggagctgaa gggcggcggc ggcagcggcg gcggcggcag cggcggcggc 60
ggcagccagc tggagaccgc caaggag 87

<210> SEQ ID NO 239
<211> LENGTH: 50
<212> TYPE: DNA
<213> ORGANISM: Artificial
<220> FEATURE:
<223> OTHER INFORMATION: pcDNA3.1-GITRL-R

<400> SEQUENCE: 239
ctgatcagcg gtttaaactt aagctttcag ctgatgaact gggggttggc 50

<210> SEQ ID NO 240
<211> LENGTH: 42
<212> TYPE: DNA
<213> ORGANISM: Artificial
<220> FEATURE:
<223> OTHER INFORMATION: IgD-GITRL-F

<400> SEQUENCE: 240
cacacccagc ccctgggcgt gcagctggag accgccaagg ag 42

<210> SEQ ID NO 241
<211> LENGTH: 87
<212> TYPE: DNA
<213> ORGANISM: Artificial
<220> FEATURE:
<223> OTHER INFORMATION: CD3-(GGGGS)3-CD70-F

<400> SEQUENCE: 241
ggcaccaagc tggagctgaa gggcggcggc ggcagcggcg gcggcggcag cggcggcggc 60
ggcagccagc gcttcgccca ggcccag 87

<210> SEQ ID NO 242
<211> LENGTH: 50
<212> TYPE: DNA
<213> ORGANISM: Artificial
<220> FEATURE:
<223> OTHER INFORMATION: pcDNA3.1-CD70-R

<400> SEQUENCE: 242
ctgatcagcg gtttaaactt aagctttcag gggcgcaccc actgcacgcc 50

<210> SEQ ID NO 243

<211> LENGTH: 42
<212> TYPE: DNA
<213> ORGANISM: Artificial
<220> FEATURE:
<223> OTHER INFORMATION: IgD-CD70-F

<400> SEQUENCE: 243
cacacccagc ccctgggcgt gcagcgcttc gcccaggccc ag 42

<210> SEQ ID NO 244
<211> LENGTH: 5
<212> TYPE: PRT
<213> ORGANISM: Artificial
<220> FEATURE:
<223> OTHER INFORMATION: The amino acid sequence of CD19-CD3-PD-1 TsAb_M monomer linker (Linker 1)

<400> SEQUENCE: 244

Gly Gly Gly Gly Ser
1 5

<210> SEQ ID NO 245
<211> LENGTH: 15
<212> TYPE: DNA
<213> ORGANISM: Artificial
<220> FEATURE:
<223> OTHER INFORMATION: The nucleotide sequence of CD19-CD3-PD-1 TsAb_M monomer linker (Linker 1)

<400> SEQUENCE: 245
ggcggcggcg gcagc 15

<210> SEQ ID NO 246
<211> LENGTH: 15
<212> TYPE: PRT
<213> ORGANISM: Artificial
<220> FEATURE:
<223> OTHER INFORMATION: The amino acid sequence of CD19-CD3-PD-1 TsAb_M monomer linker (Linker 2)

<400> SEQUENCE: 246

Gly Gly Gly Gly Ser Gly Gly Gly Gly Ser Gly Gly Gly Gly Ser
1 5 10 15

<210> SEQ ID NO 247
<211> LENGTH: 45
<212> TYPE: DNA
<213> ORGANISM: Artificial
<220> FEATURE:
<223> OTHER INFORMATION: The nucleotide sequence of CD19-CD3-PD-1 TsAb_M monomer linker (Linker 2)

<400> SEQUENCE: 247
ggcggcggcg gcagcggcgg cggcggcagc ggcggcggcg gcagc 45

<210> SEQ ID NO 248
<211> LENGTH: 5
<212> TYPE: PRT
<213> ORGANISM: Artificial
<220> FEATURE:
<223> OTHER INFORMATION: The amino acid sequence of CD19-CD3-PD-1 TsAb_D dimer linker (Linker 1)

<400> SEQUENCE: 248

Gly Gly Gly Gly Ser
1 5

<210> SEQ ID NO 249
<211> LENGTH: 15
<212> TYPE: DNA
<213> ORGANISM: Artificial
<220> FEATURE:
<223> OTHER INFORMATION: The nucleotide sequence of CD19-CD3-PD-1 TsAb_D dimer linker (Linker 1)

<400> SEQUENCE: 249
ggcggcggcg gcagc 15

<210> SEQ ID NO 250
<211> LENGTH: 81
<212> TYPE: PRT
<213> ORGANISM: Artificial
<220> FEATURE:
<223> OTHER INFORMATION: The amino acid sequence of CD19-CD3-PD-1 TsAb_D dimer linker (Linker 2)

<400> SEQUENCE: 250

Ala Ser Lys Ser Lys Lys Glu Ile Phe Arg Trp Pro Glu Ser Pro Lys
1 5 10 15

Ala Gln Ala Ser Ser Val Pro Thr Ala Gln Pro Gln Ala Glu Gly Ser
20 25 30

Leu Ala Lys Ala Thr Thr Ala Pro Ala Thr Thr Arg Asn Thr Gly Arg
35 40 45

Gly Gly Glu Glu Lys Lys Lys Glu Lys Glu Lys Glu Glu Gln Glu Glu
50 55 60

Arg Glu Thr Lys Thr Pro Glu Cys Pro Ser His Thr Gln Pro Leu Gly
65 70 75 80

Val

<210> SEQ ID NO 251
<211> LENGTH: 243
<212> TYPE: DNA
<213> ORGANISM: Artificial
<220> FEATURE:
<223> OTHER INFORMATION: The nucleotide sequence of CD19-CD3-PD-1 TsAb_D dimer linker (Linker 2)

<400> SEQUENCE: 251
gccagcaaga gcaagaagga gatcttccgc tggcccgaga gccccaaggc ccaggccagc 60
agcgtgccca ccgcccagcc ccaggccgag ggcagcctgg ccaaggccac caccgccccc 120
gccaccaccc gcaacaccgg ccgcggcggc gaggagaaga agaaggagaa ggagaaggag 180
gagcaggagg agcgcgagac caagaccccc gagtgcccca gccacaccca gcccctgggc 240
gtg 243

<210> SEQ ID NO 252
<211> LENGTH: 150
<212> TYPE: PRT
<213> ORGANISM: Artificial
<220> FEATURE:
<223> OTHER INFORMATION: The amino acid sequence of the extracellular domain of the human T cell inhibitory molecule PD-1

<400> SEQUENCE: 252

Pro Gly Trp Phe Leu Asp Ser Pro Asp Arg Pro Trp Asn Pro Pro Thr
1 5 10 15

Phe Ser Pro Ala Leu Leu Val Val Thr Glu Gly Asp Asn Ala Thr Phe
20 25 30

Thr Cys Ser Phe Ser Asn Thr Ser Glu Ser Phe Val Leu Asn Trp Tyr

```
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150


<210> SEQ ID NO 253
<211> LENGTH: 126
<212> TYPE: PRT
<213> ORGANISM: Artificial
<220> FEATURE:
<223> OTHER INFORMATION: The amino acid sequence of the extracellular
      domain of the human T cell inhibitory molecule CTLA-4

<400> SEQUENCE: 253

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp
        115                 120                 125


<210> SEQ ID NO 254
<211> LENGTH: 422
<212> TYPE: PRT
<213> ORGANISM: Artificial
<220> FEATURE:
<223> OTHER INFORMATION: The amino acid sequence of the extracellular
      domain of the human T cell inhibitory molecule LAG-3

<400> SEQUENCE: 254

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
```

-continued 50 55 60

Gly Pro Arg Pro Arg Arg Tyr Thr Val Leu Ser Val Gly Pro Gly Gly
65 70 75 80

Leu Arg Ser Gly Arg Leu Pro Leu Gln Pro Arg Val Gln Leu Asp Glu
85 90 95

Arg Gly Arg Gln Arg Gly Asp Phe Ser Leu Trp Leu Arg Pro Ala Arg
100 105 110

Arg Ala Asp Ala Gly Glu Tyr Arg Ala Ala Val His Leu Arg Asp Arg
115 120 125

Ala Leu Ser Cys Arg Leu Arg Leu Arg Leu Gly Gln Ala Ser Met Thr
130 135 140

Ala Ser Pro Pro Gly Ser Leu Arg Ala Ser Asp Trp Val Ile Leu Asn
145 150 155 160

Cys Ser Phe Ser Arg Pro Asp Arg Pro Ala Ser Val His Trp Phe Arg
165 170 175

Asn Arg Gly Gln Gly Arg Val Pro Val Arg Glu Ser Pro His His His
180 185 190

Leu Ala Glu Ser Phe Leu Phe Leu Pro Gln Val Ser Pro Met Asp Ser
195 200 205

Gly Pro Trp Gly Cys Ile Leu Thr Tyr Arg Asp Gly Phe Asn Val Ser
210 215 220

Ile Met Tyr Asn Leu Thr Val Leu Gly Leu Glu Pro Pro Thr Pro Leu
225 230 235 240

Thr Val Tyr Ala Gly Ala Gly Ser Arg Val Gly Leu Pro Cys Arg Leu
245 250 255

Pro Ala Gly Val Gly Thr Arg Ser Phe Leu Thr Ala Lys Trp Thr Pro
260 265 270

Pro Gly Gly Gly Pro Asp Leu Leu Val Thr Gly Asp Asn Gly Asp Phe
275 280 285

Thr Leu Arg Leu Glu Asp Val Ser Gln Ala Gln Ala Gly Thr Tyr Thr
290 295 300

Cys His Ile His Leu Gln Glu Gln Gln Leu Asn Ala Thr Val Thr Leu
305 310 315 320

Ala Ile Ile Thr Val Thr Pro Lys Ser Phe Gly Ser Pro Gly Ser Leu
325 330 335

Gly Lys Leu Leu Cys Glu Val Thr Pro Val Ser Gly Gln Glu Arg Phe
340 345 350

Val Trp Ser Ser Leu Asp Thr Pro Ser Gln Arg Ser Phe Ser Gly Pro
355 360 365

Trp Leu Glu Ala Gln Glu Ala Gln Leu Leu Ser Gln Pro Trp Gln Cys
370 375 380

Gln Leu Tyr Gln Gly Glu Arg Leu Leu Gly Ala Ala Val Tyr Phe Thr
385 390 395 400

Glu Leu Ser Ser Pro Gly Ala Gln Arg Ser Gly Arg Ala Pro Gly Ala
405 410 415

Leu Pro Ala Gly His Leu
420

<210> SEQ ID NO 255
<211> LENGTH: 181
<212> TYPE: PRT
<213> ORGANISM: Artificial
<220> FEATURE:
<223> OTHER INFORMATION: The amino acid sequence of the extracellular domain of the human T cell inhibitory molecule TIM-3

<400> SEQUENCE: 255

```
Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
        115                 120                 125

Arg Met Leu Thr Thr Arg Gly His Gly Pro Ala Glu Thr Gln Thr Leu
    130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly
            180
```

<210> SEQ ID NO 256
<211> LENGTH: 120
<212> TYPE: PRT
<213> ORGANISM: Artificial
<220> FEATURE:
<223> OTHER INFORMATION: The amino acid sequence of the extracellular domain of the human T cell inhibitory molecule TIGIT

<400> SEQUENCE: 256

```
Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro
        115                 120
```

<210> SEQ ID NO 257
<211> LENGTH: 127
<212> TYPE: PRT
<213> ORGANISM: Artificial
<220> FEATURE:
<223> OTHER INFORMATION: The amino acid sequence of the extracellular domain of the human T cell inhibitory molecule BTLA

<400> SEQUENCE: 257

Lys Glu Ser Cys Asp Val Gln Leu Tyr Ile Lys Arg Gln Ser Glu His
1               5                   10                  15

Ser Ile Leu Ala Gly Asp Pro Phe Glu Leu Glu Cys Pro Val Lys Tyr
            20                  25                  30

Cys Ala Asn Arg Pro His Val Thr Trp Cys Lys Leu Asn Gly Thr Thr
        35                  40                  45

Cys Val Lys Leu Glu Asp Arg Gln Thr Ser Trp Lys Glu Glu Lys Asn
    50                  55                  60

Ile Ser Phe Phe Ile Leu His Phe Glu Pro Val Leu Pro Asn Asp Asn
65                  70                  75                  80

Gly Ser Tyr Arg Cys Ser Ala Asn Phe Gln Ser Asn Leu Ile Glu Ser
                85                  90                  95

His Ser Thr Thr Leu Tyr Val Thr Asp Val Lys Ser Ala Ser Glu Arg
            100                 105                 110

Pro Ser Lys Asp Glu Met Ala Ser Arg Pro Trp Leu Leu Tyr Arg
        115                 120                 125

<210> SEQ ID NO 258
<211> LENGTH: 749
<212> TYPE: PRT
<213> ORGANISM: Artificial
<220> FEATURE:
<223> OTHER INFORMATION: The amino acid sequence of CD19-CD3-PD-1 TsAb_M monomer

<400> SEQUENCE: 258

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

```
Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Gln Val Gln Leu Val Glu Ser Gly Gly Gly Val Val Gln Pro Gly
        515                 520                 525

Arg Ser Leu Arg Leu Asp Cys Lys Ala Ser Gly Ile Thr Phe Ser Asn
    530                 535                 540

Ser Gly Met His Trp Val Arg Gln Ala Pro Gly Lys Gly Leu Glu Trp
545                 550                 555                 560

Val Ala Val Ile Trp Tyr Asp Gly Ser Lys Arg Tyr Tyr Ala Asp Ser
                565                 570                 575

Val Lys Gly Arg Phe Thr Ile Ser Arg Asp Asn Ser Lys Asn Thr Leu
            580                 585                 590

Phe Leu Gln Met Asn Ser Leu Arg Ala Glu Asp Thr Ala Val Tyr Tyr
        595                 600                 605

Cys Ala Thr Asn Asp Asp Tyr Trp Gly Gln Gly Thr Leu Val Thr Val
    610                 615                 620
```

-continued

```
Ser Ser Gly Gly Gly Gly Ser Gly Gly Gly Gly Ser Gly Gly Gly Gly
625                 630                 635                 640

Ser Glu Ile Val Leu Thr Gln Ser Pro Ala Thr Leu Ser Leu Ser Pro
                645                 650                 655

Gly Glu Arg Ala Thr Leu Ser Cys Arg Ala Ser Gln Ser Val Ser Ser
            660                 665                 670

Tyr Leu Ala Trp Tyr Gln Gln Lys Pro Gly Gln Ala Pro Arg Leu Leu
        675                 680                 685

Ile Tyr Asp Ala Ser Asn Arg Ala Thr Gly Ile Pro Ala Arg Phe Ser
    690                 695                 700

Gly Ser Gly Ser Gly Thr Asp Phe Thr Leu Thr Ile Ser Ser Leu Glu
705                 710                 715                 720

Pro Glu Asp Phe Ala Val Tyr Tyr Cys Gln Gln Ser Ser Asn Trp Pro
                725                 730                 735

Arg Thr Phe Gly Gln Gly Thr Lys Val Glu Ile Lys Arg
            740                 745
```

<210> SEQ ID NO 259
<211> LENGTH: 2247
<212> TYPE: DNA
<213> ORGANISM: Artificial
<220> FEATURE:
<223> OTHER INFORMATION: The nucleotide sequence of CD19-CD3-PD-1 TsAb_M monomer

<400> SEQUENCE: 259

```
gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180

ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggcggcggcg gcagcgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320
```

```
gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaaccccct gaccttcggc gccggcacca agctggagct gaagggcggc   1500

ggcggcagcg gcggcggcgg cagcggcggc ggcggcagcc aggtgcagct ggtggagagc   1560

ggcggcggcg tggtgcagcc cggccgcagc ctgcgcctgg actgcaaggc cagcggcatc   1620

accttcagca acagcggcat gcactgggtg cgccaggccc ccggcaaggg cctggagtgg   1680

gtggccgtga tctggtacga cggcagcaag cgctactacg ccgacagcgt gaagggccgc   1740

ttcaccatca gccgcgacaa cagcaagaac accctgttcc tgcagatgaa cagcctgcgc   1800

gccgaggaca ccgccgtgta ctactgcgcc accaacgacg actactgggg ccagggcacc   1860

ctggtgaccg tgagcagcgg cggcggcggc agcggcggcg gcggcagcgg cggcggcggc   1920

agcgagatcg tgctgaccca gagccccgcc accctgagcc tgagccccgg cgagcgcgcc   1980

accctgagct gccgcgccag ccagagcgtg agcagctacc tggcctggta ccagcagaag   2040

cccggccagg ccccccgcct gctgatctac gacgccagca accgcgccac cggcatcccc   2100

gcccgcttca gcggcagcgg cagcggcacc gacttcaccc tgaccatcag cagcctggag   2160

cccgaggact tcgccgtgta ctactgccag cagagcagca actggccccg caccttcggc   2220

cagggcacca aggtggagat caagcgc                                       2247
```

<210> SEQ ID NO 260
<211> LENGTH: 815
<212> TYPE: PRT
<213> ORGANISM: Artificial
<220> FEATURE:
<223> OTHER INFORMATION: The amino acid sequence of CD19-CD3-PD-1 TsAb_D dimer

<400> SEQUENCE: 260

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190
```

-continued

```
Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Gln Val Gln Leu Val Glu Ser Gly Gly Gly Val Val Gln
            580                 585                 590

Pro Gly Arg Ser Leu Arg Leu Asp Cys Lys Ala Ser Gly Ile Thr Phe
        595                 600                 605

Ser Asn Ser Gly Met His Trp Val Arg Gln Ala Pro Gly Lys Gly Leu
```

```
    610                 615                 620

Glu Trp Val Ala Val Ile Trp Tyr Asp Gly Ser Lys Arg Tyr Tyr Ala
625                 630                 635                 640

Asp Ser Val Lys Gly Arg Phe Thr Ile Ser Arg Asp Asn Ser Lys Asn
                645                 650                 655

Thr Leu Phe Leu Gln Met Asn Ser Leu Arg Ala Glu Asp Thr Ala Val
            660                 665                 670

Tyr Tyr Cys Ala Thr Asn Asp Asp Tyr Trp Gly Gln Gly Thr Leu Val
        675                 680                 685

Thr Val Ser Ser Gly Gly Gly Gly Ser Gly Gly Gly Gly Ser Gly Gly
    690                 695                 700

Gly Gly Ser Glu Ile Val Leu Thr Gln Ser Pro Ala Thr Leu Ser Leu
705                 710                 715                 720

Ser Pro Gly Glu Arg Ala Thr Leu Ser Cys Arg Ala Ser Gln Ser Val
                725                 730                 735

Ser Ser Tyr Leu Ala Trp Tyr Gln Gln Lys Pro Gly Gln Ala Pro Arg
            740                 745                 750

Leu Leu Ile Tyr Asp Ala Ser Asn Arg Ala Thr Gly Ile Pro Ala Arg
        755                 760                 765

Phe Ser Gly Ser Gly Ser Gly Thr Asp Phe Thr Leu Thr Ile Ser Ser
    770                 775                 780

Leu Glu Pro Glu Asp Phe Ala Val Tyr Tyr Cys Gln Gln Ser Ser Asn
785                 790                 795                 800

Trp Pro Arg Thr Phe Gly Gln Gly Thr Lys Val Glu Ile Lys Arg
                805                 810                 815


<210> SEQ ID NO 261
<211> LENGTH: 2445
<212> TYPE: DNA
<213> ORGANISM: Artificial
<220> FEATURE:
<223> OTHER INFORMATION: The nucleotide sequence of CD19-CD3-PD-1 TsAb_D
      dimer

<400> SEQUENCE: 261

gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600

agcagcagca ccgcctacat gcagctgagc agcctggcca gcgaggacag cgccgtgtac     660

ttctgcgccc gccgcgagac caccaccgtg ggccgctact actacgccat ggactactgg     720

ggccagggca ccaccgtgac cgtgagcagc ggcggcggcg gcagcgacat caagctgcag     780

cagagcggcg ccgagctggc ccgccccggc gccagcgtga agatgagctg caagaccagc     840

ggctacacct tcacccgcta caccatgcac tgggtgaagc agcgccccgg ccagggcctg     900
```

```
gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaacccccct gaccttcggc gccggcacca agctggagct gaaggccagc   1500

aagagcaaga aggagatctt ccgctggccc gagagcccca aggcccaggc cagcagcgtg   1560

cccaccgccc agccccaggc cgagggcagc ctggccaagg ccaccaccgc ccccgccacc   1620

acccgcaaca ccggccgcgg cggcgaggag aagaagaagg agaaggagaa ggaggagcag   1680

gaggagcgcg agaccaagac ccccgagtgc cccagccaca cccagcccct gggcgtgcag   1740

gtgcagctgg tggagagcgg cggcggcgtg gtgcagcccg gccgcagcct gcgcctggac   1800

tgcaaggcca gcggcatcac cttcagcaac agcggcatgc actgggtgcg ccaggccccc   1860

ggcaagggcc tggagtgggt ggccgtgatc tggtacgacg gcagcaagcg ctactacgcc   1920

gacagcgtga agggccgctt caccatcagc cgcgacaaca gcaagaacac cctgttcctg   1980

cagatgaaca gcctgcgcgc cgaggacacc gccgtgtact actgcgccac caacgacgac   2040

tactggggcc agggcaccct ggtgaccgtg agcagcggcg gcggcggcag cggcggcggc   2100

ggcagcggcg gcggcggcag cgagatcgtg ctgacccaga gccccgccac cctgagcctg   2160

agccccggcg agcgcgccac cctgagctgc cgcgccagcc agagcgtgag cagctacctg   2220

gcctggtacc agcagaagcc cggccaggcc ccccgcctgc tgatctacga cgccagcaac   2280

cgcgccaccg gcatccccgc ccgcttcagc ggcagcggca gcggcaccga cttcaccctg   2340

accatcagca gcctggagcc cgaggacttc gccgtgtact actgccagca gagcagcaac   2400

tggccccgca ccttcggcca gggcaccaag gtggagatca agcgc                   2445
```

<210> SEQ ID NO 262
<211> LENGTH: 755
<212> TYPE: PRT
<213> ORGANISM: Artificial
<220> FEATURE:
<223> OTHER INFORMATION: The amino acid sequence of CD19-CD3-CTLA-4
      TsAb_M monomer

<400> SEQUENCE: 262

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
```

-continued

```
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510
```

```
Ser Gln Val Gln Leu Val Glu Ser Gly Gly Gly Val Val Gln Pro Gly
        515                 520                 525

Arg Ser Leu Arg Leu Ser Cys Ala Ala Ser Gly Phe Thr Phe Ser Ser
    530                 535                 540

Tyr Thr Met His Trp Val Arg Gln Ala Pro Gly Lys Gly Leu Glu Trp
545                 550                 555                 560

Val Thr Phe Ile Ser Tyr Asp Gly Asn Asn Lys Tyr Tyr Ala Asp Ser
                565                 570                 575

Val Lys Gly Arg Phe Thr Ile Ser Arg Asp Asn Ser Lys Asn Thr Leu
            580                 585                 590

Tyr Leu Gln Met Asn Ser Leu Arg Ala Glu Asp Thr Ala Ile Tyr Tyr
        595                 600                 605

Cys Ala Arg Thr Gly Trp Leu Gly Pro Phe Asp Tyr Trp Gly Gln Gly
    610                 615                 620

Thr Leu Val Thr Val Ser Ser Gly Gly Gly Gly Ser Gly Gly Gly Gly
625                 630                 635                 640

Ser Gly Gly Gly Gly Ser Glu Ile Val Leu Thr Gln Ser Pro Gly Thr
                645                 650                 655

Leu Ser Leu Ser Pro Gly Glu Arg Ala Thr Leu Ser Cys Arg Ala Ser
            660                 665                 670

Gln Ser Val Gly Ser Ser Tyr Leu Ala Trp Tyr Gln Gln Lys Pro Gly
        675                 680                 685

Gln Ala Pro Arg Leu Leu Ile Tyr Gly Ala Phe Ser Arg Ala Thr Gly
    690                 695                 700

Ile Pro Asp Arg Phe Ser Gly Ser Gly Ser Gly Thr Asp Phe Thr Leu
705                 710                 715                 720

Thr Ile Ser Arg Leu Glu Pro Glu Asp Phe Ala Val Tyr Tyr Cys Gln
                725                 730                 735

Gln Tyr Gly Ser Ser Pro Trp Thr Phe Gly Gln Gly Thr Lys Val Glu
            740                 745                 750

Ile Lys Arg
        755
```

<210> SEQ ID NO 263
<211> LENGTH: 2265
<212> TYPE: DNA
<213> ORGANISM: Artificial
<220> FEATURE:
<223> OTHER INFORMATION: The nucleotide sequence of CD19-CD3-CTLA-4 TsAb_M monomer

<400> SEQUENCE: 263

```
gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600
```

agcagcagca ccgcctacat gcagctgagc agcctggcca gcgaggacag cgccgtgtac 660
ttctgcgccc gccgcgagac caccaccgtg ggccgctact actacgccat ggactactgg 720
ggccagggca ccaccgtgac cgtgagcagc ggcggcggcg gcagcgacat caagctgcag 780
cagagcggcg ccgagctggc ccgccccggc gccagcgtga agatgagctg caagaccagc 840
ggctacacct tcacccgcta caccatgcac tgggtgaagc agcgccccgg ccagggcctg 900
gagtggatcg gctacatcaa ccccagccgc ggctacacca actacaacca gaagttcaag 960
gacaaggcca ccctgaccac cgacaagagc agcagcaccg cctacatgca gctgagcagc 1020
ctgaccagcg aggacagcgc cgtgtactac tgcgcccgct actacgacga ccactactgc 1080
ctggactact ggggccaggg caccaccctg accgtgagca gcgtggaggg cggcagcggc 1140
ggcagcggcg gcagcggcgg cagcggcggc gtggacgaca tccagctgac ccagagcccc 1200
gccatcatga gcgccagccc cggcgagaag gtgaccatga cctgccgcgc cagcagcagc 1260
gtgagctaca tgaactggta ccagcagaag agcggcacca gccccaagcg ctggatctac 1320
gacaccagca aggtggccag cggcgtgccc taccgcttca gcggcagcgg cagcggcacc 1380
agctacagcc tgaccatcag cagcatggag gccgaggacg ccgccaccta ctactgccag 1440
cagtggagca gcaacccccct gaccttcggc gccggcacca agctggagct gaagggcggc 1500
ggcggcagcg gcggcggcgg cagcggcggc ggcggcagcc aggtgcagct ggtggagagc 1560
ggcggcggcg tggtgcagcc cggccgcagc ctgcgcctga gctgcgccgc cagcggcttc 1620
accttcagca gctacaccat gcactgggtg cgccaggccc ccggcaaggg cctggagtgg 1680
gtgaccttca tcagctacga cggcaacaac aagtactacg ccgacagcgt gaagggccgc 1740
ttcaccatca gccgcgacaa cagcaagaac accctgtacc tgcagatgaa cagcctgcgc 1800
gccgaggaca ccgccatcta ctactgcgcc cgcaccggct ggctgggccc cttcgactac 1860
tggggccagg gcaccctggt gaccgtgagc agcggcggcg gcggcagcgg cggcggcggc 1920
agcggcggcg gcggcagcga gatcgtgctg acccagagcc ccggcaccct gagcctgagc 1980
cccggcgagc gcgccaccct gagctgccgc gccagccaga gcgtgggcag cagctacctg 2040
gcctggtacc agcagaagcc cggccaggcc ccccgcctgc tgatctacgg cgccttcagc 2100
cgcgccaccg gcatccccga ccgcttcagc ggcagcggca gcggcaccga cttcaccctg 2160
accatcagcc gcctggagcc cgaggacttc gccgtgtact actgccagca gtacggcagc 2220
agcccctgga ccttcggcca gggcaccaag gtggagatca agcgc 2265

<210> SEQ ID NO 264
<211> LENGTH: 821
<212> TYPE: PRT
<213> ORGANISM: Artificial
<220> FEATURE:
<223> OTHER INFORMATION: The amino acid sequence of CD19-CD3-CTLA-4 TsAb_D dimer

<400> SEQUENCE: 264

Asp Ile Gln Leu Thr Gln Ser Pro Ala Ser Leu Ala Val Ser Leu Gly
1 5 10 15

Gln Arg Ala Thr Ile Ser Cys Lys Ala Ser Gln Ser Val Asp Tyr Asp
20 25 30

Gly Asp Ser Tyr Leu Asn Trp Tyr Gln Gln Ile Pro Gly Gln Pro Pro
35 40 45

Lys Leu Leu Ile Tyr Asp Ala Ser Asn Leu Val Ser Gly Ile Pro Pro
50 55 60

-continued

```
Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480
```

```
Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Gln Val Gln Leu Val Glu Ser Gly Gly Gly Val Val Gln
            580                 585                 590

Pro Gly Arg Ser Leu Arg Leu Ser Cys Ala Ala Ser Gly Phe Thr Phe
        595                 600                 605

Ser Ser Tyr Thr Met His Trp Val Arg Gln Ala Pro Gly Lys Gly Leu
    610                 615                 620

Glu Trp Val Thr Phe Ile Ser Tyr Asp Gly Asn Asn Lys Tyr Tyr Ala
625                 630                 635                 640

Asp Ser Val Lys Gly Arg Phe Thr Ile Ser Arg Asp Asn Ser Lys Asn
                645                 650                 655

Thr Leu Tyr Leu Gln Met Asn Ser Leu Arg Ala Glu Asp Thr Ala Ile
            660                 665                 670

Tyr Tyr Cys Ala Arg Thr Gly Trp Leu Gly Pro Phe Asp Tyr Trp Gly
        675                 680                 685

Gln Gly Thr Leu Val Thr Val Ser Ser Gly Gly Gly Gly Ser Gly Gly
    690                 695                 700

Gly Gly Ser Gly Gly Gly Gly Ser Glu Ile Val Leu Thr Gln Ser Pro
705                 710                 715                 720

Gly Thr Leu Ser Leu Ser Pro Gly Glu Arg Ala Thr Leu Ser Cys Arg
                725                 730                 735

Ala Ser Gln Ser Val Gly Ser Ser Tyr Leu Ala Trp Tyr Gln Gln Lys
            740                 745                 750

Pro Gly Gln Ala Pro Arg Leu Leu Ile Tyr Gly Ala Phe Ser Arg Ala
        755                 760                 765

Thr Gly Ile Pro Asp Arg Phe Ser Gly Ser Gly Ser Gly Thr Asp Phe
    770                 775                 780

Thr Leu Thr Ile Ser Arg Leu Glu Pro Glu Asp Phe Ala Val Tyr Tyr
785                 790                 795                 800

Cys Gln Gln Tyr Gly Ser Ser Pro Trp Thr Phe Gly Gln Gly Thr Lys
                805                 810                 815

Val Glu Ile Lys Arg
            820
```

<210> SEQ ID NO 265
<211> LENGTH: 2463
<212> TYPE: DNA
<213> ORGANISM: Artificial
<220> FEATURE:
<223> OTHER INFORMATION: The nucleotide sequence of CD19-CD3-CTLA-4 TsAb_D dimer

<400> SEQUENCE: 265

```
gacatccagc tgacccagag ccccgccagc ctggccgtga gcctgggcca gcgcgccacc     60
```

-continued

```
atcagctgca aggccagcca gagcgtggac tacgacggcg acagctacct gaactggtac    120
cagcagatcc ccggccagcc ccccaagctg ctgatctacg acgccagcaa cctggtgagc    180
ggcatccccc cccgcttcag cggcagcggc agcggcaccg acttcaccct gaacatccac    240
cccgtggaga aggtggacgc cgccacctac cactgccagc agagcaccga ggacccctgg    300
accttcggcg gcggcaccaa gctggagatc aagggcggcg gcggcagcgg cggcggcggc    360
agcggcggcg gcggcagcca ggtgcagctg cagcagagcg gcgccgagct ggtgcgcccc    420
ggcagcagcg tgaagatcag ctgcaaggcc agcggctacg ccttcagcag ctactggatg    480
aactgggtga agcagcgccc cggccagggc ctggagtgga tcggccagat ctggcccggc    540
gacggcgaca ccaactacaa cggcaagttc aagggcaagg ccaccctgac cgccgacgag    600
agcagcagca ccgcctacat gcagctgagc agcctggcca gcgaggacag cgccgtgtac    660
ttctgcgccc gccgcgagac caccaccgtg ggccgctact actacgccat ggactactgg    720
ggccagggca ccaccgtgac cgtgagcagc ggcggcggcg gcagcgacat caagctgcag    780
cagagcggcg ccgagctggc ccgccccggc gccagcgtga agatgagctg caagaccagc    840
ggctacacct tcacccgcta caccatgcac tgggtgaagc agcgccccgg ccagggcctg    900
gagtggatcg gctacatcaa ccccagccgc ggctacacca actacaacca gaagttcaag    960
gacaaggcca ccctgaccac cgacaagagc agcagcaccg cctacatgca gctgagcagc   1020
ctgaccagcg aggacagcgc cgtgtactac tgcgcccgct actacgacga ccactactgc   1080
ctggactact ggggccaggg caccaccctg accgtgagca gcgtggaggg cggcagcggc   1140
ggcagcggcg gcagcggcgg cagcggcggc gtggacgaca tccagctgac ccagagcccc   1200
gccatcatga gcgccagccc cggcgagaag gtgaccatga cctgccgcgc cagcagcagc   1260
gtgagctaca tgaactggta ccagcagaag agcggcacca gccccaagcg ctggatctac   1320
gacaccagca aggtggccag cggcgtgccc taccgcttca gcggcagcgg cagcggcacc   1380
agctacagcc tgaccatcag cagcatggag gccgaggacg ccgccaccta ctactgccag   1440
cagtggagca gcaacccccct gaccttcggc gccggcacca agctggagct gaaggccagc   1500
aagagcaaga aggagatctt ccgctggccc gagagcccca aggcccaggc cagcagcgtg   1560
cccaccgccc agccccaggc cgagggcagc ctggccaagg ccaccaccgc ccccgccacc   1620
acccgcaaca ccggccgcgg cggcgaggag aagaagaagg agaaggagaa ggaggagcag   1680
gaggagcgcg agaccaagac ccccgagtgc cccagccaca cccagcccct gggcgtgcag   1740
gtgcagctgg tggagagcgg cggcggcgtg gtgcagcccg gccgcagcct gcgcctgagc   1800
tgcgccgcca gcggcttcac cttcagcagc tacaccatgc actgggtgcg ccaggccccc   1860
ggcaagggcc tggagtgggt gaccttcatc agctacgacg gcaacaacaa gtactacgcc   1920
gacagcgtga agggccgctt caccatcagc cgcgacaaca gcaagaacac cctgtacctg   1980
cagatgaaca gcctgcgcgc cgaggacacc gccatctact actgcgcccg caccggctgg   2040
ctgggcccct tcgactactg gggccagggc accctggtga ccgtgagcag cggcggcggc   2100
ggcagcggcg gcggcggcag cggcggcggc ggcagcgaga tcgtgctgac ccagagcccc   2160
ggcaccctga gcctgagccc cggcgagcgc gccaccctga gctgccgcgc cagccagagc   2220
gtgggcagca gctacctggc ctggtaccag cagaagcccg gccaggcccc ccgcctgctg   2280
atctacggcg ccttcagccg cgccaccggc atccccgacc gcttcagcgg cagcggcagc   2340
ggcaccgact tcaccctgac catcagccgc ctggagcccg aggacttcgc cgtgtactac   2400
tgccagcagt acggcagcag cccctggacc ttcggccagg gcaccaaggt ggagatcaag   2460
```

cgc 2463

<210> SEQ ID NO 266
<211> LENGTH: 756
<212> TYPE: PRT
<213> ORGANISM: Artificial
<220> FEATURE:
<223> OTHER INFORMATION: The amino acid sequence of CD19-CD3-LAG-3
TsAb_M monomer

<400> SEQUENCE: 266

Asp Ile Gln Leu Thr Gln Ser Pro Ala Ser Leu Ala Val Ser Leu Gly
1 5 10 15

Gln Arg Ala Thr Ile Ser Cys Lys Ala Ser Gln Ser Val Asp Tyr Asp
20 25 30

Gly Asp Ser Tyr Leu Asn Trp Tyr Gln Gln Ile Pro Gly Gln Pro Pro
35 40 45

Lys Leu Leu Ile Tyr Asp Ala Ser Asn Leu Val Ser Gly Ile Pro Pro
50 55 60

Arg Phe Ser Gly Ser Gly Ser Gly Thr Asp Phe Thr Leu Asn Ile His
65 70 75 80

Pro Val Glu Lys Val Asp Ala Ala Thr Tyr His Cys Gln Gln Ser Thr
85 90 95

Glu Asp Pro Trp Thr Phe Gly Gly Gly Thr Lys Leu Glu Ile Lys Gly
100 105 110

Gly Gly Gly Ser Gly Gly Gly Gly Ser Gly Gly Gly Gly Ser Gln Val
115 120 125

Gln Leu Gln Gln Ser Gly Ala Glu Leu Val Arg Pro Gly Ser Ser Val
130 135 140

Lys Ile Ser Cys Lys Ala Ser Gly Tyr Ala Phe Ser Ser Tyr Trp Met
145 150 155 160

Asn Trp Val Lys Gln Arg Pro Gly Gln Gly Leu Glu Trp Ile Gly Gln
165 170 175

Ile Trp Pro Gly Asp Gly Asp Thr Asn Tyr Asn Gly Lys Phe Lys Gly
180 185 190

Lys Ala Thr Leu Thr Ala Asp Glu Ser Ser Ser Thr Ala Tyr Met Gln
195 200 205

Leu Ser Ser Leu Ala Ser Glu Asp Ser Ala Val Tyr Phe Cys Ala Arg
210 215 220

Arg Glu Thr Thr Thr Val Gly Arg Tyr Tyr Tyr Ala Met Asp Tyr Trp
225 230 235 240

Gly Gln Gly Thr Thr Val Thr Val Ser Ser Gly Gly Gly Gly Ser Asp
245 250 255

Ile Lys Leu Gln Gln Ser Gly Ala Glu Leu Ala Arg Pro Gly Ala Ser
260 265 270

Val Lys Met Ser Cys Lys Thr Ser Gly Tyr Thr Phe Thr Arg Tyr Thr
275 280 285

Met His Trp Val Lys Gln Arg Pro Gly Gln Gly Leu Glu Trp Ile Gly
290 295 300

Tyr Ile Asn Pro Ser Arg Gly Tyr Thr Asn Tyr Asn Gln Lys Phe Lys
305 310 315 320

Asp Lys Ala Thr Leu Thr Thr Asp Lys Ser Ser Ser Thr Ala Tyr Met
325 330 335

Gln Leu Ser Ser Leu Thr Ser Glu Asp Ser Ala Val Tyr Tyr Cys Ala
340 345 350

```
Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Gln Val Gln Leu Gln Gln Trp Gly Ala Gly Leu Leu Lys Pro Ser
        515                 520                 525

Glu Thr Leu Ser Leu Thr Cys Ala Val Tyr Gly Gly Ser Phe Ser Asp
    530                 535                 540

Tyr Tyr Trp Asn Trp Ile Arg Gln Pro Pro Gly Lys Gly Leu Glu Trp
545                 550                 555                 560

Ile Gly Glu Ile Asn His Arg Gly Ser Thr Asn Ser Asn Pro Ser Leu
                565                 570                 575

Lys Ser Arg Val Thr Leu Ser Leu Asp Thr Ser Lys Asn Gln Phe Ser
            580                 585                 590

Leu Lys Leu Arg Ser Val Thr Ala Ala Asp Thr Ala Val Tyr Tyr Cys
        595                 600                 605

Ala Phe Gly Tyr Ser Asp Tyr Glu Tyr Asn Trp Phe Asp Pro Trp Gly
    610                 615                 620

Gln Gly Thr Leu Val Thr Val Ser Ser Gly Gly Gly Gly Ser Gly Gly
625                 630                 635                 640

Gly Gly Ser Gly Gly Gly Gly Ser Glu Ile Val Leu Thr Gln Ser Pro
                645                 650                 655

Ala Thr Leu Ser Leu Ser Pro Gly Glu Arg Ala Thr Leu Ser Cys Arg
            660                 665                 670

Ala Ser Gln Ser Ile Ser Ser Tyr Leu Ala Trp Tyr Gln Gln Lys Pro
        675                 680                 685

Gly Gln Ala Pro Arg Leu Leu Ile Tyr Asp Ala Ser Asn Arg Ala Thr
    690                 695                 700

Gly Ile Pro Ala Arg Phe Ser Gly Ser Gly Ser Gly Thr Asp Phe Thr
705                 710                 715                 720

Leu Thr Ile Ser Ser Leu Glu Pro Glu Asp Phe Ala Val Tyr Tyr Cys
                725                 730                 735

Gln Gln Arg Ser Asn Trp Pro Leu Thr Phe Gly Gln Gly Thr Asn Leu
            740                 745                 750

Glu Ile Lys Arg
        755
```

<210> SEQ ID NO 267
<211> LENGTH: 2268
<212> TYPE: DNA
<213> ORGANISM: Artificial
<220> FEATURE:
<223> OTHER INFORMATION: The nucleotide sequence of CD19-CD3-LAG-3
TsAb_M monomer

<400> SEQUENCE: 267

```
gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180

ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggcggcggcg gcagcgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaaccccct gaccttcggc gccggcacca agctggagct gaagggcggc   1500

ggcggcagcg gcggcggcgg cagcggcggc ggcggcagcc aggtgcagct gcagcagtgg   1560

ggcgccggcc tgctgaagcc cagcgagacc ctgagcctga cctgcgccgt gtacggcggc   1620

agcttcagcg actactactg gaactggatc cgccagcccc ccggcaaggg cctggagtgg   1680

atcggcgaga tcaaccaccg cggcagcacc aacagcaacc ccagcctgaa gagccgcgtg   1740

accctgagcc tggacaccag caagaaccag ttcagcctga agctgcgcag cgtgaccgcc   1800

gccgacaccg ccgtgtacta ctgcgccttc ggctacagcg actacgagta caactggttc   1860

gacccctggg gccagggcac cctggtgacc gtgagcagcg gcggcggcgg cagcggcggc   1920

ggcggcagcg gcggcggcgg cagcgagatc gtgctgaccc agagccccgc caccctgagc   1980

ctgagccccg gcgagcgcgc caccctgagc tgccgcgcca gccagagcat cagcagctac   2040
```

-continued

```
ctggcctggt accagcagaa gcccggccag gccccccgcc tgctgatcta cgacgccagc   2100

aaccgcgcca ccggcatccc cgcccgcttc agcggcagcg gcagcggcac cgacttcacc   2160

ctgaccatca gcagcctgga gcccgaggac ttcgccgtgt actactgcca gcagcgcagc   2220

aactggcccc tgaccttcgg ccagggcacc aacctggaga tcaagcgc               2268


<210> SEQ ID NO 268
<211> LENGTH: 822
<212> TYPE: PRT
<213> ORGANISM: Artificial
<220> FEATURE:
<223> OTHER INFORMATION: The amino acid sequence of CD19-CD3-LAG-3
      TsAb_D dimer

<400> SEQUENCE: 268

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320
```

-continued

```
Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Gln Val Gln Leu Gln Gln Trp Gly Ala Gly Leu Leu Lys
            580                 585                 590

Pro Ser Glu Thr Leu Ser Leu Thr Cys Ala Val Tyr Gly Gly Ser Phe
        595                 600                 605

Ser Asp Tyr Tyr Trp Asn Trp Ile Arg Gln Pro Pro Gly Lys Gly Leu
    610                 615                 620

Glu Trp Ile Gly Glu Ile Asn His Arg Gly Ser Thr Asn Ser Asn Pro
625                 630                 635                 640

Ser Leu Lys Ser Arg Val Thr Leu Ser Leu Asp Thr Ser Lys Asn Gln
                645                 650                 655

Phe Ser Leu Lys Leu Arg Ser Val Thr Ala Ala Asp Thr Ala Val Tyr
            660                 665                 670

Tyr Cys Ala Phe Gly Tyr Ser Asp Tyr Glu Tyr Asn Trp Phe Asp Pro
        675                 680                 685

Trp Gly Gln Gly Thr Leu Val Thr Val Ser Ser Gly Gly Gly Gly Ser
    690                 695                 700

Gly Gly Gly Gly Ser Gly Gly Gly Gly Ser Glu Ile Val Leu Thr Gln
705                 710                 715                 720

Ser Pro Ala Thr Leu Ser Leu Ser Pro Gly Glu Arg Ala Thr Leu Ser
                725                 730                 735

Cys Arg Ala Ser Gln Ser Ile Ser Ser Tyr Leu Ala Trp Tyr Gln Gln
```

```
            740                 745                 750

Lys Pro Gly Gln Ala Pro Arg Leu Leu Ile Tyr Asp Ala Ser Asn Arg
        755                 760                 765

Ala Thr Gly Ile Pro Ala Arg Phe Ser Gly Ser Gly Ser Gly Thr Asp
    770                 775                 780

Phe Thr Leu Thr Ile Ser Ser Leu Glu Pro Glu Asp Phe Ala Val Tyr
785                 790                 795                 800

Tyr Cys Gln Gln Arg Ser Asn Trp Pro Leu Thr Phe Gly Gln Gly Thr
                805                 810                 815

Asn Leu Glu Ile Lys Arg
            820


<210> SEQ ID NO 269
<211> LENGTH: 2466
<212> TYPE: DNA
<213> ORGANISM: Artificial
<220> FEATURE:
<223> OTHER INFORMATION: The nucleotide sequence of CD19-CD3-LAG-3
      TsAb_D dimer

<400> SEQUENCE: 269

gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180

ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggcggcggcg gcagcgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaacccccct gaccttcggc gccggcacca agctggagct gaaggccagc   1500

aagagcaaga aggagatctt ccgctggccc gagagcccca aggcccaggc cagcagcgtg   1560
```

```
cccaccgccc agccccaggc cgagggcagc ctggccaagg ccaccaccgc ccccgccacc   1620

acccgcaaca ccggccgcgg cggcgaggag aagaagaagg agaaggagaa ggaggagcag   1680

gaggagcgcg agaccaagac ccccgagtgc cccagccaca cccagcccct gggcgtgcag   1740

gtgcagctgc agcagtgggg cgccggcctg ctgaagccca gcgagaccct gagcctgacc   1800

tgcgccgtgt acggcggcag cttcagcgac tactactgga actggatccg ccagcccccc   1860

ggcaagggcc tggagtggat cggcgagatc aaccaccgcg gcagcaccaa cagcaacccc   1920

agcctgaaga gccgcgtgac cctgagcctg gacaccagca agaaccagtt cagcctgaag   1980

ctgcgcagcg tgaccgccgc cgacaccgcc gtgtactact gcgccttcgg ctacagcgac   2040

tacgagtaca actggttcga cccctggggc cagggcaccc tggtgaccgt gagcagcggc   2100

ggcggcggca gcggcggcgg cggcagcggc ggcggcggca gcgagatcgt gctgacccag   2160

agccccgcca ccctgagcct gagccccggc gagcgcgcca ccctgagctg ccgcgccagc   2220

cagagcatca gcagctacct ggcctggtac cagcagaagc ccggccaggc cccccgcctg   2280

ctgatctacg acgccagcaa ccgcgccacc ggcatccccg cccgcttcag cggcagcggc   2340

agcggcaccg acttcaccct gaccatcagc agcctggagc ccgaggactt cgccgtgtac   2400

tactgccagc agcgcagcaa ctggcccctg accttcggcc agggcaccaa cctggagatc   2460

aagcgc                                                              2466
```

<210> SEQ ID NO 270
<211> LENGTH: 758
<212> TYPE: PRT
<213> ORGANISM: Artificial
<220> FEATURE:
<223> OTHER INFORMATION: The amino acid sequence of CD19-CD3-TIM-3
TsAb_M monomer

<400> SEQUENCE: 270

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190
```

-continued

Lys Ala Thr Leu Thr Ala Asp Glu Ser Ser Ser Thr Ala Tyr Met Gln
195 200 205

Leu Ser Ser Leu Ala Ser Glu Asp Ser Ala Val Tyr Phe Cys Ala Arg
210 215 220

Arg Glu Thr Thr Thr Val Gly Arg Tyr Tyr Tyr Ala Met Asp Tyr Trp
225 230 235 240

Gly Gln Gly Thr Thr Val Thr Val Ser Ser Gly Gly Gly Gly Ser Asp
245 250 255

Ile Lys Leu Gln Gln Ser Gly Ala Glu Leu Ala Arg Pro Gly Ala Ser
260 265 270

Val Lys Met Ser Cys Lys Thr Ser Gly Tyr Thr Phe Thr Arg Tyr Thr
275 280 285

Met His Trp Val Lys Gln Arg Pro Gly Gln Gly Leu Glu Trp Ile Gly
290 295 300

Tyr Ile Asn Pro Ser Arg Gly Tyr Thr Asn Tyr Asn Gln Lys Phe Lys
305 310 315 320

Asp Lys Ala Thr Leu Thr Thr Asp Lys Ser Ser Ser Thr Ala Tyr Met
325 330 335

Gln Leu Ser Ser Leu Thr Ser Glu Asp Ser Ala Val Tyr Tyr Cys Ala
340 345 350

Arg Tyr Tyr Asp Asp His Tyr Cys Leu Asp Tyr Trp Gly Gln Gly Thr
355 360 365

Thr Leu Thr Val Ser Ser Val Glu Gly Gly Ser Gly Gly Ser Gly Gly
370 375 380

Ser Gly Gly Ser Gly Gly Val Asp Asp Ile Gln Leu Thr Gln Ser Pro
385 390 395 400

Ala Ile Met Ser Ala Ser Pro Gly Glu Lys Val Thr Met Thr Cys Arg
405 410 415

Ala Ser Ser Ser Val Ser Tyr Met Asn Trp Tyr Gln Gln Lys Ser Gly
420 425 430

Thr Ser Pro Lys Arg Trp Ile Tyr Asp Thr Ser Lys Val Ala Ser Gly
435 440 445

Val Pro Tyr Arg Phe Ser Gly Ser Gly Ser Gly Thr Ser Tyr Ser Leu
450 455 460

Thr Ile Ser Ser Met Glu Ala Glu Asp Ala Ala Thr Tyr Tyr Cys Gln
465 470 475 480

Gln Trp Ser Ser Asn Pro Leu Thr Phe Gly Ala Gly Thr Lys Leu Glu
485 490 495

Leu Lys Gly Gly Gly Gly Ser Gly Gly Gly Gly Ser Gly Gly Gly Gly
500 505 510

Ser Gln Val Gln Leu Val Gln Ser Gly Ala Glu Val Lys Lys Pro Gly
515 520 525

Ala Ser Val Lys Val Ser Cys Lys Ala Ser Gly Tyr Thr Phe Thr Ser
530 535 540

Tyr Asn Met His Trp Val Arg Gln Ala Pro Gly Gln Gly Leu Glu Trp
545 550 555 560

Ile Gly Asp Ile Tyr Pro Gly Gln Gly Asp Thr Ser Tyr Asn Gln Lys
565 570 575

Phe Lys Gly Arg Ala Thr Met Thr Ala Asp Lys Ser Thr Ser Thr Val
580 585 590

Tyr Met Glu Leu Ser Ser Leu Arg Ser Glu Asp Thr Ala Val Tyr Tyr
595 600 605

-continued

```
Cys Ala Arg Val Gly Gly Ala Phe Pro Met Asp Tyr Trp Gly Gln Gly
    610                 615                 620

Thr Leu Val Thr Val Ser Ser Gly Gly Gly Gly Ser Gly Gly Gly Gly
625                 630                 635                 640

Ser Gly Gly Gly Gly Ser Asp Ile Val Leu Thr Gln Ser Pro Asp Ser
                645                 650                 655

Leu Ala Val Ser Leu Gly Glu Arg Ala Thr Ile Asn Cys Arg Ala Ser
            660                 665                 670

Glu Ser Val Glu Tyr Tyr Gly Thr Ser Leu Met Gln Trp Tyr Gln Gln
        675                 680                 685

Lys Pro Gly Gln Pro Pro Lys Leu Leu Ile Tyr Ala Ala Ser Asn Val
    690                 695                 700

Glu Ser Gly Val Pro Asp Arg Phe Ser Gly Ser Gly Ser Gly Thr Asp
705                 710                 715                 720

Phe Thr Leu Thr Ile Ser Ser Leu Gln Ala Glu Asp Val Ala Val Tyr
                725                 730                 735

Tyr Cys Gln Gln Ser Arg Lys Asp Pro Ser Thr Phe Gly Gly Gly Thr
            740                 745                 750

Lys Val Glu Ile Lys Arg
        755


<210> SEQ ID NO 271
<211> LENGTH: 2274
<212> TYPE: DNA
<213> ORGANISM: Artificial
<220> FEATURE:
<223> OTHER INFORMATION: The nucleotide sequence of CD19-CD3-TIM-3
      TsAb_M monomer

<400> SEQUENCE: 271

gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600

agcagcagca ccgcctacat gcagctgagc agcctggcca gcgaggacag cgccgtgtac     660

ttctgcgccc gccgcgagac caccaccgtg ggccgctact actacgccat ggactactgg     720

ggccagggca ccaccgtgac cgtgagcagc ggcggcggcg gcagcgacat caagctgcag     780

cagagcggcg ccgagctggc ccgccccggc gccagcgtga agatgagctg caagaccagc     840

ggctacacct tcacccgcta caccatgcac tgggtgaagc agcgccccgg ccagggcctg     900

gagtggatcg gctacatcaa ccccagccgc ggctacacca actacaacca gaagttcaag     960

gacaaggcca ccctgaccac cgacaagagc agcagcaccg cctacatgca gctgagcagc    1020

ctgaccagcg aggacagcgc cgtgtactac tgcgcccgct actacgacga ccactactgc    1080

ctggactact ggggccaggg caccaccctg accgtgagca gcgtggaggg cggcagcggc    1140
```

```
ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaaccccct gaccttcggc gccggcacca agctggagct gaagggcggc   1500

ggcggcagcg gcggcggcgg cagcggcggc ggcggcagcc aggtgcagct ggtgcagagc   1560

ggcgccgagg tgaagaagcc cggcgccagc gtgaaggtga gctgcaaggc cagcggctac   1620

accttcacca gctacaacat gcactgggtg cgccaggccc ccggccaggg cctggagtgg   1680

atcggcgaca tctaccccgg ccagggcgac accagctaca accagaagtt caagggccgc   1740

gccaccatga ccgccgacaa gagcaccagc accgtgtaca tggagctgag cagcctgcgc   1800

agcgaggaca ccgccgtgta ctactgcgcc cgcgtgggcg gcgccttccc catggactac   1860

tggggccagg gcaccctggt gaccgtgagc agcggcggcg gcggcagcgg cggcggcggc   1920

agcggcggcg gcggcagcga catcgtgctg acccagagcc ccgacagcct ggccgtgagc   1980

ctgggcgagc gcgccaccat caactgccgc gccagcgaga gcgtggagta ctacggcacc   2040

agcctgatgc agtggtacca gcagaagccc ggccagcccc ccaagctgct gatctacgcc   2100

gccagcaacg tggagagcgg cgtgcccgac cgcttcagcg gcagcggcag cggcaccgac   2160

ttcaccctga ccatcagcag cctgcaggcc gaggacgtgg ccgtgtacta ctgccagcag   2220

agccgcaagg accccagcac cttcggcggc ggcaccaagg tggagatcaa gcgc         2274
```

<210> SEQ ID NO 272
<211> LENGTH: 824
<212> TYPE: PRT
<213> ORGANISM: Artificial
<220> FEATURE:
<223> OTHER INFORMATION: The amino acid sequence of CD19-CD3-TIM-3 TsAb_D dimer

<400> SEQUENCE: 272

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160
```

```
Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Gln Val Gln Leu Val Gln Ser Gly Ala Glu Val Lys Lys
```

```
            580                 585                 590

Pro Gly Ala Ser Val Lys Val Ser Cys Lys Ala Ser Gly Tyr Thr Phe
        595                 600                 605

Thr Ser Tyr Asn Met His Trp Val Arg Gln Ala Pro Gly Gln Gly Leu
    610                 615                 620

Glu Trp Ile Gly Asp Ile Tyr Pro Gly Gln Gly Asp Thr Ser Tyr Asn
625                 630                 635                 640

Gln Lys Phe Lys Gly Arg Ala Thr Met Thr Ala Asp Lys Ser Thr Ser
                645                 650                 655

Thr Val Tyr Met Glu Leu Ser Ser Leu Arg Ser Glu Asp Thr Ala Val
            660                 665                 670

Tyr Tyr Cys Ala Arg Val Gly Gly Ala Phe Pro Met Asp Tyr Trp Gly
        675                 680                 685

Gln Gly Thr Leu Val Thr Val Ser Ser Gly Gly Gly Gly Ser Gly Gly
    690                 695                 700

Gly Gly Ser Gly Gly Gly Gly Ser Asp Ile Val Leu Thr Gln Ser Pro
705                 710                 715                 720

Asp Ser Leu Ala Val Ser Leu Gly Glu Arg Ala Thr Ile Asn Cys Arg
                725                 730                 735

Ala Ser Glu Ser Val Glu Tyr Tyr Gly Thr Ser Leu Met Gln Trp Tyr
            740                 745                 750

Gln Gln Lys Pro Gly Gln Pro Pro Lys Leu Leu Ile Tyr Ala Ala Ser
        755                 760                 765

Asn Val Glu Ser Gly Val Pro Asp Arg Phe Ser Gly Ser Gly Ser Gly
    770                 775                 780

Thr Asp Phe Thr Leu Thr Ile Ser Ser Leu Gln Ala Glu Asp Val Ala
785                 790                 795                 800

Val Tyr Tyr Cys Gln Gln Ser Arg Lys Asp Pro Ser Thr Phe Gly Gly
                805                 810                 815

Gly Thr Lys Val Glu Ile Lys Arg
            820


<210> SEQ ID NO 273
<211> LENGTH: 2472
<212> TYPE: DNA
<213> ORGANISM: Artificial
<220> FEATURE:
<223> OTHER INFORMATION: The nucleotide sequence of CD19-CD3-TIM-3
      TsAb_D dimer

<400> SEQUENCE: 273

gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600

agcagcagca ccgcctacat gcagctgagc agcctggcca gcgaggacag cgccgtgtac     660
```

-continued

```
ttctgcgccc gccgcgagac caccaccgtg ggccgctact actacgccat ggactactgg    720
ggccagggca ccaccgtgac cgtgagcagc ggcggcggcg gcagcgacat caagctgcag    780
cagagcggcg ccgagctggc ccgccccggc gccagcgtga agatgagctg caagaccagc    840
ggctacacct tcacccgcta caccatgcac tgggtgaagc agcgccccgg ccagggcctg    900
gagtggatcg gctacatcaa ccccagccgc ggctacacca actacaacca gaagttcaag    960
gacaaggcca ccctgaccac cgacaagagc agcagcaccg cctacatgca gctgagcagc   1020
ctgaccagcg aggacagcgc cgtgtactac tgcgcccgct actacgacga ccactactgc   1080
ctggactact ggggccaggg caccaccctg accgtgagca gcgtggaggg cggcagcggc   1140
ggcagcggcg gcagcggcgg cagcggcggc gtggacgaca tccagctgac ccagagcccc   1200
gccatcatga gcgccagccc cggcgagaag gtgaccatga cctgccgcgc cagcagcagc   1260
gtgagctaca tgaactggta ccagcagaag agcggcacca gccccaagcg ctggatctac   1320
gacaccagca aggtggccag cggcgtgccc taccgcttca gcggcagcgg cagcggcacc   1380
agctacagcc tgaccatcag cagcatggag gccgaggacg ccgccaccta ctactgccag   1440
cagtggagca gcaaccccct gaccttcggc gccggcacca agctggagct gaaggccagc   1500
aagagcaaga aggagatctt ccgctggccc gagagcccca aggcccaggc cagcagcgtg   1560
cccaccgccc agccccaggc cgagggcagc ctggccaagg ccaccaccgc ccccgccacc   1620
acccgcaaca ccggccgcgg cggcgaggag aagaagaagg agaaggagaa ggaggagcag   1680
gaggagcgcg agaccaagac ccccgagtgc cccagccaca cccagcccct gggcgtgcag   1740
gtgcagctgg tgcagagcgg cgccgaggtg aagaagcccg gcgccagcgt gaaggtgagc   1800
tgcaaggcca gcggctacac cttcaccagc tacaacatgc actgggtgcg ccaggccccc   1860
ggccagggcc tggagtggat cggcgacatc taccccggcc agggcgacac cagctacaac   1920
cagaagttca agggccgcgc caccatgacc gccgacaaga gcaccagcac cgtgtacatg   1980
gagctgagca gcctgcgcag cgaggacacc gccgtgtact actgcgcccg cgtgggcggc   2040
gccttcccca tggactactg gggccagggc accctggtga ccgtgagcag cggcggcggc   2100
ggcagcggcg gcggcggcag cggcggcggc ggcagcgaca tcgtgctgac ccagagcccc   2160
gacagcctgg ccgtgagcct gggcgagcgc gccaccatca actgccgcgc cagcgagagc   2220
gtggagtact acggcaccag cctgatgcag tggtaccagc agaagcccgg ccagcccccc   2280
aagctgctga tctacgccgc cagcaacgtg gagagcggcg tgcccgaccg cttcagcggc   2340
agcggcagcg gcaccgactt caccctgacc atcagcagcc tgcaggccga ggacgtggcc   2400
gtgtactact gccagcagag ccgcaaggac cccagcacct tcggcggcgg caccaaggtg   2460
gagatcaagc gc                                                       2472
```

<210> SEQ ID NO 274
<211> LENGTH: 762
<212> TYPE: PRT
<213> ORGANISM: Artificial
<220> FEATURE:
<223> OTHER INFORMATION: The amino acid sequence of CD19-CD3-TIGIT TsAb_M monomer

<400> SEQUENCE: 274

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30
```

```
Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445
```

```
Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Glu Val Gln Leu Gln Glu Ser Gly Pro Gly Leu Val Lys Pro Ser
        515                 520                 525

Gln Ser Leu Ser Leu Thr Cys Ser Val Thr Gly Ser Ser Ile Ala Ser
    530                 535                 540

Asp Tyr Trp Gly Trp Ile Arg Lys Phe Pro Gly Asn Lys Met Glu Trp
545                 550                 555                 560

Met Gly Phe Ile Thr Tyr Ser Gly Ser Thr Ser Tyr Asn Pro Ser Leu
                565                 570                 575

Lys Ser Arg Ile Ser Ile Thr Arg Asp Thr Ser Lys Asn Gln Phe Phe
            580                 585                 590

Leu Gln Leu His Ser Val Thr Thr Asp Asp Thr Ala Thr Tyr Ser Cys
        595                 600                 605

Ala Arg Met Pro Ser Phe Ile Thr Leu Ala Ser Leu Ser Thr Trp Glu
    610                 615                 620

Gly Tyr Phe Asp Phe Trp Gly Pro Gly Thr Met Val Thr Val Ser Ser
625                 630                 635                 640

Gly Gly Gly Gly Ser Gly Gly Gly Gly Ser Gly Gly Gly Gly Ser Asp
                645                 650                 655

Ile Gln Met Thr Gln Ser Pro Ser Leu Leu Ser Ala Ser Val Gly Asp
            660                 665                 670

Arg Val Thr Leu Asn Cys Lys Ala Ser Gln Ser Ile His Lys Asn Leu
        675                 680                 685

Ala Trp Tyr Gln Gln Lys Leu Gly Glu Ala Pro Lys Phe Leu Ile Tyr
    690                 695                 700

Tyr Ala Asn Ser Leu Gln Thr Gly Ile Pro Ser Arg Phe Ser Gly Ser
705                 710                 715                 720

Gly Ser Gly Thr Asp Phe Thr Leu Thr Ile Ser Gly Leu Gln Pro Glu
                725                 730                 735

Asp Val Ala Thr Tyr Phe Cys Gln Gln Tyr Tyr Ser Gly Trp Thr Phe
            740                 745                 750

Gly Gly Gly Thr Lys Val Glu Leu Lys Arg
        755                 760


<210> SEQ ID NO 275
<211> LENGTH: 2286
<212> TYPE: DNA
<213> ORGANISM: Artificial
<220> FEATURE:
<223> OTHER INFORMATION: The nucleotide sequence of CD19-CD3-TIGIT
      TsAb_M monomer

<400> SEQUENCE: 275

gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240
```

```
cccgtggaga aggtggacgc cgccacctac cactgccagc agagcaccga ggacccctgg    300

accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggcggcggcg gcagcgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaaccccct gaccttcggc gccggcacca agctggagct gaagggcggc   1500

ggcggcagcg gcggcggcgg cagcggcggc ggcggcagcg aggtgcagct gcaggagagc   1560

ggccccggcc tggtgaagcc cagccagagc ctgagcctga cctgcagcgt gaccggcagc   1620

agcatcgcca gcgactactg gggctggatc cgcaagttcc ccggcaacaa gatggagtgg   1680

atgggcttca tcacctacag cggcagcacc agctacaacc ccagcctgaa gagccgcatc   1740

agcatcaccc gcgacaccag caagaaccag ttcttcctgc agctgcacag cgtgaccacc   1800

gacgacaccg ccacctacag ctgcgcccgc atgcccagct tcatcaccct ggccagcctg   1860

agcacctggg agggctactt cgacttctgg ggccccggca ccatggtgac cgtgagcagc   1920

ggcggcggcg gcagcggcgg cggcggcagc ggcggcggcg gcagcgacat ccagatgacc   1980

cagagcccca gcctgctgag cgccagcgtg ggcgaccgcg tgaccctgaa ctgcaaggcc   2040

agccagagca tccacaagaa cctggcctgg taccagcaga agctgggcga ggcccccaag   2100

ttcctgatct actacgccaa cagcctgcag accggcatcc ccagccgctt cagcggcagc   2160

ggcagcggca ccgacttcac cctgaccatc agcggcctgc agcccgagga cgtggccacc   2220

tacttctgcc agcagtacta cagcggctgg accttcggcg gcggcaccaa ggtggagctg   2280

aagcgc                                                              2286
```

<210> SEQ ID NO 276
<211> LENGTH: 828
<212> TYPE: PRT
<213> ORGANISM: Artificial
<220> FEATURE:
<223> OTHER INFORMATION: The amino acid sequence of CD19-CD3-TIGIT
TsAb_D dimer

<400> SEQUENCE: 276

Asp Ile Gln Leu Thr Gln Ser Pro Ala Ser Leu Ala Val Ser Leu Gly
1 5 10 15

Gln Arg Ala Thr Ile Ser Cys Lys Ala Ser Gln Ser Val Asp Tyr Asp
20 25 30

Gly Asp Ser Tyr Leu Asn Trp Tyr Gln Gln Ile Pro Gly Gln Pro Pro
35 40 45

Lys Leu Leu Ile Tyr Asp Ala Ser Asn Leu Val Ser Gly Ile Pro Pro
50 55 60

Arg Phe Ser Gly Ser Gly Ser Gly Thr Asp Phe Thr Leu Asn Ile His
65 70 75 80

Pro Val Glu Lys Val Asp Ala Ala Thr Tyr His Cys Gln Gln Ser Thr
85 90 95

Glu Asp Pro Trp Thr Phe Gly Gly Gly Thr Lys Leu Glu Ile Lys Gly
100 105 110

Gly Gly Gly Ser Gly Gly Gly Gly Ser Gly Gly Gly Gly Ser Gln Val
115 120 125

Gln Leu Gln Gln Ser Gly Ala Glu Leu Val Arg Pro Gly Ser Ser Val
130 135 140

Lys Ile Ser Cys Lys Ala Ser Gly Tyr Ala Phe Ser Ser Tyr Trp Met
145 150 155 160

Asn Trp Val Lys Gln Arg Pro Gly Gln Gly Leu Glu Trp Ile Gly Gln
165 170 175

Ile Trp Pro Gly Asp Gly Asp Thr Asn Tyr Asn Gly Lys Phe Lys Gly
180 185 190

Lys Ala Thr Leu Thr Ala Asp Glu Ser Ser Ser Thr Ala Tyr Met Gln
195 200 205

Leu Ser Ser Leu Ala Ser Glu Asp Ser Ala Val Tyr Phe Cys Ala Arg
210 215 220

Arg Glu Thr Thr Thr Val Gly Arg Tyr Tyr Tyr Ala Met Asp Tyr Trp
225 230 235 240

Gly Gln Gly Thr Thr Val Thr Val Ser Ser Gly Gly Gly Gly Ser Asp
245 250 255

Ile Lys Leu Gln Gln Ser Gly Ala Glu Leu Ala Arg Pro Gly Ala Ser
260 265 270

Val Lys Met Ser Cys Lys Thr Ser Gly Tyr Thr Phe Thr Arg Tyr Thr
275 280 285

Met His Trp Val Lys Gln Arg Pro Gly Gln Gly Leu Glu Trp Ile Gly
290 295 300

Tyr Ile Asn Pro Ser Arg Gly Tyr Thr Asn Tyr Asn Gln Lys Phe Lys
305 310 315 320

Asp Lys Ala Thr Leu Thr Thr Asp Lys Ser Ser Ser Thr Ala Tyr Met
325 330 335

Gln Leu Ser Ser Leu Thr Ser Glu Asp Ser Ala Val Tyr Tyr Cys Ala
340 345 350

Arg Tyr Tyr Asp Asp His Tyr Cys Leu Asp Tyr Trp Gly Gln Gly Thr
355 360 365

Thr Leu Thr Val Ser Ser Val Glu Gly Gly Ser Gly Gly Ser Gly Gly
370 375 380

Ser Gly Gly Ser Gly Gly Val Asp Asp Ile Gln Leu Thr Gln Ser Pro
385 390 395 400

Ala Ile Met Ser Ala Ser Pro Gly Glu Lys Val Thr Met Thr Cys Arg
405 410 415

```
Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Glu Val Gln Leu Gln Glu Ser Gly Pro Gly Leu Val Lys
            580                 585                 590

Pro Ser Gln Ser Leu Ser Leu Thr Cys Ser Val Thr Gly Ser Ser Ile
        595                 600                 605

Ala Ser Asp Tyr Trp Gly Trp Ile Arg Lys Phe Pro Gly Asn Lys Met
    610                 615                 620

Glu Trp Met Gly Phe Ile Thr Tyr Ser Gly Ser Thr Ser Tyr Asn Pro
625                 630                 635                 640

Ser Leu Lys Ser Arg Ile Ser Ile Thr Arg Asp Thr Ser Lys Asn Gln
                645                 650                 655

Phe Phe Leu Gln Leu His Ser Val Thr Thr Asp Asp Thr Ala Thr Tyr
            660                 665                 670

Ser Cys Ala Arg Met Pro Ser Phe Ile Thr Leu Ala Ser Leu Ser Thr
        675                 680                 685

Trp Glu Gly Tyr Phe Asp Phe Trp Gly Pro Gly Thr Met Val Thr Val
    690                 695                 700

Ser Ser Gly Gly Gly Gly Ser Gly Gly Gly Gly Ser Gly Gly Gly Gly
705                 710                 715                 720

Ser Asp Ile Gln Met Thr Gln Ser Pro Ser Leu Leu Ser Ala Ser Val
                725                 730                 735

Gly Asp Arg Val Thr Leu Asn Cys Lys Ala Ser Gln Ser Ile His Lys
            740                 745                 750

Asn Leu Ala Trp Tyr Gln Gln Lys Leu Gly Glu Ala Pro Lys Phe Leu
        755                 760                 765

Ile Tyr Tyr Ala Asn Ser Leu Gln Thr Gly Ile Pro Ser Arg Phe Ser
    770                 775                 780

Gly Ser Gly Ser Gly Thr Asp Phe Thr Leu Thr Ile Ser Gly Leu Gln
785                 790                 795                 800

Pro Glu Asp Val Ala Thr Tyr Phe Cys Gln Gln Tyr Tyr Ser Gly Trp
                805                 810                 815

Thr Phe Gly Gly Gly Thr Lys Val Glu Leu Lys Arg
            820                 825
```

<210> SEQ ID NO 277
<211> LENGTH: 2484
<212> TYPE: DNA
<213> ORGANISM: Artificial
<220> FEATURE:
<223> OTHER INFORMATION: The nucleotide sequence of CD19-CD3-TIGIT
TsAb_D dimer

<400> SEQUENCE: 277

```
gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180

ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggcggcggcg gcagcgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140

ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaacccct gaccttcggc gccggcacca agctggagct gaaggccagc   1500

aagagcaaga aggagatctt ccgctggccc gagagcccca aggcccaggc cagcagcgtg   1560

cccaccgccc agccccaggc cgagggcagc ctggccaagg ccaccaccgc ccccgccacc   1620

acccgcaaca ccggccgcgg cggcgaggag aagaagaagg agaaggagaa ggaggagcag   1680

gaggagcgcg agaccaagac ccccgagtgc cccagccaca cccagcccct gggcgtggag   1740

gtgcagctgc aggagagcgg ccccggcctg gtgaagccca gccagagcct gagcctgacc   1800

tgcagcgtga ccggcagcag catcgccagc gactactggg gctggatccg caagttcccc   1860

ggcaacaaga tggagtggat gggcttcatc acctacagcg gcagcaccag ctacaacccc   1920

agcctgaaga gccgcatcag catcacccgc gacaccagca agaaccagtt cttcctgcag   1980

ctgcacagcg tgaccaccga cgacaccgcc acctacagct gcgcccgcat gcccagcttc   2040
```

```
atcaccctgg ccagcctgag cacctgggag ggctacttcg acttctgggg ccccggcacc   2100

atggtgaccg tgagcagcgg cggcggcggc agcggcggcg gcggcagcgg cggcggcggc   2160

agcgacatcc agatgaccca gagccccagc ctgctgagcg ccagcgtggg cgaccgcgtg   2220

accctgaact gcaaggccag ccagagcatc cacaagaacc tggcctggta ccagcagaag   2280

ctgggcgagg cccccaagtt cctgatctac tacgccaaca gcctgcagac cggcatcccc   2340

agccgcttca gcggcagcgg cagcggcacc gacttcaccc tgaccatcag cggcctgcag   2400

cccgaggacg tggccaccta cttctgccag cagtactaca gcggctggac cttcggcggc   2460

ggcaccaagg tggagctgaa gcgc                                          2484


<210> SEQ ID NO 278
<211> LENGTH: 758
<212> TYPE: PRT
<213> ORGANISM: Artificial
<220> FEATURE:
<223> OTHER INFORMATION: The amino acid sequence of CD19-CD3-BTLA TsAb_M
      monomer

<400> SEQUENCE: 278

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
```

```
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Gly Gly Gly Gly Ser Gly Gly Gly Gly Ser Gly Gly Gly Gly
            500                 505                 510

Ser Glu Val Gln Leu Val Glu Ser Gly Gly Gly Leu Val Gln Pro Gly
        515                 520                 525

Gly Ser Leu Arg Leu Ser Cys Ala Ala Ser Gly Phe Thr Ile Ser Ser
    530                 535                 540

Tyr Asp Met His Trp Val Arg Gln Ala Thr Gly Lys Gly Leu Glu Trp
545                 550                 555                 560

Val Ser Val Ile Gly Pro Ala Gly Asp Thr Tyr Tyr Pro Gly Ser Val
                565                 570                 575

Lys Gly Arg Phe Thr Ile Ser Arg Glu Asn Ala Lys Asn Ser Leu Tyr
            580                 585                 590

Leu Gln Met Asn Ser Leu Arg Ala Gly Asp Thr Ala Val Tyr Tyr Cys
        595                 600                 605

Ala Arg Glu Gly Met Ala Ala His Asn Tyr Tyr Gly Met Asp Val Trp
    610                 615                 620

Gly Gln Gly Thr Thr Val Thr Val Ser Ser Gly Gly Gly Gly Ser Gly
625                 630                 635                 640

Gly Gly Gly Ser Gly Gly Gly Gly Ser Glu Ile Val Leu Thr Gln Ser
                645                 650                 655

Pro Ala Thr Leu Ser Leu Ser Pro Gly Glu Arg Ala Thr Leu Ser Cys
            660                 665                 670

Arg Ala Ser Gln Ser Val Ser Ser Tyr Leu Ala Trp Tyr Gln Gln Lys
        675                 680                 685

Pro Gly Gln Ala Pro Arg Leu Leu Ile Tyr Asp Ala Ser Asn Arg Ala
    690                 695                 700
```

Thr Gly Ile Pro Ala Arg Phe Ser Gly Ser Gly Ser Gly Thr Asp Phe
705 710 715 720

Thr Leu Thr Ile Ser Ser Leu Glu Pro Glu Asp Phe Ala Val Tyr Tyr
725 730 735

Cys Gln Gln Arg Ser Asn Trp Pro Pro Ile Thr Phe Gly Gln Gly Thr
740 745 750

Arg Leu Glu Ile Lys Arg
755

<210> SEQ ID NO 279
<211> LENGTH: 2274
<212> TYPE: DNA
<213> ORGANISM: Artificial
<220> FEATURE:
<223> OTHER INFORMATION: The nucleotide sequence of CD19-CD3-BTLA TsAb_M monomer

<400> SEQUENCE: 279
gacatccagc tgacccagag ccccgccagc ctggccgtga gcctgggcca gcgcgccacc 60
atcagctgca aggccagcca gagcgtggac tacgacggcg acagctacct gaactggtac 120
cagcagatcc ccggccagcc ccccaagctg ctgatctacg acgccagcaa cctggtgagc 180
ggcatccccc cccgcttcag cggcagcggc agcggcaccg acttcaccct gaacatccac 240
cccgtggaga aggtggacgc cgccacctac cactgccagc agagcaccga ggacccctgg 300
accttcggcg gcggcaccaa gctggagatc aagggcggcg gcggcagcgg cggcggcggc 360
agcggcggcg gcggcagcca ggtgcagctg cagcagagcg gcgccgagct ggtgcgcccc 420
ggcagcagcg tgaagatcag ctgcaaggcc agcggctacg ccttcagcag ctactggatg 480
aactgggtga agcagcgccc cggccagggc ctggagtgga tcggccagat ctggcccggc 540
gacggcgaca ccaactacaa cggcaagttc aagggcaagg ccaccctgac cgccgacgag 600
agcagcagca ccgcctacat gcagctgagc agcctggcca gcgaggacag cgccgtgtac 660
ttctgcgccc gccgcgagac caccaccgtg ggccgctact actacgccat ggactactgg 720
ggccagggca ccaccgtgac cgtgagcagc ggcggcggcg gcagcgacat caagctgcag 780
cagagcggcg ccgagctggc ccgccccggc gccagcgtga agatgagctg caagaccagc 840
ggctacacct tcacccgcta caccatgcac tgggtgaagc agcgccccgg ccagggcctg 900
gagtggatcg gctacatcaa ccccagccgc ggctacacca actacaacca gaagttcaag 960
gacaaggcca ccctgaccac cgacaagagc agcagcaccg cctacatgca gctgagcagc 1020
ctgaccagcg aggacagcgc cgtgtactac tgcgcccgct actacgacga ccactactgc 1080
ctggactact ggggccaggg caccaccctg accgtgagca gcgtggaggg cggcagcggc 1140
ggcagcggcg gcagcggcgg cagcggcggc gtggacgaca tccagctgac ccagagcccc 1200
gccatcatga gcgccagccc cggcgagaag gtgaccatga cctgccgcgc cagcagcagc 1260
gtgagctaca tgaactggta ccagcagaag agcggcacca gccccaagcg ctggatctac 1320
gacaccagca aggtggccag cggcgtgccc taccgcttca gcggcagcgg cagcggcacc 1380
agctacagcc tgaccatcag cagcatggag gccgaggacg ccgccaccta ctactgccag 1440
cagtggagca gcaaccccct gaccttcggc gccggcacca agctggagct gaagggcggc 1500
ggcggcagcg gcggcggcgg cagcggcggc ggcggcagcg aggtgcagct ggtggagagc 1560
ggcggcggcc tggtgcagcc cggcggcagc ctgcgcctga gctgcgccgc cagcggcttc 1620
accatcagca gctacgacat gcactgggtg cgccaggcca ccggcaaggg cctggagtgg 1680

```
gtgagcgtga tcggccccgc cggcgacacc tactaccccg gcagcgtgaa gggccgcttc   1740

accatcagcc gcgagaacgc caagaacagc ctgtacctgc agatgaacag cctgcgcgcc   1800

ggcgacaccg ccgtgtacta ctgcgcccgc gagggcatgg ccgcccacaa ctactacggc   1860

atggacgtgt ggggccaggg caccaccgtg accgtgagca gcggcggcgg cggcagcggc   1920

ggcggcggca gcggcggcgg cggcagcgag atcgtgctga cccagagccc cgccaccctg   1980

agcctgagcc ccggcgagcg cgccaccctg agctgccgcg ccagccagag cgtgagcagc   2040

tacctggcct ggtaccagca gaagcccggc caggcccccc gcctgctgat ctacgacgcc   2100

agcaaccgcg ccaccggcat ccccgcccgc ttcagcggca gcggcagcgg caccgacttc   2160

accctgacca tcagcagcct ggagcccgag gacttcgccg tgtactactg ccagcagcgc   2220

agcaactggc cccccatcac cttcggccag ggcacccgcc tggagatcaa gcgc         2274


<210> SEQ ID NO 280
<211> LENGTH: 824
<212> TYPE: PRT
<213> ORGANISM: Artificial
<220> FEATURE:
<223> OTHER INFORMATION: The amino acid sequence of CD19-CD3-BTLA TsAb_D
      dimer

<400> SEQUENCE: 280

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255
```

```
Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys Ala Ser Lys Ser Lys Lys Glu Ile Phe Arg Trp Pro Glu Ser
            500                 505                 510

Pro Lys Ala Gln Ala Ser Ser Val Pro Thr Ala Gln Pro Gln Ala Glu
        515                 520                 525

Gly Ser Leu Ala Lys Ala Thr Thr Ala Pro Ala Thr Thr Arg Asn Thr
    530                 535                 540

Gly Arg Gly Gly Glu Glu Lys Lys Lys Glu Lys Glu Lys Glu Glu Gln
545                 550                 555                 560

Glu Glu Arg Glu Thr Lys Thr Pro Glu Cys Pro Ser His Thr Gln Pro
                565                 570                 575

Leu Gly Val Glu Val Gln Leu Val Glu Ser Gly Gly Gly Leu Val Gln
            580                 585                 590

Pro Gly Gly Ser Leu Arg Leu Ser Cys Ala Ala Ser Gly Phe Thr Ile
        595                 600                 605

Ser Ser Tyr Asp Met His Trp Val Arg Gln Ala Thr Gly Lys Gly Leu
    610                 615                 620

Glu Trp Val Ser Val Ile Gly Pro Ala Gly Asp Thr Tyr Tyr Pro Gly
625                 630                 635                 640

Ser Val Lys Gly Arg Phe Thr Ile Ser Arg Glu Asn Ala Lys Asn Ser
                645                 650                 655

Leu Tyr Leu Gln Met Asn Ser Leu Arg Ala Gly Asp Thr Ala Val Tyr
            660                 665                 670
```

-continued

```
Tyr Cys Ala Arg Glu Gly Met Ala Ala His Asn Tyr Tyr Gly Met Asp
        675                 680                 685

Val Trp Gly Gln Gly Thr Thr Val Thr Val Ser Ser Gly Gly Gly Gly
    690                 695                 700

Ser Gly Gly Gly Gly Ser Gly Gly Gly Gly Ser Glu Ile Val Leu Thr
705                 710                 715                 720

Gln Ser Pro Ala Thr Leu Ser Leu Ser Pro Gly Glu Arg Ala Thr Leu
                725                 730                 735

Ser Cys Arg Ala Ser Gln Ser Val Ser Ser Tyr Leu Ala Trp Tyr Gln
            740                 745                 750

Gln Lys Pro Gly Gln Ala Pro Arg Leu Leu Ile Tyr Asp Ala Ser Asn
        755                 760                 765

Arg Ala Thr Gly Ile Pro Ala Arg Phe Ser Gly Ser Gly Ser Gly Thr
    770                 775                 780

Asp Phe Thr Leu Thr Ile Ser Ser Leu Glu Pro Glu Asp Phe Ala Val
785                 790                 795                 800

Tyr Tyr Cys Gln Gln Arg Ser Asn Trp Pro Pro Ile Thr Phe Gly Gln
                805                 810                 815

Gly Thr Arg Leu Glu Ile Lys Arg
            820
```

<210> SEQ ID NO 281
<211> LENGTH: 2472
<212> TYPE: DNA
<213> ORGANISM: Artificial
<220> FEATURE:
<223> OTHER INFORMATION: The nucleotide sequence of CD19-CD3-BTLA TsAb_D dimer

<400> SEQUENCE: 281

```
gacatccagc tgacccagag ccccgccagc ctggccgtga gcctgggcca gcgcgccacc     60

atcagctgca aggccagcca gagcgtggac tacgacggcg acagctacct gaactggtac    120

cagcagatcc ccggccagcc ccccaagctg ctgatctacg acgccagcaa cctggtgagc    180

ggcatccccc cccgcttcag cggcagcggc agcggcaccg acttcaccct gaacatccac    240

cccgtggaga aggtggacgc cgccacctac cactgccagc agagcaccga ggacccctgg    300

accttcggcg gcggcaccaa gctggagatc aagggcggcg gcggcagcgg cggcggcggc    360

agcggcggcg gcggcagcca ggtgcagctg cagcagagcg gcgccgagct ggtgcgcccc    420

ggcagcagcg tgaagatcag ctgcaaggcc agcggctacg ccttcagcag ctactggatg    480

aactgggtga agcagcgccc cggccagggc ctggagtgga tcggccagat ctggcccggc    540

gacggcgaca ccaactacaa cggcaagttc aagggcaagg ccaccctgac cgccgacgag    600

agcagcagca ccgcctacat gcagctgagc agcctggcca gcgaggacag cgccgtgtac    660

ttctgcgccc gccgcgagac caccaccgtg ggccgctact actacgccat ggactactgg    720

ggccagggca ccaccgtgac cgtgagcagc ggcggcggcg gcagcgacat caagctgcag    780

cagagcggcg ccgagctggc ccgccccggc gccagcgtga agatgagctg caagaccagc    840

ggctacacct tcacccgcta caccatgcac tgggtgaagc agcgccccgg ccagggcctg    900

gagtggatcg gctacatcaa ccccagccgc ggctacacca actacaacca gaagttcaag    960

gacaaggcca ccctgaccac cgacaagagc agcagcaccg cctacatgca gctgagcagc   1020

ctgaccagcg aggacagcgc cgtgtactac tgcgcccgct actacgacga ccactactgc   1080

ctggactact ggggccaggg caccaccctg accgtgagca gcgtggaggg cggcagcggc   1140
```

-continued

```
ggcagcggcg gcagcggcgg cagcggcggc gtggacgaca tccagctgac ccagagcccc   1200

gccatcatga gcgccagccc cggcgagaag gtgaccatga cctgccgcgc cagcagcagc   1260

gtgagctaca tgaactggta ccagcagaag agcggcacca gccccaagcg ctggatctac   1320

gacaccagca aggtggccag cggcgtgccc taccgcttca gcggcagcgg cagcggcacc   1380

agctacagcc tgaccatcag cagcatggag gccgaggacg ccgccaccta ctactgccag   1440

cagtggagca gcaacccccct gaccttcggc gccggcacca agctggagct gaaggccagc   1500

aagagcaaga aggagatctt ccgctggccc gagagcccca aggcccaggc cagcagcgtg   1560

cccaccgccc agccccaggc cgagggcagc ctggccaagg ccaccaccgc ccccgccacc   1620

acccgcaaca ccggccgcgg cggcgaggag aagaagaagg agaaggagaa ggaggagcag   1680

gaggagcgcg agaccaagac ccccgagtgc cccagccaca cccagcccct gggcgtggag   1740

gtgcagctgg tggagagcgg cggcggcctg gtgcagcccg gcggcagcct gcgcctgagc   1800

tgcgccgcca gcggcttcac catcagcagc tacgacatgc actgggtgcg ccaggccacc   1860

ggcaagggcc tggagtgggt gagcgtgatc ggccccgccg gcgacaccta ctaccccggc   1920

agcgtgaagg gccgcttcac catcagccgc gagaacgcca agaacagcct gtacctgcag   1980

atgaacagcc tgcgcgccgg cgacaccgcc gtgtactact gcgcccgcga gggcatggcc   2040

gcccacaact actacggcat ggacgtgtgg ggccagggca ccaccgtgac cgtgagcagc   2100

ggcggcggcg gcagcggcgg cggcggcagc ggcggcggcg gcagcgagat cgtgctgacc   2160

cagagccccg ccaccctgag cctgagcccc ggcgagcgcg ccaccctgag ctgccgcgcc   2220

agccagagcg tgagcagcta cctggcctgg taccagcaga agcccggcca ggcccccccgc   2280

ctgctgatct acgacgccag caaccgcgcc accggcatcc ccgcccgctt cagcggcagc   2340

ggcagcggca ccgacttcac cctgaccatc agcagcctgg agcccgagga cttcgccgtg   2400

tactactgcc agcagcgcag caactggccc cccatcacct tcggccaggg cacccgcctg   2460

gagatcaagc gc                                                       2472
```

<210> SEQ ID NO 282
<211> LENGTH: 250
<212> TYPE: PRT
<213> ORGANISM: Artificial
<220> FEATURE:
<223> OTHER INFORMATION: The amino acid sequence of anti-CD19 scFv

<400> SEQUENCE: 282

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125
```

-continued

```
Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser
                245                 250
```

<210> SEQ ID NO 283
<211> LENGTH: 124
<212> TYPE: PRT
<213> ORGANISM: Artificial
<220> FEATURE:
<223> OTHER INFORMATION: The amino acid sequence of anti-CD19 scFv heavy chain variable region

<400> SEQUENCE: 283

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

<210> SEQ ID NO 284
<211> LENGTH: 111
<212> TYPE: PRT
<213> ORGANISM: Artificial
<220> FEATURE:
<223> OTHER INFORMATION: The amino acid sequence of anti-CD19 scFv light chain variable region

<400> SEQUENCE: 284

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45
```

```
Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110


<210> SEQ ID NO 285
<211> LENGTH: 243
<212> TYPE: PRT
<213> ORGANISM: Artificial
<220> FEATURE:
<223> OTHER INFORMATION: The amino acid sequence of anti-CD3 scFv

<400> SEQUENCE: 285

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys


<210> SEQ ID NO 286
<211> LENGTH: 119
<212> TYPE: PRT
<213> ORGANISM: Artificial
<220> FEATURE:
<223> OTHER INFORMATION: The amino acid sequence of anti-CD3 scFv heavy
      chain variable region
```

<400> SEQUENCE: 286

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 287
<211> LENGTH: 106
<212> TYPE: PRT
<213> ORGANISM: Artificial
<220> FEATURE:
<223> OTHER INFORMATION: The amino acid sequence of anti-CD3 scFv light chain variable region

<400> SEQUENCE: 287

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 288
<211> LENGTH: 236
<212> TYPE: PRT
<213> ORGANISM: Artificial
<220> FEATURE:
<223> OTHER INFORMATION: The amino acid sequence of anti-PD-1 scFv

<400> SEQUENCE: 288

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

```
Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Gly Gly Gly Gly Ser Gly Gly Gly Gly Ser Gly Gly Gly Gly Ser
        115                 120                 125

Glu Ile Val Leu Thr Gln Ser Pro Ala Thr Leu Ser Leu Ser Pro Gly
    130                 135                 140

Glu Arg Ala Thr Leu Ser Cys Arg Ala Ser Gln Ser Val Ser Ser Tyr
145                 150                 155                 160

Leu Ala Trp Tyr Gln Gln Lys Pro Gly Gln Ala Pro Arg Leu Leu Ile
                165                 170                 175

Tyr Asp Ala Ser Asn Arg Ala Thr Gly Ile Pro Ala Arg Phe Ser Gly
            180                 185                 190

Ser Gly Ser Gly Thr Asp Phe Thr Leu Thr Ile Ser Ser Leu Glu Pro
        195                 200                 205

Glu Asp Phe Ala Val Tyr Tyr Cys Gln Gln Ser Ser Asn Trp Pro Arg
    210                 215                 220

Thr Phe Gly Gln Gly Thr Lys Val Glu Ile Lys Arg
225                 230                 235
```

<210> SEQ ID NO 289
<211> LENGTH: 113
<212> TYPE: PRT
<213> ORGANISM: Artificial
<220> FEATURE:
<223> OTHER INFORMATION: The amino acid sequence of anti-PD-1 scFv heavy chain variable region

<400> SEQUENCE: 289

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser
```

<210> SEQ ID NO 290
<211> LENGTH: 108
<212> TYPE: PRT
<213> ORGANISM: Artificial
<220> FEATURE:
<223> OTHER INFORMATION: The amino acid sequence of anti-PD-1 scFv light chain variable region

<400> SEQUENCE: 290

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg
            100                 105


<210> SEQ ID NO 291
<211> LENGTH: 242
<212> TYPE: PRT
<213> ORGANISM: Artificial
<220> FEATURE:
<223> OTHER INFORMATION: The amino acid sequence of anti-CTLA-4 scFv

<400> SEQUENCE: 291

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

Ser Leu Ser Pro Gly Glu Arg Ala Thr Leu Ser Cys Arg Ala Ser Gln
145                 150                 155                 160

Ser Val Gly Ser Ser Tyr Leu Ala Trp Tyr Gln Gln Lys Pro Gly Gln
                165                 170                 175

Ala Pro Arg Leu Leu Ile Tyr Gly Ala Phe Ser Arg Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu Pro Glu Asp Phe Ala Val Tyr Tyr Cys Gln Gln
    210                 215                 220

Tyr Gly Ser Ser Pro Trp Thr Phe Gly Gln Gly Thr Lys Val Glu Ile
225                 230                 235                 240

Lys Arg
```

<210> SEQ ID NO 292
<211> LENGTH: 118
<212> TYPE: PRT
<213> ORGANISM: Artificial
<220> FEATURE:
<223> OTHER INFORMATION: The amino acid sequence of anti-CTLA-4 scFv heavy chain variable region

<400> SEQUENCE: 292

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115
```

<210> SEQ ID NO 293
<211> LENGTH: 109
<212> TYPE: PRT
<213> ORGANISM: Artificial
<220> FEATURE:
<223> OTHER INFORMATION: The amino acid sequence of anti-CTLA-4 scFv light chain variable region

<400> SEQUENCE: 293

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg
            100                 105
```

<210> SEQ ID NO 294
<211> LENGTH: 243
<212> TYPE: PRT
<213> ORGANISM: Artificial
<220> FEATURE:
<223> OTHER INFORMATION: The amino acid sequence of anti-LAG-3 scFv

<400> SEQUENCE: 294

```
Gln Val Gln Leu Gln Gln Trp Gly Ala Gly Leu Leu Lys Pro Ser Glu
1               5                   10                  15
```

```
Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Ser Ile Ser Ser Tyr Leu Ala Trp Tyr Gln Gln Lys Pro Gly
                165                 170                 175

Gln Ala Pro Arg Leu Leu Ile Tyr Asp Ala Ser Asn Arg Ala Thr Gly
            180                 185                 190

Ile Pro Ala Arg Phe Ser Gly Ser Gly Ser Gly Thr Asp Phe Thr Leu
        195                 200                 205

Thr Ile Ser Ser Leu Glu Pro Glu Asp Phe Ala Val Tyr Tyr Cys Gln
    210                 215                 220

Gln Arg Ser Asn Trp Pro Leu Thr Phe Gly Gln Gly Thr Asn Leu Glu
225                 230                 235                 240

Ile Lys Arg


<210> SEQ ID NO 295
<211> LENGTH: 120
<212> TYPE: PRT
<213> ORGANISM: Artificial
<220> FEATURE:
<223> OTHER INFORMATION: The amino acid sequence of anti-LAG-3 scFv
      heavy chain variable region

<400> SEQUENCE: 295

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser
        115                 120
```

<210> SEQ ID NO 296
<211> LENGTH: 108
<212> TYPE: PRT
<213> ORGANISM: Artificial
<220> FEATURE:
<223> OTHER INFORMATION: The amino acid sequence of anti-LAG-3 scFv
light chain variable region

<400> SEQUENCE: 296

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg
            100                 105
```

<210> SEQ ID NO 297
<211> LENGTH: 245
<212> TYPE: PRT
<213> ORGANISM: Artificial
<220> FEATURE:
<223> OTHER INFORMATION: The amino acid sequence of anti-TIM-3 scFv

<400> SEQUENCE: 297

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Leu Thr Gln Ser Pro Asp Ser Leu
    130                 135                 140

Ala Val Ser Leu Gly Glu Arg Ala Thr Ile Asn Cys Arg Ala Ser Glu
145                 150                 155                 160

Ser Val Glu Tyr Tyr Gly Thr Ser Leu Met Gln Trp Tyr Gln Gln Lys
                165                 170                 175

Pro Gly Gln Pro Pro Lys Leu Leu Ile Tyr Ala Ala Ser Asn Val Glu
            180                 185                 190

Ser Gly Val Pro Asp Arg Phe Ser Gly Ser Gly Ser Gly Thr Asp Phe
```

```
        195                 200                 205

Thr Leu Thr Ile Ser Ser Leu Gln Ala Glu Asp Val Ala Val Tyr Tyr
    210                 215                 220

Cys Gln Gln Ser Arg Lys Asp Pro Ser Thr Phe Gly Gly Gly Thr Lys
225                 230                 235                 240

Val Glu Ile Lys Arg
                245


<210> SEQ ID NO 298
<211> LENGTH: 118
<212> TYPE: PRT
<213> ORGANISM: Artificial
<220> FEATURE:
<223> OTHER INFORMATION: The amino acid sequence of anti-TIM-3 scFv
      heavy chain variable region

<400> SEQUENCE: 298

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser
        115


<210> SEQ ID NO 299
<211> LENGTH: 112
<212> TYPE: PRT
<213> ORGANISM: Artificial
<220> FEATURE:
<223> OTHER INFORMATION: The amino acid sequence of anti-TIM-3 scFv
      light chain variable region

<400> SEQUENCE: 299

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Asp Pro Ser Thr Phe Gly Gly Gly Thr Lys Val Glu Ile Lys Arg
            100                 105                 110
```

<210> SEQ ID NO 300
<211> LENGTH: 249
<212> TYPE: PRT
<213> ORGANISM: Artificial
<220> FEATURE:
<223> OTHER INFORMATION: The amino acid sequence of anti-TIGIT scFv

<400> SEQUENCE: 300

```
Glu Val Gln Leu Gln Glu Ser Gly Pro Gly Leu Val Lys Pro Ser Gln
1               5                   10                  15

Ser Leu Ser Leu Thr Cys Ser Val Thr Gly Ser Ser Ile Ala Ser Asp
            20                  25                  30

Tyr Trp Gly Trp Ile Arg Lys Phe Pro Gly Asn Lys Met Glu Trp Met
        35                  40                  45

Gly Phe Ile Thr Tyr Ser Gly Ser Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu His Ser Val Thr Thr Asp Asp Thr Ala Thr Tyr Ser Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Pro Gly Thr Met Val Thr Val Ser Ser Gly
        115                 120                 125

Gly Gly Gly Ser Gly Gly Gly Gly Ser Gly Gly Gly Gly Ser Asp Ile
    130                 135                 140

Gln Met Thr Gln Ser Pro Ser Leu Leu Ser Ala Ser Val Gly Asp Arg
145                 150                 155                 160

Val Thr Leu Asn Cys Lys Ala Ser Gln Ser Ile His Lys Asn Leu Ala
                165                 170                 175

Trp Tyr Gln Gln Lys Leu Gly Glu Ala Pro Lys Phe Leu Ile Tyr Tyr
            180                 185                 190

Ala Asn Ser Leu Gln Thr Gly Ile Pro Ser Arg Phe Ser Gly Ser Gly
        195                 200                 205

Ser Gly Thr Asp Phe Thr Leu Thr Ile Ser Gly Leu Gln Pro Glu Asp
    210                 215                 220

Val Ala Thr Tyr Phe Cys Gln Gln Tyr Tyr Ser Gly Trp Thr Phe Gly
225                 230                 235                 240

Gly Gly Thr Lys Val Glu Leu Lys Arg
                245
```

<210> SEQ ID NO 301
<211> LENGTH: 127
<212> TYPE: PRT
<213> ORGANISM: Artificial
<220> FEATURE:
<223> OTHER INFORMATION: The amino acid sequence of anti-TIGIT scFv
      heavy chain variable region

<400> SEQUENCE: 301

```
Glu Val Gln Leu Gln Glu Ser Gly Pro Gly Leu Val Lys Pro Ser Gln
1               5                   10                  15

Ser Leu Ser Leu Thr Cys Ser Val Thr Gly Ser Ser Ile Ala Ser Asp
            20                  25                  30

Tyr Trp Gly Trp Ile Arg Lys Phe Pro Gly Asn Lys Met Glu Trp Met
        35                  40                  45

Gly Phe Ile Thr Tyr Ser Gly Ser Thr Ser Tyr Asn Pro Ser Leu Lys
    50                  55                  60
```

```
Ser Arg Ile Ser Ile Thr Arg Asp Thr Ser Lys Asn Gln Phe Phe Leu
65              70                  75                  80

Gln Leu His Ser Val Thr Thr Asp Asp Thr Ala Thr Tyr Ser Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Pro Gly Thr Met Val Thr Val Ser Ser
        115                 120                 125


<210> SEQ ID NO 302
<211> LENGTH: 107
<212> TYPE: PRT
<213> ORGANISM: Artificial
<220> FEATURE:
<223> OTHER INFORMATION: The amino acid sequence of anti-TIGIT scFv
      light chain variable region

<400> SEQUENCE: 302

Asp Ile Gln Met Thr Gln Ser Pro Ser Leu Leu Ser Ala Ser Val Gly
1               5                   10                  15

Asp Arg Val Thr Leu Asn Cys Lys Ala Ser Gln Ser Ile His Lys Asn
            20                  25                  30

Leu Ala Trp Tyr Gln Gln Lys Leu Gly Glu Ala Pro Lys Phe Leu Ile
        35                  40                  45

Tyr Tyr Ala Asn Ser Leu Gln Thr Gly Ile Pro Ser Arg Phe Ser Gly
    50                  55                  60

Ser Gly Ser Gly Thr Asp Phe Thr Leu Thr Ile Ser Gly Leu Gln Pro
65              70                  75                  80

Glu Asp Val Ala Thr Tyr Phe Cys Gln Gln Tyr Tyr Ser Gly Trp Thr
                85                  90                  95

Phe Gly Gly Gly Thr Lys Val Glu Leu Lys Arg
            100                 105


<210> SEQ ID NO 303
<211> LENGTH: 245
<212> TYPE: PRT
<213> ORGANISM: Artificial
<220> FEATURE:
<223> OTHER INFORMATION: The amino acid sequence of anti-BTLA scFv

<400> SEQUENCE: 303

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
            20                  25                  30

Asp Met His Trp Val Arg Gln Ala Thr Gly Lys Gly Leu Glu Trp Val
        35                  40                  45

Ser Val Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65              70                  75                  80

Gln Met Asn Ser Leu Arg Ala Gly Asp Thr Ala Val Tyr Tyr Cys Ala
                85                  90                  95

Arg Glu Gly Met Ala Ala His Asn Tyr Tyr Gly Met Asp Val Trp Gly
            100                 105                 110

Gln Gly Thr Thr Val Thr Val Ser Ser Gly Gly Gly Gly Ser Gly Gly
        115                 120                 125
```

```
Gly Gly Ser Gly Gly Gly Gly Ser Glu Ile Val Leu Thr Gln Ser Pro
    130                 135                 140

Ala Thr Leu Ser Leu Ser Pro Gly Glu Arg Ala Thr Leu Ser Cys Arg
145                 150                 155                 160

Ala Ser Gln Ser Val Ser Ser Tyr Leu Ala Trp Tyr Gln Gln Lys Pro
                165                 170                 175

Gly Gln Ala Pro Arg Leu Leu Ile Tyr Asp Ala Ser Asn Arg Ala Thr
            180                 185                 190

Gly Ile Pro Ala Arg Phe Ser Gly Ser Gly Ser Gly Thr Asp Phe Thr
        195                 200                 205

Leu Thr Ile Ser Ser Leu Glu Pro Glu Asp Phe Ala Val Tyr Tyr Cys
    210                 215                 220

Gln Gln Arg Ser Asn Trp Pro Pro Ile Thr Phe Gly Gln Gly Thr Arg
225                 230                 235                 240

Leu Glu Ile Lys Arg
                245


<210> SEQ ID NO 304
<211> LENGTH: 121
<212> TYPE: PRT
<213> ORGANISM: Artificial
<220> FEATURE:
<223> OTHER INFORMATION: The amino acid sequence of anti-BTLA scFv heavy
      chain variable region

<400> SEQUENCE: 304

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
            20                  25                  30

Asp Met His Trp Val Arg Gln Ala Thr Gly Lys Gly Leu Glu Trp Val
        35                  40                  45

Ser Val Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Met Ala Ala His Asn Tyr Tyr Gly Met Asp Val Trp Gly
            100                 105                 110

Gln Gly Thr Thr Val Thr Val Ser Ser
        115                 120


<210> SEQ ID NO 305
<211> LENGTH: 109
<212> TYPE: PRT
<213> ORGANISM: Artificial
<220> FEATURE:
<223> OTHER INFORMATION: The amino acid sequence of anti-BTLA scFv light
      chain variable region

<400> SEQUENCE: 305

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45
```

-continued

```
Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ile Thr Phe Gly Gln Gly Thr Arg Leu Glu Ile Lys Arg
            100                 105


<210> SEQ ID NO 306
<211> LENGTH: 750
<212> TYPE: DNA
<213> ORGANISM: Artificial
<220> FEATURE:
<223> OTHER INFORMATION: The nucleotide sequence of anti-CD19 scFv

<400> SEQUENCE: 306

gacatccagc tgacccagag ccccgccagc ctggccgtga gcctgggcca gcgcgccacc      60

atcagctgca aggccagcca gagcgtggac tacgacggcg acagctacct gaactggtac     120

cagcagatcc ccggccagcc ccccaagctg ctgatctacg acgccagcaa cctggtgagc     180

ggcatccccc cccgcttcag cggcagcggc agcggcaccg acttcaccct gaacatccac     240

cccgtggaga aggtggacgc cgccacctac cactgccagc agagcaccga ggacccctgg     300

accttcggcg gcggcaccaa gctggagatc aagggcggcg gcggcagcgg cggcggcggc     360

agcggcggcg gcggcagcca ggtgcagctg cagcagagcg gcgccgagct ggtgcgcccc     420

ggcagcagcg tgaagatcag ctgcaaggcc agcggctacg ccttcagcag ctactggatg     480

aactgggtga agcagcgccc cggccagggc ctggagtgga tcggccagat ctggcccggc     540

gacggcgaca ccaactacaa cggcaagttc aagggcaagg ccaccctgac cgccgacgag     600

agcagcagca ccgcctacat gcagctgagc agcctggcca gcgaggacag cgccgtgtac     660

ttctgcgccc gccgcgagac caccaccgtg ggccgctact actacgccat ggactactgg     720

ggccagggca ccaccgtgac cgtgagcagc                                      750


<210> SEQ ID NO 307
<211> LENGTH: 372
<212> TYPE: DNA
<213> ORGANISM: Artificial
<220> FEATURE:
<223> OTHER INFORMATION: The nucleotide sequence of anti-CD19 scFv heavy
      chain variable region

<400> SEQUENCE: 307

caggtgcagc tgcagcagag cggcgccgag ctggtgcgcc ccggcagcag cgtgaagatc      60

agctgcaagg ccagcggcta cgccttcagc agctactgga tgaactgggt gaagcagcgc     120

cccggccagg gcctggagtg gatcggccag atctggcccg gcgacggcga caccaactac     180

aacggcaagt tcaagggcaa ggccaccctg accgccgacg agagcagcag caccgcctac     240

atgcagctga gcagcctggc cagcgaggac agcgccgtgt acttctgcgc ccgccgcgag     300

accaccaccg tgggccgcta ctactacgcc atggactact ggggccaggg caccaccgtg     360

accgtgagca gc                                                         372


<210> SEQ ID NO 308
<211> LENGTH: 333
<212> TYPE: DNA
<213> ORGANISM: Artificial
<220> FEATURE:
```

<223> OTHER INFORMATION: The nucleotide sequence of anti-CD19 scFv light chain variable region

<400> SEQUENCE: 308
gacatccagc tgacccagag ccccgccagc ctggccgtga gcctgggcca gcgcgccacc 60
atcagctgca aggccagcca gagcgtggac tacgacggcg acagctacct gaactggtac 120
cagcagatcc ccggccagcc ccccaagctg ctgatctacg acgccagcaa cctggtgagc 180
ggcatccccc cccgcttcag cggcagcggc agcggcaccg acttcaccct gaacatccac 240
cccgtggaga aggtggacgc cgccacctac cactgccagc agagcaccga ggacccctgg 300
accttcggcg gcggcaccaa gctggagatc aag 333

<210> SEQ ID NO 309
<211> LENGTH: 729
<212> TYPE: DNA
<213> ORGANISM: Artificial
<220> FEATURE:
<223> OTHER INFORMATION: The nucleotide sequence of anti-CD3 scFv

<400> SEQUENCE: 309
gacatcaagc tgcagcagag cggcgccgag ctggcccgcc ccggcgccag cgtgaagatg 60
agctgcaaga ccagcggcta caccttcacc cgctacacca tgcactgggt gaagcagcgc 120
cccggccagg gcctggagtg gatcggctac atcaacccca gccgcggcta caccaactac 180
aaccagaagt tcaaggacaa ggccaccctg accaccgaca agagcagcag caccgcctac 240
atgcagctga gcagcctgac cagcgaggac agcgccgtgt actactgcgc ccgctactac 300
gacgaccact actgcctgga ctactggggc cagggcacca ccctgaccgt gagcagcgtg 360
gagggcggca gcggcggcag cggcggcagc ggcggcagcg gcggcgtgga cgacatccag 420
ctgacccaga gccccgccat catgagcgcc agccccggcg agaaggtgac catgacctgc 480
cgcgccagca gcagcgtgag ctacatgaac tggtaccagc agaagagcgg caccagcccc 540
aagcgctgga tctacgacac cagcaaggtg gccagcggcg tgccctaccg cttcagcggc 600
agcggcagcg gcaccagcta cagcctgacc atcagcagca tggaggccga ggacgccgcc 660
acctactact gccagcagtg gagcagcaac cccctgacct tcggcgccgg caccaagctg 720
gagctgaag 729

<210> SEQ ID NO 310
<211> LENGTH: 357
<212> TYPE: DNA
<213> ORGANISM: Artificial
<220> FEATURE:
<223> OTHER INFORMATION: The nucleotide sequence of anti-CD3 scFv heavy chain variable region

<400> SEQUENCE: 310
gacatcaagc tgcagcagag cggcgccgag ctggcccgcc ccggcgccag cgtgaagatg 60
agctgcaaga ccagcggcta caccttcacc cgctacacca tgcactgggt gaagcagcgc 120
cccggccagg gcctggagtg gatcggctac atcaacccca gccgcggcta caccaactac 180
aaccagaagt tcaaggacaa ggccaccctg accaccgaca agagcagcag caccgcctac 240
atgcagctga gcagcctgac cagcgaggac agcgccgtgt actactgcgc ccgctactac 300
gacgaccact actgcctgga ctactggggc cagggcacca ccctgaccgt gagcagc 357

<210> SEQ ID NO 311
<211> LENGTH: 318

<212> TYPE: DNA
<213> ORGANISM: Artificial
<220> FEATURE:
<223> OTHER INFORMATION: The nucleotide sequence of anti-CD3 scFv light chain variable region

<400> SEQUENCE: 311
gacatccagc tgacccagag ccccgccatc atgagcgcca gccccggcga gaaggtgacc 60
atgacctgcc gcgccagcag cagcgtgagc tacatgaact ggtaccagca gaagagcggc 120
accagcccca agcgctggat ctacgacacc agcaaggtgg ccagcggcgt gccctaccgc 180
ttcagcggca gcggcagcgg caccagctac agcctgacca tcagcagcat ggaggccgag 240
gacgccgcca cctactactg ccagcagtgg agcagcaacc ccctgacctt cggcgccggc 300
accaagctgg agctgaag 318

<210> SEQ ID NO 312
<211> LENGTH: 708
<212> TYPE: DNA
<213> ORGANISM: Artificial
<220> FEATURE:
<223> OTHER INFORMATION: The nucleotide sequence of anti-PD-1 scFv

<400> SEQUENCE: 312
caggtgcagc tggtggagag cggcggcggc gtggtgcagc ccggccgcag cctgcgcctg 60
gactgcaagg ccagcggcat caccttcagc aacagcggca tgcactgggt gcgccaggcc 120
cccggcaagg gcctggagtg ggtggccgtg atctggtacg acggcagcaa gcgctactac 180
gccgacagcg tgaagggccg cttcaccatc agccgcgaca acagcaagaa caccctgttc 240
ctgcagatga acagcctgcg cgccgaggac accgccgtgt actactgcgc caccaacgac 300
gactactggg gccagggcac cctggtgacc gtgagcagcg gcggcggcgg cagcggcggc 360
ggcggcagcg gcggcggcgg cagcgagatc gtgctgaccc agagccccgc caccctgagc 420
ctgagccccg gcgagcgcgc caccctgagc tgccgcgcca gccagagcgt gagcagctac 480
ctggcctggt accagcagaa gcccggccag gccccccgcc tgctgatcta cgacgccagc 540
aaccgcgcca ccggcatccc cgcccgcttc agcggcagcg gcagcggcac cgacttcacc 600
ctgaccatca gcagcctgga gcccgaggac ttcgccgtgt actactgcca gcagagcagc 660
aactggcccc gcaccttcgg ccagggcacc aaggtggaga tcaagcgc 708

<210> SEQ ID NO 313
<211> LENGTH: 339
<212> TYPE: DNA
<213> ORGANISM: Artificial
<220> FEATURE:
<223> OTHER INFORMATION: The nucleotide sequence of anti-PD-1 scFv heavy chain variable region

<400> SEQUENCE: 313
caggtgcagc tggtggagag cggcggcggc gtggtgcagc ccggccgcag cctgcgcctg 60
gactgcaagg ccagcggcat caccttcagc aacagcggca tgcactgggt gcgccaggcc 120
cccggcaagg gcctggagtg ggtggccgtg atctggtacg acggcagcaa gcgctactac 180
gccgacagcg tgaagggccg cttcaccatc agccgcgaca acagcaagaa caccctgttc 240
ctgcagatga acagcctgcg cgccgaggac accgccgtgt actactgcgc caccaacgac 300
gactactggg gccagggcac cctggtgacc gtgagcagc 339

<210> SEQ ID NO 314

<211> LENGTH: 324
<212> TYPE: DNA
<213> ORGANISM: Artificial
<220> FEATURE:
<223> OTHER INFORMATION: The nucleotide sequence of anti-PD-1 scFv light chain variable region

<400> SEQUENCE: 314
gagatcgtgc tgacccagag ccccgccacc ctgagcctga gccccggcga gcgcgccacc 60
ctgagctgcc gcgccagcca gagcgtgagc agctacctgg cctggtacca gcagaagccc 120
ggccaggccc cccgcctgct gatctacgac gccagcaacc gcgccaccgg catccccgcc 180
cgcttcagcg gcagcggcag cggcaccgac ttcaccctga ccatcagcag cctggagccc 240
gaggacttcg ccgtgtacta ctgccagcag agcagcaact ggccccgcac cttcggccag 300
ggcaccaagg tggagatcaa gcgc 324

<210> SEQ ID NO 315
<211> LENGTH: 726
<212> TYPE: DNA
<213> ORGANISM: Artificial
<220> FEATURE:
<223> OTHER INFORMATION: The nucleotide sequence of anti-CTLA-4 scFv

<400> SEQUENCE: 315
caggtgcagc tggtggagag cggcggcggc gtggtgcagc ccggccgcag cctgcgcctg 60
agctgcgccg ccagcggctt caccttcagc agctacacca tgcactgggt gcgccaggcc 120
cccggcaagg gcctggagtg ggtgaccttc atcagctacg acggcaacaa caagtactac 180
gccgacagcg tgaagggccg cttcaccatc agccgcgaca acagcaagaa caccctgtac 240
ctgcagatga acagcctgcg cgccgaggac accgccatct actactgcgc ccgcaccggc 300
tggctgggcc ccttcgacta ctggggccag ggcaccctgg tgaccgtgag cagcggcggc 360
ggcggcagcg gcggcggcgg cagcggcggc ggcggcagcg agatcgtgct gacccagagc 420
cccggcaccc tgagcctgag ccccggcgag cgcgccaccc tgagctgccg cgccagccag 480
agcgtgggca gcagctacct ggcctggtac cagcagaagc ccggccaggc cccccgcctg 540
ctgatctacg gcgccttcag ccgcgccacc ggcatccccg accgcttcag cggcagcggc 600
agcggcaccg acttcaccct gaccatcagc cgcctggagc ccgaggactt cgccgtgtac 660
tactgccagc agtacggcag cagcccctgg accttcggcc agggcaccaa ggtggagatc 720
aagcgc 726

<210> SEQ ID NO 316
<211> LENGTH: 354
<212> TYPE: DNA
<213> ORGANISM: Artificial
<220> FEATURE:
<223> OTHER INFORMATION: The nucleotide sequence of anti-CTLA-4 scFv heavy chain variable region

<400> SEQUENCE: 316
caggtgcagc tggtggagag cggcggcggc gtggtgcagc ccggccgcag cctgcgcctg 60
agctgcgccg ccagcggctt caccttcagc agctacacca tgcactgggt gcgccaggcc 120
cccggcaagg gcctggagtg ggtgaccttc atcagctacg acggcaacaa caagtactac 180
gccgacagcg tgaagggccg cttcaccatc agccgcgaca acagcaagaa caccctgtac 240
ctgcagatga acagcctgcg cgccgaggac accgccatct actactgcgc ccgcaccggc 300
tggctgggcc ccttcgacta ctggggccag ggcaccctgg tgaccgtgag cagc 354

<210> SEQ ID NO 317
<211> LENGTH: 327
<212> TYPE: DNA
<213> ORGANISM: Artificial
<220> FEATURE:
<223> OTHER INFORMATION: The nucleotide sequence of anti-CTLA-4 scFv light chain variable region

<400> SEQUENCE: 317
gagatcgtgc tgacccagag ccccggcacc ctgagcctga gccccggcga gcgcgccacc 60
ctgagctgcc gcgccagcca gagcgtgggc agcagctacc tggcctggta ccagcagaag 120
cccggccagg ccccccgcct gctgatctac ggcgccttca gccgcgccac cggcatcccc 180
gaccgcttca gcggcagcgg cagcggcacc gacttcaccc tgaccatcag ccgcctggag 240
cccgaggact tcgccgtgta ctactgccag cagtacggca gcagcccctg gaccttcggc 300
cagggcacca aggtggagat caagcgc 327

<210> SEQ ID NO 318
<211> LENGTH: 729
<212> TYPE: DNA
<213> ORGANISM: Artificial
<220> FEATURE:
<223> OTHER INFORMATION: The nucleotide sequence of anti-LAG-3 scFv

<400> SEQUENCE: 318
caggtgcagc tgcagcagtg gggcgccggc ctgctgaagc ccagcgagac cctgagcctg 60
acctgcgccg tgtacggcgg cagcttcagc gactactact ggaactggat ccgccagccc 120
cccggcaagg gcctggagtg gatcggcgag atcaaccacc gcggcagcac caacagcaac 180
cccagcctga agagccgcgt gaccctgagc ctggacacca gcaagaacca gttcagcctg 240
aagctgcgca gcgtgaccgc cgccgacacc gccgtgtact actgcgcctt cggctacagc 300
gactacgagt acaactggtt cgacccctgg ggccagggca ccctggtgac cgtgagcagc 360
ggcggcggcg gcagcggcgg cggcggcagc ggcggcggcg gcagcgagat cgtgctgacc 420
cagagccccg ccaccctgag cctgagcccc ggcgagcgcg ccaccctgag ctgccgcgcc 480
agccagagca tcagcagcta cctggcctgg taccagcaga agcccggcca ggcccccgc 540 ctgctgatct acgacgccag caaccgcgcc accggcatcc ccgcccgctt cagcggcagc 600
ggcagcggca ccgacttcac cctgaccatc agcagcctgg agcccgagga cttcgccgtg 660
tactactgcc agcagcgcag caactggccc ctgaccttcg gccagggcac caacctggag 720
atcaagcgc 729

<210> SEQ ID NO 319
<211> LENGTH: 360
<212> TYPE: DNA
<213> ORGANISM: Artificial
<220> FEATURE:
<223> OTHER INFORMATION: The nucleotide sequence of anti-LAG-3 scFv heavy chain variable region

<400> SEQUENCE: 319
caggtgcagc tgcagcagtg gggcgccggc ctgctgaagc ccagcgagac cctgagcctg 60
acctgcgccg tgtacggcgg cagcttcagc gactactact ggaactggat ccgccagccc 120
cccggcaagg gcctggagtg gatcggcgag atcaaccacc gcggcagcac caacagcaac 180
cccagcctga agagccgcgt gaccctgagc ctggacacca gcaagaacca gttcagcctg 240

-continued aagctgcgca gcgtgaccgc cgccgacacc gccgtgtact actgcgcctt cggctacagc 300
gactacgagt acaactggtt cgacccctgg ggccagggca ccctggtgac cgtgagcagc 360

<210> SEQ ID NO 320
<211> LENGTH: 324
<212> TYPE: DNA
<213> ORGANISM: Artificial
<220> FEATURE:
<223> OTHER INFORMATION: The nucleotide sequence of anti-LAG-3 scFv light chain variable region

<400> SEQUENCE: 320
gagatcgtgc tgacccagag ccccgccacc ctgagcctga gccccggcga gcgcgccacc 60
ctgagctgcc gcgccagcca gagcatcagc agctacctgg cctggtacca gcagaagccc 120
ggccaggccc cccgcctgct gatctacgac gccagcaacc gcgccaccgg catccccgcc 180
cgcttcagcg gcagcggcag cggcaccgac ttcaccctga ccatcagcag cctggagccc 240
gaggacttcg ccgtgtacta ctgccagcag cgcagcaact ggcccctgac cttcggccag 300
ggcaccaacc tggagatcaa gcgc 324

<210> SEQ ID NO 321
<211> LENGTH: 735
<212> TYPE: DNA
<213> ORGANISM: Artificial
<220> FEATURE:
<223> OTHER INFORMATION: The nucleotide sequence of anti-TIM-3 scFv

<400> SEQUENCE: 321
caggtgcagc tggtgcagag cggcgccgag gtgaagaagc ccggcgccag cgtgaaggtg 60
agctgcaagg ccagcggcta caccttcacc agctacaaca tgcactgggt gcgccaggcc 120
cccggccagg gcctggagtg gatcggcgac atctaccccg gccagggcga caccagctac 180
aaccagaagt tcaagggccg cgccaccatg accgccgaca agagcaccag caccgtgtac 240
atggagctga gcagcctgcg cagcgaggac accgccgtgt actactgcgc ccgcgtgggc 300
ggcgccttcc ccatggacta ctggggccag ggcaccctgg tgaccgtgag cagcggcggc 360
ggcggcagcg gcggcggcgg cagcggcggc ggcggcagcg acatcgtgct gacccagagc 420
cccgacagcc tggccgtgag cctgggcgag cgcgccacca tcaactgccg cgccagcgag 480
agcgtggagt actacggcac cagcctgatg cagtggtacc agcagaagcc cggccagccc 540
cccaagctgc tgatctacgc cgccagcaac gtggagagcg gcgtgcccga ccgcttcagc 600
ggcagcggca gcggcaccga cttcaccctg accatcagca gcctgcaggc cgaggacgtg 660
gccgtgtact actgccagca gagccgcaag gaccccagca ccttcggcgg cggcaccaag 720
gtggagatca agcgc 735

<210> SEQ ID NO 322
<211> LENGTH: 354
<212> TYPE: DNA
<213> ORGANISM: Artificial
<220> FEATURE:
<223> OTHER INFORMATION: The nucleotide sequence of anti-TIM-3 scFv heavy chain variable region

<400> SEQUENCE: 322
caggtgcagc tggtgcagag cggcgccgag gtgaagaagc ccggcgccag cgtgaaggtg 60
agctgcaagg ccagcggcta caccttcacc agctacaaca tgcactgggt gcgccaggcc 120
cccggccagg gcctggagtg gatcggcgac atctaccccg gccagggcga caccagctac 180
aaccagaagt tcaagggccg cgccaccatg accgccgaca agagcaccag caccgtgtac 240
atggagctga gcagcctgcg cagcgaggac accgccgtgt actactgcgc ccgcgtgggc 300
ggcgccttcc ccatggacta ctggggccag ggcaccctgg tgaccgtgag cagc 354

<210> SEQ ID NO 323
<211> LENGTH: 336
<212> TYPE: DNA
<213> ORGANISM: Artificial
<220> FEATURE:
<223> OTHER INFORMATION: The nucleotide sequence of anti-TIM-3 scFv light chain variable region

<400> SEQUENCE: 323
gacatcgtgc tgacccagag ccccgacagc ctggccgtga gcctgggcga gcgcgccacc 60
atcaactgcc gcgccagcga gagcgtggag tactacggca ccagcctgat gcagtggtac 120
cagcagaagc ccggccagcc ccccaagctg ctgatctacg ccgccagcaa cgtggagagc 180
ggcgtgcccg accgcttcag cggcagcggc agcggcaccg acttcaccct gaccatcagc 240
agcctgcagg ccgaggacgt ggccgtgtac tactgccagc agagccgcaa ggaccccagc 300
accttcggcg gcggcaccaa ggtggagatc aagcgc 336

<210> SEQ ID NO 324
<211> LENGTH: 747
<212> TYPE: DNA
<213> ORGANISM: Artificial
<220> FEATURE:
<223> OTHER INFORMATION: The nucleotide sequence of anti-TIGIT scFv

<400> SEQUENCE: 324
gaggtgcagc tgcaggagag cggccccggc ctggtgaagc ccagccagag cctgagcctg 60
acctgcagcg tgaccggcag cagcatcgcc agcgactact ggggctggat ccgcaagttc 120
cccggcaaca agatggagtg gatgggcttc atcacctaca gcggcagcac cagctacaac 180
cccagcctga agagccgcat cagcatcacc cgcgacacca gcaagaacca gttcttcctg 240
cagctgcaca gcgtgaccac cgacgacacc gccacctaca gctgcgcccg catgcccagc 300
ttcatcaccc tggccagcct gagcacctgg gagggctact tcgacttctg gggccccggc 360
accatggtga ccgtgagcag cggcggcggc ggcagcggcg gcggcggcag cggcggcggc 420
ggcagcgaca tccagatgac ccagagcccc agcctgctga gcgccagcgt gggcgaccgc 480
gtgaccctga actgcaaggc cagccagagc atccacaaga acctggcctg gtaccagcag 540
aagctgggcg aggcccccaa gttcctgatc tactacgcca acagcctgca gaccggcatc 600
cccagccgct tcagcggcag cggcagcggc accgacttca ccctgaccat cagcggcctg 660
cagcccgagg acgtggccac ctacttctgc cagcagtact acagcggctg gaccttcggc 720
ggcggcacca aggtggagct gaagcgc 747

<210> SEQ ID NO 325
<211> LENGTH: 381
<212> TYPE: DNA
<213> ORGANISM: Artificial
<220> FEATURE:
<223> OTHER INFORMATION: The nucleotide sequence of anti-TIGIT scFv heavy chain variable region

<400> SEQUENCE: 325
gaggtgcagc tgcaggagag cggccccggc ctggtgaagc ccagccagag cctgagcctg 60

```
acctgcagcg tgaccggcag cagcatcgcc agcgactact ggggctggat ccgcaagttc    120

cccggcaaca agatggagtg gatgggcttc atcacctaca gcggcagcac cagctacaac    180

cccagcctga agagccgcat cagcatcacc cgcgacacca gcaagaacca gttcttcctg    240

cagctgcaca gcgtgaccac cgacgacacc gccacctaca gctgcgcccg catgcccagc    300

ttcatcaccc tggccagcct gagcacctgg gagggctact tcgacttctg gggccccggc    360

accatggtga ccgtgagcag c                                              381
```

<210> SEQ ID NO 326
<211> LENGTH: 321
<212> TYPE: DNA
<213> ORGANISM: Artificial
<220> FEATURE:
<223> OTHER INFORMATION: The nucleotide sequence of anti-TIGIT scFv light chain variable region

<400> SEQUENCE: 326

```
gacatccaga tgacccagag ccccagcctg ctgagcgcca gcgtgggcga ccgcgtgacc     60

ctgaactgca aggccagcca gagcatccac aagaacctgg cctggtacca gcagaagctg    120

ggcgaggccc ccaagttcct gatctactac gccaacagcc tgcagaccgg catccccagc    180

cgcttcagcg gcagcggcag cggcaccgac ttcaccctga ccatcagcgg cctgcagccc    240

gaggacgtgg ccacctactt ctgccagcag tactacagcg gctggacctt cggcggcggc    300

accaaggtgg agctgaagcg c                                              321
```

<210> SEQ ID NO 327
<211> LENGTH: 735
<212> TYPE: DNA
<213> ORGANISM: Artificial
<220> FEATURE:
<223> OTHER INFORMATION: The nucleotide sequence of anti-BTLA scFv

<400> SEQUENCE: 327

```
gaggtgcagc tggtggagag cggcggcggc ctggtgcagc ccggcggcag cctgcgcctg     60

agctgcgccg ccagcggctt caccatcagc agctacgaca tgcactgggt gcgccaggcc    120

accggcaagg gcctggagtg ggtgagcgtg atcggccccg ccggcgacac ctactacccc    180

ggcagcgtga agggccgctt caccatcagc cgcgagaacg ccaagaacag cctgtacctg    240

cagatgaaca gcctgcgcgc cggcgacacc gccgtgtact actgcgcccg cgagggcatg    300

gccgcccaca actactacgg catggacgtg tggggccagg gcaccaccgt gaccgtgagc    360

agcggcggcg gcggcagcgg cggcggcggc agcggcggcg gcggcagcga gatcgtgctg    420

acccagagcc ccgccaccct gagcctgagc cccggcgagc gcgccaccct gagctgccgc    480

gccagccaga gcgtgagcag ctacctggcc tggtaccagc agaagcccgg ccaggccccc    540

cgcctgctga tctacgacgc cagcaaccgc gccaccggca tccccgcccg cttcagcggc    600

agcggcagcg gcaccgactt caccctgacc atcagcagcc tggagcccga ggacttcgcc    660

gtgtactact gccagcagcg cagcaactgg ccccccatca ccttcggcca gggcacccgc    720

ctggagatca agcgc                                                     735
```

<210> SEQ ID NO 328
<211> LENGTH: 363
<212> TYPE: DNA
<213> ORGANISM: Artificial
<220> FEATURE:
<223> OTHER INFORMATION: The nucleotide sequence of anti-BTLA scFv heavy chain variable region

<400> SEQUENCE: 328
gaggtgcagc tggtggagag cggcggcggc ctggtgcagc ccggcggcag cctgcgcctg 60
agctgcgccg ccagcggctt caccatcagc agctacgaca tgcactgggt gcgccaggcc 120
accggcaagg gcctggagtg ggtgagcgtg atcggccccg ccggcgacac ctactacccc 180
ggcagcgtga agggccgctt caccatcagc cgcgagaacg ccaagaacag cctgtacctg 240
cagatgaaca gcctgcgcgc cggcgacacc gccgtgtact actgcgcccg cgagggcatg 300
gccgcccaca actactacgg catggacgtg tggggccagg gcaccaccgt gaccgtgagc 360
agc 363

<210> SEQ ID NO 329
<211> LENGTH: 327
<212> TYPE: DNA
<213> ORGANISM: Artificial
<220> FEATURE:
<223> OTHER INFORMATION: The nucleotide sequence of anti-BTLA scFv light chain variable region

<400> SEQUENCE: 329
gagatcgtgc tgacccagag ccccgccacc ctgagcctga gccccggcga gcgcgccacc 60
ctgagctgcc gcgccagcca gagcgtgagc agctacctgg cctggtacca gcagaagccc 120
ggccaggccc cccgcctgct gatctacgac gccagcaacc gcgccaccgg catccccgcc 180
cgcttcagcg gcagcggcag cggcaccgac ttcaccctga ccatcagcag cctggagccc 240
gaggacttcg ccgtgtacta ctgccagcag cgcagcaact ggcccccat caccttcggc 300 cagggcaccc gcctggagat caagcgc 327

<210> SEQ ID NO 330
<211> LENGTH: 19
<212> TYPE: PRT
<213> ORGANISM: Artificial
<220> FEATURE:
<223> OTHER INFORMATION: The amino acid sequence of the secretory signal peptide

<400> SEQUENCE: 330

Met Thr Arg Leu Thr Val Leu Ala Leu Leu Ala Gly Leu Leu Ala Ser
1 5 10 15

Ser Arg Ala

<210> SEQ ID NO 331
<211> LENGTH: 57
<212> TYPE: DNA
<213> ORGANISM: Artificial
<220> FEATURE:
<223> OTHER INFORMATION: The nucleotide sequence of the secretory signal peptide

<400> SEQUENCE: 331
atgacccgcc tgaccgtgct ggccctgctg gccggcctgc tggccagcag ccgcgcc 57

<210> SEQ ID NO 332
<211> LENGTH: 59
<212> TYPE: DNA
<213> ORGANISM: Artificial
<220> FEATURE:
<223> OTHER INFORMATION: pcDNA3.1-Sig-F

<400> SEQUENCE: 332
gtgctggata tctgcagaat tcgccgccac catgacccgg ctgaccgtgc tggccctgc 59

<210> SEQ ID NO 333
<211> LENGTH: 49
<212> TYPE: DNA
<213> ORGANISM: Artificial
<220> FEATURE:
<223> OTHER INFORMATION: Sig-R

<400> SEQUENCE: 333
ggccctggag gaggccagca ggccggccag cagggccagc acggtcagc 49

<210> SEQ ID NO 334
<211> LENGTH: 42
<212> TYPE: DNA
<213> ORGANISM: Artificial
<220> FEATURE:
<223> OTHER INFORMATION: Sig-CD19-F

<400> SEQUENCE: 334
ctgctggcct cctccagggc cgacatccag ctgacccaga gc 42

<210> SEQ ID NO 335
<211> LENGTH: 23
<212> TYPE: DNA
<213> ORGANISM: Artificial
<220> FEATURE:
<223> OTHER INFORMATION: CD19-R

<400> SEQUENCE: 335
gctgctcacg gtcacggtgg tgc 23

<210> SEQ ID NO 336
<211> LENGTH: 56
<212> TYPE: DNA
<213> ORGANISM: Artificial
<220> FEATURE:
<223> OTHER INFORMATION: CD19-G4S-CD3-F

<400> SEQUENCE: 336
ccaccgtgac cgtgagcagc ggtggcggag ggtccgacat caagctgcag cagagc 56

<210> SEQ ID NO 337
<211> LENGTH: 20
<212> TYPE: DNA
<213> ORGANISM: Artificial
<220> FEATURE:
<223> OTHER INFORMATION: CD3-R

<400> SEQUENCE: 337
cttcagctcc agcttggtgc 20

<210> SEQ ID NO 338
<211> LENGTH: 87
<212> TYPE: DNA
<213> ORGANISM: Artificial
<220> FEATURE:
<223> OTHER INFORMATION: CD3-(GGGGS)3-PD-1-F

<400> SEQUENCE: 338
ggcaccaagc tggagctgaa gggcggcggc ggcagcggcg gcggcggcag cggcggcggc 60
ggcagccagg tgcagctggt ggagagc 87

<210> SEQ ID NO 339
<211> LENGTH: 50

<212> TYPE: DNA
<213> ORGANISM: Artificial
<220> FEATURE:
<223> OTHER INFORMATION: pcDNA3.1-PD-1-R

<400> SEQUENCE: 339
ctgatcagcg gtttaaactt aagctttcag cgcttgatct ccaccttggt 50

<210> SEQ ID NO 340
<211> LENGTH: 41
<212> TYPE: DNA
<213> ORGANISM: Artificial
<220> FEATURE:
<223> OTHER INFORMATION: CD3-IgD-F

<400> SEQUENCE: 340
gcaccaagct ggagctgaag gccagcaaga gcaagaagga g 41

<210> SEQ ID NO 341
<211> LENGTH: 21
<212> TYPE: DNA
<213> ORGANISM: Artificial
<220> FEATURE:
<223> OTHER INFORMATION: IgD-R

<400> SEQUENCE: 341
cacgcccagg ggctgggtgt g 21

<210> SEQ ID NO 342
<211> LENGTH: 42
<212> TYPE: DNA
<213> ORGANISM: Artificial
<220> FEATURE:
<223> OTHER INFORMATION: IgD-PD-1-F

<400> SEQUENCE: 342
cacacccagc ccctgggcgt gcaggtgcag ctggtggaga gc 42

<210> SEQ ID NO 343
<211> LENGTH: 87
<212> TYPE: DNA
<213> ORGANISM: Artificial
<220> FEATURE:
<223> OTHER INFORMATION: CD3-(GGGGS)3-CTLA-4-F

<400> SEQUENCE: 343
ggcaccaagc tggagctgaa gggcggcggc ggcagcggcg gcggcggcag cggcggcggc 60
ggcagccagg tgcagctggt ggagagc 87

<210> SEQ ID NO 344
<211> LENGTH: 50
<212> TYPE: DNA
<213> ORGANISM: Artificial
<220> FEATURE:
<223> OTHER INFORMATION: pcDNA3.1-CTLA-4-R

<400> SEQUENCE: 344
ctgatcagcg gtttaaactt aagctttcag cgcttgatct ccaccttggt 50

<210> SEQ ID NO 345
<211> LENGTH: 42
<212> TYPE: DNA
<213> ORGANISM: Artificial
<220> FEATURE:
<223> OTHER INFORMATION: IgD-CTLA-4-F

<400> SEQUENCE: 345
cacacccagc ccctgggcgt gcaggtgcag ctggtggaga gc 42

<210> SEQ ID NO 346
<211> LENGTH: 87
<212> TYPE: DNA
<213> ORGANISM: Artificial
<220> FEATURE:
<223> OTHER INFORMATION: CD3-(GGGGS)3-LAG-3-F

<400> SEQUENCE: 346
ggcaccaagc tggagctgaa gggcggcggc ggcagcggcg gcggcggcag cggcggcggc 60
ggcagccagg tgcagctgca gcagtgg 87

<210> SEQ ID NO 347
<211> LENGTH: 50
<212> TYPE: DNA
<213> ORGANISM: Artificial
<220> FEATURE:
<223> OTHER INFORMATION: pcDNA3.1-LAG-3-R

<400> SEQUENCE: 347
ctgatcagcg gtttaaactt aagctttcag cgcttgatct ccaggttggt 50

<210> SEQ ID NO 348
<211> LENGTH: 42
<212> TYPE: DNA
<213> ORGANISM: Artificial
<220> FEATURE:
<223> OTHER INFORMATION: IgD-LAG-3-F

<400> SEQUENCE: 348
cacacccagc ccctgggcgt gcaggtgcag ctgcagcagt gg 42

<210> SEQ ID NO 349
<211> LENGTH: 87
<212> TYPE: DNA
<213> ORGANISM: Artificial
<220> FEATURE:
<223> OTHER INFORMATION: CD3-(GGGGS)3-TIM-3-F

<400> SEQUENCE: 349
ggcaccaagc tggagctgaa gggcggcggc ggcagcggcg gcggcggcag cggcggcggc 60
ggcagccagg tgcagctggt gcagagc 87

<210> SEQ ID NO 350
<211> LENGTH: 50
<212> TYPE: DNA
<213> ORGANISM: Artificial
<220> FEATURE:
<223> OTHER INFORMATION: pcDNA3.1-TIM-3-R

<400> SEQUENCE: 350
ctgatcagcg gtttaaactt aagctttcag cgcttgatct ccaccttggt 50

<210> SEQ ID NO 351
<211> LENGTH: 42
<212> TYPE: DNA
<213> ORGANISM: Artificial
<220> FEATURE:
<223> OTHER INFORMATION: IgD-TIM-3-F

<400> SEQUENCE: 351
cacacccagc ccctgggcgt gcaggtgcag ctggtgcaga gc 42

<210> SEQ ID NO 352
<211> LENGTH: 87
<212> TYPE: DNA
<213> ORGANISM: Artificial
<220> FEATURE:
<223> OTHER INFORMATION: CD3-(GGGGS)3-TIGIT-F

<400> SEQUENCE: 352
ggcaccaagc tggagctgaa gggcggcggc ggcagcggcg gcggcggcag cggcggcggc 60
ggcagcgagg tgcagctgca ggagagc 87

<210> SEQ ID NO 353
<211> LENGTH: 50
<212> TYPE: DNA
<213> ORGANISM: Artificial
<220> FEATURE:
<223> OTHER INFORMATION: pcDNA3.1-TIGIT-R

<400> SEQUENCE: 353
ctgatcagcg gtttaaactt aagctttcag cgcttcagct ccaccttggt 50

<210> SEQ ID NO 354
<211> LENGTH: 42
<212> TYPE: DNA
<213> ORGANISM: Artificial
<220> FEATURE:
<223> OTHER INFORMATION: IgD-TIGIT-F

<400> SEQUENCE: 354
cacacccagc ccctgggcgt ggaggtgcag ctgcaggaga gc 42

<210> SEQ ID NO 355
<211> LENGTH: 87
<212> TYPE: DNA
<213> ORGANISM: Artificial
<220> FEATURE:
<223> OTHER INFORMATION: CD3-(GGGGS)3-BTLA-F

<400> SEQUENCE: 355
ggcaccaagc tggagctgaa gggcggcggc ggcagcggcg gcggcggcag cggcggcggc 60
ggcagcgagg tgcagctggt ggagagc 87

<210> SEQ ID NO 356
<211> LENGTH: 50
<212> TYPE: DNA
<213> ORGANISM: Artificial
<220> FEATURE:
<223> OTHER INFORMATION: pcDNA3.1-BTLA-R

<400> SEQUENCE: 356
ctgatcagcg gtttaaactt aagctttcag cgcttgatct ccaggcgggt 50

<210> SEQ ID NO 357
<211> LENGTH: 42
<212> TYPE: DNA
<213> ORGANISM: Artificial
<220> FEATURE:
<223> OTHER INFORMATION: IgD-BTLA-F

<400> SEQUENCE: 357
cacacccagc ccctgggcgt ggaggtgcag ctggtggaga gc 42

TRIFUNCTIONAL MOLECULE AND APPLICATION THEREOF

CROSS REFERENCES TO RELATED APPLICATIONS

This is a Sect. 371 National Stage application of a PCT International Application No. PCT/CN2017/096594, filed on Aug. 9, 2017, which claims priority of four Chinese Patent Applications No. 2016112566599, filed on Dec. 30, 2016; 2016112586431, filed on Dec. 30, 2016; 2016112586910, filed on Dec. 30, 2016; 2016112608178, filed on Dec. 30, 2016. The contents of those applications are hereby incorporated by reference in their entireties for all purposes.

TECHNICAL FIELD

This disclosure relates to the technical field of biomedicine, and in particular, to a trifunctional molecule and the application thereof.

BACKGROUND

The human CD19 antigen is a transmembrane glycoprotein of 95 kDa, which belongs to the immunoglobulin superfamily. In addition to being expressed on the surface of normal B lymphocytes, CD19 is also highly expressed in B cell malignancies. Therefore, the anti-CD19 monoclonal full-length antibody has been developed for the treatment of acute/chronic lymphocytic leukemia and B-cell lymphoma (Wang K et al., Experimental Hematology & Oncology, 1:36-42, 2012). In view of the inability of anti-CD19 monoclonal antibodies to efficiently recruit cytotoxic T lymphocytes (CTLs, CD3 and CD8 positive T cells that specifically recognize antigenic peptide/MHC class I complexes on the surface of target cells, release of perforin after self-activation thus induce target cells rupture and death, can also secrete cytotoxin and granzyme to induce apoptosis of target cells by DNA damage), bispecific antibodies connecting T cells and lymphoma B cells have been designed and developed, as well as chimeric antigen receptor T-cell immunotherapy (CAR-T) (Zhukovsky E A et al., Current Opinion in Immunology, 40:24-35, 2016).

Currently, a fairly developed type of bispecific antibody targeting CD19 is an anti-CD19/anti-CD3 bispecific T cell engager (BiTE). The structure of BiTE consists of two single-chain variable fragment (scFv) domains that covalently linked by a flexible linker. (Goebeler M E et al, Leukemia & Lymphoma, 57: 1021-1032, 2016). During the cellular immunity of the body, the TCR/CD3 complex on the surface of CD8-positive T cells specifically recognizes the endogenous antigen peptide/MHC class I complex on the surface of antigen-presenting cells (APC). This leads to the interaction of CD3 with the cytoplasmic domain of the co-receptor CD8, thus activates the protein tyrosine kinase that links to the tail of the cytoplasmic domain. The activated tyrosine kinase induces tyrosine phosphorylation of immunoreceptor tyrosine-based activation motif (ITAM) of the CD3 cytoplasmic domain. This initiates a signaling cascade that activates transcription factors to activate T cells. Anti-CD19/anti-CD3 BiTE bispecific antibody with the binding activity of human CD3 and CD19 antigens, is able to form a cell-cell association between T cells and B tumor cells, which simultaneously provides T cell initial activation signal and enhances its ability of killing target tumor cells. However, the BiTE bispecific antibody does not contain the Fc region and has small molecular weight (~54 kDa), so it can cross the hematuria barrier and the cerebral blood barrier during tumor treatment. Thus it has low bioavailability and requires continuous intravenous injection. Also it is neurotoxic.

Furthermore, activation of human T cells requires a dual signaling pathway (Baxter A G et al, Nature Reviews Immunology, 2: 439-446, 2002). First, the antigen peptide-MHC complex on the membrane of APC cells interacts with the TCR/CD3 complex on the membrane of T cells to generate a first signal, allowing T cells to be partially activated. The costimulatory ligands on the membrane of APC cells (CD80, CD86, 4-1BBL, B7RP-1, OX40L, GITRL, CD40, CD70, PD-L1, PD-L2, Galectin-9, and HVEM, etc.) bind to co-stimulatory molecules on the membrane of T cells (such as CD28, 4-1BB, ICOS, OX40, GITR, CD40L, CD27, CTLA-4, PD-1, LAG-3, TIM-3, TIGIT, BTLA, etc.) to produce a second signal which fully activates T cells. Costimulatory molecules can be either positive (co-stimulation) or negative (co-inhibition). Co-stimulatory molecules include CD28 4-1BB, ICOS, OX40, GITR, CD40L and CD27, interacting with the corresponding ligands CD80, CD86, 4-1BBL, B7RP-1, OX40L, GITRL, CD70, etc. The co-stimulatory signal can lead to complete activation of T cells. While CTLA-4, PD-1, LAG-3, TIM-3, TIGIT and BTLA are negative costimulatory (co-inhibition) molecules, and the corresponding ligands include CD80, CD86, PD-L1, PD-L2, Galectin-9, HVEM, etc. The negative costimulatory signal is primarily for the down-regulation and termination of T cell activation. Studies have shown that the first signaling pathway itself cannot fully activate T cells, which usually leads to its disability and activation induced cell death (AICD). To solve this problem, a bispecific antibody against a tumor antigen and anti-T cell positive/negative costimulatory molecule can be used in combination with an anti-tumor antigen/anti-CD3 bispecific antibody to enhance T cell activation and tumor cell Killing efficacy (Jung G et al, Int J Cancer, 91: 225-230, 2001; Kodama H et al, Immunol Lett, 81: 99-106, 2002). However, this method has many inconveniences in practice. It increases the workload and manufacturing cost of recombinant bispecific antibody expression and purification, and requires optimization of relative proportion between two bispecific antibodies for T cell activation and proliferation. In contrast, CAR-T technology can active T cell in a better way. The structure of CAR typically includes a tumor-associated antigen binding region, an extracellular hinge region, a transmembrane region, and an intracellular signaling region. The intracellular signaling domain is responsible for T cell activation. The first stimulation signal is provided by the tyrosine activation motif from the CD3 chain, and then it is amplified by the CD28 costimulatory signal to promote T cell proliferation and activation. It also induces secretion of cytokines and anti-apoptotic proteins, thus delays cell death. However, CAR-T technology is deficient in some aspects. First, the technology relies on virus transduction to genetically modify T cells, which places high requirements on experimental technology. Secondly, the in vitro expanded and activated CAR-T cells need to be infused to the patient and the dosage is more difficult to control compared to the antibody drugs. In addition, the enormous number of CAR-T cells can lead to cytokine storm in a short period of time. The side effect can be high fever, hypotension, shock and even death.

SUMMARY

1) The present disclosure is able to fuse a first domain that binds to CD19, a second domain capable of binding to and activating a T cell surface CD3 molecule, and a third domain capable of binding to and activating a T cell surface CD28 molecule to the same peptide. The peptide is produced by eukaryotic cell expression system and the structure of expression product is single. The purification process is simple and the yield of protein is high. The preparation process and the product are stable and convenient in using. In contrast, in the using of the anti-CD19/anti-CD3 bispecific antibody combined with the anti-CD19/anti-CD28 bispecific antibody, the two bispecific antibodies need to be separately expressed and purified, and the preparation process is more complicated. The workload and manufacturing cost are increased. The proportion of the two needs to be optimized. The trifunctional molecule of the disclosure is capable of generating a second stimulation signal for T cell activation, and further enhancing the activation effect, thereby increasing secretion of cytokines and anti-apoptotic proteins, and effectively avoiding T cell inability and death. The T cells activated by the trifunctional molecule are able to achieve comparable or even better elimination of CD19-positive target cells than those by anti-CD19/anti-CD3 BiTE bispecific antibody, in a less amount protein level. Compared with the CAR-T technology targeting CD19, the trifunctional molecule of the present disclosure does not involve the steps of virus-mediated transgene, in vitro T cell culture and reinfusion. The trifunctional molecule is more convenient to use and dosage controllable, thereby reducing the risk of cytokines release and avoiding the side effects of using CAR-T.

2) The present disclosure is able to fuse a first domain that binds to CD19, a second domain capable of binding to and activating a T cell surface CD3 molecule, and a third domain capable of binding to and activating a T cell surface positive stimulation molecule to the same peptide. The peptide is produced by eukaryotic cell expression system and the structure of expression product a single. The purification process is simple and the yield of protein is high. The preparation process and the product are stable and convenient in using. In contrast, in the using of the anti-CD19/anti-CD3 bispecific antibody combined with the anti-CD19/anti-positive stimulation molecule bispecific antibody, the two bispecific antibodies need to be separately expressed and purified, and the preparation process is more complicated. That causes the increased workload and manufacturing cost, also the relative proportion of the two needs to be optimized. The trifunctional molecule of the disclosure is capable of generating a second (positive) stimulation signal for T cell activation, and further enhancing the activation effect, thereby increasing secretion of cytokines and anti-apoptotic proteins, and effectively avoiding T cell inability and death. The T cells activated by the trifunctional molecule are able to achieve comparable or even better elimination of CD19-positive target cells can than those by anti-CD19/anti-CD3 BiTE bispecific antibody, in a less amount protein level. Compared with the CAR-T technology targeting CD19, the trifunctional molecule of the present disclosure does not involve the steps of virus-mediated transgene, in vitro T cell culture and reinfusion. The trifunctional molecule is more convenient to use and dosage controllable, thereby reducing the risk of cytokines release and avoiding the side effects of using CAR-T.

3) The present disclosure is able to fuse a first domain that binds to CD19, a second domain capable of binding to and activating a T cell surface CD3 molecule, and a third domain capable of binding to and activating a T cell surface positive stimulation molecule to the same peptide to generate a trifunctional molecule. The peptide is produced by eukaryotic cell expression system and the structure of expression product is single. The purification process is simple and the yield of protein is high. The preparation process and the product are stable and convenient in using. In contrast, in the using of the anti-CD19/anti-CD3 bispecific antibody combined with the anti-CD19/anti-positive stimulation molecule bispecific antibody, the two bispecific antibodies need to be separately expressed and purified, and the preparation process is more complicated. That causes the increased workload and manufacturing cost, also the relative proportion of the two needs to be optimized. The trifunctional molecule of the disclosure is capable of generating a second (positive) stimulation signal for T cell activation, and further enhancing the activation effect, thereby increasing secretion of cytokines and anti-apoptotic proteins, and effectively avoiding T cell inability and death. The T cells activated by the trifunctional molecule are able to achieve comparable or even better elimination of CD19-positive target cells than those by anti-CD19/anti-CD3 BiTE bispecific antibody, in a less amount protein level. Compared with the CAR-T technology targeting CD19, the trifunctional molecule of the present disclosure does not involve the steps of virus-mediated transgene, in vitro T cell culture and reinfusion. The trifunctional molecule is more convenient to use and dosage controllable, thereby reducing the risk of cytokines release and avoiding the side effects of using CAR-T.

4) The present disclosure is able to fuse a first domain that binds to CD19, a second domain capable of binding to and activating a T cell surface CD3 molecule, and a third domain capable of binding to and inhibiting a T cell surface negative stimulation molecule to the same peptide to generate a trifunctional molecule. The peptide is produced by eukaryotic cell expression system and the structure of expression product is single. The purification process is simple and the yield of protein is high. The preparation process and the product are stable and convenient in using. In contrast, in the using of the anti-CD19/anti-CD3 bispecific antibody combined with the anti-CD19/anti-positive (negative) stimulation molecule bispecific antibody, the two bispecific antibodies need to be separately expressed and purified, and the preparation process is more complicated. That causes the increased workload and manufacturing cost, also the relative proportion of the two needs to be optimized. The trifunctional molecule of the disclosure is capable of blocking a second (negative) inhibitory signal for T cell activation, and further enhancing the activation effect, thereby increasing secretion of cytokines and anti-apoptotic proteins, and effectively avoiding T cell inability and death. The T cells activated by the trifunctional molecule are able to achieve comparable or even better elimination of CD19-positive target cells can than those by anti-CD19/anti-CD3 BiTE bispecific antibody, in a less amount protein level. Compared with the CAR-T technology targeting CD19, the trifunctional molecule of the present disclosure does not involve the steps of virus-mediated transgene, in vitro T cell culture and reinfusion. The trifunctional molecule is more convenient to use and dosage controllable, thereby reducing the risk of cytokines release and avoiding the side effects of using CAR-T.

BRIEF DESCRIPTION OF THE DRAWINGS

FIG. 1-2: The SDS-PAGE analysis diagrams of final purified CD19-CD3-CD28 TsAb_M and CD19-CD3-CD28 TsAb_D.

FIG. 1-3: EILSA results for CD19-CD3-CD28 TsAb_M and CD19-CD3-CD28 TsAb_D.

FIG. 1-4: Trispecific antibody and bispecific antibody-mediated cell-binding experiments.

FIG. 1-5: Trispecific antibody and bispecific antibody-mediated cell killing assay.

FIG. 2-1: The structure diagrams of monomeric CD19-CD3-T cell positive costimulatory molecule TsAb_M and CD19-CD3-T cell positive costimulatory molecule TsAb_D.

FIG. 2-2: The SDS-PAGE analysis diagrams of final purified CD19-CD3-4-1BB TsAb_M and CD19-CD3-4-1BB TsAb_D.

FIG. 2-3: EILSA results for CD19-CD3-4-1BB TsAb_M and CD19-CD3-4-1BB TsAb_D.

FIG. 2-4: Trispecific antibody and bispecific antibody-mediated cell killing assay.

FIG. 2-5: The SDS-PAGE analysis diagrams of final purified CD19-CD3-ICOS TsAb_M and CD19-CD3-ICOS TsAb_D;

FIG. 2-6: EILSA results for CD19-CD3-ICOS TsAb_M and EILSA results for CD19-CD3-ICOS TsAb_D.

FIG. 2-7: Trispecific antibody CD19-CD3-ICOS mediated cell killing assay.

FIG. 2-8: The SDS-PAGE analysis diagrams of final purified CD19-CD3-OX40 TsAb_M and CD19-CD3-OX40 TsAb_D.

FIG. 2-9: EILSA results for CD19-CD3-OX40 TsAb_M and 9-CD3-OX40 TsAb_D.

FIG. 2-10: Trispecific antibody CD19-CD3-OX40 mediated cell killing assay.

FIG. 2-11: The SDS-PAGE analysis diagram of final purified CD19-CD3-GITR TsAb_M and CD19-CD3-GITR TsAb_D.

FIG. 2-12: EILSA results for CD19-CD3-GITR TsAb_M and CD19-CD3-GITR TsAb_D.

FIG. 2-13: Trispecific antibody CD19-CD3-GITR mediated cell killing assay.

FIG. 2-14: The SDS-PAGE analysis diagram of final purified CD19-CD3-OX40L TsAb_M and CD19-CD3-OX40L TsAb_D.

FIG. 2-15: EILSA results for CD19-CD3-OX40L TsAb_M and CD19-CD3-OX40L TsAb_D.

FIG. 2-16: Trispecific antibody CD19-CD3-OX40L mediated cell killing assay.

FIG. 2-17: The SDS-PAGE analysis diagram of final purified CD19-CD3-CD27 TsAb_M and CD19-CD3-CD27 TsAb_D.

FIG. 2-18: EILSA results for CD19-CD3-CD27 TsAb_M and CD19-CD3-CD27 TsAb_D.

FIG. 2-19: Trispecific antibody CD19-CD3-CD27 mediated cell killing assay.

FIG. 3-1: The structure diagrams of monomeric CD19-CD3-T cell positive costimulatory molecule ligand trifunctional molecule TsM and dimeric CD19-CD3-T cell positive costimulatory molecule ligand trifunctional molecule TsM.

FIG. 3-2: The SDS-PAGE analysis diagrams of final purified CD19-CD3-4-1BBL TsM_M and CD19-CD3-4-1BBL TsM_D.

FIG. 3-3: EILSA results for CD19-CD3-4-1BBL TsM_M and CD19-CD3-4-1BBL TsM_D.

FIG. 3-4: Trispecific molecule CD19-CD3-4-1BBL mediated cell killing assay.

FIG. 3-5: The SDS-PAGE analysis diagrams of final purified CD19-CD3-B7RP-1 TsM_M and CD19-CD3-B7RP-1 TsM_D.

FIG. 3-6: EILSA results for CD19-CD3-B7RP-1 TsM_M and EILSA results for CD19-CD3-B7RP-1 TsM_D.

FIG. 3-7: Trispecific molecule CD19-CD3-B7RP-1 mediated cell killing assay.

FIG. 3-8: The SDS-PAGE analysis diagram of final purified CD19-CD3-OX40L TsM_M and CD19-CD3-OX40L TsM_D.

FIG. 3-9A: EILSA results for CD19-CD3-OX40L TsM_M and CD19-CD3-OX40L TsM_D.

FIG. 3-10: Trispecific molecule CD19-CD3-OX40L mediated cell killing assay.

FIG. 3-11: The SDS-PAGE analysis diagram of final purified CD19-CD3-GITRL TsM_M and CD19-CD3-GITRL TsM_D.

FIG. 3-12: EILSA results for CD19-CD3-GITRL TsM_M and CD19-CD3-GITRL TsM_D.

FIG. 3-13: Trispecific molecule CD19-CD3-GITRL mediated cell killing assay.

FIG. 3-14: The SDS-PAGE analysis diagram of final purified CD19-CD3-CD70 TsM_M and CD19-CD3-CD70 TsM_D.

FIG. 3-15A: EILSA results for CD19-CD3-CD70 TsM_M and CD19-CD3-CD27 TsM_D.

FIG. 3-16: Trispecific molecule CD19-CD3-CD27 mediated cell killing assay.

FIG. 4-1: the structure diagram of monomeric CD19-CD3-T cell negative costimulatory molecule trifunctional antibody and dimeric CD19-CD3-T cell negative costimulatory molecule trifunctional antibody.

FIG. 4-2: The SDS-PAGE analysis diagrams of final purified CD19-CD3-PD-1 TsAb_M and CD19-CD3-PD-1 TsAb_D.

FIG. 4-3: EILSA results for CD19-CD3-PD-1 TsAb_M and CD19-CD3-PD-1 TsAb_D.

FIG. 4-4: Trispecific antibody CD19-CD3-PD-1 mediated cell killing assay.

FIG. 4-5: The SDS-PAGE analysis diagrams of final purified CD19-CD3-CTLA-4 TsAb_M and CD19-CD3-CTLA-4 TsAb_D.

FIG. 4-6: EILSA results for CD19-CD3-CTLA-4 TsAb_M and CD19-CD3-CTLA-4 TsAb_D.

FIG. 4-7: Trispecific antibody CD19-CD3-CTLA-4 mediated cell killing assay.

FIG. 4-8: The SDS-PAGE analysis diagrams of final purified CD19-CD3-LAG-3 TsAb_M and CD19-CD3-LAG-3 TsAb_D.

FIG. 4-9: EILSA results for CD19-CD3-LAG-3 TsAb_M and CD19-CD3-LAG-3 TsAb_D.

FIG. 4-10: Trispecific antibody CD19-CD3-LAG-3 mediated cell killing assay.

FIG. 4-11: A. The SDS-PAGE analysis diagrams of final purified CD19-CD3-TIM-3 TsAb_M and CD19-CD3-TIM-3 TsAb_D.

FIG. 4-12A: EILSA results for CD19-CD3-TIM-3 TsAb_M and CD19-CD3-TIM-3 TsAb_D.

FIG. 4-13: Trispecific antibody CD19-CD3-TIM-3 mediated cell killing assay.

FIG. 4-14: The SDS-PAGE analysis diagrams of final purified CD19-CD3-TIGIT TsAb_M and CD19-CD3-TIGIT TsAb_D.

FIG. 4-15: EILSA results for CD19-CD3-TIGIT TsAb_M and CD19-CD3-TIGIT TsAb_D.

FIG. 4-16: Trispecific antibody CD19-CD3-TIGIT mediated cell killing assay.

FIG. 4-17: The SDS-PAGE analysis diagrams of final purified CD19-CD3-BTLA TsAb_M and CD19-CD3-BTLA TsAb_D.

FIG. 4-18A: EILSA results for CD19-CD3-BTLA TsAb_M and CD19-CD3-BTLA TsAb_D.

FIG. 4-19: Trispecific antibody CD19-CD3-BTLA mediated cell killing assay.

DETAILED DESCRIPTION OF THE PREFERRED EMBODIMENTS

1, Terms and Abbreviations

Figure 1:
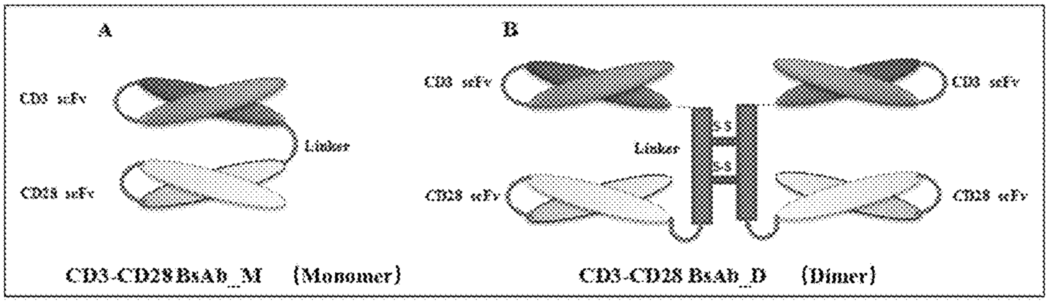
FIG. 1-1: the structure diagrams of CD19-CD3-CD28 TsAb_M and CD19-CD3-CD28 TsAb_D.

CTL, Cytotoxic T lymphocyte
BsAb, Bi-specific Antibody
TsAb, Tri-specific Antibody
TsM, Tri-specific Molecule
BiTE, Bi-specific T cell engager
TiTE, Tri-specific T cell engager
Fab, Fragment of antigen binding
Fv, Variable fragment
scFv, Single-chain variable fragment
VH, Heavy chain variable region
VL, Light chain variable region
Linker
Linker1
Linker2
Extracellular domain
Co-stimulatory molecule CD19-CD3-CD28 TsAb_M, Monomeric form of anti-CD19/anti-CD3/anti-CD28 trispecific antibody CD19-CD3-CD28 TsAb_D, Dimeric form of anti-CD19/anti-CD3/anti-CD28 trispecific antibody CD19-CD3-4-1BB TsAb_M, Monomeric form of anti-CD19/anti-CD3/anti-4-1BB trispecific antibody CD19-CD3-4-1BB TsAb_D, Dimeric form of anti-CD19/anti-CD3/anti-4-1BB trispecific antibody CD19-CD3-ICOS TsAb_M, Monomeric form of anti-CD19/anti-CD3/anti-ICOS trispecific antibody CD19-CD3-ICOS TsAb_D, Dimeric form of anti-CD19/anti-CD3/anti-ICOS trispecific antibody CD19-CD3-OX40 TsAb_M, Monomeric form of anti-CD19/anti-CD3/anti-OX40 trispecific antibody CD19-CD3-OX40 TsAb_D, Dimeric form of anti-CD19/anti-CD3/anti-OX40 trispecific antibody CD19-CD3-GITR TsAb_M, Monomeric form of anti-CD19/anti-CD3/anti-GITR trispecific antibody CD19-CD3-GITR TsAb_D, Dimeric form of anti-CD19/anti-CD3/anti-GITR trispecific antibody CD19-CD3-CD40L TsAb_M, Monomeric form of anti-CD19/anti-CD3/anti-CD40L trispecific antibody CD19-CD3-CD40L TsAb_D, Dimeric form of anti-CD19/anti-CD3/anti-CD40L trispecific antibody CD19-CD3-CD27 TsAb_M, Monomeric form of anti-CD19/anti-CD3/anti-CD27 trispecific antibody CD19-CD3-CD27 TsAb_D, Dimeric form of anti-CD19/anti-CD3/anti-CD27 trispecific antibody 4-1BBL, T cell positive costimulatory molecule 4-1BB ligand B7RP-1, T cell positive costimulatory molecule ICOS ligand OX4oL, T cell positive costimulatory molecule IOX4o ligand GITRL, T cell positive costimulatory molecule GITRL ligand CD70, T cell positive costimulatory molecule CD27 ligand CD19-CD3-4-1BBL TsM_M, Monomeric form of anti-CD19/anti-CD3/4-BBL trispecific molecules CD19-CD3-4-1BBL TsM_D, Dimeric form of anti-CD19/anti-CD3/4-1BBL trispecific molecules CD19-CD3-B7RP-1 TsM_M, Monomeric form of anti-CD19/anti-CD3/B7RP-1 trispecific molecules CD19-CD3-B7RP-1 TsM_D, Dimeric form of anti-CD19/anti-CD3/B7RP-1 trispecific molecules CD19-CD3-OX40L TsM_M, Monomeric form of anti-CD19/anti-CD3/OX40L trispecific molecules CD19-CD3-OX40L TsM_D, Dimeric form of anti-CD19/anti-CD3/OX40L trispecific molecules CD19-CD3-GITRL TsM_M, Monomeric form of anti-CD19/anti-CD3/GITRL trispecific molecules CD19-CD3-GITRL TsM_D: Dimeric form of anti-CD19/anti-CD3/GITRL trispecific molecules CD19-CD3-CD70 TsM_M, Monomeric form of anti-CD19/anti-CD3/CD70 trispecific molecules CD19-CD3-CD70 TsM_D, Donomeric form of anti-CD19/anti-CD3/CD70 trispecific molecules CD19-CD3-PD-1 TsAb_M, Monomeric form of anti-CD19/anti-CD3/anti-PD-1 trispecific antibody CD19-CD3-PD-1 TsAb_D, Dimeric form of anti-CD19/anti-CD3/anti-PD-1 trispecific antibody CD19-CD3-CTLA-4 TsAb_M, Monomeric form of anti-CD19/anti-CD3/anti-CTLA-4 trispecific antibody CD19-CD3-CTLA-4 TsAb_D, Dimeric form of anti-CD19/anti-CD3/anti-CTLA-4 trispecific antibody CD19-CD3-LAG-3 TsAb_M, Monomeric form of anti-CD19/anti-CD3/anti-LAG-3 trispecific antibody CD19-CD3-LAG-3 TsAb_D, Dimeric form of anti-CD19/anti-CD3/anti-LAG-3 trispecific antibody CD19-CD3-TIM-3 TsAb_M, Monomeric form of anti-CD19/anti-CD3/anti-TIM-3 trispecific antibody CD19-CD3-TIM-3 TsAb_D, Dimeric form of anti-CD19/anti-CD3/anti-TIM-3 trispecific antibody CD19-CD3-TIGIT TsAb_M, Monomeric form of anti-CD19/anti-CD3/anti-TIGIT trispecific antibody CD19-CD3-TIGIT TsAb_D, Dimeric form of anti-CD19/anti-CD3/anti-TIGIT trispecific antibody CD19-CD3-BTLA TsAb_M, Monomeric form of anti-CD19/anti-CD3/anti-BTLA trispecific antibody CD19-CD3-BTLA TsAb_D, Donomeric form of anti-CD19/anti-CD3/anti-BTLA trispecific antibody

2, Trifunctional Molecule

A trifunctional molecule of the disclosure including a first domain capable of binding to CD19, a second domain capable of binding to and activating a T cell surface CD3 molecule, and a third capable of binding and activating a T cell surface CD28 molecule.

Further, the trifunctional molecule is capable of binding to and activating the T cell surface CD3 molecule and the CD28 molecule while recognizing CD19, thereby generating a first signal and a second signal required for T cell activation.

The present disclosure has no particular limitation on the first functional domain, the second functional domain, and the third functional domain, as long as it can bind and activate the T cell surface CD3 molecule and the CD28 molecule while recognizing CD19, thereby generating the first and second signal for T cell activation. For example, the first functional domain can be an anti-CD19 antibody, the second functional domain can be an anti-CD3 antibody, and the third functional domain can be an anti-CD28 antibody. The antibody can be in any form. However, regardless of the form of the antibody, the antigen binding site thereof contains a heavy chain variable region and a light chain variable region. The antibody can preferably be a small molecule antibody. The small molecule antibody is a small molecular weight antibody fragment, and the antigen binding site thereof includes a heavy chain variable region and a light chain variable region. The small molecule antibody has a small molecular weight but retains the affinity of the parental monoclonal antibody and has the same specificity as the parental monoclonal antibody. The types of the small molecule antibodies include Fab antibodies, Fv antibodies and single chain antibodies (scFv). The Fab antibody is formed by a disulfide bond between the intact light chain (variable region VL and constant region CL) and the heavy chain Fd segment (variable region VH and first constant region CH1). An Fv antibody is the minimal functional fragment of an antibody molecule that retains the entire antigen binding site and is joined by a variable region of the light and heavy chains through a non-covalent bond. The scFv is a single-protein peptide chain molecule in which a heavy chain variable region and a light chain variable region are joined by a linker.

The first functional domain and the second functional domain are connected by a linker 1, and the second functional domain and the third functional domain are connected by a linker 2. The present disclosure has no particular requirements for the order of connection as long as the object of the present disclosure is not limited. For example, the C-terminus of the first functional domain can be linked to the N-terminus of the second functional domain, and the C-terminus of the second functional domain can be linked to the N-terminus of the third functional domain. The present disclosure is also not particularly limited to the linker 1 and the linker 2 as long as it does not limit the object of the present disclosure.

Further, the linker 1 and the linker 2 are selected from a G4S linker or a hinge domain of immunoglobulin IgD.

The G4S is GGGGS. The G4S linker includes one or more G4S units. For example, one, two, three or more G4S units can be included. In some embodiments of the present disclosure, a trifunctional molecule in a monomeric form is exemplified, wherein the first functional domain and the second functional domain are connected by a linker 1 in a G4S unit. The second functional domain and the third functional function are connected by a linker 2 in units of G4S. The linker 1 contains a G4S unit, and the amino acid sequence of the linker is set forth in SEQ ID NO. 23. The linker 2 contains three G4S units, and the amino acid sequence of the ligated fragment is set forth in SEQ ID NO. 25.

The hinge domain of the immunoglobulin IgD could be the hinge Ala90-Val170 of IgD. In some embodiments of the disclosure, wherein a trifunctional molecule in demeric form is exemplified, the first functional domain and the second functional domain are linked by a linker 1 in units of G4S, a second functional domain and a third functional domains are linked by a hinge domain of immunoglobulin IgD, which is Ala90-Val170. The linker 1 contains a G4S unit, and the amino acid sequence of the linker is shown in SEQ ID NO. 27. The amino acid sequence of the linker 2 is shown in SEQ ID NO. 29. The linking 2 can be linked to each other by a disulfide bond to form a dimer.

In a preferred embodiment of the disclosure, the structure of the trifunctional molecule is shown in FIG. 1-1. The trifunctional molecule can be in a monomeric form or a dimeric form. A diagram of the structure of the monomeric form of the trifunctional molecule of the present disclosure is shown in FIG. 1-1A. The structure of the trifunctional molecule contains a first functional domain that binds to the CD19 antigen, a second function that binds to the CD3 antigen, and a third domain that binds to the CD28 antigen. The first domain is a scFv that binds to the CD19 antigen, the second domain is a scFv that binds to a CD3 antigen, and the third domain is a scFv that binds to the CD28 antigen. A schematic diagram of the structure of the dimeric form of the trifunctional molecule of the present disclosure is shown in FIG. 1-1B. The structure of the trifunctional molecule contains two first domains that bind to the CD19 antigen, two second domain bind to the CD3 antigen, and two third domains that bind to the CD28 antigen. The first domain is a scFv that binds to the CD19 antigen, the second domain is a s scFv that binds to the CD3 antigen, and the third domain is a scFv that binds to the CD28 antigen. The dimeric form of the trifunctional molecule of the disclosure has an antigen binding affinity that is twice that of the monomeric form. Due to the doubling of the first signal (CD3) and the second signal (CD28) of T cell activation, T cell activation is more sufficient, and the killing ability on target cells is stronger. The doubling of the CD19 single-chain antibody domain makes it more accurate in recognizing of target cells, so the dimer has a better use effect than the monomer.

Specifically, the first functional domain is a single-chain antibody against CD19. The anti-CD19 single-chain antibody consists of a heavy chain variable region and a light chain variable region. The amino acid sequence of the heavy chain variable region of the anti-CD19 single-chain antibody is set forth in SEQ ID NO. 6. The amino acid sequence of the light chain variable region of the anti-CD19 single-chain antibody is set forth in SEQ ID NO. 7 Further, the amino acid sequence of the anti-CD19 single-chain antibody is shown in SEQ ID NO. 5.

The second domain is a single-chain antibody against CD3. The anti-CD3 single-chain antibody consists of a heavy chain variable region and a light chain variable region. The amino acid sequence of the heavy chain variable region of the anti-CD3 single-chain antibody is set forth in SEQ ID NO. 9. The amino acid sequence of the light chain variable region of the anti-CD3 single-chain antibody is set forth in SEQ ID NO. 10. Further, the amino acid sequence of the anti-CD3 single-chain antibody is shown in SEQ ID NO. 8.

The third domain is a single-chain antibody against CD28. The anti-CD28 single-chain antibody consists of a heavy chain variable region and a light chain variable region. The amino acid sequence of the heavy chain variable region of the anti-CD28 single-chain antibody is set forth in SEQ ID NO. 12. The amino acid sequence of the light chain variable region of the anti-CD28 single-chain antibody is set forth in SEQ ID NO. 13. The amino acid sequence of the anti-CD28 single-chain antibody is shown in SEQ ID NO. 11.

In a preferred embodiment of the present disclosure, the amino acid sequence of the monomeric form of the trifunctional molecule is set forth in SEQ ID NO. 1. The amino acid sequence of the dimeric form of the trifunctional molecule is set forth in SEQ ID NO. 3. It is not limited to the specific forms listed in the preferred cases of the present disclosure.

Another trifunctional molecule of the disclosure including a first domain capable of binding to CD19, a second domain capable of binding to and activating a T cell surface CD3 molecule, and a third functional domain capable of binding and activating T cell positive costimulatory molecule.

Further, the trifunctional molecule is capable of binding to and activating a T cell surface CD3 molecule and a T cell positive costimulatory molecule while recognizing CD19, thereby generating a first signal and a second signal required for T cell activation.

The T cell positive costimulatory molecules include, but are not limited to, human CD28, 4-1BB, ICOS, OX40, GITR, CD40L or CD27, et al.

The present disclosure has no particular limitation on the first functional domain, the second functional domain and the third functional domain. As long as it can bind and activate T cell surface CD3 molecules and T cell positive costimulatory molecules while recognizing CD19, thereby producing the first signal and the second signal required for activation of T cells. For example, the first functional domain can be an antibody against CD19, the second functional domain can be an anti-CD3 antibody, and the third functional domain can be an antibody against a T cell positive costimulatory molecule. The antibody can be in any form. However, regardless of the form of the antibody, the antigen binding site thereof contains a heavy chain variable region and a light chain variable region. The antibody may preferably be a small molecule antibody. The small molecule antibody is a small molecular weight antibody fragment, and the antigen binding site thereof includes a heavy chain variable region and a light chain variable region. The small molecule antibody has a small molecular weight but retains the affinity of the parental monoclonal antibody and has the same specificity as the parental monoclonal antibody. The types of the small molecule antibodies mainly include Fab, Fv and scFv. The Fab antibody is formed by a disulfide bond between the intact light chain (variable region VL and constant region CL) and the heavy chain Fd segment (variable region VH and first constant region CH1). Fv antibodies are joined by non-covalent bonds by the variable regions of the light and heavy chains. They are the minimal functional fragments of the antibody molecule that retain the intact antigen binding site. A scFv is a single-protein peptide chain molecule in which a heavy chain variable region and a light chain variable region are joined by a linker.

The first functional domain and the second functional domain are connected by linker 1, and the second functional domain and the third functional domain are connected by linker 2. The present disclosure has no particular requirements for the order of connection as long as the object of the present disclosure is not limited. For example, the C-terminus of the first functional domain can be linked to the N-terminus of the second functional domain, and the C-terminus of the second functional domain can be linked to the N-terminus of the third functional domain. The present disclosure is also not particularly limited to the linker 1 and the linker 2 as long as it does not limit the object of the present disclosure.

Further, the linker 1 and the linker 2 are selected from a G4S linker or a hinge region fragment of immunoglobulin IgD.

The G4S is GGGGS. The G4S linker includes one or more G4S units. For example, one, two, three or more G4S units can be included. In some embodiments of the present disclosure, a trifunctional molecule in a monomeric form is exemplified, wherein the first functional domain and the second functional domain are connected by a linker 1 in a G4S unit. The second functional domain and the third functional function are connected by a linker 2 in units of G4S. The linker 1 contains a G4S unit, and the amino acid sequence of the linker is set forth in SEQ ID NO. 44. The linker 2 contains three G4S units, and the amino acid sequence of the ligated fragment is set forth in SEQ ID NO. 46.

The hinge domain of the immunoglobulin IgD could be the hinge Ala90-Val170 of IgD. In some embodiments of the disclosure, wherein a trifunctional molecule in dimeric form is exemplified, the first functional domain and the second functional domain are linked by a linker 1 in units of G4S, a second functional domain and a third functional domains are linked by a hinge domain of immunoglobulin IgD, which is Ala90-Val170. The linker 1 contains a G4S unit, and the amino acid sequence of the linker is shown in SEQ ID NO. 48. The amino acid sequence of the linker 2 is shown in SEQ ID NO. 50. The linking 2 can be linked to each other by a disulfide bond to form a dimer.

Figures 1, 2:
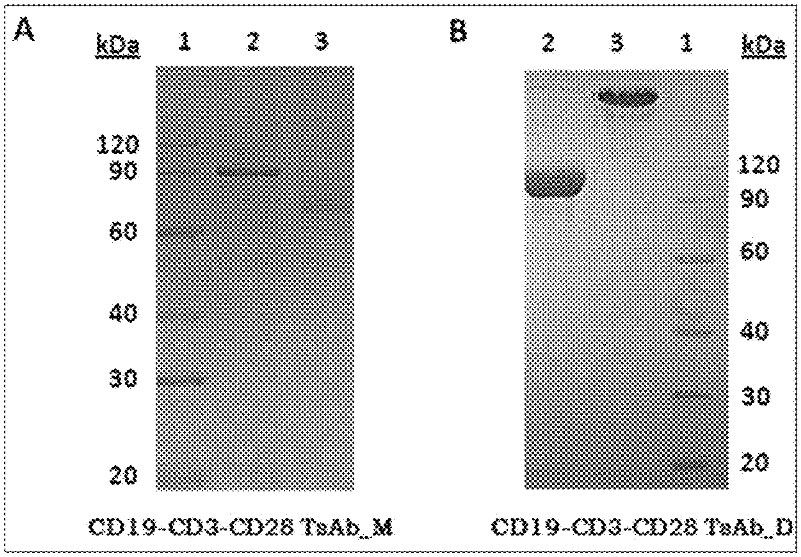

In a preferred embodiment of the disclosure, the schematic structure of the trifunctional molecule is shown in FIG. 2-1. The trifunctional molecule can be in a monomeric form or a dimeric form. A schematic diagram of the structure of the monomeric form of the trifunctional molecule of the present disclosure is shown in FIG. 2-1A. The trifunctional molecule consists of a first functional domain that binds to the CD19 antigen, a second functional domain that binds to the CD3 antigen, and a third domain that binds to a T cell positive costimulatory molecule. The first domain is a scFv that binds to the CD19 antigen, the second domain is a scFv that binds to the CD3 antigen, and the third domain is a scFv that binds to a T cell positive costimulatory molecule antigen. A schematic diagram of the structure of a dimeric form of a trifunctional molecule of the present disclosure is shown in FIG. 2-1B. The structure of the trifunctional molecule contains two first domains that bind to the CD19 antigen, and two second domains bind to the CD3 antigen, and two third domains that bind to a T cell positive co-stimulatory molecule antigen. The trifunctional molecule consists of two first functional domains that bind to the CD19 antigen, two second functional domains that bind to the CD3 antigen, and two third domains that bind to a T cell positive costimulatory molecule. The first domain is a scFv that binds to the CD19 antigen, the second domain is a scFv that binds to the CD3 antigen, and the third domain is a scFv that binds to a T cell positive costimulatory molecule antigen. The dimeric form of the trifunctional molecule of the disclosure has an antigen binding affinity that is twice that of the monomeric form. Due to the doubling of the first signal (CD3) and the second signal (CD28) of T cell activation, T cell activation is more sufficient, and the killing ability on target cells is stronger. The doubling of the CD19 single-chain antibody domain makes it more accurate in recognizing of target cells, so the dimer has a better use effect than the monomer.

The T cell positive costimulatory molecule can be CD28, 4-1BB, ICOS, OX40, GITR, CD40L or CD27, et al.

The amino acid sequence of the human T cell positive costimulatory molecule CD28 extracellular domain is set forth in SEQ ID NO. 52.

The amino acid sequence of the human T cell positive costimulatory molecule 4-1BB extracellular domain is set forth in SEQ ID NO. 53.

The amino acid sequence of the human T cell positive costimulatory molecule ICOS extracellular domain is set forth in SEQ ID NO. 54.

The amino acid sequence of the human T cell positive costimulatory molecule OX40 extracellular domain is set forth in SEQ ID NO. 55.

The amino acid sequence of the human T cell positive costimulatory molecule GITR extracellular domain is set forth in SEQ ID NO. 56.

The amino acid sequence of the human T cell positive costimulatory molecule CD40L extracellular domain is set forth in SEQ ID NO. 57.

The amino acid sequence of the human T cell positive costimulatory molecule CD27 extracellular domain is set forth in SEQ ID NO. 58.

Specifically, the first functional domain is a single-chain antibody against CD19. The anti-CD19 single-chain antibody contains a heavy chain variable region and a light chain variable region. The amino acid sequence of the heavy chain variable region of the anti-CD19 single-chain antibody is set forth in SEQ ID NO. 84. The amino acid sequence of the light chain variable region of the anti-CD19 single-chain antibody is set forth in SEQ ID NO. 85. The amino acid sequence of the anti-CD19 single-chain antibody is shown in SEQ ID NO. 83.

The second domain is a single-chain antibody against CD3. The anti-CD3 single-chain antibody contains a heavy chain variable region and a light chain variable region. The amino acid sequence of the heavy chain variable region of the anti-CD3 single-chain antibody is set forth in SEQ ID NO. 87. The amino acid sequence of the light chain variable region of the anti-CD3 single-chain antibody is set forth in SEQ ID NO. 88. Further, the amino acid sequence of the anti-CD3 single-chain antibody is shown in SEQ ID NO. 86.

The third domain is a single-chain antibody against a T cell positive costimulatory molecule. The single-chain antibody of the anti-T cell positive costimulatory molecule contains a heavy chain variable region and a light chain variable region.

The single-chain antibody of the anti-T cell positive costimulatory molecule can be one of any single chain antibodies against 4-1BB, ICOS, OX40, GITR, CD40L or CD27.

The amino acid sequence of the heavy chain variable region of the anti-4-1BB single-chain antibody is set forth in SEQ ID NO. 90. The amino acid sequence of the light chain variable region of the anti-4-1BB single-chain antibody is set forth in SEQ ID NO. 91. The amino acid sequence of the anti-4-1BB single-chain antibody is shown in SEQ ID NO. 89.

The amino acid sequence of the heavy chain variable region of the anti-ICOS single-chain antibody is set forth in SEQ ID NO. 93. The amino acid sequence of the light chain variable region of the anti-4-1BB single-chain antibody is set forth in SEQ ID NO. 94. The amino acid sequence of the anti-4-1BB single-chain antibody is shown in SEQ ID NO. 92.

The amino acid sequence of the heavy chain variable region of the anti-OX40 single-chain antibody is set forth in SEQ ID NO. 96. The amino acid sequence of the light chain variable region of the anti-4-1BB single-chain antibody is set forth in SEQ ID NO. 97. The amino acid sequence of the anti-4-1BB single-chain antibody is shown in SEQ ID NO. 95.

The amino acid sequence of the heavy chain variable region of the anti-GITR single-chain antibody is set forth in SEQ ID NO. 99. The amino acid sequence of the light chain variable region of the anti-4-1BB single-chain antibody is set forth in SEQ ID NO. 100. The amino acid sequence of the anti-4-1BB single-chain antibody is shown in SEQ ID NO. 98.

The amino acid sequence of the heavy chain variable region of the anti-CD40L single-chain antibody is set forth in SEQ ID NO. 102. The amino acid sequence of the light chain variable region of the anti-4-1BB single-chain antibody is set forth in SEQ ID NO. 103. The amino acid sequence of the anti-4-1BB single-chain antibody is shown in SEQ ID NO. 101

The amino acid sequence of the heavy chain variable region of the anti-CD27 single-chain antibody is set forth in SEQ ID NO. 105. The amino acid sequence of the light chain variable region of the anti-4-1BB single-chain antibody is set forth in SEQ ID NO. 106. The amino acid sequence of the anti-4-1BB single-chain antibody is shown in SEQ ID NO. 104

In a preferred embodiment of the disclosure, the amino acid sequence of the trifunctional molecule in monomeric form is shown as any of SEQ ID NO. 59, SEQ ID NO. 63, SEQ ID NO. 67, SEQ ID NO. 71, SEQ ID NO. 75 or SEQ ID NO. 79. The amino acid sequence of the dimeric form of the trifunctional molecule is any one of SEQ ID NO. 61, SEQ ID NO. 65, SEQ ID NO. 69, SEQ ID NO. 73, SEQ ID NO. 77 or SEQ ID NO. 81. However, it is not limited to the specific forms listed in the preferred cases of the present disclosure.

Another trifunctional molecule of the disclosure including a first domain capable of binding to CD19, a second domain capable of binding to and activating a T cell surface CD3 molecule, and a third functional domain capable of binding and activating T cell positive costimulatory molecule.

Further, the trifunctional molecule is capable of binding to and activating the T cell surface CD3 molecule and the T cell positive costimulatory molecule while binding to CD19, thereby generating a first signal and a second signal required for T cell activation. The T cell positive costimulatory molecules include, but are not limited to, human 4-1BB, ICOS, OX40, GITR, CD40L or CD27.

The present disclosure has no particular limitation on the first functional domain, the second functional domain, and the third functional domain. As long as it can bind and activate T cell surface CD3 molecules and T cell positive costimulatory molecules while recognizing CD19, thereby producing the first and the second signal required for activation of T cell. For example, the first functional domain can be an antibody against CD19, the second functional domain can be an anti-CD3 antibody, and the third functional domain can be a ligand extracellular domain of a T cell positive costimulatory molecule. The antibody can be in any form. However, regardless of the form of the antibody, the antigen binding site thereof contains a heavy chain variable region and a light chain variable region. The antibody can preferably be a small molecule antibody. The small molecule antibody is a small molecular weight antibody fragment, and the antigen binding site thereof contains a heavy chain variable region and a light chain variable region. The small molecule antibody has a small molecular weight but retains the affinity of the parental monoclonal antibody and has the same specificity as the parental monoclonal antibody. The types of the small molecule antibodies mainly include Fab, Fv and scFv. The Fab antibody is formed by a disulfide bond between the intact light chain (variable region VL and constant region CL) and the heavy chain Fd segment (variable region VH and first constant region CH1). Fv antibodies are joined by non-covalent bonds by the variable regions of the light and heavy chains. They are the minimal functional fragments of the antibody molecule that retain the intact antigen binding site. A scFv is a single-protein peptide chain molecule in which a heavy chain variable region and a light chain variable region are joined by a linker.

The first functional domain and the second functional domain are connected by linker 1, and the second functional domain and the third functional domain are connected by linker 2. The present disclosure has no particular requirements for the order of connection as long as the object of the present disclosure is not limited. For example, the C-terminus of the first functional domain can be linked to the N-terminus of the second functional domain, and the C-terminus of the second functional domain can be linked to the N-terminus of the third functional domain. The present disclosure is also not particularly limited to the linker 1 and the linker 2 as long as it does not limit the object of the present disclosure.

Further, the linker 1 and the linker 2 are selected from a G4S linker or a hinge region fragment of immunoglobulin IgD.

The G4S is GGGGS. The G4S linker includes one or more G4S units. For example, one, two, three or more G4S units can be included. In some embodiments of the present disclosure, a trifunctional molecule in a monomeric form is exemplified, wherein the first functional domain and the second functional domain are connected by a linker 1 in a G4S unit. The second functional domain and the third functional function are connected by a linker 2 in units of G4S. The linker 1 contains a G4S unit, and the amino acid sequence of the linker is set forth in SEQ ID NO. 159. The linker 2 contains three G4S units, and the amino acid sequence of the ligated fragment is set forth in SEQ ID NO. 161.

The hinge domain of the immunoglobulin IgD could be the hinge Ala90-Val170 of IgD. In some embodiments of the disclosure, wherein a trifunctional molecule in dimeric form is exemplified, the first functional domain and the second functional domain are linked by a linker 1 in units of G4S, a second functional domain and a third functional domains are linked by a hinge domain of immunoglobulin IgD, which is Ala90-Val170. The linker 1 contains a G4S unit, and the amino acid sequence of the linker is shown in SEQ ID NO. 163. The amino acid sequence of the linker 2 is shown in SEQ ID NO. 165. The linking 2 can be linked to each other by a disulfide bond to form a dimer.

Figures 1, 2, 3, 3A:
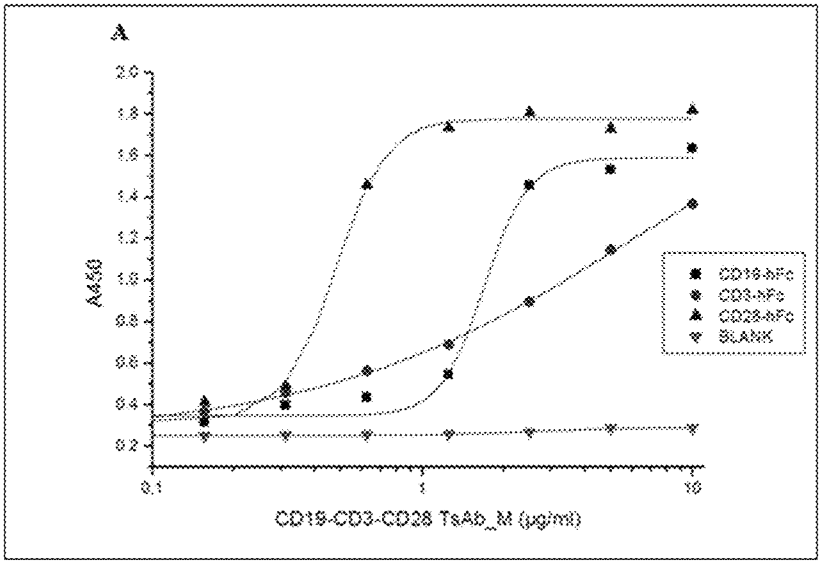

In a preferred embodiment of the disclosure, the schematic structure of the trifunctional molecule is shown in FIG. 3-1. The trifunctional molecule can be in a monomeric form or a dimeric form. A schematic diagram of the structure of the monomeric form of the trifunctional molecule of the present disclosure is shown in FIG. 3-1A. The trifunctional molecule consists of a first functional domain that binds to the CD19 antigen, a second functional domain that binds to the CD3 antigen, and a third domain that binds to a T cell positive costimulatory molecule. The first domain is a scFv that binds to the CD19 antigen, the second domain is a scFv that binds to the CD3 antigen, and the third domain is a scFv that binds to a T cell positive costimulatory molecule antigen. A schematic diagram of the structure of a dimeric form of a trifunctional molecule of the present disclosure is shown in FIG. 3-1B. The structure of the trifunctional molecule contains two first domains that bind to the CD19 antigen, and two second domains bind to the CD3 antigen, and two third domains that bind to a T cell positive co-stimulatory molecule antigen. The trifunctional molecule consists of two first functional domains that bind to the CD19 antigen, two second functional domains that bind to the CD3 antigen, and two third domains that bind to a T cell positive costimulatory molecule. The first domain is a scFv that binds to the CD19 antigen, the second domain is a scFv that binds to the CD3 antigen, and the third domain is a scFv that binds to a T cell positive costimulatory molecule antigen. The dimeric form of the trifunctional molecule of the disclosure has an antigen binding affinity that is twice that of the monomeric form. Due to the doubling of the first signal (CD3) and the second signal (CD28) of T cell activation, T cell activation is more sufficient, and the killing ability on target cells is stronger. The doubling of the CD19 single-chain antibody domain makes it more accurate in recognizing of target cells, so the dimer has a better use effect than the monomer.

Further, the T cell positive costimulatory molecule can be human 4-1BB (UniProt ID: Q07011), the amino acid sequence is shown in SEQ ID NO. 167. The ligand is human 4-1BBL (UniProt ID: P41273). The amino acid sequence is shown in SEQ ID NO. 168.

The T cell positive costimulatory molecule can be human ICOS (UniProt ID: Q9Y6W8), the amino acid sequence is shown as SEQ ID NO. 169. The ligand is human B7RP-1 (UniProt ID: 075144), and the amino acid sequence is shown in SEQ ID NO. 170.

The T cell positive costimulatory molecule can be human OX40 (UniProt ID: P43489), the amino acid sequence is shown as SEQ ID NO. 171. The ligand is human OX40L (UniProt ID: P23510), and the amino acid sequence is shown in SEQ ID NO. 172.

The T cell positive costimulatory molecule can be human GITR (UniProt ID: Q9Y5U5), the amino acid sequence is shown as SEQ ID NO. 173. The ligand is human GITRL (UniProt ID:Q9UNG2), and the amino acid sequence is shown in SEQ ID NO. 174.

The T cell positive costimulatory molecule can be human CD27 (UniProt ID: P26842), the amino acid sequence is shown as SEQ ID NO. 175. The ligand is human CD70 (UniProt ID: P32970), and the amino acid sequence is shown in SEQ ID NO. 176.

Specifically, the first functional domain is a single-chain antibody against CD19. The anti-CD19 single-chain antibody contains a heavy chain variable region and a light chain variable region. The amino acid sequence of the heavy chain variable region of the anti-CD19 single-chain antibody is set forth in SEQ ID NO. 198. The amino acid sequence of the light chain variable region of the anti-CD19 single-chain antibody is set forth in SEQ ID NO. 199. The amino acid sequence of the anti-CD19 single-chain antibody is shown in SEQ ID NO. 197.

The second domain is a single-chain antibody against CD3. The anti-CD3 single-chain antibody contains a heavy chain variable region and a light chain variable region. The amino acid sequence of the heavy chain variable region of the anti-CD3 single-chain antibody is set forth in SEQ ID NO. 201. The amino acid sequence of the light chain variable region of the anti-CD3 single-chain antibody is set forth in SEQ ID NO. 202. Further, the amino acid sequence of the anti-CD3 single-chain antibody is shown in SEQ ID NO. 200.

The third domain is the ligand extracellular domain of a T cell positive costimulatory molecule. The ligand extracellular domain of the T cell positive costimulatory molecule can be any one of 4-1BBL extracellular domain domain, B7RP-1 extracellular domain domain, OX40L extracellular domain domain, GITRL extracellular domain domain or CD70 extracellular domain domain.

The amino acid sequence of the 4-1BBL extracellular domain is set forth in SEQ ID NO. 203.

The amino acid sequence of the B7RP-1 extracellular domain is set forth in SEQ ID NO. 204.

The amino acid sequence of the OX40L extracellular domain is set forth in SEQ ID NO. 205.

The amino acid sequence of the GITRL extracellular domain is set forth in SEQ ID NO. 206.

The amino acid sequence of the CD70 extracellular domain is set forth in SEQ ID NO. 207.

In a preferred embodiment of the present disclosure, the amino acid sequence of the monomeric form of the trifunctional molecule is as defined in any one of SEQ ID NO. 177, SEQ ID NO. 181, SEQ ID NO. 185, SEQ ID NO. 189 or SEQ ID NO. 193. The amino acid sequence of the dimeric form of the trifunctional molecule is as defined in any one of SEQ ID NO. 179, SEQ ID NO. 183, SEQ ID NO. 187, SEQ ID NO. 191 or SEQ ID NO. 195. It is not limited to the specific forms listed in the preferred cases of the present disclosure.

Another trifunctional molecule of the disclosure including a first domain capable of binding to CD19, a second domain capable of binding to and activating a T cell surface CD3 molecule, and a third functional domain capable of binding and blocking T cell inhibitory molecule.

Further, the trifunctional molecule is capable of binding to and activating a T cell surface CD3 molecule, binding and blocking a T cell inhibitory molecule while recognizing CD19, thereby generating a first signal and a second signal required for T cell activation. The T cell inhibitory molecules include, but are not limited to, human PD-1, CTLA-4, LAG-3, TIM-3, TIGIT, and BTLA.

The present disclosure has no particular limitation on the first functional domain, the second functional domain, and the third functional domain. As long as it can bind and activate the T cell surface CD3 molecule, bind and block the T cell inhibitory molecule while recognizing CD19. Thereby, the first signal and the second signal required for T cell activation can be produced. For example, the first functional domain can be an antibody against CD19, the second functional domain can be an anti-CD3 antibody, and the third functional domain can be an antibody against an anti-T cell inhibitory molecule. The antibody can be in any form. However, regardless of the form of the antibody, the antigen binding site thereof contains a heavy chain variable region and a light chain variable region. The antibody can preferably be a small molecule antibody. The small molecule antibody is a small molecular weight antibody fragment, and the antigen binding site thereof contains a heavy chain variable region and a light chain variable region. The small molecule antibody has a small molecular weight but retains the affinity of the parental monoclonal antibody and has the same specificity as the parental monoclonal antibody. The types of the small molecule antibodies mainly include Fab, Fv and scFv. The Fab antibody is formed by a disulfide bond between the intact light chain (variable region VL and constant region CL) and the heavy chain Fd segment (variable region VH and first constant region CH1). Fv antibodies are joined by non-covalent bonds by the variable regions of the light and heavy chains. They are the minimal functional fragments of the antibody molecule that retain the intact antigen binding site. A scFv is a single-protein peptide chain molecule in which a heavy chain variable region and a light chain variable region are joined by a linker.

The first functional domain and the second functional domain are connected by linker 1, and the second functional domain and the third functional domain are connected by linker 2. The present disclosure has no particular requirements for the order of connection as long as the object of the present disclosure is not limited. For example, the C-terminus of the first functional domain can be linked to the N-terminus of the second functional domain, and the C-terminus of the second functional domain can be linked to the N-terminus of the third functional domain. The present disclosure is also not particularly limited to the linker 1 and the linker 2 as long as it does not limit the object of the present disclosure.

Further, the linker 1 and the linker 2 are selected from a G4S linker or a hinge region fragment of immunoglobulin IgD.

The G4S is GGGGS. The G4S linker includes one or more G4S units. For example, one, two, three or more G4S units can be included. In some embodiments of the present disclosure, a trifunctional molecule in a monomeric form is exemplified, wherein the first functional domain and the second functional domain are connected by a linker 1 in a G4S unit. The second functional domain and the third functional function are connected by a linker 2 in units of G4S. The linker 1 contains a G4S unit, and the amino acid sequence of the linker is set forth in SEQ ID NO. 244. The linker 2 contains three G4S units, and the amino acid sequence of the ligated fragment is set forth in SEQ ID NO. 246.

The hinge domain of the immunoglobulin IgD could be the hinge Ala90-Val170 of IgD. In some embodiments of the disclosure, wherein a trifunctional molecule in dimeric form is exemplified, the first functional domain and the second functional domain are linked by a linker 1 in units of G4S, a second functional domain and a third functional domains are linked by a hinge domain of immunoglobulin IgD, which is Ala90-Val170. The linker 1 contains a G4S unit, and the amino acid sequence of the linker is shown in SEQ ID NO. 248. The amino acid sequence of the linker 2 is shown in SEQ ID NO. 250. The linking 2 can be linked to each other by a disulfide bond to form a dimer.

Figures 1, 2, 3, 3B:
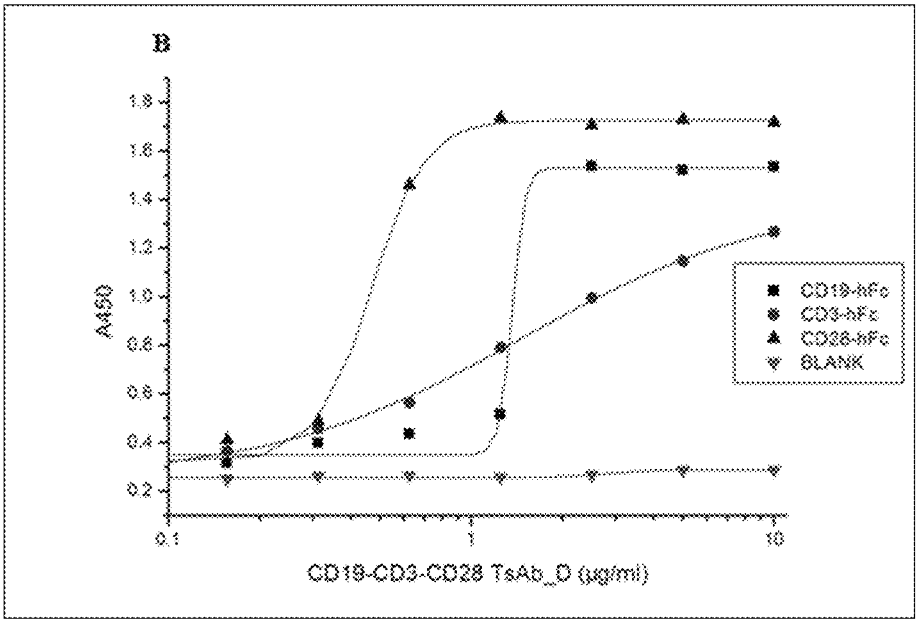
Figures 1, 2, 3, 4:
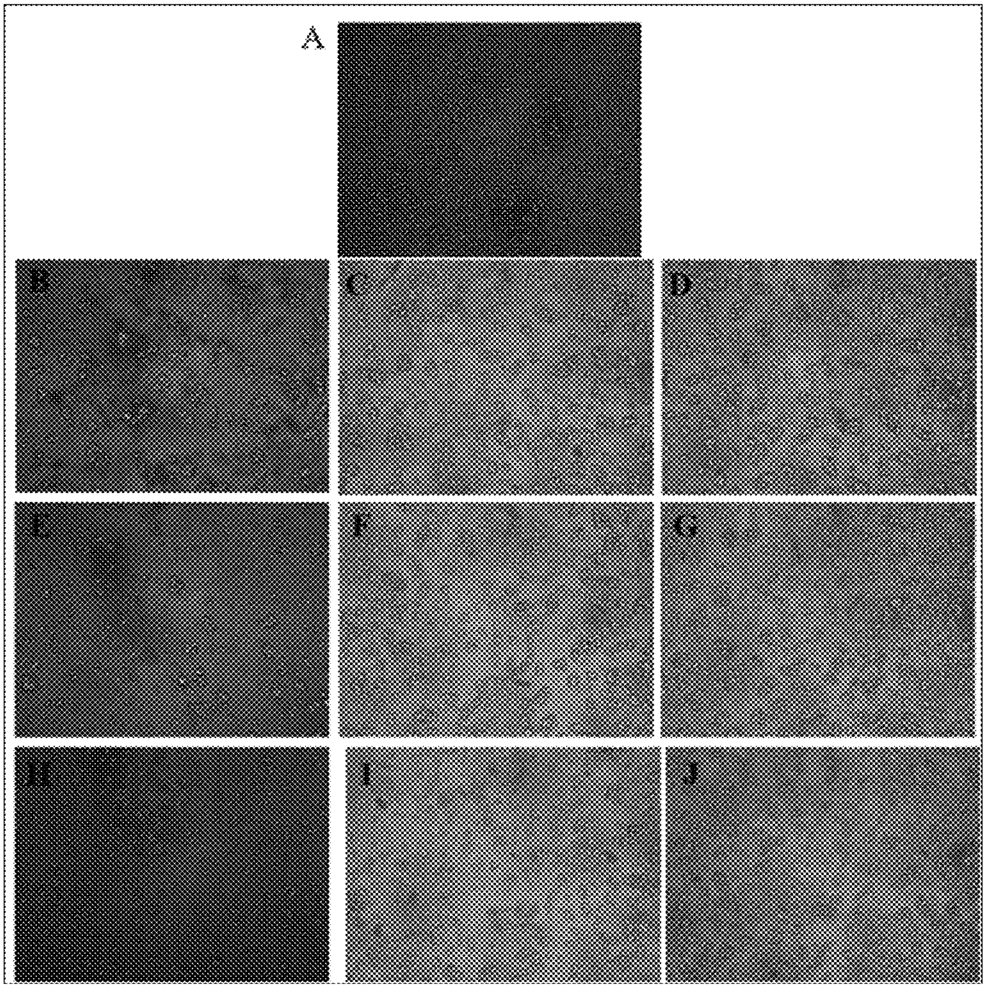

In a preferred embodiment of the disclosure, the schematic structure of the trifunctional molecule is shown in FIG. 4-1. The trifunctional molecule can be in a monomeric form or a dimeric form. A schematic diagram of the structure of the monomeric form of the trifunctional molecule of the present disclosure is shown in FIG. 4-1A. The trifunctional molecule consists of a first functional domain that binds to the CD19 antigen, a second functional domain that binds to the CD3 antigen, and a third domain that binds to a T cell positive costimulatory molecule. The first domain is a scFv that binds to the CD19 antigen, the second domain is a scFv that binds to the CD3 antigen, and the third domain is a scFv that binds to a T cell positive costimulatory molecule antigen. A schematic diagram of the structure of a dimeric form of a trifunctional molecule of the present disclosure is shown in FIG. 4-1B. The structure of the trifunctional molecule contains two first domains that bind to the CD19 antigen, and two second domains bind to the CD3 antigen, and two third domains that bind to a T cell inhibitory molecule antigen. The trifunctional molecule consists of two first functional domains that bind to the CD19 antigen, two second functional domains that bind to the CD3 antigen, and two third domains that bind to a T cell inhibitory molecule. The first domain is a scFv that binds to the CD19 antigen, the second domain is a scFv that binds to the CD3 antigen, and the third domain is a scFv that binds to a T cell inhibitory molecule antigen. The dimeric form of the trifunctional molecule of the disclosure has an antigen binding affinity that is twice that of the monomeric form. Due to the doubling of the first active signal (CD3) and the second signal (blocking of inhibitory molecule) of T cell, T cell activation is more sufficient, and the killing ability on target cells is stronger. The doubling of the CD19 single-chain antibody domain makes it more accurate in recognizing of target cells, so the dimer has a better use effect than the monomer.

The T cell inhibitory molecules can be PD-1, CTLA-4, LAG-3, TIM-3, TIGIT, BTLA, et al.

The amino acid sequence of the extracellular domain of the human T cell inhibitory molecule PD-1 (Uniprot ID: Q15116) is shown in SEQ ID NO. 252.

The amino acid sequence of the extracellular domain of the human T cell inhibitory molecule CTLA-4 (Uniprot ID: P16410) is shown in SEQ ID NO. 253.

The amino acid sequence of the extracellular domain of the human T cell inhibitory molecule LAG-3 (Uniprot ID: P18627) is shown in SEQ ID NO. 254.

The amino acid sequence of the extracellular domain of the human T cell inhibitory molecule TIM-3 (Uniprot ID: Q8TDQ0) is shown in SEQ ID NO. 255.

The amino acid sequence of the extracellular domain of the human T cell inhibitory molecule TIGIT (Uniprot ID: Q495A1) is shown in SEQ ID NO. 256.

The amino acid sequence of the extracellular domain of the human T cell inhibitory molecule BTLA (Uniprot ID: Q7Z6A9) is shown in SEQ ID NO. 257.

Specifically, the first functional domain is a single-chain antibody against CD19. The anti-CD19 single-chain antibody contains a heavy chain variable region and a light chain variable region. The amino acid sequence of the heavy chain variable region of the anti-CD19 single-chain antibody is set forth in SEQ ID NO. 283. The amino acid sequence of the light chain variable region of the anti-CD19 single-chain antibody is set forth in SEQ ID NO. 284. The amino acid sequence of the anti-CD19 single-chain antibody is shown in SEQ ID NO. 282.

The second domain is a single-chain antibody against CD3. The anti-CD3 single-chain antibody contains a heavy chain variable region and a light chain variable region. The amino acid sequence of the heavy chain variable region of the anti-CD3 single-chain antibody is set forth in SEQ ID NO. 286. The amino acid sequence of the light chain variable region of the anti-CD3 single-chain antibody is set forth in SEQ ID NO. 287. Further, the amino acid sequence of the anti-CD3 single-chain antibody is shown in SEQ ID NO. 285.

The third domain is a single-chain antibody against an anti-T cell inhibitory molecule. The single-chain antibody of the anti-T cell inhibitiv molecule includes a heavy chain variable region and a light chain variable region.

The single-chain antibody against the T cell inhibitory molecule can be a single-chain antibody against PD-1, CTLA-4, LAG-3, TIM-3, TIGIT or BTLA.

The amino acid sequence of the heavy chain variable region of the anti-PD-1 single-chain antibody is set forth in SEQ ID NO. 289. The amino acid sequence of the light chain variable region of the anti-PD-1 single-chain antibody is set forth in SEQ ID NO. 290. The amino acid sequence of the single-chain antibody against PD-1 is set forth in SEQ ID NO. 288.

The amino acid sequence of the heavy chain variable region of the anti-CTLA-4 single-chain antibody is set forth in SEQ ID NO. 292. The amino acid sequence of the light chain variable region of the anti-CTLA-4 single-chain antibody is set forth in SEQ ID NO. 293. The amino acid sequence of the single-chain antibody against CTLA-4 is set forth in SEQ ID NO. 291.

The amino acid sequence of the heavy chain variable region of the anti-LAG-3 single-chain antibody is set forth in SEQ ID NO. 295. The amino acid sequence of the light chain variable region of the anti-LAG-3 single-chain antibody is set forth in SEQ ID NO. 296. The amino acid sequence of the single-chain antibody against LAG-3 is set forth in SEQ ID NO. 294.

The amino acid sequence of the heavy chain variable region of the anti-TIM-3 single-chain antibody is set forth in SEQ ID NO. 298. The amino acid sequence of the light chain variable region of the anti-TIM-3 single-chain antibody is set forth in SEQ ID NO. 299. The amino acid sequence of the single-chain antibody against TIM-3 is set forth in SEQ ID NO. 297.

The amino acid sequence of the heavy chain variable region of the anti-TIGIT single-chain antibody is set forth in SEQ ID NO. 301. The amino acid sequence of the light chain variable region of the anti-TIGIT single-chain antibody is set forth in SEQ ID NO. 302. The amino acid sequence of the single-chain antibody against TIGIT is set forth in SEQ ID NO. 300.

The amino acid sequence of the heavy chain variable region of the anti-BTLA single-chain antibody is set forth in SEQ ID NO. 304. The amino acid sequence of the light chain variable region of the anti-BTLA single-chain antibody is set forth in SEQ ID NO. 305. The amino acid sequence of the single-chain antibody against BTLA is set forth in SEQ ID NO. 303.

In a preferred embodiment of the disclosure, the amino acid sequence of the monomeric form of the trifunctional molecule is shown as any of SEQ ID NO. 258, SEQ ID NO. 262, SEQ ID NO. 266, SEQ ID NO. 270, SEQ ID NO. 274 or SEQ ID NO. 278. The amino acid sequence of the dimeric form of the trifunctional molecule is shown as any one of SEQ ID NO. 260, SEQ ID NO. 264, SEQ ID NO. 268, SEQ ID NO. 272, SEQ ID NO. 276 or SEQ ID NO. 280. However, it is not limited to the specific forms listed in the preferred cases of the present disclosure.

3, Polynucleotide Encoding Trifunctional Molecule

The polynucleotide encoding the trifunctional molecule of the present disclosure can be in the form of DNA or RNA. DNA forms include cDNA, genomic DNA or synthetic DNA. DNA can be single-stranded or double-stranded.

The polynucleotide encoding the trifunctional molecule of the disclosure can be prepared by any suitable technique well known to those skilled in the field. Such techniques are described in the general description of the field, such as Molecular Cloning: A Laboratory Manual (J. Sambrook et al., Science Press, 1995). Methods are including, but not limited to, recombinant DNA techniques, chemical synthesis. For example, overlapping extension PCR.

In some preferred embodiments of the disclosure, the nucleotide sequence encoding the heavy chain variable region of the anti-CD19 single-chain antibody is set forth in SEQ ID NO. 15.

The nucleotide sequence encoding the light chain variable region of the anti-CD19 single-chain antibody is set forth in SEQ ID NO. 16.

The nucleotide sequence encoding the anti-CD19 single-chain antibody is set forth in SEQ ID NO. 14.

The nucleotide sequence encoding the heavy chain variable region of the anti-CD3 single-chain antibody is set forth in SEQ ID NO. 18.

The nucleotide sequence encoding the light chain variable region of the anti-CD3 single-chain antibody is set forth in SEQ ID NO. 19.

The nucleotide sequence encoding the anti-CD3 single-chain antibody is set forth in SEQ ID NO. 17.

The nucleotide sequence encoding the heavy chain variable region of the anti-CD28 single-chain antibody is set forth in SEQ ID NO. 21.

The nucleotide sequence encoding the light chain variable region of the anti-CD28 single-chain antibody is set forth in SEQ ID NO. 22.

The nucleotide sequence encoding the anti-CD28 single-chain antibody is set forth in SEQ ID NO. 20.

The nucleotide sequence encoding the amino acid sequence SEQ ID NO. 23 of linker 1 is set forth in SEQ ID NO. 24.

The nucleotide sequence encoding the amino acid sequence SEQ ID NO. 25 of linker 2 is set forth in SEQ ID NO. 26.

The nucleotide sequence encoding the amino acid sequence SEQ ID NO. 27 of linker 1 is set forth in SEQ ID NO. 28.

The nucleotide sequence encoding the amino acid sequence SEQ ID NO. 29 of linker 2 is set forth in SEQ ID NO. 30.

Further, the nucleotide sequence encoding the trifunctional molecule in monomeric form is set forth in SEQ ID NO. 2. The nucleotide sequence encoding the trifunctional molecule in the dimeric form is set forth in SEQ ID NO. 4.

In other preferred embodiments of the disclosure, the nucleotide sequence encoding the heavy chain variable region of the anti-CD19 single-chain antibody is set forth in SEQ ID NO. 108. The nucleotide sequence of the light chain variable region encoding the anti-CD19 single-chain antibody is set forth in SEQ ID NO. 109. The nucleotide sequence of the single-chain antibody encoding the anti-CD19 is shown in SEQ ID NO. 107.

The nucleotide sequence of the heavy chain variable region encoding the anti-CD3 single-chain antibody is set forth in SEQ ID NO. 111. The nucleotide sequence of the light chain variable region encoding the anti-CD3 single-chain antibody is set forth in SEQ ID NO. 112. The nucleotide sequence of the single-chain antibody encoding the anti-CD3 is set forth in SEQ ID NO. 110.

The nucleotide sequence of the heavy chain variable region encoding the anti-4-1BB single-chain antibody is set forth in SEQ ID NO. 114. The nucleotide sequence of the light chain variable region encoding the anti-4-1BB single-chain antibody is set forth in SEQ ID NO. 115. The nucleotide sequence of the single-chain antibody encoding the anti-4-1BB is shown in SEQ ID NO. 113.

The nucleotide sequence of the heavy chain variable region encoding the anti-ICOS single-chain antibody is set forth in SEQ ID NO. 117. The nucleotide sequence of the light chain variable region encoding t the anti-ICOS single-chain antibody is set forth in SEQ ID NO. 118. The nucleotide sequence of the single-chain antibody encoding the anti-ICOS is shown in SEQ ID NO. 116.

The nucleotide sequence of the heavy chain variable region encoding the anti-OX40 single-chain antibody is set forth in SEQ ID NO. 120. The nucleotide sequence of the light chain variable region encoding the s anti-OX40 single-chain antibody is set forth in SEQ ID NO. 121. The nucleotide sequence of the single-chain antibody encoding the anti-OX40 is shown in SEQ ID NO. 119.

The nucleotide sequence of the heavy chain variable region encoding the anti-GITR single-chain antibody is set forth in SEQ ID NO. 123. The nucleotide sequence of the light chain variable region encoding the s anti-GITR single-chain antibody is set forth in SEQ ID NO. 124. The nucleotide sequence of the single-chain antibody encoding the anti-GITR is shown in SEQ ID NO. 122.

The nucleotide sequence of the heavy chain variable region encoding the anti-CD40L single-chain antibody is set forth in SEQ ID NO. 126. The nucleotide sequence of the light chain variable region encoding the s anti-CD40L single-chain antibody is set forth in SEQ ID NO. 127. The nucleotide sequence of the single-chain antibody encoding the anti-CD40L is shown in SEQ ID NO. 125.

The nucleotide sequence of the heavy chain variable region encoding the anti-CD27 single-chain antibody is set forth in SEQ ID NO. 129. The nucleotide sequence of the light chain variable region encoding the s anti-CD27 single-chain antibody is set forth in SEQ ID NO. 130. The nucleotide sequence of the single-chain antibody encoding the anti-CD27 is shown in SEQ ID NO. 128.

The nucleotide sequence encoding the amino acid sequence SEQ ID NO. 44 of linker 1 is set forth in SEQ ID NO. 45.

The nucleotide sequence encoding the amino acid sequence SEQ ID NO. 46 of linker 2 is set forth in SEQ ID NO. 47.

The nucleotide sequence encoding the amino acid sequence SEQ ID NO. 48 of linker 1 is set forth in SEQ ID NO. 49.

The nucleotide sequence encoding the amino acid sequence SEQ ID NO. 50 of linker 2 is set forth in SEQ ID NO. 51.

Further, the nucleotide sequence encoding the trifunctional molecule in monomeric form is set forth in any one of SEQ ID NO. 60, SEQ ID NO. 64, SEQ ID NO. 68, SEQ ID NO. 72, SEQ ID NO. 76 or SEQ ID NO. 80. The nucleotide sequence encoding the trifunctional molecule in the dimeric form is set forth in any one of SEQ ID NO. 62, SEQ ID NO. 66, SEQ ID NO. 70, SEQ ID NO. 74, SEQ ID NO. 78 or SEQ ID NO. 82.

In other preferred embodiments of the disclosure, the nucleotide sequence encoding the heavy chain variable region of the anti-CD19 single-chain antibody is set forth in SEQ ID NO. 209. The nucleotide sequence of the light chain variable region encoding the anti-CD19 single-chain antibody is set forth in SEQ ID NO. 210. The nucleotide sequence of the single-chain antibody encoding the anti-CD19 is set forth in SEQ ID NO. 208.

The nucleotide sequence of the heavy chain variable region encoding the anti-CD3 single-chain antibody is set forth in SEQ ID NO. 212. The nucleotide sequence of the light chain variable region encoding the anti-CD3 single-chain antibody is set forth in SEQ ID NO. 213. The nucleotide sequence of the anti-CD3 single-chain antibody is shown in SEQ ID NO. 211.

The nucleotide sequence encoding the 4-1BBL extracellular domain domain is set forth in SEQ ID NO. 214.

The nucleotide sequence encoding the B7RP-1 extracellular domain domain is set forth in SEQ ID NO. 215.

The nucleotide sequence encoding the OX40L extracellular domain domain is set forth in SEQ ID NO. 216.

The nucleotide sequence encoding the GITRL extracellular domain domain is set forth in SEQ ID NO. 217.

The nucleotide sequence encoding the D70 extracellular domain domain is set forth in SEQ ID NO. 218.

The nucleotide sequence encoding the amino acid sequence SEQ ID NO. 159 of linker is set forth in SEQ ID NO. 160.

The nucleotide sequence encoding the amino acid sequence SEQ ID NO. 161 of linker is set forth in SEQ ID NO. 162.

The nucleotide sequence encoding the amino acid sequence SEQ ID NO. 163 of linker is set forth in SEQ ID NO. 164.

The nucleotide sequence encoding the amino acid sequence SEQ ID NO. 165 of linker is set forth in SEQ ID NO. 166.

Further, the nucleotide sequence encoding the trifunctional molecule in monomeric form is set forth in any one of SEQ ID NO. 178, SEQ ID NO. 182, SEQ ID NO. 186, SEQ ID NO. 190 or SEQ ID NO. 194. The nucleotide sequence encoding the trifunctional molecule in the dimeric form is set forth in any one of SEQ ID NO. 180, SEQ ID NO. 184, SEQ ID NO. 188, SEQ ID NO. 192 or SEQ ID NO. 196.

In other preferred embodiments of the disclosure, the nucleotide sequence encoding the heavy chain variable region of the anti-CD19 single-chain antibody is set forth in SEQ ID NO. 307. The nucleotide sequence encoding the light chain variable region of the anti-CD19 single-chain antibody is set forth in SEQ ID NO. 308. The nucleotide sequence encoding the single-chain antibody of the anti-CD19 is set forth in SEQ ID NO. 306.

The nucleotide sequence encoding the heavy chain variable region of the anti-CD3 single-chain antibody is set forth in SEQ ID NO. 310. The nucleotide sequence encoding the light chain variable region of the anti-CD3 single-chain antibody is set forth in SEQ ID NO. 311. The nucleotide sequence encoding the anti-CD3 single-chain antibody is shown in SEQ ID NO. 309.

The nucleotide sequence encoding the heavy chain variable region of the anti-PD-1 single-chain antibody is set forth in SEQ ID NO. 313. The nucleotide sequence encoding the light chain variable region of the anti-PD-1 single-chain antibody is set forth in SEQ ID NO. 314. The nucleotide sequence encoding the anti-PD-1 single-chain antibody is shown in SEQ ID NO. 312.

The nucleotide sequence encoding the heavy chain variable region of the anti-CTLA-4 single-chain antibody is set forth in SEQ ID NO. 316. The nucleotide sequence encoding the light chain variable region of the anti-CTLA-4 single-chain antibody is set forth in SEQ ID NO. 317. The nucleotide sequence encoding the anti-CTLA-4 single-chain antibody is shown in SEQ ID NO. 315.

The nucleotide sequence encoding the heavy chain variable region of the anti-LAG-3 single-chain antibody is set forth in SEQ ID NO. 319. The nucleotide sequence encoding the light chain variable region of the anti-LAG-3 single-chain antibody is set forth in SEQ ID NO. 320. The nucleotide sequence encoding the anti-LAG-3 single-chain antibody is shown in SEQ ID NO. 318.

The nucleotide sequence encoding the heavy chain variable region of the anti-TIM-3 single-chain antibody is set forth in SEQ ID NO. 322. The nucleotide sequence encoding the light chain variable region of the anti-TIM-3 single-chain antibody is set forth in SEQ ID NO. 323. The nucleotide sequence encoding the anti-TIM-3 single-chain antibody is shown in SEQ ID NO. 321.

The nucleotide sequence encoding the heavy chain variable region of the anti-TIGIT single-chain antibody is set forth in SEQ ID NO. 325. The nucleotide sequence encoding the light chain variable region of the anti-TIGIT single-chain antibody is set forth in SEQ ID NO. 326. The nucleotide sequence encoding the anti-TIGIT single-chain antibody is shown in SEQ ID NO. 324.

The nucleotide sequence encoding the heavy chain variable region of the anti-BTLA single-chain antibody is set forth in SEQ ID NO. 328. The nucleotide sequence encoding the light chain variable region of the anti-BTLA single-chain antibody is set forth in SEQ ID NO. 329. The nucleotide sequence encoding the anti-BTLA single-chain antibody is shown in SEQ ID NO. 327.

The nucleotide sequence encoding the amino acid sequence SEQ ID NO. 244 of linker 1 is set forth in SEQ ID NO. 245.

The nucleotide sequence encoding the amino acid sequence SEQ ID NO. 246 of linker 2 is set forth in SEQ ID NO. 247.

The nucleotide sequence encoding the amino acid sequence SEQ ID NO. 248 of linker 1 is set forth in SEQ ID NO. 249.

The nucleotide sequence encoding the amino acid sequence SEQ ID NO. 250 of linker 2 is set forth in SEQ ID NO. 251.

Further, the nucleotide sequence encoding the trifunctional molecule in monomeric form is set forth in any one of SEQ ID NO. 259, SEQ ID NO. 263, SEQ ID NO. 267, SEQ ID NO. 271, SEQ ID NO. 275 or SEQ ID NO. 279. The nucleotide sequence encoding the trifunctional molecule in the dimeric form is set forth in any one of SEQ ID NO. 261, SEQ ID NO. 265, SEQ ID NO. 269, SEQ ID NO. 273, SEQ ID NO. 277 or SEQ ID NO. 281.

4, Expression Vector

The expression vector of the present disclosure contains the polynucleotide encoding the trifunctional molecule. Methods well known to those skilled in the field can be used to construct the expression vector. These methods include recombinant DNA techniques, DNA synthesis techniques, et al. The DNA encoding the fusion protein can be cloned to a multiple cloning site in the vector to direct mRNA synthesis to express the protein, or for homologous recombination. In a preferred embodiment of the disclosure, the expression vector is pcDNA3.1. The host cell line is Chinese hamster ovary cell (CHO).

5, Method for Preparing Trifunctional Molecules

The method for preparing the trifunctional molecule of the present disclosure includes: constructing an expression vector containing a DNA sequence of a trifunctional molecule, followed by transforming vector into a host cell to induce expression, and isolating the expression product. In a preferred embodiment of the disclosure, the expression vector is pcDNA3.1. The host cell line is Chinese hamster ovary cell (CHO).

6, Use of Trifunctional Molecules

The trifunctional molecule of the present disclosure can be used as a tumor therapeutic drug. The tumor is CD19 positive.

In some preferred embodiments of the present disclosure, human peripheral blood mononuclear cells (PBMC) are used in the experiment. The trifunctional molecule prepared by the present disclosure and the purchased anti-CD19/anti-CD3 BiTE bispecific antibody (CD19-CD3 BsAb) was applied to CIK cells (CD3+CD56+) and CCL-86 Raji lymphoma cells (CD19+) prepared from human blood PBMC of the same donor, respectively. The monomer and dimer form of trifunctional molecules consist of the first function capable of binding to CD19, a second functional domain capable of binding and activating T cell surface CD3 molecule, and a third functional domain capable of binding and activating T cell surface CD28 molecule. It was found that after the adding of the trifunctional molecule of the present disclosure, the killing efficacy of the CIK cells to the Raji cells was significantly improved, and the targeted killing activity against the CD19 positive tumor cells was superior to the anti-CD19/anti-CD3 BiTE bispecific antibody (CD19-CD3 BsAb).

In other preferred embodiments of the present disclosure, it has been found through experiments that the structure prepared by the present disclosure including a first functional domain capable of binding to CD19, a second functional domain capable of binding and activating T cell surface CD3 molecules, and a third functional domain capable of binding and activating T cell positive costimulatory molecule has in vitro binding activity to CD19, CD3 and the corresponding T cell positive costimulatory molecule recombinant antigen, which can promote the targeted killing of CD19 positive target cells by T cells. And the dimer has a better effect than the monomer.

In other preferred embodiments of the present disclosure, it has been found through experiments that the structure prepared by the present disclosure including a first functional domain capable of binding to CD19, a second functional domain capable of binding and activating T cell surface CD3 molecules, and a third functional domain capable of binding and activating T cell positive costimulatory molecule has in vitro binding activity to CD19 recombinant antigen, CD3 recombinant antigen and the corresponding T cell positive costimulatory molecule recombinant protein, which can promote the targeted killing of CD19 positive target cells by T cells. And the dimer has a better effect than the monomer.

In other preferred embodiments of the present disclosure, it has been found through experiments that the structure prepared by the present disclosure including a first functional domain capable of binding to CD19, a second functional domain capable of binding and activating T cell surface CD3 molecules, and a third functional domain capable of binding and blocking T cell inhibitory molecule has in vitro binding activity to CD19, CD3 and the corresponding T cell inhibitory molecule recombinant antigen, which can promote the targeted killing of CD19 positive target cells by T cells. And the dimer has a better effect than the monomer.

7, Pharmaceutical Composition in Tumor Treatment

The tumor therapeutic pharmaceutical composition of the present disclosure includes the aforementioned trifunctional molecule and at least one pharmaceutically acceptable carrier or excipient. The tumor is CD19 positive.

The pharmaceutical composition provided by the present disclosure can be present in various dosage forms, such as an injection for intravenous injection, a percutaneous absorption agent for subcutaneous injection, external application of the epidermis, etc. It can be a spray for nose, throat, oral cavity, epidermis and mucous membrane, etc., drops for nose, eyes, ears, etc. Used in suppositories, tablets, powders, granules, capsules, oral liquids, ointments, creams, etc. It can be pulmonary administration preparations and other compositions for parenteral administration. The above various dosage forms of the drug can be prepared according to the conventional method in the pharmaceutical field.

The carrier includes conventional diluents, excipients, fillers, binders, wetting agents, disintegrating agents, absorption enhancers, surfactants, adsorption carriers, lubricants, etc. The pharmaceutical composition can also contain a flavoring agent, a sweetener, etc.

The pharmaceutical preparations as described above can be used clinically in mammals, including humans and animals, and can be administered by intravenous injection or by mouth, nose, skin, lung inhalation, etc. A preferred weekly dose of the above drug is 0.1-5 mg/kg body weight, and a preferred course of treatment is 10 to 30 days. Administration can be once or in divided doses. Regardless of the method of administration, the optimal dosage for an individual should be based on the particular treatment.

8, Method for Treating Tumor In Vitro

The method of treating a tumor in vitro of the present disclosure includes administering the aforementioned trifunctional molecule or tumor therapeutic pharmaceutical composition to a tumor patient. The tumor is CD19 positive. The method can be for non-therapeutic purposes. In some preferred embodiments of the present disclosure, human peripheral blood mononuclear cells (PBMC) are used in the experiment. The trifunctional molecule prepared by the present disclosure and the purchased anti-CD19/anti-CD3 BiTE bispecific antibody (CD19-CD3 BsAb) was applied to CIK cells (CD3+CD56+) and CCL-86 Raji lymphoma cells (CD19+) prepared from human blood PBMC of the same donor, respectively. The monomer and dimer form of trifunctional molecules consist of the first function capable of binding to CD19, a second functional domain capable of binding and activating T cell surface CD3 molecule, and a third functional domain capable of binding and activating T cell surface CD28 molecule. It was found that after the adding of the trifunctional molecule of the present disclosure, the killing efficacy of the CIK cells to the Raji cells was significantly improved, and the targeted killing activity against the CD19 positive tumor cells was superior to the anti-CD19/anti-CD3 BiTE bispecific antibody (CD19-CD3 BsAb).

The present disclosure aims at the deficiency of anti-CD19/anti-CD3 BiTE bispecific antibody and CAR-T technology targeting CD19, and constructs a trifunctional molecule capable of simultaneously recognizing CD19, CD3 and CD28 by genetic engineering and antibody engineering. There are distinct advantages of the molecule in the preparation process and practical application. It further enhances the efficacy of activating T cells while endowing T cells in targeting of CD19 positive cells. The T cells activated by the trifunctional molecule are able to achieve comparable or even better elimination of CD19-positive target cells can than those by anti-CD19/anti-CD3 BiTE bispecific antibody, and it is superior to the CAR-T technology targeting CD19 in term of use.

In other preferred embodiments of the present disclosure, it has been found through experimentation that the structure prepared by the present disclosure includes a first functional domain capable of binding to CD19, a second functional domain capable of binding and activating T cell surface CD3 molecules, and a third domain capable of binding and activating the of the T cell positive costimulatory molecule. It has in vitro binding activity to CD19, CD3 and the corresponding T cell positive costimulatory molecule recombinant antigen, which can promote the targeted killing of CD19 positive target cells by T cells. And the dimer has a better effect than the monomer.

The present disclosure is directed to the deficiency of anti-CD19/anti-CD3 BiTE bispecific antibody and CAR-T technology targeting CD19. By genetic engineering and antibody engineering methods, the trifunctional molecule is constructed which is capable of simultaneously recognizing CD19, CD3 and any T cell positive costimulatory molecule. There are distinct advantages of the molecule in the preparation process and practical application. It further enhances the efficacy of activating T cells while endowing T cells in targeting of CD19 positive cells. The T cells activated by the trifunctional molecule are able to achieve comparable or even better elimination of CD19-positive target cells can than those by anti-CD19/anti-CD3 BiTE bispecific antibody, and it is superior to the CAR-T technology targeting CD19 in term of use.

In other preferred embodiments of the present disclosure, it has been found through experimentation that the structure prepared by the present disclosure includes a first functional domain capable of binding to CD19, a second functional domain capable of binding and activating T cell surface CD3 molecules, and a third domain capable of binding and activating the of the T cell positive costimulatory molecule. It has in vitro binding activity to CD19, CD3 and the corresponding T cell positive costimulatory molecule recombinant protein, which can promote the targeted killing of CD19 positive target cells by T cells. And the dimer has a better effect than the monomer.

The present disclosure is directed to the deficiency of anti-CD19/anti-CD3 BiTE bispecific antibody and CAR-T technology targeting CD19. By genetic engineering and antibody engineering methods, the Tri-specific Molecule (TsM) is constructed which is capable of simultaneously recognizing CD19, CD3 and any T cell positive costimulatory molecule. There are distinct advantages of the molecule in the preparation process and practical application. It further enhances the efficacy of activating T cells while endowing T cells in targeting of CD19 positive cells. The T cells activated by the trifunctional molecule are able to achieve comparable or even better elimination of CD19-positive target cells can than those by anti-CD19/anti-CD3 BiTE bispecific antibody, and it is superior to the CAR-T technology targeting CD19 in term of use.

In other preferred embodiments of the present disclosure, it has been found through experimentation that the structure prepared by the present disclosure includes a first functional domain capable of binding to CD19, a second functional domain capable of binding and activating T cell surface CD3 molecules, and a third domain capable of blocking the of the T cell inhibitory molecule. It has in vitro binding activity to CD19, CD3 and the corresponding T cell inhibitory molecule recombinant protein, which can promote the targeted killing of CD19 positive target cells by T cells. And the dimer has a better effect than the monomer.

The present disclosure is directed to the deficiency of anti-CD19/anti-CD3 BiTE bispecific antibody and CAR-T technology targeting CD19. By genetic engineering and antibody engineering methods, the Tri-specific Molecule (TsM) is constructed which is capable of simultaneously recognizing CD19, CD3 and any T cell inhibitory molecule. There are distinct advantages of the molecule in the preparation process and practical application. It further enhances the efficacy of activating T cells while endowing T cells in targeting of CD19 positive cells. The T cells activated by the trifunctional molecule are able to achieve comparable or even better elimination of CD19-positive target cells can than those by anti-CD19/anti-CD3 BiTE bispecific antibody, and it is superior to the CAR-T technology targeting CD19 in term of use.

Before the present disclosure is further described, it is to be understood that the scope of the present disclosure is not limited to the specific embodiments described below. The terms used in the embodiments of the present disclosure are intended to describe specific embodiments, and are not intended to limit the scope of the disclosure. The test methods which do not specify the specific conditions in the following examples are usually carried out according to conventional conditions or according to the conditions recommended by each manufacturer.

When the numerical values are given by the embodiments, it is to be understood that two endpoints of each range of values and any value between the two endpoints can be selected. Unless otherwise defined, all technical and scientific terms used in the present disclosure have the same meaning as commonly understood by those skilled in the field. In addition to the specific methods, devices, and materials used in the embodiments, the methods, devices, and materials described in the embodiments of the present disclosure can also be used according to the current technology and the description of the present disclosure by those skilled in the field. Any method, devices, and material of the current technology, similar or equivalent, can be used to practice the disclosure.

Unless otherwise defined, the experimental methods, detection methods, and preparation methods disclosed in the present disclosure employ conventional techniques of molecular biology, biochemistry, chromatin structure and analysis, analytical chemistry, cell culture, recombinant DNA technology, and conventional technology in related fields. These techniques have been well described in the existing literature, according to Sambrook et al. MOLECULAR CLONING: A LABORATORY MANUAL, Second edition, Cold Spring Harbor Laboratory Press, 1989 and Third edition, 2001; Ausubel et al, CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304; Chromatin (P M Wassarman and A P Wolffe, eds.), Academic Press, San Diego, 1999; METHODS IN MOLECULAR BIOLOGY, Vol. 119, Chromatin Protocols (P. B. Becker, ed.) Humana Press, Totowa, 1999, et al.

Embodiment 1-1 The Eukaryotic Expression Vector Construction of CD19-CD3-CD28 TsAb_M and CD19-CD3-CD28 TsAb_D In this disclosure, the tri-specific antibody targeted CD19 on B lymphoma cells, CD3 and CD28 on human T cell is named as CD19-CD3-CD28 TsAb.

1. Construction Design of CD19-CD3-CD28 TsAb_M and CD19-CD3-CD28 TsAb_D

Construction design of CD19-CD3-CD28 TsAb_M Monomer:

The sequences of the anti-CD19 scFv, anti-CD3 scFv and anti-CD28 scFv are linked by linkers. Specifically, the sequence of anti-CD19 scFv and the anti-CD3 scFv are linked by Linker 1, the sequence of anti-CD3 scFv and anti-CD28 scFv are linked by Linker 2.

Construction design of CD19-CD3-CD28 TsAb_D Dimer:

The sequences of the anti-CD19 scFv, anti-CD3 scFv and anti-CD28 scFv are linked by linkers. Specifically, the sequences of anti-CD19 scFv and anti-CD3 scFv are linked by Linker 1, the sequences of anti-CD3 scFv and anti-CD28 scFv are linked by IgD hinge region (Ala90-Val170) as Linker 2.

In order to express the tri-specific antibody in mammalian cells, codon optimization of mammalian system was performed for the sequence of anti-CD19 scFv, anti-CD3 scFv, and anti-CD28 scFv.

The nucleotide sequence of anti-CD19 scFv heavy chain variable region is shown as SEQ ID NO. 15.

The nucleotide sequence of anti-CD19 scFv light chain variable region is shown as SEQ ID NO. 16.

The nucleotide sequence of anti-CD19 scFv is shown as SEQ ID NO. 14.

The nucleotide sequence of anti-CD3 scFv heavy chain variable region is shown as SEQ ID NO. 18.

The nucleotide sequence of anti-CD3 scFv light chain variable region is shown as SEQ ID NO. 19.

The nucleotide sequence of anti-CD3 scFv is shown as SEQ ID NO. 17.

The nucleotide sequence of anti-CD28 heavy chain variable region is shown as SEQ ID NO. 21.

The nucleotide sequence of anti-CD28 scFv light chain variable region is shown as SEQ ID NO. 22.

The nucleotide sequence of anti-CD28 is shown as SEQ ID NO. 20.

The nucleotide sequence of CD19-CD3-CD28 TsAb_M monomer linker (Linker 1) is shown as SEQ ID NO. 24.

The nucleotide sequence of CD19-CD3-CD28 TsAb_M monomer linker (Linker 2) is shown as SEQ ID NO. 26.

The nucleotide sequence of CD19-CD3-CD28 TsAb_D dimer linker (Linker 1) is shown as SEQ ID NO. 28.

The nucleotide sequence of CD19-CD3-CD28 TsAb_D dimer linker (Linker 2) is shown as SEQ ID NO. 30.

In order to express tri-specific antibody successfully in CHO-S cells and secret into medium, signal peptide of antibody secretory expression was selected in this embodiment.

The amino acid sequence of this secretory signal peptide is shown as SEQ ID NO. 31.

The nucleotide sequence of this secretory signal peptide is shown as SEQ ID NO. 32.

2. CD19-CD3-CD28 TsAb_M and CD19-CD3-CD28 TsAb_D Eukaryotic Expression Vector Construction The construction and expression of this tri-specific antibody in the present disclosure selected mammalian cell protein transient expression vector pcDNA3.1 (purchased from Invitrogen, Shanghai). In order to construct the tri-specific antibody in monomer and dimer form, primers were designed as in table 1-1. All the primers were synthesized by Genewiz, Suzhou, and DNA template for PCR was synthesized by Synbio Technologies, Suzhou.

The cloning construct for CD19-CD3-CD28 TsAb_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker+anti-CD28 scFv sequence by primer pairs Sig-CD19-F and CD19-R, CD19-G4S-CD3-F and CD3-R, and CD3-$(GGGGS)_3$—CD28-F and pcDNA3.1-CD28-R, respectively. The cloning construct for CD19-CD3-CD28 TsAb_D includes: amplifying signal peptide by primers pcDNA3.1-Sig-F and Sig-R, amplifying anti-CD19 scFv, GGGGS Linker 1+anti-CD3 scFv, and IgD hinge region Linker2+anti-CD28 scFv sequence by primer pairs Sig-CD19-F and CD19-R, CD19-G4S-CD3-F and CD3-R, CD3-IgD-F and IgD-R, and IgD-CD28-F and pcDNA3.1-CD28-R, respectively. After PCR amplification, by using NovoRec® PCR One-Step Cloning Kit (purchased from Wujiang Novoprotein Technology Co., Ltd.), the full length of tri-specific antibody monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-CD28 TsAb monomer and CD19-CD3-CD28 TsAb dimer both had the correct full DNA sequence as expected.

The nucleotide sequence of CCD19-CD3-CD28 TsAb_M monomer is shown as SEQ ID NO. 2.

The nucleotide sequence of CD19-CD3-CD28 TsAb_D dimer is shown as SEQ ID NO. 4.

TABLE 1-1

Primers used in tri-specific antibody gene cloning

| Primer name | Sequence | No. |
|---|---|---|
| pcDNA3.1-Sig-F | GTGCTGGATATCTGCAGAATTCGCCGCCACCATGACCCGGCT GACCGTGCTGGCCCTGC | SEQ ID NO. 33 |
| Sig-R | GGCCCTGGAGGAGGCCAGCAGGCCGGCCAGCAGGGCCAGCAC GGTCAGC | SEQ ID NO. 34 |
| Sig-CD19-F | CTGCTGGCCTCCTCCAGGGCCGACATCCAGCTGACCCAGAGC | SEQ ID NO. 35 |
| CD19-R | GCTGCTCACGGTCACGGTGGTGC | SEQ ID NO. 36 |
| CD19-G4S-CD3-F | CCACCGTGACCGTGAGCAGCGGTGGCGGAGGGTCCGACATCA AGCTGCAGCAGAGC | SEQ ID NO. 37 |
| CD3-R | CTTCAGCTCCAGCTTGGTGC | SEQ ID NO. 38 |
| CD3-(GGGGS)3-CD28-F | GCACCAAGCTGGAGCTGAAGGGAGGCGGAGGTTCCGGCGGTG GGGGATCGGGGGGTGGAGGGAGTCAGGTGCAGCTGGTGCAGA GC | SEQ ID NO. 39 |
| pcDNA3.1-CD28-R | CTGATCAGCGGTTTAAACTTAAGCTTTCAGCGCTTGATCTCC ACCTTGGTG | SEQ ID NO. 40 |
| CD3-IgD-F | GCACCAAGCTGGAGCTGAAGGCCAGCAAGAGCAAGAAGGAG | SEQ ID NO. 41 |
| IgD-R | CACGCCCAGGGGCTGGGTGTG | SEQ ID NO. 42 |
| IgD-CD28-F | CACACCCAGCCCCTGGGCGTGCAGGTGCAGCTGGTGCAGAGC | SEQ ID NO. 43 |

Embodiment 1-2: The Expression and Purification of CD19-CD3-CD28 TsAb_M and CD19-CD3-CD28 TsAb_D 1. The Expression of CD19-CD3-CD28 TsAb_M and CD19-CD3-CD28 TsAb_D 1.1 The cell density of CHO-S cells (purchased from Thermo Fisher Scientific) was 0.5~0.6×$10^6$/ml one day before transfection.

1.2 Calculating cell density at the day of transfection, plasmid transfection can be performed when the density is 1~1.4×$10^6$/ml and cell viability is >90%.

1.3 Transfecting complex recipes: each project (CD19-CD3-CD28 TsAb_M and CD19-CD3-CD28 TsAb_D) requires two centrifuge tubes/flasks. Take 20 ml as example, the recombinant plasmids from Embodiment 1-1 were taken: Tube 1: 600 μl PBS, 20 μg recombinant plasmid, mix well; Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well, to obtain transfection complex.

1.5 Keeping transfection complex for 15~20 min, adding it into cell culture dropwise steadily.

1.6 Keeping cell culture at 37° C., $CO_2$ concentration of 8%, concentration 130 rpm on. Collecting medium after 5 days for the target protein test.

2. The Purification of D19-CD3-CD28 TsAb_M and CD19-CD3-CD28 TsAb_D 2.1 Sample pretreatment Taking 20 ml cell medium after transfection, adding 20 mM PB, 200 mM NaCl, and adjust pH to 7.5;

2.2 Purification of Protein L affinity chromatography column Protein purification chromatography column: Protein L affinity chromatography column (purchased from GE Healthcare, column volume: 1.0 ml) Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collect flowthrough sample. After running sample, balancing chromatography column with at least 1.5 ml Buffer A, then washing with Buffer B and Buffer C respectively, collecting flowthrough sample with target protein (the collection tube for flowthrough sample needs pretreated with 1% 1M Tris, pH8.0 to neutralize the pH of flowthrough sample, and the final concentration of Tris is about 10 mM). Finally, concentrating and dialysing the flowthrough sample into buffer PBS.

The final purified CD19-CD3-CD28 TsAb_M and CD19-CD3-CD28 TsAb_D recombinant protein was analyzed by SDS-PAGE, and the protein electrophoresis data under reduced and unreduced conditions were shown as FIG. 1-2. It shows that both purity of CD19-CD3-CD28 TsAb_M and CD19-CD3-CD28 recombinant protein are >95%. The theoretical molecule weight of CD19-CD3-CD28 TsAb_M is 81.3 kDa, and protein displayed the same single band under reduced and unreduced conditions. The molecule weight of these bands is consistent with monomer, so this tri-specific antibody is monomer (FIG. 1-2A, Lane 1: protein marker for molecule weight; Lane 2: reduced CD19-CD3-CD28 TsAb_M; Lane 3: unreduced CD19-CD3-CD28 TsAb_M). The theoretical molecule weight for CD19-CD3-CD28 TsAb_D is 89.1 kDa, and protein displayed the same molecule weight as monomer under reduced condition, but the molecule weight is consistent with dimer under unreduced condition (~180 kDa) (FIG. 1-2B, Lane 1: protein marker for molecule weight; Lane 2: reduced CD19-CD3-CD28 TsAb_D; Lane 3: unreduced CD19-CD3-CD28 TsAb_D), which indicate two protein link to each other by disulfide bond formed through IgD hinge region so that this tri-specific antibody is dimer.

Moreover, the N/C terminal sequence analysis for purified recombinant protein shows the reading frame has no error, it is consistent with the theoretical N/C terminal amino acid sequence. Mass spectrometry analysis further confirmed that CD19-CD3-CD28 TsAb_M is monomer and CD19-CD3-CD28 TsAb_D is dimer.

Therefore, the amino acid sequence of CD19-CD3-CD28 TsAb_M monomer is shown as SEQ ID NO. 1.

The amino acid sequence of CD19-CD3-CD28 TsAb_D dimer is shown as SEQ ID NO. 3.

The amino acid sequence of anti-CD19 scFv is shown as SEQ ID NO. 5.

The amino acid sequence of anti-CD19 scFv heavy chain variable region is shown as SEQ ID NO. 6.

The amino acid sequence of anti-CD19 scFv light chain variable region is shown as SEQ ID NO. 7.

The amino acid sequence of anti-CD3 scFv is shown as SEQ ID NO. 8.

The amino acid sequence of anti-CD3 scFv heavy chain variable region is shown as SEQ ID NO. 9.

The amino acid sequence of anti-CD3 scFv light chain variable region is shown as SEQ ID NO. 10.

The amino acid sequence of anti-CD28 scFv is shown as SEQ ID NO. 11.

The amino acid sequence of anti-CD28 scFv heavy chain variable region is shown as SEQ ID NO. 12.

The amino acid sequence of anti-CD28 scFv light chain variable region is shown as SEQ ID NO. 13.

The amino acid sequence of CD19-CD3-CD28 TsAb_M monomer linker (Linker 1) is shown as SEQ ID NO. 23 in details: GGGGS The amino acid sequence of CD19-CD3-CD28 TsAb_M monomer linker (Linker 2) is shown as SEQ ID NO. 25 in details: GGGGSGGGGSGGGGS The amino acid sequence of CD19-CD3-CD28 TsAb_D dimer linker (Linker 1) is shown as SEQ ID NO. 27 in details: GGGGS The amino acid sequence of CD19-CD3-CD28 TsAb_D dimer linker (Linker 2) is shown as SEQ ID NO. 29.

Embodiment 1-3: Antigen Binding Activity Test of CD19-CD3-CD28 TsAb_M and CD19-CD3-CD28 TsAb_D by ELISA ELISA procedure:

1. Recombinant antigen coating: 96-well plates were coated by human CD19-hFc, CD3-hFc and human CD28-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g Na2HPO4, 0.24 g NaH2PO4, 0.2 g KCl, 8.2 g NaCl, 950 ml H2O, adjusting pH to 7.4 with 1 mol/L HCl or 1 mol/L NaOH, adding water to 1 L for total volume.

2. Blocking: washing plates with PBS for 4 times, and adding PBSA (PBS+2% BSA(V/W)) 200 μl per well to block at 37° C. for 1 hour.

3. Adding sample: washing plates with PBS for 4 times, adding 100 μl per well tri-specific antibody samples respectively and keeping plates at 37° C. for 1 hour. Sample serial dilution includes: using 10 μg/ml purified CD19-CD3-CD28 TsAb_M or CD19-CD3-CD28 TsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, add 100 μl per well and keeping plates at 37° C. for 1 hour. Washing plates with PBS for 4 times, adding 1041 per well color-developing TMB (purchased from KPL), developing in dark for 5~10 min at room temperature.

5. Reaction termination and result test: adding 100 μl per well 1M HCl to stop reaction, and reading OD value of 450 nm absorbance on ELISA reader.

The results of ELISA are shown in FIGS. 1-3A and 1-3B, The four curves in the figure represent four results: ■ coated with 1 μg/ml CD19-hFc recombinant antigen, ● coated with 1 μg/ml CD3-hFc recombinant antigen; ▲ coated with 1 μg/ml CD28-hFc recombinant antigen; ▼ no antigen coated result. FIG. 1-3A indicates that CD19-CD3-CD28 TsAb_M has antigen binding activity with CD19-hFc, CD3-hFc and CD28-hFc in vitro. CD28 has the highest binding activity, CD19 has the second highest binding activity, CD3 has the weakest binding activity. FIG. 1-3B indicates that CD19-CD3-CD28 TsAb_D has antigen binding activity with CD19-hFc, CD3-hFc and CD28-hFc in vitro as well. CD28 has the highest binding activity, CD19 has the second highest binding activity, CD3 has the weakest binding activity.

Embodiment 1-4: Tri-Specific Antibody and Bispecific Antibody-Mediated Cell Junction Assay Using CCL-86 Raji lymphoma cells (purchased from ATCC) as CD19-positive target cells, TIB-152 Jurkat cells (purchased from ATCC) as CD3 and CD28-positive effector cells, comparing with the TiTE in monomeric form of the present disclosure (CD19-CD3-CD28 TsAb_M), TiTE tri-specific antibody in dimeric form (CD19-CD3-CD28 TsAb_D) and anti-CD19/anti-CD3 BiTE (CD19-CD3 BsAb, purchased from Novoprotein, Wujiang) mediated differences in cell-binding activity.

Cell Junction Assay Procedure:

1. Taking Raji cells ~1×10$^5$, setting 3 experimental groups as high, medium and low concentration, adding CD19-CD3 BsAb with concentration of 45 ng/ml, CD19-CD3-CD28 TsAb_M with concentration of 0.45 ng/ml and CD19-CD3-CD28 TsAb_D with concentration of 0.0045 ng/ml respectively. Keeping for 5 min. Cells without antibody added was a blank control.

2. Taking the same amount of Jurkat cells, adding the Jurkat cells to the above Raji cell samples, placing the samples in the incubator at 37° C. for 1 h, taking out the cells and shaking gently for 30 s, keeping for 2 min, observing the cell formation and photograph under the microscope.

The results are shown in FIG. 1-4, A: blank control without antibody added; B: experimental group supplemented with high concentration CD19-CD3 BsAb (45 ng/ml) was added; C: experimental group with high concentration of CD19-CD3-CD28 TsAb_M (45 ng/ml) was added; D: experimental group with high concentration of CD19-CD3-CD28 TsAb_D (45 ng/ml) was added; and E: experimental group with medium concentration of CD19-CD3 BsAb (0.45 ng/ml) was added; F: experimental group with medium concentration CD19-CD3-CD28 TsAb_M (0.45 ng/ml) was added; G: experimental group with medium concentration CD19-CD3-CD28 TsAb_D (0.45 ng/ml) was added H: experimental group with low concentration of CD19-CD3 BsAb (0.0045 ng/ml) was added; I: experimental group with low concentration of CD19-CD3-CD28 TsAb_M (0.0045 ng/ml) was added; J: experimental group with low concentration of CD19-CD3-CD28 TsAb_D (0.0045 ng/ml) was added. Raji cells were not aggregated with Jurkat cells without any antibody (FIG. 1-4A), which indicated that there was no non-specific binding between the two cells. Under the conditions of antibody (45 ng/ml), both Raji cells and Jurkat cells in the three experimental groups were significantly aggregated (FIG. 1-4B-D), which indicated that two forms TiTE tri-specific antibody (CD19-CD3-CD28 TsAb_M and CD19-CD3-CD28 TsAb_D) and anti-CD19/anti-CD3 BiTE bispecific antibody (CD19-CD3 BsAb) showed little difference in cell binding activity at higher concentrations. Under the condition of adding medium concentration antibody (0.45 ng/ml), CD19-CD3-CD28 TsAb_M and CD19-CD3-CD28 TsAb_D can still induce Raji cells to form aggregation with Jurkat cells, CD19-CD3 BsAb can cause a small amount of aggregation of two cells (FIG. 1-4E-G), which indicated that cell binding activity of two tri-specific antibody is superior to BiTE bispecific antibody at medium concentration. Under the condition of adding low concentration antibody (0.0045 ng/ml), CD19-CD3-CD28 TsAb_D can still induce Raji cells to form aggregation with Jurkat cells. CD19-CD3-CD28 TsAb_M can induce a small amount of two cells to form a aggregation, while CD19-CD3 BsAb is unable to agglomerate cells (FIG. 1-4H-J), which indicated that the TiTE tri-specific antibody of dimeric form has better cell binding activity at low concentrations than the TiTE tri-specific antibody of monomeric form, while BiTE bispecific antibodies have no cell-binding activity at low concentrations.

Embodiment 1-5: Tri-Specific Antibody and Bispecific Antibody-Mediated Cell Killing Assay Human PBMC (Peripheral blood mononuclear cell, PBMC) was used as experiment material. The above-mentioned the TiTE tri-specific antibody CD19-CD3-CD28 TsAb_M in monomeric form and the TiTE tri-specific antibody CD19-CD3-CD28 TsAb_D in dimeric form and purchased anti-CD19/anti-CD3 BiTE bispecific antibody (CD19-CD3 BsAb) were applied to CIK cells (CD3+ CD56+) and CCL-86 Raji lymphoma cells (CD19+) prepared from the same donor, respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Fresh bloods were collected from volunteers. Adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. extractinging white fluffy cell layer in the middle into a new tube, adding PBS buffer with volume more than 2 times of the extracted cell layer, centrifuging at 1100 rpm for 10 min, washing again, and using a small amount of pre-cooled X-vivo 15 serum-free medium (purchased from Lonza) to resuspended the cells. Counting cells for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity, and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 μL, $1\times10^5$ of the cultured CIK cells were taken, and $5\times10^5$ Raji cells were added (CIK effector cells: Raji target cells (E:T ratio) is 1:5) or $1\times10^5$ Raji cells were added (E:T ratio is 1:1). Then CD19-CD3 BsAb and CD19-CD3-CD28 TsAb_M and CD19-CD3-CD28 TsAb_D antibody are added at different final concentrations (25, 12.5, 6.25, 3.125 ng/ml). Mixing at room temperature for 3-5 min, after culture at 37° C. for 3 h, adding 10 μl CCK8 per well, and keeping reaction at 37° C. for 2-3 h. Then $OD_{450}$ was detected by using OD reader. Killing efficacy was calculated by the following formula. Each group was detected for 3 times. The cytotoxicity of CIK cultured without any antibody was blank control of killing efficacy.

$$\text{Killing efficacy (\%)} = \frac{OD\text{ value of Raji cells} + OD\text{ value of } CIK\text{ cells} - \text{detected } OD\text{ value}}{OD\text{ value of Raji cells}} \times 100\%$$

The results are shown in FIG. 1-5. When CIK effector cells: Raji target cells (E:T ratio) were 1:5 and 1:1, respectively, the killing efficacy was about 17% (FIG. 1-5A) and 21% (FIG. 1-5B) after 3 h without adding any antibody. The killing efficacy of CIK cells on Raji cells was significantly improved under the conditions of adding higher concentrations of antibodies (25, 12.5, 6.25 ng/ml). Cells mediated by CD19-CD3-CD28 TsAb_D have the best cell killing effect. When the E:T ratio is 1:5, the killing efficacy is about 36%, 29% and 30%, respectively. When the E:T ratio is 1:1, the killing efficacy is about 85%, 90% and 85%, respectively. The effect of CD19-CD3-CD28 TsAb_M is in second place. When the E:T ratio is 1:5, the killing efficacy is about 30%, 23% and 26% respectively. When the E:T ratio is 1:1, the killing efficacy is about 86%, 82% and 81%. The effect of CD19-CD3 BsAb is the weakest. When the E:T ratio is 1:5, the killing efficacy is about 23%, 22% and 22% respectively. When the E:T ratio is 1:1, the killing efficacy is about 80%, 55% and 56%. Under the condition of adding lower concentration antibody (3.125 ng/ml), the killing efficacy of CIK cells mediated by CD19-CD3-CD28 TsAb_D and CD19-CD3-CD28 TsAb_M against Raji cells is improved to some extent. when E When the T is 1:5, the killing efficacy is about 23% and 22% respectively. When the E:T ratio is 1:1, the killing efficacy is about 82% and 70%, respectively. While CD19-CD3 BsAb had no effect compared with the blank control. The above results indicated that the two forms of TiTE tri-specific antibody-mediated T cell-targeted killing activity against CD19-positive tumor cells were superior to that of BiTE bispecific antibody. The dimeric form has a better effect than the monomer form.

Embodiment 2-1 the Eukaryotic Expression Vector Construction of CD19-CD3-4-1BB TsAb_M and CD19-CD3-4-1BB TsAb_D In the present disclosure, a TiTE tri-specific antibody targeting human CD19 protein on the surface of lymphoma B cells, T cell surface human CD3 and T cell positive costimulatory molecule 4-1BB protein is named as CD19-CD3-4-1BB TsAb.

1. Construction design of CD19-CD3-4-1BB TsAb_M and CD19-CD3-4-1BB TsAb_D

Construction Design of CD19-CD3-4-1BB TsAb_M Monomer:

The sequences of the anti-CD19 scFv, anti-CD3 scFv and anti-4-1BB scFv are linked by a linker. Specifically, the sequence of anti-CD19 scFv and the anti-CD3 scFv are linked by Linker 1, the sequence of anti-CD3 scFv and anti-4-1BB scFv are linked by Linker 2.

Construction design of CD19-CD3-4-1BB TsAb_D Dimer:

The sequences of the anti-CD19 scFv, anti-CD3 scFv and anti-4-1BB scFv are linked by linkers. Specifically, the sequences of anti-CD19 scFv and anti-CD3 scFv are linked by Linker 1, the sequences of anti-CD3 scFv and anti-4-1BB scFv are linked by IgD hinge region (Ala90-Val170) as Linker 2.

In order to express the tri-specific antibody in mammalian cells, codon optimization of mammalian system was performed for the sequence of anti-CD19 scFv, anti-CD3 scFv, and anti-4-1BB scFv.

The nucleotide sequence of anti-CD19 scFv heavy chain variable region is shown as SEQ ID NO. 108.

The nucleotide sequence of anti-CD19 scFv light chain variable region is shown as SEQ ID NO. 109.

The nucleotide sequence of anti-CD19 scFv is shown as SEQ ID NO. 107.

The nucleotide sequence of anti-CD3 scFv heavy chain variable region is shown as SEQ ID NO. 111.

The nucleotide sequence of anti-CD3 scFv light chain variable region is shown as SEQ ID NO. 112.

The nucleotide sequence of anti-CD3 scFv is shown as SEQ ID NO. 110.

The nucleotide sequence of anti-4-1BB scFv heavy chain variable region is shown as SEQ ID NO. 114.

The nucleotide sequence of anti-4-1BB scFv light chain variable region is shown as SEQ ID NO. 115.

The nucleotide sequence of anti-4-1BB scFv is shown as SEQ ID NO. 113.

The nucleotide sequence of CD19-CD3-4-1BB TsAb_M monomer linker (Linker 1) is shown as SEQ ID NO. 45.

The nucleotide sequence of CD19-CD3-4-1BB TsAb_M monomer linker (Linker 2) is shown as SEQ ID NO. 47.

The nucleotide sequence of CD19-CD3-4-1BB TsAb_D dimer linker (Linker 1) is shown as SEQ ID NO. 49.

The nucleotide sequence of CD19-CD3-4-1BB TsAb_D dimer linker (Linker 2) is shown as SEQ ID NO. 51.

In order to expresstri-specific antibody successfully in CHO-S cells and secret into medium, signal peptide of antibody secretory expression was selected in this Embodiment.

The amino acid sequence of this secretory signal peptide is shown as SEQ ID NO. 131.

The nucleotide sequence of this secretory signal peptide is shown as SEQ ID NO. 132.

2. CD19-CD3-4-1BB TsAb_M and CD19-CD3-4-1BB TsAb_D Eukaryotic Expression Vector Construction The construction and expression of this tri-specific antibody in the present disclosure selected mammalian cell protein transient expression vector pcDNA3.1 (purchased from Invitrogen, Shanghai). In order to construct the tri-specific antibody in monomer and dimer form, primers were designed as in table 2-1. All the primers were synthesized by Genewiz, Suzhou, and DNA template for PCR was synthesized by Synbio Technologies, Suzhou.

The cloning construct for CD19-CD3-4-1BB TsAb_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+anti-4-1BB scFv sequence by primer pairs Sig-CD19-F and CD19-R, CD19-G4S-CD3-F and CD3-R, and CD3-$(GGGGS)_3$-4-1BB-F and pcDNA3.1-4-1BB-R, respectively. The cloning construct for CD19-CD3-4-1BB TsAb_D includes: amplifying signal peptide by primers pcDNA3.1-Sig-F and Sig-R, and then amplifying anti-CD19 scFv, GGGGS Linker 1+anti-CD3 scFv, IgD hinge region Linker2 and anti-4-1BB scFv sequence by primer pairs Sig-CD19-F and CD19-R, CD19-G4S-CD3-F and CD3-R, CD3-IgD-F and IgD-R, and IgD-4-1BB-F and pcDNA3.1-4-1BB-R, respectively. After PCR amplification, by using NovoRec® PCR One-Step Cloning Kit (purchased from Wujiang Novoprotein Technology Co., Ltd.), the full length of tri-specific antibody monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-4-1BB TsAb_M monomer and CD19-CD3-4-1BB TsAb_D dimer both had the right full DNA sequence as expected.

The nucleotide sequence of CD19-CD3-4-1BB TsAb_M monomer is shown as SEQ ID NO. 60.

The nucleotide sequence of CD19-CD3-4-1BB TsAb_D dimer is shown as SEQ ID NO. 62.

TABLE 2-1

Primers used in CD3-4-1BB tri-specific antibody gene cloning

| Primer name | sequence | No. |
|---|---|---|
| pcDNA3.1-Sig-F | GTGCTGGATATCTGCAGAATTCGCCGCCACCATGACCCGGCTGACCGT GCTGGCCCTGC | SEQ ID NO. 133 |
| Sig-R | GGCCCTGGAGGAGGCCAGCAGGCCGGCCAGCAGGGCCAGCACGGTCAG C | SEQ ID NO. 134 |
| Sig-CD19-F | CTGCTGGCCTCCTCCAGGGCCGACATCCAGCTGACCCAGAGC | SEQ ID NO. 135 |
| CD19-R | GCTGCTCACGGTCACGGTGGTGC | SEQ ID NO. 136 |
| CD19-G4S-CD3-F | CCACCGTGACCGTGAGCAGCGGTGGCGGAGGGTCCGACATCAAGCTGC AGCAGAGC | SEQ ID NO. 137 |
| CD3-R | CTTCAGCTCCAGCTTGGTGC | SEQ ID NO. 138 |
| CD3-$(GGGGS)_3$-4-1BB-F | GCACCAAGCTGGAGCTGAAGGGCGGCGGCGGCAGCGGCGGCGGCGGCA GCGGCGGCGGCGGCAGCCAGGTGC | SEQ ID NO. 139 |
| pcDNA3.1-4-1BB-R | CTGATCAGCGGTTTAAACTTAAGCTTTCAGCGCTTGATCTCCACCTTG GTG | SEQ ID NO. 140 |
| CD3-IgD-F | GCACCAAGCTGGAGCTGAAGGCCAGCAAGAGCAAGAAGGAG | SEQ ID NO. 141 |
| IgD-R | CACGCCCAGGGGCTGGGTGTG | SEQ ID NO. 142 |
| IgD-4-1BB-F | CACACCCAGCCCCTGGGCGTGCAGGTGCAGCTGCAGCAGTGG | SEQ ID NO. 143 |

Embodiment 2-2: The Expression and Purification of CD19-CD3-4-1BB TsAb_M and CD19-CD3-4-1BB TsAb_D 1. The Expression of CD19-CD3-4-1BB TsAb_M and CD19-CD3-4-1BB TsAb_D 1.1 The cell density of CHO-S cells (purchased from Thermo Fisher Scientific) was $0.5\sim0.6\times10^6$/ml one day before transfection.

1.2 Calculating cell density at the day of transfection, plasmid transfection can be performed when the density is in the range of $1\sim1.4\times10^6$/ml and live percentage is >90%.

1.3 Transfection complex recipes: each project (CD19-CD3-4-1BB TsAb_M and CD19-CD3-4-1BB TsAb_D) requires two centrifuge tubes/flasks. Take total 20 ml as an example, the recombinant plasmids from Embodiment 1-1 were taken: Tube 1: 600 μl PBS, 20 μg recombinant plasmid, mix well; Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15~20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-4-1BB TsAb_M and CD19-CD3-4-1BB TsAb_D 2.1 Sample pretreatment Taking 20 ml cell medium after transfection, adding 20 mM PB, 200 mM NaCl, and adjusting pH to 7.5;

2.2 Purification of Protein L affinity chromatography column Protein purification chromatography column: Protein L affinity chromatography column (purchased from GE Healthcare, column volume: 1.0 ml) Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-4-1BB TsAb_M and CD19-CD3-4-1BB TsAb_D recombinant protein was analyzed by SDS-PAGE, and the protein electrophoresis data under reduced and unreduced conditions were shown as FIG. 2-2. It shows that both purity of CD19-CD3-4-1BB TsAb_M and CD19-CD3-4-1BB TsAb_D recombinant protein are >95%. The theoretical molecule weight for CD19-CD3-4-1BB TsAb_M is 80.6 kDa, and protein displayed the same single band under reduced and unreduced conditions. The molecule weight of these bands is consistent with monomer, so this tri-specific antibody is monomer (FIG. 2-2A, Lane 1: protein marker for molecule weight; Lane 2: reduced CD19-CD3-4-1BB TsAb_M; Lane 3: unreduced CD19-CD3-4-1BB TsAb_M. B). The theoretical molecule weight for CD19-CD3-4-1BB TsAb_D is 88.4 kDa, and protein displayed the same molecular weight as monomer under reduced condition, but the molecular weight is consistent with dimer under unreduced condition (~180 kDa)(FIG. 2-2B, Lane 1: protein marker for molecule weight; Lane 2: reduced CD19-CD3-4-1BB TsAb_D; Lane 3: unreduced CD19-CD3-4-1BB TsAb_D), which indicate two protein link to each other by disulfide bond formed through IgD hinge region so that this tri-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-4-1BB TsAb_M is monomer and CD19-CD3-4-1BB TsAb_D is dimer.

Therefore, the amino acid sequence of CD19-CD3-4-1BB TsAb_M monomer is shown as SEQ ID NO. 59.

The amino acid sequence of CD19-CD3-4-1BB TsAb_D dimer is shown as SEQ ID NO. 61.

The amino acid sequence of anti-CD19 scFv is shown as SEQ ID NO. 83.

The amino acid sequence of anti-CD19 scFv heavy chain variable region is shown as SEQ ID NO. 84.

The amino acid sequence of anti-CD19 scFv light chain variable region is shown as SEQ ID NO. 85.

The amino acid sequence of anti-CD3 scFv is shown as SEQ ID NO. 86.

The amino acid sequence of anti-CD3 scFv heavy chain variable region is shown as SEQ ID NO. 87.

The amino acid sequence of anti-CD3 scFv light chain variable region is shown as SEQ ID NO. 88.

The amino acid sequence of anti-4-1BB scFv is shown as SEQ ID NO. 89.

The amino acid sequence of anti-4-1BB scFv heavy chain variable region is shown as SEQ ID NO. 90.

The amino acid sequence of anti-4-1BB scFv light chain variable region is shown as SEQ ID NO. 91.

The amino acid sequence of CD19-CD3-4-1BB TsAb_M monomer linker (Linker 1) is shown as SEQ ID NO. 44.

The amino acid sequence of CD19-CD3-4-1BB TsAb_M monomer linker (Linker 2) is shown as SEQ ID NO. 46.

The amino acid sequence of CD19-CD3-4-1BB TsAb_D dimer linker (Linker 1) is shown as SEQ ID NO. 48.

The amino acid sequence of CD19-CD3-4-1BB TsAb_D dimer linker is shown as SEQ ID NO. 50.

Embodiment 2-3: Antigen Binding Activity Test of CD19-CD3-4-1BB TsAb_M and CD19-CD3-4-1BB TsAb_D by ELISA ELISA procedure:

1. Recombinant antigen coating: 96-well plates were coated by human CD19-hFc, CD3-hFc and human 4-1BB-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific antibody samples respectively and keeping plates at 37° C. for 1 hour. Sample serial dilution includes: using 10 μg/ml purified CD19-CD3-4-1BB TsAb_M or CD19-CD3-4-1BB TsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5~10 min at room temperature.

5. Reaction termination and result test: adding 100 μl per well of 1M HCl to stop reaction, and reading OD value of 450 nm absorbance on ELISA reader.

The results of ELISA are shown in FIGS. 2-3A and 2-3B. The four curves in the figure represent three test results: ■ coated with 1 μg/ml CD19-hFc recombinant antigen, ✺ coated with 1 μg/ml CD3-hFc recombinant antigen; ▲ coated with 1 μg/ml 4-1BB-hFc recombinant antigen; ▽ no antigen coated result. FIG. 2-3A indicates that CD19-CD3-4-1BB TsAb_M has antigen binding activity with CD19-hFc, CD3-hFc and 4-1BB-hFc in vitro, among which 4-1BB has the highest binding activity, CD19 has the second highest binding activity, and CD3 has the weakest binding activity. FIG. 2-3B indicates that CD19-CD3-CD28 TsAb_D has antigen binding activity with CD19-hFc, CD3-hFc and CD28-hFc in vitro as well, among which 4-1BB has the highest binding activity, CD19 has the second highest binding activity, and CD3 has the weakest binding activity.

Embodiment 2-4: CD19-CD3-4-1BB Tri-Specific Antibody-Mediated Cell Killing Assay Human PBMC (Peripheral blood mononuclear cell, PBMC) was used as experiment material. The above-mentioned TiTE tri-specific antibody CD19-CD3-4-1BB TsAb_M in monomeric form, TiTE tri-specific antibody CD19-CD3-4-1BB TsAb_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Counting cells for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ (200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb, CD19-CD3-4-1BB TsAb_M and CD19-CD3-4-1BB TsAb_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{OD \text{ value of Raji cells} + OD \text{ value of } CIK \text{ cells} - \text{detected } OD \text{ value}}{OD \text{ value of Raji cells}} \times 100\%$$

The results are shown in FIG. 2-4: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-4-1BB TsAb_D have the best cell killing effect. The killing efficacy is about 96%, 96% and 92%. The effect of CD19-CD3-4-1BB TsAb_M is in the second place, the killing efficacy is about 92%, 90% and 86%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-4-1BB TsAb_D and CD19-CD3-4-1BB TsAb_M against Raji cells is improved to some extent, and the killing efficacy is about 87% and 80%, respectively. While CD19-CD3 BsAb had no effect compared with the blank control. The above results indicated that the two forms of CD19-CD3-4-1BB TiTE tri-specific antibody-mediated T cell-targeted killing activity against CD19-positive tumor cells were superior to that of BiTE bispecific antibody. The dimeric form has a better effect than the monomer form.

Embodiment 2-5 the Eukaryotic Expression Vector Construction of CD19-CD3-ICOS TsAb_M and CD19-CD3-ICOS TsAb_D In the present disclosure, a TiTE tri-specific antibody targeting human CD19 protein on the surface of lymphoma B cells, T cell surface human CD3 and T cell positive costimulatory molecule ICOS protein is named as CD19-CD3-ICOS TsAb.

1. Construction Design of CD19-CD3-ICOS TsAb_M and CD19-CD3-ICOS TsAb_D

Construction design of CD19-CD3-ICOS TsAb_M Monomer:

The sequences of the anti-CD19 scFv, anti-CD3 scFv and anti-ICOS scFv are linked by a linker. Specifically, the sequence of anti-CD19 scFv and the anti-CD3 scFv are linked by Linker 1, the sequence of anti-CD3 scFv and anti-ICOS scFv are linked by Linker 2.

Construction design of CD19-CD3-ICOS TsAb_D Dimer:

The sequences of the anti-CD19 scFv, anti-CD3 scFv and anti-ICOS scFv are linked by linkers. Specifically, the sequences of anti-CD19 scFv and anti-CD3 scFv are linked by Linker 1, the sequences of anti-CD3 scFv and anti-ICOS scFv are linked by IgD hinge region (Ala90-Val170) as Linker 2.

In order to express the tri-specific antibody in mammalian cells, codon optimization of mammalian system was performed for the sequence of anti-CD19 scFv, anti-CD3 scFv, and anti-ICOS scFv.

The nucleotide sequence of anti-CD19 scFv heavy chain variable region is shown as SEQ ID NO. 108.

The nucleotide sequence of anti-CD19 scFv light chain variable region is shown as SEQ ID NO. 109.

The nucleotide sequence of anti-CD19 scFv is shown as SEQ ID NO. 107.

The nucleotide sequence of anti-CD3 scFv heavy chain variable region is shown as SEQ ID NO. 111.

The nucleotide sequence of anti-CD3 scFv light chain variable region is shown as SEQ ID NO. 112.

The nucleotide sequence of anti-CD3 scFv is shown as SEQ ID NO. 110.

The nucleotide sequence of anti-ICOS scFv heavy chain variable region is shown as SEQ ID NO. 117.

The nucleotide sequence of anti-ICOS scFv light chain variable region is shown as SEQ ID NO. 118.

The nucleotide sequence of anti-ICOS scFv is shown as SEQ ID NO. 116.

The nucleotide sequence of CD19-CD3-ICOS TsAb_M monomer linker (Linker 1) is shown as SEQ ID NO. 45.

The nucleotide sequence of CD19-CD3-ICOS TsAb_M monomer linker (Linker 2) is shown as SEQ ID NO. 47.

The nucleotide sequence of CD19-CD3-ICOS TsAb_D dimer linker (Linker 1) is shown as SEQ ID NO. 49.

The nucleotide sequence of CD19-CD3-ICOS TsAb_D dimer linker (Linker 2) is shown as SEQ ID NO. 51.

IgD-F and IgD-R, and IgD-ICOS-F and pcDNA3.1-ICOS-R, respectively. After PCR amplification, by using NovoRec® PCR One-Step Cloning Kit (purchased from Wujiang Novoprotein Technology Co., Ltd.), the full length of tri-specific antibody monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-ICOS TsAb_M monomer and CD19-CD3-ICOS TsAb_D dimer both had the right full DNA sequence as expected.

The nucleotide sequence of CD19-CD3-ICOS TsAb_M monomer is shown as SEQ ID NO. 64.

The nucleotide sequence of CD19-CD3-ICOS TsAb_D dimer is shown as SEQ ID NO. 66.

TABLE 2-2

Primers used in CD19-CD3-ICOS tri-specific antibody gene cloning

| Primer name | Sequence | No. |
|---|---|---|
| CD3-(GGGGS)$_3$-ICOS-F | GCACCAAGCTGGAGCTGAAGGGCGGCGGCGGCAGCGGCGG CGGCGGCAGCGGCGGCGGCGGCAGCCAGGTGCAGCTGGTG CAGAGC | SEQ ID NO. 144 |
| pcDNA3.1-ICOS-R | CTGATCAGCGGTTTAAACTTAAGCTTTCACTTGATCTCCA CCTTGGTGCC | SEQ ID NO. 145 |
| IgD-ICOS-F | CACACCCAGCCCCTGGGCGTGCAGGTGCAGCTGGTGCAGA GC | SEQ ID NO. 146 |

In order to express tri-specific antibody successfully in CHO-S cells and secret into medium, signal peptide of antibody secretory expression was selected in this Embodiment.

The amino acid sequence of this secretory signal peptide is shown as SEQ ID NO. 131.

The nucleotide sequence of this secretory signal peptide is shown as SEQ ID NO. 132.

2. CD19-CD3-ICOS TsAb_M and CD19-CD3-ICOS TsAb_D Eukaryotic Expression Vector Construction The construction and expression of this tri-specific antibody in the present disclosure selected mammalian cell protein transient expression vector pcDNA3.1 (purchased from Invitrogen, Shanghai). In order to construct the tri-specific antibody in monomer and dimer form, primers were designed as in table 2-2. All the primers were synthesized by Genewiz, Suzhou, and DNA template for PCR was synthesized by Synbio Technologies, Suzhou.

The cloning construct for CD19-CD3-ICOS TsAb_M includes: amplifying signal peptide by primers pcDNA3.1-Sig-F and Sig-R, and then amplifying anti-CD19 scFv, GGGGS Linker 1+anti-CD3 scFv, and (GGGGS)$_3$ Linker 2+anti-ICOS scFv sequence by primer pairs Sig-CD19-F and CD19-R, CD19-G4S-CD3-F and CD3-R, and CD3-(GGGGS)3-ICOS-F and pcDNA3.1-ICOS-R, respectively. The cloning construct for CD19-CD3-ICOS TsAb_D includes: amplifying signal peptide by primers pcDNA3.1-Sig-F and Sig-R, and then amplifying anti-CD19 scFv, GGGGS Linker 1+anti-CD3 scFv, and IgD hinge region Linker2+anti-ICOS scFv sequence by primer pairs Sig-CD19-F and CD19-R, CD19-G4S-CD3-F and CD3-R, CD3-

Embodiment 2-6: The Expression and Purification of CD19-CD3-ICOS TsAb_M and CD19-CD3-ICOS TsAB_D 1. The Expression of CD19-CD3-ICOS TsAb_M and CD19-CD3-ICOS TsAb_D 1.1 The cell density of CHO-S cells (purchased from Thermo Fisher Scientific) was 0.5~0.6×$10^6$/ml one day before transfection.

1.2 Calculating cell density at the day of transfection, plasmid transfection can be performed when the density is in the range of 1-1.4×$10^6$/ml and live percentage is >90%.

1.3 Transfection complex recipes: each project (CD19-CD3-ICOS TsAb_M and CD19-CD3-ICOS TsAb_D) requires two centrifuge tubes/flasks. Take total 20 ml as an example, the recombinant plasmids from Embodiment 2-5 were taken: Tube 1: 600 μl PBS, 20 μg recombinant plasmid, mix well.

Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15-20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-ICOS TsAb_M and CD19-CD3-ICOS TsAb_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4

Buffer B:0.1M Glycine, pH3.0

Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-ICOS TsAb_M and CD19-CD3-ICOS TsAb_D recombinant protein was analyzed by SDS-PAGE, and the protein electrophoresis data under reduced and unreduced conditions were shown as FIG. 2-5. It shows that both purity of CD19-CD3-ICOS TsAb_M and CD19-CD3-ICOS TsAb_D recombinant protein are >95%. The theoretical molecule weight for CD19-CD3-ICOS TsAb_M is 80.7 kDa, and protein displayed the same single band under reduced and unreduced conditions. The molecule weight of these bands is consistent with monomer, so this tri-specific antibody is monomer (FIG. 2-5A, Lane 1: protein marker for molecule weight; Lane 2: reduced CD19-CD3-ICOS TsAb_M; Lane 3: unreduced CD19-CD3-ICOS TsAb_M. B.). The theoretical molecule weight for CD19-CD3-ICOS TsAb_D is 88.6 kDa, and protein displayed the same molecular weight as monomer under reduced condition, but the molecular weight is consistent with dimer under unreduced condition (~180 kDa) (FIG. 2-5B, Lane 1: protein marker for molecule weight; Lane 2: reduced CD19-CD3-ICOS TsAb_D; Lane 3: unreduced CD19-CD3-ICOS TsAb_D), which indicate two protein link to each other by disulfide bond formed through IgD hinge region so that this tri-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-ICOS TsAb_M is monomer and CD19-CD3-ICOS TsAb_D is dimer.

Therefore, the amino acid sequence of CD19-CD3-ICOS TsAb_M monomer is shown as SEQ ID NO. 63.

The amino acid sequence of CD19-CD3-ICOS TsAb_D dimer is shown as SEQ ID NO. 65.

The amino acid sequence of CD19 scFv is shown as SEQ ID NO. 83.

The amino acid sequence of CD19 scFv heavy chain variable region is shown as SEQ ID NO. 84.

The amino acid sequence of CD19 scFv light chain variable region is shown as SEQ ID NO. 85.

The amino acid sequence of CD3 scFv is shown as SEQ ID NO. 86.

The amino acid sequence of CD3 scFv heavy chain variable region is shown as SEQ ID NO. 87.

The amino acid sequence of CD3 scFv light chain variable region is shown as SEQ ID NO. 88.

The amino acid sequence of ICOS scFv is shown as SEQ ID NO. 92.

The amino acid sequence of ICOS scFv heavy chain variable region is shown as SEQ ID NO. 93.

The amino acid sequence of ICOS scFv light chain variable region is shown as SEQ ID NO. 94.

The amino acid sequence of CD19-CD3-ICOS TsAb_M monomer linker (Linker 1) is shown as SEQ ID NO. 44.

The amino acid sequence of CD19-CD3-ICOS TsAb_M monomer linker (Linker 2) is shown as SEQ ID NO. 46.

The amino acid sequence of CD19-CD3-ICOS TsAb_D dimer linker (Linker 1) is shown as SEQ ID NO. 48.

The amino acid sequence of CD19-CD3-ICOS TsAb_D dimer linker (Linker 2) is shown as SEQ ID NO. 50.

Embodiment 2-7: Antigen Binding Activity Test of CD19-CD3-ICOS TsAb_M and CD19-CD3-ICOS TsAb_D by ELISA ELISA procedure:

1. Recombinant antigen coating: 96-well plates were coated by human CD19-hFc, CD3-hFc and human ICOS-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific antibody samples respectively and keeping plates at 37° C. for 1 hour. Sample serial dilution includes: using 10 μg/ml purified CD19-CD3-ICOS TsAb_M or CD19-CD3-ICOS TsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5-10 min at room temperature.

5. Reaction termination and result test: adding 100 μl per well of 1M HCl to stop reaction, and reading OD value of 450 nm absorbance on ELISA reader.

The results of ELISA are shown in FIGS. 2-6A and 2-6B. The four curves in the figure represent three test results: ■ coated with 1 μg/ml CD19-hFc recombinant antigen, ◆ coated with 1 μg/ml CD3-hFc recombinant antigen; ▲ coated with 1 μg/ml ICOS-hFc recombinant antigen; ▽ no antigen coated result. FIG. 2-6A indicates that CD19-CD3-ICOS TsAb_M has antigen binding activity with CD19-hFc, CD3-hFc and ICOS-hFc in vitro, among which ICOS has the highest binding activity, CD19 has the second highest binding activity, and CD3 has the weakest binding activity. FIG. 2-6B indicates that CD19-CD3-ICOS TsAb_D has antigen binding activity with CD19-hFc, CD3-hFc and ICOS-hFc in vitro as well, among which ICOS has the highest binding activity, CD19 has the second highest binding activity, and CD3 has the weakest binding activity.

Embodiment 2-8: CD19-CD3-ICOS Tri-Specific Antibody-Mediated Cell Killing Assay

Human PBMC (Peripheral blood mononuclear cell, PBMC) was used as experiment material. The above-mentioned TiTE tri-specific antibody CD19-CD3-ICOS TsAb_M in monomeric form, TiTE tri-specific antibody CD19-CD3-ICOS TsAb_D in dimeric form, and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Counting cells for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-ICOS TsAb_M and CD19-CD3-ICOS TsAb_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{OD \text{ value of Raji cells} + OD \text{ value of } CIK \text{ cells} - \text{detected } OD \text{ value}}{OD \text{ value of Raji cells}} \times 100\%$$

The results are shown in FIG. 2-7: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-ICOS TsAb_D have the best cell killing effect. The killing efficacy is about 94%, 94% and 82%. The effect of CD19-CD3-ICOS TsAb_M is in the second place, the killing efficacy is about 92%, 86% and 84%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-ICOS TsAb_D and CD19-CD3-ICOS TsAb_M against Raji cells is improved to some extent, and the killing efficacy is about 76% and 71%, respectively. While CD19-CD3 BsAb had no effect compared with the blank control. The above results indicated that the two forms of CD19-CD3-ICOS TiTE tri-specific antibody-mediated T cell-targeted killing activity against CD19-positive tumor cells were superior to that of BiTE bispecific antibody. The dimeric form has a better effect than the monomer form.

Embodiment 2-9 the Eukaryotic Expression Vector Construction of CD19-CD3-OX40 TsAb_M and CD19-CD3-OX40 TsAb_D In the present disclosure, a TiTE tri-specific antibody targeting human CD19 protein on the surface of lymphoma B cells, T cell surface human CD3 and T cell positive costimulatory molecule OX40 protein is named as CD19-CD3-OX40 TsAb.

1. Construction design of CD19-CD3-OX40 TsAb_M and CD19-CD3-OX40 TsAb_D

Construction design of CD19-CD3-OX40 TsAb_M Monomer:

The sequences of the anti-CD19 scFv, anti-CD3 scFv and anti-OX40 scFv are linked by a linker. Specifically, the sequence of anti-CD19 scFv and the anti-CD3 scFv are linked by Linker 1, the sequence of anti-CD3 scFv and anti-OX40 scFv are linked by Linker 2.

Construction design of CD19-CD3-OX40 TsAb_D Dimer:

The sequences of the anti-CD19 scFv, anti-CD3 scFv and anti-OX40 scFv are linked by linkers. Specifically, the sequences of anti-CD19 scFv and anti-CD3 scFv are linked by Linker 1, the sequences of anti-CD3 scFv and anti-OX40 scFv are linked by IgD hinge region (Ala90-Val170) as Linker 2.

In order to express the tri-specific antibody in mammalian cells, codon optimization of mammalian system was performed for the sequence of anti-CD19 scFv, anti-CD3 scFv, and anti-OX40 scFv.

The nucleotide sequence of anti-CD19 scFv heavy chain variable region is shown as SEQ ID NO. 108.

The nucleotide sequence of anti-CD19 scFv light chain variable region is shown as SEQ ID NO. 109.

The nucleotide sequence of anti-CD19 scFv is shown as SEQ ID NO. 107.

The nucleotide sequence of anti-CD3 scFv heavy chain variable region is shown as SEQ ID NO. 111.

The nucleotide sequence of anti-CD3 scFv light chain variable region is shown as SEQ ID NO. 112.

The nucleotide sequence of anti-CD3 scFv is shown as SEQ ID NO. 110.

The nucleotide sequence of anti-OX40 scFv heavy chain variable region is shown as SEQ ID NO. 120.

The nucleotide sequence of anti-OX40 scFv light chain variable region is shown as SEQ ID NO. 121.

The nucleotide sequence of anti-OX40 scFv is shown as SEQ ID NO. 119.

The nucleotide sequence of CD19-CD3-OX40 TsAb_M monomer linker (Linker 1) is shown as SEQ ID NO. 45.

The nucleotide sequence of CD19-CD3-OX40 TsAb_M monomer linker (Linker 2) is shown as SEQ ID NO. 47.

The nucleotide sequence of CD19-CD3-OX40 TsAb_D dimer linker (Linker 1) is shown as SEQ ID NO. 49.

The nucleotide sequence of CD19-CD3-OX40 TsAb_D dimer linker (Linker 2) is shown as SEQ ID NO. 51.

In order to express tri-specific antibody successfully in CHO-S cells and secret into medium, signal peptide of antibody secretory expression was selected in this Embodiment.

The amino acid sequence of this secretory signal peptide is shown as SEQ ID NO. 131.

The nucleotide sequence of this secretory signal peptide is shown as SEQ ID NO. 132.

2. CD19-CD3-OX40 TsAb_M and CD19-CD3-OX40 TsAb_D Eukaryotic Expression Vector Construction The construction and expression of this tri-specific antibody in the present disclosure selected mammalian cell protein transient expression vector pcDNA3.1 (purchased from Invitrogen, Shanghai). In order to construct the tri-specific antibody in monomer and dimer form, primers were designed as in table 2-2. All the primers were synthesized by Genewiz, Suzhou, and DNA template for PCR was synthesized by Synbio Technologies, Suzhou.

The cloning construct for CD19-CD3-OX40 TsAb_M includes: amplifying signal peptide by primers pcDNA3.1-Sig-F and Sig-R, and then amplifying anti-CD19 scFv, GGGGS Linker 1+anti-CD3 scFv, $(GGGGS)_3$ Linker 2+anti-OX40 scFv sequence by primer pairs Sig-CD19-F and CD19-R, CD19-G4S-CD3-F and CD3-R, and CD3-(GGGGS)3-OX40-F and pcDNA3.1-OX40-R, respectively. The cloning construct for CD19-CD3-OX40 TsAb_D includes: amplifying signal peptide by primers pcDNA3.1-Sig-F and Sig-R, and then amplifying anti-CD19 scFv, GGGGS Linker 1+anti-CD3 scFv, and IgD hinge region Linker2+anti-OX40 scFv sequence by primer pairs Sig-CD19-F and CD19-R, CD19-G4S-CD3-F and CD3-R, CD3-IgD-F and IgD-R, and IgD-OX40-F and pcDNA3.1-OX40-R, respectively. After PCR amplification, by using NovoRec® PCR One-Step Cloning Kit (purchased from Wujiang Novoprotein Technology Co., Ltd.), the full length of tri-specific antibody monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-OX40 TsAb_M monomer and CD19-CD3-OX40 TsAb_D dimer both had the right full DNA sequence as expected.

The nucleotide sequence of CD19-CD3-OX40 TsAb_M monomer is shown as SEQ ID NO. 68.

The nucleotide sequence of CD19-CD3-OX40 TsAb_D dimer is shown as SEQ ID NO. 70.

TABLE 2-3

Primers used in CD19-CD3-OX40 tri-specific antibody gene cloning

| Primer name | Sequence | No. |
|---|---|---|
| CD3-$(GGGGS)_3$-OX40-F | GCACCAAGCTGGAGCTGAAGGGCGGCGGCGGCAGCGGCGGCGGCGGCAGCGGCGGCGGCGGCAGCCAGCTGGTGGAGAGCGGCGG | SEQ ID NO. 147 |
| pcDNA3.1-OX40-R | CTGATCAGCGGTTTAAACTTAAGCTTTCACTTGATCTCCACCTTGGTGCC | SEQ ID NO. 148 |
| IgD-OX40-F | GCCACACCCAGCCCCTGGGCGTGCAGCTGGTGGAGAGCGGCGGCG | SEQ ID NO. 149 |

Embodiment 2-10: The Expression and Purification of CD19-CD3-OX40 TsAb_M and CD19-CD3-OX40 TsAB_D 1. The Expression of CD19-CD3-OX40 TsAb_M and CD19-CD3-OX40 TsAb_D 1.1 The cell density of CHO-S cells (purchased from Thermo Fisher Scientific) was 0.5~$0.6\times10^6$/ml one day before transfection.

1.2 Calculating cell density at the day of transfection, plasmid transfection can be performed when the density is in the range of 1~$1.4\times10^6$/ml and live percentage is >90%.

1.3 Transfection complex recipes: each project (CD19-CD3-OX40 TsAb_M and CD19-CD3-OX40 TsAb_D) requires two centrifuge tubes/flasks. Take total 20 ml as an example, the recombinant plasmids from Embodiment 2-9 were taken:

Tube 1: 600 μl PBS, 20 μg recombinant plasmid, mix well.
Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15-20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-OX40 TsAb_M and CD19-CD3-OX40 TsAb_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml) Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-OX40 TsAb_M and CD19-CD3-OX40 TsAb_D recombinant protein was analyzed by SDS-PAGE, and the protein electrophoresis data under reduced and unreduced conditions were shown as FIG. 2-8. It shows that both purity of CD19-CD3-OX40 TsAb_M and CD19-CD3-OX40 TsAb_D recombinant protein are >95%. The theoretical molecule weight for CD19-CD3-OX40 TsAb_M is 80.1 kDa, and protein displayed the same single band under reduced and unreduced conditions. The molecule weight of these bands is consistent with monomer, so this tri-specific antibody is monomer (FIG. 2-8A, Lane 1: protein marker for molecule weight; Lane 2: reduced CD19-CD3-OX40 TsAb_M; Lane 3: unreduced CD19-CD3-OX40 TsAb_M. B). The theoretical molecule weight for CD19-CD3-OX40 TsAb_D is 88.0 kDa, and protein displayed the same molecular weight as monomer under reduced condition, but the molecular weight is consistent with dimer under unreduced condition (~180 kDa) (FIG. 2-8B, Lane 1: protein marker for molecule weight; Lane 2: reduced CD19-CD3-OX40 TsAb_D; Lane 3: unreduced CD19-CD3-OX40 TsAb_D), which indicate two protein link to each other by disulfide bond formed through IgD hinge region so that this tri-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-OX40 TsAb_M is monomer and CD19-CD3-OX40 TsAb_D is dimer.

Therefore, the amino acid sequence of CD19-CD3-OX40 TsAb_M monomer is shown as SEQ ID NO. 67.

The amino acid sequence of CD19-CD3-OX40 TsAb_D dimer is shown as SEQ ID NO. 69.

The amino acid sequence of CD19 scFv is shown as SEQ ID NO. 83.

The amino acid sequence of CD19 scFv heavy chain variable region is shown as SEQ ID NO. 84.

The amino acid sequence of CD19 scFv light chain variable region is shown as SEQ ID NO. 85.

The amino acid sequence of CD3 scFv is shown as SEQ ID NO. 86.

The amino acid sequence of CD3 scFv heavy chain variable region is shown as SEQ ID NO. 87.

The amino acid sequence of CD3 scFv light chain variable region is shown as SEQ ID NO. 88.

The amino acid sequence of OX40 scFv is shown as SEQ ID NO. 95.

The amino acid sequence of OX40 scFv heavy chain variable region is shown as SEQ ID NO. 96.

The amino acid sequence of OX40 scFv light chain variable region is shown as SEQ ID NO. 97.

The amino acid sequence of CD19-CD3-OX40 TsAb_M monomer linker (Linker 1) is shown as SEQ ID NO. 44.

The amino acid sequence of CD19-CD3-OX40 TsAb_M monomer linker (Linker 2) is shown as SEQ ID NO. 46.

The amino acid sequence of CD19-CD3-OX40 TsAb_D dimer linker (Linker 1) is shown as SEQ ID NO. 48.

The amino acid sequence of CD19-CD3-OX40 TsAb_D dimer linker (Linker 2) is shown as SEQ ID NO. 50.

Embodiment 2-11: Antigen Binding Activity Test of CD19-CD3-OX40 TsAb_M and CD19-CD3-OX40 TsAb_D by ELISA ELISA procedure:

1. Recombinant antigen coating: 96-well plates were coated by human CD19-hFc, CD3-hFc and human OX40-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific antibody samples respectively and keeping plates at 37° C. for 1 hour. Sample serial dilution includes: using 10 μg/ml purified CD19-CD3-OX40 TsAb_M or CD19-CD3-OX40 TsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5-10 min at room temperature.

5. Reaction termination and result test: adding 100 μl per well of 1M HCl to stop reaction, and reading OD value of 450 nm absorbance on ELISA reader.

The results of ELISA are shown in FIGS. 2-9A and 2-9B. The four curves in the figure represent three four results: ■ coated with 1 μg/ml CD19-hFc recombinant antigen, ◆ coated with 1 μg/ml CD3-hFc recombinant antigen; ▲ coated with 1 μg/ml OX40-hFc recombinant antigen; ▼ no antigen coated result. FIG. 2-9A indicates that CD19-CD3-OX40 TsAb_M has antigen binding activity with CD19-hFc, CD3-hFc and OX40-hFc in vitro, among which CD19 has the highest binding activity, OX40 has the second highest binding activity, and CD3 has the weakest binding activity. FIG. 2-9B indicates that CD19-CD3-OX40 TsAb_D has antigen binding activity with CD19-hFc, CD3-hFc and OX40-hFc in vitro as well, among which CD19 has the highest binding activity, OX40 has the second highest binding activity, and CD3 has the weakest binding activity.

Embodiment 2-12: CD19-CD3-OX40 Tri-Specific Antibody-Mediated Cell Killing Assay Human PBMC (Peripheral blood mononuclear cell, PBMC) was used as experiment material. The above-mentioned TiTE tri-specific antibody CD19-CD3-OX40 TsAb_M in monomeric form, TiTE tri-specific antibody CD19-CD3-OX40 TsAb_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Counting cells for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ (200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-OX40 TsAb_M and CD19-CD3-OX40 TsAb_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{OD \text{ value of } Raji \text{ cells} + OD \text{ value of } CIK \text{ cells} - \text{detected } OD \text{ value}}{OD \text{ value of } Raji \text{ cells}} \times 100\%$$

The results are shown in FIG. 2-10: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-OX40 TsAb_D have the best cell killing effect. The killing efficacy is about 96%, 92% and 86%. The effect of CD19-CD3-OX40 TsAb_M is in the second place, the killing efficacy is about 89%, 82% and 80%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-OX40 TsAb_D and CD19-CD3-OX40 TsAb_M against Raji cells is improved to some extent, and the killing efficacy is about 72% and 68%, respectively. While CD19-CD3 BsAb had no effect compared with the blank control. The above results indicated that the two forms of CD19-CD3-OX40 TiTE tri-specific antibody-mediated T cell-targeted killing activity against CD19-positive tumor cells were superior to that of BiTE bispecific antibody. The dimeric form has a better effect than the monomer form.

Embodiment 2-13 the Eukaryotic Expression Vector Construction of CD19-CD3-GITR TsAb_M and CD19-CD3-GITR TsAb_D In the present disclosure, a TiTE tri-specific antibody targeting human CD19 protein on the surface of lymphoma B cells, T cell surface human CD3 and T cell positive costimulatory molecule GITR protein is named as CD19-CD3-GITR TsAb.

1. CD19-CD3-GITR TsAb_M and CD19-CD3-GITR TsAb_D

Construction design of CD19-CD3-GITR TsAb_M Monomer construction design:

The sequences of the anti-CD19 scFv, anti-CD3 scFv and anti-GITR scFv are linked by a linker. Specifically, the sequence of anti-CD19 scFv and the anti-CD3 scFv are linked by Linker 1, the sequence of anti-CD3 scFv and anti-GITR scFv are linked by Linker 2.

Construction design of CD19-CD3-GITR TsAb_D Dimer:

The sequences of the anti-CD19 scFv, anti-CD3 scFv and anti-GITR scFv are linked by linkers. Specifically, the sequences of anti-CD19 scFv and anti-CD3 scFv are linked by Linker 1, the sequences of anti-CD3 scFv and anti-GITR scFv are linked by IgD hinge region (Ala90-Val170) as Linker 2.

In order to express the tri-specific antibody in mammalian cells, codon optimization of mammalian system was performed for the sequence of anti-CD19 scFv, anti-CD3 scFv, and anti-GITR scFv.

The nucleotide sequence of anti-CD19 scFv heavy chain variable region is shown as SEQ ID NO. 108.

The nucleotide sequence of anti-CD19 scFv light chain variable region is shown as SEQ ID NO. 109.

The nucleotide sequence of anti-CD19 scFv is shown as SEQ ID NO. 107.

The nucleotide sequence of anti-CD3 scFv heavy chain variable region is shown as SEQ ID NO. 111.

The nucleotide sequence of anti-CD3 scFv light chain variable region is shown as SEQ ID NO. 112.

The nucleotide sequence of anti-CD3 scFv is shown as SEQ ID NO. 110.

The nucleotide sequence of anti-GITR scFv heavy chain variable region is shown as SEQ ID NO. 123.

The nucleotide sequence of anti-GITR scFv light chain variable region is shown as SEQ ID NO. 124.

The nucleotide sequence of anti-GITR scFv is shown as SEQ ID NO. 122.

The nucleotide sequence of CD19-CD3-GITR TsAb_M monomer linker (Linker 1) is shown as SEQ ID NO. 45.

The nucleotide sequence of CD19-CD3-GITR TsAb_M monomer linker (Linker 2) is shown as SEQ ID NO. 47.

The nucleotide sequence of CD19-CD3-GITR TsAb_D dimer linker (Linker 1) is shown as SEQ ID NO. 49.

The nucleotide sequence of CD19-CD3-GITR TsAb_D dimer linker (Linker 2) is shown as SEQ ID NO. 51.

In order to express tri-specific antibody successfully in CHO-S cells and secret into medium, signal peptide of antibody secretory expression was selected in this Embodiment.

The amino acid sequence of this secretory signal peptide is shown as SEQ ID NO. 131.

The nucleotide sequence of this secretory signal peptide is shown as SEQ ID NO. 132.

2. CD19-CD3-GITR TsAb_M and CD19-CD3-GITR TsAb_D Eukaryotic Expression Vector Construction The construction and expression of this tri-specific antibody in the present disclosure selected mammalian cell protein transient expression vector pcDNA3.1 (purchased from Invitrogen, Shanghai). In order to construct the tri-specific antibody in monomer and dimer form, primers were designed as in table 2-4. All the primers were synthesized by Genewiz, Suzhou, and DNA template for PCR was synthesized by Synbio Technologies, Suzhou.

The cloning construct for CD19-CD3-GITR TsAb_M includes: amplifying signal peptide by primers pcDNA3.1-Sig-F and Sig-R, and then amplifying anti-CD19 scFv, GGGGS Linker 1+anti-CD3 scFv, $(GGGGS)_3$ Linker 2+anti-GITR scFv sequence by primer pairs Sig-CD19-F and CD19-R, CD19-G4S-CD3-F and CD3-R, and CD3-(GGGGS)3-GITR-F and pcDNA3.1-GITR-R, respectively. The cloning construct for CD19-CD3-GITR TsAb_D includes: amplifying signal peptide by primers pcDNA3.1-Sig-F and Sig-R, and then amplifying anti-CD19 scFv, GGGGS Linker 1+anti-CD3 scFv, and IgD hinge region Linker2+anti-GITR scFv sequence by primer pairs Sig-CD19-F and CD19-R, CD19-G4S-CD3-F and CD3-R, CD3-IgD-F and IgD-R, and IgD-GITR-F and pcDNA3.1-GITR-R, respectively. After PCR amplification, by using NovoRec® PCR One-Step Cloning Kit (purchased from Wujiang Novoprotein Technology Co., Ltd.), the full length of tri-specific antibody monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-GITR TsAb_M monomer and CD19-CD3-GITR TsAb_D dimer both had the right full DNA sequence as expected.

The nucleotide sequence of CD19-CD3-GITR TsAb_M monomer is shown as SEQ ID NO. 72.

The nucleotide sequence of CD19-CD3-GITR TsAb_D dimer is shown as SEQ ID NO. 74.

TABLE 2-4

Primers used in CD19-CD3-GITR tri-specific antibody gene cloning

| Primer name | Sequence | No. |
|---|---|---|
| CD3-$(GGGGS)_3$-GITR-F | GCACCAAGCTGGAGCTGAAGGGCGGCGGCGGCAGCGGCGGCGGCGGCAGCGGCGGCGGCGGCAGCCAGGTGACCCTGAAGGAGAG | SEQ ID NO. 150 |

TABLE 2-4-continued

Primers used in CD19-CD3-GITR tri-specific antibody gene cloning

| Primer name | Sequence | No. |
|---|---|---|
| pcDNA3.1-GITR-R | CTGATCAGCGGTTTAAACTTAAGCTTTCACTTGATCTCCAGCTTGGTGCCGG | SEQ ID NO. 151 |
| IgD-GITR-F | GCCACACCCAGCCCCTGGGCGTGCAGGTGACCCTGAAGGAGAG | SEQ ID NO. 152 |

Embodiment 2-14: The Expression and Purification of CD19-CD3-GITR TsAb_M and CD19-CD3-GITR TsAb_D 1. The Expression of CD19-CD3-GITR TsAb_M and CD19-CD3-GITR TsAb_D 1.1 The cell density of CHO-S cells (purchased from Thermo Fisher Scientific) was 0.5~0.6×$10^6$/ml one day before transfection.

1.2 Calculating cell density at the day of transfection, plasmid transfection can be performed when the density is in the range of 1~1.4×$10^6$/ml and live percentage is >90%.

1.3 Transfection complex recipes: each project (CD19-CD3-GITR TsAb_M and CD19-CD3-GITR TsAb_D) requires two centrifuge tubes/flasks. Take total 20 ml as an example, the recombinant plasmids from Embodiment 2-13 were taken:

Tube 1: 600p, 1 PBS, 20 μg recombinant plasmid, mix well;

Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15~20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-GITR TsAb_M and CD19-CD3-GITR TsAb_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-GITR TsAb_M and CD19-CD3-GITR TsAb_D recombinant protein was analyzed by SDS-PAGE, and the protein electrophoresis data under reduced and unreduced conditions were shown as FIG. 2-11. It shows that both purity of CD19-CD3-GITR TsAb_M and CD19-CD3-GITR TsAb_D recombinant protein are >95%. The theoretical molecule weight for CD19-CD3-GITR TsAb_M is 80.1 kDa, and protein displayed the same single band under reduced and unreduced conditions. The molecule weight of these bands is consistent with monomer, so this tri-specific antibody is monomer (FIG. 2-11A, Lane 1: protein marker for molecule weight; Lane 2: reduced CD19-CD3-GITR TsAb_M; Lane 3: unreduced CD19-CD3-GITR TsAb_M. B). The theoretical molecule weight for CD19-CD3-GITR TsAb_D is 88.0 kDa, and protein displayed the same molecular weight as monomer under reduced condition, but the molecular weight is consistent with dimer under unreduced condition (~180 kDa) (FIG. 2-11B, Lane 1: protein marker for molecule weight; Lane 2: reduced CD19-CD3-GITR TsAb_D; Lane 3: unreduced CD19-CD3-GITR TsAb_D), which indicate two protein link to each other by disulfide bond formed through IgD hinge region so that this tri-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-GITR TsAb_M is monomer and CD19-CD3-GITR TsAb_D is dimer.

Therefore, the amino acid sequence of CD19-CD3-GITR TsAb_M monomer is shown as SEQ ID NO. 71.

The amino acid sequence of CD19-CD3-GITR TsAb_D dimer is shown as SEQ ID NO. 73.

The amino acid sequence of CD19 scFv is shown as SEQ ID NO. 83.

The amino acid sequence of CD19 scFv heavy chain variable region is shown as SEQ ID NO. 84.

The amino acid sequence of CD19 scFv light chain variable region is shown as SEQ ID NO. 85.

The amino acid sequence of CD3 scFv is shown as SEQ ID NO. 86.

The amino acid sequence of CD3 scFv heavy chain variable region is shown as SEQ ID NO. 87.

The amino acid sequence of CD3 scFv light chain variable region is shown as SEQ ID NO. 88.

The amino acid sequence of GITR scFv is shown as SEQ ID NO. 98.

The amino acid sequence of GITR scFv heavy chain variable region is shown as SEQ ID NO. 99.

The amino acid sequence of GITR scFv light chain variable region is shown as SEQ ID NO. 100.

The amino acid sequence of CD19-CD3-GITR TsAb_M monomer linker (Linker 1) is shown as SEQ ID NO. 44.

The amino acid sequence of CD19-CD3-GITR TsAb_M monomer linker (Linker 2) is shown as SEQ ID NO. 46.

The amino acid sequence of CD19-CD3-GITR TsAb_D dimer linker (Linker 1) is shown as SEQ ID NO. 48.

The amino acid sequence of CD19-CD3-GITR TsAb_D dimer linker (Linker 2) is shown as SEQ ID NO. 50.

Embodiment 2-15: Antigen Binding Activity Test of CD19-CD3-GITR TsAb_M and CD19-CD3-GITR TsAb_D by ELISA ELISA procedure:

1. Recombinant antigen coating: 96-well plates were coated by human CD19-hFc, CD3-hFc and human GITR-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific antibody samples respectively and keeping plates at 37° C. for 1 hour. Sample serial dilution includes: using 10 μg/ml purified CD19-CD3-GITR TsAb_M or CD19-CD3-GITR TsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5~10 min at room temperature.

5. Reaction termination and result test: adding 100 μl per well of 1M HCl to stop reaction, and reading OD value of 450 nm absorbance on ELISA reader.

The results of ELISA are shown in FIGS. 2-12A and 2-12B. The four curves in the figure represent three four results: ■ coated with 1 μg/ml CD19-hFc recombinant antigen, ● coated with 1 μg/ml CD3-hFc recombinant antigen; ▲ coated with 1 μg/ml GITR-hFc recombinant antigen; ▼ no antigen coated result. FIG. 2-12A indicates that CD19-CD3-GITR TsAb_M has antigen binding activity with CD19-hFc, CD3-hFc and GITR-hFc in vitro, among which GITR and CD19 have higher binding activity, and CD3 has weaker binding activity. FIG. 2-12B indicates that CD19-CD3-GITR TsAb_D has antigen binding activity with CD19-hFc, CD3-hFc and GITR-hFc in vitro as well, among which GITR and CD19 has higher binding activity, and CD3 has weaker binding activity.

Embodiment 2-16: CD19-CD3-GITR Tri-Specific Antibody-Mediated Cell Killing Assay Human PBMC (Peripheral blood mononuclear cell, PBMC) was used as experiment material. The above-mentioned TiTE tri-specific antibody CD19-CD3-GITR TsAb_M in monomeric form, TiTE tri-specific antibody CD19-CD3-GITR TsAb_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Counting cells for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-GITR TsAb_M and CD19-CD3-GITR TsAb_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{OD \text{ value of } Raji \text{ cells} + OD \text{ value of } CIK \text{ cells} - \text{detected } OD \text{ value}}{OD \text{ value of } Raji \text{ cells}} \times 100\%$$

The results are shown in FIG. 2-13: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-GITR TsAb_D have the best cell killing effect. The killing efficacy is about 93%, 77% and 73%. The effect of CD19-CD3-GITR TsAb_M is in the second place, the killing efficacy is about 88%, 83% and 66%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-GITR TsAb_D and CD19-CD3-GITR TsAb_M against Raji cells is improved to some extent, and the killing efficacy is about 57% and 49%, respectively. While CD19-CD3 BsAb had no effect compared with the blank control. The above results indicated that the two forms of CD19-CD3-GITR TiTE tri-specific antibody-mediated T cell-targeted killing activity against CD19-positive tumor cells were superior to that of BiTE bispecific antibody. The dimeric form has a better effect than the monomer form.

Embodiment 2-17 the Eukaryotic Expression Vector Construction of CD19-CD3-CD40L TsAb_M and CD19-CD3-CD40L TsAb_D In the present disclosure, a TiTE tri-specific antibody targeting human CD19 protein on the surface of lymphoma B cells, T cell surface human CD3 and T cell positive costimulatory molecule CD40L protein is named as CD19-CD3-CD40L TsAb.

1. Construction Design of CD19-CD3-CD40L TsAb_M and CD19-CD3-CD40L TsAb_D

Construction design of CD19-CD3-CD40L TsAb_M Monomer:

The sequences of the anti-CD19 scFv, anti-CD3 scFv and anti-CD40L scFv are linked by a linker. Specifically, the sequence of anti-CD19 scFv and the anti-CD3 scFv are linked by Linker 1, the sequence of anti-CD3 scFv and anti-CD40L scFv are linked by Linker 2.

Construction design of CD19-CD3-CD40L TsAb_D Dimer:

The sequences of the anti-CD19 scFv, anti-CD3 scFv and anti-CD40L scFv are linked by linkers. Specifically, the sequences of anti-CD19 scFv and anti-CD3 scFv are linked by Linker 1, the sequences of anti-CD3 scFv and anti-CD40L scFv are linked by IgD hinge region (Ala90-Val170) as Linker 2.

In order to express the tri-specific antibody in mammalian cells, codon optimization of mammalian system was performed for the sequence of anti-CD19 scFv, anti-CD3 scFv, and anti-CD40L scFv.

The nucleotide sequence of anti-CD19 scFv heavy chain variable region is shown as SEQ ID NO. 108.

The nucleotide sequence of anti-CD19 scFv light chain variable region is shown as SEQ ID NO. 109.

The nucleotide sequence of anti-CD19 scFv is shown as SEQ ID NO. 107.

The nucleotide sequence of anti-CD3 scFv heavy chain variable region is shown as SEQ ID NO. 111.

The nucleotide sequence of anti-CD3 scFv light chain variable region is shown as SEQ ID NO. 112.

The nucleotide sequence of anti-CD3 scFv is shown as SEQ ID NO. 110.

The nucleotide sequence of anti-CD40L scFv heavy chain variable region is shown as SEQ ID NO. 126.

The nucleotide sequence of anti-CD40L scFv light chain variable region is shown as SEQ ID NO. 127.

The nucleotide sequence of anti-CD40L scFv is shown as SEQ ID NO. 125.

The nucleotide sequence of CD19-CD3-CD40L TsAb_M monomer linker (Linker 1) is shown as SEQ ID NO. 45.

The nucleotide sequence of CD19-CD3-CD40L TsAb_M monomer linker (Linker 2) is shown as SEQ ID NO. 47.

The nucleotide sequence of CD19-CD3-CD40L TsAb_D dimer linker (Linker 1) is shown as SEQ ID NO. 49.

The nucleotide sequence of CD19-CD3-CD40L TsAb_D dimer linker (Linker 2) is shown as SEQ ID NO. 51.

In order to express tri-specific antibody successfully in CHO-S cells and secret into medium, signal peptide of antibody secretory expression was selected in this Embodiment.

The amino acid sequence of this secretory signal peptide is shown as SEQ ID NO. 131.

The nucleotide sequence of this secretory signal peptide is shown as SEQ ID NO. 132.

2. CD19-CD3-CD40L TsAb_M and CD19-CD3-CD40L TsAb_D Eukaryotic Expression Vector Construction The construction and expression of this tri-specific antibody in the present disclosure selected mammalian cell protein transient expression vector pcDNA3.1 (purchased from Invitrogen, Shanghai). In order to construct the tri-specific antibody in monomer and dimer form, primers were designed as in table 2-5. All the primers were synthesized by Genewiz, Suzhou, and DNA template for PCR was synthesized by Synbio Technologies, Suzhou.

The cloning construct for CD19-CD3-CD40L TsAb_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+anti-CD40L scFv sequence by primer pairs Sig-CD19-F and CD19-R, CD19-G4S-CD3-F and CD3-R, and CD3-(GGGGS)3-CD40L-F and pcDNA3.1-CD40L-R, respectively. The cloning construct for CD19-CD3-CD40L TsAb_D includes: amplifying signal peptide by primers pcDNA3.1-Sig-F and Sig-R, and then amplifying anti-CD19 scFv, GGGGS Linker 1+anti-CD3 scFv, and IgD hinge region Linker2+anti-CD40L scFv sequence by primer pairs Sig-CD19-F and CD19-R, CD19-G4S-CD3-F and CD3-R, CD3-IgD-F and IgD-R, and IgD-CD40L-F and pcDNA3.1-CD40L-R, respectively. After PCR amplification, by using NovoRec® PCR One-Step Cloning Kit (purchased from Wujiang Novoprotein Technology Co., Ltd.), the full length of tri-specific antibody monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-CD40L TsAb_M monomer and CD19-CD3-CD40L TsAb_D dimer both had the right full DNA sequence as expected.

The nucleotide sequence of CD19-CD3-CD40L TsAb_M monomer is shown as SEQ ID NO. 76.

The nucleotide sequence of CD19-CD3-CD40L TsAb_D dimer is shown as SEQ ID NO. 78.

TABLE 2-5

Primers used in CD19-CD3-CD40L tri-specific antibody gene cloning

| Primer name | Sequence | No. |
|---|---|---|
| CD3-$(GGGGS)_3$-CD40L-F | GGCACCAAGCTGGAGCTGAAGGGCGGCGGCGGCAGCGGCGGCGGCGGCAGCGGCGGCGGCGGCAGCGAGGTGCAGCTGCTGGAGAGC | SEQ ID NO. 153 |
| pcDNA3.1-CD40L-R | CTGATCAGCGGTTTAAACTTAAGCTTTCAGCGCTTGATCTCCACCTTGGTG | SEQ ID NO. 154 |
| IgD-CD40L-F | GCCACACCCAGCCCCTGGGCGTGGAGGTGCAGCTGCTGGAGAG | SEQ ID NO. 155 |

Embodiment 2-18: The Expression and Purification of CD19-CD3-CD40L TsAb_M and CD19-CD3-CD40L TsAb_D 1. The Expression of CD19-CD3-CD40L TsAb_M and CD19-CD3-CD40L TsAb_D 1.1 The cell density of CHO-S cells (purchased from Thermo Fisher Scientific) was 0.5~0.6×$10^6$/ml one day before transfection.

1.2 Calculating cell density at the day of transfection, plasmid transfection can be performed when the density is in the range of 1-1.4×$10^6$/ml and live percentage is >90%.

1.3 Transfection complex recipes: each project (CD19-CD3-CD40L TsAb_M and CD19-CD3-CD40L TsAb_D) requires two centrifuge tubes/flasks. Take total 20 ml as an example, the recombinant plasmids from Embodiment 2-17 were taken: Tube 1: 600 μl PBS, 20 μg recombinant plasmid, mix well; Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15-20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-CD40L TsAb_M and CD19-CD3-CD40L TsAb_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialysing the flowthrough sample into buffer PBS.

The final purified CD19-CD3-CD40L TsAb_M and CD19-CD3-CD40L TsAb_D recombinant protein was analyzed by SDS-PAGE, and the protein electrophoresis data under reduced and unreduced conditions were shown as FIG. 2-14. It shows that both purity of CD19-CD3-CD40L TsAb_M and CD19-CD3-CD40L TsAb_D recombinant protein are >95%. The theoretical molecule weight for CD19-CD3-CD40L TsAb_M is 79.2 kDa, and protein displayed the same single band under reduced and unreduced conditions. The molecule weight of these bands is consistent with monomer, so this tri-specific antibody is monomer (FIG. 2-14A, Lane 1: protein marker for molecule weight; Lane 2: reduced CD19-CD3-OX40L TsAb_M; Lane 3: unreduced CD19-CD3-OX40L TsAb_M). The theoretical molecule weight for CD19-CD3-CD40L TsAb_D is 87.1 kDa, and protein displayed the same molecular weight as monomer under reduced condition, but the molecular weight is consistent with dimer under unreduced condition (~180 kDa) (FIG. 2-14B, Lane 1: protein marker for molecule weight; Lane 2: reduced CD19-CD3-OX40L TsAb_D; Lane 3: unreduced CD19-CD3-OX40L TsAb_D), which indicate two protein link to each other by disulfide bond formed through IgD hinge region so that this tri-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-CD40L TsAb_M is monomer and CD19-CD3-CD40L TsAb_D is dimer.

Therefore, the amino acid sequence of CD19-CD3-CD40L TsAb_M monomer is shown as SEQ ID NO. 75.

The amino acid sequence of CD19-CD3-CD40L TsAb_D dimer is shown as SEQ ID NO. 77.

The amino acid sequence of CD19 scFv is shown as SEQ ID NO. 83.

The amino acid sequence of CD19 scFv heavy chain variable region is shown as SEQ ID NO. 84.

The amino acid sequence of CD19 scFv light chain variable region is shown as SEQ ID NO. 85.

The amino acid sequence of CD3 scFv is shown as SEQ ID NO. 86.

The amino acid sequence of CD3 scFv heavy chain variable region is shown as SEQ ID NO. 87.

The amino acid sequence of CD3 scFv light chain variable region is shown as SEQ ID NO. 88.

The amino acid sequence of CD40L scFv is shown as SEQ ID NO. 101.

The amino acid sequence of CD40L scFv heavy chain variable region is shown as SEQ ID NO. 102.

The amino acid sequence of CD40L scFv light chain variable region is shown as SEQ ID NO. 103.

The amino acid sequence of CD19-CD3-CD40L TsAb_M monomer linker (Linker 1) is shown as SEQ ID NO. 44.

The amino acid sequence of CD19-CD3-CD40L TsAb_M monomer linker (Linker 2) is shown as SEQ ID NO. 46.

The amino acid sequence of CD19-CD3-CD40L TsAb_D dimer linker (Linker 1) is shown as SEQ ID NO. 48.

The amino acid sequence of CD19-CD3-CD40L TsAb_D dimer linker (Linker 2) is shown as SEQ ID NO. 50.

Embodiment 2-19: Antigen Binding Activity Test of CD19-CD3-CD40L TsAb_M and CD19-CD3-CD40L TsAb_D by ELISA ELISA procedure:

1. Recombinant antigen coating: 96-well plates were coated by human CD19-hFc, CD3-hFc and human CD40L-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific antibody samples respectively and keeping plates at 37° C. for 1 hour. Sample serial dilution includes: using 10 μg/ml purified CD19-CD3-CD40L TsAb_M or CD19-CD3-CD40L TsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5~10 min at room temperature.

5. Reaction termination and result test: adding 100 μl per well of 1M HCl to stop reaction, and reading OD value of 450 nm absorbance on ELISA reader.

The results of ELISA are shown in FIGS. 2-15A and 2-15B. The four curves in the figure represent three four results: ■ coated with 1 μg/ml CD19-hFc recombinant antigen, ◈ coated with 1 μg/ml CD3-hFc recombinant antigen; ■ coated with 1 μg/ml OX40L-hFc recombinant antigen; ▼ no antigen coated result. FIG. 2-15A indicates that CD19-CD3-CD40L TsAb_M has antigen binding activity with CD19-hFc, CD3-hFc and CD40L-hFc in vitro, among which CD40L has the highest binding activity, CD19 has the second highest binding activity, and CD3 has the weakest binding activity. FIG. 2-15B indicates that CD19-CD3-CD40L TsAb_D has antigen binding activity with CD19-hFc, CD3-hFc and CD40L-hFc in vitro as well, among which CD40L has the highest binding activity, CD19 has the second highest binding activity, and CD3 has the weakest binding activity.

Embodiment 2-20: CD19-CD3-CD40L Tri-Specific Antibody-Mediated Cell Killing Assay Human PBMC (Peripheral blood mononuclear cell, PBMC) was used as experiment material. The above-mentioned TiTE tri-specific antibody CD19-CD3-CD40L TsAb_M in monomeric form, TiTE tri-specific antibody CD19-CD3-CD40L TsAb_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Count cell number and cells are ready for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-CD40L TsAb_M and CD19-CD3-CD40L TsAb_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{\begin{array}{c} OD \text{ value of } Raji \text{ cells} + \\ OD \text{ value of } CIK \text{ cells} - \text{detected } OD \text{ value} \end{array}}{OD \text{ value of } Raji \text{ cells}} \times 100\%$$

The results are shown in FIG. 2-16: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-CD40L TsAb_D have the best cell killing effect. The killing efficacy is about 94%, 90% and 82%. The effect of CD19-CD3-CD40L TsAb_M is in the second place, the killing efficacy is about 91%, 88% and 73%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-CD40L TsAb_D and CD19-CD3-CD40L TsAb_M against Raji cells is improved to some extent, and the killing efficacy is about 68% and 61%, respectively. While CD19-CD3 BsAb had no effect compared with the blank control. The above results indicated that the two forms of CD19-CD3-CD40L TiTE tri-specific antibody-mediated T cell-targeted killing activity against CD19-positive tumor cells were superior to that of BiTE bispecific antibody. The dimeric form has a better effect than the monomer form.

Embodiment 2-21 the Eukaryotic Expression Vector Construction of CD19-CD3-CD27 TsAb_M and CD19-CD3-CD27 TsAb_D In the present disclosure, a TiTE tri-specific antibody targeting human CD19 protein on the surface of lymphoma B cells, T cell surface human CD3 and T cell positive costimulatory molecule CD27 protein is named as CD19-CD3-CD27 TsAb.

1. Construction Design of CD19-CD3-CD27 TsAb_M and CD19-CD3-CD27 TsAb_D

Construction design of CD19-CD3-CD27 TsAb_M Monomer:

The sequences of the anti-CD19 scFv, anti-CD3 scFv and anti-CD27 scFv are linked by a linker. Specifically, the sequence of anti-CD19 scFv and the anti-CD3 scFv are linked by Linker 1, the sequence of anti-CD3 scFv and anti-CD27 scFv are linked by Linker 2.

Construction design of CD19-CD3-CD27 TsAb_D Dimer:

The sequences of the anti-CD19 scFv, anti-CD3 scFv and anti-CD27 scFv are linked by linkers. Specifically, the sequences of anti-CD19 scFv and anti-CD3 scFv are linked by Linker 1, the sequences of anti-CD3 scFv and anti-CD27 scFv are linked by IgD hinge region (Ala90-Val170) as Linker 2.

In order to express the tri-specific antibody in mammalian cells, codon optimization of mammalian system was performed for the sequence of anti-CD19 scFv, anti-CD3 scFv, and anti-CD27 scFv.

The nucleotide sequence of anti-CD19 scFv heavy chain variable region is shown as SEQ ID NO. 108.

The nucleotide sequence of anti-CD19 scFv light chain variable region is shown as SEQ ID NO. 109.

The nucleotide sequence of anti-CD19 scFv is shown as SEQ ID NO. 107.

The nucleotide sequence of anti-CD3 scFv heavy chain variable region is shown as SEQ ID NO. 111.

The nucleotide sequence of anti-CD3 scFv light chain variable region is shown as SEQ ID NO. 112.

The nucleotide sequence of anti-CD3 scFv is shown as SEQ ID NO. 110.

The nucleotide sequence of anti-CD27 scFv heavy chain variable region is shown as SEQ ID NO. 129.

The nucleotide sequence of anti-CD27 scFv light chain variable region is shown as SEQ ID NO. 130.

The nucleotide sequence of anti-CD27 scFv is shown as SEQ ID NO. 128.

The nucleotide sequence of CD19-CD3-CD27 TsAb_M monomer linker (Linker 1) is shown as SEQ ID NO. 45.

The nucleotide sequence of CD19-CD3-CD27 TsAb_M monomer linker (Linker 2) is shown as SEQ ID NO. 47.

The nucleotide sequence of CD19-CD3-CD27 TsAb_D dimer linker (Linker 1) is shown as SEQ ID NO. 49.

The nucleotide sequence of CD19-CD3-CD27 TsAb_D dimer linker (Linker 2) is shown as SEQ ID NO. 51.

In order to express tri-specific antibody successfully in CHO-S cells and secret into medium, signal peptide of antibody secretory expression was selected in this Embodiment.

The amino acid sequence of this secretory signal peptide is shown as SEQ ID NO. 131.

The nucleotide sequence of this secretory signal peptide is shown as SEQ ID NO. 132.

2. CD19-CD3-CD27 TsAb_M and CD19-CD3-CD27 TsAb_D Eukaryotic Expression Vector Construction The construction and expression of this tri-specific antibody in the present disclosure selected mammalian cell protein transient expression vector pcDNA3.1 (purchased from Invitrogen, Shanghai). In order to construct the tri-specific antibody in monomer and dimer form, primers were designed as in table 2-6. All the primers were synthesized by Genewiz, Suzhou, and DNA template for PCR was synthesized by Synbio Technologies, Suzhou.

The cloning construct for CD19-CD3-CD27 TsAb_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+anti-CD27 scFv sequence by primer pairs Sig-CD19-F+CD19-R, CD19-G4S-CD3-F+CD3-R, and CD3-$(GGGGS)_3$—CD27-F+pcDNA3.1-CD27-R, respectively. The cloning construct for CD19-CD3-CD27 TsAb_D includes: amplifying signal peptide by primers pcDNA3.1-Sig-F and Sig-R, and then amplifying anti-CD19 scFv, GGGGS Linker 1+anti-CD3 scFv, IgD hinge region Linker2, and anti-CD27 scFv sequence by primer pairs Sig-CD19-F+CD19-R, CD19-G4S-CD3-F+CD3-R, CD3-IgD-F+IgD-R, and IgD-CD27-F+pcDNA3.1-CD27-R, respectively. After PCR amplification, by using NovoRec® PCR One-Step Cloning Kit (purchased from Wujiang Novoprotein Technology Co., Ltd.), the full length of tri-specific antibody monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-CD27 TsAb_M monomer and CD19-CD3-CD27 TsAb_D dimer both had the right full DNA sequence as expected.

The nucleotide sequence of CD19-CD3-CD27 TsAb_M monomer is shown as SEQ ID NO. 80.

The nucleotide sequence of CD19-CD3-CD27 TsAb_D dimer is shown as SEQ ID NO. 82.

TABLE 2-6

Primers used in CD19-CD3-CD27 tri-specific antibody gene cloning

| Primer name | Sequence | No. |
|---|---|---|
| CD3-$(GGGGS)_3$-CD27-F | GCACCAAGCTGGAGCTGAAGGGCGGCGGCGGCAGCGGCGGCGGCGGCAGCGGCGGCGGCGGCAGCCAGGTGCAGCTGGTGGAGAGC | SEQ ID NO. 156 |
| pcDNA3.1-CD27-R | CTGATCAGCGGTTTAAACTTAAGCTTTCACTTGATCTCCACCTTGGTGCCC | SEQ ID NO. 157 |
| IgD-CD27-F | GCCACACCCAGCCCCTGGGCGTGCAGGTGCAGCTGGTGGAGAG | SEQ ID NO. 158 |

Embodiment 2-22: The Expression and Purification of CD19-CD3-CD27 TsAb_M and CD19-CD3-CD27 TsAb_D 1. The Expression of CD19-CD3-CD27 TsAb_M and CD19-CD3-CD27 TsAb_D 1.1 The cell density of CHO-S cells (purchased from Thermo Fisher Scientific) was 0.5~0.6×$10^6$/ml one day before transfection.

1.2 Calculating cell density at the day of transfection, plasmid transfection can be performed when the density is in the range of 1~1.4×$10^6$/ml and live percentage is >90%.

1.3 Transfection complex recipes: each project (CD19-CD3-CD27 TsAb_M and CD19-CD3-CD27 TsAb_D) requires two centrifuge tubes/flasks. Take total 20 ml as an example, the recombinant plasmids from Embodiment 2-21 were taken: Tube 1: 600 μl PBS, 20 μg recombinant plasmid, mix well; Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15-20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-CD27 TsAb_M and CD19-CD3-CD27 TsAb_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialysing the flowthrough sample into buffer PBS.

The final purified CD19-CD3-CD27 TsAb_M and CD19-CD3-CD27 TsAb_D recombinant protein was analyzed by SDS-PAGE, and the protein electrophoresis data under reduced and unreduced conditions were shown as FIG. 2-17. It shows that both purity of CD19-CD3-CD27 TsAb_M and CD19-CD3-CD27 TsAb_D recombinant protein are >95%. The theoretical molecule weight for CD19-CD3-CD27 TsAb_M is 80.1 kDa, and protein displayed the same single band under reduced and unreduced conditions. The molecule weight of these bands is consistent with monomer, so this tri-specific antibody is monomer (FIG. 2-17A, Lane 1: protein marker for molecule weight; Lane 2: reduced CD19-CD3-CD27 TsAb_M; Lane 3: unreduced CD19-CD3-CD27 TsAb_M). The theoretical molecule weight for CD19-CD3-CD27 TsAb_D is 88.0 kDa, and protein displayed the same molecular weight as monomer under reduced condition, but the molecular weight is consistent with dimer under unreduced condition (~180 kDa) (FIG. 2-17B, Lane 1: protein marker for molecule weight; Lane 2: reduced CD19-CD3-CD27 TsAb_D; Lane 3: unreduced CD19-CD3-CD27 TsAb_D), which indicate two protein link to each other by disulfide bond formed through IgD hinge region so that this tri-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-CD27 TsAb_M is monomer and CD19-CD3-CD27 TsAb_D is dimer.

Therefore, the amino acid sequence of CD19-CD3-CD27 TsAb_M monomer is shown as SEQ ID NO. 79.

The amino acid sequence of CD19-CD3-CD27 TsAb_D dimer is shown as SEQ ID NO. 81.

The amino acid sequence of CD19 scFv is shown as SEQ ID NO. 83.

The amino acid sequence of CD19 scFv heavy chain variable region is shown as SEQ ID NO. 84.

The amino acid sequence of CD19 scFv light chain variable region is shown as SEQ ID NO. 85.

The amino acid sequence of CD3 scFv is shown as SEQ ID NO. 86.

The amino acid sequence of CD3 scFv heavy chain variable region is shown as SEQ ID NO. 87.

The amino acid sequence of CD3 scFv light chain variable region is shown as SEQ ID NO. 88.

The amino acid sequence of CD27 scFv is shown as SEQ ID NO. 104.

The amino acid sequence of CD27 scFv heavy chain variable region is shown as SEQ ID NO. 105.

The amino acid sequence of CD27 scFv light chain variable region is shown as SEQ ID NO. 106.

The amino acid sequence of CD19-CD3-CD27 TsAb_M monomer linker (Linker 1) is shown as SEQ ID NO. 44.

The amino acid sequence of CD19-CD3-CD27 TsAb_M monomer linker (Linker 2) is shown as SEQ ID NO. 46.

The amino acid sequence of CD19-CD3-CD27 TsAb_D dimer linker (Linker 1) is shown as SEQ ID NO. 48.

The amino acid sequence of CD19-CD3-CD27 TsAb_D dimer linker (Linker 2) is shown as SEQ ID NO. 50.

Embodiment 2-23: Antigen Binding Activity Test of CD19-CD3-CD27 TsAb_M and CD19-CD3-CD27 TsAb_D by ELISA ELISA procedure:

1. Recombinant antigen coating: 96-well plates were coated by human CD19-hFc, CD3-hFc and human CD27-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific antibody samples respectively and keeping plates at 37° C. for 1 hour. Sample serial dilution includes: using 10 μg/ml purified CD19-CD3-CD27 TsAb_M or CD19-CD3-CD27 TsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5-10 min at room temperature.

5. Reaction termination and result test: adding 100 μl per well of 1M HCl to stop reaction, and reading OD value of 450 nm absorbance on ELISA reader.

The results of ELISA are shown in FIGS. 2-18A and 2-18B. The four curves in the figure represent three four results: ■ coated with 1 μg/ml CD19-hFc recombinant antigen, ◆ coated with 1 μg/ml CD3-hFc recombinant antigen; ▲ coated with 1 μg/ml CD27-hFc recombinant antigen; ▼ no antigen coated result. FIG. 2-18A indicates that CD19-CD3-CD27 TsAb_M has antigen binding activity with CD19-hFc, CD3-hFc and CD27-hFc in vitro, among which CD27 has the highest binding activity, CD19 has the second highest binding activity, and CD3 has the weakest binding activity. FIG. 2-18B indicates that CD19-CD3-CD27 TsAb_D has antigen binding activity with CD19-hFc, CD3-hFc and CD27-hFc in vitro as well, among which CD27 has the highest binding activity, CD19 has the second highest binding activity, and CD3 has the weakest binding activity.

Embodiment 2-24: CD19-CD3-CD27 Tri-Specific Antibody-Mediated Cell Killing Assay Human PBMC (Peripheral blood mononuclear cell, PBMC) was used as experiment material. The above-mentioned TiTE tri-specific antibody CD19-CD3-CD27 TsAb_M in monomeric form, TiTE tri-specific antibody CD19-CD3-CD27 TsAb_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Count cell number and cells are ready for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-CD27 TsAb_M and CD19-CD3-CD27 TsAb_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{OD \text{ value of } Raji \text{ cells} + OD \text{ value of } CIK \text{ cells} - \text{detected } OD \text{ value}}{OD \text{ value of } Raji \text{ cells}} \times 100\%$$

The results are shown in FIG. 2-19: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-CD27 TsAb_D have the best cell killing effect. The killing efficacy is about 89%, 84% and 74%. The effect of CD19-CD3-CD27 TsAb_M is in the second place, the killing efficacy is about 89%, 84% and 67%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-CD27 TsAb_D and CD19-CD3-CD27 TsAb_M against Raji cells is improved to some extent, and the killing efficacy is about 55% and 49%, respectively. While CD19-CD3 BsAb had no effect compared with the blank control. The above results indicated that the two forms of CD19-CD3-CD27 TiTE tri-specific antibody-mediated T cell-targeted killing activity against CD19-positive tumor cells were superior to that of BiTE bispecific antibody. The dimeric form has a better effect than the monomer form.

Embodiment 3-1: The Eukaryotic Expression Vector Construction of CD19-CD3-4-1BBL TsM_M and CD19-CD3-4-1BBL TsM_D In this disclosure, the TiTE tri-specific molecule including anti-CD19 scFv, anti-CD3 scFv, and co-stimulatory molecule ligand 4-1BBL extracellular domain on human T cell is named as CD19-CD3-4-1BBL TsM.

1. Construction Design of CD19-CD3-4-1BBL TsM_M and CD19-CD3-4-1BBL TsM_D

Construction design of CD19-CD3-4-1BBL TsM_M Monomer:

The sequences of the anti-CD19 scFv, anti-CD3 scFv and 4-1BBL extracellular domain are linked by a linker. Specifically, the sequence of anti-CD19 scFv and the anti-CD3 scFv are linked by Linker 1, the sequence of anti-CD3 scFv and 4-1BBL extracellular domain are linked by Linker 2.

Construction design of CD19-CD3-4-1BBL TsM_D Dimer:

The sequences of the anti-CD19 scFv, anti-CD3 scFv and 4-1BBL extracellular domain are linked by linkers. Specifically, the sequences of anti-CD19 scFv and anti-CD3 scFv are linked by Linker 1, the sequences of anti-CD3 scFv and 4-1BBL extracellular domain are linked by IgD hinge region (Ala90-Val170) as Linker 2.

In order to express the tri-specific molecule in mammalian cells, codon optimization of mammalian system was performed for the sequence of anti-CD19 scFv, anti-CD3 scFv, and 4-1BBL extracellular domain.

The nucleotide sequence of anti-CD19 scFv heavy chain variable region is shown as SEQ ID NO. 209.

The nucleotide sequence of anti-CD19 scFv light chain variable region is shown as SEQ ID NO. 210.

The nucleotide sequence of anti-CD19 scFv is shown as SEQ ID NO. 208.

The nucleotide sequence of anti-CD3 scFv heavy chain variable region is shown as SEQ ID NO. 212.

The nucleotide sequence of anti-CD3 scFv light chain variable region is shown as SEQ ID NO. 213.

The nucleotide sequence of anti-CD3 scFv is shown as SEQ ID NO. 211.

The nucleotide sequence of 4-1BBL extracellular region is shown as SEQ ID NO. 214.

The nucleotide sequence of CD19-CD3-4-1BBL TsM_M monomer linker (Linker 1) is shown as SEQ ID NO. 160.

The nucleotide sequence of CD19-CD3-4-1BBL TsM_M monomer linker (Linker 2) is shown as SEQ ID NO. 162.

The nucleotide sequence of CD19-CD3-4-1BBL TsM_D dimer linker (Linker 1) is shown as SEQ ID NO. 164.

The nucleotide sequence of CD19-CD3-4-1BBL TsM_D dimer linker (Linker 2) is shown as SEQ ID NO. 166.

In order to express make tri-specific molecule successfully in CHO-S cells and secret into medium, signal peptide of antibody secretory expression was selected in this Embodiment.

The amino acid sequence of this secretory signal peptide is shown as SEQ ID NO. 219.

The nucleotide sequence of this secretory signal peptide is shown as SEQ ID NO. 220.

2. CD19-CD3-4-1BBL TsM_M and CD19-CD3-4-1BBL TsM_D Eukaryotic Expression Vector Construction The construction and expression of this tri-specific molecule in the present disclosure selected mammalian cell protein transient expression vector pcDNA3.1 (purchased from Invitrogen, Shanghai). In order to construct the tri-specific molecules in monomer and dimer form, primers were designed as in table 3-1. All the primers were synthesized by Genewiz, Suzhou, and DNA template for PCR was synthesized by Synbio Technologies, Suzhou.

The cloning construct for CD19-CD3-4-1BBL TsM_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+4-1BBL extracellular domain sequence by primer pairs Sig-CD19-F and CD19-R, CD19-G4S-CD3-F and CD3-R, and CD3-$(GGGGS)_3$-4-1BBL-F and pcDNA3.1-4-1BBL-R, respectively. The cloning construct for CD19-CD3-4-1BBL TsM_D includes: amplifying signal peptide by primers pcDNA3.1-Sig-F and Sig-R, and then amplifying anti-CD19 scFv, GGGGS Linker 1+anti-CD3 scFv, and IgD hinge region Linker2+4-1BBL extracellular domain sequence by primer pairs Sig-CD19-F and CD19-R, CD19-G4S-CD3-F and CD3-R, CD3-IgD-F and IgD-R, and IgD-4-1BBL-F and pcDNA3.1-4-1BBL-R, respectively. After PCR amplification, by using NovoRec® PCR One-Step Cloning Kit (purchased from Wujiang Novoprotein Technology Co., Ltd.), the full length of tri-specific molecule monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-4-1BBL TsM_M monomer and CD19-CD3-4-1BBL TsM_D dimer both had the right full DNA sequence as expected.

The nucleotide sequence of CD19-CD3-4-1BBL TsM_M monomer is shown as SEQ ID NO. 178.

The nucleotide sequence of CD19-CD3-4-1BBL TsM_D dimer is shown as SEQ ID NO. 180.

TABLE 3-1

Primers used in CD19-CD3-4-1BBL tri-specific molecule gene cloning

| Primer name | Sequence | No. |
|---|---|---|
| pcDNA3.1-Sig-F | GTGCTGGATATCTGCAGAATTCGCCGCCACCATGACCCGGCTGACCGTGCTGGCCCTGC | SEQ ID NO. 221 |
| Sig-R | GGCCCTGGAGGAGGCCAGCAGGCCGGCCAGCAGGGCCAGCACGGTCAGC | SEQ ID NO. 222 |
| Sig-CD19-F | CTGCTGGCCTCCTCCAGGGCCGACATCCAGCTGACCCAGAGC | SEQ ID NO. 223 |
| CD19-R | GCTGCTCACGGTCACGGTGGTGC | SEQ ID NO. 224 |
| CD19-G4S-CD3-F | CCACCGTGACCGTGAGCAGCGGTGGCGGAGGGTCCGACATCAAGCTGCAGCAGAGC | SEQ ID NO. 225 |
| CD3-R | CTTCAGCTCCAGCTTGGTGC | SEQ ID NO. 226 |
| CD3-$(GGGGS)_3$-4-1BBL-F | GGCACCAAGCTGGAGCTGAAGGGCGGCGGCGGCAGCGGCGGCGGCGGCAGCGGCGGCGGCGGCAGCGCCTGCCCCTGGGCCGTGAGC | SEQ ID NO. 227 |
| pcDNA3.1-4-1BBL-R | CTGATCAGCGGTTTAAACTTAAGCTTTCACTCGCTGCGGGGGCTGGGCAGGCC | SEQ ID NO. 228 |
| CD3-IgD-F | GCACCAAGCTGGAGCTGAAGGCCAGCAAGAGCAAGAAGGAG | SEQ ID NO. 229 |
| IgD-R | CACGCCCAGGGGCTGGGTGTG | SEQ ID NO. 230 |
| IgD-4-1BBL-F | CACACCCAGCCCCTGGGCGTGGCCTGCCCCTGGGCCGTGAGC | SEQ ID NO. 231 |

Embodiment 3-2: The Expression and Purification of CD19-CD3-4-1BBL TsM_M and CD19-CD3-4-1BBL TsM_D 1. The Expression of CD19-CD3-4-1BBL TsM_M and CD19-CD3-4-1BBL TsM_D 1.1 The cell density of CHO-S cells (purchased from Thermo Fisher Scientific) was 0.5~0.6×$10^6$/ml one day before transfection.

1.2 Calculating cell density at the day of transfection, plasmid transfection can be performed when the density is in the range of 1~1.4×$10^6$/ml and live percentage is >90%.

1.3 Transfection complex recipes: each project (CD19-CD3-4-1BBL TsM_M and CD19-CD3-4-1BBL TsM_D) requires two centrifuge tubes/flasks. Take total 20 ml as an example, the recombinant plasmids from Embodiment 3-1 were taken: Tube 1: 600 μl PBS, 20 μg recombinant plasmid, mix well; Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15~20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-4-1BBL TsM_M and CD19-CD3-4-1BBL TsM_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-4-1BBL TsM_M and CD19-CD3-4-1BBL TsM_D recombinant protein was analyzed by SDS-PAGE, and the protein electrophoresis data under reduced and unreduced conditions were shown as FIG. 3-2. It shows that both purity of CD19-CD3-4-1BBL TsM_M and CD19-CD3-4-1BBL TsM_D recombinant protein are >95%. The theoretical molecule weight for CD19-CD3-4-1BBL TsM_M is 75.6 kDa, and protein displayed the same single band under reduced and unreduced conditions. The molecule weight of these bands is consistent with monomer, so this tri-specific molecule is monomer (FIG. 3-2A, Lane 1: protein marker for molecule weight; Lane 2: reduced CD19-CD3-4-1BBL TsM_M; Lane 3: unreduced CD19-CD3-4-1BBL TsM_M). The theoretical molecule weight for CD19-CD3-4-1BBL TsM_D is 83.5 kDa, and protein displayed the same molecular weight as monomer under reduced condition, but the molecular weight is consistent with dimer under unreduced condition (FIG. 3-2B, Lane 1: protein marker for molecule weight; Lane 2: reduced CD19-CD3-4-1BBL TsM_D; Lane 3: unreduced CD19-CD3-4-1BBL TsM_D), which indicate two protein molecules link to each other by disulfide bond formed through IgD hinge region so that this tri-specific molecule is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-4-1BBL TsM_M is monomer and CD19-CD3-4-1BBL TsM_D is dimer.

Therefore, the amino acid sequence of CD19-CD3-4-1BBL TsM_M monomer is shown as SEQ ID NO. 177.

The amino acid sequence of CD19-CD3-4-1BBL TsM_D dimer is shown as SEQ ID NO. 179.

The amino acid sequence of anti-CD19 scFv is shown as SEQ ID NO. 197.

The amino acid sequence of anti-CD19 scFv heavy chain variable region is shown as SEQ ID NO. 198.

The amino acid sequence of anti-CD19 scFv light chain variable region is shown as SEQ ID NO. 199.

The amino acid sequence of anti-CD3 scFv is shown as SEQ ID NO. 200.

The amino acid sequence of anti-CD3 scFv heavy chain variable region is shown as SEQ ID NO. 201.

The amino acid sequence of anti-CD3 scFv light chain variable region is shown as SEQ ID NO. 202.

The amino acid sequence of 4-1BBL extracellular domain is shown as SEQ ID NO. 203.

The amino acid sequence of CD19-CD3-4-1BBL TsM_M monomer linker (Linker 1) is shown as SEQ ID NO. 159.

The amino acid sequence of CD19-CD3-4-1BBL TsM_M monomer linker (Linker 2) is shown as SEQ ID NO. 161.

The amino acid sequence of CD19-CD3-4-1BBL TsM_D dimer linker (Linker 1) is shown as SEQ ID NO. 163.

The amino acid sequence of CD19-CD3-4-1BBL TsM_D dimer linker (Linker 2) is shown as SEQ ID NO. 165.

Embodiment 3-3: CD19, CD3 Antigen Binding and Co-Stimulatory Molecule 4-1BB Binding Activity Test of CD19-CD3-4-1BBL TsM_M and CD19-CD3-4-1BBL TsM_D by ELISA ELISA Procedure:

1. Recombinant antigen coating: 96-well plates were coated by human CD19-hFc, human CD3-hFc and human 4-1BB-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific molecule samples respecitvely and keeping plates at 37° C. for 1 hour. Sample serial dilution includes: using 10 μg/ml purified CD19-CD3-4-1BBL TsM_M or CD19-CD3-4-1BBL TsM_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5~10 min at room temperature.

5. Reaction termination and result test: adding 100 μl per well of 1M HCl to stop reaction, and reading OD value of 450 nm absorbance on ELISA reader.

The results of ELISA are shown in FIGS. 3-3A and 3-3B. The four curves in the figure represent three four results: ■ coated with 1 μg/ml CD19-hFc recombinant antigen, ◆ coated with 1 μg/ml CD3-hFc recombinant antigen; ▲ coated with 1 μg/ml 4-1BB-hFc recombinant antigen; ▼ no antigen coated result. FIG. 3-3A indicates that CD19-CD3-4-1BBL TsM_M has antigen binding activity with CD19-hFc, CD3-hFc and 4-1BB-hFc in vitro, among which 4-1BB has the highest binding activity, CD19 has the second highest binding activity, and CD3 has the weakest binding activity. FIG. 3-3B indicates that CD19-CD3-4-1BBL TsM_D has antigen binding activity with CD19-hFc, CD3-hFc and 4-1BB-hFc in vitro as well, among which 4-1BB has the highest binding activity, CD19 has the second highest binding activity, and CD3 has the weakest binding activity.

Embodiment 3-4: Cell Proliferation of CIK (Cytokine Induced Killer) Mediated by CD19-CD3-4-1BBL Tri-Specific Molecule Human PBMC (Peripheral blood mononuclear cell, PBMC) was used as experiment material. The above-mentioned TiTE tri-specific molecule CD19-CD3-4-1BBL TsM_M in monomeric form, TiTE tri-specific molecule CD19-CD3-4-1BBL TsM_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three protein-mediated CIK effector cells was compared.

Cell killing assay procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Count cell number and cells are ready for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-4-1BBL TsM_M and CD19-CD3-4-1BBL TsM_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{OD \text{ value of } Raji \text{ cells} + OD \text{ value of } CIK \text{ cells} - \text{detected } OD \text{ value}}{OD \text{ value of } Raji \text{ cells}} \times 100\%$$

The results are shown in FIG. 3-4: When the CIK effector cells: Raji target cells (E:T ratio) were 1:1, the killing efficacy was about 23% after 3 h without adding any protein. The killing efficacy of CIK cells on Raji cells was significantly improved under the conditions of adding higher concentrations of antibodies (25, 12.5, 6.25 ng/ml). Among them, Cells mediated by CD19-CD3-4-1BBL TsM_D have the best cell killing effect. The killing efficacy is about 96%, 92% and 87%. The effect of CD19-CD3-4-1BBL TsM_M is in the second place, the killing efficacy is about 93%, 88% and 83%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-4-1BBL TsM_D and CD19-CD3-4-1BBL TsM_M against Raji cells is improved to some extent, and the killing efficacy is about 82% and 72%, respectively. While CD19-CD3 BsAb had no effect compared with the blank control. The above results indicated that the two forms of CD19-CD3-4-1BBL TiTE tri-specific molecule-mediated T cell-targeted killing activity against CD19-positive tumor cells were superior to that of CD19-CD3 BiTE bispecific antibody. The dimeric form has a better effect than the monomer form.

Embodiment 3-5: The Eukaryotic Expression Vector Construction of CD19-CD3-B7RP-1 TsM_M and CD19-CD3-B7RP-1 TsM_D In this disclosure, the TiTE tri-specific molecule including anti-CD19 scFv, anti-CD3 scFv, and co-stimulatory molecule ligand B7RP-1 extracellular domain on human T cell is named as CD19-CD3-B7RP-1 TsM.

1. Construction Design of CD19-CD3-B7RP-1 TsM_M and CD19-CD3-B7RP-1 TsM_D

Construction design of CD19-CD3-B7RP-1 TsM_M Monomer:

The sequences of the anti-CD19 scFv, anti-CD3 scFv and B7RP-1 extracellular domain are linked by a linker. Specifically, the sequence of anti-CD19 scFv and the anti-CD3 scFv are linked by Linker 1, the sequence of anti-CD3 scFv and B7RP-1 extracellular domain are linked by Linker 2.

Construction design of CD19-CD3-B7RP-1 TsM_D Dimer:

The sequences of the anti-CD19 scFv, anti-CD3 scFv and B7RP-1 extracellular domain are linked by linkers. Specifically, the sequences of anti-CD19 scFv and anti-CD3 scFv are linked by Linker 1, the sequences of anti-CD3 scFv and B7RP-1 extracellular domain are linked by IgD hinge region (Ala90-Val170) as Linker 2.

In order to express the tri-specific molecule in mammalian cells, codon optimization of mammalian system was performed for the sequence of anti-CD19 scFv, anti-CD3 scFv, and B7RP-1 extracellular domain.

The nucleotide sequence of anti-CD19 scFv heavy chain variable region is shown as SEQ ID NO. 209.

The nucleotide sequence of anti-CD19 scFv light chain variable region is shown as SEQ ID NO. 210.

The nucleotide sequence of anti-CD19 scFv is shown as SEQ ID NO. 208.

The nucleotide sequence of anti-CD3 scFv heavy chain variable region is shown as SEQ ID NO. 212.

The nucleotide sequence of anti-CD3 scFv light chain variable region is shown as SEQ ID NO. 213.

The nucleotide sequence of anti-CD3 scFv is shown as SEQ ID NO. 211.

The nucleotide sequence of B7RP-1 extracellular domain sequence is shown as SEQ ID NO. 215.

The nucleotide sequence of CD19-CD3-B7RP-1 TsM_M monomer linker (Linker 1) is shown as SEQ ID NO. 160.

The nucleotide sequence of CD19-CD3-B7RP-1 TsM_M monomer linker (Linker 2) is shown as SEQ ID NO. 162.

The nucleotide sequence of CD19-CD3-B7RP-1 TsM_D dimer linker (Linker 1) is shown as SEQ ID NO. 164.

The nucleotide sequence of CD19-CD3-B7RP-1 TsM_D dimer linker (Linker 2) is shown as SEQ ID NO. 166.

In order to express tri-specific molecule successfully in CHO-S cells and secret into medium, signal peptide of antibody secretory expression was selected in this Embodiment.

The amino acid sequence of this secretory signal peptide is shown as SEQ ID NO. 219.

The nucleotide sequence of this secretory signal peptide is shown as SEQ ID NO. 220.

2. CD19-CD3-B7RP-1 TsM_M and CD19-CD3-B7RP-1 TsM_D Eukaryotic Expression Vector Construction The construction and expression of this tri-specific molecule in the present disclosure selected mammalian cell protein transient expression vector pcDNA3.1 (purchased from Invitrogen, Shanghai). In order to construct the tri-specific molecules in monomer and dimer form, primers were designed as in table 3-2. All the primers were synthesized by Genewiz, Suzhou, and DNA template for PCR was synthesized by Synbio Technologies, Suzhou.

The cloning construct for CD19-CD3-B7RP-1 TsM_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+B7RP-1 extracellular domain sequence by primer pairs Sig-CD19-F and CD19-R, CD19-G4S-CD3-F and CD3-R, and CD3-$(GGGGS)_3$-B7RP-1-F and pcDNA3.1-B7RP-1-R, respectively. The cloning construct for CD19-CD3-B7RP-1 TsM_D includes: amplifying signal peptide by primers pcDNA3.1-Sig-F and Sig-R, and then amplifying anti-CD19 scFv, GGGGS Linker 1+anti-CD3 scFv, IgD hinge region Linker2, and B7RP-1 extracellular domain sequence by primer pairs Sig-CD19-F and CD19-R, CD19-G4S-CD3-F and CD3-R, CD3-IgD-F and IgD-R, and IgD-B7RP-1-F and pcDNA3.1-B7RP-1-R, respectively. After PCR amplification, by using NovoRec® PCR One-Step Cloning Kit (purchased from Wujiang Novoprotein Technology Co., Ltd.), the full length of tri-specific molecule monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-B7RP-1 TsM_M monomer and CD19-CD3-B7RP-1 TsM_D dimer both had the right full DNA sequence as expected.

The nucleotide sequence of CD19-CD3-B7RP-1 TsM_M monomer is shown as SEQ ID NO. 182.

The nucleotide sequence of CD19-CD3-B7RP-1 TsM_D dimer is shown as SEQ ID NO. 184.

TABLE 3-2

Primers used in CD19-CD3-B7RP-1 tri-specific molecule gene cloning

| Primer name | Sequence | No. |
|---|---|---|
| CD3-(GGGGS)$_3$-B7RP-1-F | GGCACCAAGCTGGAGCTGAAGGGCGGCGGCGGCAGCGGCGGCGGCGGCAGCGGCGGCGGCGGCAGCGACACCCAGGAGAAGGAGGTG | SEQ ID NO. 232 |
| pcDNA3.1-B7RP-1-R | CTGATCAGCGGTTTAAACTTAAGCTTTCAGGTGGCGGCGTTCTTCTCGCC | SEQ ID NO. 233 |
| IgD-B7RP-1-F | CACACCCAGCCCCTGGGCGTGGACACCCAGGAGAAGGAGGTG | SEQ ID NO. 234 |

Embodiment 3-6: The Expression and Purification of CD19-CD3-B7RP-1 TsM_M and CD19-CD3-B7RP-1 TsM_D 1. The Expression of CD19-CD3-B7RP-1 TsM_M and CD19-CD3-B7RP-1 TsM_D 1.1 The cell density of CHO-S cells (purchased from Thermo Fisher Scientific) was 0.5~0.6×10$^6$/ml one day before transfection.

1.2 Calculating cell density at the day of transfection, plasmid transfection can be performed when the density is in the range of 1~1.4×10$^6$/ml and live percentage is >90%.

1.3 Transfection complex recipes: each project (CD19-CD3-B7RP-1 TsM_M and CD19-CD3-B7RP-1 TsM_D) requires two centrifuge tubes/flasks. Take total 20 ml as an example, the recombinant plasmids from Embodiment 3-5 were taken:

Tube 1: 600 μl PBS, 20 μg recombinant plasmid, mix well.

Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15-20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-B7RP-1 TsM_M and CD19-CD3-B7RP-1 TsM_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

Figures 1, 2, 3, 4, 5, 5A:
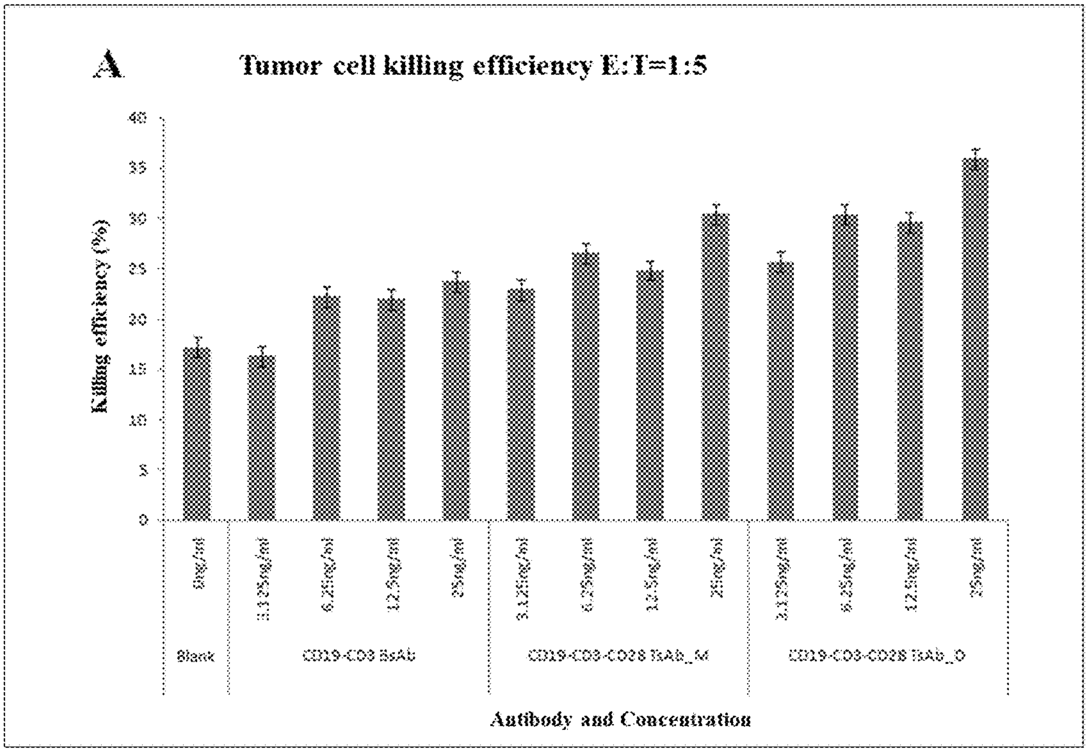
Figures 1, 2, 3, 4, 5, 5B:
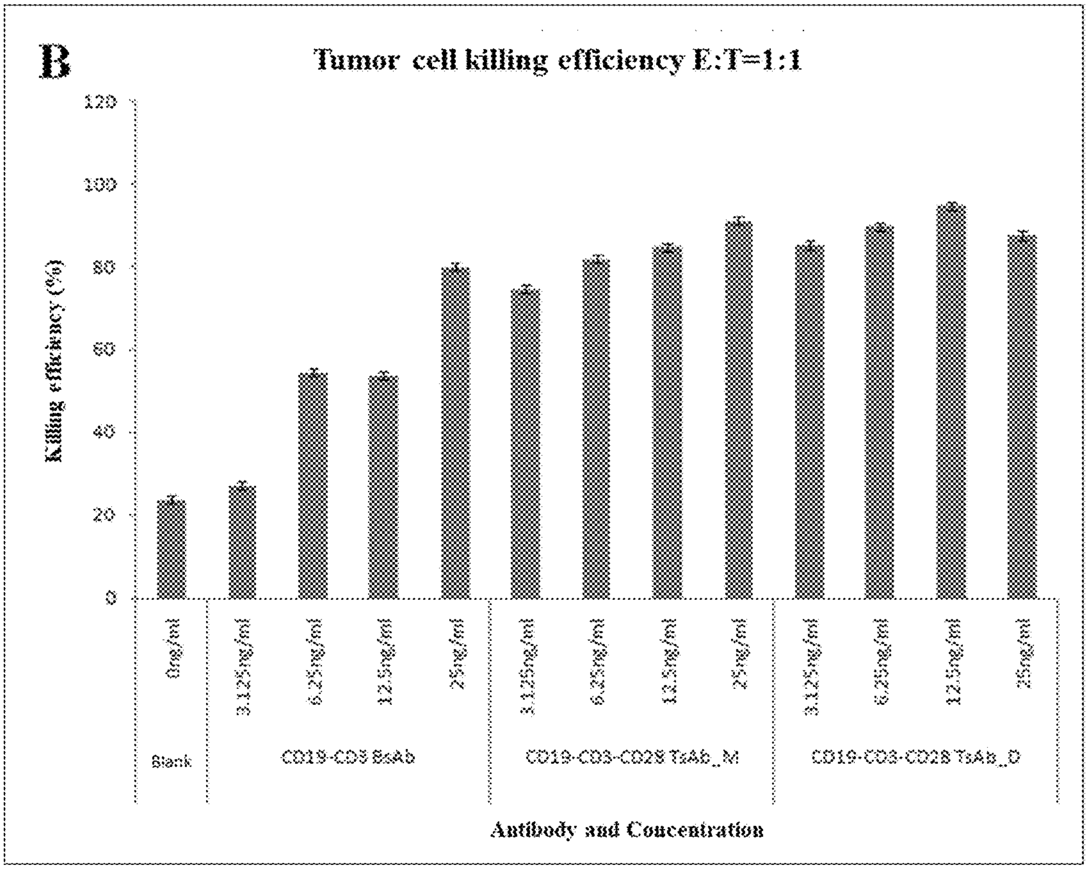
Figures 1, 2:
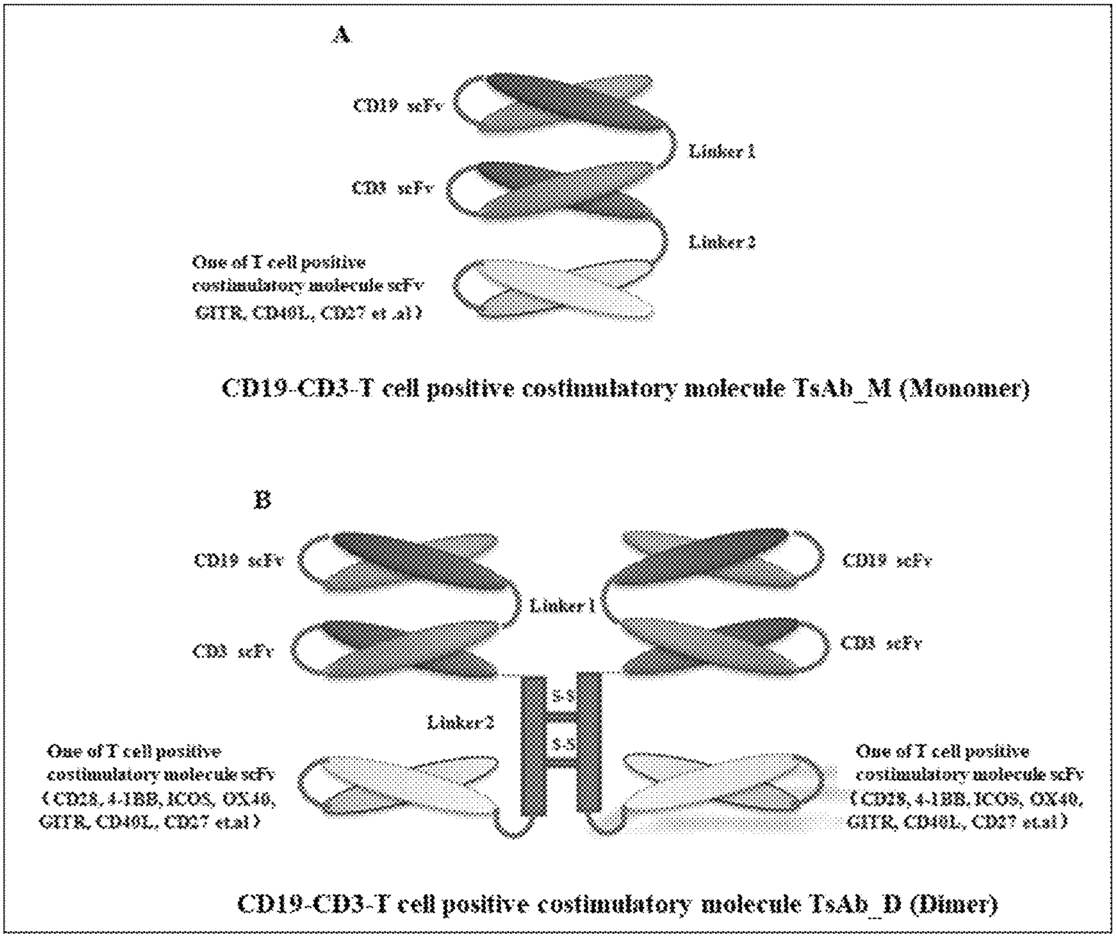
Figure 2:
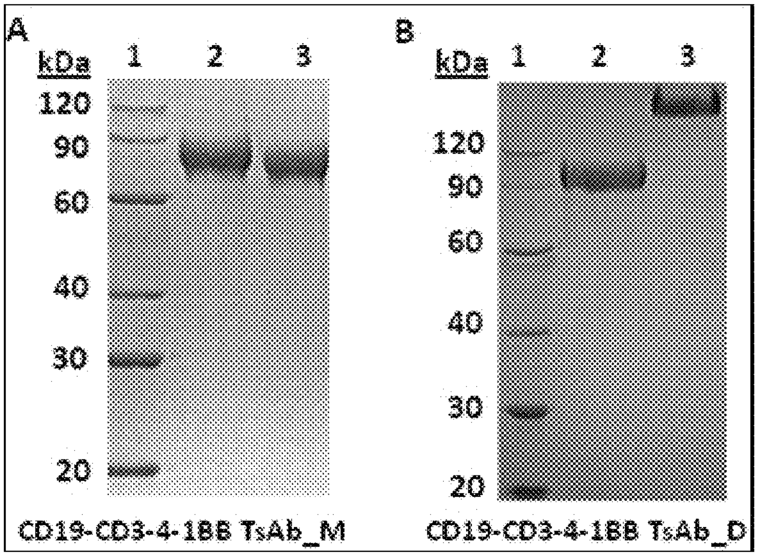
Figures 2, 3, 3A:
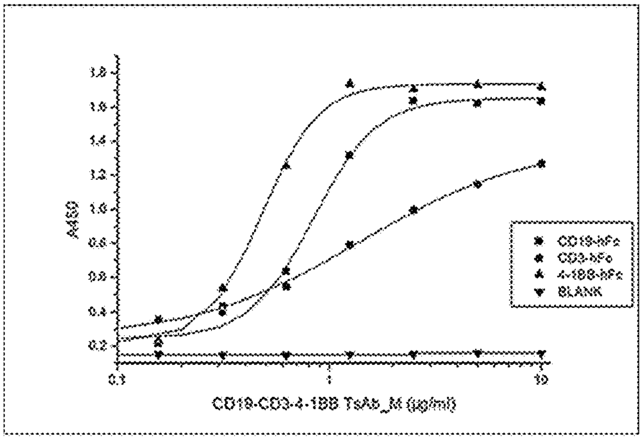
Figures 2, 3, 3B:
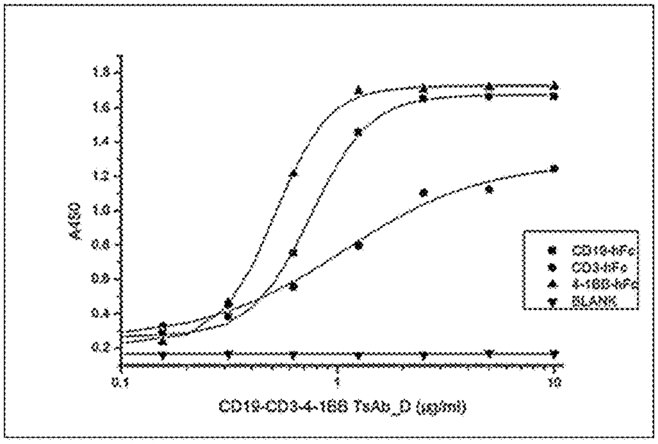
Figures 2, 3, 4:
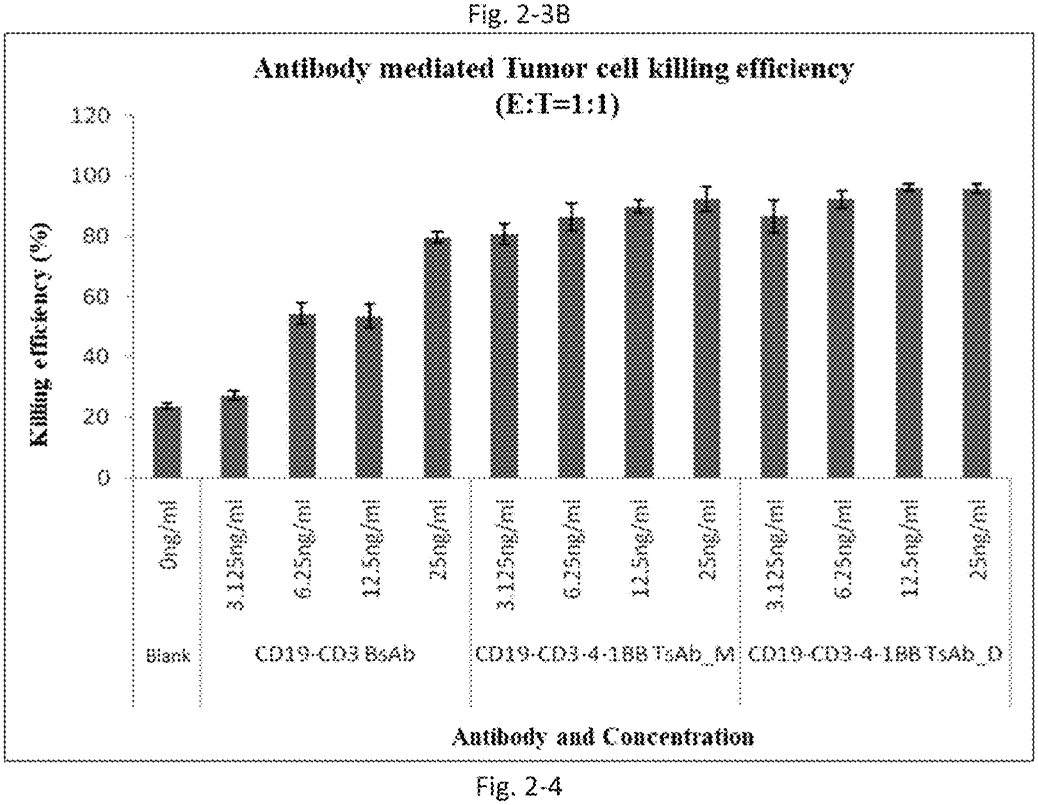
Figures 2, 3, 4, 5:
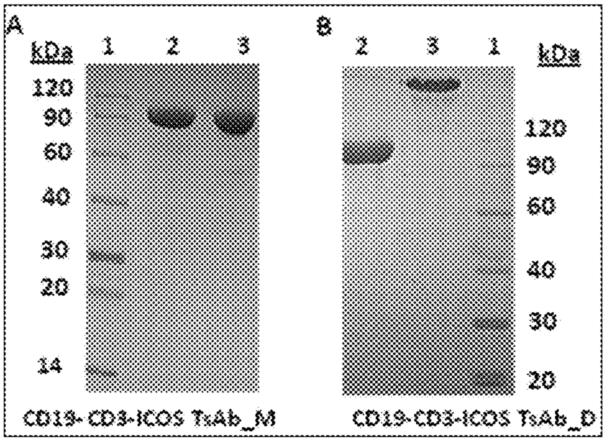
Figures 2, 3, 4, 5, 6, 6A:
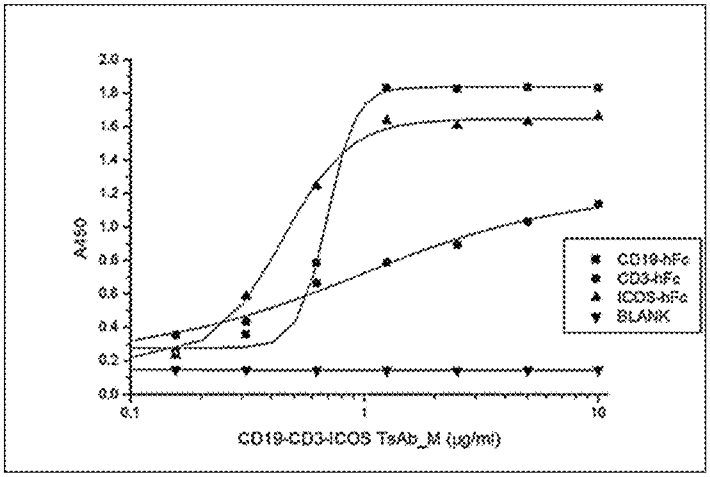
Figures 2, 3, 4, 5, 6, 6B:
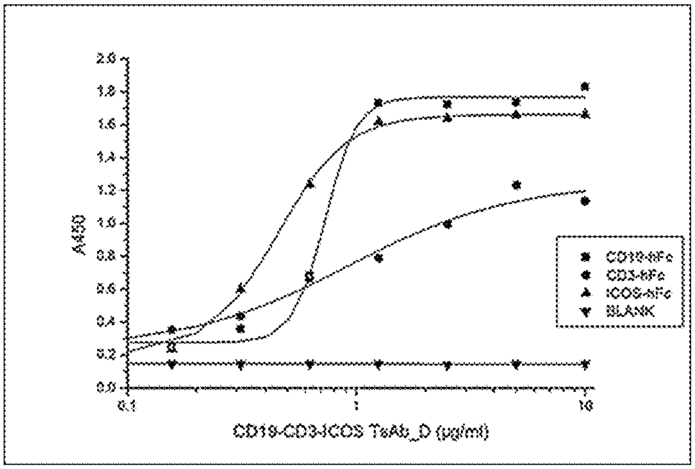
Figures 2, 3, 4, 5, 6, 7:
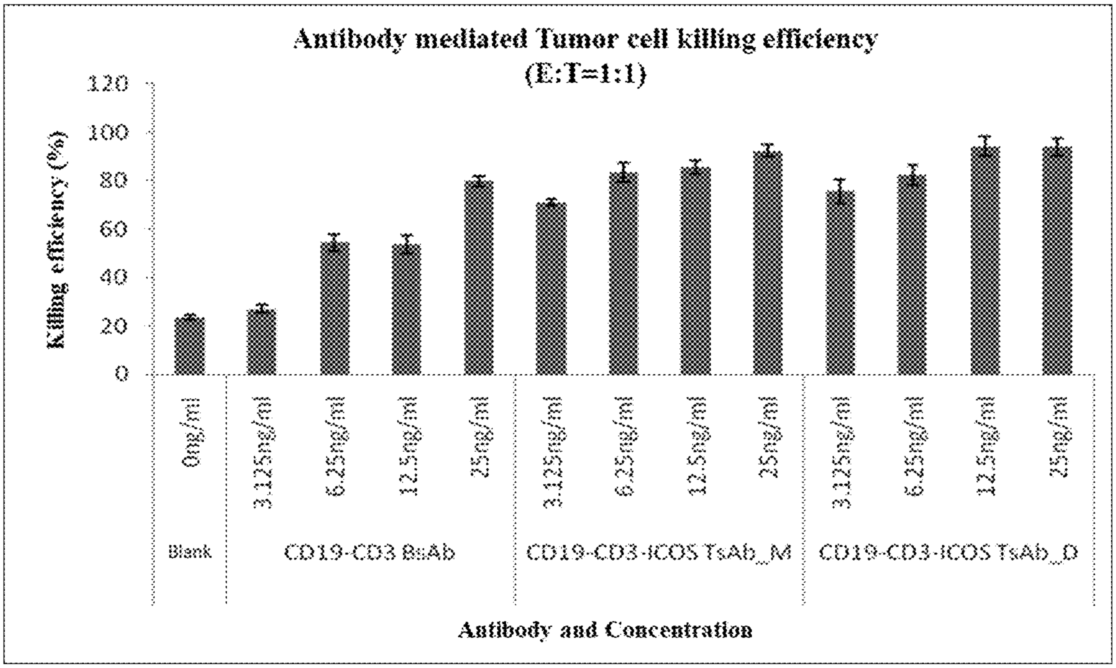
Figures 2, 3, 4, 5, 6, 7, 8:
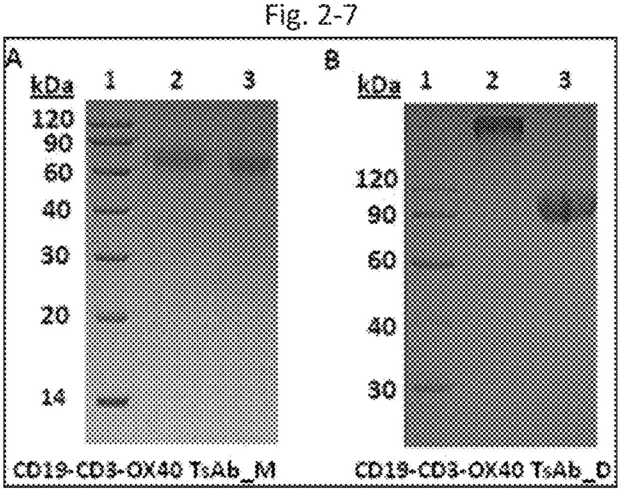
Figures 2, 3, 4, 5, 6, 7, 8, 9, 9A:
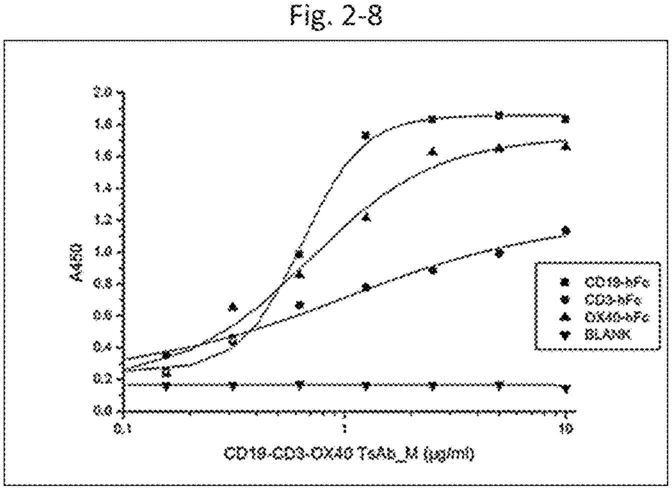
Figures 2, 3, 4, 5, 6, 7, 8, 9, 9B:
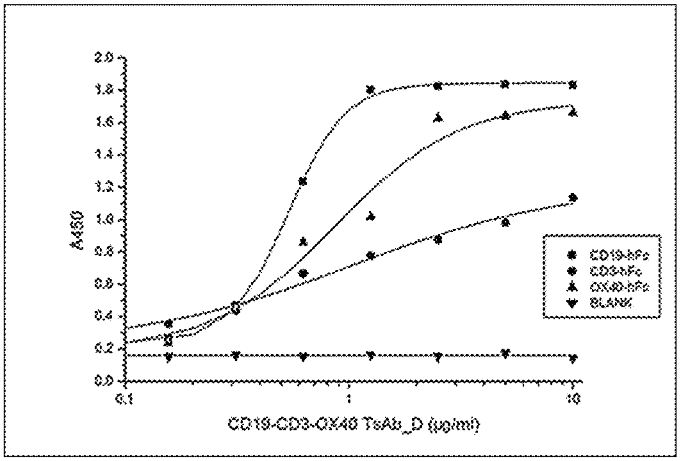
Figures 2, 3, 4, 5, 6, 7, 8, 9, 10:
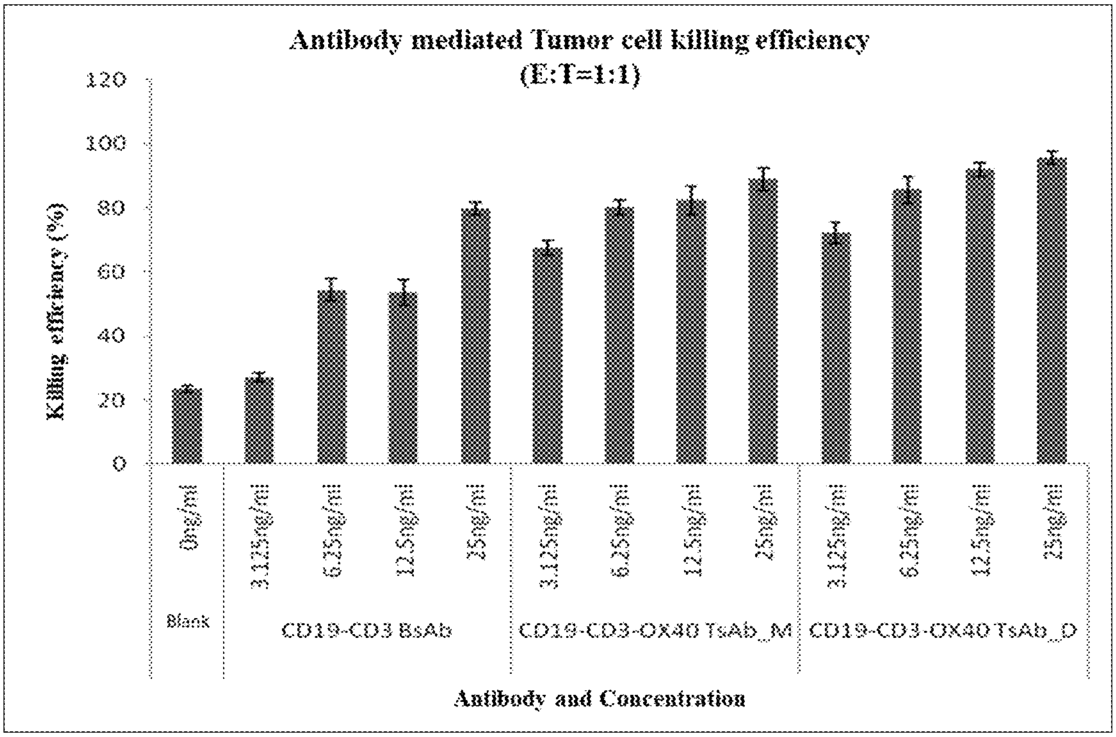
Figures 2, 3, 4, 5, 6, 7, 8, 9, 10, 11:
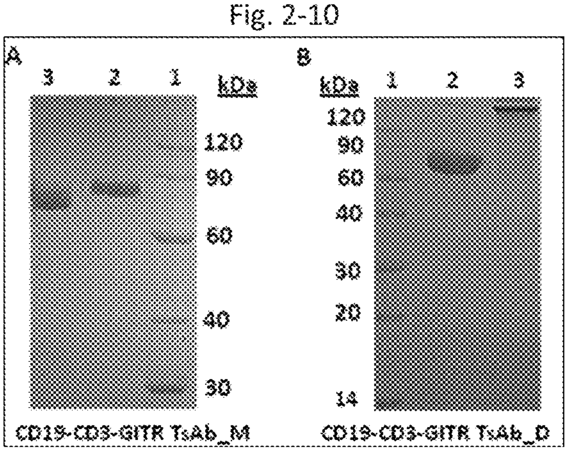
Figures 2, 3, 4, 5, 6, 7, 8, 9, 10, 11, 12, 12A:
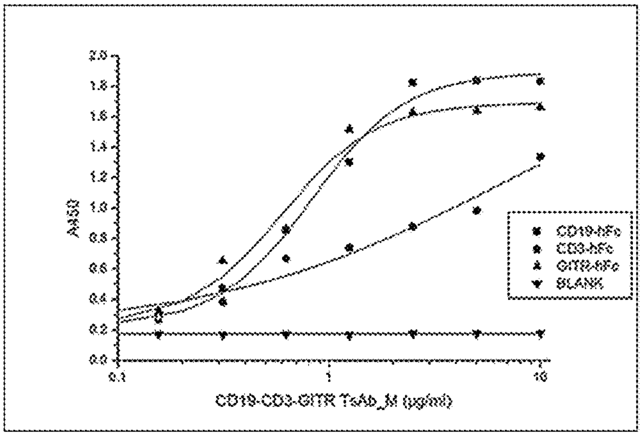
Figures 2, 3, 4, 5, 6, 7, 8, 9, 10, 11, 12, 12B:
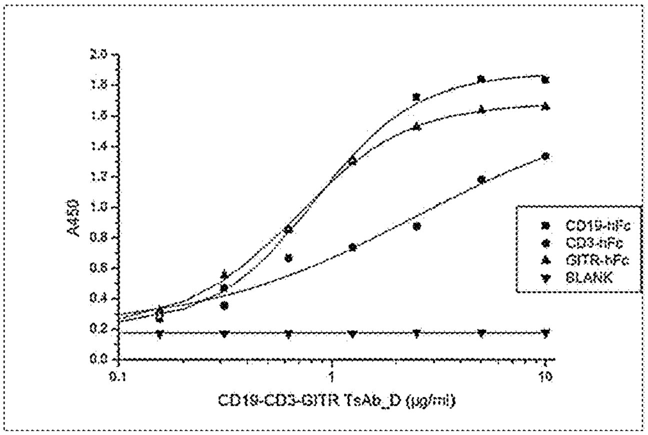
Figures 2, 3, 4, 5, 6, 7, 8, 9, 10, 11, 12, 13:
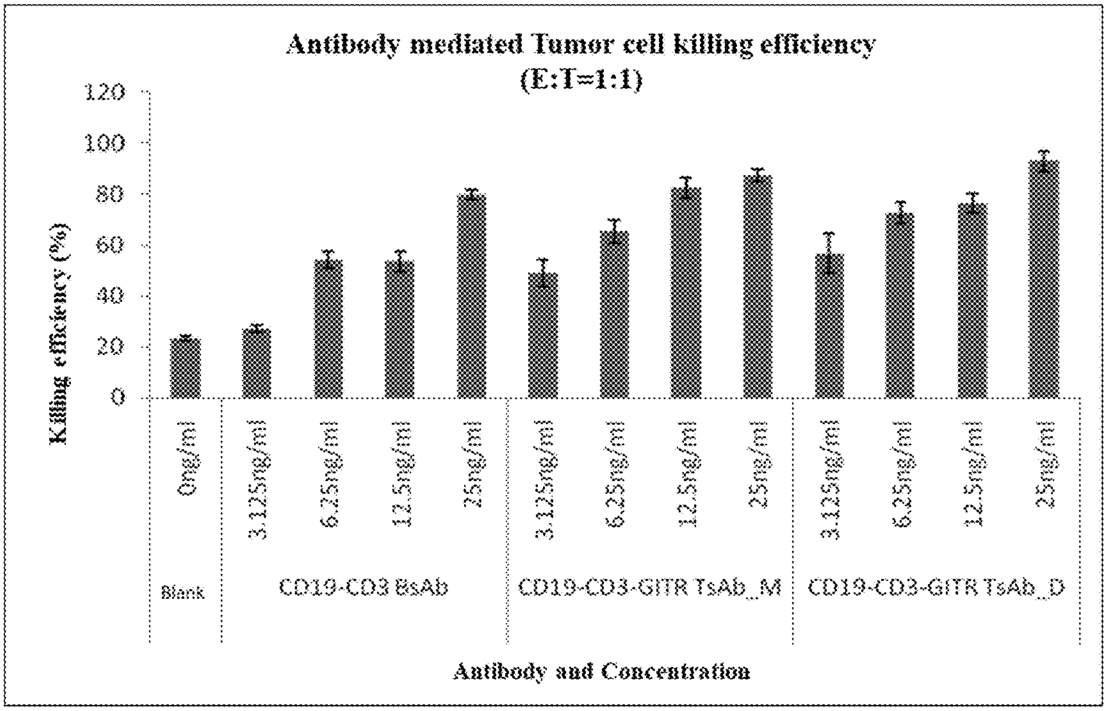
Figures 2, 3, 4, 5, 6, 7, 8, 9, 10, 11, 12, 13, 14:
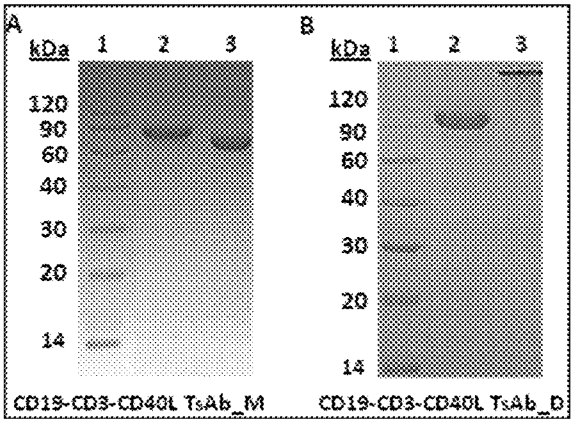
Figures 2, 3, 4, 5, 6, 7, 8, 9, 10, 11, 12, 13, 14, 15, 15A:
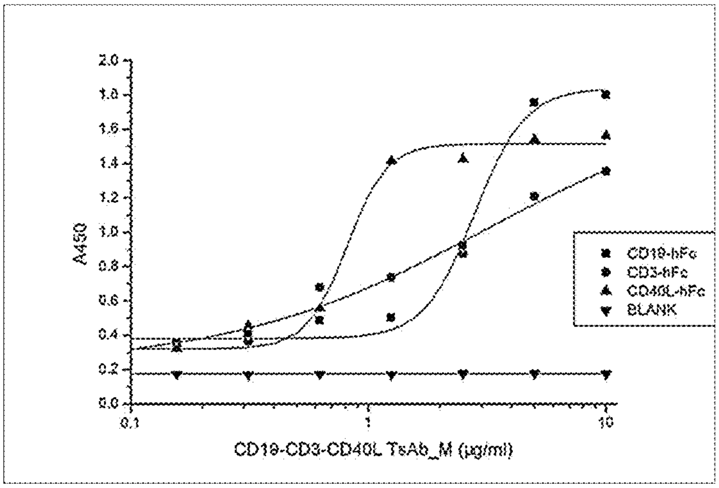
Figures 2, 3, 4, 5, 6, 7, 8, 9, 10, 11, 12, 13, 14, 15, 15B:
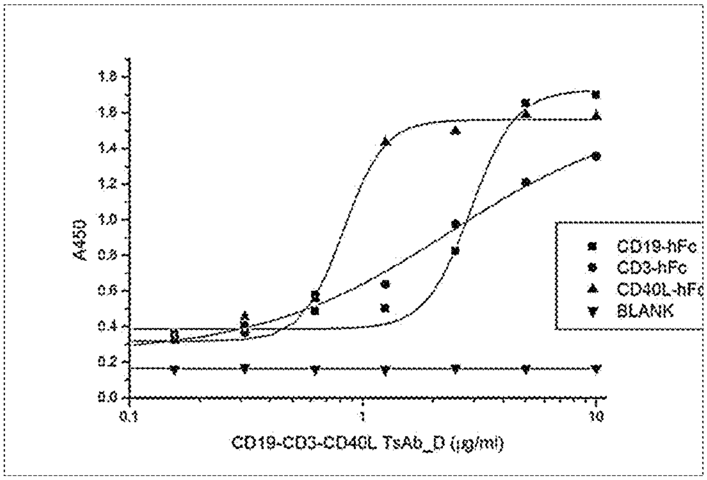
Figures 2, 3, 4, 5, 6, 7, 8, 9, 10, 11, 12, 13, 14, 15, 16:
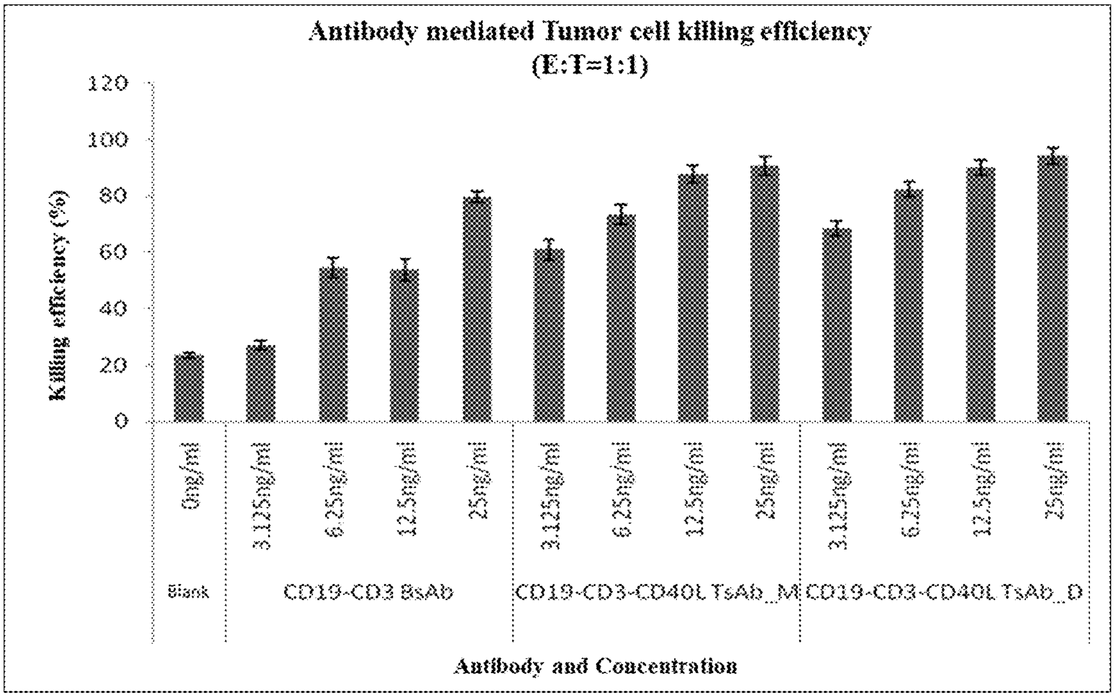
Figures 2, 3, 4, 5, 6, 7, 8, 9, 10, 11, 12, 13, 14, 15, 16, 17:
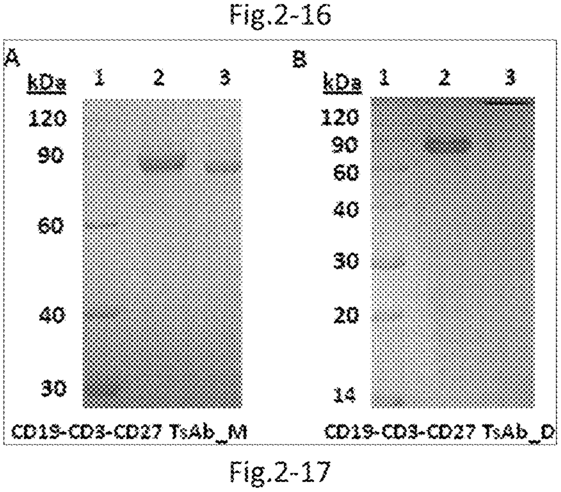
Figures 2, 3, 4, 5, 6, 7, 8, 9, 10, 11, 12, 13, 14, 15, 16, 17, 18, 18A:
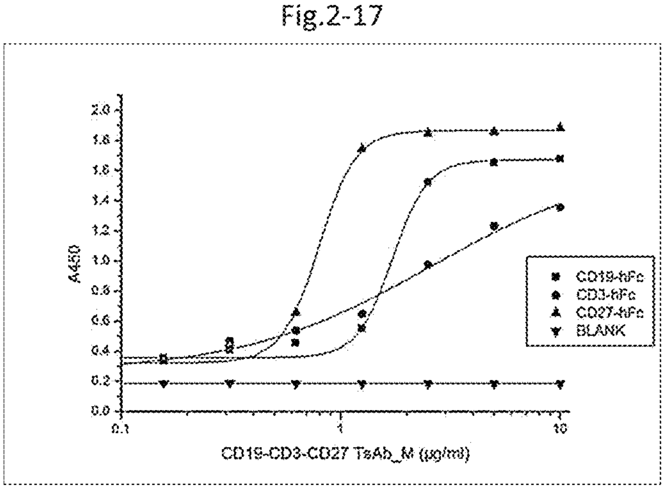
Figures 2, 3, 4, 5, 6, 7, 8, 9, 10, 11, 12, 13, 14, 15, 16, 17, 18, 18B:
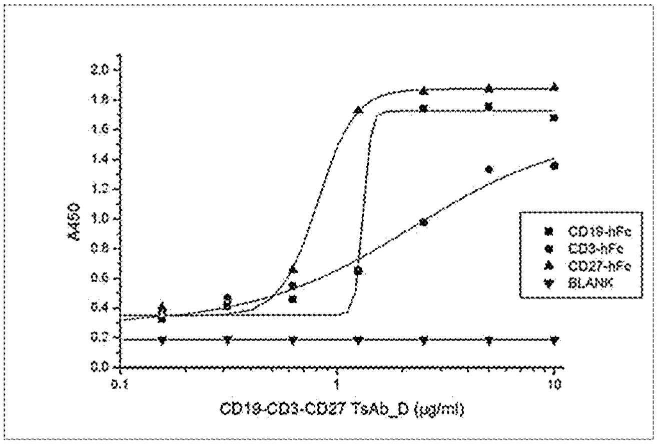
Figures 2, 3, 4, 5, 6, 7, 8, 9, 10, 11, 12, 13, 14, 15, 16, 17, 18, 19:
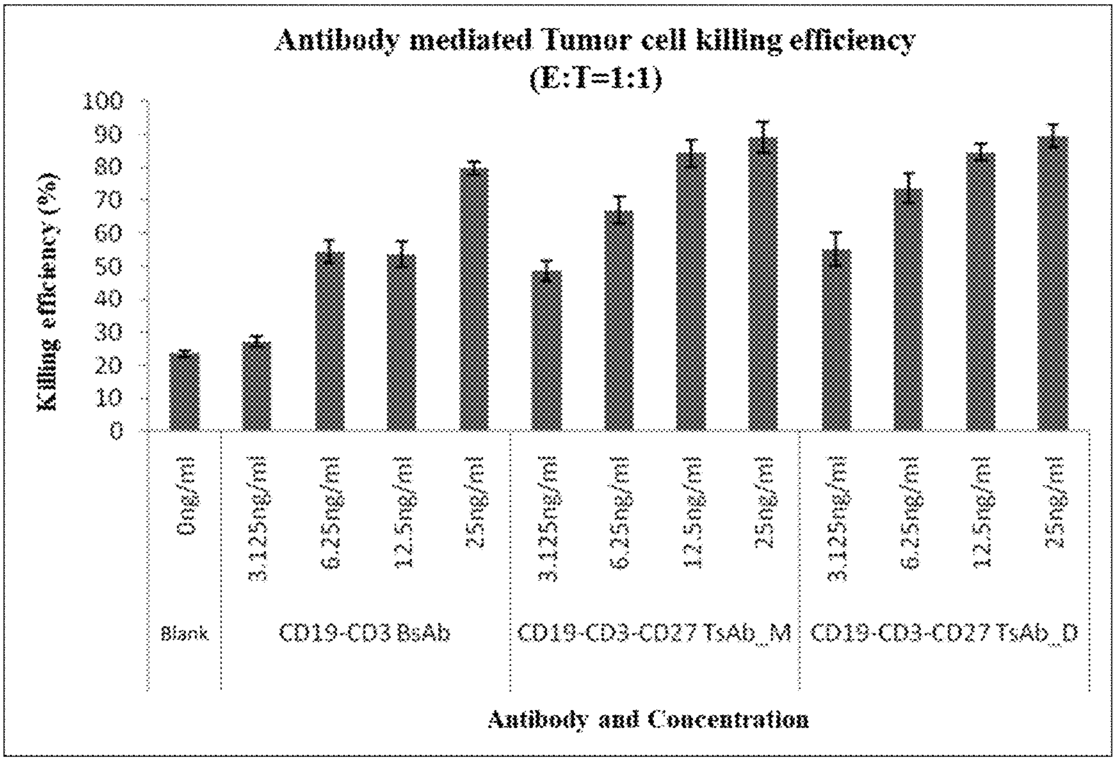
Figures 1, 3:
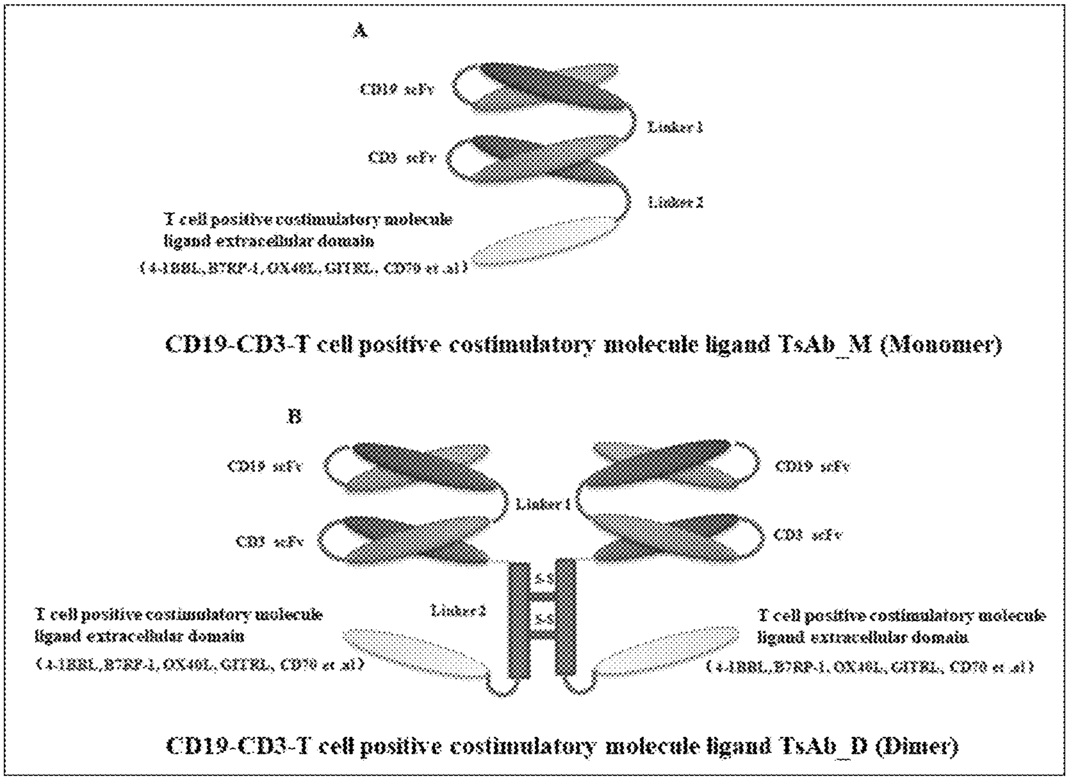
Figures 2, 3:
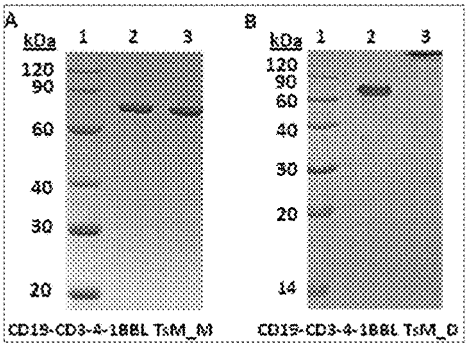
Figures 3, 3A:
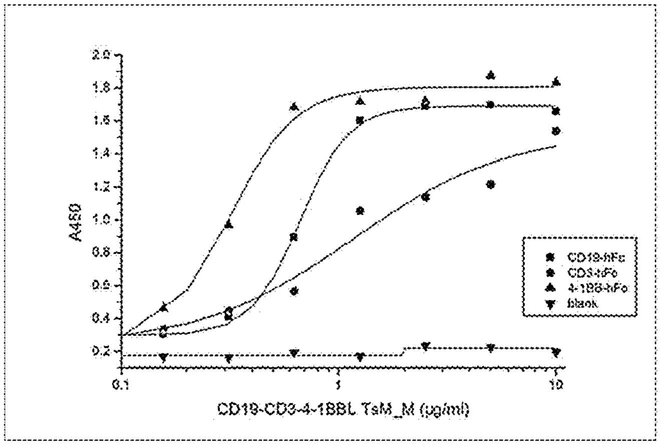
Figures 3, 3B:
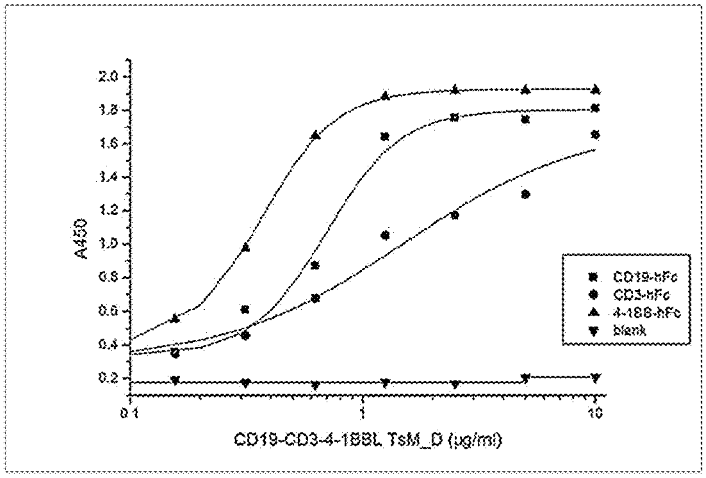
Figures 3, 4:
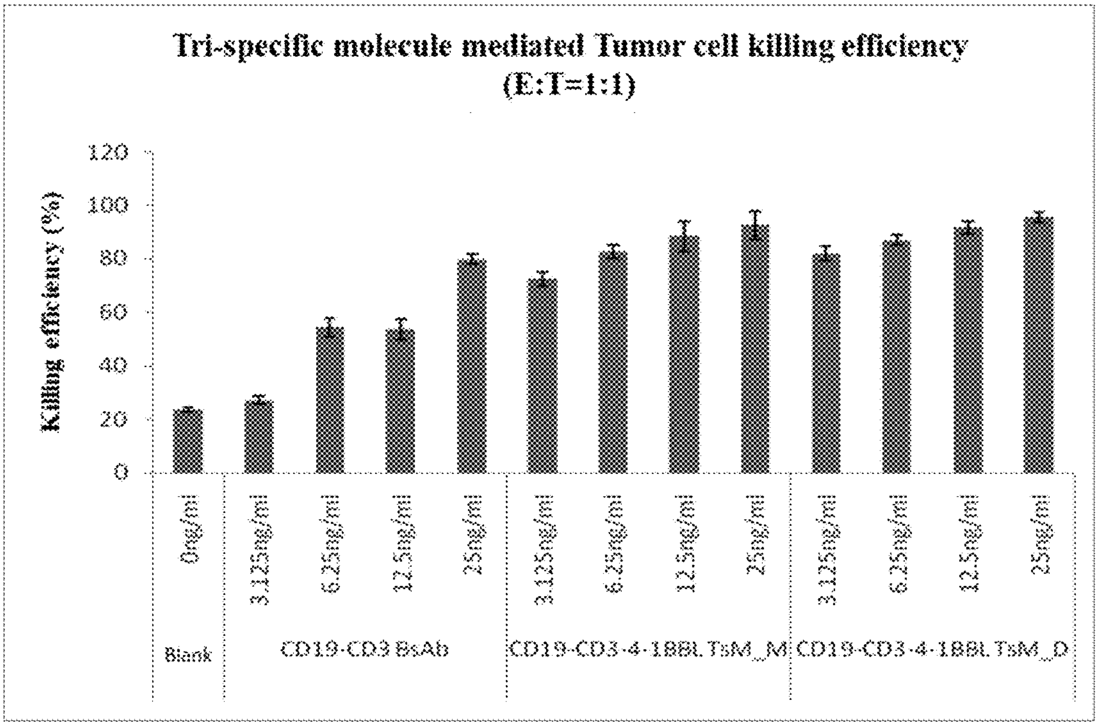
Figures 3, 4, 5:
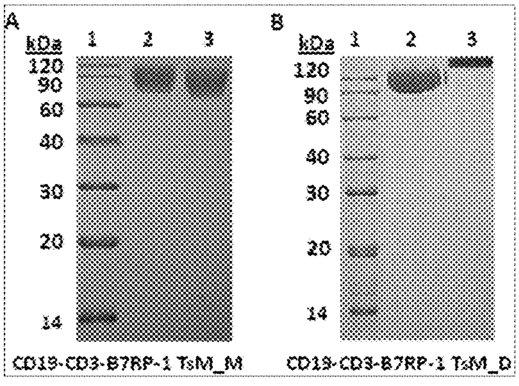
Figures 3, 4, 5, 6, 6A:
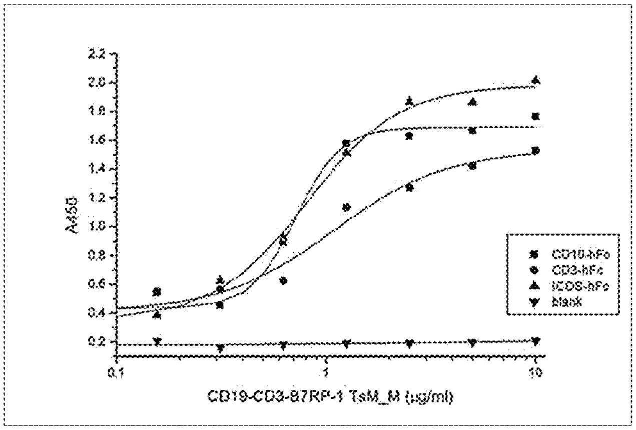
Figures 3, 4, 5, 6, 6B:
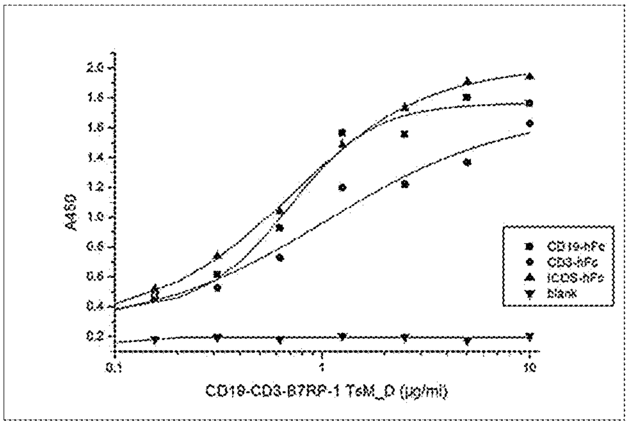
Figures 3, 4, 5, 6, 7:
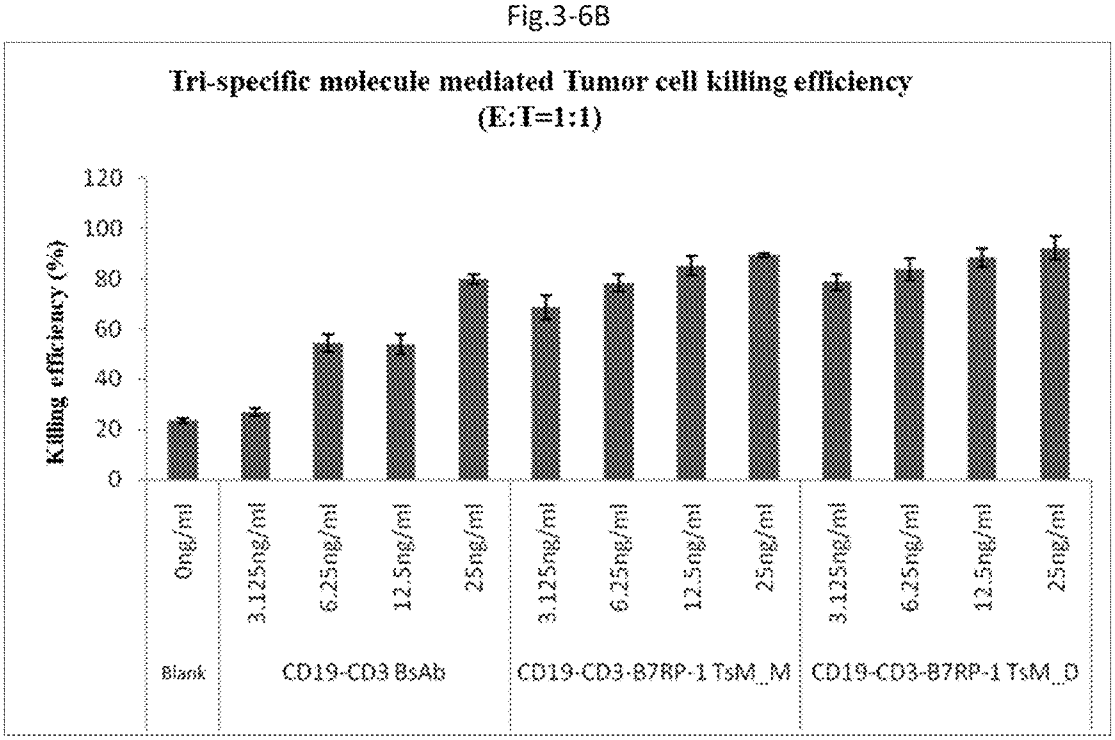
Figures 3, 4, 5, 6, 7, 8:
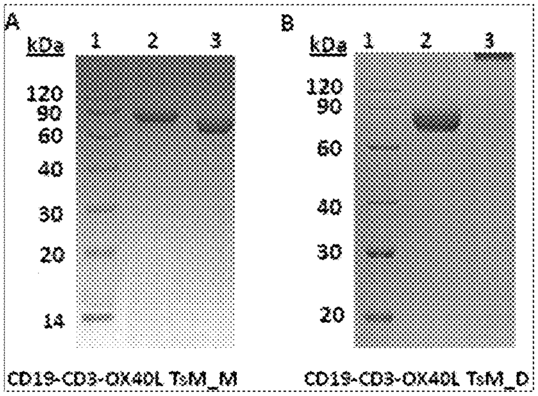
Figures 3, 4, 5, 6, 7, 8, 9, 9A:
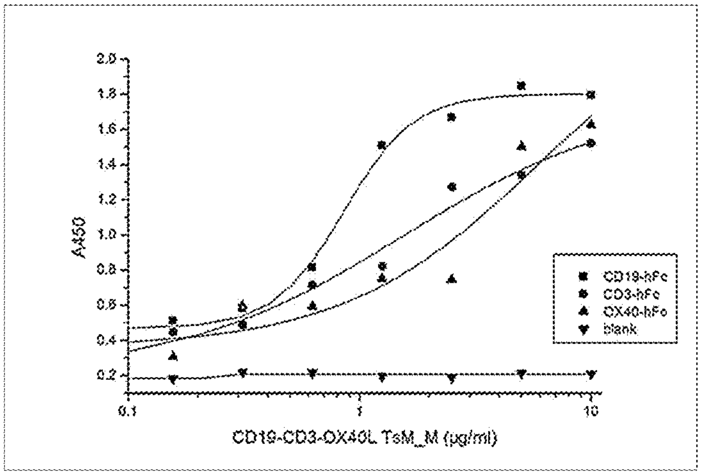
Figures 3, 4, 5, 6, 7, 8, 9, 9B:
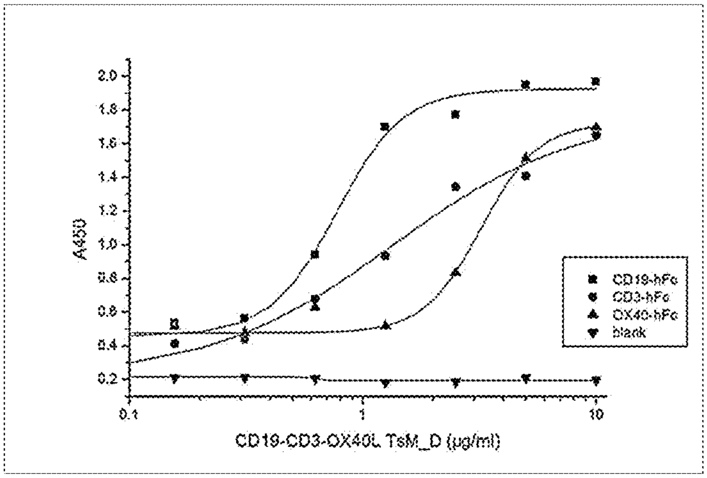
Figures 3, 4, 5, 6, 7, 8, 9, 10:
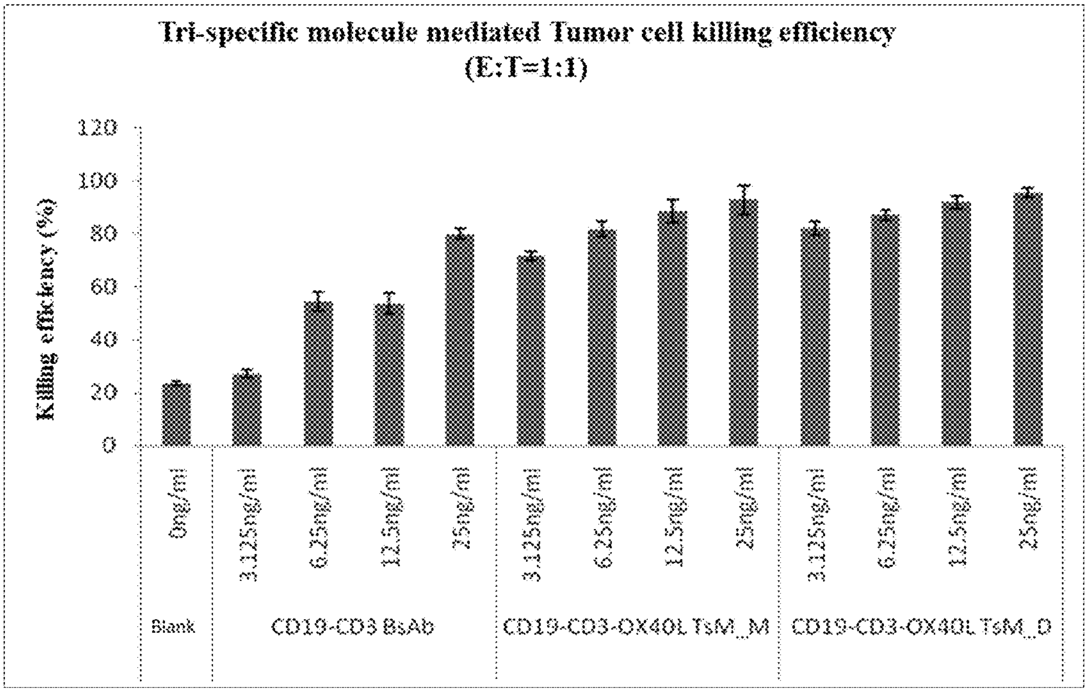
Figures 3, 4, 5, 6, 7, 8, 9, 10, 11:
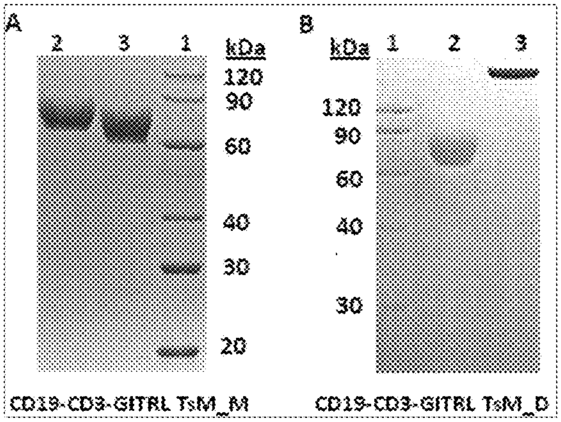
Figures 3, 4, 5, 6, 7, 8, 9, 10, 11, 12, 12A:
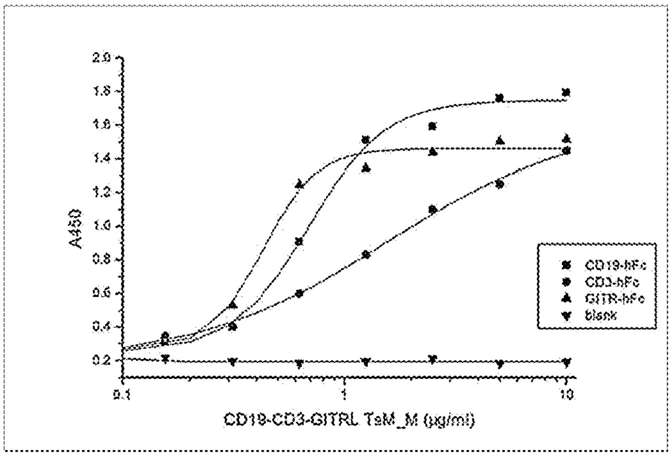
Figures 3, 4, 5, 6, 7, 8, 9, 10, 11, 12, 12B:
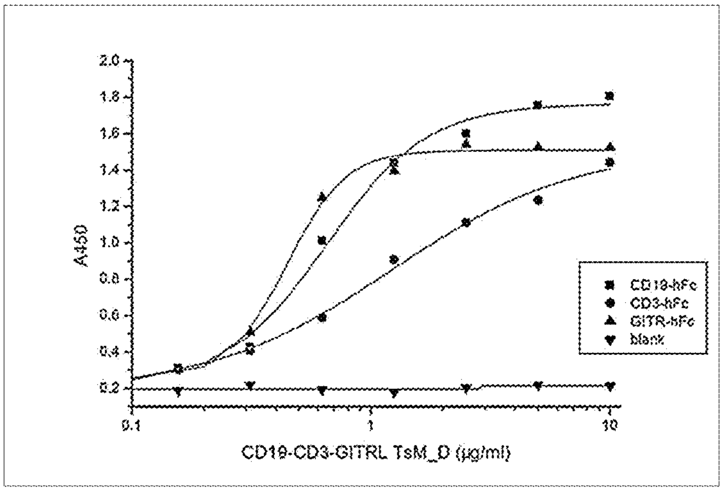
Figures 3, 4, 5, 6, 7, 8, 9, 10, 11, 12, 13:
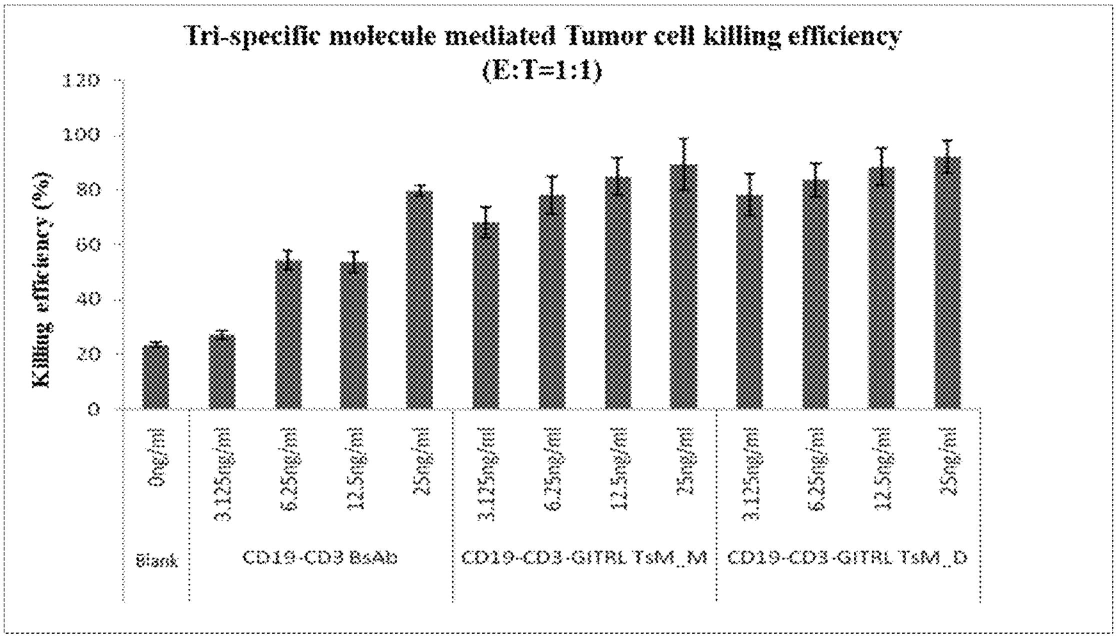
Figures 3, 4, 5, 6, 7, 8, 9, 10, 11, 12, 13, 14:
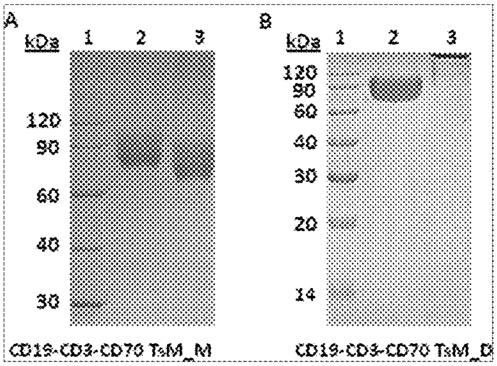
Figures 3, 4, 5, 6, 7, 8, 9, 10, 11, 12, 13, 14, 15, 15A:
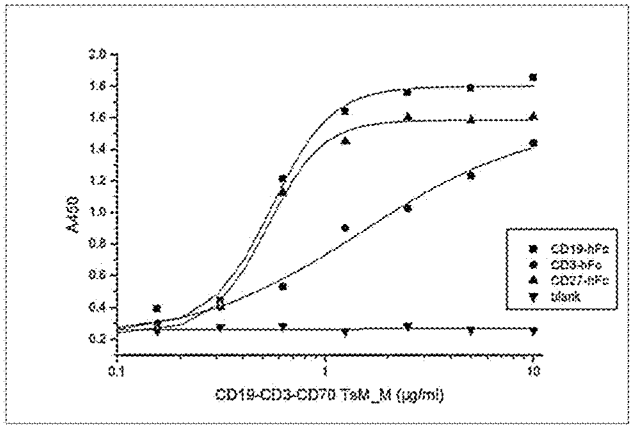
Figures 3, 4, 5, 6, 7, 8, 9, 10, 11, 12, 13, 14, 15, 15B:
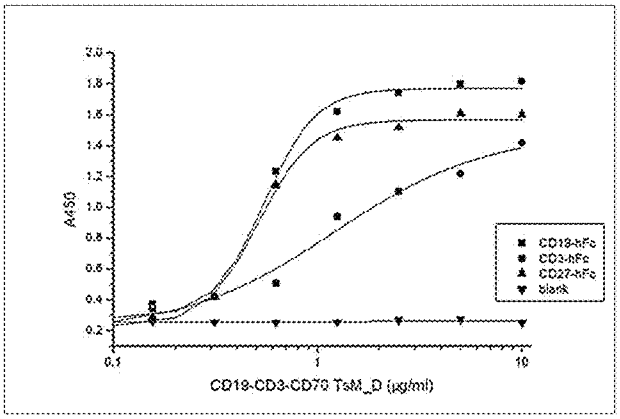
Figures 3, 4, 5, 6, 7, 8, 9, 10, 11, 12, 13, 14, 15, 16:
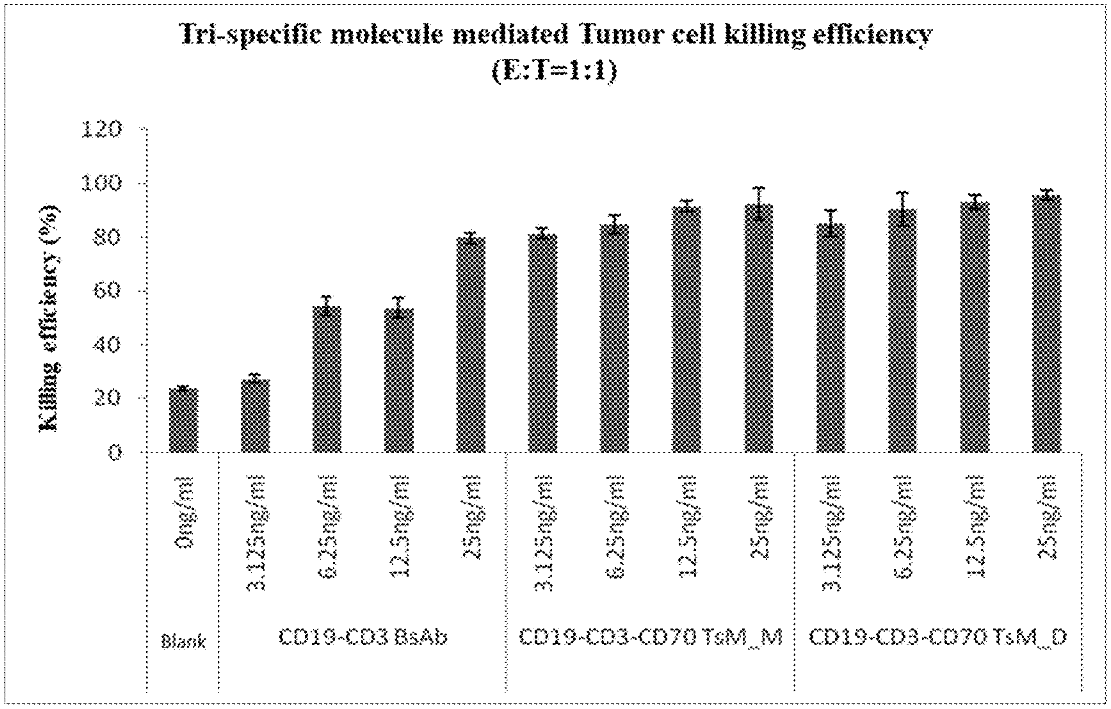
Figures 1, 4:
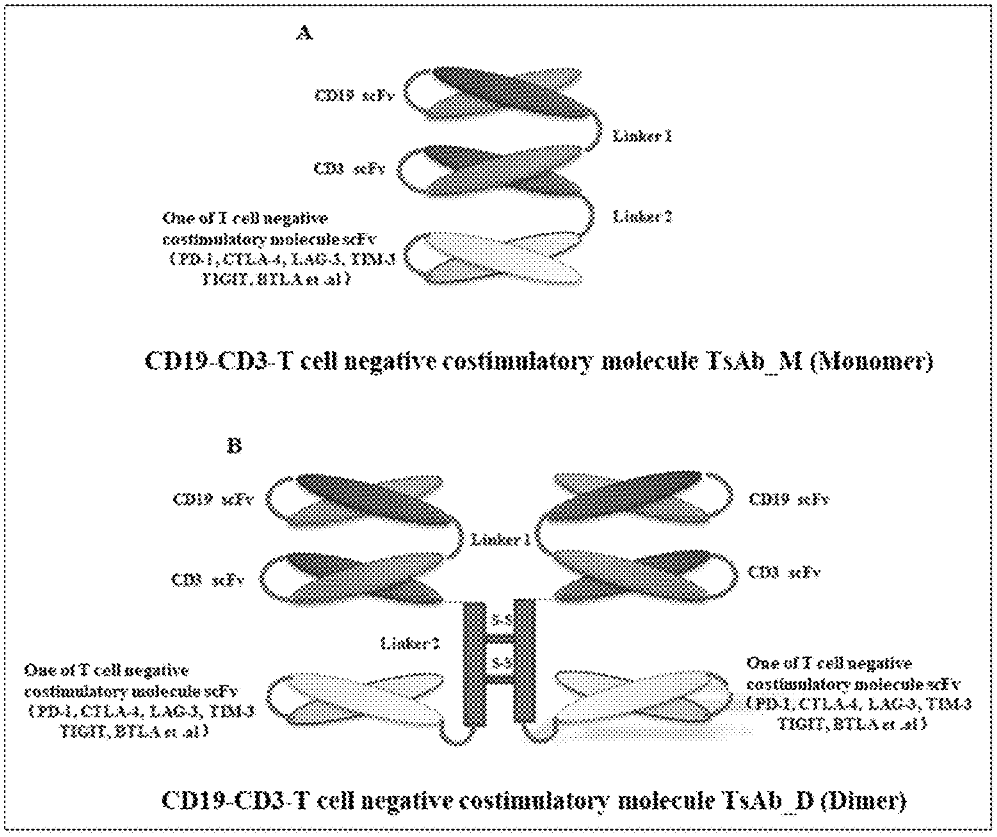
Figures 2, 4:
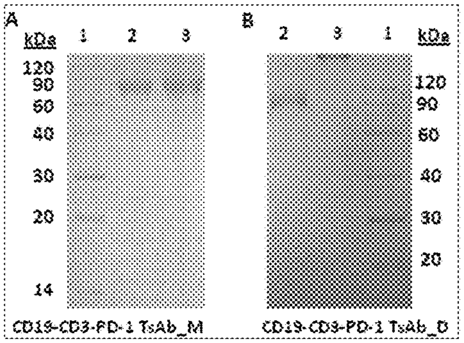
Figures 3A, 4:
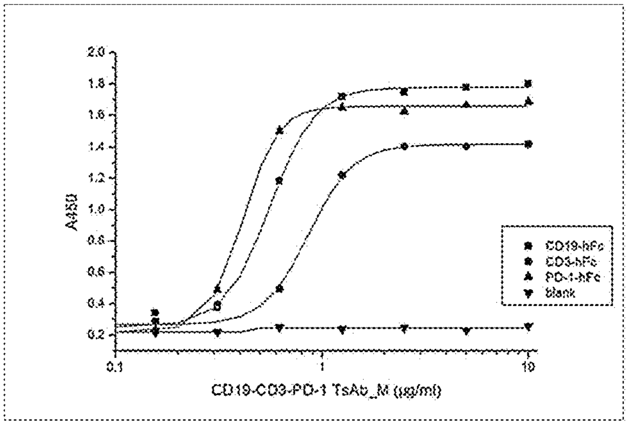
Figures 3B, 4:
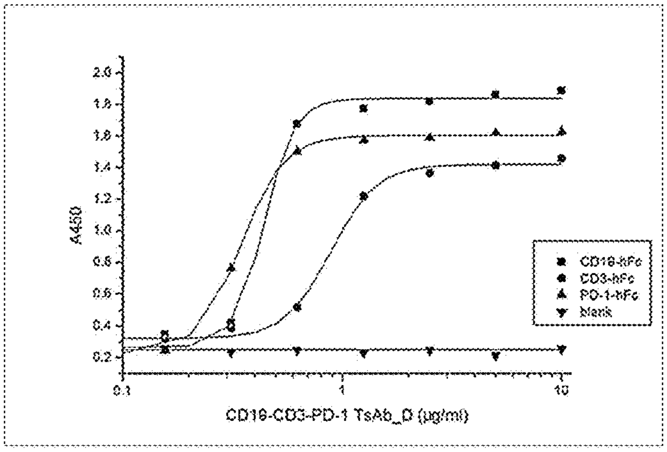
Figure 4:
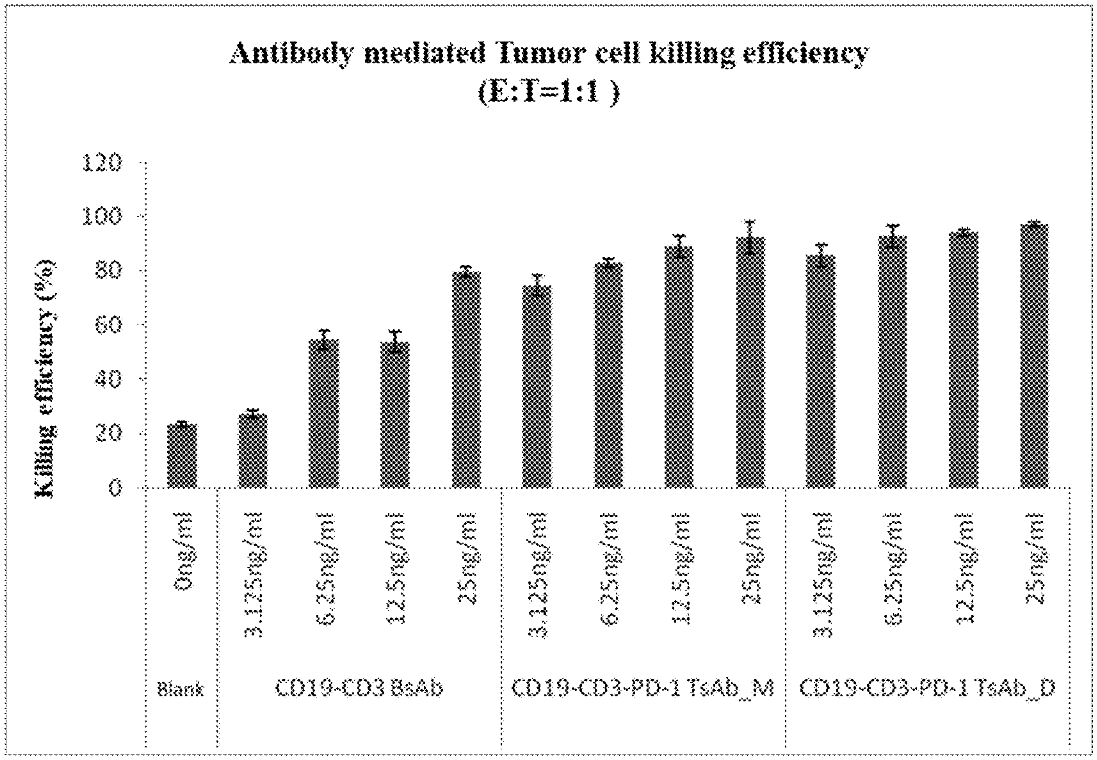
Figures 4, 5:
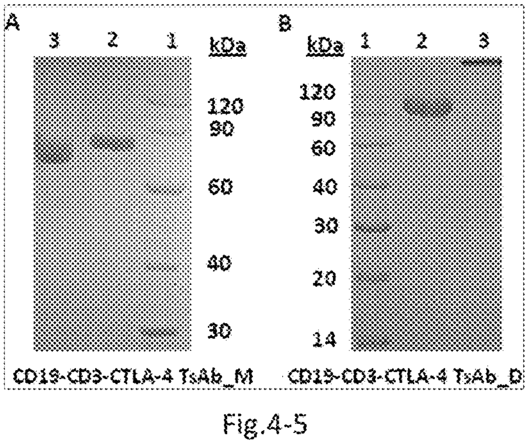
Figures 4, 5, 6, 6A:
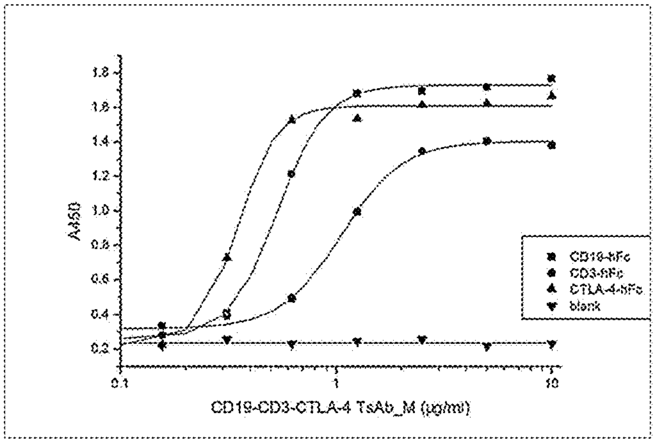
Figures 4, 5, 6, 6B:
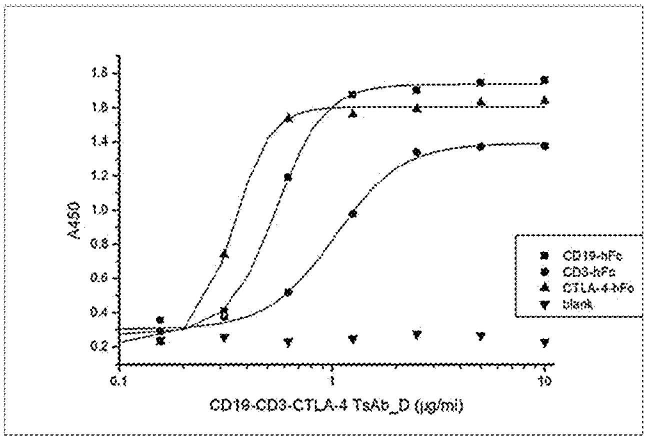
Figures 4, 5, 6, 7:
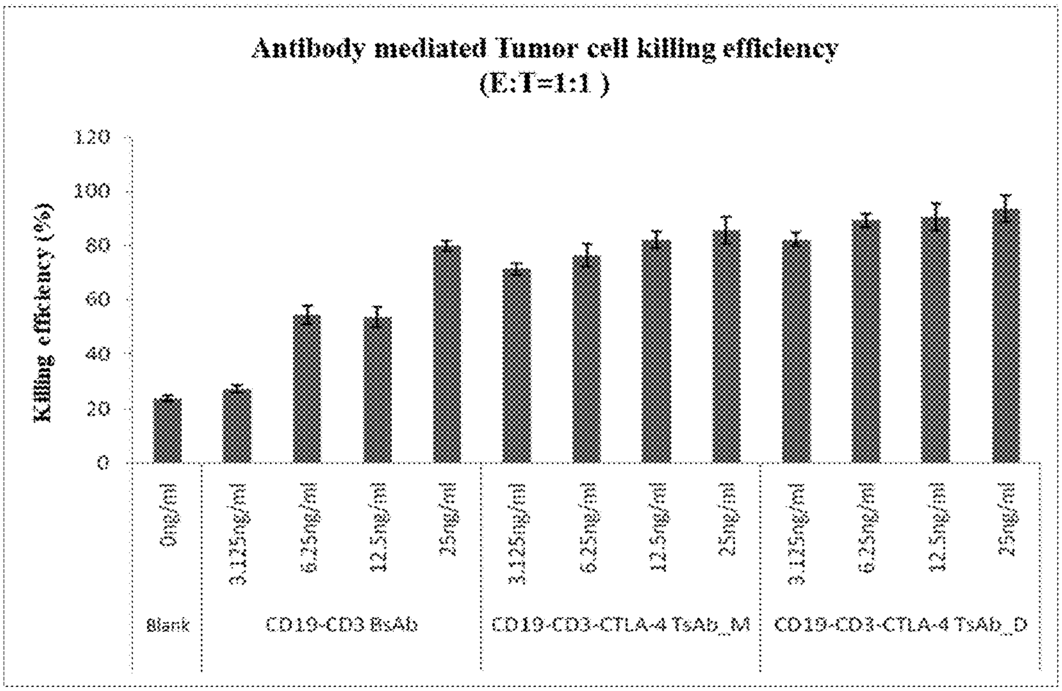
Figures 4, 5, 6, 7, 8:
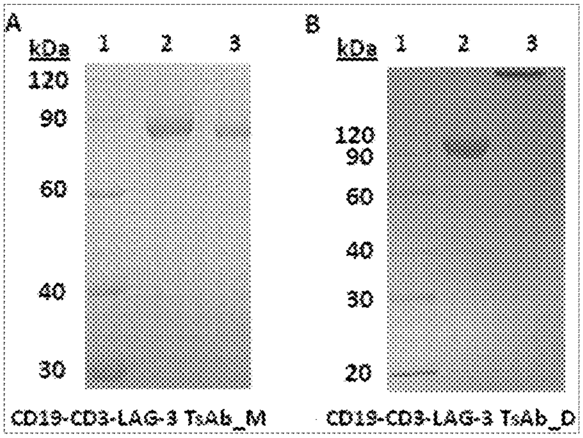
Figures 4, 5, 6, 7, 8, 9, 9A:
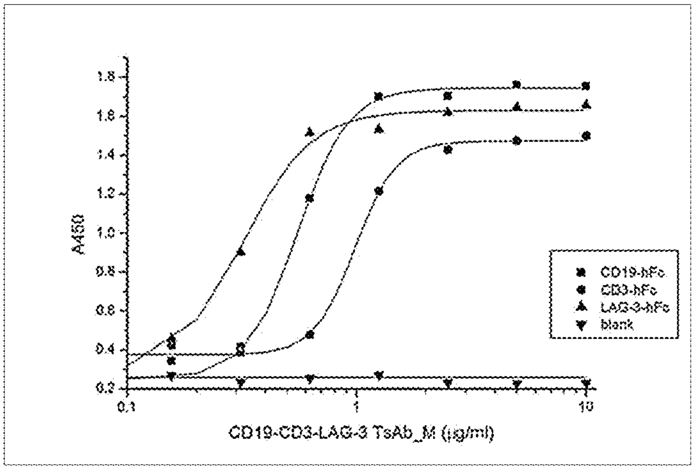
Figures 4, 5, 6, 7, 8, 9, 9B:
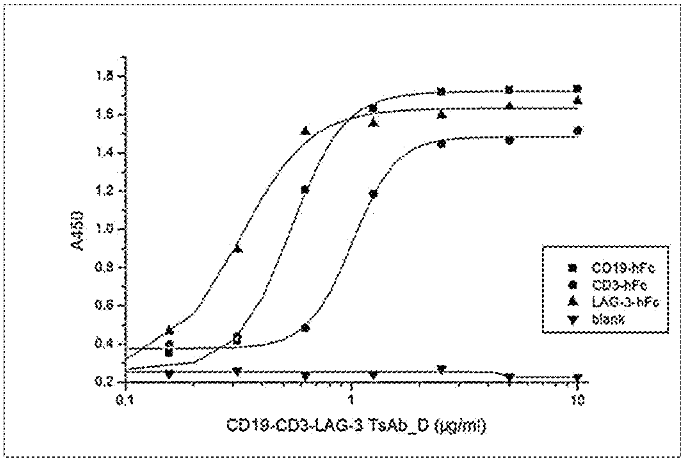
Figures 4, 5, 6, 7, 8, 9, 10:
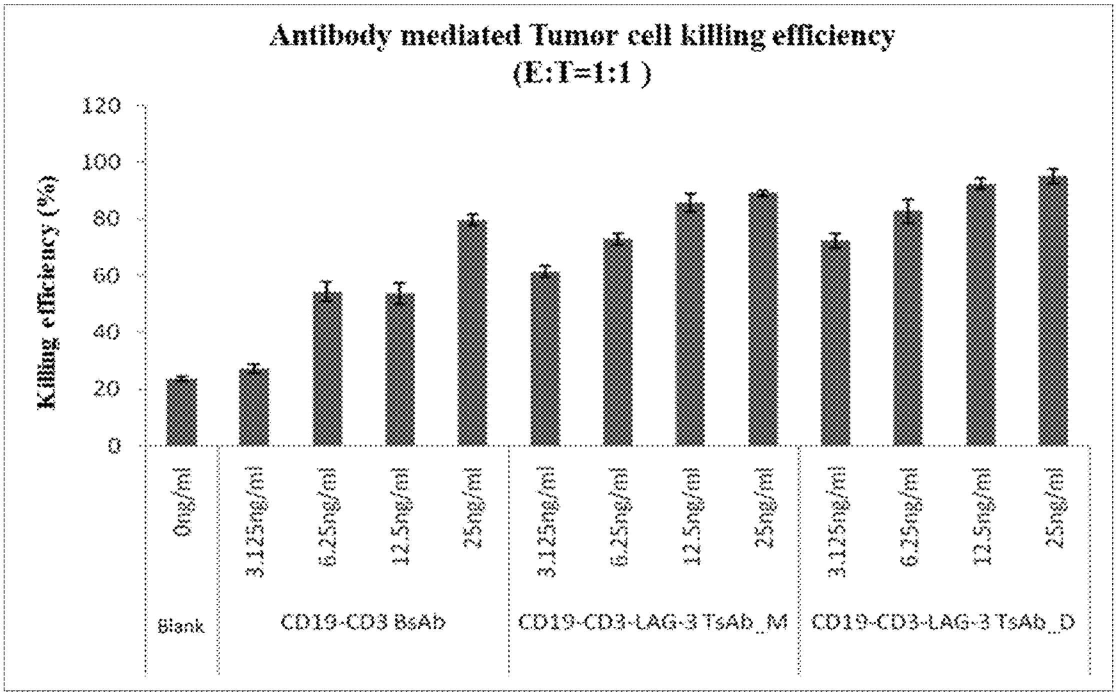
Figures 4, 5, 6, 7, 8, 9, 10, 11:
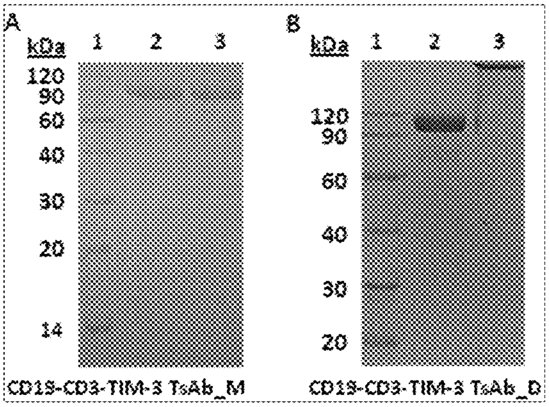
Figures 4, 5, 6, 7, 8, 9, 10, 11, 12, 12A:
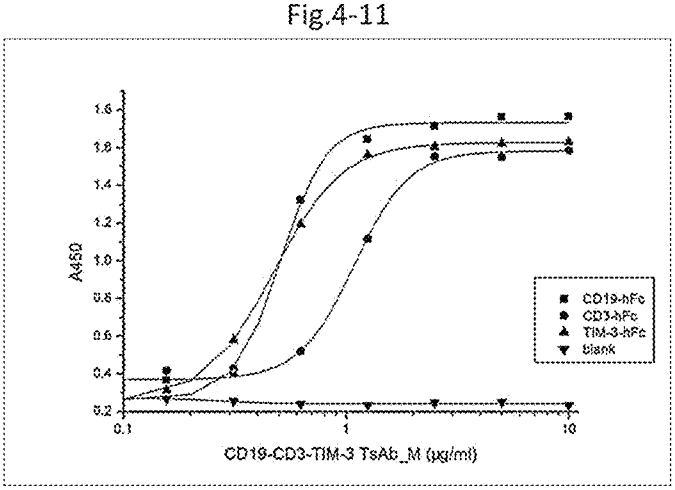
Figures 4, 5, 6, 7, 8, 9, 10, 11, 12, 12B:
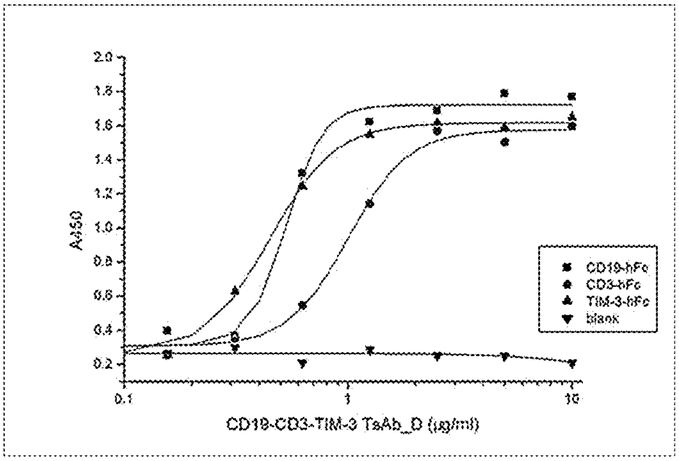
Figures 4, 5, 6, 7, 8, 9, 10, 11, 12, 13:
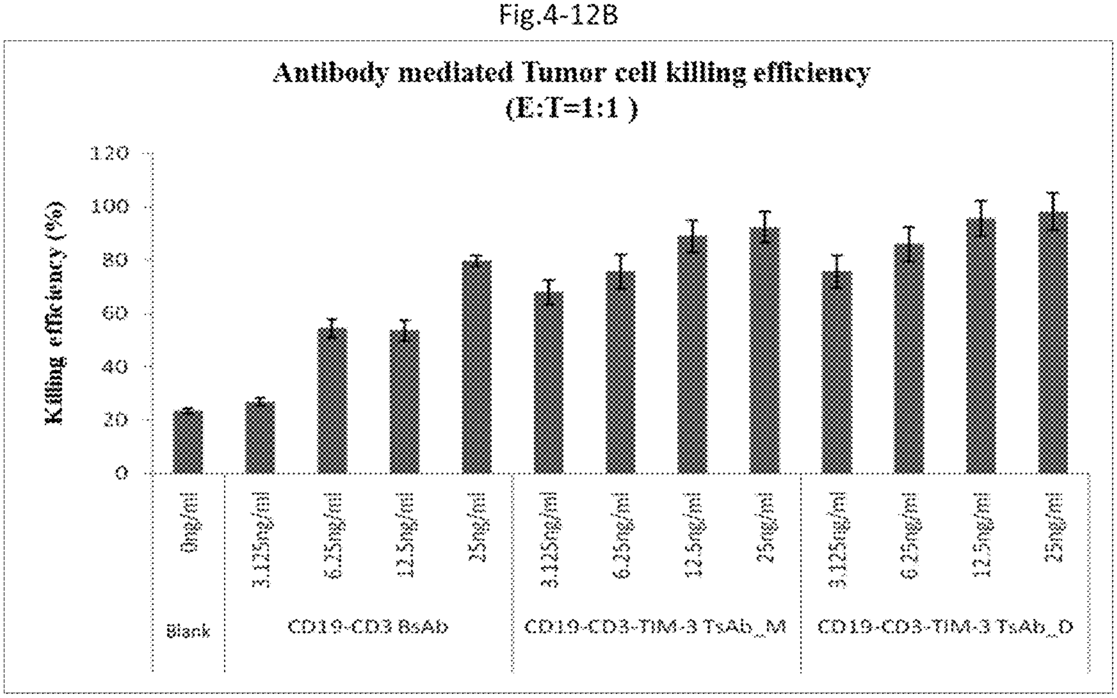
Figures 4, 5, 6, 7, 8, 9, 10, 11, 12, 13, 14:
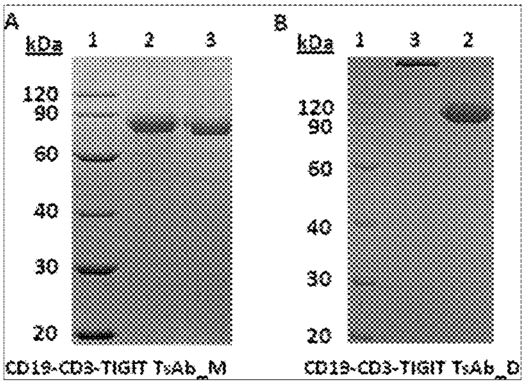
Figures 4, 5, 6, 7, 8, 9, 10, 11, 12, 13, 14, 15, 15A:
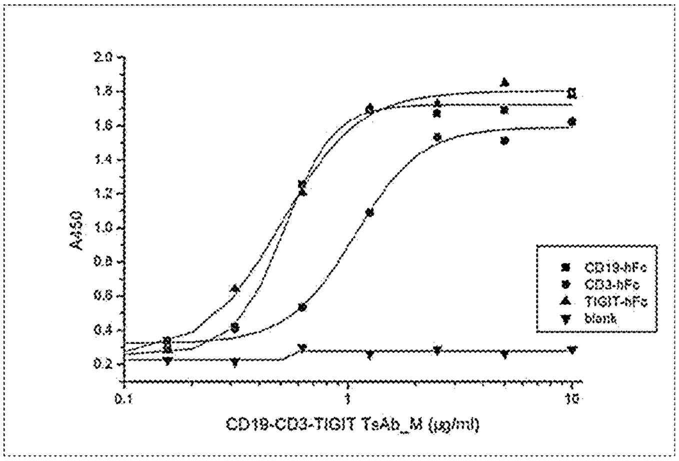
Figures 4, 5, 6, 7, 8, 9, 10, 11, 12, 13, 14, 15, 15B:
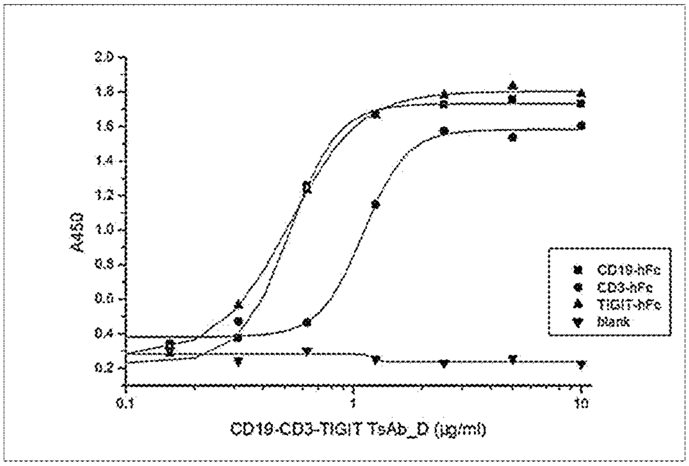
Figures 4, 5, 6, 7, 8, 9, 10, 11, 12, 13, 14, 15, 16:
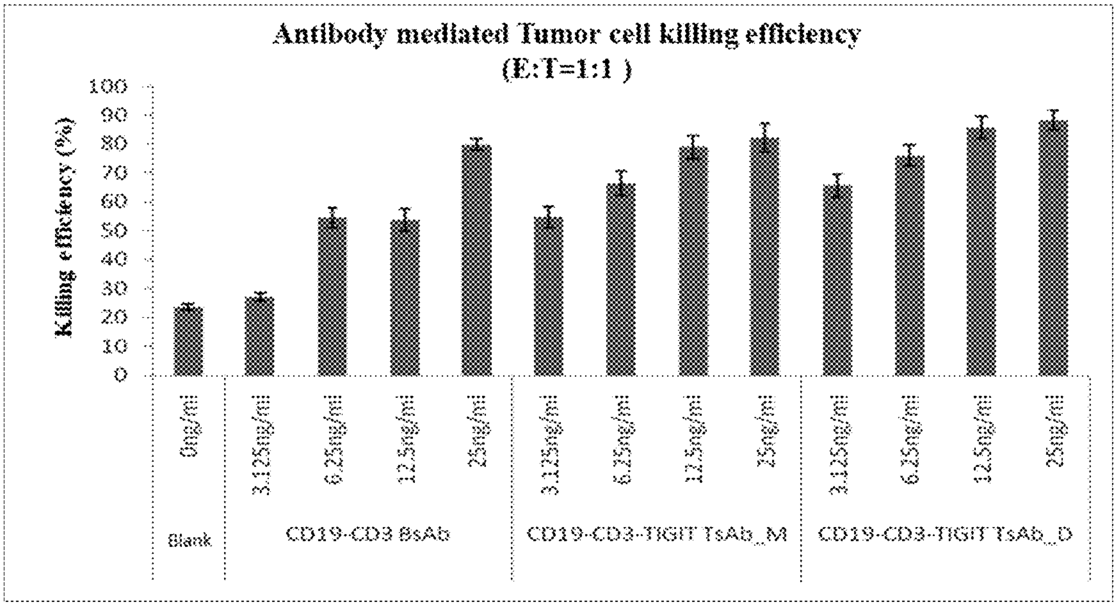
Figures 4, 5, 6, 7, 8, 9, 10, 11, 12, 13, 14, 15, 16, 17:
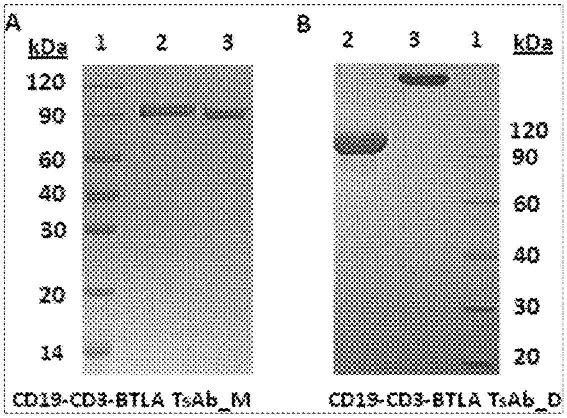
Figures 4, 5, 6, 7, 8, 9, 10, 11, 12, 13, 14, 15, 16, 17, 18, 18A:
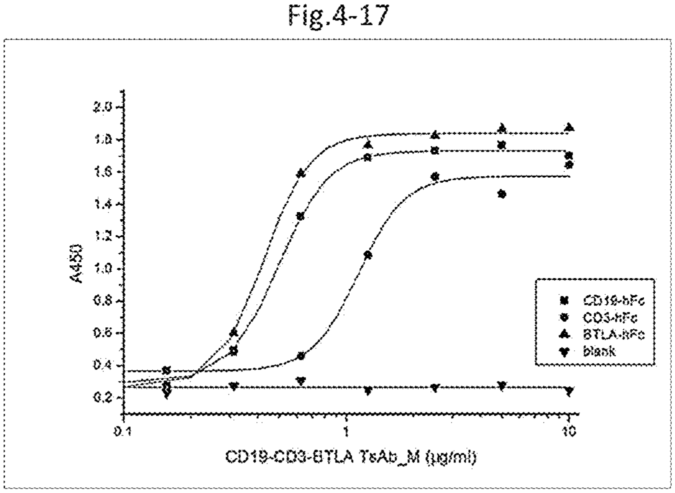
Figures 4, 5, 6, 7, 8, 9, 10, 11, 12, 13, 14, 15, 16, 17, 18, 18B:
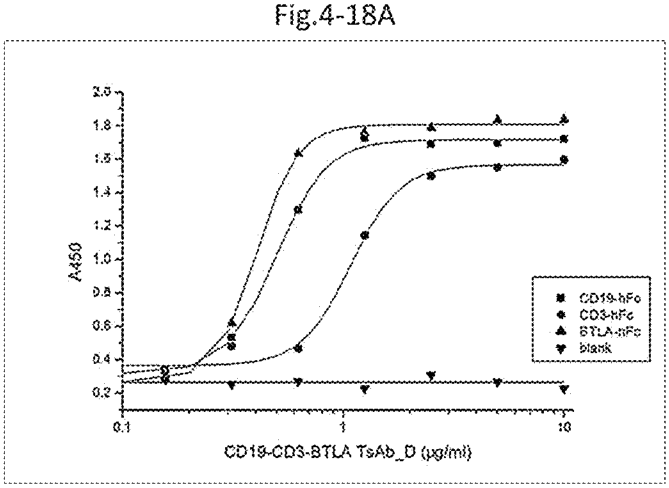
Figures 4, 5, 6, 7, 8, 9, 10, 11, 12, 13, 14, 15, 16, 17, 18, 19:
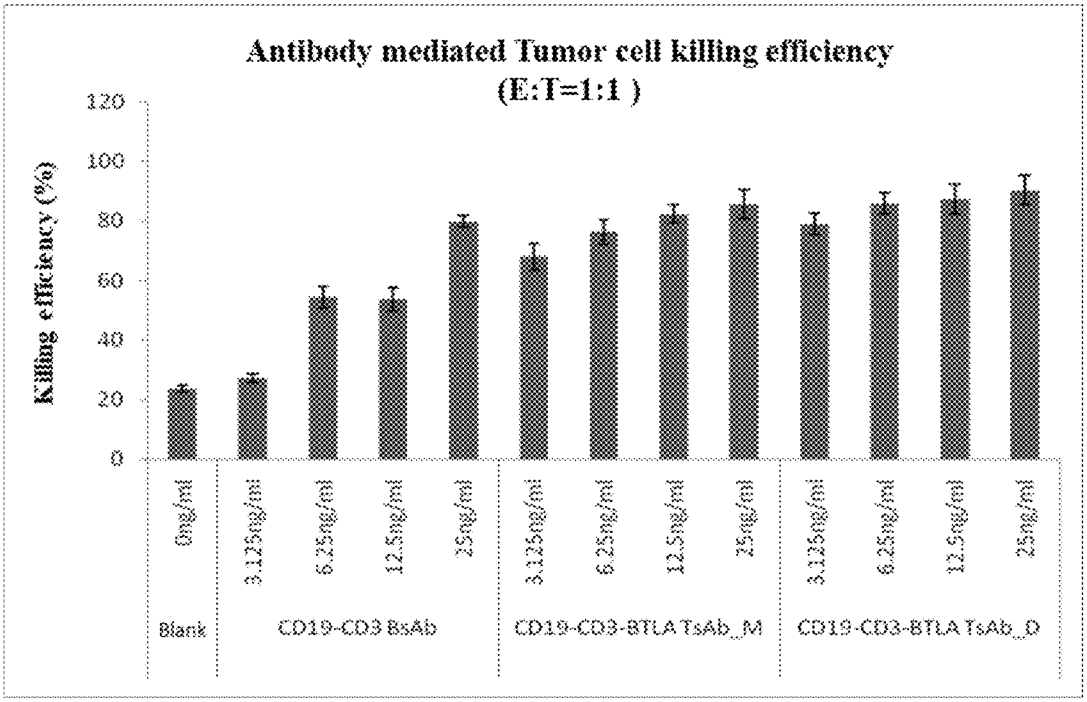

The final purified CD19-CD3-B7RP-1 TsM_M and CD19-CD3-B7RP-1 TsM_D recombinant protein was analyzed by SDS-PAGE, and the protein electrophoresis data under reduced and unreduced conditions were shown as FIG. 3-5. It shows that both purity of CD19-CD3-B7RP-1 TsM_M and CD19-CD3-B7RP-1 TsM_D recombinant protein are >95%. The theoretical molecule weight for CD19-CD3-B7RP-1 TsM_M is 80.6 kDa, and protein displayed the same single band under reduced and unreduced conditions. Because of the post-translational N-glycosylation modification on B7RP-1 extracellular domain, the real molecule weight of the band is bigger than theoretical value, so this tri-specific molecule is glycosylated monomer (FIG. 3-5A, Lane 1: protein marker for molecule weight; Lane 2: reduced CD19-CD3-B7RP-1 TsM_M; Lane 3: unreduced CD19-CD3-B7RP-1 TsM_M). The theoretical molecule weight for CD19-CD3-B7RP-1 TsM_D is 88.5 kDa, and protein displayed the same molecular weight as glycosylated monomer under reduced condition, the molecular weight is consistent with glycosylated dimer under non-reduced condition (FIG. 3-5B, Lane 1: protein marker for molecule weight; Lane 2: reduced CD19-CD3-B7RP-1 TsM_D; Lane 3: unreduced CD19-CD3-B7RP-1 TsM_D), which indicate two protein molecules link to each other by disulfide bond formed through IgD hinge region so that this tri-specific molecule is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-B7RP-1 TsM_M is monomer and CD19-CD3-B7RP-1 TsM_D is dimer.

Therefore, the amino acid sequence of CD19-CD3-B7RP-1 TsM_M monomer is shown as SEQ ID NO. 181.

The amino acid sequence of CD19-CD3-B7RP-1 TsM_D dimer is shown as SEQ ID NO. 183.

The amino acid sequence of anti-CD19 scFv is shown as SEQ ID NO. 197.

The amino acid sequence of anti-CD19 scFv heavy chain variable region is shown as SEQ ID NO. 198.

The amino acid sequence of anti-CD19 scFv light chain variable region is shown as SEQ ID NO. 199.

The amino acid sequence of anti-CD3 scFv is shown as SEQ ID NO. 200.

The amino acid sequence of anti-CD3 scFv heavy chain variable region is shown as SEQ ID NO. 201.

The amino acid sequence of anti-CD3 scFv light chain variable region is shown as SEQ ID NO. 202.

The amino acid sequence of B7RP-1 extracellular domain is shown as SEQ ID NO. 204.

The amino acid sequence of CD19-CD3-B7RP-1 TsM_M monomer linker (Linker 1) is shown as SEQ ID NO. 159.

The amino acid sequence of CD19-CD3-B7RP-1 TsM_M monomer linker (Linker 2) is shown as SEQ ID NO. 161.

The amino acid sequence of CD19-CD3-B7RP-1 TsM_D dimer linker (Linker 1) is shown as SEQ ID NO. 163.

The amino acid sequence of CD19-CD3-B7RP-1 TsM_D dimer linker (Linker 2) is shown as SEQ ID NO. 165.

Embodiment 3-7: CD19, CD3 Antigen Binding and Co-Stimulatory Molecule ICOS Binding Activity Test of CD19-CD3-B7RP-1 TsM_M and CD19-CD3-B7RP-1 TsM_D by ELISA ELISA Procedure:

1. Recombinant antigen coating: 96-well plates were coated by human CD19-hFc, human CD3-hFc and human ICOS-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific molecule samples respectively and keeping plates at 37° C. for 1 hour. Sample serial dilution includes: using 10 μg/ml purified CD19-CD3-B7RP-1 TsM_M or CD19-CD3-B7RP-1 TsM_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5-10 min at room temperature.

5. Reaction termination and result test: adding 100 μl per well of 1M HCl to stop reaction, and reading OD value of 450 nm absorbance on ELISA reader.

The results of ELISA are shown in FIGS. 3-6A and 3-6B. The four curves in the figure represent three four results: ■ coated with 1 μg/ml CD19-hFc recombinant antigen, ● coated with 1 μg/ml CD3-hFc recombinant antigen; ▲ coated with 1 μg/ml ICOS-hFc recombinant antigen; ▼ no antigen coated result. FIG. 3-6A indicates that CD19-CD3-B7RP-1 TsM_M has antigen binding activity with CD19-hFc, CD3-hFc and ICOS-hFc in vitro, among which ICOS and CD19 have higher binding activity, and CD3 has the weaker binding activity. FIG. 3-6B indicates that CD19-CD3-B7RP-1 TsM_D has antigen binding activity with CD19-hFc, CD3-hFc and ICOS-hFc in vitro as well, among which ICOS and CD19 have higher binding activity, and CD3 has weaker binding activity.

Embodiment 3-8: CD19-CD3-B7RP-1 Tri-Specific Molecule-Mediated Cell Killing Assay Human PBMC (Peripheral blood mononuclear cell, PBMC) was used as experiment material. The above-mentionedTiTE tri-specific molecule CD19-CD3-B7RP-1 TsM_M in monomeric form, TiTE tri-specific molecule CD19-CD3-B7RP-1 TsM_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Count cell number and cells are ready for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-B7RP-1 TsM_M and CD19-CD3-B7RP-1 TsM_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{OD \text{ value of } Raji \text{ cells} + OD \text{ value of } CIK \text{ cells} - \text{detected } OD \text{ value}}{OD \text{ value of } Raji \text{ cells}} \times 100\%$$

The results are shown in FIG. 3-7: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-B7RP-1 TsM_D have the best cell killing effect. The killing efficacy is about 92%, 88% and 84%. The effect of CD19-CD3-B7RP-1 TsM_M is in the second place, the killing efficacy is about 89%, 85% and 78%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-B7RP-1 TsM_D and CD19-CD3-B7RP-1 TsM_M against Raji cells is improved to some extent, and the killing efficacy is about 79% and 68%, respectively. While CD19-CD3 BsAb had no effect compared with the blank control. The above results indicated that the two forms of CD19-CD3-B7RP-1 TiTE tri-specific molecule-mediated T cell-targeted killing activity against CD19-positive tumor cells were superior to that of CD19-CD3 BiTE bispecific antibody. The dimeric form has a better effect than the monomer form.

Embodiment 3-9: The Eukaryotic Expression Vector Construction of CD19-CD3-OX40L TsM_M and CD19-CD3-OX40L TsM_D In this disclosure, the TiTE tri-specific molecule including anti-CD19 scFv, anti-CD3 scFv, and co-stimulatory molecule ligand OX40L extracellular domain on human T cell is named as CD19-CD3-OX40L TsM.

1. Construction Design of CD19-CD3-OX40L TsM_M and CD19-CD3-OX40L TsM_D

Construction design of CD19-CD3-OX40L TsM_M Monomer:

The sequences of the anti-CD19 scFv, anti-CD3 scFv and OX40L extracellular domain are linked by a linker. Specifically, the sequence of anti-CD19 scFv and the anti-CD3 scFv are linked by Linker 1, the sequence of anti-CD3 scFv and OX40L extracellular domain are linked by Linker 2.

Construction design of CD19-CD3-OX40L TsM_D Dimer:

The sequences of the anti-CD19 scFv, anti-CD3 scFv and OX40L extracellular domain are linked by linkers. Specifically, the sequences of anti-CD19 scFv and anti-CD3 scFv are linked by Linker 1, the sequences of anti-CD3 scFv and OX40L extracellular domain are linked by IgD hinge region (Ala90-Val170) as Linker 2.

In order to express the tri-specific molecule in mammalian cells, codon optimization of mammalian system was performed for the sequence of anti-CD19 scFv, anti-CD3 scFv, and OX40L extracellular domain.

The nucleotide sequence of anti-CD19 scFv heavy chain variable region is shown as SEQ ID NO. 209.

The nucleotide sequence of anti-CD19 scFv light chain variable region is shown as SEQ ID NO. 210.

The nucleotide sequence of anti-CD19 scFv is shown as SEQ ID NO. 208.

The nucleotide sequence of anti-CD3 scFv heavy chain variable region is shown as SEQ ID NO. 212.

The nucleotide sequence of anti-CD3 scFv light chain variable region is shown as SEQ ID NO. 213.

The nucleotide sequence of anti-CD3 scFv is shown as SEQ ID NO. 211.

The nucleotide sequence of OX40L extracellular domain sequence is shown as SEQ ID NO. 216.

The nucleotide sequence of CD19-CD3-OX40L TsM_M monomer linker (Linker 1) is shown as SEQ ID NO. 160.

The nucleotide sequence of CD19-CD3-OX40L TsM_M monomer linker (Linker 2) is shown as SEQ ID NO. 162.

The nucleotide sequence of CD19-CD3-OX40L TsM_D dimer linker (Linker 1) is shown as SEQ ID NO. 164.

The nucleotide sequence of CD19-CD3-OX40L TsM_D dimer linker (Linker 2) is shown as SEQ ID NO. 166.

In order to express tri-specific molecule successfully in CHO-S cells and secret into medium, signal peptide of antibody secretory expression was selected in this Embodiment.

The amino acid sequence of this secretory signal peptide is shown as SEQ ID NO. 219.

The nucleotide sequence of this secretory signal peptide is shown as SEQ ID NO. 220 in details.

2. CD19-CD3-OX40L TsM_M and CD19-CD3-OX40L TsM_D Eukaryotic Expression Vector Construction The construction and expression of this tri-specific molecule in the present disclosure selected mammalian cell protein transient expression vector pcDNA3.1 (purchased from Invitrogen, Shanghai). In order to construct the tri-specific molecules in monomer and dimer form, primers were designed as in table 3-3. All the primers were synthesized by Genewiz, Suzhou, and DNA template for PCR was synthesized by Synbio Technologies, Suzhou.

The cloning construct for CD19-CD3-OX40L TsM_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+OX40L extracellular domain sequence by primer pairs Sig-CD19-F and CD19-R, CD19-G4S-CD3-F and CD3-R, and CD3-$(GGGGS)_3$-OX40L-F and pcDNA3.1-OX40L-R, respectively. The cloning construct for CD19-CD3-OX40L TsM_D includes: amplifying signal peptide by primers pcDNA3.1-Sig-F and Sig-R, and then amplifying anti-CD19 scFv, GGGGS Linker 1+anti-CD3 scFv, and IgD hinge region Linker2+OX40L extracellular domain sequence by primer pairs Sig-CD19-F and CD19-R, CD19-G4S-CD3-F and CD3-R, CD3-IgD-F and IgD-R, and IgD-OX40L-F and pcDNA3.1-OX40L-R, respectively. After PCR amplification, by using NovoRec® PCR One-Step Cloning Kit (purchased from Wujiang Novoprotein Technology Co., Ltd.), the full length of tri-specific molecule monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-OX40L TsM_M monomer and CD19-CD3-OX40L TsM_D dimer both had the right full DNA sequence as expected.

The nucleotide sequence of CD19-CD3-OX40L TsM_M monomer is shown as SEQ ID NO. 186.

The nucleotide sequence of CD19-CD3-OX40L TsM_D dimer is shown as SEQ ID NO. 188.

TABLE 3-3

Primers used in CD19-CD3-OX40L tri-specific molecule gene cloning

| Primer name | Sequence | No. |
|---|---|---|
| CD3-$(GGGGS)_3$-OX40L-F | GGCACCAAGCTGGAGCTGAAGGGCGGCGGCGGCAGCGGCGGCGGCGGCAGCGGCGGCGGCGGCAGCCAGGTGAGCCACCGCTACCCC | SEQ ID NO. 235 |
| pcDNA3.1-OX40L-R | CTGATCAGCGGTTTAAACTTAAGCTTTCACAGCACGCAGAACTCGCCGGG | SEQ ID NO. 236 |
| IgD-OX40L-F | CACACCCAGCCCCTGGGCGTGCAGGTGAGCCACCGCTACCCC | SEQ ID NO. 237 |

Embodiment 3-10: The Expression and Purification of CD19-CD3-OX40L TsM_M and CD19-CD3-OX40L TsM_D 1. The Expression of CD19-CD3-OX40L TsM_M and CD19-CD3-OX40L TsM_D 1.1 The cell density of CHO-S cells (purchased from Thermo Fisher Scientific) was 0.5~$0.6\times10^6$/ml one day before transfection.

1.2 Calculating cell density at the day of transfection, plasmid transfection can be performed when the density is in the range of 1-$1.4\times10^6$/ml and live percentage is >90%.

1.3 Transfection complex recipes: each project (CD19-CD3-OX40L TsM_M and CD19-CD3-OX40L TsM_D) requires two centrifuge tubes/flasks. Take total 20 ml as an example, the recombinant plasmids from Embodiment 3-9 were taken: Tube 1: 600 μl PBS, 20 μg recombinant plasmid, mix well; Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15-20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-OX40L TsM_M and CD19-CD3-OX40L TsM_D 2.1 Sample pretreatment Taking 20 ml cell medium after transfection, adding 20 mM PB, 200 mM NaCl, and adjusting pH to 7.5;

2.2 Purification of Protein L affinity chromatography column Protein purification chromatography column: Protein L affinity chromatography column (purchased from GE Healthcare, column volume: 1.0 ml) Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-OX40L TsM_M and CD19-CD3-OX40L TsM_D recombinant protein was analyzed by SDS-PAGE, and the protein electrophoresis data under reduced and unreduced conditions were shown as FIG. 3-8. It shows that both purity of CD19-CD3-OX40L TsM_M and CD19-CD3-OX40L TsM_D recombinant protein are >95%. The theoretical molecule weight for CD19-CD3-OX40L TsM_M is 69.6 kDa, and protein displayed the same single band under reduced and unreduced conditions. Because of the post-translational N-glycosylation modification on OX40L extracellular domain, the real molecule weight of the band is bigger than theoretical value, so this tri-specific molecule is glycosylated monomer (FIG. 3-8A, Lane 1: protein marker for molecule weight; Lane 2: reduced CD19-CD3-OX40L TsM_M; Lane 3: unreduced CD19-CD3-OX40L TsM_M). The theoretical molecule weight for CD19-CD3-OX40L TsM_D is 77.5 kDa, and protein displayed the same molecular weight as glycosylated monomer under reduced condition, the molecular weight is consistent with glycosylated dimer under non-reduced condition (FIG. 3-8B, Lane 1: protein marker for molecule weight; Lane 2: reduced CD19-CD3-OX40L TsM_D; Lane 3: unreduced CD19-CD3-OX40L TsM_D), which indicate two protein molecules link to each other by disulfide bond formed through IgD hinge region so that this tri-specific molecule is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-OX40L TsM_M is monomer and CD19-CD3-OX40L TsM_D is dimer.

Therefore, the amino acid sequence of CD19-CD3-OX40L TsM_M monomer is shown as SEQ ID NO. 185.

The amino acid sequence of CD19-CD3-OX40L TsM_D dimer is shown as SEQ ID NO. 187.

The amino acid sequence of anti-CD19 scFv is shown as SEQ ID NO. 197.

The amino acid sequence of anti-CD19 scFv heavy chain variable region is shown as SEQ ID NO. 198.

The amino acid sequence of anti-CD19 scFv light chain variable region is shown as SEQ ID NO. 199.

The amino acid sequence of anti-CD3 scFv is shown as SEQ ID NO. 200.

The amino acid sequence of anti-CD3 scFv heavy chain variable region is shown as SEQ ID NO. 201.

The amino acid sequence of anti-CD3 scFv light chain variable region is shown as SEQ ID NO. 202.

The amino acid sequence of OX40L extracellular domain is shown as SEQ ID NO. 205.

The amino acid sequence of CD19-CD3-OX40L TsM_M monomer linker (Linker 1) is shown as SEQ ID NO. 159.

The amino acid sequence of CD19-CD3-OX40L TsM_M monomer linker (Linker 2) is shown as SEQ ID NO. 161.

The amino acid sequence of CD19-CD3-OX40L TsM_D dimer linker (Linker 1) is shown as SEQ ID NO. 163.

The amino acid sequence of CD19-CD3-OX40L TsM_D dimer linker (Linker 2) is shown as SEQ ID NO. 165.

Embodiment 3-11: CD19, CD3 Antigen Binding and Co-Stimulatory Molecule OX40 Binding Activity Test of CD19-CD3-OX40L TsM_M and CD19-CD3-OX40L TsM_D by ELISA ELISA Procedure:

1. Recombinant antigen coating: 96-well plates were coated by human CD19-hFc, human CD3-hFc and human OX40-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific molecule samples respectively and keeping plates at 37° C. for 1 hour. Sample serial dilution includes: using 10 μg/ml purified CD19-CD3-OX40L TsM_M or CD19-CD3-OX40L TsM_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5~10 min at room temperature.

5. Reaction termination and result test: adding 100 μl per well of 1M HCl to stop reaction, and reading OD value of 450 nm absorbance on ELISA reader.

The results of ELISA are shown in FIGS. 3-9A and 3-9B. The four curves in the figure represent three four results: ■ coated with 1 μg/ml CD19-hFc recombinant antigen, ● coated with 1 μg/ml CD3-hFc recombinant antigen; ▲ coated with 1 μg/ml OX40-hFc recombinant antigen; ▼ no antigen coated result. FIG. 3-9A indicates that CD19-CD3-OX40L TsM_M has antigen binding activity with CD19-hFc, CD3-hFc and OX40-hFc in vitro, among which CD19 has the highest binding activity, CD3 has the second highest binding activity, and OX40 has the weakest binding activity. FIG. 3-9B indicates that CD19-CD3-OX40L TsM_D has antigen binding activity with CD19-hFc, CD3-hFc and OX40-hFc in vitro as well, among which CD19 has the highest binding activity, CD3 has the second highest binding activity, and OX40 has the weakest binding activity.

Embodiment 3-12: CD19-CD3-OX40L Tri-Specific Molecule-Mediated Cell Killing Assay Human PBMC (Peripheral blood mononuclear cell, PBMC) was used as experiment material. The above-mentioned TiTE tri-specific molecule CD19-CD3-OX40L TsM_M in monomeric form, TiTE tri-specific molecule CD19-CD3-OX40L TsAb_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Count cell number and cells are ready for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-OX40L TsM_M and CD19-CD3-OX40L TsM_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any protein was blank control of killing efficacy.

$$\text{Killing efficacy (\%)} = \frac{OD \text{ value of } Raji \text{ cells} + OD \text{ value of } CIK \text{ cells} - \text{detected } OD \text{ value}}{OD \text{ value of } Raji \text{ cells}} \times 100\%$$

The results are shown in FIG. 3-10: When the CIK effector cells: Raji target cells (E:T ratio) were 1:1, the killing efficacy was about 23% after 3 h without adding any protein. The killing efficacy of CIK cells on Raji cells was significantly improved under the conditions of adding higher concentrations of antibodies (25, 12.5, 6.25 ng/ml). Among them, Cells mediated by CD19-CD3-OX40L TsM_D have the best cell killing effect. The killing efficacy is about 96%, 92% and 87%. The effect of CD19-CD3-OX40L TsM_M is in the second place, the killing efficacy is about 93%, 88% and 82%. The effect of CD19-CD3 BsAb is the weakest and the killing efficacy is about 80%, 54% and 54%. Under the condition of adding lower concentration protein (3.125 ng/ml), the killing efficacy of CIK cells mediated by CD19-

CD3-OX40L TsM_D and CD19-CD3-OX40L TsM_M against Raji cells is improved to some extent, and the killing efficacy is about 82% and 72%, respectively. While CD19-CD3 BsAb had no effect compared with the blank control. The above results indicated that the two forms of CD19-CD3-OX40L TiTE tri-specific molecule-mediated T cell-targeted killing activity against CD19-positive tumor cells were superior to that of BiTE bispecific antibody. The dimeric form has a better effect than the monomer form.

Embodiment 3-13: The Eukaryotic Expression Vector Construction of CD19-CD3-GITRL TsM_M and CD19-CD3-GITRL TsM_D In this disclosure, the TiTE tri-specific molecule including anti-CD19 scFv, anti-CD3 scFv, and co-stimulatory molecule ligand GITRL extracellular domain on human T cell is named as CD19-CD3-GITRL TsM.

1. Construction Design of CD19-CD3-GITRL TsM_M and CD19-CD3-GITRL TsM_D

Construction design of CD19-CD3-GITRL TsM_M Monomer:

The sequences of the anti-CD19 scFv, anti-CD3 scFv and GITRL extracellular domain are linked by a linker. Specifically, the sequence of anti-CD19 scFv and the anti-CD3 scFv are linked by Linker 1, the sequence of anti-CD3 scFv and GITRL extracellular domain are linked by Linker 2.

Construction design of CD19-CD3-GITRL TsM_D Dimer:

The sequences of the anti-CD19 scFv, anti-CD3 scFv and GITRL extracellular domain are linked by linkers. Specifically, the sequences of anti-CD19 scFv and anti-CD3 scFv are linked by Linker 1, the sequences of anti-CD3 scFv and GITRL extracellular domain are linked by IgD hinge region (Ala90-Val170) as Linker 2.

In order to express the tri-specific molecule in mammalian cells, codon optimization of mammalian system was performed for the sequence of anti-CD19 scFv, anti-CD3 scFv, and GITRL extracellular domain.

The nucleotide sequence of anti-CD19 scFv heavy chain variable region is shown as SEQ ID NO. 209.

The nucleotide sequence of anti-CD19 scFv light chain variable region is shown as SEQ ID NO. 210.

The nucleotide sequence of anti-CD19 scFv is shown as SEQ ID NO. 208.

The nucleotide sequence of anti-CD3 scFv heavy chain variable region is shown as SEQ ID NO. 212.

The nucleotide sequence of anti-CD3 scFv light chain variable region is shown as SEQ ID NO. 213.

The nucleotide sequence of anti-CD3 scFv is shown as SEQ ID NO. 211.

The nucleotide sequence of GITRL extracellular domain sequence is shown as SEQ ID NO. 217.

The nucleotide sequence of CD19-CD3-GITRL TsM_M monomer linker (Linker 1) is shown as SEQ ID NO. 160.

The nucleotide sequence of CD19-CD3-GITRL TsM_M monomer linker (Linker 2) is shown as SEQ ID NO. 162.

The nucleotide sequence of CD19-CD3-GITRL TsM_D dimer linker (Linker 1) is shown as SEQ ID NO. 164.

The nucleotide sequence of CD19-CD3-GITRL TsM_D dimer linker (Linker 2) is shown as SEQ ID NO. 166.

In order to express tri-specific molecule successfully in CHO-S cells and secret into medium, signal peptide of antibody secretory expression was selected in this Embodiment.

The amino acid sequence of this secretory signal peptide is shown as SEQ ID NO. 219.

The nucleotide sequence of this secretory signal peptide is shown as SEQ ID NO. 220.

2. CD19-CD3-GITRL TsM_M and CD19-CD3-GITRL TsM_D Eukaryotic Expression Vector Construction The construction and expression of this tri-specific molecule in the present disclosure selected mammalian cell protein transient expression vector pcDNA3.1 (purchased from Invitrogen, Shanghai). In order to construct the tri-specific molecules in monomer and dimer form, primers were designed as in table 3-4. All the primers were synthesized by Genewiz, Suzhou, and DNA template for PCR was synthesized by Synbio Technologies, Suzhou.

The cloning construct for CD19-CD3-GITRL TsM_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+GITRL extracellular domain sequence by primer pairs Sig-CD19-F and CD19-R, CD19-G4S-CD3-F and CD3-R, and CD3-$(GGGGS)_3$-GITRL-F and pcDNA3.1-GITRL-R, respectively. The cloning construct for CD19-CD3-GITRL TsM_D includes: amplifying signal peptide by primers pcDNA3.1-Sig-F and Sig-R, and then amplifying anti-CD19 scFv, GGGGS Linker 1+anti-CD3 scFv, IgD hinge region Linker2, and GITRL extracellular domain sequence by primer pairs Sig-CD19-F and CD19-R, CD19-G4S-CD3-F and CD3-R, CD3-IgD-F and IgD-R, and IgD-GITRL-F and pcDNA3.1-GITRL-R, respectively. After PCR amplification, by using NovoRec® PCR One-Step Cloning Kit (purchased from Wujiang Novoprotein Technology Co., Ltd.), the full length of tri-specific molecule monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-GITRL TsM_M monomer and CD19-CD3-GITRL TsM_D dimer both had the right full DNA sequence as expected.

The nucleotide sequence of CD19-CD3-GITRL TsM_M monomer is shown as SEQ ID NO. 190.

The nucleotide sequence of CD19-CD3-GITRL TsM_D dimer is shown as SEQ ID NO. 192.

TABLE 3-4

Primers used in CD19-CD3-GITRL tri-specific molecule gene cloning

| Primer name | Sequence | No. |
|---|---|---|
| CD3-$(GGGGS)_3$-GITRL-F | GGCACCAAGCTGGAGCTGAAGGGCGGCGGCGGCAGCGGCGGCGGCGGCAGCGGCGGCGGCGGCAGCCAGCTGGAGACCGCCAAGGAG | SEQ ID NO. 238 |
| pcDNA3.1-GITRL-R | CTGATCAGCGGTTTAAACTTAAGCTTTCAGCTGATGAACTGGGGGTTGGC | SEQ ID NO. 239 |
| IgD-GITRL-F | CACACCCAGCCCCTGGGCGTGCAGCTGGAGACCGCCAAGGAG | SEQ ID NO. 240 |

Embodiment 3-14: The Expression and Purification of CD19-CD3-GITRL TsM_M and CD19-CD3-GITRL TsM_D 1. The Expression of CD19-CD3-GITRL TsM_M and CD19-CD3-GITRL TsM_D 1.1 The cell density of CHO-S cells (purchased from Thermo Fisher Scientific) was 0.5~0.6×$10^6$/ml one day before transfection.

1.2 Calculating cell density at the day of transfection, plasmid transfection can be performed when the density is in the range of 1~1.4×$10^6$/ml and live percentage is >90%.

1.3 Transfection complex recipes: each project (CD19-CD3-GITRL TsM_M and CD19-CD3-GITRL TsM_D) requires two centrifuge tubes/flasks. Take total 20 ml as an example, the recombinant plasmids from Embodiment 3-13 were taken: Tube 1: 600 μl PBS, 20 μg recombinant plasmid, mix well; Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15-20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-GITRL TsM_M and CD19-CD3-GITRL TsM_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-GITRL TsM_M and CD19-CD3-GITRL TsM_D recombinant protein was analyzed by SDS-PAGE, and the protein electrophoresis data under reduced and unreduced conditions were shown as FIG. 3-11. It shows that both purity of CD19-CD3-GITRL TsM_M and CD19-CD3-GITRL TsM_D recombinant protein are >95%. The theoretical molecule weight for CD19-CD3-GITRL TsM_M is 68.7 kDa, and protein displayed the same single band under reduced and unreduced conditions. Because of the post-translational N-glycosylation modification on GITRL extracellular domain, the real molecule weight of the band is bigger than theoretical value, so this tri-specific molecule is glycosylated monomer (FIG. 3-11A, Lane 1: protein marker for molecule weight; Lane 2: reduced CD19-CD3-GITRL TsM_M; Lane 3: unreduced CD19-CD3-GITRL TsM_M). The theoretical molecule weight for CD19-CD3-GITRL TsM_D is 76.6 kDa, and protein displayed the same molecular weight as glycosylated monomer under reduced condition, the molecular weight is consistent with glycosylated dimer under non-reduced condition (FIG. 3-11B, Lane 1: protein marker for molecule weight; Lane 2: reduced CD19-CD3-GITRL TsM_D; Lane 3: unreduced CD19-CD3-GITRL TsM_D), which indicate two protein molecules link to each other by disulfide bond formed through IgD hinge region so that this tri-specific molecule is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-GITRL TsM_M is monomer and CD19-CD3-GITRL TsM_D is dimer.

Therefore, the amino acid sequence of CD19-CD3-GITRL TsM_M monomer is shown as SEQ ID NO. 189.

The amino acid sequence of CD19-CD3-GITRL TsM_D dimer is shown as SEQ ID NO. 191.

The amino acid sequence of anti-CD19 scFv is shown as SEQ ID NO. 197.

The amino acid sequence of anti-CD19 scFv heavy chain variable region is shown as SEQ ID NO. 198.

The amino acid sequence of anti-CD19 scFv light chain variable region is shown as SEQ ID NO. 199.

The amino acid sequence of anti-CD3 scFv is shown as SEQ ID NO. 200.

The amino acid sequence of anti-CD3 scFv heavy chain variable region is shown as SEQ ID NO. 201.

The amino acid sequence of anti-CD3 scFv light chain variable region is shown as SEQ ID NO. 202.

The amino acid sequence of GITRL extracellular domain is shown as SEQ ID NO. 206.

The amino acid sequence of CD19-CD3-GITRL TsM_M monomer linker (Linker 1) is shown as SEQ ID NO. 159.

The amino acid sequence of CD19-CD3-GITRL TsM_M monomer linker (Linker 2) is shown as SEQ ID NO. 161.

The amino acid sequence of CD19-CD3-GITRL TsM_D dimer linker (Linker 1) is shown as SEQ ID NO. 163.

The amino acid sequence of CD19-CD3-GITRL TsM_D dimer linker (Linker 2) is shown as SEQ ID NO. 165.

Embodiment 3-15: CD19, CD3 Antigen Binding and Co-Stimulatory Molecule GITR Binding Activity Test of CD19-CD3-GITRL TsM_M and CD19-CD3-GITRL TsM_D by ELISA ELISA Procedure:

1. Recombinant antigen coating: 96-well plates were coated by human CD19-hFc, human CD3-hFc and human GITR-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific molecule samples respectively and keeping plates at 37° C. for 1 hour. Sample serial dilution includes: using 10 μg/ml purified CD19-CD3-GITRL TsM_M or CD19-CD3-GITRL TsM_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5-10 min at room temperature.

5. Reaction termination and result test: adding 100 μl per well of 1M HCl to stop reaction, and reading OD value of 450 nm absorbance on ELISA reader.

The results of ELISA are shown in FIGS. 3-12A and 3-12B. The four curves in the figure represent three four results: ■ coated with 1 μg/ml CD19-hFc recombinant antigen, ◆ coated with 1 μg/ml CD3-hFc recombinant antigen; ▲ coated with 1 μg/ml GITR-hFc recombinant antigen; ⧗ no antigen coated result. FIG. 3-12A indicates that CD19-CD3-GITRL TsM_M has antigen binding activity with CD19-hFc, CD3-hFc and GITR-hFc in vitro, among which GITR has the highest binding activity, CD19 has the second highest binding activity, and CD3 has the weakest binding activity. FIG. 3-12B indicates that CD19-CD3-GITRL TsM_D has antigen binding activity with CD19-hFc, CD3-hFc and GITR-hFc in vitro as well, among which GITR has the highest binding activity, CD19 has the second highest binding activity, and CD3 has the weakest binding activity.

Embodiment 3-16: CD19-CD3-GITRL Tri-Specific Molecule-Mediated Cell Killing Assay Human PBMC (Peripheral blood mononuclear cell, PBMC) was used as experiment material. The above-mentioned TiTE tri-specific molecule CD19-CD3-GITRL TsM_M in monomeric form, TiTE tri-specific molecule CD19-CD3-GITRL TsM_D in dimeric form and purchased anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three protein-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Count cell number and cells are ready for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ (200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-GITRL TsM_M and CD19-CD3-GITRL TsM_D protein are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{OD \text{ value of } Raji \text{ cells} + OD \text{ value of } CIK \text{ cells} - \text{detected } OD \text{ value}}{OD \text{ value of } Raji \text{ cells}} \times 100\%$$

The results are shown in FIG. 3-13: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-GITRL TsM_D have the best cell killing effect. The killing efficacy is about 92%, 88% and 84%. The effect of CD19-CD3-GITRL TsM_M is in the second place, the killing efficacy is about 89%, 85% and 78%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-GITRL TsM_D and CD19-CD3-GITRL TsM_M against Raji cells is improved to some extent, and the killing efficacy is about 78% and 68%, respectively. While CD19-CD3 BsAb had no effect compared with the blank control. The above results indicated that the two forms of CD19-CD3-GITRL TiTE tri-specific molecule-mediated T cell-targeted killing activity against CD19-positive tumor cells were superior to that of BiTE bispecific antibody. The dimeric form has a better effect than the monomer form.

Embodiment 3-17: The Eukaryotic Expression Vector Construction of CD19-CD3-CD70 TsM_M and CD19-CD3-CD70 TsM_D In this disclosure, the TiTE tri-specific molecule including anti-CD19 scFv, anti-CD3 scFv, and co-stimulatory molecule ligand CD70 extracellular domain on human T cell is named as CD19-CD3-CD70 TsM.

1. Construction Design of CD19-CD3-CD70 TsM_M and CD19-CD3-CD70 TsM_D

Construction design of CD19-CD3-CD70 TsM_M Monomer:

The sequences of the anti-CD19 scFv, anti-CD3 scFv and CD70 extracellular domain are linked by a linker. Specifically, the sequence of anti-CD19 scFv and the anti-CD3 scFv are linked by Linker 1, the sequence of anti-CD3 scFv and CD70 extracellular domain are linked by Linker 2.

Construction design of CD19-CD3-CD70 TsM_D Dimer:

The sequences of the anti-CD19 scFv, anti-CD3 scFv and CD70 extracellular domain are linked by linkers. Specifically, the sequences of anti-CD19 scFv and anti-CD3 scFv are linked by Linker 1, the sequences of anti-CD3 scFv and CD70 extracellular domain are linked by IgD hinge region (Ala90-Val170) as Linker 2.

In order to express the tri-specific molecule in mammalian cells, codon optimization of mammalian system was performed for the sequence of anti-CD19 scFv, anti-CD3 scFv, and CD70 extracellular domain.

The nucleotide sequence of anti-CD19 scFv heavy chain variable region is shown as SEQ ID NO. 209.

The nucleotide sequence of anti-CD19 scFv light chain variable region is shown as SEQ ID NO. 210.

The nucleotide sequence of anti-CD19 scFv is shown as SEQ ID NO. 208.

The nucleotide sequence of anti-CD3 scFv heavy chain variable region is shown as SEQ ID NO. 212.

The nucleotide sequence of anti-CD3 scFv light chain variable region is shown as SEQ ID NO. 213.

The nucleotide sequence of anti-CD3 scFv is shown as SEQ ID NO. 211.

The nucleotide sequence of CD70 extracellular domain sequence is shown as SEQ ID NO. 218.

The nucleotide sequence of CD19-CD3-CD70 TsM_M monomer linker (Linker 1) is shown as SEQ ID NO. 160.

The nucleotide sequence of CD19-CD3-CD70 TsM_M monomer linker (Linker 2) is shown as SEQ ID NO. 162.

The nucleotide sequence of CD19-CD3-CD70 TsM_D dimer linker (Linker 1) is shown as SEQ ID NO. 164.

The nucleotide sequence of CD19-CD3-CD70 TsM_D dimer linker (Linker 2) is shown as SEQ ID NO. 166.

In order to express tri-specific molecule successfully in CHO-S cells and secret into medium, signal peptide of antibody secretory expression was selected in this Embodiment.

The amino acid sequence of this secretory signal peptide is shown as SEQ ID NO. 219.

The nucleotide sequence of this secretory signal peptide is shown as SEQ ID NO. 220.

2. CD19-CD3-CD70 TsM_M and CD19-CD3-CD70 TsM_D Eukaryotic Expression Vector Construction The construction and expression of this tri-specific molecule in the present disclosure selected mammalian cell protein transient expression vector pcDNA3.1 (purchased from Invitrogen, Shanghai). In order to construct the tri-specific molecules in monomer and dimer form, primers were designed as in table 3-5. All the primers were synthesized by Genewiz, Suzhou, and DNA template for PCR was synthesized by Synbio Technologies, Suzhou.

The cloning construct for CD19-CD3-CD70 TsM_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+CD70 extracellular domain sequence by primer pairs Sig-CD19-F and CD19-R, CD19-G4S-CD3-F and CD3-R, and CD3-$(GGGGS)_3$—CD70-F and pcDNA3.1-CD70-R, respectively. The cloning construct for CD19-CD3-CD70 TsM_D includes: amplifying signal peptide by primers pcDNA3.1-Sig-F and Sig-R, and then amplifying anti-CD19 scFv, GGGGS Linker 1+anti-CD3 scFv, IgD hinge region Linker2, and CD70 extracellular domain sequence by primer pairs Sig-CD19-F and CD19-R, CD19-G4S-CD3-F and CD3-R, CD3-IgD-F and IgD-R, and IgD-CD70-F and pcDNA3.1-CD70-R, respectively. After PCR amplification, by using NovoRec® PCR One-Step Cloning Kit (purchased from Wujiang Novoprotein Technology Co., Ltd.), the full length of tri-specific molecule monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-CD70 TsM_M monomer and CD19-CD3-CD70 TsM_D dimer both had the right full DNA sequence as expected.

The nucleotide sequence of CD19-CD3-CD70 TsM_M monomer is shown as SEQ ID NO. 194.

The nucleotide sequence of CD19-CD3-CD70 TsM_D dimer is shown as SEQ ID NO. 196.

TABLE 3-5

Primers used in CD19-CD3-CD70 tri-specific molecule gene cloning

| Primer name | Sequence | No. |
|---|---|---|
| CD3-$(GGGGS)_3$-CD70-F | GGCACCAAGCTGGAGCTGAAGGGCGGCGGCGGCAGCGGCGGCGGCGGCAGCGGCGGCGGCGGCAGCCAGCGCTTCGCCCAGGCCCAG | SEQ ID NO. 241 |
| pcDNA3.1-CD70-R | CTGATCAGCGGTTTAAACTTAAGCTTTCAGGGGCGCACCCACTGCACGCC | SEQ ID NO. 242 |
| IgD-CD70-F | CACACCCAGCCCCTGGGCGTGCAGCGCTTCGCCCAGGCCCAG | SEQ ID NO. 243 |

Embodiment 3-18: The Expression and Purification of CD19-CD3-CD70 TsM_M and CD19-CD3-CD70 TsM_D 1. The Expression of CD19-CD3-CD70 TsM_M and CD19-CD3-CD70 TsM_D 1.1 The cell density of CHO-S cells (purchased from Thermo Fisher Scientific) was $0.5\sim0.6\times10^6$/ml one day before transfection.

1.2 Calculating cell density at the day of transfection, plasmid transfection can be performed when the density is in the range of $1\sim1.4\times10^6$/ml and live percentage is >90%.

1.3 Transfection complex recipes: each project (CD19-CD3-CD70 TsM_M and CD19-CD3-CD70 TsM_D) requires two centrifuge tubes/flasks. Take total 20 ml as an example, the recombinant plasmids from Embodiment 3-17 were taken: Tube 1: 600 μl PBS, 20 μg recombinant plasmid, mix well; Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15-20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-CD70 TsM_M and CD19-CD3-CD70 TsM_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-CD70 TsM_M and CD19-CD3-CD70 TsM_D recombinant protein was analyzed by SDS-PAGE, and the protein electrophoresis data under reduced and unreduced conditions were shown as FIG. 3-14. It shows that both purity of CD19-CD3-CD70 TsM_M and CD19-CD3-CD70 TsM_D recombinant protein are >95%. The theoretical molecule weight for CD19-CD3-CD70 TsM_M is 71.3 kDa, and protein displayed the same single band under reduced and unreduced conditions. Because of the post-translational N-glycosylation modification on CD70 extracellular domain, the real molecule weight of the band is bigger than theoretical value, so this tri-specific molecule is glycosylated monomer (FIG. 3-14A, Lane 1: protein marker for molecule weight; Lane 2: reduced CD19-CD3-CD70 TsM_M; Lane 3: unreduced CD19-CD3-CD70 TsM_M). The theoretical molecule weight for CD19-CD3-CD70 TsM_D is 79.2 kDa, and protein displayed the same molecular weight as glycosylated monomer under reduced condition, the molecular weight is consistent with glycosylated dimer under non-reduced condition (FIG. 3-14B, Lane 1: protein marker for molecule weight; Lane 2: reduced CD19-CD3-CD70 TsM_D; Lane 3: unreduced CD19-CD3-CD70 TsM_D), which indicate two protein molecules link to each other by disulfide bond formed through IgD hinge region so that this tri-specific molecule is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-CD70 TsM_M is monomer and CD19-CD3-CD70 TsM_D is dimer.

Therefore, the amino acid sequence of CD19-CD3-CD70 TsM_M monomer is shown as SEQ ID NO. 193.

The amino acid sequence of CD19-CD3-CD70 TsM_D dimer is shown as SEQ ID NO. 195.

The amino acid sequence of anti-CD19 scFv is shown as SEQ ID NO. 197.

The amino acid sequence of anti-CD19 scFv heavy chain variable region is shown as SEQ ID NO. 198.

The amino acid sequence of anti-CD19 scFv light chain variable region is shown as SEQ ID NO. 199.

The amino acid sequence of anti-CD3 scFv is shown as SEQ ID NO. 200.

The amino acid sequence of anti-CD3 scFv heavy chain variable region is shown as SEQ ID NO. 201.

The amino acid sequence of anti-CD3 scFv light chain variable region is shown as SEQ ID NO. 202.

The amino acid sequence of CD70 extracellular domain is shown as SEQ ID NO. 207.

The amino acid sequence of CD19-CD3-CD70 TsM_M monomer linker (Linker 1) is shown as SEQ ID NO. 159.

The amino acid sequence of CD19-CD3-CD70 TsM_M monomer linker (Linker 2) is shown as SEQ ID NO. 161.

The amino acid sequence of CD19-CD3-CD70 TsM_D dimer linker (Linker 1) is shown as SEQ ID NO. 163.

The amino acid sequence of CD19-CD3-CD70 TsM_D dimer linker (Linker 2) is shown as SEQ ID NO. 165.

Embodiment 3-19: CD19, CD3 Antigen Binding and Co-Stimulatory Molecule CD27 Binding Activity Test of CD19-CD3-CD70 TsM_M and CD19-CD3-CD70 TsM_D by ELISA ELISA Procedure:

1. Recombinant antigen coating: 96-well plates were coated by human CD19-hFc, human CD3-hFc and human CD27-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific molecule samples respectively and keeping plates at 37° C. for 1 hour. Sample serial dilution includes: using 10 μg/ml purified CD19-CD3-CD70 TsM_M or CD19-CD3-CD70 TsM_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5-10 min at room temperature.

5. Reaction termination and result test: adding 100 μl per well of 1M HCl to stop reaction, and reading OD value of 450 nm absorbance on ELISA reader.

The results of ELISA are shown in FIGS. 3-15A and 3-15B. The four curves in the figure represent three four results: ■ coated with 1 μg/ml CD19-hFc recombinant antigen, ● coated with 1 μg/ml CD3-hFc recombinant antigen; ▲ coated with 1 μg/ml CD27-hFc recombinant antigen; ▼ no antigen coated result. FIG. 3-15A indicates that CD19-CD3-CD70 TsM_M has antigen binding activity with CD19-hFc, CD3-hFc and CD27-hFc in vitro, among which CD27 and CD19 have higher binding activity, CD3 has weaker binding activity. FIG. 3-15B indicates that CD19-CD3-CD70 TsM_D has antigen binding activity with CD19-hFc, CD3-hFc and CD27-hFc in vitro as well, among which CD27 and CD19 have higher binding activity, CD3 has weaker binding activity.

Embodiment 3-20: CD19-CD3-CD70 Tri-Specific Molecule-Mediated Cell Killing Assay Human PBMC (Peripheral blood mononuclear cell, PBMC) was used as experiment material. The above-mentioned TiTE tri-specific molecule CD19-CD3-CD70 TsM_M in monomeric form, TiTE tri-specific molecule CD19-CD3-CD70 TsM_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three protein-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Count cell number and cells are ready for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-CD70 TsM_M and CD19-CD3-CD70 TsM_D protein are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any protein was blank control of killing efficacy.

$$\text{Killing efficacy (\%)} = \frac{OD \text{ value of } Raji \text{ cells} + OD \text{ value of } CIK \text{ cells} - \text{detected } OD \text{ value}}{OD \text{ value of } Raji \text{ cells}} \times 100\%$$

The results are shown in FIG. 3-16: When the CIK effector cells: Raji target cells (E:T ratio) were 1:1, the killing efficacy was about 23% after 3 h without adding any protein. The killing efficacy of CIK cells on Raji cells was significantly improved under the conditions of adding higher concentrations of antibodies (25, 12.5, 6.25 ng/ml). Among them, Cells mediated by CD19-CD3-CD70 TsM_D have the best cell killing effect. The killing efficacy is about 96%, 92% and 87%. The effect of CD19-CD3-CD70 TsM_M is in the second place, the killing efficacy is about 93%, 88% and 83%. The effect of CD19-CD3 BsAb is the weakest and the killing efficacy is about 80%, 54% and 54%. Under the condition of adding lower concentration protein (3.125 ng/ml), the killing efficacy of CIK cells mediated by CD19-CD3-CD70 TsM_D and CD19-CD3-CD70 TsM_M against Raji cells is improved to some extent, and the killing efficacy is about 82% and 72%, respectively. While CD19-CD3 BsAb had no effect compared with the blank control. The above results indicated that the two forms of CD19-CD3-CD70 TiTE tri-specific molecule-mediated T cell-targeted killing activity against CD19-positive tumor cells were superior to that of BiTE bispecific antibody. The dimeric form has a better effect than the monomer form.

Embodiment 4-1 the Eukaryotic Expression Vector Construction of CD19-CD3-PD-1 TsAb_M and CD19-CD3-PD-1 TsAb_D In the present disclosure, a TiTE tri-specific antibody targeting human CD19 protein on the surface of lymphoma B cells, T cell surface human CD3 and T cell inhibitory molecule PD-1 protein is named as CD19-CD3-PD-1 TsAb.

1. Construction Design of CD19-CD3-PD-1 TsAb_M and CD19-CD3-PD-1 TsAb_D

Construction design of CD19-CD3-PD-1 TsAb_M Monomer:

The sequences of the anti-CD19 scFv, anti-CD3 scFv and anti-PD-1 scFv are linked by a linker. Specifically, the sequence of anti-CD19 scFv and the anti-CD3 scFv are linked by Linker 1, the sequence of anti-CD3 scFv and anti-PD-1 scFv are linked by Linker 2.

Construction design of CD19-CD3-PD-1 TsAb_D Dimer:

The sequences of the anti-CD19 scFv, anti-CD3 scFv and anti-PD-1 scFv are linked by linkers. Specifically, the sequences of anti-CD19 scFv and anti-CD3 scFv are linked by Linker 1, the sequences of anti-CD3 scFv and anti-PD-1 scFv are linked by IgD hinge region (Ala90-Val170) as Linker 2.

In order to express the tri-specific antibody in mammalian cells, codon optimization of mammalian system was performed for the sequence of anti-CD19 scFv, anti-CD3 scFv, and anti-PD-1 scFv.

The nucleotide sequence of anti-CD19 scFv heavy chain variable region is shown as SEQ ID NO. 307.

The nucleotide sequence of anti-CD19 scFv light chain variable region is shown as SEQ ID NO. 308.

The nucleotide sequence of anti-CD19 scFv is shown as SEQ ID NO. 306.

The nucleotide sequence of anti-CD3 scFv heavy chain variable region is shown as SEQ ID NO. 310.

The nucleotide sequence of anti-CD3 scFv light chain variable region is shown as SEQ ID NO. 311.

The nucleotide sequence of anti-CD3 scFv is shown as SEQ ID NO. 309.

The nucleotide sequence of anti-PD-1 scFv heavy chain variable region is shown as SEQ ID NO. 313.

The nucleotide sequence of anti-PD-1 scFv light chain variable region is shown as SEQ ID NO. 314.

The nucleotide sequence of anti-PD-1 scFv is shown as SEQ ID NO. 312.

The nucleotide sequence of CD19-CD3-PD-1 TsAb_M monomer linker (Linker 1) is shown as SEQ ID NO. 245.

The nucleotide sequence of CD19-CD3-PD-1 TsAb_M monomer linker (Linker 2) is shown as SEQ ID NO. 247.

The nucleotide sequence of CD19-CD3-PD-1 TsAb_D dimer linker (Linker 1) is shown as SEQ ID NO. 249.

The nucleotide sequence of CD19-CD3-PD-1 TsAb_D dimer linker (Linker 2) is shown as SEQ ID NO. 251.

In order to express tri-specific antibody successfully in CHO-S cells and secret into medium, signal peptide of antibody secretory expression was selected in this Embodiment.

The amino acid sequence of this secretory signal peptide is shown as SEQ ID NO. 330.

The nucleotide sequence of this secretory signal peptide is shown as SEQ ID NO. 331.

2. CD19-CD3-PD-1 TsAb_M and CD19-CD3-PD-1 TsAb_D Eukaryotic Expression Vector Construction The construction and expression of this tri-specific antibody in the present disclosure selected mammalian cell protein transient expression vector pcDNA3.1 (purchased from Invitrogen, Shanghai). In order to construct the tri-specific antibody in monomer and dimer form, primers were designed as in table 4-1. All the primers were synthesized by Genewiz, Suzhou, and DNA template for PCR was synthesized by Synbio Technologies, Suzhou.

The cloning construct for CD19-CD3-PD-1 TsAb_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+anti-PD-1 scFv sequence by primer pairs Sig-CD19-F and CD19-R, CD19-G4S-CD3-F and CD3-R, and CD3-$(GGGGS)_3$—PD-1-F and pcDNA3.1-PD-1-R, respectively. The cloning construct for CD19-CD3-PD-1 TsAb_D includes: amplifying signal peptide by primers pcDNA3.1-Sig-F and Sig-R, and then amplifying anti-CD19 scFv, GGGGS Linker 1+anti-CD3 scFv, and IgD hinge region Linker2+anti-PD-1 scFv sequence by primer pairs Sig-CD19-F and CD19-R, CD19-G4S-CD3-F and CD3-R, CD3-IgD-F and IgD-R, and IgD-PD-1-F and pcDNA3.1-PD-1-R, respectively. After PCR amplification, by using NovoRec® PCR One-Step Cloning Kit (purchased from Wujiang Novoprotein Technology Co., Ltd.), the full length of tri-specific antibody monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-PD-1 TsAb_M monomer and CD19-CD3-PD-1 TsAb_D dimer both had the right full DNA sequence as expected.

The nucleotide sequence of CD19-CD3-PD-1 TsAb_M monomer is shown as SEQ ID NO. 259.

The nucleotide sequence of CD19-CD3-PD-1 TsAb_D dimer is shown as SEQ ID NO. 261.

TABLE 4-1

Primers used in CD19-CD3-PD-1 tri-specific antibody gene cloning

| Primer name | sequence | No. |
|---|---|---|
| pcDNA3.1-Sig-F | GTGCTGGATATCTGCAGAATTCGCCGCCACCATGACCCGGCTGACCGTGCTGGCCCTGC | SEQ ID NO. 332 |
| Sig-R | GGCCCTGGAGGAGGCCAGCAGGCCGGCCAGCAGGGCCAGCACGGTCAGC | SEQ ID NO. 333 |
| Sig-CD19-F | CTGCTGGCCTCCTCCAGGGCCGACATCCAGCTGACCCAGAGC | SEQ ID NO. 334 |
| CD19-R | GCTGCTCACGGTCACGGTGGTGC | SEQ ID NO. 335 |
| CD19-G4S-CD3-F | CCACCGTGACCGTGAGCAGCGGTGGCGGAGGGTCCGACATCAAGCTGCAGCAGAGC | SEQ ID NO. 336 |
| CD3-R | CTTCAGCTCCAGCTTGGTGC | SEQ ID NO. 337 |
| CD3-$(GGGGS)_3$-PD-1-F | GGCACCAAGCTGGAGCTGAAGGGCGGCGGCGGCAGCGGCGGCGGCGGCAGCGGCGGCGGCGGCAGCCAGGTGCAGCTGGTGGAGAGC | SEQ ID NO. 338 |
| pcDNA3.1-PD-1-R | CTGATCAGCGGTTTAAACTTAAGCTTTCAGCGCTTGATCTCCACCTTGGT | SEQ ID NO. 339 |
| CD3-IgD-F | GCACCAAGCTGGAGCTGAAGGCCAGCAAGAGCAAGAAGGAG | SEQ ID NO. 340 |
| IgD-R | CACGCCCAGGGGCTGGGTGTG | SEQ ID NO. 341 |
| IgD-PD-1-F | CACACCCAGCCCCTGGGCGTGCAGGTGCAGCTGGTGGAGAGC | SEQ ID NO. 342 |

Embodiment 4-2: The Expression and Purification of CD19-CD3-PD-1 TsAb_M and CD19-CD3-PD-1 TsAb_D 1. The Expression of CD19-CD3-PD-1 TsAb_M and CD19-CD3-PD-1 TsAb_D 1.1 The cell density of CHO-S cells (purchased from Thermo Fisher Scientific) was $0.5\sim0.6\times10^6$/ml one day before transfection.

1.2 Calculating cell density at the day of transfection, plasmid transfection can be performed when the density is in the range of $1\sim1.4\times10^6$/ml and live percentage is >90%.

1.3 Transfection complex recipes: each project (CD19-CD3-PD-1 TsAb_M and CD19-CD3-PD-1 TsAb_D) requires two centrifuge tubes/flasks. Take total 20 ml as an example, the recombinant plasmids from Embodiment 4-1 were taken: Tube 1: 600 μl PBS, 20 μg recombinant plasmid, mix well; Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15-20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-PD-1 TsAb_M and CD19-CD3-PD-1 TsAb_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-PD-1 TsAb_M and CD19-CD3-PD-1 TsAb_D recombinant protein was analyzed by SDS-PAGE, and the protein electrophoresis data under reduced and unreduced conditions were shown as FIG. 4-2. It shows that, after the purification of protein L affinity chromatography column, both purity of CD19-CD3-PD-1 TsAb_M and CD19-CD3-PD-1 TsAb_D recombinant protein are >95%. The theoretical molecule weight for CD19-CD3-PD-1 TsAb_M is 79.4 kDa, and protein displayed the same single band under reduced and unreduced conditions. The molecule weight of these bands is consistent with monomer, so this tri-specific antibody is monomer (FIG. 4-2A, Lane 1: protein marker for molecule weight; Lane 2: reduced CD19-CD3-PD-1 TsAb_M; Lane 3: unreduced CD19-CD3-PD-1 TsAb_M). The theoretical molecule weight for CD19-CD3-PD-1 TsAb_D is 87.3 kDa, and protein displayed the same molecular weight as monomer under reduced condition, but the molecular weight is consistent with dimer under unreduced condition (~180 kDa) (~180 kDa)(FIG. 4-2B, Lane 1: protein marker for molecule weight; Lane 2: reduced CD19-CD3-PD-1 TsAb_D; Lane 3: unreduced CD19-CD3-PD-1 TsAb_D), which indicate two protein link to each other by disulfide bond formed through IgD hinge region so that this tri-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-PD-1 TsAb_M is monomer and CD19-CD3-PD-1 TsAb_D is dimer.

Therefore, the amino acid sequence of CD19-CD3-PD-1 TsAb_M monomer is shown as SEQ ID NO. 258.

The amino acid sequence of CD19-CD3-PD-1 TsAb_D dimer is shown as SEQ ID NO. 260.

The amino acid sequence of anti-CD19 scFv is shown as SEQ ID NO. 282.

The amino acid sequence of anti-CD19 scFv heavy chain variable region is shown as SEQ ID NO. 283.

The amino acid sequence of anti-CD19 scFv light chain variable region is shown as SEQ ID NO. 284.

The amino acid sequence of anti-CD3 scFv is shown as SEQ ID NO. 285.

The amino acid sequence of anti-CD3 scFv heavy chain variable region is shown as SEQ ID NO. 286.

The amino acid sequence of anti-CD3 scFv light chain variable region is shown as SEQ ID NO. 287.

The amino acid sequence of anti-PD-1 scFv is shown as SEQ ID NO. 288.

The amino acid sequence of anti-PD-1 scFv heavy chain variable region is shown as SEQ ID NO. 289.

The amino acid sequence of anti-PD-1 scFv light chain variable region is shown as SEQ ID NO. 290.

The amino acid sequence of CD19-CD3-PD-1 TsAb_M monomer linker (Linker 1) is shown as SEQ ID NO. 244.

The amino acid sequence of CD19-CD3-PD-1 TsAb_M monomer linker (Linker 2) is shown as SEQ ID NO. 246.

The amino acid sequence of CD19-CD3-PD-1 TsAb_D dimer linker (Linker 1) is shown as SEQ ID NO. 248.

The amino acid sequence of CD19-CD3-PD-1 TsAb_D dimer linker (Linker 2) is shown as SEQ ID NO. 250.

Embodiment 4-3: Antigen Binding Activity Test of CD19-CD3-PD-1 TsAb_M and CD19-CD3-PD-1 TsAb_D by ELISA ELISA procedure:

1. Recombinant antigen coating: 96-well plates were coated by human CD19-hFc, CD3-hFc and human PD-1-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific antibody samples respecitvely and keeping plates at 37° C. for 1 hour. Sample serial dilution includes: using 10 μg/ml purified CD19-CD3-PD-1 TsAb_M or CD19-CD3-PD-1 TsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5~10 min at room temperature.

5. Reaction termination and result test: adding 100 μl per well of 1M HCl to stop reaction, and reading OD value of 450 nm absorbance on ELISA reader.

The results of ELISA are shown in FIGS. 4-3A and 4-3B. The four curves in the figure represent three four results: ■ coated with 1 μg/ml CD19-hFc recombinant antigen, ◆ coated with 1 μg/ml CD3-hFc recombinant antigen; ▲ coated with 1 μg/ml PD-1-hFc recombinant antigen; ▼ no antigen coated result. FIG. 4-3A indicates that CD19-CD3-PD-1 TsAb_M has antigen binding activity with CD19-hFc, CD3-hFc and PD-1-hFc in vitro, among which PD-1 has the highest binding activity, CD19 has the second highest binding activity, and CD3 has the weakest binding activity. FIG. 4-3B indicates that CD19-CD3-PD-1 TsAb_D has antigen binding activity with CD19-hFc, CD3-hFc and PD-1-hFc in vitro as well, among which PD-1 has the highest binding activity, CD19 has the second highest binding activity, and CD3 has the weakest binding activity to.

Embodiment 4-4: CD19-CD3-PD-1 Tri-Specific Antibody-Mediated Cell Killing Assay

Human PBMC (Peripheral blood mononuclear cell, PBMC) was used as experiment material. The above-mentioned TiTE tri-specific antibody CD19-CD3-PD-1 TsAb_M in monomeric form, TiTE tri-specific antibody CD19-CD3-PD-1 TsAb_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Counting cells for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-PD-1 TsAb_M and CD19-CD3-PD-1 TsAb_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{OD \text{ value of } Raji \text{ cells} + OD \text{ value of } CIK \text{ cells} - \text{detected } OD \text{ value}}{OD \text{ value of } Raji \text{ cells}} \times 100\%$$

The results are shown in FIG. 4-4: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-PD-1 TsAb_D have the best cell killing effect. The killing efficacy is about 97%, 94% and 93%. The effect of CD19-CD3-PD-1 TsAb_M is in the second place, the killing efficacy is about 92%, 89% and 83%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-PD-1 TsAb_D and CD19-CD3-PD-1 TsAb_M against Raji cells is improved to some extent, and the killing efficacy is about 86% and 75%, respectively. While CD19-CD3 BsAb had no effect compared with the blank control. The above results indicated that the two forms of CD19-CD3-PD-1 TiTE tri-specific antibody-mediated T cell-targeted killing activity against CD19-positive tumor cells were superior to that of BiTE bispecific antibody. The dimeric form has a better effect than the monomer form.

Embodiment 4-5: The Eukaryotic Expression Vector Construction of CD19-CD3-CTLA-4 TsAb_M and CD19-CD3-CTLA-4 TsAb_D In the present disclosure, a TiTE tri-specific antibody targeting human CD19 protein on the surface of lymphoma B cells, T cell surface human CD3 and T cell inhibitory molecule CTLA-4 protein is named as CD19-CD3-CTLA-4 TsAb.

1. Construction Design of CD19-CD3-CTLA-4 TsAb_M and CD19-CD3-CTLA-4 TsAb_D

Construction design of CD19-CD3-CTLA-4 TsAb_M Monomer:

The sequences of the anti-CD19 scFv, anti-CD3 scFv and anti-CTLA-4 scFv are linked by linkers. Specifically, the sequence of anti-CD19 scFv and the anti-CD3 scFv are linked by Linker 1, the sequence of anti-CD3 scFv and anti-CTLA-4 scFv are linked by Linker 2.

Construction design of CD19-CD3-CTLA-4 TsAb_D Dimer:

The sequences of the anti-CD19 scFv, anti-CD3 scFv and anti-CTLA-4 scFv are linked by linkers. Specifically, the sequences of anti-CD19 scFv and anti-CD3 scFv are linked by Linker 1, the sequences of anti-CD3 scFv and anti-CTLA-4 scFv are linked by IgD hinge region (Ala90-Val170) as Linker 2.

In order to express the tri-specific antibody in mammalian cells, codon optimization of mammalian system was performed for the sequence of anti-CD19 scFv, anti-CD3 scFv, and anti-CTLA-4 scFv.

The nucleotide sequence of anti-CD19 scFv heavy chain variable region is shown as SEQ ID NO. 307.

The nucleotide sequence of anti-CD19 scFv light chain variable region is shown as SEQ ID NO. 308.

The nucleotide sequence of anti-CD19 scFv is shown as SEQ ID NO. 306.

The nucleotide sequence of anti-CD3 scFv heavy chain variable region is shown as SEQ ID NO. 310.

The nucleotide sequence of anti-CD3 scFv light chain variable region is shown as SEQ ID NO. 311.

The nucleotide sequence of anti-CD3 scFv is shown as SEQ ID NO. 309.

The nucleotide sequence of anti-CTLA-4 scFv heavy chain variable region is shown as SEQ ID NO. 316.

The nucleotide sequence of anti-CTLA-4 scFv light chain variable region is shown as SEQ ID NO. 317.

The nucleotide sequence of anti-CTLA-4 scFv is shown as SEQ ID NO. 315.

The nucleotide sequence of CD19-CD3-CTLA-4 TsAb_M monomer linker (Linker 1) is shown as SEQ ID NO. 245.

The nucleotide sequence of CD19-CD3-CTLA-4 TsAb_M monomer linker (Linker 2) is shown as SEQ ID NO. 247.

The nucleotide sequence of CD19-CD3-CTLA-4 TsAb_D dimer linker (Linker 1) is shown as SEQ ID NO. 249.

The nucleotide sequence of CD19-CD3-CTLA-4 TsAb_D dimer linker (Linker 2) is shown as SEQ ID NO. 251.

In order to express tri-specific antibody successfully in CHO-S cells and secret into medium, signal peptide of antibody secretory expression was selected in this Embodiment.

The amino acid sequence of this secretory signal peptide is shown as SEQ ID NO. 330.

The nucleotide sequence of this secretory signal peptide is shown as SEQ ID NO. 331.

2. CD19-CD3-CTLA-4 TsAb_M and CD19-CD3-CTLA-4 TsAb_D Eukaryotic Expression Vector Construction The construction and expression of this tri-specific antibody in the present disclosure selected mammalian cell protein transient expression vector pcDNA3.1 (purchased from Invitrogen, Shanghai). In order to construct the tri-specific antibody in monomer and dimer form, primers were designed as in table 4-2. All the primers were synthesized by Genewiz, Suzhou, and DNA template for PCR was synthesized by Synbio Technologies, Suzhou.

The cloning construct for CD19-CD3-CTLA-4 TsAb_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+anti-CTLA-4 scFv sequence by primer pairs Sig-CD19-F and CD19-R, CD19-G4S-CD3-F and CD3-R, and CD3-$(GGGGS)_3$—CTLA-4-F and pcDNA3.1-CTLA-4-R, respectively. The cloning construct for CD19-CD3-CTLA-4 TsAb_D includes: amplifying signal peptide by primers pcDNA3.1-Sig-F and Sig-R, and then amplifying anti-CD19 scFv, GGGGS Linker 1+anti-CD3 scFv, IgD hinge region Linker2, and anti-CTLA-4 scFv sequence by primer pairs Sig-CD19-F and CD19-R, CD19-G4S-CD3-F and CD3-R, CD3-IgD-F and IgD-R, and IgD-CTLA-4-F and pcDNA3.1-CTLA-4-R, respectively. After PCR amplification, by using NovoRec® PCR One-Step Cloning Kit (purchased from Wujiang Novoprotein Technology Co., Ltd.), the full length of tri-specific antibody monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-CTLA-4 TsAb_M monomer and CD19-CD3-CTLA-4 TsAb_D dimer both had the right full DNA sequence as expected.

The nucleotide sequence of CD19-CD3-CTLA-4 TsAb_M monomer is shown as SEQ ID NO. 263.

The nucleotide sequence of CD19-CD3-CTLA-4 TsAb_D dimer is shown as SEQ ID NO. 265.

TABLE 4-2

Primers used in CD19-CD3-CTLA-4 tri-specific antibody gene cloning

| Primer name | sequence | No. |
|---|---|---|
| CD3-$(GGGGS)_3$-CTLA-4-F | GGCACCAAGCTGGAGCTGAAGGGCGGCGGCGGCAGCGGCGGCGGCGGCAGCGGCGGCGGCGGCAGCCAGGTGCAGCTGGTGGAGAGC | SEQ ID NO. 343 |
| pcDNA3.1-CTLA-4-R | CTGATCAGCGGTTTAAACTTAAGCTTTCAGCGCTTGATCTCCACCTTGGT | SEQ ID NO. 344 |
| IgD-CTLA-4-F | CACACCCAGCCCCTGGGCGTGCAGGTGCAGCTGGTGGAGAGC | SEQ ID NO. 345 |

Embodiment 4-6: The Expression and Purification of CD19-CD3-CTLA-4 TsAb_M and CD19-CD3-CTLA-4 TsAb_D 1. The Expression of CD19-CD3-CTLA-4 TsAb_M and CD19-CD3-CTLA-4 TsAb_D 1.1 The cell density of CHO-S cells (purchased from Thermo Fisher Scientific) was $0.5\sim0.6\times10^6$/ml one day before transfection.

1.2 Calculating cell density at the day of transfection, plasmid transfection can be performed when the density is in the range of $1\sim1.4\times10^6$/ml and live percentage is >90%.

1.3 Transfection complex recipes: each project (CD19-CD3-CTLA-4 TsAb_M and CD19-CD3-CTLA-4 TsAb_D) requires two centrifuge tubes/flasks. Take total 20 ml as an example, the recombinant plasmids from Embodiment 4-5 were taken: Tube 1: 600 μl PBS, 20 μg recombinant plasmid, mix well; Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15-20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-CTLA-4 TsAb_M and CD19-CD3-CTLA-4 TsAb_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-CTLA-4 TsAb_M and CD19-CD3-CTLA-4 TsAb_D recombinant protein was analyzed by SDS-PAGE, and the protein electrophoresis data under reduced and unreduced conditions were shown as FIG. 4-5. It shows that, after the purification of protein L affinity chromatography column, both purity of CD19-CD3-CTLA-4 TsAb_M and CD19-CD3-CTLA-4 TsAb_D recombinant protein are >95%. The theoretical molecule weight for CD19-CD3-CTLA-4 TsAb_M is 80.1 kDa, and protein displayed the same single band under reduced and unreduced conditions. The molecule weight of these bands is consistent with monomer, so this tri-specific antibody is monomer (FIG. 4-5A, Lane 1: protein marker for molecule weight; Lane 2: reduced CD19-CD3-CTLA-4 TsAb_M; Lane 3: unreduced CD19-CD3-CTLA-4 TsAb_M). The theoretical molecule weight for CD19-CD3-CTLA-4 TsAb_D is 88.0 kDa, and protein displayed the same molecular weight as monomer under reduced condition, but the molecular weight is consistent with dimer under unreduced condition (~180 kDa)(FIG. 4-5B, Lane 1: protein marker for molecule weight; Lane 2: reduced CD19-CD3-CTLA-4 TsAb_D; Lane 3: unreduced CD19-CD3-CTLA-4 TsAb_D), which indicate two protein link to each other by disulfide bond formed through IgD hinge region so that this tri-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-CTLA-4 TsAb_M is monomer and CD19-CD3-CTLA-4 TsAb_D is dimer.

Therefore, the amino acid sequence of CD19-CD3-CTLA-4 TsAb_M monomer is shown as SEQ ID NO. 262.

The amino acid sequence of CD19-CD3-CTLA-4 TsAb_D dimer is shown as SEQ ID NO. 264.

The amino acid sequence of anti-CD19 scFv is shown as SEQ ID NO. 282.

The amino acid sequence of anti-CD19 scFv heavy chain variable region is shown as SEQ ID NO. 283.

The amino acid sequence of anti-CD19 scFv light chain variable region is shown as SEQ ID NO. 284.

The amino acid sequence of anti-CD3 scFv is shown as SEQ ID NO. 285.

The amino acid sequence of anti-CD3 scFv heavy chain variable region is shown as SEQ ID NO. 286.

The amino acid sequence of anti-CD3 scFv light chain variable region is shown as SEQ ID NO. 287.

The amino acid sequence of anti-CTLA-4 scFv is shown as SEQ ID NO. 291.

The amino acid sequence of anti-CTLA-4 scFv heavy chain variable region is shown as SEQ ID NO. 292.

The amino acid sequence of anti-CTLA-4 scFv light chain variable region is shown as SEQ ID NO. 293.

The amino acid sequence of CD19-CD3-CTLA-4 TsAb_M monomer linker (Linker 1) is shown as SEQ ID NO. 244.

The amino acid sequence of CD19-CD3-CTLA-4 TsAb_M monomer linker (Linker 2) is shown as SEQ ID NO. 246.

The amino acid sequence of CD19-CD3-CTLA-4 TsAb_D dimer linker (Linker 1) is shown as SEQ ID NO. 248.

The amino acid sequence of CD19-CD3-CTLA-4 TsAb_D dimer linker (Linker 2) is shown as SEQ ID NO. 250.

Embodiment 4-7: Antigen Binding Activity Test of CD19-CD3-CTLA-4 TsAb_M and CD19-CD3-CTLA-4 TsAb_D by ELISA ELISA procedure:

1. Recombinant antigen coating: 96-well plates were coated by human CD19-hFc, CD3-hFc and human CTLA-4-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific antibody samples respectively and keeping plates at 37° C. for 1 hour. Sample serial dilution includes: using 10 μg/ml purified CD19-CD3-CTLA-4 TsAb_M or CD19-CD3-CTLA-4 TsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5-10 min at room temperature.

5. Reaction termination and result test: adding 100 μl per well of 1M HCl to stop reaction, and reading OD value of 450 nm absorbance on ELISA reader.

The results of ELISA are shown in FIGS. 4-6A and 4-6B. The four curves in the figure represent three four results: ■ coated with 1 μg/ml CD19-hFc recombinant antigen, ● coated with 1 μg/ml CD3-hFc recombinant antigen; ▲ coated with 1 μg/ml CTLA-4-hFc recombinant antigen; ▼ no antigen coated result. FIG. 4-6A indicates that CD19-CD3-CTLA-4 TsAb_M has antigen binding activity with CD19-hFc, CD3-hFc and CTLA-4-hFc in vitro, among which CTLA-4 has the highest binding activity, CD19 has the second highest binding activity, and CD3 has the weakest binding activity. FIG. 4-6B indicates that CD19-CD3-CTLA-4 TsAb_D has antigen binding activity with CD19-hFc, CD3-hFc and CTLA-4-hFc in vitro as well, among which CTLA-4 has the highest binding activity, CD19 has the second highest binding activity, and CD3 has the weakest binding activity.

Embodiment 4-8: CD19-CD3-CTLA-4 Tri-Specific Antibody-Mediated Cell Killing Assay Human PBMC (Peripheral blood mononuclear cell, PBMC) was used as experiment material. The above-mentioned TiTE tri-specific antibody CD19-CD3-CTLA-4 TsAb_M in monomeric form, TiTE tri-specific antibody CD19-CD3-CTLA-4 TsAb_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Counting cells for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-CTLA-4 TsAb_M and CD19-CD3-CTLA-4 TsAb_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{OD \text{ value of } Raji \text{ cells} + OD \text{ value of } CIK \text{ cells} - \text{detected } OD \text{ value}}{OD \text{ value of } Raji \text{ cells}} \times 100\%$$

The results are shown in FIG. 4-7: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-CTLA-4 TsAb_D have the best cell killing effect. The killing efficacy is about 94%, 91% and 89%. The effect of CD19-CD3-CTLA-4 TsAb_M is in the second place, the killing efficacy is about 86%, 82% and 76%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-CTLA-4 TsAb_D and CD19-CD3-CTLA-4 TsAb_M against Raji cells is improved to some extent, and the killing efficacy is about 82% and 71%, respectively. While CD19-CD3 BsAb had no effect compared with the blank control. The above results indicated that the two forms of CD19-CD3-CTLA-4 TiTE tri-specific antibody-mediated T cell-targeted killing activity against CD19-positive tumor cells were superior to that of BiTE bispecific antibody. The dimeric form has a better effect than the monomer form.

Embodiment 4-9: The Eukaryotic Expression Vector Construction of CD19-CD3-LAG-3 TsAb_M and CD19-CD3-LAG-3 TsAb_D In the present disclosure, a TiTE tri-specific antibody targeting human CD19 protein on the surface of lymphoma B cells, T cell surface human CD3 and T cell inhibitory molecule LAG-3 protein is named as CD19-CD3-LAG-3 TsAb.

1. Construction Design of CD19-CD3-LAG-3 TsAb_M and CD19-CD3-LAG-3 TsAb_D

Construction design of CD19-CD3-LAG-3 TsAb_M Monomer:

The sequences of the anti-CD19 scFv, anti-CD3 scFv and anti-LAG-3 scFv are linked by a linker. Specifically, the sequence of anti-CD19 scFv and the anti-CD3 scFv are linked by Linker 1, the sequence of anti-CD3 scFv and anti-LAG-3 scFv are linked by Linker 2.

Construction design of CD19-CD3-LAG-3 TsAb_D Dimer:

The sequences of the anti-CD19 scFv, anti-CD3 scFv and anti-LAG-3 scFv are linked by linkers. Specifically, the sequences of anti-CD19 scFv and anti-CD3 scFv are linked by Linker 1, the sequences of anti-CD3 scFv and anti-LAG-3 scFv are linked by IgD hinge region (Ala90-Val170) as Linker 2.

In order to express the tri-specific antibody in mammalian cells, codon optimization of mammalian system was performed for the sequence of anti-CD19 scFv, anti-CD3 scFv, and anti-LAG-3 scFv.

The nucleotide sequence of anti-CD19 scFv heavy chain variable region is shown as SEQ ID NO. 307.

The nucleotide sequence of anti-CD19 scFv light chain variable region is shown as SEQ ID NO. 308.

The nucleotide sequence of anti-CD19 scFv is shown as SEQ ID NO. 306.

The nucleotide sequence of anti-CD3 scFv heavy chain variable region is shown as SEQ ID NO. 310 in details.

The nucleotide sequence of anti-CD3 scFv light chain variable region is shown as SEQ ID NO. 311.

The nucleotide sequence of anti-CD3 scFv is shown as SEQ ID NO. 309.

The nucleotide sequence of anti-LAG-3 scFv heavy chain variable region is shown as SEQ ID NO. 319.

The nucleotide sequence of anti-LAG-3 scFv light chain variable region is shown as SEQ ID NO. 320.

The nucleotide sequence of anti-LAG-3 scFv is shown as SEQ ID NO. 318.

The nucleotide sequence of CD19-CD3-LAG-3 TsAb_M monomer linker (Linker 1) is shown as SEQ ID NO. 245.

The nucleotide sequence of CD19-CD3-LAG-3 TsAb_M monomer linker (Linker 2) is shown as SEQ ID NO. 247.

The nucleotide sequence of CD19-CD3-LAG-3 TsAb_D dimer linker (Linker 1) is shown as SEQ ID NO. 249.

The nucleotide sequence of CD19-CD3-LAG-3 TsAb_D dimer linker (Linker 2) is shown as SEQ ID NO. 251.

In order to express tri-specific antibody successfully in CHO-S cells and secret into medium, signal peptide of antibody secretory expression was selected in this Embodiment.

The amino acid sequence of this secretory signal peptide is shown as SEQ ID NO. 330.

The nucleotide sequence of this secretory signal peptide is shown as SEQ ID NO. 331.

2. CD19-CD3-LAG-3 TsAb_M and CD19-CD3-LAG-3 TsAb_D Eukaryotic Expression Vector Construction The construction and expression of this tri-specific antibody in the present disclosure selected mammalian cell protein transient expression vector pcDNA3.1 (purchased from Invitrogen, Shanghai). In order to construct the tri-specific antibody in monomer and dimer form, primers were designed as in table 4-3. All the primers were synthesized by Genewiz, Suzhou, and DNA template for PCR was synthesized by Synbio Technologies, Suzhou.

The cloning construct for CD19-CD3-LAG-3 TsAb_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+anti-LAG-3 scFv sequence by primer pairs Sig-CD19-F and CD19-R, CD19-G4S-CD3-F and CD3-R, and CD3-$(GGGGS)_3$-LAG-3-F and pcDNA3.1-LAG-3-R, respectively. The cloning construct for CD19-CD3-LAG-3 TsAb_D includes: amplifying signal peptide by primers pcDNA3.1-Sig-F and Sig-R, and then amplifying anti-CD19 scFv, GGGGS Linker 1+anti-CD3 scFv, IgD hinge region Linker2, and anti-LAG-3 scFv sequence by primer pairs Sig-CD19-F and CD19-R, CD19-G4S-CD3-F and CD3-R, CD3-IgD-F and IgD-R, and IgD-LAG-3-F and pcDNA3.1-LAG-3-R, respectively. After PCR amplification, by using NovoRec® PCR One-Step Cloning Kit (purchased from Wujiang Novoprotein Technology Co., Ltd.), the full length of tri-specific antibody monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-LAG-3 TsAb_M monomer and CD19-CD3-LAG-3 TsAb_D dimer both had the right full DNA sequence as expected.

The nucleotide sequence of CD19-CD3-LAG-3 TsAb_M monomer is shown as SEQ ID NO. 267.

The nucleotide sequence of CD19-CD3-LAG-3 TsAb_D dimer is shown as SEQ ID NO. 269.

TABLE 4-3

Primers used in CD19-CD3-LAG-3 tri-specific antibody gene cloning

| Primer name | sequence | No. |
|---|---|---|
| CD3-$(GGGGS)_3$-LAG-3-F | GGCACCAAGCTGGAGCTGAAGGGCGGCGGCGGCAGCGGCGGCGGCGGCAGCGGCGGCGGCGGCAGCCAGGTGCAGCTGCAGCAGTGG | SEQ ID NO. 346 |
| pcDNA3.1-LAG-3-R | CTGATCAGCGGTTTAAACTTAAGCTTTCAGCGCTTGATCTCCAGGTTGGT | SEQ ID NO. 347 |
| IgD-LAG-3-F | CACACCCAGCCCCTGGGCGTGCAGGTGCAGCTGCAGCAGTGG | SEQ ID NO. 348 |

Embodiment 4-10: The Expression and Purification of CD19-CD3-LAG-3 TsAb_M and CD19-CD3-LAG-3 TsAb_D 1. The Expression of CD19-CD3-LAG-3 TsAb_M and CD19-CD3-LAG-3 TsAb_D 1.1 The cell density of CHO-S cells (purchased from Thermo Fisher Scientific) was 0.5~0.6×$10^6$/ml one day before transfection.

1.2 Calculating cell density at the day of transfection, plasmid transfection can be performed when the density is in the range of 1-1.4×$10^6$/ml and live percentage is >90%.

1.3 Transfection complex recipes: each project (CD19-CD3-LAG-3 TsAb_M and CD19-CD3-LAG-3 TsAb_D) requires two centrifuge tubes/flasks. Take total 20 ml as an example, the recombinant plasmids from Embodiment 4-9 were taken: Tube 1: 600 μl PBS, 20 μg recombinant plasmid, mix well; Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15-20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-LAG-3 TsAb_M and CD19-CD3-LAG-3 TsAb_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-LAG-3 TsAb_M and CD19-CD3-LAG-3 TsAb_D recombinant protein was analyzed by SDS-PAGE, and the protein electrophoresis data under reduced and unreduced conditions were shown as FIG. 4-8. It shows that, after the purification of protein L affinity chromatography column, both purity of CD19-CD3-LAG-3 TsAb_M and CD19-CD3-LAG-3 TsAb_D recombinant protein are >95%. The theoretical molecule weight for CD19-CD3-LAG-3 TsAb_M is 80.4 kDa, and protein displayed the same single band under reduced and unreduced conditions. The molecule weight of these bands is consistent with monomer, so this tri-specific antibody is monomer (FIG. 4-8A, Lane 1: protein marker for molecule weight; Lane 2: reduced CD19-CD3-LAG-3 TsAb_M; Lane 3: unreduced CD19-CD3-LAG-3 TsAb_M). The theoretical molecule weight for CD19-CD3-LAG-3 TsAb_D is 88.3 kDa, and protein displayed the same molecular weight as monomer under reduced condition, but the molecular weight is consistent with dimer under unreduced condition (~180 kDa)(FIG. 4-8B, Lane 1: protein marker for molecule weight; Lane 2: reduced CD19-CD3-LAG-3 TsAb_D; Lane 3: unreduced CD19-CD3-LAG-3 TsAb_D), which indicate two protein link to each other by disulfide bond formed through IgD hinge region so that this tri-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-LAG-3 TsAb_M is monomer and CD19-CD3-LAG-3 TsAb_D is dimer.

Therefore, the amino acid sequence of CD19-CD3-LAG-3 TsAb_M monomer is shown as SEQ ID NO. 266.

The amino acid sequence of CD19-CD3-LAG-3 TsAb_D dimer is shown as SEQ ID NO. 268.

The amino acid sequence of anti-CD19 scFv is shown as SEQ ID NO. 282.

The amino acid sequence of anti-CD19 scFv heavy chain variable region is shown as SEQ ID NO. 283.

The amino acid sequence of anti-CD19 scFv light chain variable region is shown as SEQ ID NO. 284.

The amino acid sequence of anti-CD3 scFv is shown as SEQ ID NO. 285.

The amino acid sequence of anti-CD3 scFv heavy chain variable region is shown as SEQ ID NO. 286.

The amino acid sequence of anti-CD3 scFv light chain variable region is shown as SEQ ID NO. 287.

The amino acid sequence of anti-LAG-3 scFv is shown as SEQ ID NO. 294.

The amino acid sequence of anti-LAG-3 scFv heavy chain variable region is shown as SEQ ID NO. 295.

The amino acid sequence of anti-LAG-3 scFv light chain variable region is shown as SEQ ID NO. 296.

The amino acid sequence of CD19-CD3-LAG-3 TsAb_M monomer linker (Linker 1) is shown as SEQ ID NO. 244.

The amino acid sequence of CD19-CD3-LAG-3 TsAb_M monomer linker (Linker 2) is shown as SEQ ID NO. 246.

The amino acid sequence of CD19-CD3-LAG-3 TsAb_D dimer linker (Linker 1) is shown as SEQ ID NO. 248.

The amino acid sequence of CD19-CD3-LAG-3 TsAb_D dimer linker (Linker 2) is shown as SEQ ID NO. 250.

Embodiment 4-11: Antigen Binding Activity Test of CD19-CD3-LAG-3 TsAb_M and CD19-CD3-LAG-3 TsAb_D by ELISA ELISA procedure:

1. Recombinant antigen coating: 96-well plates were coated by human CD19-hFc, CD3-hFc and human LAG-3-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific antibody samples respectively and keeping plates at 37° C. for 1 hour. Sample serial dilution includes: using 10 μg/ml purified CD19-CD3-LAG-3 TsAb_M or CD19-CD3-LAG-3 TsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5-10 min at room temperature.

5. Reaction termination and result test: adding 100 μl per well of 1M HCl to stop reaction, and reading OD value of 450 nm absorbance on ELISA reader.

The results of ELISA are shown in FIGS. 4-9A and 4-9B. The four curves in the figure represent three four results: ■ coated with 1 μg/ml CD19-hFc recombinant antigen, ● coated with 1 μg/ml CD3-hFc recombinant antigen; ▲ coated with 1 μg/ml LAG-3-hFc recombinant antigen; ▼ no antigen coated result. FIG. 4-9A indicates that CD19-CD3-LAG-3 TsAb_M has antigen binding activity with CD19-hFc, CD3-hFc and LAG-3-hFc in vitro, among which LAG-3 has the highest binding activity, CD19 has the second highest binding activity, and CD3 has the weakest binding activity. FIG. 4-9B indicates that CD19-CD3-LAG-3 TsAb_D has antigen binding activity with CD19-hFc, CD3-hFc and LAG-3-hFc in vitro as well, among which LAG-3 has the highest binding activity, CD19 has the second highest binding activity, and CD3 has the weakest binding activity.

Embodiment 4-12: CD19-CD3-LAG-3 Tri-Specific Antibody-Mediated Cell Killing Assay Human PBMC (Peripheral blood mononuclear cell, PBMC) was used as experiment material. The above-mentioned TiTE tri-specific antibody CD19-CD3-LAG-3 TsAb_M in monomeric form, TiTE tri-specific antibody CD19-CD3-LAG-3 TsAb_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Counting cells for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ (200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-LAG-3 TsAb_M and CD19-CD3-LAG-3 TsAb_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{OD\text{ value of }Raji\text{ cells} + OD\text{ value of }CIK\text{ cells} - \text{detected }OD\text{ value}}{OD\text{ value of }Raji\text{ cells}} \times 100\%$$

The results are shown in FIG. 4-10: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-LAG-3 TsAb_D have the best cell killing effect. The killing efficacy is about 95%, 92% and 83%. The effect of CD19-CD3-LAG-3 TsAb_M is in the second place, the killing efficacy is about 89%, 86% and 73%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-LAG-3 TsAb_D and CD19-CD3-LAG-3 TsAb_M against Raji cells is improved to some extent, and the killing efficacy is about 72% and 61%, respectively. While CD19-CD3 BsAb had no effect compared with the blank control. The above results indicated that the two forms of CD19-CD3-LAG-3 TiTE tri-specific antibody-mediated T cell-targeted killing activity against CD19-positive tumor cells were superior to that of BiTE bispecific antibody. The dimeric form has a better effect than the monomer form.

Embodiment 4-13: The Eukaryotic Expression Vector Construction of CD19-CD3-TIM-3 TsAb_M and CD19-CD3-TIM-3 TsAb_D In the present disclosure, a TiTE tri-specific antibody targeting human CD19 protein on the surface of lymphoma B cells, T cell surface human CD3 and T cell inhibitory molecule TIM-3 protein is named as CD19-CD3-TIM-3 TsAb.

1. Construction Design of CD19-CD3-TIM-3 TsAb_M and CD19-CD3-TIM-3 TsAb_D

Construction design of CD19-CD3-TIM-3 TsAb_M Monomer:

The sequences of the anti-CD19 scFv, anti-CD3 scFv and anti-TIM-3 scFv are linked by a linker. Specifically, the sequence of anti-CD19 scFv and the anti-CD3 scFv are linked by Linker 1, the sequence of anti-CD3 scFv and anti-TIM-3 scFv are linked by Linker 2.

Construction design of CD19-CD3-TIM-3 TsAb_D Dimer:

The sequences of the anti-CD19 scFv, anti-CD3 scFv and anti-TIM-3 scFv are linked by linkers. Specifically, the sequences of anti-CD19 scFv and anti-CD3 scFv are linked by Linker 1, the sequences of anti-CD3 scFv and anti-TIM-3 scFv are linked by IgD hinge region (Ala90-Val170) as Linker 2.

In order to express the tri-specific antibody in mammalian cells, codon optimization of mammalian system was performed for the sequence of anti-CD19 scFv, anti-CD3 scFv, and anti-TIM-3 scFv.

The nucleotide sequence of anti-CD19 scFv heavy chain variable region is shown as SEQ ID NO. 307.

The nucleotide sequence of anti-CD19 scFv light chain variable region is shown as SEQ ID NO. 308.

The nucleotide sequence of anti-CD19 scFv is shown as SEQ ID NO. 306.

The nucleotide sequence of anti-CD3 scFv heavy chain variable region is shown as SEQ ID NO. 310 in details.

The nucleotide sequence of anti-CD3 scFv light chain variable region is shown as SEQ ID NO. 311.

The nucleotide sequence of anti-CD3 scFv is shown as SEQ ID NO. 309.

The nucleotide sequence of anti-TIM-3 scFv heavy chain variable region is shown as SEQ ID NO. 322.

The nucleotide sequence of anti-TIM-3 scFv light chain variable region is shown as SEQ ID NO. 323.

The nucleotide sequence of anti-TIM-3 scFv is shown as SEQ ID NO. 321.

The nucleotide sequence of CD19-CD3-TIM-3 TsAb_M monomer linker (Linker 1) is shown as SEQ ID NO. 245.

The nucleotide sequence of CD19-CD3-TIM-3 TsAb_M monomer linker (Linker 2) is shown as SEQ ID NO. 247.

The nucleotide sequence of CD19-CD3-TIM-3 TsAb_D dimer linker (Linker 1) is shown as SEQ ID NO. 249.

The nucleotide sequence of CD19-CD3-TIM-3 TsAb_D dimer linker (Linker 2) is shown as SEQ ID NO. 251.

In order to express tri-specific antibody successfully in CHO-S cells and secret into medium, signal peptide of antibody secretory expression was selected in this Embodiment.

The amino acid sequence of this secretory signal peptide is shown as SEQ ID NO. 330.

The nucleotide sequence of this secretory signal peptide is shown as SEQ ID NO. 331.

2. CD19-CD3-TIM-3 TsAb_M and CD19-CD3-TIM-3 TsAb_D Eukaryotic Expression Vector Construction The construction and expression of this tri-specific antibody in the present disclosure selected mammalian cell protein tra Osi t expression vector pcDNA3.1 (purchased from Invitrogen, Shanghai). In order to construct the tri-specific antibody in monomer and dimer form, primers were designed as in table 4-4. All the primers were synthesized by Genewiz, Suzhou, and DNA template for PCR was synthesized by Synbio Technologies, Suzhou.

The cloning construct for CD19-CD3-TIM-3 TsAb_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+anti-TIM-3 scFv sequence by primer pairs Sig-CD19-F and CD19-R, CD19-G4S-CD3-F and CD3-R, and CD3-$(GGGGS)_3$-TIM-3-F and pcDNA3.1-TIM-3-R, respectively. The cloning construct for CD19-CD3-TIM-3 TsAb_D includes: amplifying signal peptide by primers pcDNA3.1-Sig-F and Sig-R, and then amplifying anti-CD19 scFv, GGGGS Linker 1+anti-CD3 scFv, IgD hinge region Linker2, and anti-TIM-3 scFv sequence by primer pairs Sig-CD19-F and CD19-R, CD19-G4S-CD3-F and CD3-R, CD3-IgD-F&IgD-R, and IgD-TIM-3-F and pcDNA3.1-TIM-3-R, respectively. After PCR amplification, by using NovoRec® PCR One-Step Cloning Kit (purchased from Wujiang Novoprotein Technology Co., Ltd.), the full length of tri-specific antibody monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-TIM-3 TsAb_M monomer and CD19-CD3-TIM-3 TsAb_D dimer both had the right full DNA sequence as expected.

The nucleotide sequence of CD19-CD3-TIM-3 TsAb_M monomer is shown as SEQ ID NO. 271.

The nucleotide sequence of CD19-CD3-TIM-3 TsAb_D dimer is shown as SEQ ID NO. 273.

TABLE 4-4

Primers used in CD19-CD3-TIM-3 tri-specific antibody gene cloning

| Primer name | sequence | No. |
|---|---|---|
| CD3-$(GGGGS)_3$-TIM-3-F | GGCACCAAGCTGGAGCTGAAGGGCGGCGGCGGCAGCGGCGGCGGCGGCAGCGGCGGCGGCGGCAGCCAGGTGCAGCTGGTGCAGAGC | SEQ ID NO. 349 |
| pcDNA3.1-TIM-3-R | CTGATCAGCGGTTTAAACTTAAGCTTTCAGCGCTTGATCTCCACCTTGGT | SEQ ID NO. 350 |
| IgD-TIM-3-F | CACACCCAGCCCCTGGGCGTGCAGGTGCAGCTGGTGCAGAGC | SEQ ID NO. 351 |

Embodiment 4-14: The Expression and Purification of CD19-CD3-TIM-3 TsAb_M and CD19-CD3-TIM-3 TsAb_D 1. The Expression of CD19-CD3-TIM-3 TsAb_M and CD19-CD3-TIM-3 TsAb_D 1.1 The cell density of CHO-S cells (purchased from Thermo Fisher Scientific) was $0.5\sim0.6\times10^6$/ml one day before transfection.

1.2 Calculating cell density at the day of transfection, plasmid transfection can be performed when the density is in the range of $1\sim1.4\times10^6$/ml and live percentage is >90%.

1.3 Transfection complex recipes: each project (CD19-CD3-TIM-3 TsAb_M and CD19-CD3-TIM-3 TsAb_D) requires two centrifuge tubes/flasks. Take total 20 ml as an example, the recombinant plasmids from Embodiment 4-13 were taken:

Tube 1: 600 μl PBS, 20 μg recombinant plasmid, mix well.

Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15-20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-TIM-3 TsAb_M and CD19-CD3-TIM-3 TsAb_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-TIM-3 TsAb_M and CD19-CD3-TIM-3 TsAb_D recombinant protein was analyzed by SDS-PAGE, and the protein electrophoresis data under reduced and unreduced conditions were shown as FIG. 4-11. It shows that, after the purification of protein L affinity chromatography column, both purity of CD19-CD3-TIM-3 TsAb_M and CD19-CD3-TIM-3 TsAb_D recombinant protein are >95%. The theoretical molecule weight for CD19-CD3-TIM-3 TsAb_M is 80.1 kDa, and protein displayed the same single band under reduced and unreduced conditions. The molecule weight of these bands is consistent with monomer, so this tri-specific antibody is monomer (FIG. 4-11A, Lane 1: protein marker for molecule weight; Lane 2: reduced CD19-CD3-TIM-3 TsAb_M; Lane 3: unreduced CD19-CD3-TIM-3 TsAb_M). The theoretical molecule weight for CD19-CD3-TIM-3 TsAb_D is 88.0 kDa, and protein displayed the same molecular weight as monomer under reduced condition, but the molecular weight is consistent with dimer under unreduced condition (~180 kDa) (FIG. 4-11B, Lane 1: protein marker for molecule weight; Lane 2: reduced CD19-CD3-TIM-3 TsAb_D; Lane 3: unreduced CD19-CD3-TIM-3 TsAb_D), which indicate two protein link to each other by disulfide bond formed through IgD hinge region so that this tri-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-TIM-3 TsAb_M is monomer and CD19-CD3-TIM-3 TsAb_D is dimer.

Therefore, the amino acid sequence of CD19-CD3-TIM-3 TsAb_M monomer is shown as SEQ ID NO. 270.

The amino acid sequence of CD19-CD3-TIM-3 TsAb_D dimer is shown as SEQ ID NO. 272.

The amino acid sequence of anti-CD19 scFv is shown as SEQ ID NO. 282.

The amino acid sequence of anti-CD19 scFv heavy chain variable region is shown as SEQ ID NO. 283.

The amino acid sequence of anti-CD19 scFv light chain variable region is shown as SEQ ID NO. 284.

The amino acid sequence of anti-CD3 scFv is shown as SEQ ID NO. 285.

The amino acid sequence of anti-CD3 scFv heavy chain variable region is shown as SEQ ID NO. 286.

The amino acid sequence of anti-CD3 scFv light chain variable region is shown as SEQ ID NO. 287.

The amino acid sequence of anti-TIM-3 scFv is shown as SEQ ID NO. 297.

The amino acid sequence of anti-TIM-3 scFv heavy chain variable region is shown as SEQ ID NO. 298.

The amino acid sequence of anti-TIM-3 scFv light chain variable region is shown as SEQ ID NO. 299.

The amino acid sequence of CD19-CD3-TIM-3 TsAb_M monomer linker (Linker 1) is shown as SEQ ID NO. 244.

The amino acid sequence of CD19-CD3-TIM-3 TsAb_M monomer linker (Linker 2) is shown as SEQ ID NO. 246.

The amino acid sequence of CD19-CD3-TIM-3 TsAb_D dimer linker (Linker 1) is shown as SEQ ID NO. 248.

The amino acid sequence of CD19-CD3-TIM-3 TsAb_D dimer linker (Linker 2) is shown as SEQ ID NO. 250.

Embodiment 4-15: Antigen Binding Activity Test of CD19-CD3-TIM-3 TsAb_M and CD19-CD3-TIM-3 TsAb_D by ELISA ELISA procedure:

1. Recombinant antigen coating: 96-well plates were coated by human CD19-hFc, CD3-hFc and human TIM-3-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific antibody samples respectively and keeping plates at 37° C. for 1 hour. Sample serial dilution includes: using 10 μg/ml purified CD19-CD3-TIM-3 TsAb_M or CD19-CD3-TIM-3 TsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5~10 min at room temperature.

5. Reaction termination and result test: adding 100 μl per well of 1M HCl to stop reaction, and reading OD value of 450 nm absorbance on ELISA reader.

The results of ELISA are shown in FIGS. 4-12A and 4-12B. The four curves in the figure represent three four results: ■ coated with 1 μg/ml CD19-hFc recombinant antigen, ◆ coated with 1 μg/ml CD3-hFc recombinant antigen; ▲ coated with 1 μg/ml TIM-3-hFc recombinant antigen; ▼ no antigen coated result. FIG. 4-12A indicates that CD19-CD3-TIM-3 TsAb_M has antigen binding activity with CD19-hFc, CD3-hFc and TIM-3-hFc in vitro, among which TIM-3 has the highest binding activity, CD19 has the second highest binding activity, and CD3 has the weakest binding activity. FIG. 4-12B indicates that CD19-CD3-TIM-3 TsAb_D has antigen binding activity with CD19-hFc, CD3-hFc and TIM-3-hFc in vitro as well, among which TIM-3 has the highest binding activity, CD19 has the second highest binding activity, and CD3 has the weakest binding activity.

Embodiment 4-16: CD19-CD3-TIM-3 Tri-Specific Antibody-Mediated Cell Killing Assay Human PBMC (Peripheral blood mononuclear cell, PBMC) was used as experiment material. The above-mentioned TiTE tri-specific antibody CD19-CD3-TIM-3 TsAb_M in monomeric form, TiTE tri-specific antibody CD19-CD3-TIM-3 TsAb_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Counting cells for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β(2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-TIM-3 TsAb_M and CD19-CD3-TIM-3 TsAb_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{\begin{array}{c}OD \text{ value of } Raji \text{ cells} + \\ OD \text{ value of } CIK \text{ cells} - \text{detected } OD \text{ value}\end{array}}{OD \text{ value of } Raji \text{ cells}} \times 100\%$$

The results are shown in FIG. 4-13: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-TIM-3 TsAb_D have the best cell killing effect. The killing efficacy is about 98%, 97% and 86%. The effect of CD19-CD3-TIM-3 TsAb_M is in the second place, the killing efficacy is about 92%, 89% and 76%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-TIM-3 TsAb_D and CD19-CD3-TIM-3 TsAb_M against Raji cells is improved to some extent, and the killing efficacy is about 76% and 68%, respectively. While CD19-CD3 BsAb had no effect compared with the blank control. The above results indicated that the two forms of CD19-CD3-TIM-3 TiTE tri-specific antibody-mediated T cell-targeted killing activity against CD19-positive tumor cells were superior to that of BiTE bispecific antibody. The dimeric form has a better effect than the monomer form.

Embodiment 4-17: The Eukaryotic Expression Vector Construction of CD19-CD3-TIGIT TsAb_M and CD19-CD3-TIGIT TsAb_D In the present disclosure, a TiTE tri-specific antibody targeting human CD19 protein on the surface of lymphoma B cells, T cell surface human CD3 and T cell inhibitory molecule TIGIT protein is named as CD19-CD3-TIGIT TsAb.

1. Construction Design of CD19-CD3-TIGIT TsAb_M and CD19-CD3-TIGIT TsAb_D

Construction design of CD19-CD3-TIGIT TsAb_M Monomer:

The sequences of the anti-CD19 scFv, anti-CD3 scFv and anti-TIGIT scFv are linked by a linker. Specifically, the sequence of anti-CD19 scFv and the anti-CD3 scFv are linked by Linker 1, the sequence of anti-CD3 scFv and anti-TIGIT scFv are linked by Linker 2.

Construction design of CD19-CD3-TIGIT TsAb_D Dimer:

The sequences of the anti-CD19 scFv, anti-CD3 scFv and anti-TIGIT scFv are linked by linkers. Specifically, the sequences of anti-CD19 scFv and anti-CD3 scFv are linked by Linker 1, the sequences of anti-CD3 scFv and anti-TIGIT scFv are linked by IgD hinge region (Ala90-Val170) as Linker 2.

In order to express the tri-specific antibody in mammalian cells, codon optimization of mammalian system was performed for the sequence of anti-CD19 scFv, anti-CD3 scFv, and anti-TIGIT scFv.

The nucleotide sequence of anti-CD19 scFv heavy chain variable region is shown as SEQ ID NO. 307.

The nucleotide sequence of anti-CD19 scFv light chain variable region is shown as SEQ ID NO. 308.

The nucleotide sequence of anti-CD19 scFv is shown as SEQ ID NO. 306.

The nucleotide sequence of anti-CD3 scFv heavy chain variable region is shown as SEQ ID NO. 310 in details.

The nucleotide sequence of anti-CD3 scFv light chain variable region is shown as SEQ ID NO. 311.

The nucleotide sequence of anti-CD3 scFv is shown as SEQ ID NO. 309.

The nucleotide sequence of anti-TIGIT scFv heavy chain variable region is shown as SEQ ID NO. 325.

The nucleotide sequence of anti-TIGIT scFv light chain variable region is shown as SEQ ID NO. 326.

The nucleotide sequence of anti-TIGIT scFv is shown as SEQ ID NO. 324.

The nucleotide sequence of CD19-CD3-TIGIT TsAb_M monomer linker (Linker 1) is shown as SEQ ID NO. 245.

The nucleotide sequence of CD19-CD3-TIGIT TsAb_M monomer linker (Linker 2) is shown as SEQ ID NO. 247.

The nucleotide sequence of CD19-CD3-TIGIT TsAb_D dimer linker (Linker 1) is shown as SEQ ID NO. 249.

The nucleotide sequence of CD19-CD3-TIGIT TsAb_D dimer linker (Linker 2) is shown as SEQ ID NO. 251.

In order to express tri-specific antibody successfully in CHO-S cells and secret into medium, signal peptide of antibody secretory expression was selected in this Embodiment.

The amino acid sequence of this secretory signal peptide is shown as SEQ ID NO. 330.

The nucleotide sequence of this secretory signal peptide is shown as SEQ ID NO. 331.

2. CD19-CD3-TIGIT TsAb_M and CD19-CD3-TIGIT TsAb_D Eukaryotic Expression Vector Construction The construction and expression of this tri-specific antibody in the present disclosure selected mammalian cell protein transient expression vector pcDNA3.1 (purchased from Invitrogen, Shanghai). In order to construct the tri-specific antibody in monomer and dimer form, primers were designed as in table 4-5. All the primers were synthesized by Genewiz, Suzhou, and DNA template for PCR was synthesized by Synbio Technologies, Suzhou.

The cloning construct for CD19-CD3-TIGIT TsAb_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+anti-TIGIT scFv sequence by primer pairs Sig-CD19-F and CD19-R, CD19-G4S-CD3-F and CD3-R, and CD3-$(GGGGS)_3$-TIGIT-F and pcDNA3.1-TIGIT-R, respectively. The cloning construct for CD19-CD3-TIGIT TsAb_D includes: amplifying signal peptide by primers pcDNA3.1-Sig-F and Sig-R, and then amplifying anti-CD19 scFv, GGGGS Linker 1+anti-CD3 scFv, IgD hinge region Linker2, and anti-TIGIT scFv sequence by primer pairs Sig-CD19-F and CD19-R, CD19-G4S-CD3-F and CD3-R, CD3-IgD-F and IgD-R, and IgD-TIGIT-F and pcDNA3.1-TIGIT-R, respectively. After PCR amplification, by using NovoRec® PCR One-Step Cloning Kit (purchased from Wujiang Novoprotein Technology Co., Ltd.), the full length of tri-specific antibody monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-TIGIT TsAb_M monomer and CD19-CD3-TIGIT TsAb_D dimer both had the right full DNA sequence as expected.

The nucleotide sequence of CD19-CD3-TIGIT TsAb_M monomer is shown as SEQ ID NO. 275.

The nucleotide sequence of CD19-CD3-TIGIT TsAb_D dimer is shown as SEQ ID NO. 277.

TABLE 4-5

Primers used in CD19-CD3-TIGIT tri-specific antibody gene cloning

| Primer name | sequence | No. |
|---|---|---|
| CD3-$(GGGGS)_3$-TIGIT-F | GGCACCAAGCTGGAGCTGAAGGGCGGCGGCGGCAGCGGCGGCGGCGGCAGCGGCGGCGGCGGCAGCGAGGTGCAGCTGCAGGAGAGC | SEQ ID NO. 352 |

TABLE 4-5-continued

Primers used in CD19-CD3-TIGIT tri-specific antibody gene cloning

| Primer name | sequence | No. |
|---|---|---|
| pcDNA3.1-TIGIT-R | CTGATCAGCGGTTTAAACTTAAGCTTTCAGCGCTTCAGCTCCACCTTGGT | SEQ ID NO. 353 |
| IgD-TIGIT-F | CACACCCAGCCCCTGGGCGTGGAGGTGCAGCTGCAGGAGAGC | SEQ ID NO. 354 |

Embodiment 4-18: The Expression and Purification of CD19-CD3-TIGIT TsAb_M and CD19-CD3-TIGIT TsAb_D 1. The Expression of CD19-CD3-TIGIT TsAb_M and CD19-CD3-TIGIT TsAb_D The cell density of CHO-S cells (purchased from Thermo Fisher Scientific) was 0.5~0.6×$10^6$/ml one day before transfection.

Calculating cell density at the day of transfection, plasmid transfection can be performed when the density is in the range of 1~1.4×$10^6$/ml and live percentage is >90%.

Transfection complex recipes: each project (CD19-CD3-TIGIT TsAb_M and CD19-CD3-TIGIT TsAb_D) requires two centrifuge tubes/flasks. Take total 20 ml as an example, the recombinant plasmids from Embodiment 4-17 were taken: Tube 1: 600 μl PBS, 20 μg recombinant plasmid, mix well; Tube 2: 600 μl PBS, 20 μl FreeStyle™ MAX Transfection Reagent (purchased from Thermo Fisher Scientific), mix well.

Adding the diluted transfection reagent into the diluted recombinant plasmid, mixing well to obtain transfection complex.

Keeping transfection complex for 15~20 min, adding it into cell culture dropwise steadily.

Keeping cell culture at 37° C., 8% $CO_2$ and 130 rpm on cell shaker. Collecting medium after 5 days for the target protein test.

2. The Purification of CD19-CD3-TIGIT TsAb_M and CD19-CD3-TIGIT TsAb_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-TIGIT TsAb_M and CD19-CD3-TIGIT TsAb_D recombinant protein was analyzed by SDS-PAGE, and the protein electrophoresis data under reduced and unreduced conditions were shown as FIG. 4-14. It shows that, after the purification of protein L affinity chromatography column, both purity of CD19-CD3-TIGIT TsAb_M and CD19-CD3-TIGIT TsAb_D recombinant protein are >95%. The theoretical molecule weight for CD19-CD3-TIGIT TsAb_M is 80.9 kDa, and protein displayed the same single band under reduced and unreduced conditions. The molecule weight of these bands is consistent with monomer, so this tri-specific antibody is monomer (FIG. 4-14A, Lane 1: protein marker for molecule weight; Lane 2: reduced CD19-CD3-TIGIT TsAb_M; Lane 3: unreduced CD19-CD3-TIGIT TsAb_M). The theoretical molecule weight for CD19-CD3-TIGIT TsAb_D is 88.8 kDa, and protein displayed the same molecular weight as monomer under reduced condition, but the molecular weight is consistent with dimer under unreduced condition (~180 kDa) (FIG. 4-14B, Lane 1: protein marker for molecule weight; Lane 2: reduced CD19-CD3-TIGIT TsAb_D; Lane 3: unreduced CD19-CD3-TIGIT TsAb_D), which indicate two protein link to each other by disulfide bond formed through IgD hinge region so that this tri-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-TIGIT TsAb_M is monomer and CD19-CD3-TIGIT TsAb_D is dimer.

Therefore, the amino acid sequence of CD19-CD3-TIGIT TsAb_M monomer is shown as SEQ ID NO. 274.

The amino acid sequence of CD19-CD3-TIGIT TsAb_D dimer is shown as SEQ ID NO. 276.

The amino acid sequence of anti-CD19 scFv is shown as SEQ ID NO. 282.

The amino acid sequence of anti-CD19 scFv heavy chain variable region is shown as SEQ ID NO. 283.

The amino acid sequence of anti-CD19 scFv light chain variable region is shown as SEQ ID NO. 284.

The amino acid sequence of anti-CD3 scFv is shown as SEQ ID NO. 285.

The amino acid sequence of anti-CD3 scFv heavy chain variable region is shown as SEQ ID NO. 286.

The amino acid sequence of anti-CD3 scFv light chain variable region is shown as SEQ ID NO. 287.

The amino acid sequence of anti-TIGIT scFv is shown as SEQ ID NO. 300.

The amino acid sequence of anti-TIGIT scFv heavy chain variable region is shown as SEQ ID NO. 301.

The amino acid sequence of anti-TIGIT scFv light chain variable region is shown as SEQ ID NO. 302.

The amino acid sequence of CD19-CD3-TIGIT TsAb_M monomer linker (Linker 1) is shown as SEQ ID NO. 244.

The amino acid sequence of CD19-CD3-TIGIT TsAb_M monomer linker (Linker 2) is shown as SEQ ID NO. 246.

The amino acid sequence of CD19-CD3-TIGIT TsAb_D dimer linker (Linker 1) is shown as SEQ ID NO. 248.

The amino acid sequence of CD19-CD3-TIGIT TsAb_D dimer linker (Linker 2) is shown as SEQ ID NO. 250.

Embodiment 4-19: Antigen Binding Activity Test of CD19-CD3-TIGIT TsAb_M and CD19-CD3-TIGIT TsAb_D by ELISA ELISA procedure:

1. Recombinant antigen coating: 96-well plates were coated by human CD19-hFc, CD3-hFc and human TIGIT-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g Na2HPO4, 0.24 g NaH2PO4, 0.2 g KCl, 8.2 g NaCl, 950 ml H2O, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific antibody samples respectively and keeping plates at 37° C. for 1 hour. Sample serial dilution includes: using 10 μg/ml purified CD19-CD3-TIGIT TsAb_M or CD19-CD3-TIGIT TsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5~10 min at room temperature.

5. Reaction termination and result test: adding 100 μl per well of 1M HCl to stop reaction, and reading OD value of 450 nm absorbance on ELISA reader.

The results of ELISA are shown in FIGS. 4-15A and 4-15B. The four curves in the figure represent three four results: ■ coated with 1 μg/ml CD19-hFc recombinant antigen, ◈ coated with 1 μg/ml CD3-hFc recombinant antigen; ▲ coated with 1 μg/ml TIGIT-hFc recombinant antigen; ▼ no antigen coated result. FIG. 4-15A indicates that CD19-CD3-TIGIT TsAb_M has antigen binding activity with CD19-hFc, CD3-hFc and TIGIT-hFc in vitro, TIGIT and CD19 have higher binding activity, CD3 has weaker binding activity. FIG. 4-15B indicates that CD19-CD3-TIGIT TsAb_D has antigen binding activity with CD19-hFc, CD3-hFc and TIGIT-hFc in vitro as well, among which TIGIT and CD19 have higher binding activity, CD3 has weaker binding activity.

Embodiment 4-20: CD19-CD3-TIGIT Tri-Specific Antibody-Mediated Cell Killing Assay Human PBMC (Peripheral blood mononuclear cell, PBMC) was used as experiment material. The above-mentioned TiTE tri-specific antibody CD19-CD3-TIGIT TsAb_M in monomeric form, TiTE tri-specific antibody CD19-CD3-TIGIT TsAb_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, washing again, and using a small amount of pre-cooled X-vivo 15 serum-free medium (purchased from Lonza) to resuspend the cells. Counting cells for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-TIGIT TsAb_M and CD19-CD3-TIGIT TsAb_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{OD \text{ value of } Raji \text{ cells} + OD \text{ value of } CIK \text{ cells} - \text{detected } OD \text{ value}}{OD \text{ value of } Raji \text{ cells}} \times 100\%$$

The results are shown in FIG. 4-16: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-TIGIT TsAb_D have the best cell killing effect. The killing efficacy is about 88%, 86% and 76%. The effect of CD19-CD3-TIGIT TsAb_M is in the second place, the killing efficacy is about 82%, 79% and 66%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-TIGIT TsAb_D and CD19-CD3-TIGIT TsAb_M against Raji cells is improved to some extent, and the killing efficacy is about 66% and 65%, respectively. While CD19-CD3 BsAb had no effect compared with the blank control. The above results indicated that the two forms of CD19-CD3-TIGIT TiTE tri-specific antibody-mediated T cell-targeted killing activity against CD19-positive tumor cells were superior to that of BiTE bispecific antibody. The dimeric form has a better effect than the monomer form.

Embodiment 4-21: The Eukaryotic Expression Vector Construction of CD19-CD3-BTLA TsAb_M and CD19-CD3-BTLA TsAb_D In the present disclosure, a TiTE tri-specific antibody targeting human CD19 protein on the surface of lymphoma B cells, T cell surface human CD3 and T cell inhibitory molecule BTLA protein is named as CD19-CD3-BTLA TsAb.

1. Construction Design of CD19-CD3-BTLA TsAb_M and CD19-CD3-BTLA TsAb_D

Construction design of CD19-CD3-BTLA TsAb_M Monomer:

The sequences of the anti-CD19 scFv, anti-CD3 scFv and anti-BTLA scFv are linked by a linker. Specifically, the sequence of anti-CD19 scFv and the anti-CD3 scFv are linked by Linker 1, the sequence of anti-CD3 scFv and anti-BTLA scFv are linked by Linker 2.

Construction design of CD19-CD3-BTLA TsAb_D Dimer:

The sequences of the anti-CD19 scFv, anti-CD3 scFv and anti-BTLA scFv are linked by linkers. Specifically, the sequences of anti-CD19 scFv and anti-CD3 scFv are linked by Linker 1, the sequences of anti-CD3 scFv and anti-BTLA scFv are linked by IgD hinge region (Ala90-Val170) as Linker 2.

In order to express the tri-specific antibody in mammalian cells, codon optimization of mammalian system was performed for the sequence of anti-CD19 scFv, anti-CD3 scFv, and anti-BTLA scFv.

The nucleotide sequence of anti-CD19 scFv heavy chain variable region is shown as SEQ ID NO. 307.

The nucleotide sequence of anti-CD19 scFv light chain variable region is shown as SEQ ID NO. 308.

The nucleotide sequence of anti-CD19 scFv is shown as SEQ ID NO. 306.

The nucleotide sequence of anti-CD3 scFv heavy chain variable region is shown as SEQ ID NO. 310 in details.

The nucleotide sequence of anti-CD3 scFv light chain variable region is shown as SEQ ID NO. 311.

The nucleotide sequence of anti-CD3 scFv is shown as SEQ ID NO. 309.

The nucleotide sequence of anti-BTLA scFv heavy chain variable region is shown as SEQ ID NO. 328.

The nucleotide sequence of anti-BTLA scFv light chain variable region is shown as SEQ ID NO. 329.

The nucleotide sequence of anti-BTLA scFv is shown as SEQ ID NO. 327.

The nucleotide sequence of CD19-CD3-BTLA TsAb_M monomer linker (Linker 1) is shown as SEQ ID NO. 245.

The nucleotide sequence of CD19-CD3-BTLA TsAb_M monomer linker (Linker 2) is shown as SEQ ID NO. 247.

The nucleotide sequence of CD19-CD3-BTLA TsAb_D dimer linker (Linker 1) is shown as SEQ ID NO. 249.

The nucleotide sequence of CD19-CD3-BTLA TsAb_D dimer linker (Linker 2) is shown as SEQ ID NO. 251.

In order to express tri-specific antibody successfully in CHO-S cells and secret into medium, signal peptide of antibody secretory expression was selected in this Embodiment.

The amino acid sequence of this secretory signal peptide is shown as SEQ ID NO. 330.

The nucleotide sequence of this secretory signal peptide is shown as SEQ ID NO. 331.

2. CD19-CD3-BTLA TsAb_M and CD19-CD3-BTLA TsAb_D Eukaryotic Expression Vector Construction The construction and expression of this tri-specific antibody in the present disclosure selected mammalian cell protein transient expression vector pcDNA3.1 (purchased from Invitrogen, Shanghai). In order to construct the tri-specific antibody in monomer and dimer form, primers were designed as in table 4-6. All the primers were synthesized by Genewiz, Suzhou, and DNA template for PCR was synthesized by Synbio Technologies, Suzhou.

The cloning construct for CD19-CD3-BTLA TsAb_M includes: amplifying signal peptide by primers pcDNA3.1-Sig-F and Sig-R, and then amplifying anti-CD19 scFv, GGGGS Linker 1+anti-CD3 scFv, and $(GGGGS)_3$ Linker 2+anti-BTLA scFv sequence by primer pairs Sig-CD19-F and CD19-R, CD19-G4S-CD3-F and CD3-R, and CD3-$(GGGGS)_3$—BTLA-F and pcDNA3.1-BTLA-R, respectively. The cloning construct for CD19-CD3-BTLA TsAb_D includes: amplifying signal peptide by primers pcDNA3.1-Sig-F and Sig-R, and then amplifying anti-CD19 scFv, GGGGS Linker 1+anti-CD3 scFv, IgD hinge region Linker2, and anti-BTLA scFv sequence by primer pairs Sig-CD19-F+CD19-R, CD19-G4S-CD3-F+CD3-R, CD3-IgD-F+IgD-R, and IgD-BTLA-F+pcDNA3.1-BTLA-R, respectively. After PCR amplification, by using NovoRec® PCR One-Step Cloning Kit (purchased from Wujiang Novoprotein Technology Co., Ltd.), the full length of tri-specific antibody monomer and dimer were separately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with correct sequence were purified by midi-prep, and then transfected into CHO-S cells.

After sequencing, the CD19-CD3-BTLA TsAb_M monomer and CD19-CD3-BTLA TsAb_D dimer both had the right full DNA sequence as expected.

The nucleotide sequence of CD19-CD3-BTLA TsAb_M monomer is shown as SEQ ID NO. 279.

The nucleotide sequence of CD19-CD3-BTLA TsAb_D dimer is shown as SEQ ID NO. 281.

TABLE 4-6

Primers used in CD19-CD3-BTLA tri-specific antibody gene cloning

| Primer name | sequence | No. |
|---|---|---|
| CD3-$(GGGGS)_3$-BTLA-F | GGCACCAAGCTGGAGCTGAAGGGCGGCGGCGGCAGCGGCGGCGGCGGCAGCGGCGGCGGCGGCAGCGAGGTGCAGCTGGTGGAGAGC | SEQ ID NO. 355 |
| pcDNA3.1-BTLA-R | CTGATCAGCGGTTTAAACTTAAGCTTTCAGCGCTTGATCTCCAGGCGGGT | SEQ ID NO. 356 |

TABLE 4-6-continued

Primers used in CD19-CD3-BTLA tri-specific antibody gene cloning

| Primer name | sequence | No. |
|---|---|---|
| IgD-BTLA-F | CACACCCAGCCCCTGGGCGTGGAGGTGCAGCTGGTGGAGAGC | SEQ ID NO. 357 |

Embodiment 4-22: The Expression and Purification of CD19-CD3-BTLA TsAb_M and CD19-CD3-BTLA TsAb_D 1. The Expression of CD19-CD3-BTLA TsAb_M and CD19-CD3-BTLA TsAb_D 1.1 The cell density of CHO-S cells (purchased from Thermo Fisher Scientific) was $0.5\sim0.6\times10^6$/ml one day before transfection.

1.2 Calculating cell density at the day of transfection, plasmid transfection can be performed when the density is in the range of $1\sim1.4\times10^6$/ml and live percentage is >90%.

1.3 Transfection complex recipes: each project (CD19-CD3-BTLA TsAb_M and CD19-CD3-BTLA TsAb_D) requires two centrifuge tubes/flasks. Take total 20 ml as an example, the recombinant plasmids from Embodiment 4-21 were taken: Tube 1: 600 μl PBS, 20 μg recombinant plasmid, mix well; Tube 2: 600 μl PBS, 20 μl FreeStyle™ MAX Transfection Reagent (purchased from Thermo Fisher Scientific), mix well.

1.4 Adding the diluted transfection reagent into the diluted recombinant plasmid, mixing well to obtain transfection complex.

1.5 Keeping transfection complex for 15-20 min, adding it into cell culture dropwise steadily.

1.6 Keeping cell culture at 37° C., 8% $CO_2$ and 130 rpm on cell shaker. Collecting medium after 5 days for the target protein test.

2. The Purification of CD19-CD3-BTLA TsAb_M and CD19-CD3-BTLA TsAb_D 2.1 Sample pretreatment Taking 20 ml cell medium after transfection, adding 20 mM PB, 200 mM NaCl, and adjusting pH to 7.5;

2.2 Purification of Protein L affinity chromatography column

Protein purification chromatography column: Protein L affinity chromatography column (purchased from GE Healthcare, column volume: 1.0 ml)

Buffer A:PBS, pH7.4; Buffer B:0.1M Glycine, pH3.0; Buffer C:0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C, collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrating and dialyzing the flowthrough sample into buffer PBS.

The final purified CD19-CD3-BTLA TsAb_M and CD19-CD3-BTLA TsAb_D recombinant protein was analyzed by SDS-PAGE, and the protein electrophoresis data under reduced and unreduced conditions were shown as FIG. 4-17. It shows that, after the purification of protein L affinity chromatography column, both purity of CD19-CD3-BTLA TsAb_M and CD19-CD3-BTLA TsAb_D recombinant protein are >95%. The theoretical molecule weight for CD19-CD3-BTLA TsAb_M is 80.0 kDa, and protein displayed the same single band under reduced and unreduced conditions. The molecule weight of these bands is consistent with monomer, so this tri-specific antibody is monomer (FIG. 4-17A, Lane 1: protein marker for molecule weight; Lane 2: reduced CD19-CD3-BTLA TsAb_M; Lane 3: unreduced CD19-CD3-BTLA TsAb_M). The theoretical molecule weight for CD19-CD3-BTLA TsAb_D is 87.9 kDa, and protein displayed the same molecular weight as monomer under reduced condition, but the molecular weight is consistent with dimer under unreduced condition (~180 kDa) (FIG. 4-17B, Lane 1: protein marker for molecule weight; Lane 2: reduced CD19-CD3-BTLA TsAb_D; Lane 3: unreduced CD19-CD3-BTLA TsAb_D), which indicate two protein link to each other by disulfide bond formed through IgD hinge region so that this tri-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD19-CD3-BTLA TsAb_M is monomer and CD19-CD3-BTLA TsAb_D is dimer.

Therefore, the amino acid sequence of CD19-CD3-BTLA TsAb_M monomer is shown as SEQ ID NO. 278.

The amino acid sequence of CD19-CD3-BTLA TsAb_D dimer is shown as SEQ ID NO. 280.

The amino acid sequence of anti-CD19 scFv is shown as SEQ ID NO. 282.

The amino acid sequence of anti-CD19 scFv heavy chain variable region is shown as SEQ ID NO. 283.

The amino acid sequence of anti-CD19 scFv light chain variable region is shown as SEQ ID NO. 284.

The amino acid sequence of anti-CD3 scFv is shown as SEQ ID NO. 285.

The amino acid sequence of anti-CD3 scFv heavy chain variable region is shown as SEQ ID NO. 286.

The amino acid sequence of anti-CD3 scFv light chain variable region is shown as SEQ ID NO. 287.

The amino acid sequence of anti-BTLA scFv is shown as SEQ ID NO. 303.

The amino acid sequence of anti-BTLA scFv heavy chain variable region is shown as SEQ ID NO. 304.

The amino acid sequence of anti-BTLA scFv light chain variable region is shown as SEQ ID NO. 305.

The amino acid sequence of CD19-CD3-BTLA TsAb_M monomer linker (Linker 1) is shown as SEQ ID NO. 244.

The amino acid sequence of CD19-CD3-BTLA TsAb_M monomer linker (Linker 2) is shown as SEQ ID NO. 246.

The amino acid sequence of CD19-CD3-BTLA TsAb_D dimer linker (Linker 1) is shown as SEQ ID NO. 248.

The amino acid sequence of CD19-CD3-BTLA TsAb_D dimer linker (Linker 2) is shown as SEQ ID NO. 250.

Embodiment 4-23: Antigen Binding Activity Test of CD19-CD3-BTLA TsAb_M and CD19-CD3-BTLA TsAb_D by ELISA ELISA procedure:

1. Recombinant antigen coating: 96-well plates were coated by human CD19-hFc, CD3-hFc and human BTLA-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding 200 μl per well of PBSA (PBS+2% BSA(V/W)) to block at 37° C. for 1 hour.

3. Adding sample: washing plates with PBS for 4 times, adding 100 μl per well of purified tri-specific antibody samples respectively and keeping plates at 37° C. for 1 hour. Sample serial dilution includes: using 10 μg/ml purified CD19-CD3-BTLA TsAb_M or CD19-CD3-BTLA TsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well of color-developing TMB (purchased from KPL), developing in dark for 5~10 min at room temperature.

5. Reaction termination and result test: adding 100 μl per well of 1M HCl to stop reaction, and reading OD value of 450 nm absorbance on ELISA reader.

The results of ELISA are shown in FIGS. 4-18A and 4-18B. The four curves in the figure represent three four results: ■ coated with 1 μg/ml CD19-hFc recombinant antigen, ● coated with 1 μg/ml BTLA-hFc recombinant antigen; ▲ coated with 1 μg/ml TIGIT-hFc recombinant antigen; ▼ no antigen coated result. FIG. 4-18A indicates that CD19-CD3-BTLA TsAb_M has antigen binding activity with CD19-hFc, CD3-hFc and BTLA-hFc in vitro, among which BTLA has the highest binding activity, CD19 has the second highest binding activity, and CD3 has the weakest binding activity. FIG. 4-18B indicates that CD19-CD3-BTLA TsAb_D has antigen binding activity with CD19-hFc, CD3-hFc and BTLA-hFc in vitro as well, among which BTLA has the highest binding activity, CD19 has the second highest binding activity, and CD3 has the weakest binding activity.

Embodiment 4-24: CD19-CD3-BTLA Tri-Specific Antibody-Mediated Cell Killing Assay Human PBMC (Peripheral blood mononuclear cell, PBMC) was used as experiment material. The above-mentioned TiTE tri-specific antibody CD19-CD3-BTLA TsAb_M in monomeric form, TiTE tri-specific antibody CD19-CD3-BTLA TsAb_D in dimeric form and anti-CD19/anti-CD3 BiTE bispecific antibody (CD19-CD3 BsAb, purchased from Novoprotein, Wujiang) were applied to CIK cells (CD3+CD56+) prepared by PBMC from the same donor and CCL-86 Raji lymphoma cells (CD19+, purchased from ATCC), respectively. Tumor cells (CD19+) were tested for cell death, and the difference in killing efficacy of CCL-86 Raji target cells by three antibody-mediated CIK effector cells was compared.

Cell Killing Assay Procedure:

1. Separating PBMC: Using a fresh anticoagulant blood from volunteers, adding an equal volume of medical saline, and slowly adding an equal volume of lymphocyte separation solution (purchased from GE Healthcare) along the wall of the centrifuge tube to maintain the liquid level. Centrifuging at 2000 rpm for 20 min. Pipetting white fluffy cell layer in the middle into a new tube, washing with PBS buffer with volume more than 2 times of the pipetted cell layer, centrifuging at 1100 rpm for 10 min, repeat the washing once, and using a small amount of pre-cooled X-vivo 15 serum-free medium (purchased from Lonza) to resuspend the cells. Counting cells for use.

2. CIK cell culture and expansion: Resuspending PBMC with CIK basic medium (90% X-vivo 15+10% FBS, Gibco), adjusting cell density to $1\times10^6$/ml. Adding cells into T25 flask coated by full-length antibody Anti-CD3 (5 μg/ml), full-length antibody Anti-CD28 (5 μg/ml) and NovoNectin (25 μg/ml) (full length antibody and NovoNectin were purchased from Novoprotein, Wujiang), IFN-γ(200 ng/ml, purchased from Novoprotein, Wujiang) and IL-1β (2 ng/ml, purchased from Novoprotein, Wujiang) were added to the T25 flask, keeping cell culture in incubator at 37° C., with saturated humidity and $CO_2$ concentration of 5.0%. After overnight, adding 500 U/ml IL-2 (purchased from Novoprotein, Wujiang) into cell medium and keeping culture. Every 2-3 days, counting cells and passaging cells as $1\times10^6$/ml density in CIK basic medium with 500 U/ml IL-2.

3. Killing efficacy of CIK cells against Raji cells: Cell killing experiments were carried out in 96-well plates. The reaction volume was 100 uL, $1\times10^5$ of the cultured CIK cells were taken, and $1\times10^5$ of Raji cells were added (CIK effector cells: Raji target cells (E:T ratio) is 1:1). Then CD19-CD3 BsAb and CD19-CD3-BTLA TsAb_M and CD19-CD3-BTLA TsAb_D antibody are added at different final concentrations (25, 12.5, 6.25, 3.125 ng/ml). Mixing at room temperature for 3-5 min, after culturing at 37° C. for 3 h, adding 10 μl CCK8 per well, and keeping reaction at 37° C. for 2-3 h. Then using OD reader to detect $OD_{450}$, calculating cytotoxicity efficacy by the following formula. Each group was detected for 3 times. The cytotoxicity of CIK cultured without any antibody was blank control of killing efficacy.

$$\text{Killing efficacy (\%)} = \frac{OD \text{ value of } Raji \text{ cells} + OD \text{ value of } CIK \text{ cells} - \text{detected } OD \text{ value}}{OD \text{ value of } Raji \text{ cells}} \times 100\%$$

The results are shown in FIG. 4-19: When the CIK effector cells: Raji target cells (E:T ratio) were 1:1, the killing efficacy was about 23% after 3 h without adding any antibody. The killing efficacy of CIK cells on Raji cells was significantly improved under the conditions of adding higher concentrations of antibodies (25, 12.5, 6.25 ng/ml). Among them, Cells mediated by CD19-CD3-BTLA TsAb_D have the best cell killing effect. The killing efficacy is about 90%, 87% and 86%. The effect of CD19-CD3-BTLA TsAb_M is in the second place, the killing efficacy is about 86%, 82% and 76%. The effect of CD19-CD3 BsAb is the weakest and the killing efficacy is about 80%, 54% and 54%. Under the condition of adding lower concentration antibody (3.125 ng/ml), the killing efficacy of CIK cells mediated by CD19-CD3-BTLA TsAb_D and CD19-CD3-BTLA TsAb_M against Raji cells is improved to some extent, and the killing efficacy is about 79% and 68%, respectively. While CD19-CD3 BsAb had no effect compared with the blank control. The above results indicated that the two forms of CD19-CD3-BTLA TiTE tri-specific antibody-mediated T cell-targeted killing activity against CD19-positive tumor cells were superior to that of BiTE bispecific antibody. The dimeric form has a better effect than the monomer form.

The above is only a preferred embodiment of the present disclosure, and is not intended to limit the scope of the present disclosure. It should be noted that for those skilled in the field, a number of modifications and additions may be made without departing from the method of the disclosure, and such modifications and additions are also considered to be within the scope of the disclosure. Any changes, modifications, and evolutions that can be made based on the above-disclosed technical content by those skilled in the field are still the equivalents of the present embodiment, without departing from the spirit and scope of the present disclosure. At the same time, any changes, modifications and evolutions of any equivalent changes made to the above-described embodiments in accordance with the essential techniques of the present disclosure are still within the scope of the technical solutions of the present disclosure.

The invention claimed is:

1. A trifunctional molecule, selected from any one of the following:

(1) the trifunctional molecule comprising a first functional domain capable of binding to CD19, a second functional domain capable of binding to and activating CD3 molecule on a surface of T cell, and a third functional domain capable of binding to and activating a T cell positive costimulatory molecule, wherein the first functional domain is an anti-CD19 scFv, the second functional domain is an anti-CD3 scFv, and the third functional domain is an scFv against T cell positive costimulatory molecule or the extracellular domain of a ligand of the T cell positive costimulatory molecule;

(2) the trifunctional molecule comprising a first functional domain capable of binding to CD19, a second functional domain capable of binding to and activating CD3 molecule on the surface of T cell, and a third functional domain capable of binding to and blocking a T cell negative costimulatory molecule, wherein the first functional domain is an anti-CD19 scFv, the second functional domain is an anti-CD3 scFv, and the third functional domain is an scFv against T cell negative costimulatory molecule, wherein each of the scFvs comprises a heavy chain variable region and a light chain variable region;

wherein the first functional domain and the second functional domain are connected by a first linker, and the second functional domain and the third functional domain are connected by a second linker;

wherein the first linker is a linker fragment consisting of G4S units, and the amino acid sequence of the linker fragment consisting of the G4S units comprises any one of SEQ ID NO. 23, SEQ ID NO. 25 or SEQ ID NO. 27; and wherein the second linker is a hinge domain fragment of immunoglobulin IgD, and the amino acid sequence of the hinge domain fragment of immunoglobulin IgD comprises SEQ ID NO. 29.

2. The trifunctional molecule according to claim 1, wherein the trifunctional molecule is:

capable of binding to and activating CD3 molecule on a surface of T cell and T cell positive costimulatory molecules while recognizing CD19, thereby generating a first signal and a second signal required for T cell activation; or, capable of binding to and activating CD3 molecule on a surface of T cell, binding to and blocking a T cell negative costimulatory molecule while recognizing CD19, thereby generating a first signal and a second signal required for T cell activation.

3. The trifunctional molecule according to claim 1, wherein the scFv against T cell positive costimulatory molecule is selected from the group consisting of anti-CD28 scFv, anti-4-1BB scFv, anti-ICOS scFv, anti-OX40 scFv, anti-GITR scFv, anti-CD40L scFv, and anti-CD27 scFv;

the ligand extracellular domain of the T cell positive costimulatory molecule is selected from the group consisting of 4-1BBL, B7RP-1, OX40L, GITRL and CD70 ligand extracellular domains; and the scFv against T cell negative costimulatory molecule is selected from the group consisting of anti-PD-1 scFv, anti-CTLA-4 scFv, anti-LAG-3 scFv, anti-TIM-3 scFv, anti-TIGIT scFv, and anti-BTLA scFv.

4. The trifunctional molecule according to claim 3, wherein the amino acid sequence of the heavy chain variable region of the anti-CD19 scFv comprises SEQ ID NO. 6, the amino acid sequence of the light chain variable region of the anti-CD19 scFv comprises SEQ ID NO. 7;

the amino acid sequence of the heavy chain variable region of the anti-CD3 scFv comprises SEQ ID NO. 9, the amino acid sequence of the light chain variable region of the anti-CD3 scFv comprises SEQ ID NO. 10;

the amino acid sequence of the heavy chain variable region of the anti-CD28 scFv comprises SEQ ID NO. 12, the amino acid sequence of the light chain variable region of the anti-CD28 scFv comprises SEQ ID NO. 13;

the amino acid sequence of the heavy chain variable region of the anti-4-1BB scFv comprises SEQ ID NO. 90, the amino acid sequence of the light chain variable region of the anti-4-1BB scFv comprises SEQ ID NO. 91;

the amino acid sequence of the heavy chain variable region of the anti-ICOS scFv comprises SEQ ID NO. 93, the amino acid sequence of the light chain variable region of the anti-ICOS scFv comprises SEQ ID NO. 94;

the amino acid sequence of the heavy chain variable region of the anti-OX40 scFv comprises SEQ ID NO. 96, the amino acid sequence of the light chain variable region of the anti-OX40 scFv comprises SEQ ID NO. 97;

the amino acid sequence of the heavy chain variable region of the anti-GITR scFv comprises SEQ ID NO. 99, the amino acid sequence of the light chain variable region of the anti-GITR scFv comprises SEQ ID NO. 100;

the amino acid sequence of the heavy chain variable region of the anti-CD40L scFv comprises SEQ ID NO. 102, the amino acid sequence of the light chain variable region of the anti-CD40L scFv comprises SEQ ID NO. 103;

the amino acid sequence of the heavy chain variable region of the anti-CD27 scFv comprises SEQ ID NO. 105, the amino acid sequence of the light chain variable region of the anti-CD27 scFv comprises SEQ ID NO. 106;

the amino acid sequence of the heavy chain variable region of the anti-PD-1 scFv comprises SEQ ID NO. 289, the amino acid sequence of the light chain variable region of the anti-PD-1 scFv comprises SEQ ID NO. 290;

the amino acid sequence of the heavy chain variable region of the anti-CTLA-4 scFv comprises SEQ ID NO. 292, the amino acid sequence of the light chain variable region of the anti-CTLA-4 scFv comprises SEQ ID NO. 293;

the amino acid sequence of the heavy chain variable region of the anti-LAG-3 scFv comprises SEQ ID NO. 295, the amino acid sequence of the light chain variable region of the anti-LAG-3 scFv comprises SEQ ID NO. 296;

the amino acid sequence of the heavy chain variable region of the anti-TIM-3 scFv comprises SEQ ID NO. 298, the amino acid sequence of the light chain variable region of the anti-TIM-3 scFv comprises SEQ ID NO. 299;

the amino acid sequence of the heavy chain variable region of the anti-TIGIT scFv comprises SEQ ID NO. 301, the amino acid sequence of the light chain variable region of the anti-TIGIT scFv comprises SEQ ID NO. 302; or the amino acid sequence of the heavy chain variable region of the anti-BTLA scFv comprises SEQ ID NO. 304, the amino acid sequence of the light chain variable region of the anti-BTLA scFv comprises SEQ ID NO. 305.

5. The trifunctional molecule according to claim 3, wherein the amino acid sequence of the anti-CD19 scFv comprises SEQ ID NO. 5;

the amino acid sequence of the anti-CD3 scFv comprises SEQ ID NO. 8;

the amino acid sequence of the anti-CD28 scFv comprises SEQ ID NO. 11;

the amino acid sequence of the anti-4-1BB scFv comprises SEQ ID NO. 89;

the amino acid sequence of the anti-ICOS scFv comprises SEQ ID NO. 92;

the amino acid sequence of the anti-OX40 scFv comprises SEQ ID NO. 95;

the amino acid sequence of the anti-GITR scFv comprises SEQ ID NO. 98;

the amino acid sequence of the anti-CD40L scFv comprises SEQ ID NO. 101;

the amino acid sequence of the anti-CD27 scFv comprises SEQ ID NO. 104;

the amino acid sequence of 4-1BBL extracellular domain comprises SEQ ID NO. 203;

the amino acid sequence of B7RP-1 extracellular domain comprises SEQ ID NO. 204;

the amino acid sequence of OX40L extracellular domain comprises SEQ ID NO. 205;

the amino acid sequence of GITRL extracellular domain comprises SEQ ID NO. 206;

the amino acid sequence of CD70 extracellular domain comprises SEQ ID NO. 207;

the amino acid sequence of the anti-PD-1 scFv comprises SEQ ID NO. 288;

the amino acid sequence of the anti-CTLA-4 scFv comprises SEQ ID NO. 291;

the amino acid sequence of the anti-LAG-3 scFv comprises SEQ ID NO. 294;

the amino acid sequence of the anti-TIM-3 scFv comprises SEQ ID NO. 297;

the amino acid sequence of the anti-TIGIT scFv comprises SEQ ID NO. 300; or, the amino acid sequence of the anti-BTLA scFv comprises SEQ ID NO. 303.

6. The trifunctional molecule according to claim 1, wherein the amino acid sequence of the trifunctional molecule comprises any one of SEQ ID NO. 1, SEQ ID NO. 3, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 177, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, SEQ ID NO. 258, SEQ ID NO. 260, SEQ ID NO. 262, SEQ ID NO. 264, SEQ ID NO. 266, SEQ ID NO. 268, SEQ ID NO. 270, SEQ ID NO. 272, SEQ ID NO. 274, SEQ ID NO. 276, SEQ ID NO. 278 and SEQ ID NO. 280.

7. A polynucleotide encoding a trifunctional molecule according to claim 1.

8. An expression vector comprising the polynucleotide of claim 7.

9. A host cell transfected with the expression vector of claim 8.

10. A method for preparing a trifunctional molecule of claim 1, comprising:

constructing an expression vector comprising a trifunctional molecule gene sequence, transfecting the expression vector into a host cell to induce expression, and separating the trifunctional molecule from an expression product.

11. A therapeutic composition for tumor therapy, comprising the trifunctional molecule according to claim 1 and at least one pharmaceutically acceptable carrier or excipient.

12. A method for treating a subject with a tumor, comprising administering the trifunctional molecule of claim 1 to the subject.

* * * * *